US010138225B2

(12) United States Patent
Wiles et al.

(10) Patent No.: US 10,138,225 B2
(45) Date of Patent: Nov. 27, 2018

(54) AMIDE COMPOUNDS FOR TREATMENT OF MEDICAL DISORDERS

(71) Applicant: Achillion Pharmaceuticals, Inc., New Haven, CT (US)

(72) Inventors: Jason Allan Wiles, Madison, CT (US); Avinash S. Phadke, Branford, CT (US); Milind Deshpande, Madison, CT (US); Atul Agarwal, Hamden, CT (US); Dawei Chen, Guilford, CT (US); Venkat Rao Gadhachanda, Hamden, CT (US); Akihiro Hashimoto, Branford, CT (US); Godwin Pais, Hamden, CT (US); Qiuping Wang, Bethany, CT (US); Xiangzhu Wang, Branford, CT (US)

(73) Assignee: Achillion Pharmaceuticals, Inc., New Haven, CT (US)

(*) Notice: Subject to any disclaimer, the term of this patent is extended or adjusted under 35 U.S.C. 154(b) by 0 days.

(21) Appl. No.: 15/247,440

(22) Filed: Aug. 25, 2016

(65) Prior Publication Data

US 2017/0057950 A1 Mar. 2, 2017

Related U.S. Application Data

(60) Provisional application No. 62/209,931, filed on Aug. 26, 2015.

(51) Int. Cl.
| | |
|---|---|
| *A61K 31/416* | (2006.01) |
| *A61K 31/404* | (2006.01) |
| *C07D 403/14* | (2006.01) |
| *C07D 403/06* | (2006.01) |
| *C07D 401/14* | (2006.01) |
| *C07D 413/14* | (2006.01) |
| *C07D 471/08* | (2006.01) |
| *C07D 513/04* | (2006.01) |
| *C07D 495/04* | (2006.01) |

(52) U.S. Cl.
CPC .......... *C07D 403/14* (2013.01); *A61K 31/404* (2013.01); *A61K 31/416* (2013.01); *C07D 401/14* (2013.01); *C07D 403/06* (2013.01); *C07D 413/14* (2013.01); *C07D 471/08* (2013.01); *C07D 495/04* (2013.01); *C07D 513/04* (2013.01)

(58) Field of Classification Search
None
See application file for complete search history.

(56) References Cited

U.S. PATENT DOCUMENTS

| | | |
|---|---|---|
| 6,489,476 B1 | 12/2002 | Dang et al. |
| 6,653,340 B1 | 11/2003 | Babu et al. |
| 2005/0228000 A1 | 10/2005 | Smallheer et al. |
| 2005/0267108 A1 | 12/2005 | Hsieh et al. |
| 2007/0155712 A1 | 7/2007 | Zahn et al. |
| 2008/0075720 A1 | 3/2008 | Holers et al. |
| 2008/0075728 A1 | 3/2008 | Newman et al. |
| 2008/0108691 A1 | 5/2008 | Hamann et al. |
| 2010/0041628 A1 | 2/2010 | Enomoto et al. |
| 2011/0280808 A1 | 11/2011 | Kroth et al. |
| 2012/0231471 A1 | 9/2012 | Sato et al. |
| 2012/0295884 A1 | 11/2012 | Altmann et al. |
| 2013/0296377 A1 | 11/2013 | Adams et al. |
| 2014/0371133 A1 | 12/2014 | Francois et al. |
| 2015/0141455 A1 | 5/2015 | Altmann et al. |
| 2015/0148374 A1 | 5/2015 | Hommel et al. |
| 2015/0239837 A1 | 8/2015 | Wiles et al. |
| 2015/0239838 A1 | 8/2015 | Phadke et al. |
| 2015/0239893 A1 | 8/2015 | Wang et al. |
| 2015/0239894 A1 | 8/2015 | Gadhachanda et al. |
| 2015/0239895 A1 | 8/2015 | Gadhachanda et al. |
| 2015/0239919 A1 | 8/2015 | Gadhachanda et al. |
| 2015/0239920 A1 | 8/2015 | Gadhachanda et al. |
| 2015/0239921 A1 | 8/2015 | Wiles et al. |
| 2015/0269868 A1 | 8/2015 | Pais et al. |

FOREIGN PATENT DOCUMENTS

| | | |
|---|---|---|
| WO | WO 1993/020099 A2 | 10/1993 |
| WO | WO 1995/029697 A1 | 11/1995 |
| WO | WO 1999/048492 A1 | 9/1999 |
| WO | WO 2004/007501 A1 | 1/2004 |
| WO | WO 2004/045518 A2 | 6/2004 |
| WO | WO 2004/111041 A1 | 12/2004 |
| WO | WO 2008/047831 A1 | 4/2008 |
| WO | WO 2009/091826 A2 | 7/2009 |
| WO | WO 2012/093101 A1 | 7/2012 |

(Continued)

OTHER PUBLICATIONS

Airey et al. "A Convenient Preparation of Thieno[3,2-c]pyrazole" Synthesis, 2014; 46: 96-100.
Barraclough et al. "Synthesis of (2S,3R)- and (@S,3S)-[3-2H1]-proline via highly selective hydrolysis of a silyl enol ether" Tetrahedron Letters, 2005; 46: 4653-4655.
Barraclough et al. "Two separate and distinct syntheses of stereospecifically deuteriated samples of (2S)-proline" Organic & Biomolecular Chemistry, 2006; 4: 1483-1491.
Cole et al. "Structure of 3,4-Dichloroisocoumarin-Inhibited Factor D" Acta Crystallographica, 1998; D54: 711-717.
De Luca et al. "HIV-1 integrase strand-transfer inhibitors: Design, synthesis and molecular modeling investigation" European Journal of Medicinal Chemistry, 2011; 46: 756-764.

(Continued)

*Primary Examiner* — Samantha L Shterengarts
(74) *Attorney, Agent, or Firm* — Knowles Intellectual Property Strategies, LLC

(57) ABSTRACT

Compounds, methods of use, and processes for making inhibitors of complement Factor D comprising Formula I, or a pharmaceutically acceptable salt or composition thereof wherein $R^{12}$ or $R^{13}$ on the A group is an amide substituent ($R^{32}$) are provided. The inhibitors described herein target Factor D and inhibit or regulate the complement cascade. The inhibitors of Factor D described herein are capable of reducing the excessive activation of complement.

31 Claims, 55 Drawing Sheets

(56) References Cited

FOREIGN PATENT DOCUMENTS

| WO | WO 2012/177782 A1 | 12/2012 |
|---|---|---|
| WO | WO 2013/166436 A1 | 11/2013 |
| WO | WO 2014/002051 A2 | 1/2014 |
| WO | WO 2014/002052 A1 | 1/2014 |
| WO | WO 2014/002053 A1 | 1/2014 |
| WO | WO 2014/002054 A1 | 1/2014 |
| WO | WO 2014/002057 A1 | 1/2014 |
| WO | WO 2014/002058 A2 | 1/2014 |
| WO | WO 2014/002059 A1 | 1/2014 |
| WO | WO 2014/005150 A1 | 1/2014 |
| WO | WO 2014/009833 A2 | 1/2014 |
| WO | WO 2014/037480 A1 | 3/2014 |
| WO | WO 2014/116880 A1 | 7/2014 |
| WO | WO 2015/130784 A1 | 9/2015 |
| WO | WO 2015/130795 A1 | 9/2015 |
| WO | WO 2015/130806 A1 | 9/2015 |
| WO | WO 2015/130830 A1 | 9/2015 |
| WO | WO 2015/130838 A1 | 9/2015 |
| WO | WO 2015/130842 A2 | 9/2015 |
| WO | WO 2015/130845 A1 | 9/2015 |
| WO | WO 2015/130854 A1 | 9/2015 |
| WO | WO 2017/035348 A1 | 3/2017 |
| WO | WO 2017/035349 A1 | 3/2017 |
| WO | WO 2017/035351 A1 | 3/2017 |
| WO | WO 2017/035352 A1 | 3/2017 |
| WO | WO 2017/035353 A1 | 3/2017 |
| WO | WO 2017/035355 A1 | 3/2017 |
| WO | WO 2017/035357 A1 | 3/2017 |
| WO | WO 2017/035360 A1 | 3/2017 |
| WO | WO 2017/035361 A1 | 3/2017 |
| WO | WO 2017/035362 A1 | 3/2017 |
| WO | WO 2017/035401 A1 | 3/2017 |
| WO | WO 2017/035405 A1 | 3/2017 |
| WO | WO 2017/035408 A1 | 3/2017 |
| WO | WO 2017/035409 A1 | 3/2017 |
| WO | WO 2017/035411 A1 | 3/2017 |
| WO | WO 2017/035413 A1 | 3/2017 |
| WO | WO 2017/035415 A1 | 3/2017 |
| WO | WO 2017/035417 A1 | 3/2017 |
| WO | WO 2017/035418 A1 | 3/2017 |
| WO | WO 2017/098328 A2 | 6/2017 |

OTHER PUBLICATIONS

Donthiri et al. "Copper-Catalyzed C—H Functionalization of Pyridines and Isoquinolines with Vinyl Azides: Synthesis of Imidazo Heterocycles" Journal of Organic Chemistry, 2014; 79: 11277-11284.

Dormoy et al. "Synthesis of N-t-Butoxycarbonyl-4,4-dideuterio-L-proline" Synthesis, 1986; 1: 81-82.

Hecker et al. "Liver-Targeted Prodrugs of 2'-C-Methyladenosine for Therapy of Hepatitis C Virus Infection" Journal of Medicinal Chemistry, 2007; 50(16): 3891-3896.

Hruby et al. "Carbon-13 NMR studies of the Peptide hormones oxytocin, arginine vasopressin, isotocin, mesotocin, glumitocin, aspartocin, related analogs, and diastereoisomers. Use of specifically deuterated hormone derivatives for assignments and effects of structural changes on carbon-13 NMR chemical shifts in peptides" Journal of the American Chemical Society, 1979; 101(1): 202-212.

International Search Report and Written Opinion for PCT/US2015/017523 dated May 14, 2015.

International Search Report and Written Opinion for PCT/US2015/017538 dated May 14, 2015.

International Search Report and Written Opinion for PCT/US2015/017554 dated May 14, 2015.

International Search Report and Written Opinion for PCT/US2015/017583 dated May 27, 2015.

International Search Report and Written Opinion for PCT/US2015/017593 dated Jun. 16, 2015.

International Search Report and Written Opinion for PCT/US2015/017597 dated Jan. 29, 2016.

International Search Report and Written Opinion for PCT/US2015/17600 dated May 27, 2015.

International Search Report and Written Opinion for PCT/US2015/017609 dated May 29, 2015.

Kobayashi et al. "Carboxylation of alkynylsilanes with carbon dioxide mediated by cesium fluoride in DMSO" Organic & Biomolecular Chemistry, 2013; 11: 3773-3775.

Kuang et al. "Synthesis of (Z)-1-bromo-1-alkenes and terminal alkynes from anti-2,3-dibromoalkanoic acids by microwave-induced reaction" Tetrahedron, 2006; 61(16): 4043-4052.

Mackay et al. "Rapid Synthesis of the N-Methylwelwitindolinone Skeleton" Organic Letters, 2005; 7: 3421-3424.

Okutani et al. "Conversion of Bromoalkenes into Alkynes by Wet Tetra-n-butylammonium Fluoride" Journal of Organic Chemistry, 2009; 74: 442-444.

Quesada et al. "One-pot conversion of activated alcohols into terminal alkynes using manganese dioxide in combination with the Bestmann-Ohira reagent" Tetrahedron Letters, 2005; 46: 6473-6476.

Roth et al. "Further Improvements of the Synthesis of Alkynes from Aldehydes" Synthesis, 2004; 1: 59-62.

Ruiz-Gomez et al. "Structure—Activity Relationships for Substrate-Based Inhibitors of Human Complement Factor B" Journal of Medicinal Chemistry, 2009; 52: 6042-6052.

Tandon et al. "Substrate specificity of human prolyl-4-hydroxylase" Bioorganic and Medicinal Chemistry Letters, 1998; 8(10): 1139-1144.

Tang et al. "Palladium-Catalyzed Carbonylative Sonogashira Coupling of Aryl Bromides via tert-Butyl Isocyanide Insertion" Journal of Organic Chemistry, 2013; 78(7): 3170-3175.

9,598,446 B2, U.S. Appl. No. 14/631,312, Gadhachanda et al., dated Mar. 21, 2017.

9,643,986 A1, U.S. Appl. No. 14/630,959, Wiles et al., dated May 9, 2017.

9,663,543 B2, U.S. Appl. No. 14/631,785, Wiles et al., dated May 30, 2017.

9,695,205 B2, U.S. Appl. No. 14/631,233, Wiles et al., dated Jul. 4, 2017.

2016-0361329 A1, U.S. Appl. No. 15/246,049, Wiles et al., filed Dec. 15, 2016.

2016-0362398 A1, U.S. Appl. No. 15/245,712, Wiles et al., dated Dec. 15, 2016.

2016-0362399 A1, U.S. Appl. No. 15/245,788, Wiles et al., dated Dec. 15, 2016.

2016-0362432 A1, U.S. Appl. No. 15/245,945, Wiles et al., dated Dec. 15, 2016.

2016-0362433 A1, U.S. Appl. No. 15/245,872, Wiles et al., dated Dec. 15, 2016.

2017-0056428 A1, U.S. Appl. No. 15/247,429, Wiles et al., dated Mar. 2, 2017.

2017-0057983 A1, U.S. Appl. No. 15/247,424, Wiles et al., dated Mar. 2, 2017.

2017-0057993 A1, U.S. Appl. No. 15/247,410, Wiles et al., dated Mar. 2, 2017.

2017-0066783 A1, U.S. Appl. No. 15/247,399, Wiles et al., dated Mar. 9, 2017.

2017-0189410 A1, U.S. Appl. No. 15/463,701, Gadhachanda et al., dated Jul. 6, 2017.

2015-0239837 A1, U.S. Appl. No. 14/630,959, Wiles et al., dated Aug. 27, 2015.

2015-0239868 A1, U.S. Appl. No. 14/631,090, Pais et al., dated Aug. 27, 2015.

2015-0239893 A1, U.S. Appl. No. 14/631,233, Wang et al., dated Aug. 27, 2015.

2015-0239894 A1, U.S. Appl. No. 14/631,312, Gadhachanda et al., dated Aug. 27, 2015.

2015-0239919 A1, U.S. Appl. No. 14/631,440, Gadhachanda et al., dated Aug. 27, 2015.

2015-0239895 A1, U.S. Appl. No. 14/631,625, Gadhachanda et al., dated Aug. 27, 2015.

2015-0239920 A1, U.S. Appl. No. 14/631,683, Gadhachanda et al., dated Aug. 27, 2015.

2015-0239921 A1, U.S. Appl. No. 14/631,785, Wiles et al., dated Aug. 27, 2015.

(56) References Cited

OTHER PUBLICATIONS 2015-0239838 A1, U.S. Appl. No. 14/631,828, Phadke et al., dated Aug. 27, 2015.
Peifer et al. "Design, Synthesis, and Biological Evaluation of Novel 3-Aryl-4-(1H-indole-3yl)-1,5-dihydro-2H-pyrrole-2-ones as Vascular Endothelial Growth Factor Receptor (VEGF-R) Inhibitors", J. Med. Chem. 2008, vol. 51, pp. 3814-3824.
Qu et al. "Recent Developments in Low Molecular Weight Complement Inhibitors", Mol. Immunol. 2009. vol. 47 (2-3). pp. 185-195.
International Search Report and Written Opinion for PCT/US2016/048688 dated Dec. 28, 2016.
International Search Report and Written Opinion for PCT/US2016/048690 dated Dec. 28, 2016.
International Search Report and Written Opinion for PCT/US2016/048693 dated Jan. 13, 2017.
International Search Report and Written Opinion for PCT/US2016/048695 dated Dec. 30, 2016.
International Search Report and Written Opinion for PCT/US2016/048696 dated Jan. 5, 2017.
International Search Report and Written Opinion for PCT/US2016/048701 dated Jan. 10, 2017.
International Search Report and Written Opinion for PCT/US2016/048704 dated Dec. 27, 2016.
International Search Report and Written Opinion for PCT/US2016/048707 dated Jan. 5, 2017.
International Search Report and Written Opinion for PCT/US2016/048709 dated Jan. 17, 2017.
International Search Report and Written Opinion for PCT/US2016/048797 dated Jan. 5, 2017.
International Search Report and Written Opinion for PCT/US2016/048779 dated Dec. 27, 2016.
International Search Report and Written Opinion for PCT/US2016/048783 dated Feb. 3, 2017.
International Search Report and Written Opinion for PCT/US2016/048795 dated Feb. 17, 2017.
International Search Report and Written Opinion for PCT/US2016/048788 dated Jan. 5, 2017.
International Search Report and Written Opinion for PCT/US2016/048793 dated Dec. 28, 2016.
International Search Report and Written Opinion for PCT/US2016/048799 dated Dec. 28, 2016.
International Search Report and Written Opinion for PCT/US2016/048787 dated Jan. 5, 2017.
International Search Report and Written Opinion for PCT/US2016/048800 dated Jan. 5, 2017.
International Search Report and Written Opinion for PCT/US2016/048710 dated Jan. 5, 2017.

AMIDE COMPOUNDS FOR TREATMENT OF MEDICAL DISORDERS

CROSS-REFERENCE TO RELATED APPLICATIONS

This application claims the benefit of provisional U.S. Application No. 62/209,931, filed Aug. 26, 2015 and the entirety of the application is hereby incorporated by reference for all purposes.

BACKGROUND

An immune disorder occurs when the immune system is not performing in a normal manner. Inflammation is a protective response that involves the immune system, blood vessels, and molecular mediators. A wide variety of medical disorders are caused by detrimental immune or inflammatory responses, or the inability of a cell to respond to a normal immune or inflammatory process.

The complement system is a part of the innate immune system which does not adapt to changes over the course of the host's life, but instead is recruited and used by the adaptive immune system. For example, it assists, or complements, the ability of antibodies and phagocytic cells to clear pathogens. This sophisticated regulatory pathway allows rapid reaction to pathogenic organisms while protecting host cells from destruction. Over thirty proteins and protein fragments make up the complement system. These proteins act through opsonization (enhancing phagocytosis of antigens), chemotaxis (attracting macrophages and neutrophils), cell lysis (rupturing membranes of foreign cells) and agglutination (clustering and binding of pathogens together).

The complement system has three pathways: classical, alternative and lectin. Complement Factor D plays an early and central role in activation of the alternative pathway of the complement cascade. Activation of the alternative complement pathway is initiated by spontaneous hydrolysis of a thioester bond within C3 to produce C3($H_2O$), which associates with Factor B to form the C3($H_2O$)B complex. Complement Factor D acts to cleave Factor B within the C3($H_2O$)B complex to form Ba and Bb. The Bb fragment remains associated with C3($H_2O$) to form the alternative pathway C3 convertase C3($H_2O$)Bb. Additionally, C3b generated by any of the C3 convertases also associates with Factor B to form C3bB, which Factor D cleaves to generate the later stage alternative pathway C3 convertase C3bBb. This latter form of the alternative pathway C3 convertase may provide important downstream amplification within all three of the defined complement pathways, leading ultimately to the recruitment and assembly of additional factors in the complement cascade pathway, including the cleavage of C5 to C5a and C5b. C5b acts in the assembly of factors C6, C7, C8, and C9 into the membrane attack complex, which can destroy pathogenic cells by lysing the cell.

The dysfunction of or excessive activation of complement has been linked to certain autoimmune, inflammatory, and neurodegenerative diseases, as well as ischemia-reperfusion injury and cancer. For example, activation of the alternative pathway of the complement cascade contributes to the production of C3a and C5a, both potent anaphylatoxins, which also have roles in a number of inflammatory disorders. Therefore, in some instances, it is desirable to decrease the response of the complement pathway, including the alternative complement pathway. Some examples of disorders mediated by the complement pathway include age-related macular degeneration (AMD), paroxysmal nocturnal hemoglobinuria (PNH), multiple sclerosis, and rheumatoid arthritis.

Age-related macular degeneration (AMD) is a leading cause of vision loss in industrialized countries. Based on a number of genetic studies, there is evidence of the link between the complement cascade and macular degeneration. Individuals with mutations in the gene encoding complement Factor H have a fivefold increased risk of macular degeneration and individuals with mutations in other complement factor genes also have an increased risk of AMD. Individuals with mutant Factor H also have increased levels of C-reactive protein, a marker of inflammation. Without adequate functioning of Factor H, the alternative pathway of the complement cascade is overly activated leading to cellular damage. Inhibition of the alternative pathway under these circumstances is thus desired.

Paroxysmal nocturnal hemoglobinuria (PNH) is a non-malignant, hematological disorder characterized by the expansion of hematopoietic stem cells and progeny mature blood cells which are deficient in some surface proteins. PNH erythrocytes are not capable of modulating their surface complement activation, which leads to the typical hallmark of PNH—the chronic activation of complement mediated intravascular anemia. Alexion Pharmaceutical's anti-C5 antibody eculizumab (Soliris®) is currently the only complement-specific antibody on the market, and is the first and only approved treatment for paroxysmal nocturnal hemoglobinuria (PNH). Exciluzimab is also approved for atypical hemolytic uremic syndrome (aHUS). However, many of the patients treated with eculizumab remain anemic, and many patients continue to require blood transfusions. In addition, treatment with eculizumab requires lifelong intravenous injections. Thus, there is an unmet need to develop novel inhibitors of the complement pathway.

Other disorders that have been linked to the complement cascade include aHUS, hemolytic uremic syndrome (HUS), abdominal aortic aneurysm, hemodialysis complications, hemolytic anemia, or hemodialysis, neuromylitis (NMO), myasthenia gravis (MG), fatty liver, nonalcoholic steatohepatitis (NASH), liver inflammation, cirrhosis, liver failure, dermatomyocitis, and amyotrophic lateral sclerosis.

Factor D is an attractive target for inhibition or regulation of the complement cascade due to its early and essential role in the alternative complement pathway, and its potential role in signal amplification within the classical and lectin complement pathways. Inhibition of Factor D effectively interrupts the pathway and attenuates the formation of the membrane attack complex.

While initial attempts have been made to develop inhibitors of Factor D, there are currently no small molecule Factor D inhibitors in clinical trials. Examples of Factor D inhibitors or prolyl compounds are described in the following disclosures.

Biocryst Pharmaceuticals U.S. Pat. No. 6,653,340 titled "Compounds useful in the complement, coagulat and kallikrein pathways and method for their preparation" describes fused bicyclic ring compounds that are potent inhibitors of Factor D. Development of the Factor D inhibitor BCX1470 was discontinued due to lack of specificity and short half-life of the compound.

Novartis PCT patent publication WO2012/093101 titled "Indole compounds or analogues thereof useful for the treatment of age-related macular degeneration" describes certain Factor D inhibitors. Additional Factor D inhibitors are described in Novartis PCT patent publications WO2014/002051, WO2014/002052, WO2014/002053, WO2014/

002054, WO2014/002057, WO2014/002058, WO2014/002059, WO2014/005150, and WO2014/009833.

Bristol-Myers Squibb PCT patent publication WO2004/045518 titled "Open chain prolyl urea-related modulators of androgen receptor function" describes open chain prolyl urea and thiourea related compounds for the treatment of androgen receptor-associated conditions, such as age-related diseases, for example, sarcopenia.

Japan Tobacco Inc. PCT patent publication WO1999/048492 titled "Amide derivatives and nociceptin antagonists" describes compounds with a proline-like core and aromatic substituents connected to the proline core through amide linkages useful for the treatment of pain.

Ferring B. V. and Yamanouchi Pharmaceutical Co. 1TD. PCT patent publication WO1993/020099 titled "CCK and/or gastrin receptor ligands" describes compounds with a proline-like core and heterocyclic substituents connected to the proline core through amide linkages for the treatment of, for example, gastric disorders or pain.

Alexion Pharmaceuticals PCT patent publication WO1995/029697 titled "Methods and compositions for the treatment of glomerulonephritis and other inflammatory diseases" discloses antibodies directed to C5 of the complement pathway for the treatment of glomerulonephritis and inflammatory conditions involving pathologic activation of the complement system.

On Feb. 25, 2015, Achillion Pharmaceuticals filed PCT Patent Application No. PCT/US2015/017523 and U.S. patent application Ser. No. 14/631,090 titled "Alkyne Compounds for Treatment of Complement Mediated Disorders"; PCT Patent Application No. PCT/US2015/017538 and U.S. patent application Ser. No. 14/631,233 titled "Amide Compounds for Treatment of Complement Mediated Disorders"; PCT Patent Application No. PCT/US2015/017554 and U.S. patent application Ser. No. 14/631,312 titled "Amino Compounds for Treatment of Complement Mediated Disorders"; PCT Patent Application No. PCT/US2015/017583 and U.S. patent application Ser. No. 14/631,440 titled "Carbamate, Ester, and Ketone Compounds for Treatment of Complement Mediated Disorders"; PCT Patent Application No. PCT/US2015/017593 and U.S. patent application Ser. No. 14/631,625 titled "Aryl, Heteroaryl, and Heterocyclic Compounds for Treatment of Complement Mediated Disorders"; PCT Patent Application No. PCT/US2015/017597 and U.S. patent application Ser. No. 14/631,683 titled "Ether Compounds for Treatment of Complement Mediated Disorders"; PCT Patent Application No. PCT/US2015/017600 and U.S. patent application Ser. No. 14/631,785 titled "Phosphonate Compounds for Treatment of Complement Mediated Disorders"; and PCT Patent Application No. PCT/US2015/017609 and U.S. patent application Ser. No. 14/631,828 titled "Compounds for Treatment of Complement Mediated Disorders."

Given the wide variety of medical disorders that are caused by detrimental immune or inflammatory responses, new uses and compounds are needed for medical treatment. In one aspect, new uses and compounds are needed to mediate the complement pathway, and for example, which act as Factor D inhibitors for treatment of disorders in a host, including a human, associated with dysregulation of the complement cascade, or with undesired result of the complement cascade performing its normal function.

SUMMARY

In a first embodiment, the invention is the use of a compound of Formula I, or a pharmaceutically acceptable salt or composition thereof, wherein at least one of $R^{12}$ or $R^{13}$ on the A group is an Amide substituent including those compounds set out in Table 1, for the treatment of a disorder in a host, typically a human, wherein the disorder is selected from the group disclosed in the Detailed Description, Part IV, Section A. The compounds of Table 1 were first disclosed in PCT Patent Application No. PCT/US2015/017538 and U.S. patent application Ser. No. 14/631,233 titled "Amide Compounds for Treatment of Complement Mediated Disorders", however, not for the indications now provided in the Detailed Description, Part IV, Section A. The compound is provided in an effective amount to treat the disorder, and is optionally provided in a pharmaceutically acceptable carrier. Therefore, in particular, this first embodiment includes uses of compounds to treat a disorder selected from the group disclosed in the Detailed Description, Part IV, Section A.

Non-limiting examples of disorders described in the Detailed Description, Part IV, Section A include: fatty liver and conditions stemming from fatty liver, nonalcoholic steatohepatitis (NASH), liver inflammation, cirrhosis, liver failure, dermatomyocitis, and amyotrophic lateral sclerosis. In another embodiment of Section A disorders, the active compound is used to modulate an immune response prior to, during, or after surgery or other medical procedure, or as adjunctive therapy to dampen the immune or inflammatory response during a pharmaceutical or biopharmaceutical drug treatment, a blood transfusion, or other allogenic tissue or fluid administration. In one embodiment, a Section A method is provided for the treatment or prevention of cytokine or inflammatory reactions in response to the administration of biotherapeutics (e.g. CAR T-cell therapy) in a host by administering an effective amount of a designated compound herein, or a pharmaceutically acceptable salt thereof, optionally in a pharmaceutically acceptable carrier.

Non-limiting examples of disorders in the Detailed Description, Part IV, Section B of this invention include paroxysmal nocturnal hemoglobinuria (PNH), rheumatoid arthritis, multiple sclerosis, age-related macular degeneration (AMD), retinal degeneration, other ophthalmic diseases (e.g., geographic atrophy), a respiratory disease or a cardiovascular disease. In one aspect, an active compound or its salt or composition can be used to treat a medical disorder which is mediated by either a dysfunctional complement cascade or a disorder or abnormality of a cell that adversely affects the ability of the cell to engage in or respond to normal complement activity, for example, including but not limited to sparing certain cells from complement mediated lysis. PNH is one example of such a disorder, wherein host blood cells are missing the gene PIG-A that expresses a protein that protects the blood cells from complement mediated lysis. Other embodiments of Section B disorders include complement associated disorders that are induced by antibody-antigen interactions, a component of an immune or autoimmune disorder, hereditary angioedema, capillary leak syndrome, atypical hemolytic uremic syndrome (aHUS), hemolytic uremic syndrome (HUS), abdominal aortic aneurysm, hemodialysis complications, hemolytic anemia and hemodialysis.

In a second embodiment of the invention, an amide compound is selected from Table 2 or an active compound that is prepared from or consists of moieties selected from FIGS. 1B, 1C, 2B, 2C, 2D, 2E, 3B, 3C, 3D, 3E, 3F, 3G, 3H, 3I, 3J, 3K, 3L, 3M, 3N, 5, 6A, and 6B; and optionally 4B, 4C, 4D, 4E, 4F or a pharmaceutically acceptable composition, salt, isotopic analog or prodrug thereof, for the treatment of an immune or inflammatory disorder in a host, typically a human, including a disorder selected from the group disclosed in the Detailed Description, Part IV, Section A or B. In one embodiment, the compound of Table 2 is used to treat a disorder associated with a dysfunction, including increased activity of the complement pathway that includes the administration of an effective amount of a compound selected from Table 2 or a pharmaceutically acceptable salt thereof, optionally in a pharmaceutically acceptable carrier, as described in more detail below. In one embodiment, the disorder is associated with the alternative complement cascade pathway. In yet another embodiment, the disorder is associated with the complement classical pathway. In a further embodiment, the disorder is associated with the complement lectin pathway. The compound in Table in one embodiment is used to dampen or inhibit detrimental complement activity in a host, by administration of an effective amount in a suitable manner to a host in need thereof. Therefore, in particular, this second embodiment includes compound species, and uses of these species to treat disorders selected from the group disclosed in the Detailed Description, Part IV, Section A or B.

In a third embodiment of the invention, an amide compound is provided selected from Table 3 or a pharmaceutically acceptable composition, salt, isotopic analog or prodrug thereof, for the treatment of an immune or inflammatory disorder in a host, typically a human, including a disorder selected from the group disclosed in the Detailed Description, Part IV, Section A or B. In one embodiment, the compound of Table 3 is used to treat a disorder associated with a dysfunction, including increased activity, of the complement pathway that includes the administration of an effective amount of a compound selected from Table 3 or a pharmaceutically acceptable salt thereof, optionally in a pharmaceutically acceptable carrier, as described in more detail below. In one embodiment, the disorder is associated with the alternative complement cascade pathway. In yet another embodiment, the disorder is associated with the complement classical pathway. In a further embodiment, the disorder is associated with the complement lectin pathway. The compound in Table 3 in one embodiment is used to dampen or inhibit detrimental complement activity in a host, by administration of an effective amount in a suitable manner to a host in need thereof. Therefore, in particular, this third embodiment includes compound species and uses of these species to treat a disorder selected from the group disclosed in the Detailed Description, Part IV, Section A or B.

In a fourth embodiment of the invention, an amide compound is provided that is prepared from or consists of moieties selected from FIGS. 1D, 1E, 5, 6A, 6B, 7A, 7B, 7C, 7D, 7E, and 8; and optionally 4B, 4C, 4D, 4E or 4F or a pharmaceutically acceptable composition, salt, isotopic analog or prodrug thereof, for the treatment of an immune or inflammatory disorder in a host, typically a human, including a disorder selected from the group disclosed in the Detailed Description, Part IV, Section A. In one embodiment, the compound that is prepared from or consists of moieties selected from FIGS. 1D, 1E, 5, 6A, 6B, 7A, 7B, 7C, 7D, 7E, and 8; and optionally 4B, 4C, 4D, 4E, or 4F is used to treat a disorder associated with a dysfunction, including increased activity, of the complement pathway that includes the administration of an effective amount of the compound or an embodiment of the active compound, or a pharmaceutically acceptable salt thereof, optionally in a pharmaceutically acceptable carrier, as described in more detail below. In one embodiment, the disorder is associated with the alternative complement cascade pathway. In yet another embodiment, the disorder is associated with the complement clas-
sical pathway. In a further embodiment, the disorder is associated with the complement lectin pathway. The compound in one embodiment provided herein is used to dampen or inhibit detrimental complement activity in a host, by administration of an effective amount in a suitable manner to a host in need thereof. Therefore, in particular, this fourth embodiment includes uses of these compounds to treat disorder selected from the group disclosed in the Detailed Description, Part IV, Section A.

In a fifth embodiment of the invention, an amide compound is provided that is prepared from or consists of moieties selected from FIGS. 1B, 1C, 1D, 1E, 3A, 3B, 3C, 3D, 3E, 3F, 3G, 3H, 3I, 3J, 3K, 3L, 3M, 3N, 3O, 3P, 3Q, 5, 6A, 6B, 6C, and 7F; and optionally 4B, 4C, 4D, 4E, and 4F or a pharmaceutically acceptable composition, salt, isotopic analog or prodrug thereof, for the treatment of an immune or inflammatory disorder in a host, typically a human, including a disorder selected from the group disclosed in the Detailed Description, Part IV, Section A or B. In one embodiment, the compound that is prepared from or consists of moieties selected from FIGS. 1B, 1C, 1D, 1E, 3A, 3B, 3C, 3D, 3E, 3F, 3G, 3H, 3I, 3J, 3K, 3L, 3M, 3N, 3O, 3P, 3Q, 5, 6A, 6B, 6C, and 7F; and optionally 4B, 4C, 4D, 4E, and 4F is used to treat a disorder associated with a dysfunction, including increased activity, of the complement pathway that includes the administration of an effective amount of the compound or an embodiment of the active compound, or a pharmaceutically acceptable salt thereof, optionally in a pharmaceutically acceptable carrier, as described in more detail below. In one embodiment, the disorder is associated with the alternative complement cascade pathway. In yet another embodiment, the disorder is associated with the complement classical pathway. In a further embodiment, the disorder is associated with the complement lectin pathway. The compound in one embodiment provided herein is used to dampen or inhibit detrimental complement activity in a host, by administration of an effective amount in a suitable manner to a host in need thereof. Therefore, in particular, this fifth embodiment includes compound species and uses of these species to treat disorder selected from the group disclosed in the Detailed Description, Part IV, Section A or B.

In a sixth embodiment of the invention, an amide compound is provided that is prepared from or consists of moieties selected from FIGS. 1B, 1C, 1D, 1E, 3A, 3B, 3C, 3D, 3E, 3F, 3G, 3H, 3I, 3J, 3K, 3L, 3M, 3N, 3O, 3P, 3Q, 5, 6A, 6B, 6C, 7G and 8; and optionally 4B, 4C, 4D, 4E, 4F or a pharmaceutically acceptable composition, salt, isotopic analog or prodrug thereof, for the treatment of an immune or inflammatory disorder in a host, typically a human, including a disorder selected from the group disclosed in the Detailed Description, Part IV, Section A. In one embodiment, the compound that is prepared from or consists of moieties selected from FIGS. 1B, 1C, 1D, 1E, 3A, 3B, 3C, 3D, 3E, 3F, 3G, 3H, 3I, 3J, 3K, 3L, 3M, 3N, 3O, 3P, 3Q, 5, 6A, 6B, 6C, 7G and 8; and optionally 4B, 4C, 4D, 4E, 4F is used to treat a disorder associated with a dysfunction, including increased activity, of the complement pathway that includes the administration of an effective amount of the compound or an embodiment of the active compound, or a pharmaceutically acceptable salt thereof, optionally in a pharmaceutically acceptable carrier, as described in more detail below. In one embodiment, the disorder is associated with the alternative complement cascade pathway. In yet another embodiment, the disorder is associated with the complement classical pathway. In a further embodiment, the disorder is associated with the complement lectin pathway.

The compound in one embodiment provided herein is used to dampen or inhibit detrimental complement activity in a host, by administration of an effective amount in a suitable manner to a host in need thereof. Therefore, in particular, this sixth embodiment includes uses of these species to treat disorder selected from the group disclosed in the Detailed Description, Part IV, Section A.

In a seventh embodiment of the invention, an amide compound as described and used herein is selected from those depicted in FIGS. 9A, 9B, 9C, 9D, 9E, 9F, 9G and 9H, and FIGS. 6A, and 6B or a pharmaceutically acceptable composition, salt, isotopic analog or prodrug thereof, for the treatment of an immune or inflammatory disorder in a host, typically a human, including a disorder selected from the group disclosed in the Detailed Description, Part IV, Section A or B. In one embodiment, the compound of FIG. 9A, 9B, 9C, 9D, 9E, 9F, 9G or 9H, and FIG. 6A, or 6B is used to treat a disorder associated with a dysfunction, including increased activity of the complement pathway that includes the administration of an effective amount of a compound selected from FIG. 9A, 9B, 9C, 9D, 9E, 9F, 9G or 9H, and FIG. 6A, or 6B or a pharmaceutically acceptable salt thereof, optionally in a pharmaceutically acceptable carrier, as described in more detail below. In one embodiment, the disorder is associated with the alternative complement cascade pathway. In yet another embodiment, the disorder is associated with the complement classical pathway. In a further embodiment, the disorder is associated with the complement lectin pathway. The compound in FIG. 9A, 9B, 9C, 9D, 9E, 9F, 9G or 9H, and FIG. 6A, or 6B in one embodiment is used to dampen or inhibit detrimental complement activity in a host, by administration of an effective amount in a suitable manner to a host in need thereof. Therefore, in particular, this seventh embodiment includes compound species, and uses of these species to treat disorder selected from the group disclosed in the Detailed Description, Part IV, Section A or B.

Compounds disclosed herein or used as described herein may be administered in any desired route according to the direction of the healthcare provider, for example, oral, topical, parenteral, by inhalation or spray, sublingual, via implant, including ocular implant, transdermal, via buccal administration, rectal, as an ophthalmic solution, injection, including ocular injection, intravenous, intra-aortal, intracranial, subdermal, intraperitoneal, subcutaneous, transnasal, sublingual, or rectal or by other means, in dosage unit formulations optionally containing conventional pharmaceutically acceptable carriers, and in an immediate or controlled release fashion. For use in the eye, any of the compounds described herein can be administered to the eye in any desired form of administration, including via intravitreal, intrastromal, intracameral, sub-tenon, sub-retinal, retro-bulbar, peribulbar, suprachoroidal, choroidal, subchoroidal, conjunctival, subconjunctival, episcleral, posterior juxtasclearlscleral, circumcorneal, and tear duct injections, or through a mucus, mucin, or a mucosal barrier, in an immediate or controlled release fashion.

The compounds of Formula I as described in PCT Patent Application No. PCT/US2015/017538 and U.S. patent application Ser. No. 14/631,233 titled "Amide Compounds for Treatment of Complement Mediated Disorders" are of the formula:

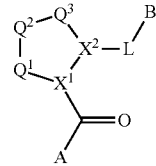

and the pharmaceutically acceptable salts and compositions thereof, wherein:

$Q^1$ is $N(R^1)$ or $C(R^1R^{1'})$;

$Q^2$ is $C(R^2R^{2'})$, $C(R^2R^{2'})$—$C(R^2R^{2+'})$, S, O, $N(R^2)$ or $C(R^2R^{2'})O$;

$Q^3$ is $N(R^3)$, S, or $C(R^3R^{3'})$;

$X^1$ and $X^2$ are independently N, CH, or CZ, or $X^1$ and $X^2$ together are C=C; and wherein $Q^1$, $Q^2$, $Q^3$, $X^1$, and $X^2$ are selected such that a stable compound results.

Any of the structures illustrated herein, e.g., A, B, L or central core can be optionally substituted with 0, 1, 2, 3, or 4, as appropriate, and independently, selected from $R^{75}$, wherein $R^{75}$ is selected from hydrogen, halogen, hydroxyl, nitro, cyano, amino, $C_1$-$C_6$alkyl, $C_1$-$C_6$haloalkyl, $C_2$-$C_6$alkenyl, $C_2$-$C_6$alkynyl, $C_1$-$C_6$thioalkyl, $C_1$-$C_6$alkoxy, -$JC_3$-$C_7$cycloalkyl, —$B(OH)_2$, -$JC(O)NR^9R^{23}$, -$JOSO_2OR^{21}$, —$C(O)(CH_2)_{1-4}S(O)R^{21}$, —$O(CH_2)_{1-4}S(O)NR^{21}R^{22}$, -$JOP(O)(OR^{21})(OR^{22})$, -$JP(O)(OR^{21})(OR^{22})$, -$JOP(O)(OR^{21})R^{22}$, -$JP(O)(OR^{21})R^{22}$, -$JOP(O)R^{21}R^{22}$, -$JP(O)R^{21}R^{22}$, -$JSP(O)(OR^{21})(OR^{22})$, -$JSP(O)(OR^{21})(R^{22})$, -$JSP(O)(R^{21})(R^{22})$, -$JNR^9P(O)(NHR^{21})(NHR^{22})$, -$JNR^9P(O)(OR^{21})(NHR^{22})$, -$JNR^9P(O)(OR^{21})(OR^{22})$, -$JC(S)R^{21}$, -$JNR^{21}SO_2R^{22}$, -$JNR^9S(O)NR^{10}R^{22}$, -$JNR^9SO_2NR^{10}R^{22}$, -$JSO_2NR^9COR^{22}$, -$JSO_2NR^9CONR^{21}R^{22}$, -$JNR^{21}SO_2R^{22}$, -$JC(O)NR^{21}SO_2R^{22}$, -$JC(NH_2)$=$NR^{22}$, -$JCH(NH_2)NR^9S(O)_2R^{22}$, -$JOC(O)NR^{21}R^{22}$, -$JNR^{21}C(O)OR^{22}$, -$JNR^{21}OC(O)R^{22}$, —$(CH_2)_{1-4}C(O)NR^{21}R^{22}$, -$JC(O)NR^{24}R^{25}$, -$JNR^9C(O)R^{21}$, -$JC(O)R^{21}$, -$JNR^9C(O)NR^{10}R^{22}$, —$CCR^{21}$, —$(CH_2)_{1-4}OC(O)R^{21}$, -$JC(O)OR^{23}$; each of which $R^{75}$ may be unsubstituted or substituted with one or more substituents independently selected from halogen, hydroxyl, nitro, cyano, amino, oxo, —$B(OH)_2$, —$Si(CH_3)_3$, —$COOH$, —$CONH_2$, —$P(O)(OH)_2$, $C_1$-$C_6$alkyl, —$C_0$-$C_4$alkyl($C_3$-$C_7$cycloalkyl), $C_1$-$C_6$alkoxy, —$C_0$-$C_4$alkyl(mono- and)di-$C_1$-$C_4$alkylNR$^9R^{10}$, $C_1$-$C_6$alkylester, $C_1$-$C_4$alkylamino, $C_1$-$C_4$hydroxylalkyl, $C_1$-$C_2$haloalkyl, $C_1$-$C_2$haloalkoxy, —$OC(O)R^9$, —$NR^9C(O)R^{10}$, —$C(O)NR^9R^{10}$, —$OC(O)NR^9R^{10}$, —$NR^9C(O)OR^{10}$, $C_1$-$C_2$haloalkyl, and $C_1$-$C_2$haloalkoxy, $S(O)$=$NHR^{21}$, $SF_5$, and $JC(R^9)$=$NR^{21}$ and $SO_2OR^{21}$.

In an alternate embodiment, the

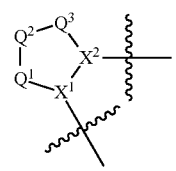

ring is replaced by one of the following core structures:

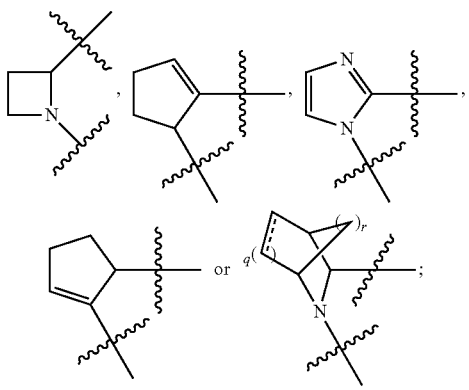

wherein q is 0, 1, 2 or 3, r is 1, 2 or 3, ≈≈≈≈ is a single or double bond. Examples of core structures are provided in FIGS. 3B, 3C, 3D, 3E, 3F, 3G, 3H, 3I, 3J, 3K, 3L, 3M, 3N, 3O, 3P, 3Q, and 5.

It is clear that when q is 0, ≈≈≈≈ is not a double bond.

R and R' (see FIG. 5) are independently selected from H, alkyl, cycloalkyl, cycloalkylalkyl, heterocycle, heterocycloalkyl, aryl, arylalkyl, heteroaryl, heteroarylalkyl wherein each group can be optionally substituted or any other substituent group herein that provides the desired properties. In some embodiments, the core ring includes one or more chiral carbon atoms. The invention includes the use of compounds with embodiments in which the chiral carbon can be provided as an enantiomer, or mixtures of enantiomers, including a racemic mixture. Where the core ring includes more than one stereocenter, all of the enantiomers and diastereomers are included in the invention as individual species.

Z is F, Cl, $NH_2$, $CH_3$, $CH_2D$, $CHD_2$, or $CD_3$.

$R^1$, $R^{1'}$, $R^2$, $R^{2'}$, $R^3$, and $R^{3'}$ are independently selected at each occurrence, as appropriate, and only where a stable compound results, from hydrogen, halogen, hydroxyl, nitro, cyano, amino, $C_1$-$C_6$alkyl, $C_2$-$C_6$alkenyl, $C_2$-$C_6$alkynyl, $C_1$-$C_6$alkoxy, $C_2$-$C_6$alkynyl, $C_2$-$C_6$alkanoyl, $C_1$-$C_6$thioalkyl, hydroxy$C_1$-$C_6$alkyl, amino$C_1$-$C_6$alkyl, —$C_0$-$C_4$alkylN$R^9R^{10}$, —C(O)O$R^9$, —OC(O)$R^9$, —N$R^9$C(O)$R^{10}$, —C(O)NR$^9R^{10}$, —OC(O)NR$^9R^{10}$, —NR$^9$C(O)OR$^{10}$, $C_1$-$C_2$haloalkyl, and $C_1$-$C_2$haloalkoxy, where $R^9$ and $R^{10}$ are independently selected at each occurrence from hydrogen, $C_1$-$C_6$alkyl, ($C_3$-$C_7$cycloalkyl)$C_0$-$C_4$alkyl, —$C_0$-$C_4$alkyl($C_3$-$C_7$cycloalkyl), and —O—$C_0$-$C_4$alkyl($C_3$-$C_7$cycloalkyl).

In alternative embodiments, $R^1$ and $R^{1'}$ or $R^3$ and $R^{3'}$ may be taken together to form a 3- to 6-membered carbocyclic spiro ring or a 3- to 6-membered heterocyclic spiro ring containing 1 or 2 heteroatoms independently selected from N, O, or S; $R^2$ and $R^{2'}$ may be taken together to form a 3- to 6-membered carbocyclic spiro ring; or $R^2$ and $R^{2'}$ may be taken together to form a 3- to 6-membered heterocyclic spiro ring; each of which spiro ring may be unsubstituted or substituted with 1 or more substituents independently selected from halogen (and in particular F), hydroxyl, cyano, —COOH, $C_1$-$C_4$alkyl (including in particular methyl), $C_2$-$C_4$alkenyl, $C_2$-$C_4$alkynyl, $C_1$-$C_4$alkoxy, $C_2$-$C_4$alkanoyl, hydroxy$C_1$-$C_4$alkyl, (mono- and di-$C_1$-$C_4$alkylamino)$C_0$-$C_4$alkyl, —$C_0$-$C_4$alkyl($C_3$-$C_7$cycloalkyl), —O—$C_0$-$C_4$alkyl($C_3$-$C_7$cycloalkyl), $C_1$-$C_2$haloalkyl, and $C_1$-$C_2$haloalkoxy.

In alternative embodiments, $R^1$ and $R^2$ may be taken together to form a 3-membered carbocyclic ring; $R^1$ and $R^2$ may be taken together to form a 4- to 6-membered carbocyclic or aryl ring or a 4- to 6-membered heterocyclic or heteroaryl ring containing 1 or 2 heteroatoms independently selected from N, O, and S; or $R^2$ and $R^3$, if bound to adjacent carbon atoms, may be taken together to form a 3- to 6-membered carbocyclic or aryl ring or a 3- to 6-membered heterocyclic or heteroaryl ring; each of which ring may be unsubstituted or substituted with 1 or more substituents independently selected from halogen (and in particular F), hydroxyl, cyano, —COOH, $C_1$-$C_4$alkyl (including in particular methyl), $C_2$-$C_4$alkenyl, $C_2$-$C_4$alkynyl, $C_1$-$C_4$alkoxy, $C_2$-$C_4$alkanoyl, hydroxy$C_1$-$C_4$alkyl, (mono- and di-$C_1$-$C_4$alkylamino)$C_0$-$C_4$alkyl, —$C_0$-$C_4$alkyl($C_3$-$C_7$cycloalkyl), —O—$C_0$-$C_4$alkyl($C_3$-$C_7$cycloalkyl), $C_1$-$C_2$haloalkyl, and $C_1$-$C_2$haloalkoxy.

In alternative embodiments, $R^1$ and $R^{1'}$, $R^2$ and $R^{2'}$, or $R^3$ and $R^{3'}$ can be taken together to form a carbonyl group. In alternative embodiments, $R^1$ and $R^2$ or $R^2$ and $R^3$ can be taken together to form a carbon-carbon double bond.

Non-limiting examples of the

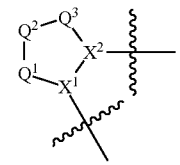

ring are illustrated, for example, in FIG. 5 (any of which can be otherwise substituted with $R^1$, $R^{1'}$, $R^2$, $R^{2'}$, $R^3$, and $R^{3'}$).

A is a group selected from:

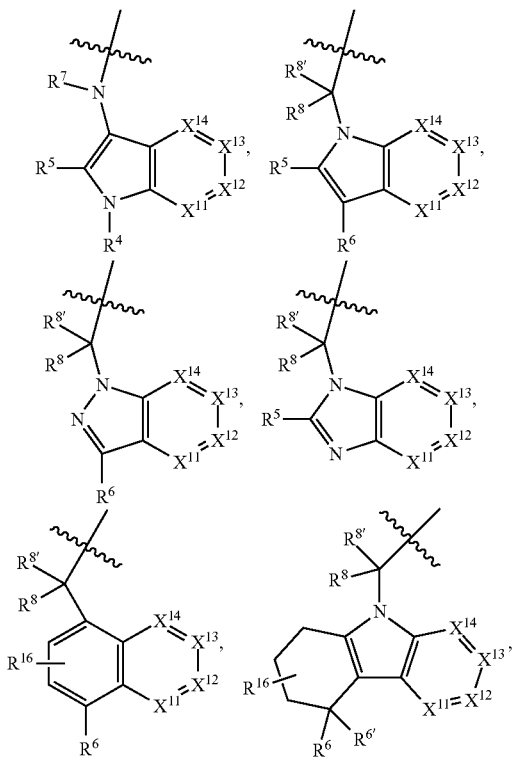

-continued

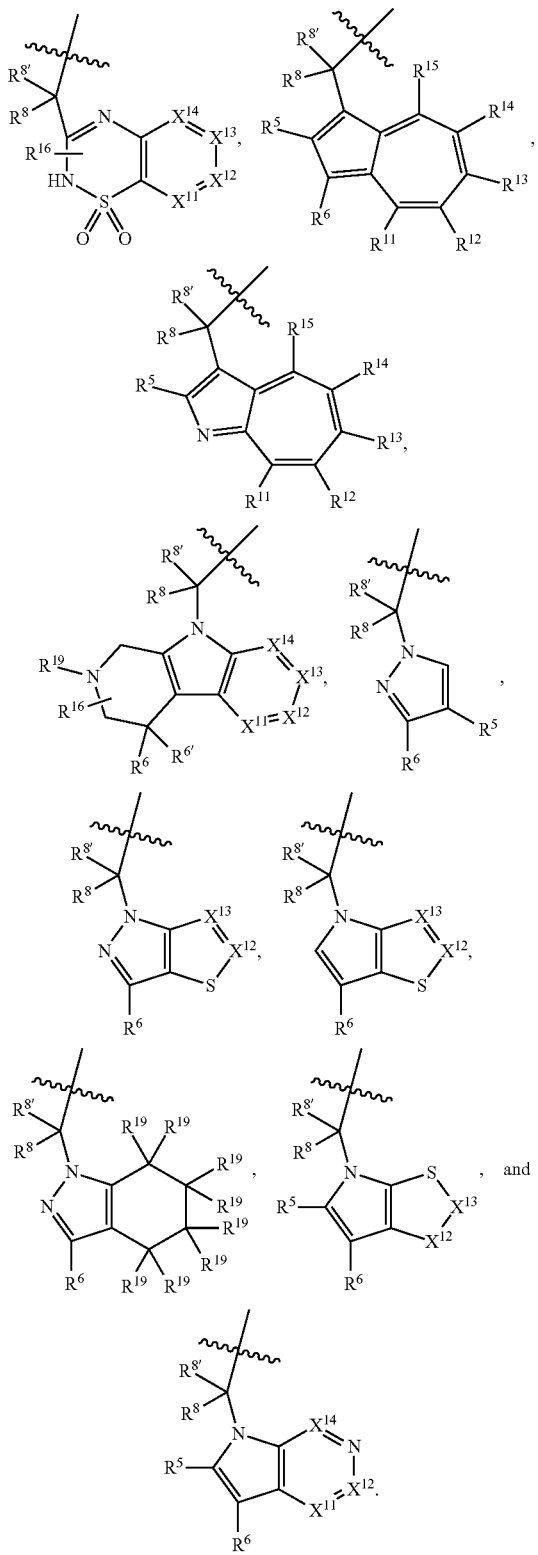
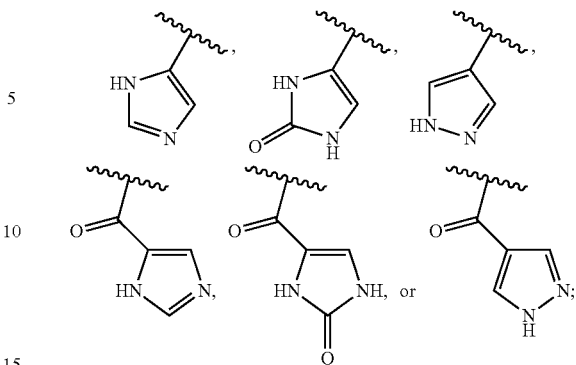

Examples of "A" groups are in FIGS. 1B, 1C, 1D, and 1E.

$R^4$ is selected from —CHO, —CONH$_2$, C$_2$-C$_6$alkanoyl, hydrogen, —SO$_2$NH$_2$, —C(CH$_2$)$_2$F, —CH(CF$_3$)NH$_2$, C$_1$-C$_6$alkyl, —C$_0$-C$_4$alkyl(C$_3$-C$_7$cycloalkyl), —C(O)C$_0$-C$_2$alkyl(C$_3$-C$_7$cycloalkyl), each of which $R^4$ other than hydrogen, —CHO, and —CONH$_2$, is unsubstituted or substituted with one or more of amino, imino, halogen, hydroxyl, cyano, cyanoimino, C$_1$-C$_2$alkyl, C$_1$-C$_2$alkoxy, —C$_0$-C$_2$alkyl(mono- and di-C$_1$-C$_4$alkylamino), C$_1$-C$_2$haloalkyl, and C$_1$-C$_2$haloalkoxy.

$R^5$ and $R^6$ are independently selected from —CHO, —C(O)NH$_2$, —C(O)NH(CH$_3$), C$_2$-C$_6$alkanoyl, hydrogen, hydroxyl, halogen, cyano, nitro, —COOH, —SO$_2$NH$_2$, vinyl, C$_1$-C$_6$alkyl (including methyl), C$_2$-C$_6$alkenyl, C$_1$-C$_6$alkoxy, —C$_0$-C$_4$alkyl(C$_3$-C$_7$cycloalkyl), —C(O)C$_0$-C$_4$alkyl(C$_3$-C$_7$cycloalkyl), —P(O)(OR$^9$)$_2$, —OC(O)R$^9$, —C(O)OR$^9$, —C(O)N(CH$_2$CH$_2$R$^9$)(R$^{10}$), —NR$^9$C(O)R$^{10}$, phenyl, or 5- to 6-membered heteroaryl.

Each $R^5$ and $R^6$ other than hydrogen, hydroxyl, cyano, and —COOH is unsubstituted or optionally substituted. For example, $R^5$ and $R^6$ other than hydrogen, hydroxyl, cyano, and —COOH may be substituted with one or more substituents independently selected from halogen, hydroxyl, amino, imino, cyano, cyanoimino, C$_1$-C$_2$alkyl, C$_1$-C$_4$alkoxy, —C$_0$-C$_2$alkyl(mono- and di-C$_1$-C$_4$alkylamino), C$_1$-C$_2$haloalkyl, and C$_1$-C$_2$haloalkoxy.

$R^{6'}$ is hydrogen, halogen, hydroxyl, C$_1$-C$_4$alkyl, —C$_0$-C$_4$alkyl(C$_3$-C$_7$cycloalkyl), or C$_1$-C$_4$alkoxy; or $R^6$ and $R^{6'}$ may be taken together to form an oxo, vinyl, or imino group.

$R^7$ is hydrogen, C$_1$-C$_6$alkyl, or —C$_0$-C$_4$alkyl(C$_3$-C$_7$cycloalkyl).

$R^8$ and $R^{8'}$ are independently selected from hydrogen, halogen, hydroxyl, C$_1$-C$_6$alkyl, —C$_0$-C$_4$alkyl(C$_3$-C$_7$cycloalkyl), C$_1$-C$_6$alkoxy, and (C$_1$-C$_4$alkylamino)C$_0$-C$_2$alkyl; or $R^8$ and $R^{8'}$ are taken together to form an oxo group; or $R^8$ and $R^{8'}$ can be taken together with the carbon that they are bonded to form a 3-membered carbocyclic ring.

$R^{16}$ is absent or be independently selected from halogen, hydroxyl, nitro, cyano, C$_1$-C$_6$alkyl, C$_2$-C$_6$alkenyl, C$_2$-C$_6$alkanoyl, C$_1$-C$_6$alkoxy, —C$_0$-C$_4$alkyl(mono- and di-C$_1$-C$_6$alkylamino), —C$_0$-C$_4$alkyl(C$_3$-C$_7$cycloalkyl), C$_1$-C$_2$haloalkyl, and C$_1$-C$_2$haloalkoxy.

$R^{19}$ is hydrogen, C$_1$-C$_6$alkyl, C$_2$-C$_6$alkenyl, C$_2$-C$_6$alkanoyl, —SO$_2$C$_1$-C$_6$alkyl, (mono- and di-C$_1$-C$_6$alkylamino)C$_1$-C$_4$alkyl, —C$_0$-C$_4$alkyl(C$_3$-C$_7$cycloalkyl), —C$_0$-C$_4$alkyl(C$_3$-C$_7$heterocycloalkyl), —C$_0$-C$_4$alkyl(aryl), C$_0$-C$_4$alkyl(heteroaryl), and wherein $R^{19}$ other than hydrogen is unsubstituted or substituted with one or more substituents independently selected from halogen, hydroxyl, amino, —COOH, and —C(O)OC$_1$-C$_4$alkyl.

$X^{11}$ is N or CR$^{11}$.
$X^{12}$ is N or CR$^{12}$.
$X^{13}$ is N or CR$^{13}$.
$X^{14}$ is N or CR$^{14}$.
No more than 2 of $X^{11}$, $X^1$, $X^{13}$, and $X^{14}$ are N.

One of $R^{12}$ or $R^{13}$ is $R^{32}$. In one embodiment, one of $R^{12}$ and $R^{13}$ is selected from $R^{31}$ and the other of $R^{12}$ and $R^{13}$ is selected from $R^{32}$. In an alternative embodiment, $R^{12}$ and $R^{13}$ are each independently selected from an $R^{32}$ moiety.

$R^{31}$ is selected from hydrogen, halogen, hydroxyl, nitro, cyano, amino, —COOH, $C_1$-$C_2$haloalkyl, $C_1$-$C_2$haloalkoxy, $C_1$-$C_6$alkyl, —$C_0$-$C_4$alkyl($C_3$-$C_7$cycloalkyl), $C_2$-$C_6$alkenyl, $C_2$-$C_6$alkanoyl, $C_1$-$C_6$alkoxy, $C_2$-$C_6$alkenyloxy, —C(O)OR$^9$, $C_1$-$C_6$thioalkyl, —$C_0$-$C_4$alkylNR$^9$R$^{10}$, —C(O)NR$^9$R$^{10}$, —SO$_2$R$^9$, —SO$_2$NR$^9$R$^{10}$, —OC(O)R$^9$, and —C(NR$^9$)NR$^9$R$^{10}$, each of which $R^{31}$ other than hydrogen, halogen, hydroxyl, nitro, cyano, $C_1$-$C_2$haloalkyl, and $C_1$-$C_2$haloalkoxy is unsubstituted or substituted with one or more substituents independently selected from halogen, hydroxyl, nitro, cyano, amino, —COOH, —CONH$_2$ $C_1$-$C_2$haloalkyl, and $C_1$-$C_2$haloalkoxy, and each of which $R^{31}$ is also optionally substituted with one substituent selected from phenyl and 4- to 7-membered heterocycle containing 1, 2, or 3 heteroatoms independently selected from N, O, and S; which phenyl or 4- to 7-membered heterocycle is unsubstituted or substituted with one or more substituents independently selected from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl)($C_3$-$C_7$cycloalkyl), $C_1$-$C_2$haloalkyl, and $C_1$-$C_2$haloalkoxy;

$R^{32}$ is selected from C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, and —NR$^9$C(O)NR$^{24}$R$^{25}$, each of which is optionally substituted.

$R^{32}$ is the same as $Z_{32}$.

In one embodiment, when $R^{32}$ is C(O)NR$^{21}$R$^{37}$, —C(O)NR$^{24}$R$^{25}$, —C(O)NR$^9$R$^{37}$, B is not $C_2$-$C_6$ alkenyl; ($C_0$-$C_4$ alkyl)(heteroaryl); monocyclic or bicyclic carbocyclic; or monocyclic heterocyclic.

$R^{21}$ and $R^{22}$ are independently selected at each occurrence from hydrogen, hydroxyl, cyano, amino, $C_1$-$C_6$alkyl, $C_1$-$C_6$haloalkyl, $C_1$-$C_6$alkoxy, ($C_3$-$C_7$cycloalkyl)$C_0$-$C_4$alkyl, (phenyl)$C_0$-$C_4$alkyl, —$C_1$-$C_4$alkylOC(O)OC$_1$-$C_6$alkyl, —$C_1$-$C_4$alkylOC(O)C$_1$-$C_6$alkyl, —$C_1$-$C_4$alkylC(O)OC$_1$-$C_6$alkyl, (4- to 7-membered heterocycloalkyl)$C_0$-$C_4$alkyl having 1, 2, or 3 heteroatoms independently selected from N, O, and S, and (5- or 6-membered unsaturated or aromatic heterocycle)$C_0$-$C_4$alkyl having 1, 2, or 3 heteroatoms independently selected from N, O, and S, and each $R^{21}$ and $R^{22}$ can be optionally substituted.

$R^{23}$ is independently selected at each occurrence from $C_1$-$C_6$alkyl, $C_1$-$C_6$haloalkyl, ($C_3$-$C_7$cycloalkyl)$C_0$-$C_4$alkyl, (aryl)$C_0$-$C_4$alkyl, (4- to 7-membered heterocycloalkyl)$C_0$-$C_4$alkyl having 1, 2, or 3 heteroatoms independently selected from N, O, and S, and (5- or 6-membered unsaturated or aromatic heterocycle)$C_0$-$C_4$alkyl having 1, 2, or 3 heteroatoms independently selected from N, O, and S.

$R^{24}$ and $R^{25}$ are taken together with the nitrogen to which they are attached to form a 4- to 7-membered monocyclic heterocycloalkyl group, or a 6- to 10-membered bicyclic heterocyclic group having fused, spiro, or bridged rings and each $R^{24}$ and $R^{25}$ can be optionally substituted.

$R^{37}$ is selected at each occurrence from hydroxyl, $C_1$-$C_6$alkoxy, ($C_3$-$C_7$cycloalkyl)$C_0$-$C_4$alkyl, (phenyl)$C_0$-$C_4$alkyl, —$C_1$-$C_4$alkylOC(O)OC$_1$-$C_6$alkyl, —$C_1$-$C_4$alkylOC(O)C$_1$-$C_6$alkyl, —$C_1$-$C_4$alkylC(O)OC$_1$-$C_6$alkyl, (4- to 7-membered heterocycloalkyl)$C_0$-$C_4$alkyl having 1, 2, or 3 heteroatoms independently selected from N, O, and S, and (5- or 6-membered unsaturated or aromatic heterocycle) $C_0$-$C_4$alkyl having 1, 2, or 3 heteroatoms independently selected from N, O, and S, and each can be optionally substituted.

When A is an indole or indazole and $X^{12}$ is N, $X^{13}$ is CR$^{13}$, wherein $R^{13}$ is $R^{32}$.

When A is an indole or indazole and $X^{13}$ is N, $X^{12}$ is CR$^{12}$, wherein $R^{12}$ is $R^{32}$.

$R^{11}$, $R^{14}$, and $R^{15}$ are independently selected at each occurrence from hydrogen, halogen, hydroxyl, nitro, cyano, —O(PO)(OR$^9$)$_2$, —(PO)(OR$^9$)$_2$, $C_1$-$C_6$alkyl, $C_2$-$C_6$alkenyl, $C_2$-$C_6$alkynyl, $C_2$-$C_6$alkenyl(aryl), $C_2$-$C_6$alkenyl(cycloalkyl), $C_2$-$C_6$alkenyl(heterocycle), $C_2$-$C_6$alkenyl(heteroaryl), $C_2$-$C_6$alkynyl, $C_2$-$C_6$alkynyl(aryl), $C_2$-$C_6$alkynyl (cycloalkyl), $C_2$-$C_6$alkynyl(heterocycle), $C_2$-$C_6$alkynyl (heteroaryl), $C_2$-$C_6$alkanoyl, $C_1$-$C_6$alkoxy, $C_1$-$C_6$thioalkyl, —$C_0$-$C_4$alkyl(mono- and di-$C_1$-$C_6$alkylamino), —$C_0$-$C_4$alkyl($C_3$-$C_7$cycloalkyl), —$C_0$-$C_4$alkoxy($C_3$-$C_7$cycloalkyl), $C_1$-$C_2$haloalkyl, and $C_1$-$C_2$haloalkoxy.

L is a bond or is selected from the formulas

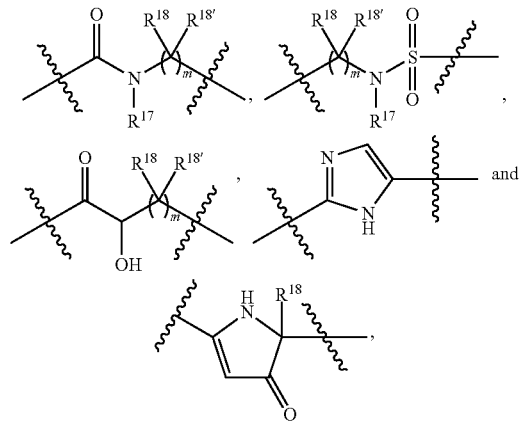

where $R^{17}$ is hydrogen, $C_1$-$C_6$alkyl, or —$C_0$-$C_4$alkyl($C_3$-$C_7$cycloalkyl) and $R^{18}$ and $R^{18'}$ are independently selected from hydrogen, halogen, hydroxymethyl, and methyl; and m is 0, 1, 2, or 3.

Linkers are also illustrated in FIGS. 4B, 4C, 4D, 4E, 4F, and 4G.

B is a monocyclic or bicyclic carbocyclic; a monocyclic or bicyclic carbocyclicoxy group; a monocyclic, bicyclic, or tricyclic heterocyclic group having 1, 2, 3, or 4 heteroatoms independently selected from N, O, and S and from 4 to 7 ring atoms per ring; $C_2$-$C_6$alkenyl; $C_2$-$C_6$alkynyl; —($C_0$-$C_4$alkyl)(aryl); —($C_0$-$C_4$alkyl)(heteroaryl); or —($C_0$-$C_4$alkyl)(biphenyl), and B is unsubstituted or substituted with one or more substituents independently selected from $R^{33}$ and $R^{34}$, and 0 or 1 substituents selected from $R^{35}$ and $R^{36}$.

$R^{33}$ is independently selected from halogen, hydroxyl, —COOH, cyano, $C_1$-$C_6$alkyl, $C_2$-$C_6$alkanoyl, $C_1$-$C_6$alkoxy, —$C_0$-$C_4$alkylNR$^9$R$^{10}$, —SO$_2$R$^9$, $C_1$-$C_2$haloalkyl, and $C_1$-$C_2$haloalkoxy;

$R^{34}$ is independently selected from nitro, $C_2$-$C_6$alkenyl, $C_2$-$C_6$alkynyl, $C_1$-$C_6$thioalkyl, -J$C_3$-$C_7$cycloalkyl, —B(OH)$_2$, -JC(O)NR$^9$R$^{23}$, -JOSO$_2$OR$^{21}$, —C(O)(CH$_2$)$_{1-4}$S (O)R$^{21}$, —O(CH$_2$)$_{1-4}$S)NR$^{21}$R$^{22}$, -JOP(O)(OR$^{21}$)(OR$^{22}$), -JP(O)(OR$^{21}$)(OR$^{22}$), -JOP(O)(OR$^{21}$)R$^{22}$, -JP(O)(OR$^{21}$) R$^{22}$, -JOP(O)R$^{21}$R$^{22}$, -JP(O)R$^{21}$R$^{22}$, -JSP(O)(OR$^{21}$)(OR$^{22}$), -JSP(O)(OR$^{21}$)(R$^{22}$), -JSP(O)(R$^{21}$)(R$^{22}$), -JNR$^9$P(O) (NHR$^{21}$)(NHR$^{22}$), -JNR$^9$P(O)(OR$^{21}$)(NHR$^{22}$), -JNR$^9$P(O)

$(OR^{21})(OR^{22})$, -JC(S)R$^{21}$, -JNR$^{21}$SO$_2$R$^{22}$, -JNR$^9$S(O)NR$^{10}$R$^{22}$, -JNR$^9$SO$_2$NR$^{10}$R$^{22}$, -JSO$_2$NR$^9_{COR}{}^{22}$, -JSO$_2$NR$^9$CONR$^{21}$R$^{22}$, -JNR$^{21}$SO$_2$R$^{22}$, -JC(O)NR$^{21}$SO$_2$R$^{22}$, -JC(NH$_2$)NR$^{22}$, -JC(NH$_2$)NR$^9$S(O)$_2$R$^{22}$, -JOC(O)NR$^{21}$R$^{22}$, -JNR$^{21}$C(O)OR$^{22}$, -JNR$^{21}$OC(O)R$^{22}$, —(CH$_2$)$_{1-4}$C(O)NR$^{21}$R$^{22}$, -JC(O)NR$^{24}$R$^{25}$, -JNR$^9$C(O)R$^{22}$, -JC(O)R$_{21}$, -JNR$^9$C(O)NR$^{10}$R$^{22}$, —CCR$^{21}$, —(CH$_2$)$_{1-4}$OC(O)R$^{21}$, and -JC(O)OR$^{23}$; each of which R$^{34}$ may be unsubstituted or substituted with one or more substituents independently selected from halogen, hydroxyl, nitro, cyano, amino, oxo, —B(OH)$_2$, —Si(CH$_3$)$_3$, —COOH, —CONH$_2$, —P(O)(OH)$_2$, C$_1$-C$_6$alkyl, —C$_0$-C$_4$alkyl(C$_3$-C$_7$cycloalkyl), C$_1$-C$_6$alkoxy, —C$_0$-C$_2$alkyl(mono- and di-C$_1$-C$_4$alkylamino), C$_1$-C$_6$alkylester, C$_1$-C$_4$alkylamino, C$_1$-C$_4$hydroxylalkyl, C$_1$-C$_2$haloalkyl, and C$_1$-C$_2$haloalkoxy.

R$^{35}$ is independently selected from naphthyl, naphthyloxy, indanyl, (4- to 7-membered heterocycloalkyl)C$_0$-C$_4$alkyl containing 1 or 2 heteroatoms selected from N, O, and S, and bicyclic heterocycle containing 1, 2, or 3 heteroatoms independently selected from N, O, and S, and containing 4- to 7-ring atoms in each ring; each of which R$^{35}$ is unsubstituted or substituted with one or more substituents independently selected from halogen, hydroxyl, nitro, cyano, C$_1$-C$_6$alkyl, C$_2$-C$_6$alkenyl, C$_2$-C$_6$alkanoyl, C$_1$-C$_6$alkoxy, (mono- and di-C$_1$-C$_6$alkylamino)C$_0$-C$_4$alkyl, C$_1$-C$_6$alkylester, —C$_0$-C$_4$alkyl(C$_3$-C$_7$cycloalkyl), —SO$_2$R$^9$, C$_1$-C$_2$haloalkyl, and C$_1$-C$_2$haloalkoxy.

R$^{36}$ is independently selected from tetrazolyl, (phenyl)C$_0$-C$_2$alkyl, (phenyl)C$_1$-C$_2$alkoxy, phenoxy, and 5- or 6-membered heteroaryl containing 1, 2, or 3 heteroatoms independently selected from N, O, B, and S, each of which R$^{36}$ is unsubstituted or substituted with one or more substituents independently selected from halogen, hydroxyl, nitro, cyano, C$_1$-C$_6$alkyl, C$_2$-C$_6$alkenyl, C$_2$-C$_6$alkanoyl, C$_1$-C$_6$alkoxy, (mono- and di-C$_1$-C$_6$alkylamino)C$_0$-C$_4$alkyl, C$_1$-C$_6$alkylester, —C$_0$-C$_4$alkyl(C$_3$-C$_7$cycloalkyl), —SO$_2$R$^9$, —OSi(CH$_3$)$_2$C(CH$_3$)$_3$, —Si(CH$_3$)$_2$C(CH$_3$)$_3$, C$_1$-C$_2$haloalkyl, and C$_1$-C$_2$haloalkoxy.

J is independently selected at each occurrence from a covalent bond, C$_1$-C$_4$alkylene, —OC$_1$-C$_4$alkylene, C$_2$-C$_4$alkenylene, and C$_2$-C$_4$alkynylene.

In one additional alternative embodiment B is selected from:

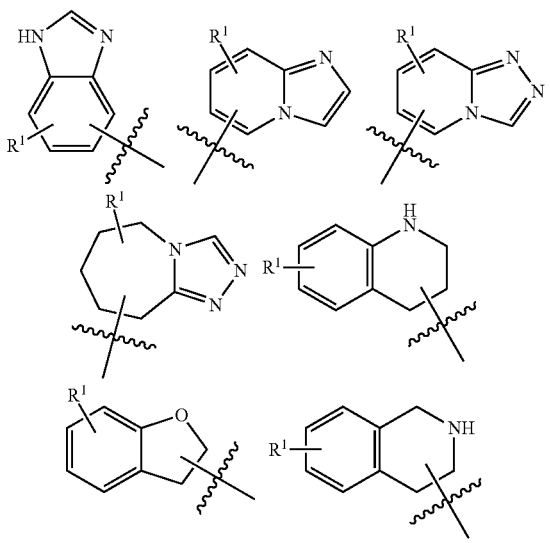

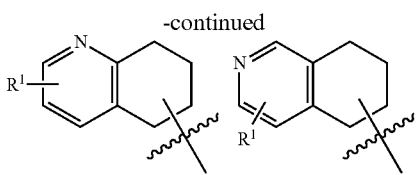

In one additional alternative embodiment R$^{36}$ is selected from:

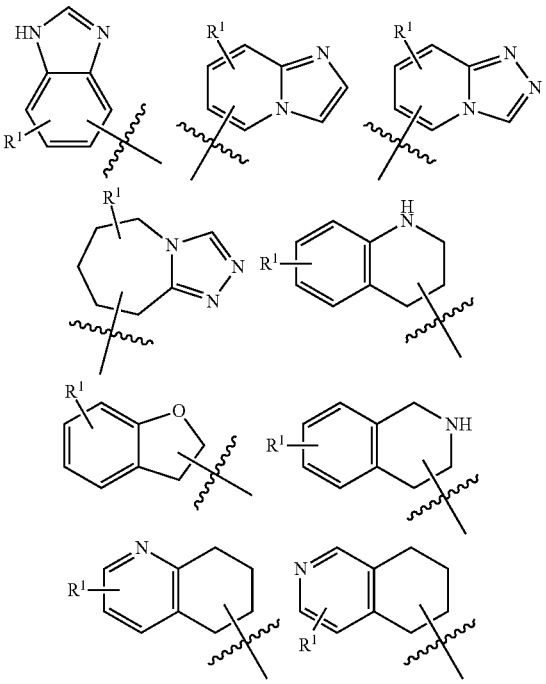

In one embodiment R$^1$ is selected from F, Cl, Br, and C$_1$-C$_6$alkyl.

In one embodiment R$^1$ is selected from hydroxyl and C$_1$-C$_6$alkoxy.

In one embodiment R$^1$ is selected from C$_2$-C$_6$alkynyl, C$_2$-C$_6$alkanoyl, and C$_1$-C$_6$thioalkyl.

In one embodiment R$^1$ is selected from aminoC$_1$-C$_6$alkyl and —C$_0$-C$_4$alkylNR$^9$R$^{10}$.

The present invention thus includes at least the following features:

(a) An amide compound of Formula I, including those compounds listed in Table 1, as described herein, and pharmaceutically acceptable salts and prodrugs thereof, for use in treating or preventing a disorder listed in the Detailed Description, Part IV, Section A, including but not limited to the development of fatty liver and conditions stemming from fatty liver, such as nonalcoholic steatohepatitis (NASH), liver inflammation, cirrhosis, liver failure; dermatomyocitis; amyotrophic lateral sclerosis; and cytokine or inflammatory reactions in response to biotherapeutics (e.g. CAR T-cell therapy);

(b) An amide compound of Table 2 or Table 3 or an active compound that is prepared from or consists of moieties selected from FIGS. 1B, 1C, 2B, 2C, 2D, 2E, 3B, 3C, 3D, 3E, 3F, 3G, 3H, 3I, 3J, 3K, 3L, 3M, 3N, 6A, and 6B, optionally 4B, 4C, 4D, 4E or 4F, as described herein, and pharmaceutically acceptable salts and prodrugs thereof, for use in treating or preventing a disorder listed in the Detailed Description, Part IV, Section A, including but not limited to the development of fatty liver and conditions stemming from fatty liver, such as nonalcoholic steatohepatitis (NASH), liver inflammation, cirrhosis, liver failure, dermatomyocitis; amyotrophic lateral sclerosis; and cytokine or inflammatory reactions in response to the administration of biotherapeutics (e.g. CAR T-cell therapy);

(c) An amide compound of Table 2 or Table 3 or an embodiment of the active compound as described in FIGS. 1B, 1C, 2B, 2C, 2D, 2E, 3B, 3C, 3D, 3E, 3F, 3G, 3H, 3I, 3J, 3K, 3L, 3M, 3N, 6A, and 6B, optionally 4B, 4C, 4D, 4E or 4F, as described herein, and pharmaceutically acceptable salts and prodrugs thereof, for use in treating or preventing a disorder listed in the Detailed Description, Part IV, Section B of this invention, including but not limited to paroxysmal nocturnal hemoglobinuria (PNH), rheumatoid arthritis, multiple sclerosis, age-related macular degeneration (AMD), retinal degeneration, other ophthalmic diseases (e.g., geographic atrophy), a respiratory disease or a cardiovascular disease;

(d) A pharmaceutically acceptable composition of an amide compound of Table 2 or Table 3 or a amide compound that is prepared from or consists of moieties selected from FIGS. 1B, 1C, 2B, 2C, 2D, 2E, 3B, 3C, 3D, 3E, 3F, 3G, 3H, 3I, 3J, 3K, 3L, 3M, 3N, 6A, and 6B, optionally 4B, 4C, 4D, 4E or 4F, or its pharmaceutically acceptable salt in a pharmaceutically acceptable carrier;

(e) An amide compound selected from Table 2 or Table 3 or a compound that is prepared from or consists of moieties selected from FIGS. 1B, 1C, 2B, 2C, 2D, 2E, 3B, 3C, 3D, 3E, 3F, 3G, 3H, 3I, 3J, 3K, 3L, 3M, 3N, 6A, and 6B, optionally 4B, 4C, 4D, 4E or 4F, as described herein, and pharmaceutically acceptable salts, prodrugs and pharmaceutically acceptable compositions thereof;

(f) An amide compound selected from Table 2 or Table 3 or a compound that is prepared from or consists of moieties selected from FIGS. 1B, 1C, 2B, 2C, 2D, 2E, 3B, 3C, 3D, 3E, 3F, 3G, 3H, 3I, 3J, 3K, 3L, 3M, 3N, 6A, and 6B, optionally 4B, 4C, 4D, 4E or 4F, as described herein, and pharmaceutically acceptable salts and prodrugs thereof, for use in treating or preventing disorders mediated by the complement pathway, and for example, cascade Factor D;

(g) Use of a compound of Formula I, including those compounds listed in Table 1, as described herein, and pharmaceutically acceptable salts and prodrugs thereof, in the manufacture of a medicament for treating or preventing a disorder listed in the Detailed Description, Part IV, Section A, including but not limited to the development of fatty liver and conditions stemming from fatty liver, such as nonalcoholic steatohepatitis (NASH), liver inflammation, cirrhosis, liver failure; dermatomyocitis; amyotrophic lateral sclerosis; and cytokine or inflammatory reactions in response to biotherapeutics (e.g. CAR T-cell therapy);

(h) Use of a compound of Table 2 or Table 3 that is prepared from or consists of moieties selected from FIGS. 1B, 1C, 2B, 2C, 2D, 2E, 3B, 3C, 3D, 3E, 3F, 3G, 3H, 3I, 3J, 3K, 3L, 3M, 3N, 6A, and 6B, optionally 4B, 4C, 4D, 4E or 4F, as described herein, and pharmaceutically acceptable salts and prodrugs thereof, in the manufacture of a medicament for treating or preventing a disorder listed in the Detailed Description, Part IV, Section A, including but not limited to the development of fatty liver and conditions stemming from fatty liver, such as nonalcoholic steatohepatitis (NASH), liver inflammation, cirrhosis, liver failure; dermatomyocitis; amyotrophic lateral sclerosis; and cytokine or inflammatory reactions in response to biotherapeutics (e.g. CAR T-cell therapy);

(i) Use of a compound of Table 2 or Table 3 or a compound that is prepared from or consists of moieties selected from FIGS. 1B, 1C, 2B, 2C, 2D, 2E, 3B, 3C, 3D, 3E, 3F, 3G, 3H, 3I, 3J, 3K, 3L, 3M, 3N, 6A, and 6B, optionally 4B, 4C, 4D, 4E or 4F, as described herein, and pharmaceutically acceptable salts and prodrugs thereof, in the manufacture of a medicament for treating or preventing a disorder listed in the Detailed Description, Part IV, Section B of this invention, including but not limited to paroxysmal nocturnal hemoglobinuria (PNH), rheumatoid arthritis, multiple sclerosis, age-related macular degeneration (AMD), retinal degeneration, other ophthalmic diseases (e.g., geographic atrophy), a respiratory disease or a cardiovascular disease;

(j) A process for manufacturing a medicament intended for the therapeutic use for treating or preventing a disorder listed in the Detailed Description, Part IV, Section A or Section B, or generally for treating or preventing disorders mediated by complement cascade Factor D, including age-related macular degeneration (AMD), retinal degeneration, paroxysmal nocturnal hemoglobinuria (PNH), multiple sclerosis (MS), and rheumatoid arthritis (RA) and other disorders described further herein characterized in that a compound selected from Table 2 or Table 3 or a compound that is prepared from or consists of moieties selected from FIGS. 1B, 1C, 2B, 2C, 2D, 2E, 3B, 3C, 3D, 3E, 3F, 3G, 3H, 3I, 3J, 3K, 3L, 3M, 3N, 6A, and 6B, optionally 4B, 4C, 4D, 4E or 4F, is used in the manufacture;

(k) A compound selected from Table 2 or Table 3 or a compound that is prepared from or consists of moieties selected from FIGS. 1B, 1C, 2B, 2C, 2D, 2E, 3B, 3C, 3D, 3E, 3F, 3G, 3H, 3I, 3J, 3K, 3L, 3M, 3N, 6A, and 6B, optionally 4B, 4C, 4D, 4E or 4F, as described herein in substantially pure form (e.g., at least 90 or 95%);

(l) An amide compound of Formula I, including those compounds listed in Table 1, as described herein, and pharmaceutically acceptable salts and prodrugs thereof, for use in treating a medical disorder which is an inflammatory or immune condition, a disorder mediated by the complement cascade (including a dysfunctional cascade), a disorder or abnormality of a cell that adversely affects the ability of the cell to engage in or respond to normal complement activity, or an undesired complement-mediated response to a medical treatment, such as surgery or other medical procedure or a pharmaceutical or biopharmaceutical drug administration, a blood transfusion, or other allogenic tissue or fluid administration;

(m) An amide compound of Table 2 or Table 3 or a compound that is prepared from or consists of moieties in FIGS. 1B, 1C, 2B, 2C, 2D, 2E, 3B, 3C, 3D, 3E, 3F, 3G, 3H, 3I, 3J, 3K, 3L, 3M, 3N, 6A, and 6B, optionally 4B, 4C, 4D, 4E or 4F, as described herein, and pharmaceutically acceptable salts and prodrugs thereof, for use in treating a medical disorder which is an inflammatory or immune condition, a disorder mediated by the complement cascade (including a dysfunctional cascade), a disorder or abnormality of a cell that adversely affects the ability of the cell to engage in or respond to normal complement activity, or an undesired complement-mediated response to a medical treatment, such as surgery or other medical procedure or a pharmaceutical or biopharmaceutical drug administration, a blood transfusion, or other allogenic tissue or fluid administration;

(n) An amide compound that is prepared from or consists of moieties selected from FIG. 1D or 1E; 5; 6A, 6B, 7A, 7B, 7C, 7D or 7E; and 8; optionally including a moiety of FIG. 4B, 4C, 4D, 4E or 4F, as described herein, and pharmaceutically acceptable salts and prodrugs thereof, for use in treating or preventing a disorder listed in the Detailed Description, Part IV, Section A, including but not limited to the development of fatty liver and conditions stemming from fatty liver, such as nonalcoholic steatohepatitis (NASH), liver inflammation, cirrhosis, liver failure; dermatomyocitis; amyotrophic lateral sclerosis; and cytokine or inflammatory reactions in response to biotherapeutics (e.g. CAR T-cell therapy);

(o) An amide compound that is prepared from or consists of moieties selected from one of the following groups: (i) any of FIG. 1B, 1C, 1D or 1E; FIG. 5; FIG. 6A, 6B, or 6C and FIG. 7F; optionally including a moiety of FIG. 4B, 4C, 4D, 4E or 4F; (ii) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6A, 6B, 6C, and 7F; optionally including a moiety of FIG. 4B, 4C, 4D, 4E or 4F; (iii) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6A, 6B, 6C, and 7G; optionally including a moiety of FIG. 4B, 4C, 4D, 4E or 4F; (iv) FIG. 1B, 1C, 1D or 1E; FIG. 5; FIG. 6E; any of FIGS. 7A, 7B, 7C, 7D, 7E, 7F, 7G and 8; optionally including a moiety of FIG. 4B, 4C, 4D, 4E or 4F or (v) FIGS. 9A, 9B, 9C, 9D, 9E, 9F, 9G, 9H and FIGS. 6A, 6B and 6C; as described herein, and pharmaceutically acceptable salts and prodrugs thereof, for use in treating or preventing a disorder listed in the Detailed Description, Part IV, Section A, including but not limited to the development of fatty liver and conditions stemming from fatty liver, such as nonalcoholic steatohepatitis (NASH), liver inflammation, cirrhosis, liver failure, dermatomyocitis; amyotrophic lateral sclerosis; and cytokine or inflammatory reactions in response to the administration of biotherapeutics (e.g. CAR T-cell therapy);

(p) An amide compound that is prepared from or consists of moieties selected from one of the following groups: (i) any of FIG. 1B, 1C, 1D or 1E; FIG. 5; any one of FIGS. 6A, 6B, 6C and FIG. 7F, optionally including a moiety of FIG. 4B, 4C, 4D, 4E or 4F; (ii FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6A, 6B, 6C, and 7F; optionally including a moiety of FIG. 4B, 4C, 4D, 4E or 4F; (iii) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6A, 6B, 6C, and 7G; optionally including a moiety of FIG. 4B, 4C, 4D, 4E or 4F; (iv) FIG. 1B, 1C, 1D or 1E; FIG. 5; FIG. 6E; any of FIGS. 7A, 7B, 7C, 7D, 7E, 7F, 7G and 8; optionally including a moiety of FIG. 4B, 4C, 4D, 4E or 4F or (v) FIGS. 9A, 9B, 9C, 9D, 9E, 9F, 9G, 9H and FIGS. 6A, 6B and 6C; as described herein, and pharmaceutically acceptable salts and prodrugs thereof, for use in treating or preventing a disorder listed in the Detailed Description, Part IV, Section B of this invention, including but not limited to paroxysmal nocturnal hemoglobinuria (PNH), rheumatoid arthritis, multiple sclerosis, age-related macular degeneration (AMD), retinal degeneration, other ophthalmic diseases (e.g., geographic atrophy), a respiratory disease or a cardiovascular disease;

(q) A pharmaceutically acceptable composition of a compound of any species consisting of moieties selected from one of the following groups: (i) any of FIG. 1B, 1C, 1D or 1E; FIG. 5; any one of FIGS. 6A, 6B, 6C and FIG. 7F; optionally including a moiety of FIG. 4B, 4C, 4D, 4E or 4F; (ii) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6A, 6B, 6C, and 7F; optionally including a moiety of FIG. 4B, 4C, 4D, 4E or 4F; (iii) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6A, 6B, 6C, and 7G; optionally including a moiety of FIG. 4B, 4C, 4D, 4E or 4F; (iv) FIG. 1B, 1C, 1D or 1E; FIG. 5; FIG. 6E; any of FIGS. 7A, 7B, 7C, 7D, 7E, 7F, 7G and 8; optionally including a moiety of FIG. 4B, 4C, 4D, 4E or 4F or (v) FIGS. 9A, 9B, 9C, 9D, 9E, 9F, 9G, 9H and FIGS. 6A, 6B and 6C; or its pharmaceutically acceptable salt in a pharmaceutically acceptable carrier;

(r) A compound that is prepared from or consists of moieties selected from one of the following groups (i) any of FIG. 1B, 1C, 1D or 1E; FIG. 5; any one of FIGS. 6A, 6B, 6C and FIG. 7F; optionally including a moiety of FIG. 4B, 4C, 4D, 4E or 4F; or (ii) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6A, 6B, 6C, and 7F; optionally including a moiety of FIG. 4B, 4C, 4D, 4E or 4F; as described herein, and pharmaceutically acceptable salts, prodrugs and pharmaceutically acceptable compositions thereof;

(s) A compound that is prepared from or consists of moieties selected from one of the following groups (i) any of FIG. 1B, 1C, 1D or 1E; FIG. 5; any one of FIGS. 6A, 6B, and 6C and FIG. 7F; optionally including a moiety of FIG. 4B, 4C, 4D, 4E or 4F; (ii) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6A, 6B, 6C, and 7F; optionally including a moiety of FIG. 4B, 4C, 4D, 4E or 4F; or (iii) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6A, 6B, 6C, and 7G; optionally including a moiety of FIG. 4B, 4C, 4D, 4E or 4F; as described herein, and pharmaceutically acceptable salts and prodrugs thereof, for use in treating or preventing disorders mediated by the complement pathway, and for example, cascade Factor D;

(t) Use of a compound that is prepared from or consists of moieties selected from FIG. 1D or 1E; 5; 6A, 6B, 6C; 7A, 7B, 7C, 7D or 7E; and 8; optionally including a moiety of FIG. 4B, 4C, 4D, 4E or 4F as described herein, and pharmaceutically acceptable salts and prodrugs thereof, in the manufacture of a medicament for treating or preventing a disorder listed in the Detailed Description, Part IV, Section A, including but not limited to the development of fatty liver and conditions stemming from fatty liver, such as nonalcoholic steatohepatitis (NASH), liver inflammation, cirrhosis, liver failure; dermatomyocitis; amyotrophic lateral sclerosis; and cytokine or inflammatory reactions in response to biotherapeutics (e.g. CAR T-cell therapy);

(u) Use of a compound of that is prepared from or consists of moieties selected from (i) any of FIG. 1B, 1C, 1D or 1E; FIG. 5; any one of FIGS. 6A, 6B, 6C and FIG. 7F; optionally including a moiety of FIG. 4B, 4C, 4D, 4E or 4F; (ii) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6A, 6B, 6C, and 7F; optionally including a moiety of FIG. 4B, 4C, 4D, 4E or 4F; or (iii) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6A, 6B, 6C, and 7G; optionally including a moiety of FIG. 4B, 4C, 4D, 4E or 4F; as described herein, and pharmaceutically acceptable salts and prodrugs thereof, in the manufacture of a medicament for treating or preventing a disorder listed in the Detailed Description, Part IV, Section A, including but not limited to the development of fatty liver and conditions stemming from fatty liver, such as nonalcoholic steatohepatitis (NASH), liver inflammation, cirrhosis, liver failure; dermatomyocitis; amyotrophic lateral sclerosis; and cytokine or inflammatory reactions in response to biotherapeutics (e.g. CAR T-cell therapy);

(v) Use of a compound that is prepared from or consists of moieties selected from (i) any of FIG. 1B, 1C, 1D or 1E; FIG. 5; any one of FIGS. 6A, 6B, 6C and FIG. 7F; optionally including a moiety of FIG. 4B, 4C, 4D, 4E or 4F; (ii) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6A, 6B, 6C, and 7F; optionally including a moiety of FIG. 4B, 4C, 4D, 4E or 4F; or (iii) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6A, 6B, 6C, and 7G; optionally including a moiety of FIG. 4B, 4C, 4D, 4E or 4F; as described herein, and pharmaceutically acceptable salts and prodrugs thereof, in the manufacture of a medicament for treating or preventing a disorder listed in the Detailed Description, Part IV, Section B of this invention, including but not limited to paroxysmal nocturnal hemoglobinuria (PNH), rheumatoid arthritis, multiple sclerosis, age-related macular degeneration (AMD), retinal degeneration, other ophthalmic diseases (e.g., geographic atrophy), a respiratory disease or a cardiovascular disease;

(w) A process for manufacturing a medicament intended for the therapeutic use for treating or preventing a disorder listed in the Detailed Description, Part IV, Section A or Section B, or generally for treating or preventing disorders mediated by complement cascade Factor D, including age-related macular degeneration (AMD), retinal degeneration, paroxysymal nocturnal hemoglobinuria (PNH), multiple sclerosis (MS), and rheumatoid arthritis (RA) and other disorders described further herein characterized in that a compound selected for use is a compound that is prepared from or consists of moieties selected from (i) any of FIG. 1B, 1C, 1D or 1E; FIG. 5; any one of FIGS. 6A, 6B, 6C and FIG. 7F; optionally including a moiety of FIG. 4B, 4C, 4D, 4E or 4F; (ii) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6A, 6B, 6C, and 7F; optionally including a moiety of FIG. 4B, 4C, 4D, 4E or 4F; or (iii) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6A, 6B, 6C, and 7G; optionally including a moiety of FIG. 4B, 4C, 4D, 4E or 4F; as described herein is used in the manufacture;

(x) A compound that is prepared from or consists of moieties selected from (i) any of FIG. 1B, 1C, 1D or 1E; FIG. 5; any one of FIGS. 6A, 6B, 6C, and FIG. 7F; optionally including a moiety of FIG. 4B, 4C, 4D, 4E or 4F or (ii) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6A, 6B, 6C, and 7F; optionally including a moiety of FIG. 4B, 4C, 4D, 4E or 4F; as described herein as described herein in substantially pure form (e.g., at least 90 or 95%);

(y) A compound that is prepared from or consists of moieties selected from FIG. 1D or 1E; 5; 6A, 6B, or 6C; 7A, 7B, 7C, 7D or 7E; and 8; optionally including a moiety of FIG. 4B, 4C, 4D, 4E or 4F; as described herein, and pharmaceutically acceptable salts and prodrugs thereof, for use in treating a medical disorder which is an inflammatory or immune condition, a disorder mediated by the complement cascade (including a dysfunctional cascade), a disorder or abnormality of a cell that adversely affects the ability of the cell to engage in or respond to normal complement activity, or an undesired complement-mediated response to a medical treatment, such as surgery or other medical procedure or a pharmaceutical or biopharmaceutical drug administration, a blood transfusion, or other allogenic tissue or fluid administration; and (z) A compound of that is prepared from or consists of moieties selected from (i) any of FIG. 1B, 1C, 1D or 1E; FIG. 5; any one of FIGS. 6A, 6B, 6C and FIG. 7F; optionally including a moiety of FIG. 4 (ii) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6A, 6B, 6C, and 7F; optionally including a moiety of FIG. 4B, 4C, 4D, 4E or 4F; or (iii) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6A, 6B, 6C, and 7G; optionally including a moiety of FIG. 4B, 4C, 4D, 4E or 4F; as described herein, and pharmaceutically acceptable salts and prodrugs thereof, for use in treating a medical disorder which is an inflammatory or immune condition, a disorder mediated by the complement cascade (including a dysfunctional cascade), a disorder or abnormality of a cell that adversely affects the ability of the cell to engage in or respond to normal complement activity, or an undesired complement-mediated response to a medical treatment, such as surgery or other medical procedure or a pharmaceutical or biopharmaceutical drug administration, a blood transfusion, or other allogenic tissue or fluid administration.

(aa) For each of (a) through (z) above, and otherwise herein, each assembly of moieties in the Figures and each active compound made therefrom or its use is considered and deemed specifically and individually disclosed, as such depiction is for convenience of space only and not intended to describe a only a genus or even a subgenus for such indication.

(bb) in another embodiment, any moiety of "A" (FIG. 1B, C, D or E); any moiety of "B" ((FIG. 2B, C, D, or E), FIG. 7(A, B, C, D, E, F or G) or FIG. 8); any moiety of the core ((FIG. 3B, C, D, E, F, G. H, I, J, K, L, M. N, O, P or Q) or FIG. 5), any moiety of Linker (FIG. 4B, C, D, E, F, or (i) and any moiety of $R^{32}$ (FIG. 6A, B, or C) can be combined to treat an indication of Section A; and the assembly of moieties from the Figures and each active compound made therefrom is considered and deemed specifically and individually disclosed, as such depiction is for convenience of space only and not intended to describe a only a genus or even a subgenus for such indication;

(cc) In another embodiment, any moiety of "A" (FIG. 1B, C, or F); any moiety of "B" ((FIG. 2B, C, D, or E), FIG. 7(A, B, C, D, E, F or G) or FIG. 8); any moiety of the core ((FIG. 3B, C, D, E, F, G, H, I, J, K, L, M, N, O, P or Q) or FIG. 5), any moiety of Linker (FIG. 4B, C, D, E, F, or G) and any moiety of $R^{32}$ (FIG. 6A, B, or C) can be combined to treat an indication of Section B with the proviso that there is at least one moiety selected from FIG. 1(B, C, or F); or FIG. 7F; FIG. 4F; or FIG. 6(C); and the assembly of moieties from the Figures and each active compound made therefrom is considered and deemed specifically and individually disclosed, as such depiction is for convenience of space only and not intended to describe a only a genus or even a subgenus for such indication.

DETAILED DESCRIPTION

I. Terminology

Figure 1A:
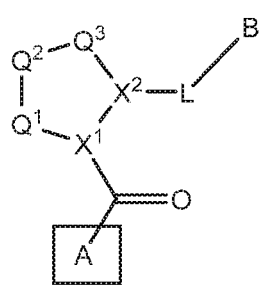
FIG. 1A is an illustration of Formula I which highlights the location of the A ring.
Figure 1B:
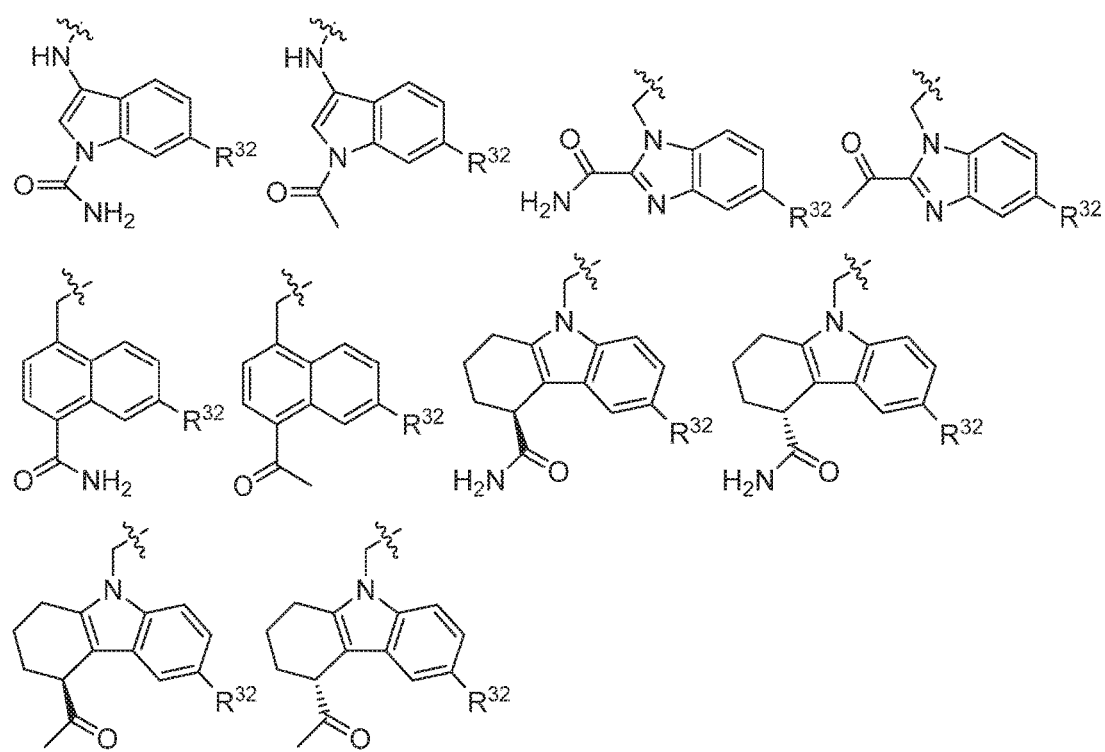
FIGS. 1B and 1C provide non-limiting embodiments of the A ring, wherein $R^{32}$ is defined below.
Figure 1C:
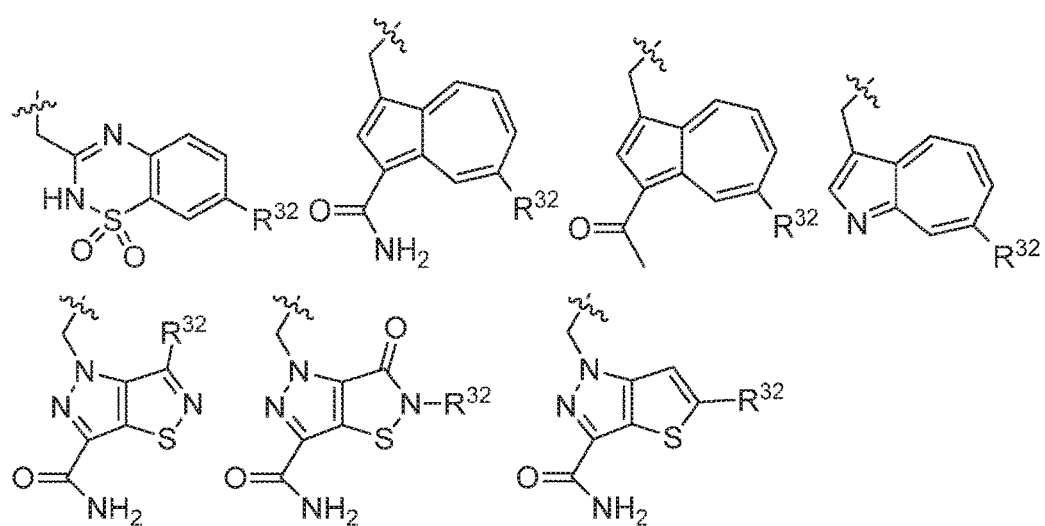
Figure 1D:
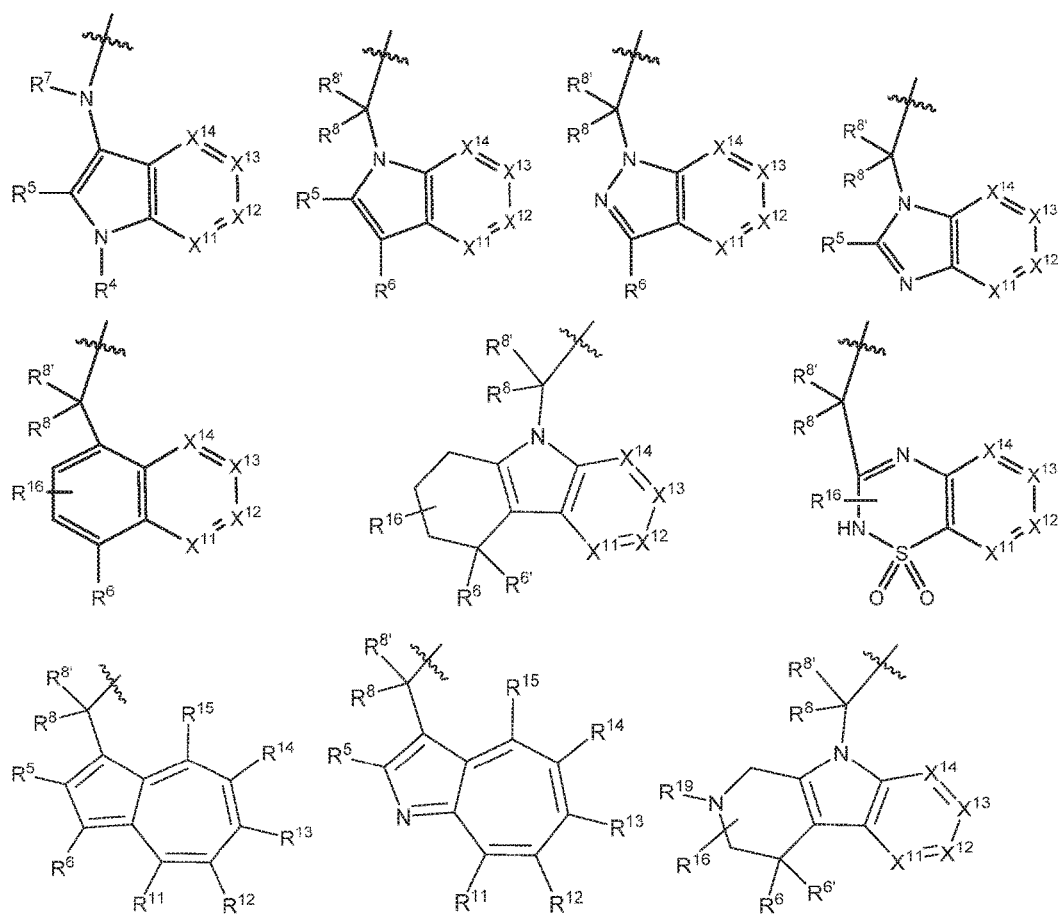
FIGS. 1D, 1E, and 1F illustrate non-limiting embodiments of the A ring of FIG. 1A, wherein $R^4$, $R^5$, $R^6$, $R^7$, $R^8$, $R^{8'}$, $R^{11}$, $R^{12}$, $R^{13}$, $R^{14}$, $R^{15}$, $R^{16}$, $R^{19}$, $R^{32}$, $X^{11}$, $X^{12}$, $X^{13}$, and $X^{14}$ are defined below.
Figure 1E:
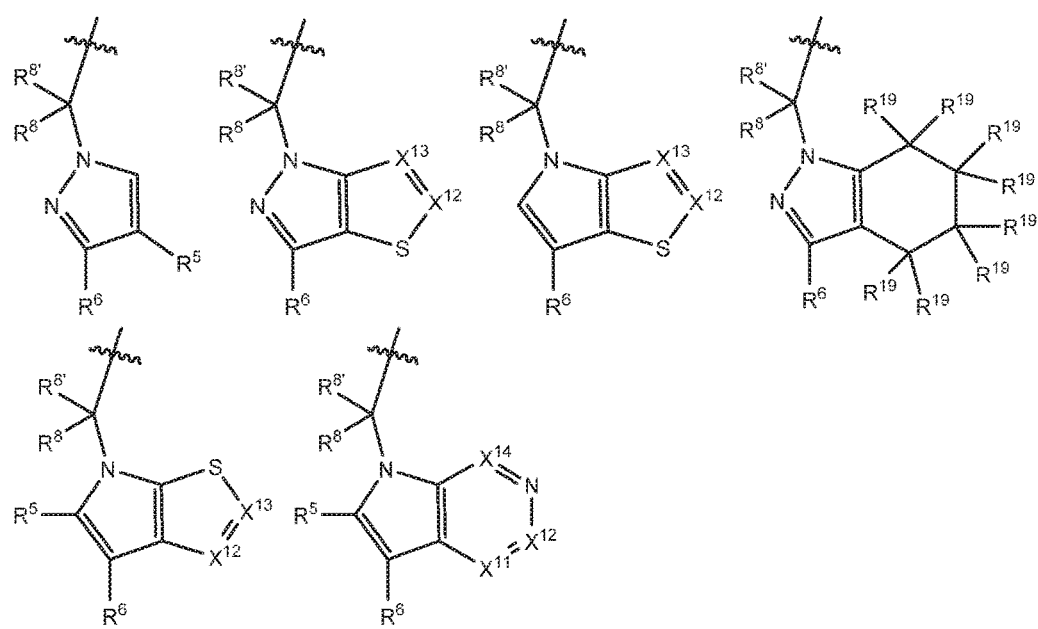
Figure 1F:
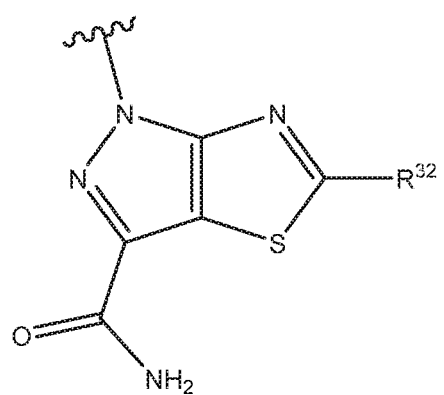
Figure 2A:
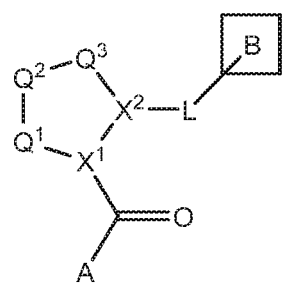
FIG. 2A illustrates the location of the B ring of Formula I.
Figure 2B:
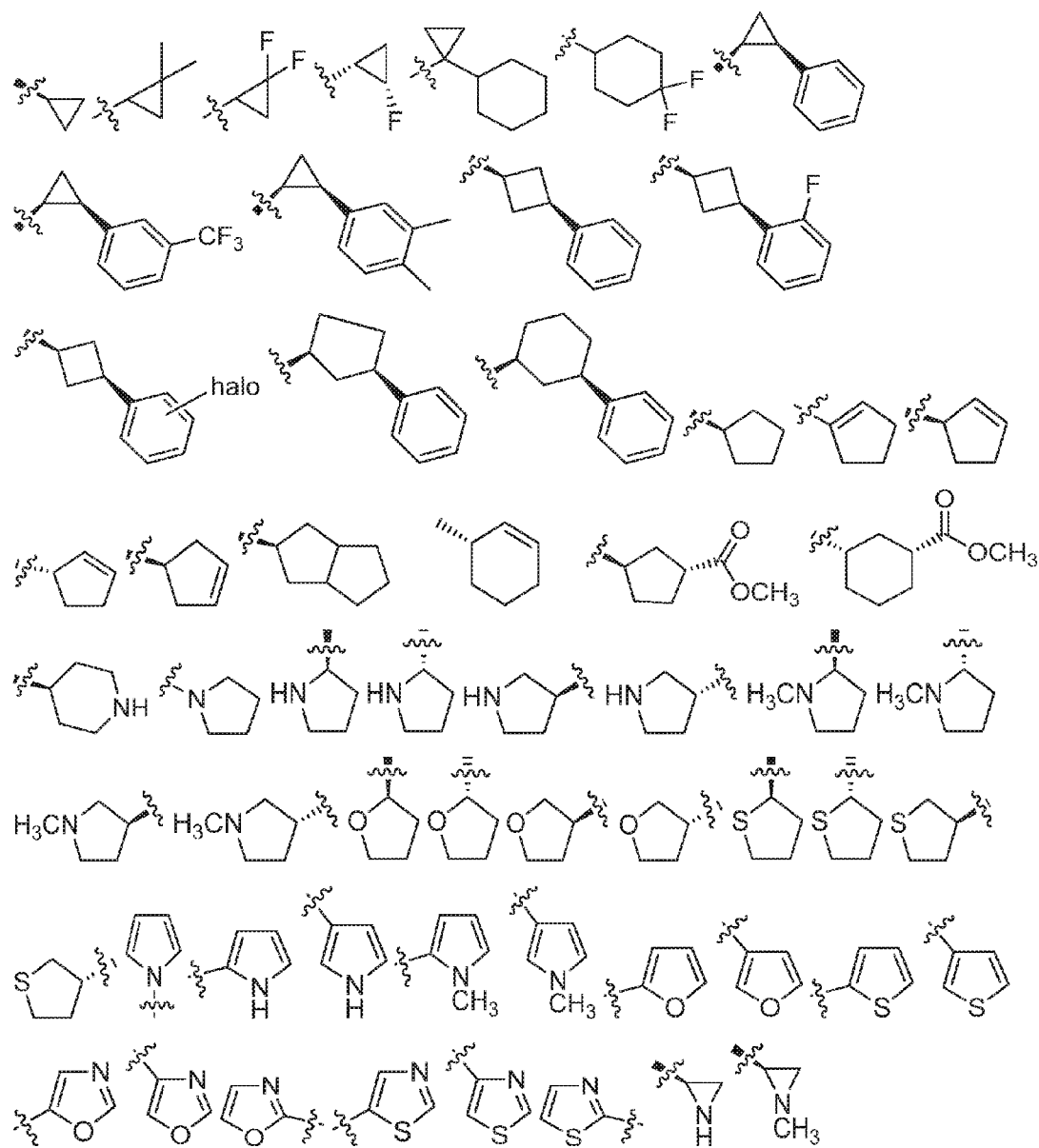
FIGS. 2B, 2C, 2D and 2E provide certain embodiments of the B ring, wherein "halo" can be F, Cl, Br, or I.
Figure 2C:
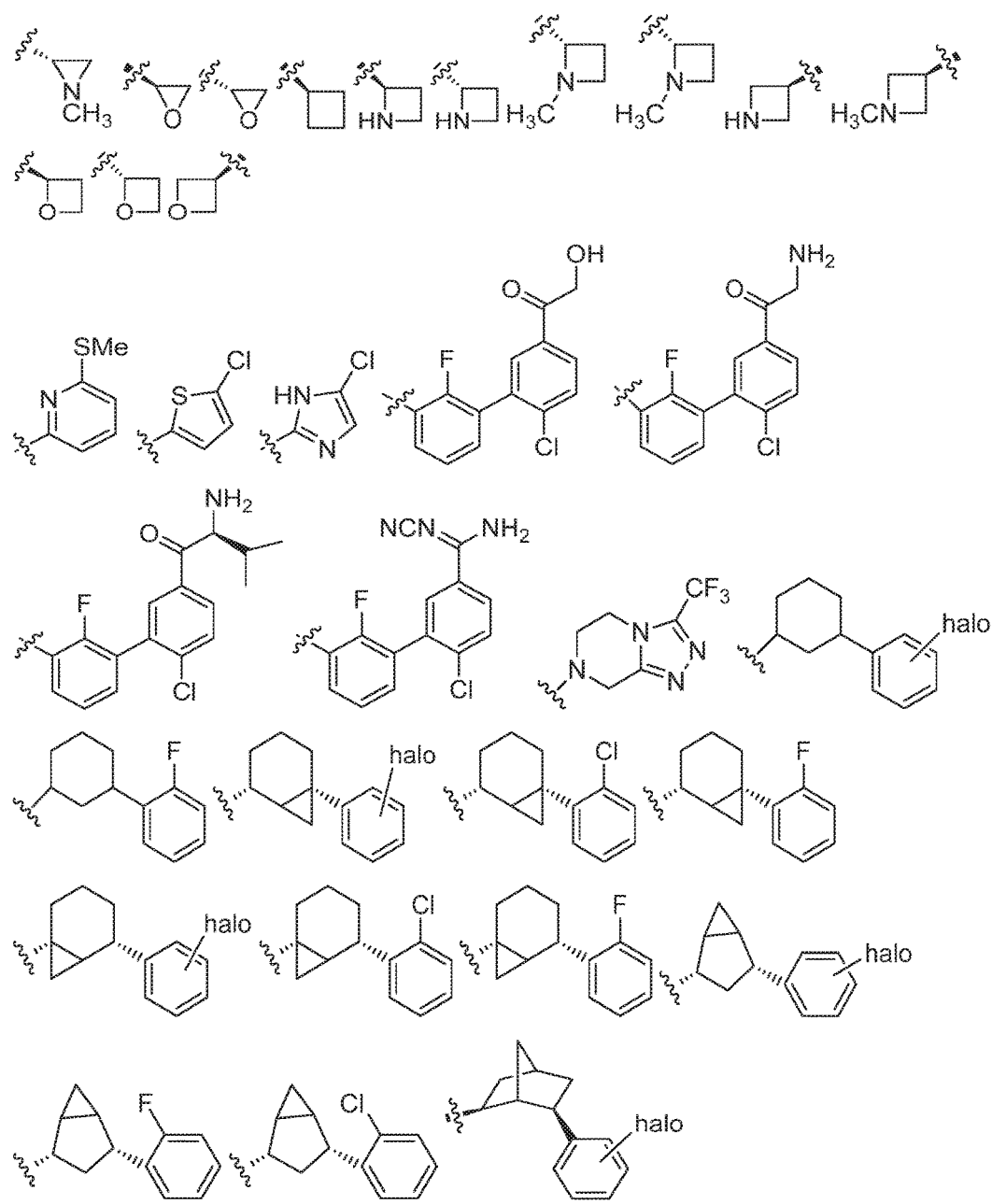
Figure 2D:
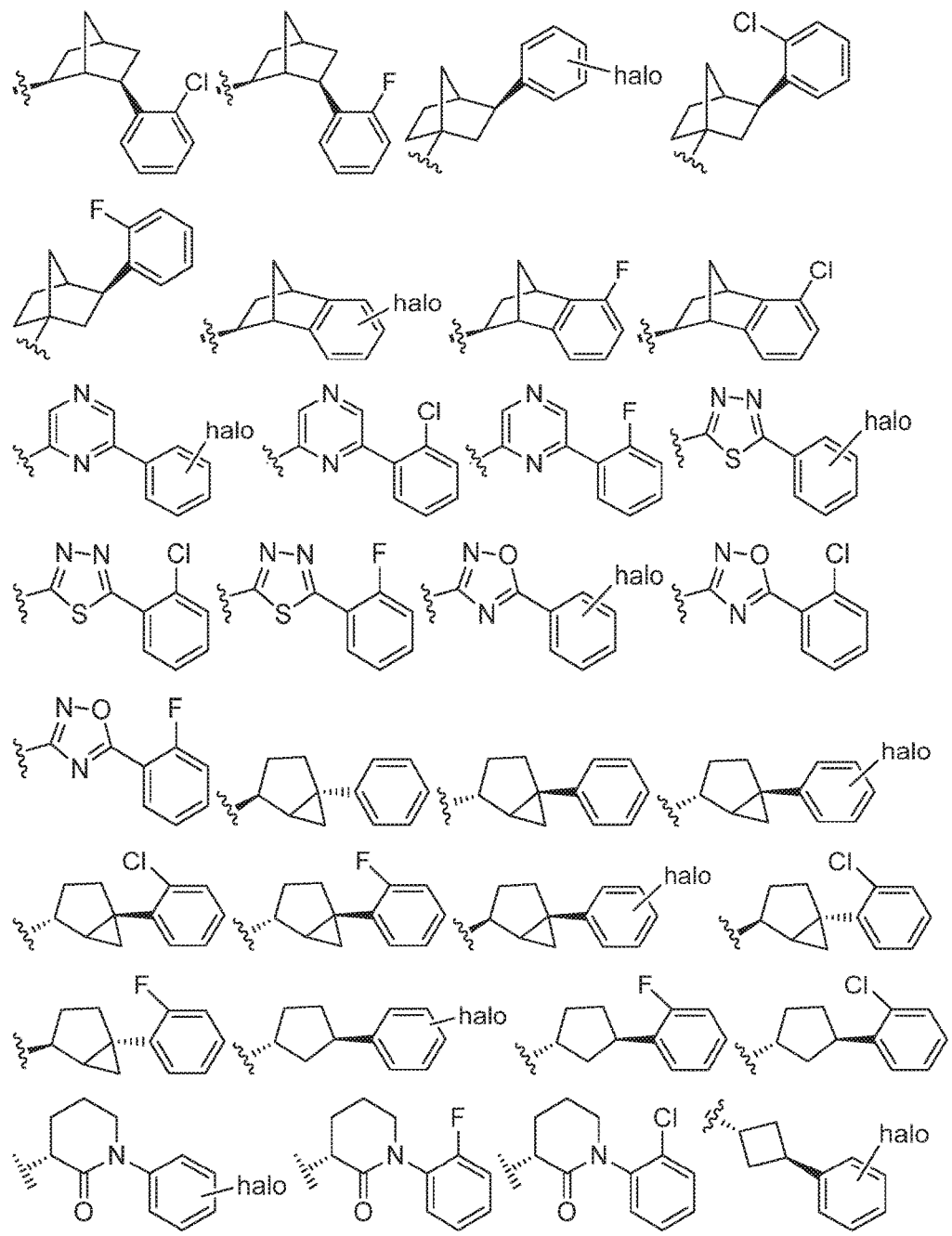
Figure 2E:
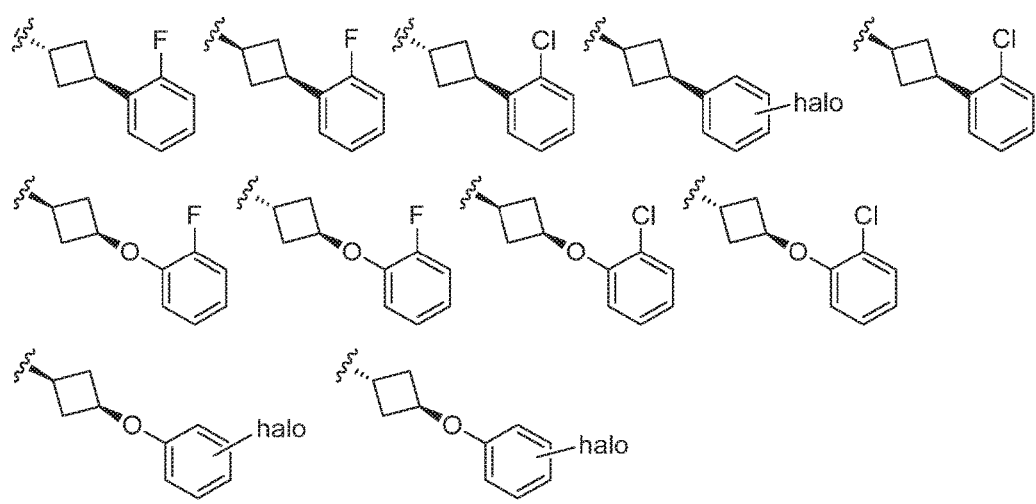
Figure 3A:
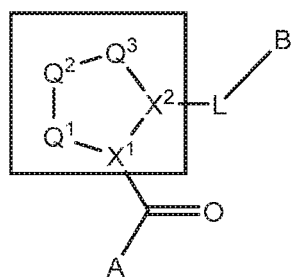
FIG. 3A illustrates the location of the Central Core of Formula I.
Figure 3B:
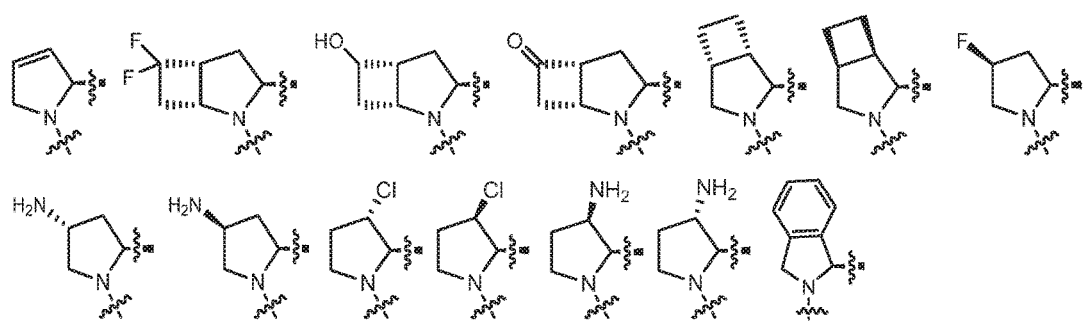
FIGS. 3B, 3C, 3D, 3E, 3F, 3G, 3H, 3I, 3J, 3K, 3L, 3M, 3N, 3O, 3P, and 3Q provide non-limiting embodiments of the Central Core ring (C ring), wherein q is 0, 1, 2 or 3, r is 1, 2 or 3, ≡≡≡ is a single or double bond, and $R^{44}$, $R^{44'}$, $R^{45}$, $R^{45'}$ are described below; wherein each group can be optionally substituted.
Figure 3C:
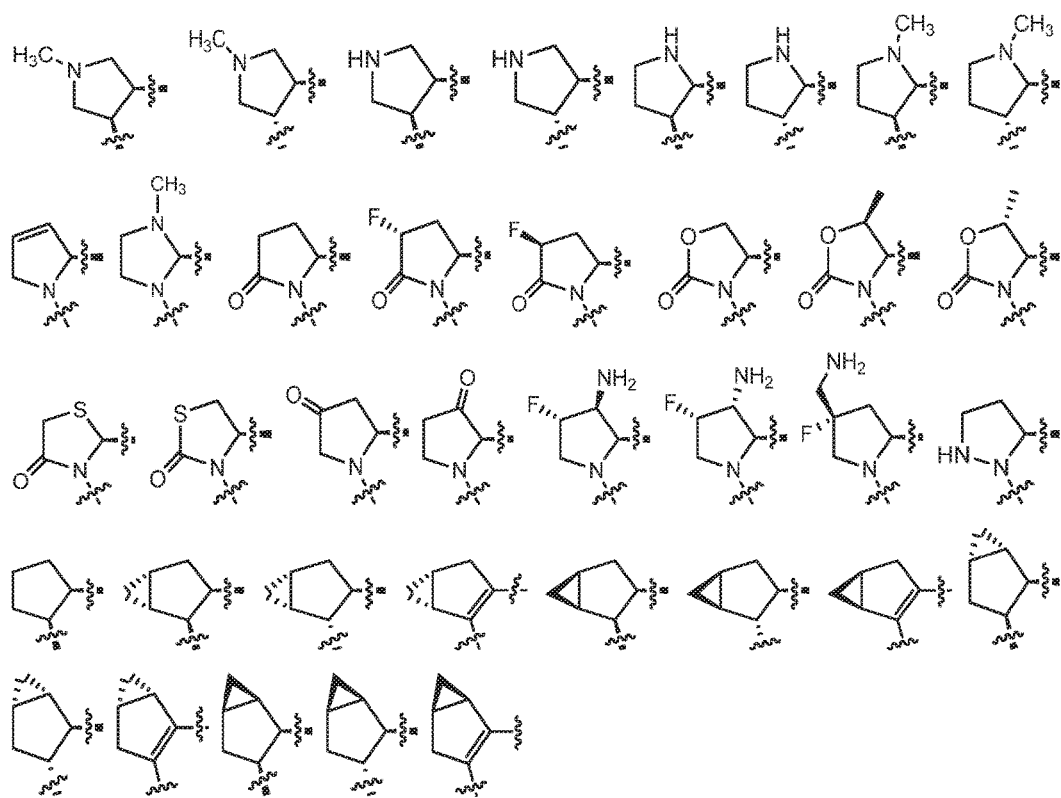
Figure 3D:
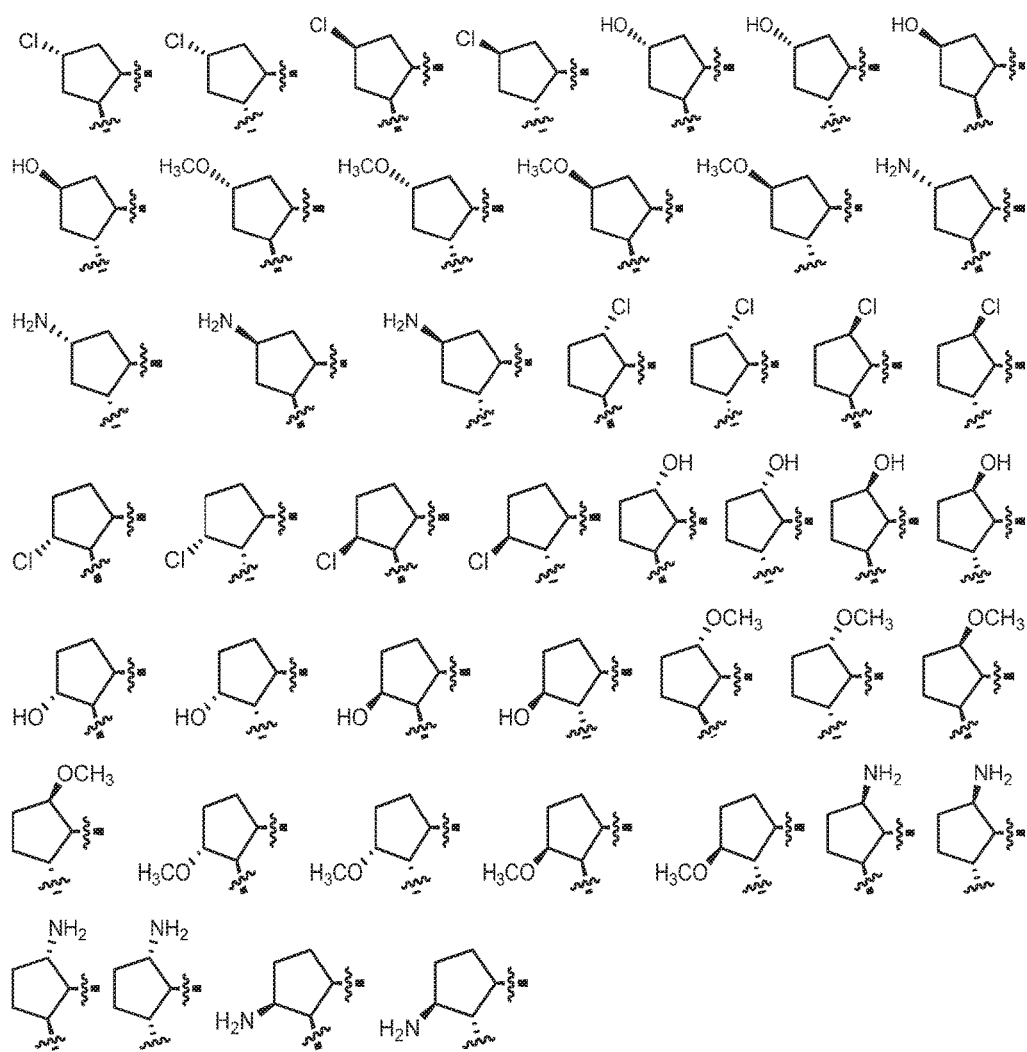
Figure 3E:
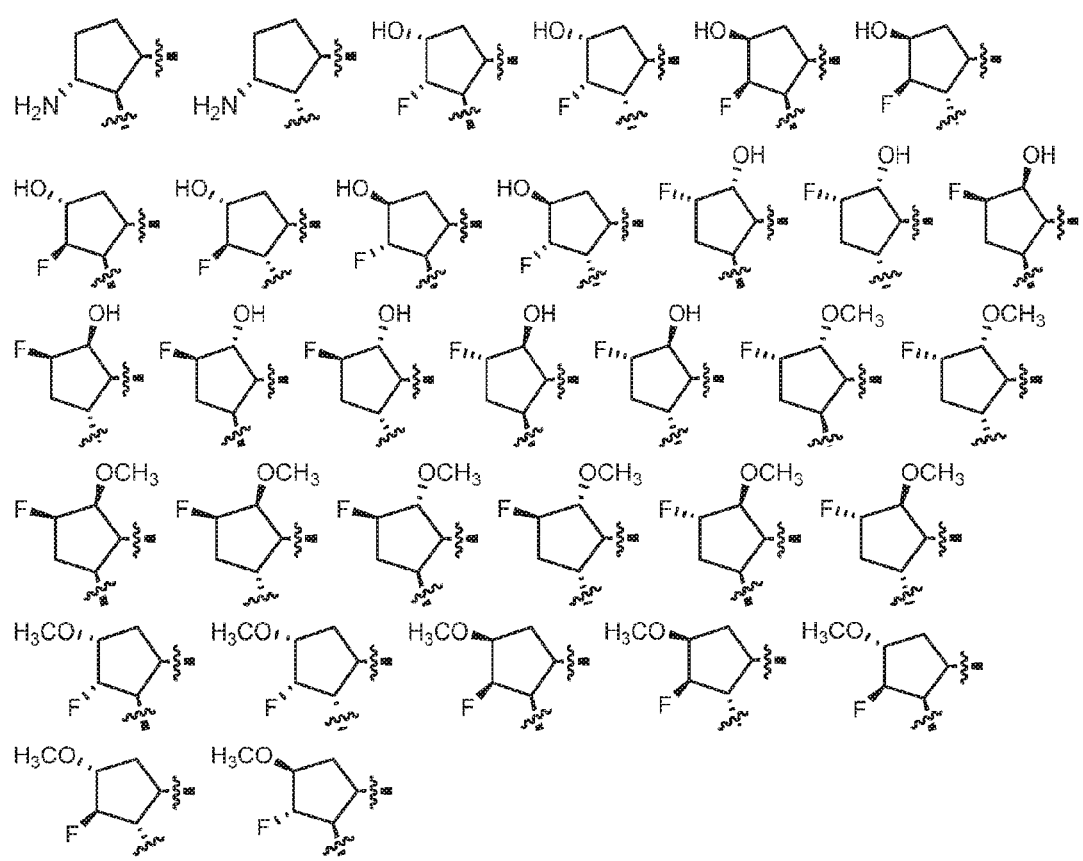
Figure 3F:
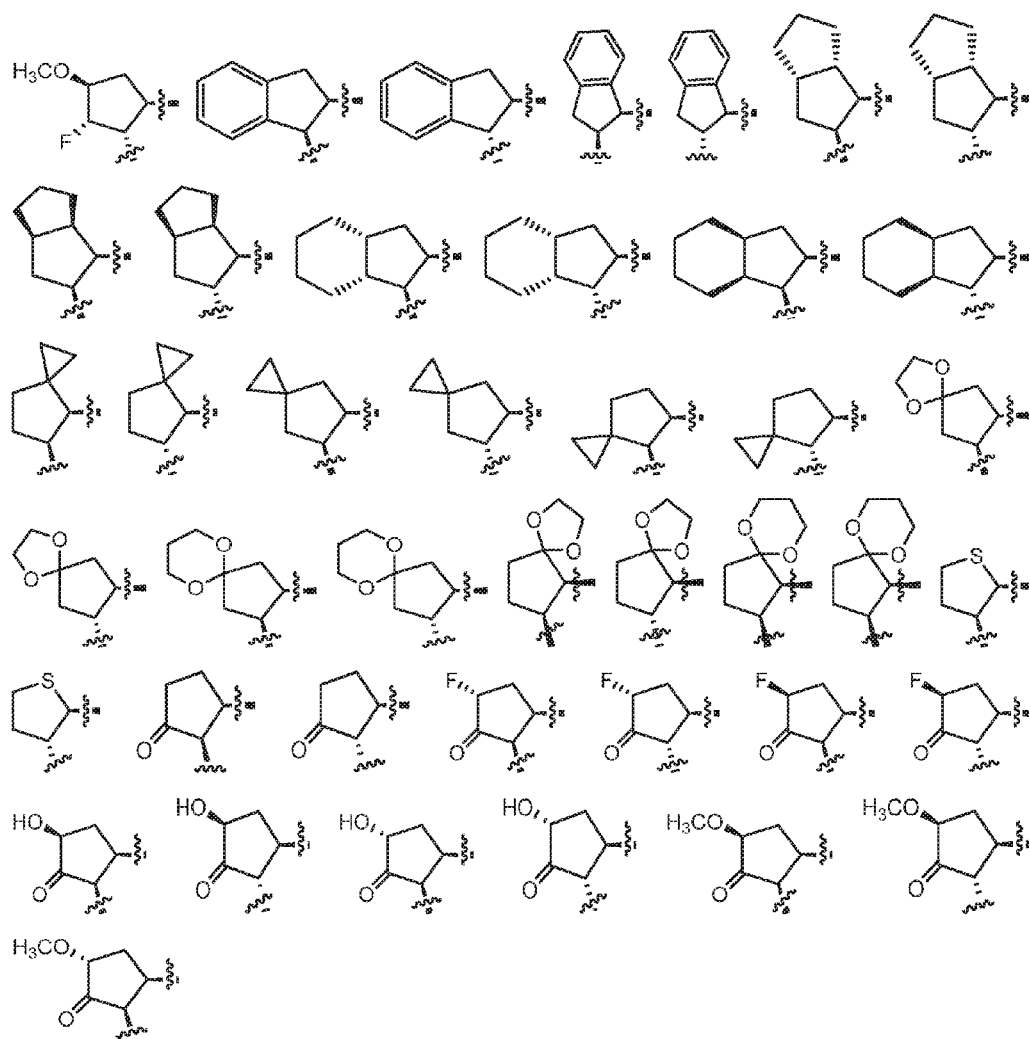
Figure 3G:
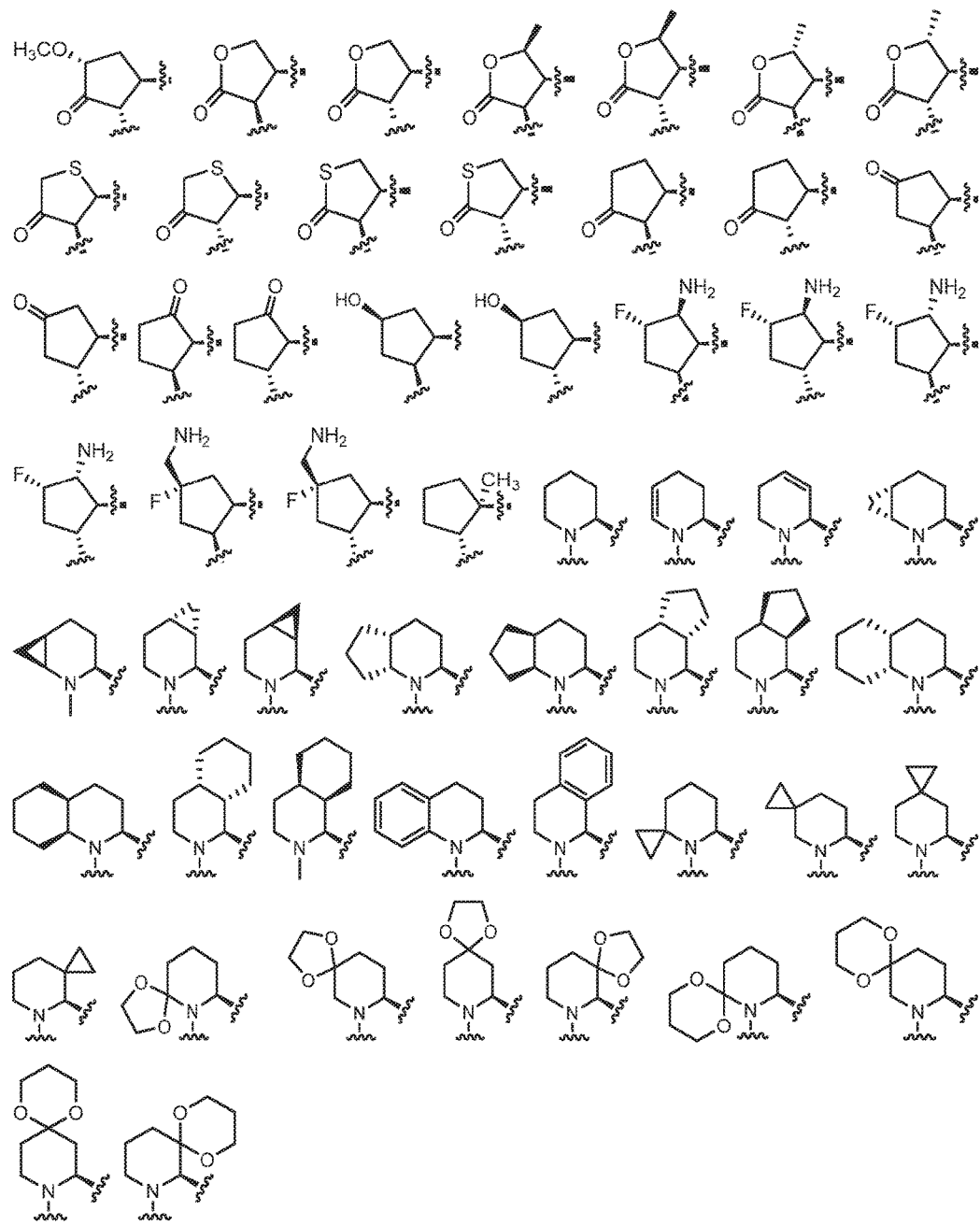
Figure 3H:
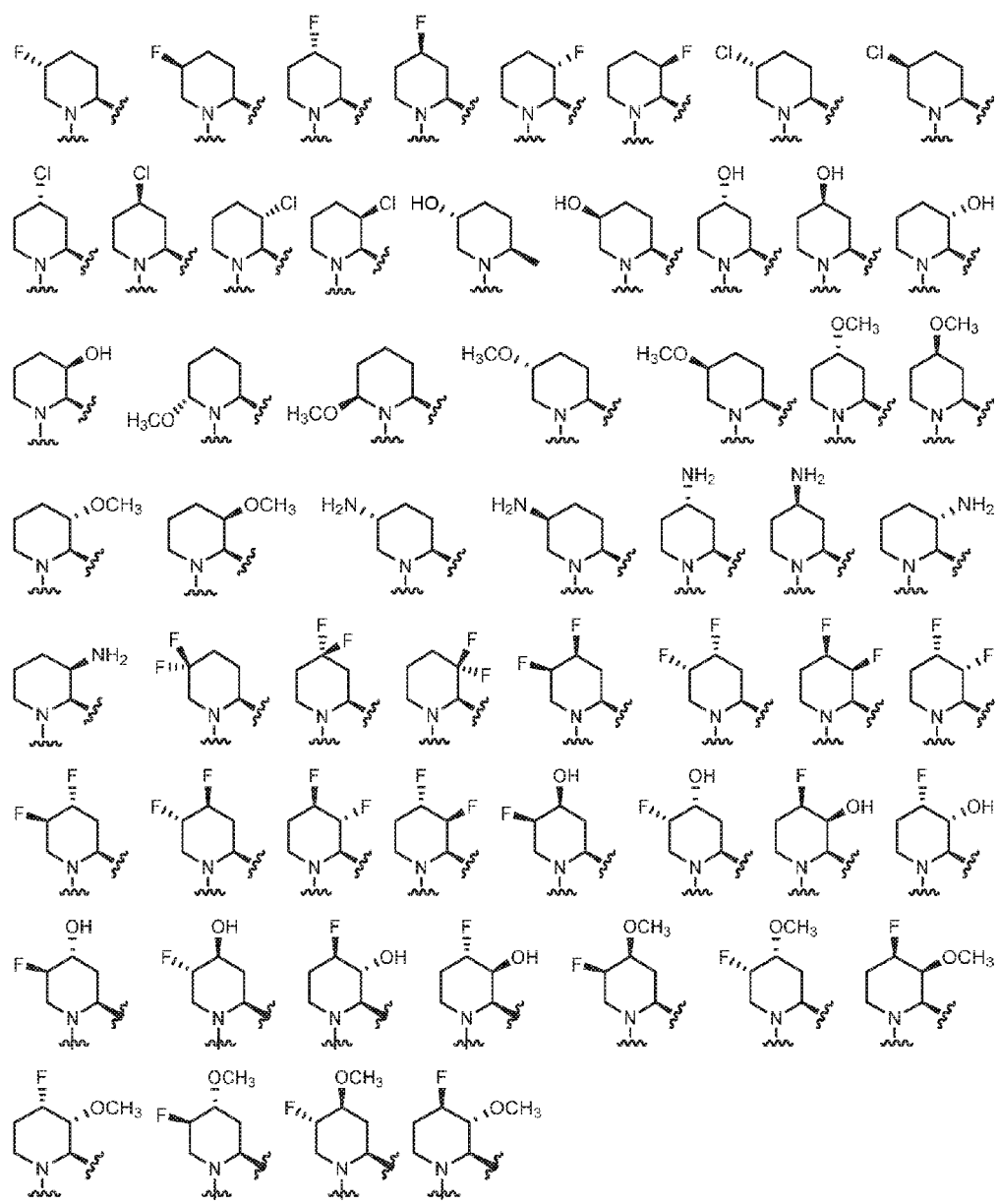
Figure 3I:
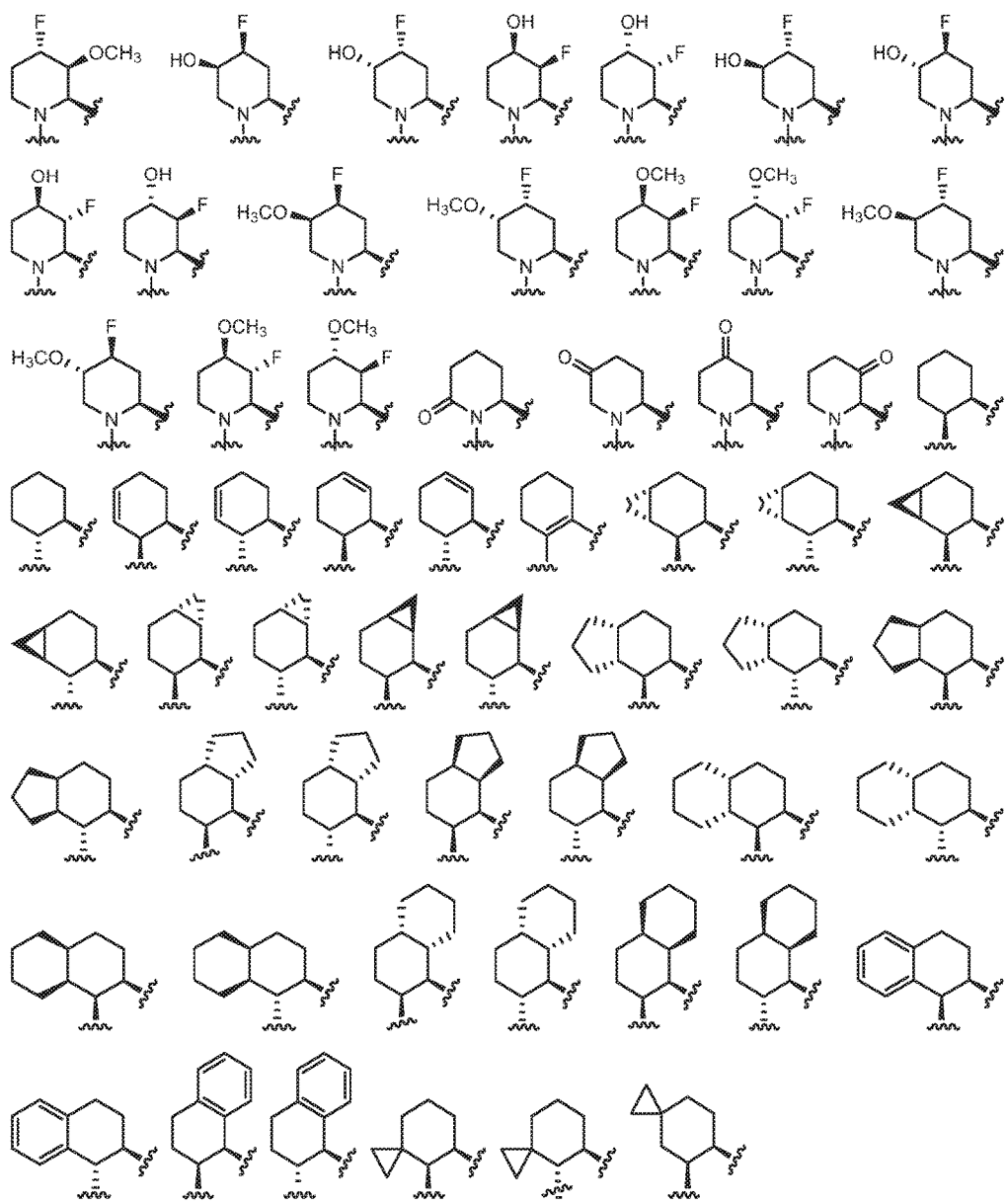
Figure 3J:
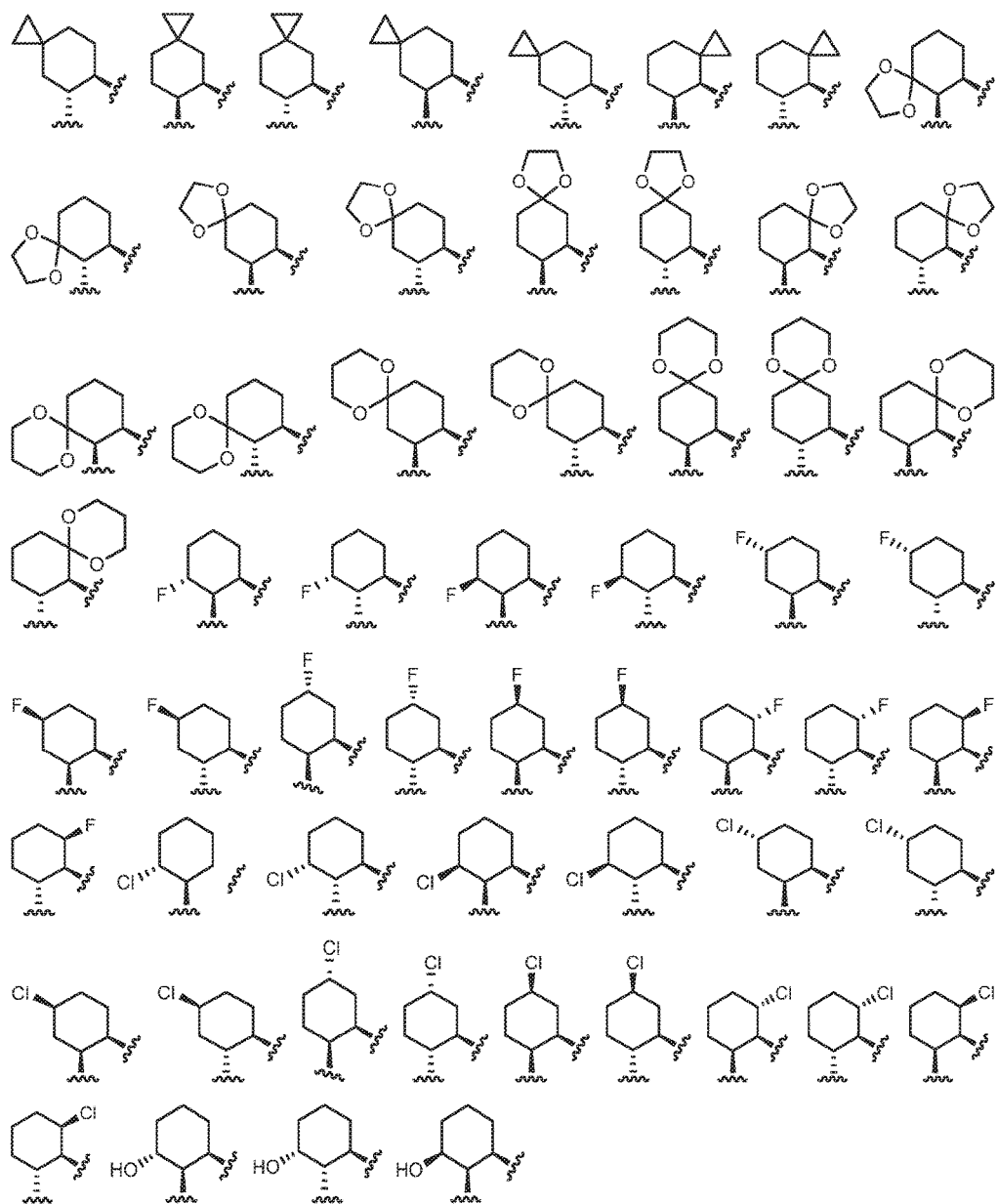
Figure 3K:
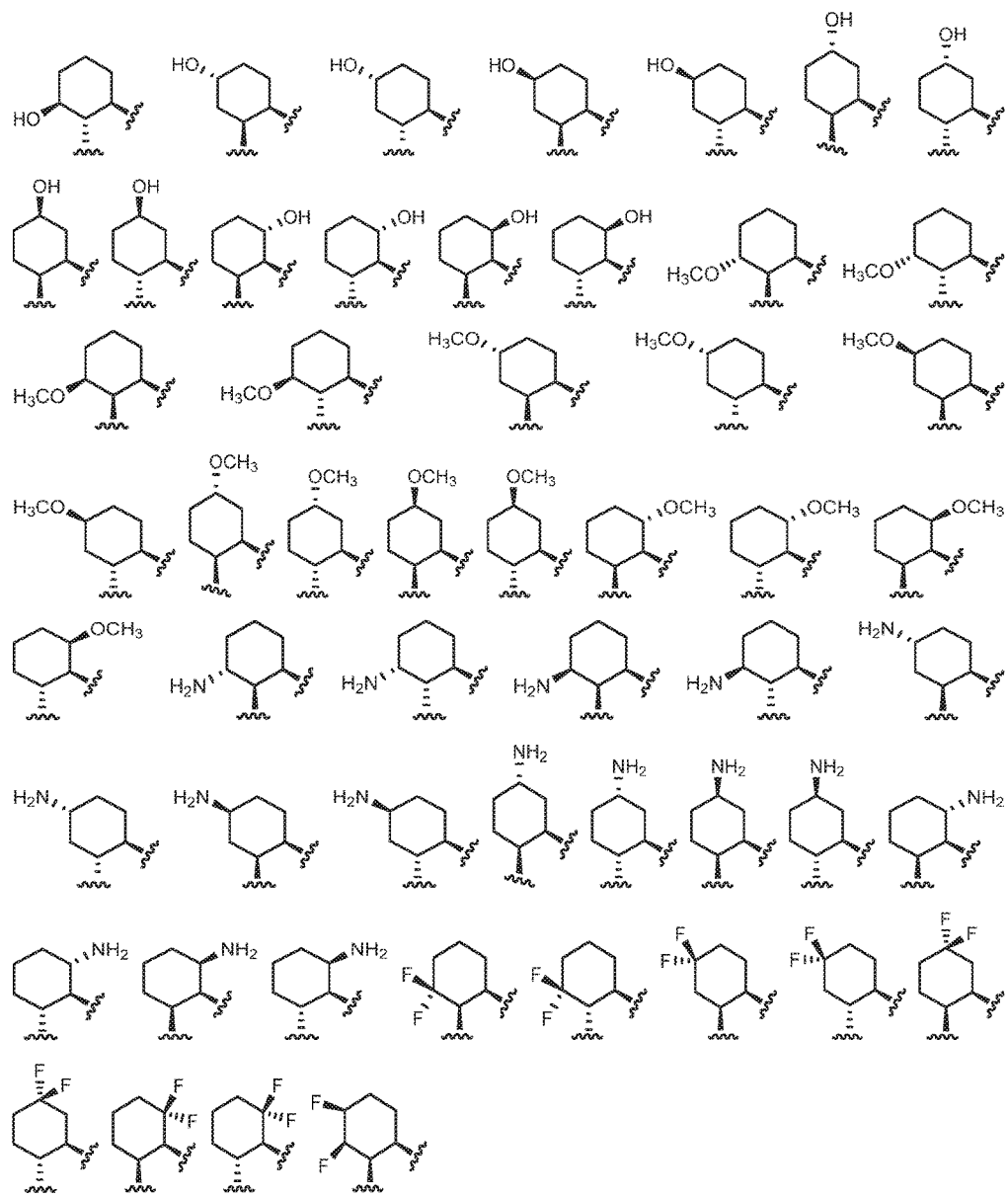
Figure 3L:
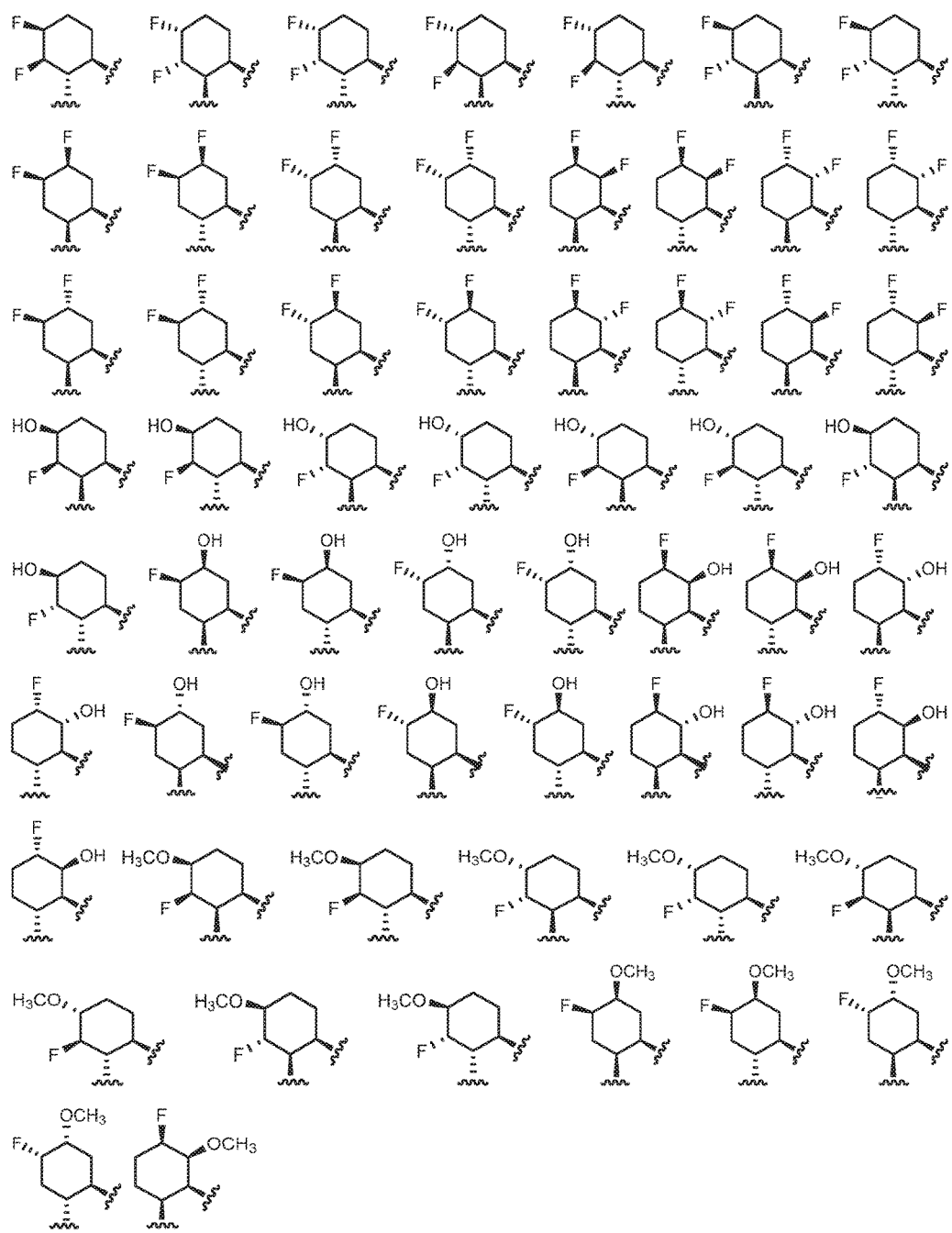
Figure 3M:
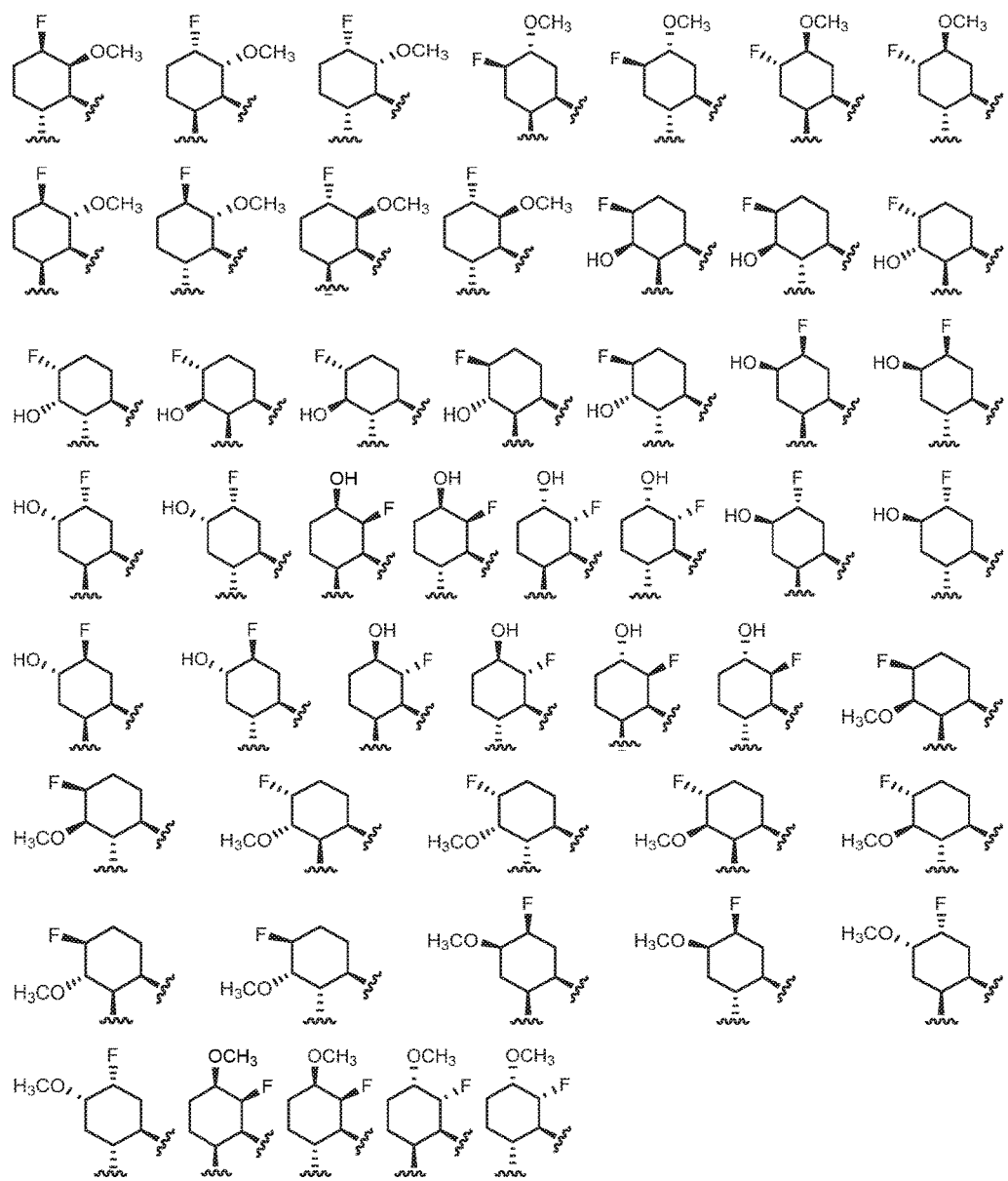
Figure 3N:
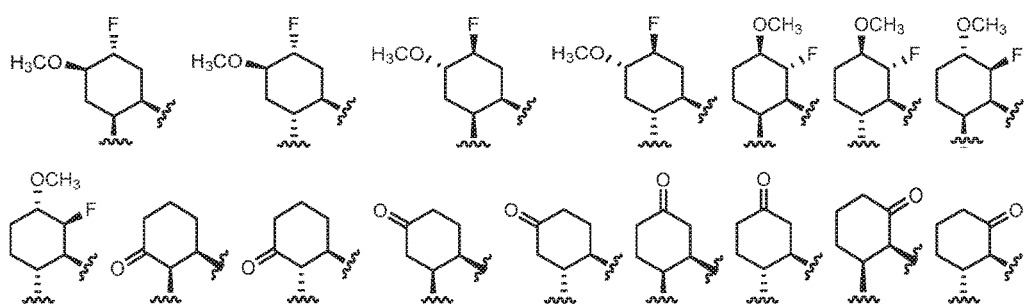
Figure 3O:
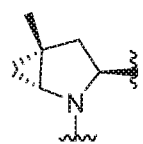
Figure 3P:
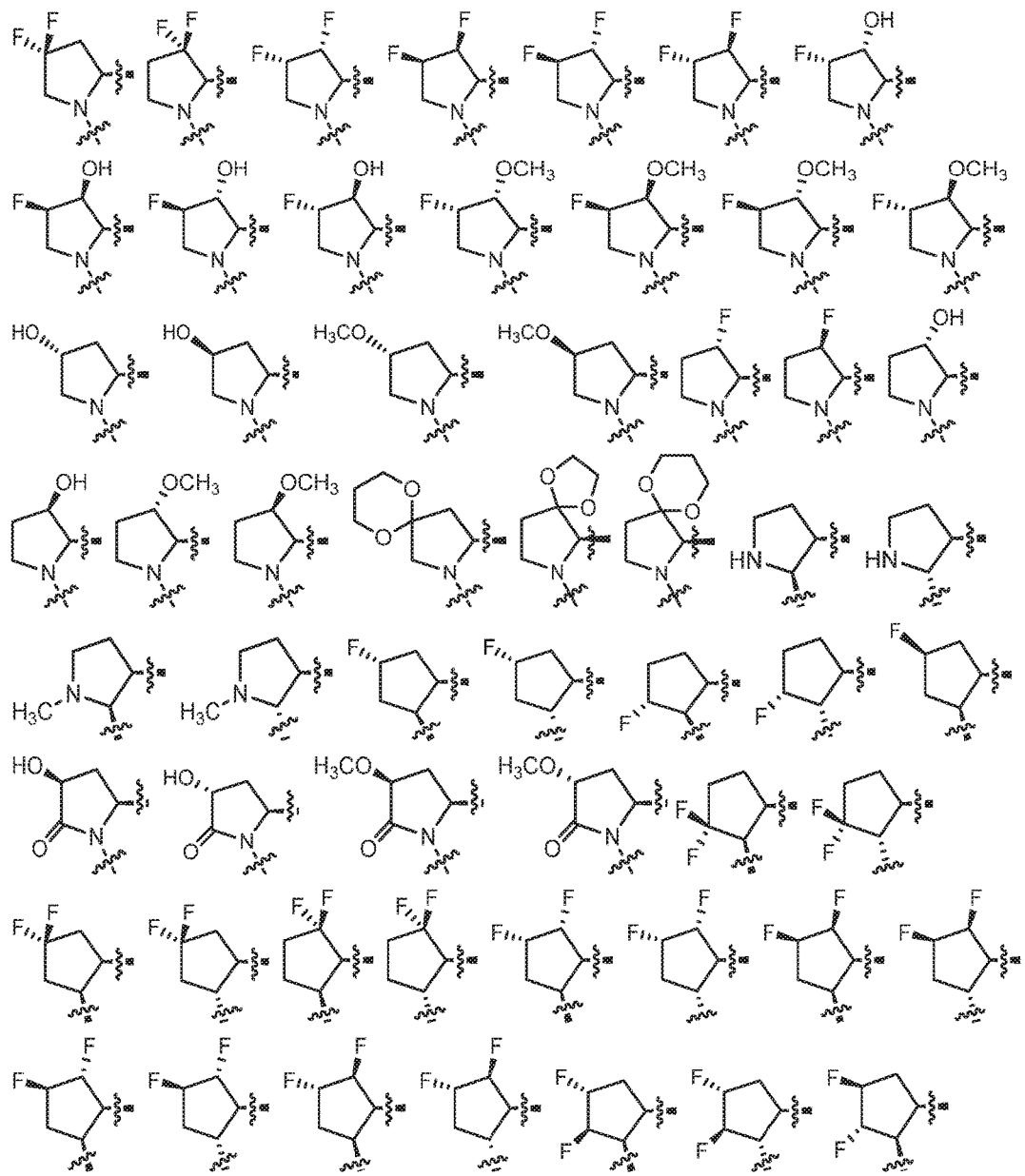
Figure 3Q:
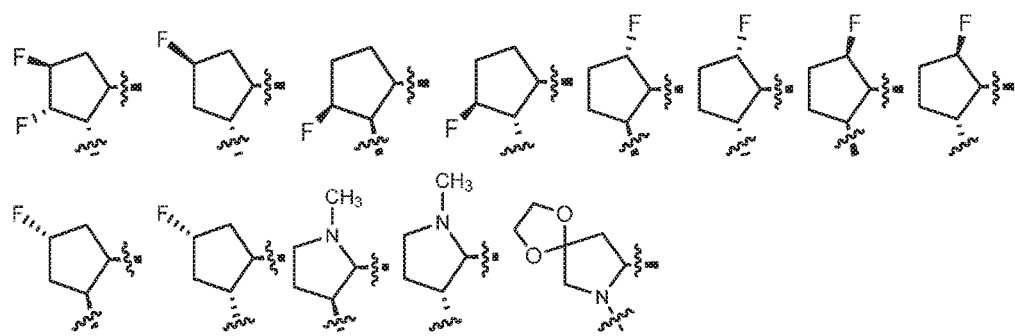
Figure 4A:
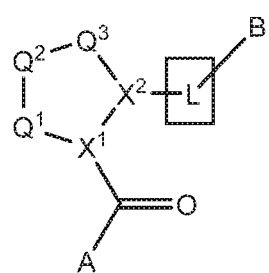
FIG. 4A illustrates the location of the Linker in Formula I.
Figure 4B:
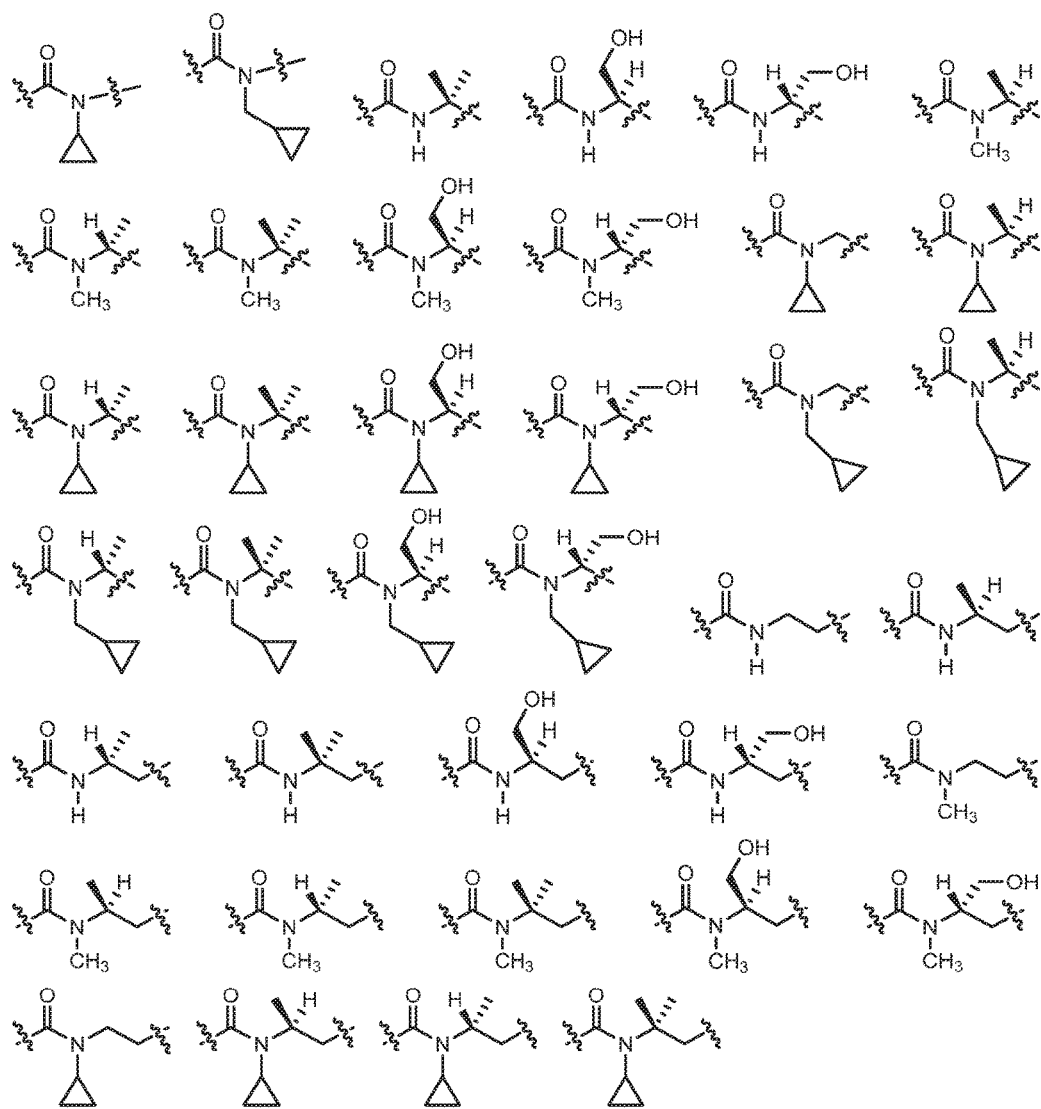
FIGS. 4B, 4C, 4D, 4E, 4F and 4G, provide non-limiting specific embodiments of the Linker (L), wherein $R^{17}$, $R^{18}$, $R^{18'}$, and m are defined below.
Figure 4C:
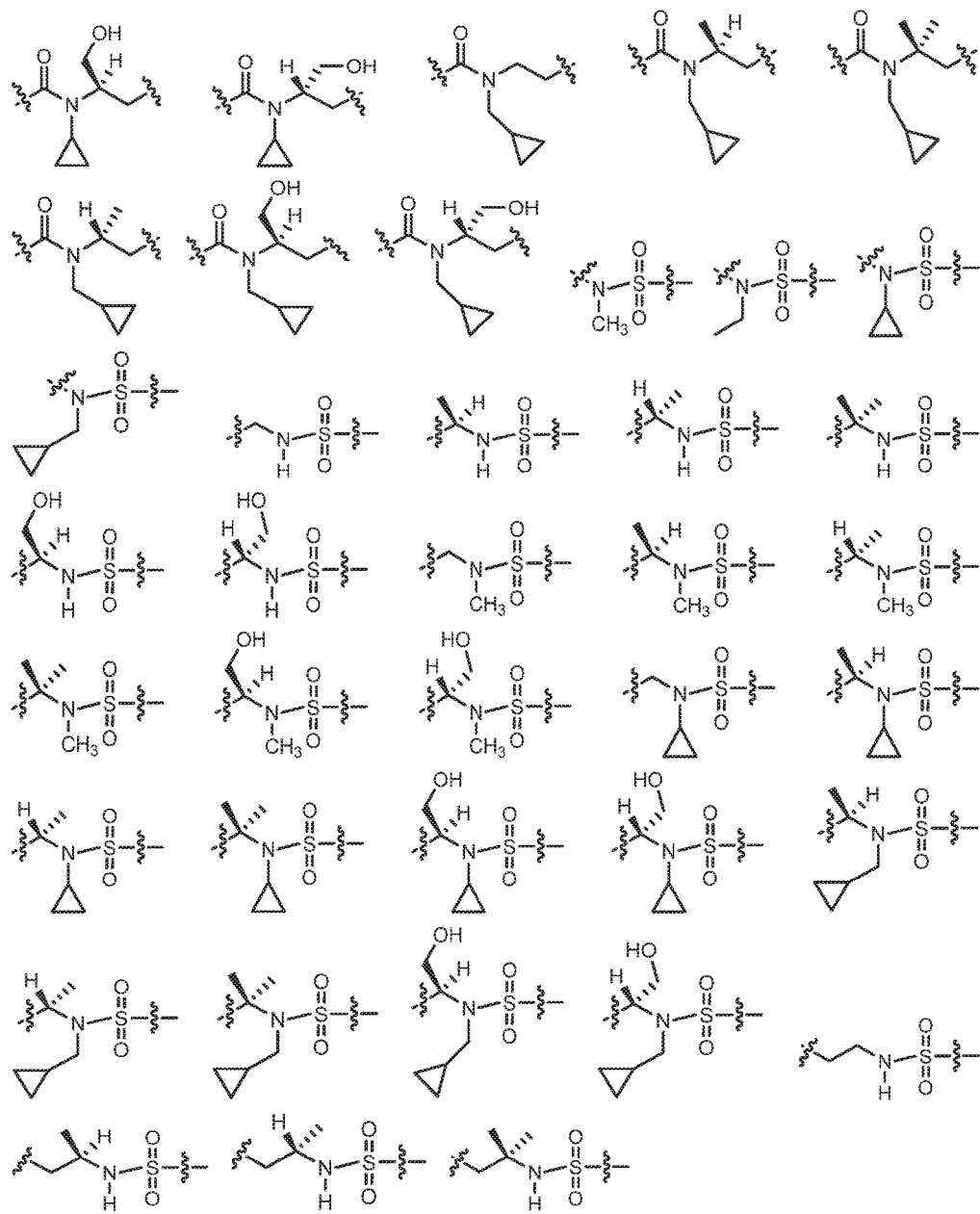
Figure 4D:
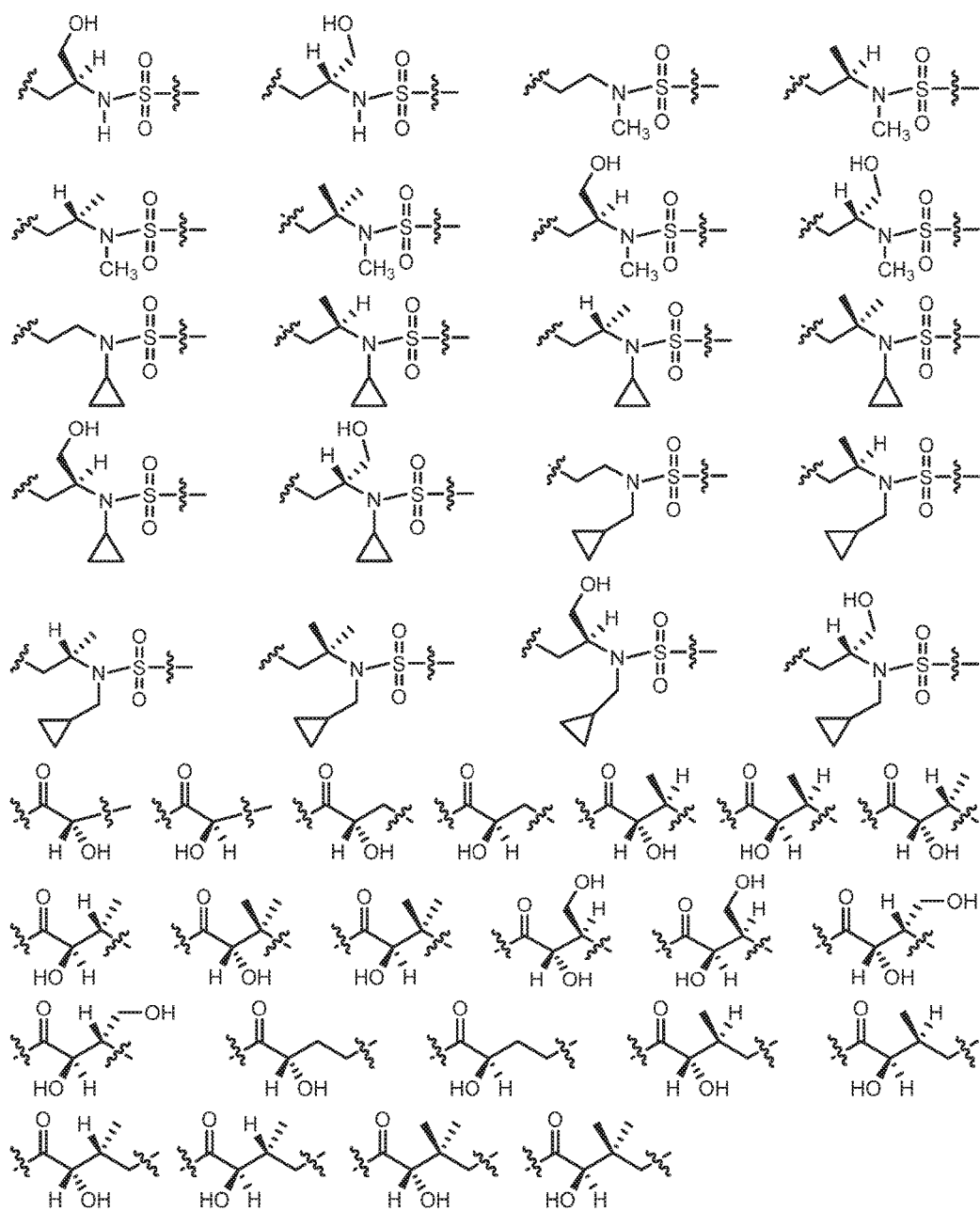
Figure 4E:
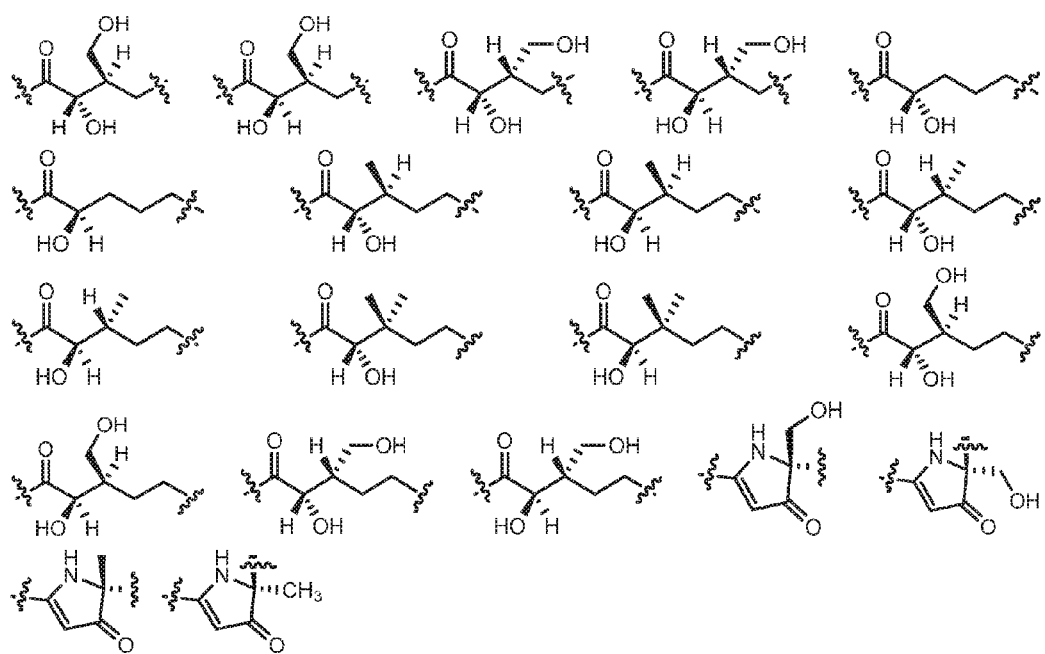
Figure 4F:
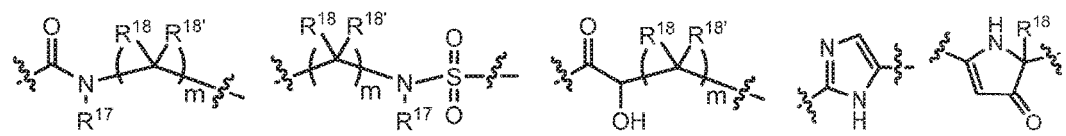
Figure 4G:
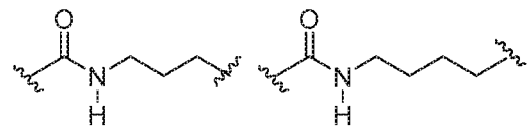

Compounds are described using standard nomenclature. Unless defined otherwise, all technical and scientific terms used herein have the same meaning as is commonly understood by one of skill in the art to which this invention belongs.

The compounds in any of the Formulas described herein include enantiomers, mixture of enantiomers, diasteromers, tautomers, racemates and other isomers, such as rotamers, as if each is specifically described, unless otherwise indicated in the text or drawing or otherwise indicated in context. "Formula I" includes all subgeneric groups of Formula I, such as Formula IA and Formula IB and also includes pharmaceutically acceptable salts of a compound of Formula I, unless clearly contraindicated by the context in which this phrase is used. "Formula I" also includes all subgeneric groups of Formula I, such as Formulas IC-ID, and Formulas II-XXX, and also includes pharmaceutically acceptable salts of all subgeneric groups of Formula I, such as Formulas IA-ID, and Formulas II-XXX, unless contraindicated by the context in which this phrase is used.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed. Unless defined otherwise, technical and scientific terms used herein have the same meaning as is commonly understood by one of skill in the art to which this invention belongs.

The present invention includes compounds of Table 2 or an embodiment of the active compound as described in the Figures and the use of compounds of Formula I, Table 1 and Table 2 or an embodiment of the active compound as described in the Figures with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. In one embodiment, isotopically labelled compounds can be used in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^2H$) and tritium ($^3H$) may be used anywhere in described structures that achieves the desired result. Alternatively or in addition, isotopes of carbon, e.g., $^{13}C$ and $^{14}C$, may be used. In one embodiment, the isotopic substitution is deuterium for hydrogen at one or more locations on the molecule to improve the performance of the drug, for example, the pharmacodynamics, pharmacokinetics, biodistribution, half-life, stability, AUC, Tmax, Cmax, etc. For example, the deuterium can be bound to carbon in a location of bond breakage during metabolism (an α-deuterium kinetic isotope effect) or next to or near the site of bond breakage (a β-deuterium kinetic isotope effect).

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one embodiments deuterium is 90, 95 or 99% enriched at a desired location. Unless otherwise stated, the enrichment at any point is above natural abundance and enough to alter a detectable property of the drug in a human.

In one embodiment, the substitution of a hydrogen atom for a deuterium atom can be provided in any of the A, B, L, or central core moieties. In one embodiment, the substitution of a hydrogen atom for a deuterium atom occurs within an R group selected from any of $R^{1'}$, $R^2$, $R^{2'}$, $R^3$, $R^{3'}$, $R^4$, $R^5$, $R^6$, $R^{6'}$, $R^7$, $R^8$, $R^{8'}$, $R^9$, $R^{10}$, $R^{11}$, $R^{12}$, $R^{13}$, $R^{14}$, $R^{15}$, $R^{16}$, $R^{17}$, $R^{18}$, $R^{18'}$, $R^{19}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$ and $R^{75}$. For example, when any of R groups are, or contain for example through substitution, methyl, ethyl, or methoxy, the alkyl residue may be deuterated (in non-limiting embodiments, $CD_3$, $CH_2CD_3$, $CD_2CD_3$, $CDH_2$, $CD_2H$, $CD_3$, $CHDCH_2D$, $CH_2CD_3$, $CHDCHD_2$, $OCDH_2$, $OCD_2H$, or $OCD_3$ etc.). In some embodiments, an R group has a "'" or an "a" designation, which in one embodiment can be deuterated. In certain other embodiments, when two substituents of the central core ring are combined to form a cyclopropyl ring, the unsubstituted methylene carbon may be deuterated.

The substitution of a hydrogen atom for a deuterium atom occurs within an R group when at least one of the variables within the R group is hydrogen (e.g., $^2H$ or D) or alkyl. For example, when any of R groups are, or contain for example through substitution, methyl or ethyl, the alkyl residue may be deuterated (in non-limiting embodiments, $CD_3$, $CH_2CD_3$, $CD_2CD_3$, $CDH_2$, $CD_2H$, $CD_3$, $CHDCH_2D$, $CH_2CD_3$, $CHDCHD_2$, etc.).

The compound of the present invention may form a solvate with solvents (including water). Therefore, in one embodiment, the invention includes a solvated form of the active compound. The term "solvate" refers to a molecular complex of a compound of the present invention (including a salt thereof) with one or more solvent molecules. Non-limiting examples of solvents are water, ethanol, dimethyl sulfoxide, acetone and other common organic solvents. The term "hydrate" refers to a molecular complex comprising a compound of the invention and water. Pharmaceutically acceptable solvates in accordance with the invention include those wherein the solvent of crystallization may be isotopically substituted, e.g. $D_2O$, $d_6$-acetone, $d_6$-DMSO. A solvate can be in a liquid or solid form.

A dash ("-") that is not between two letters or symbols is used to indicate a point of attachment for a substituent. For example, —(C=O)NH$_2$ is attached through carbon of the keto (C=O) group.

The term "substituted", as used herein, means that any one or more hydrogens on the designated atom or group is replaced with a moiety selected from the indicated group, provided that the designated atom's normal valence is not exceeded and the resulting compound is stable. For example, when the substituent is oxo (i.e., =O) then two hydrogens on the atom are replaced. For example a pyridyl group substituted by oxo is a pyridone. Combinations of substituents and/or variables are permissible only if such combinations result in stable compounds or useful synthetic intermediates.

A stable active compound refers to a compound that can be isolated and can be formulated into a dosage form with a shelf life of at least one month. A stable manufacturing intermediate or precursor to an active compound is stable if it does not degrade within the period needed for reaction or other use. A stable moiety or substituent group is one that does not degrade, react or fall apart within the period necessary for use. Non-limiting examples of unstable moieties are those that combine heteroatoms in an unstable arrangement, as typically known and identifiable to those of skill in the art.

Any suitable group may be present on a "substituted" or "optionally substituted" position that forms a stable molecule and meets the desired purpose of the invention and includes, but is not limited to, e.g., halogen (which can independently be F, Cl, Br or I); cyano; hydroxyl; nitro; azido; alkanoyl (such as a $C_2$-$C_6$ alkanoyl group); carboxamide; alkyl, cycloalkyl, alkenyl, alkynyl, alkoxy, aryloxy such as phenoxy; alkylthio including those having one or more thioether linkages; alkylsulfinyl; alkylsulfonyl groups including those having one or more sulfonyl linkages; aminoalkyl groups including groups having one or more N atoms; aryl (e.g., phenyl, biphenyl, naphthyl, or the like, each ring either substituted or unsubstituted aromatic); arylalkyl having for example, 1 to 3 separate or fused rings and from 6 to about 14 or 18 ring carbon atoms, with benzyl being an exemplary arylalkyl group; arylalkoxy, for example, having 1 to 3 separate or fused rings with benzyloxy being an exemplary arylalkoxy group; or a saturated, unsaturated, or aromatic heterocyclic group having 1 to 3 separate or fused rings with one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino. In certain embodiments "optionally substituted" includes one or more substituents independently selected from halogen, hydroxyl, amino, cyano, —CHO, —COOH, —CONH$_2$, $C_1$-$C_6$alkyl, $C_2$-$C_6$alkenyl, $C_2$-$C_6$alkynyl, —$C_1$-$C_6$alkoxy, $C_2$-$C_6$alkanoyl, $C_1$-$C_6$alkylester, (mono- and di-$C_1$-$C_6$alkylamino)$C_0$-$C_2$alkyl, $C_1$-$C_2$haloalkyl, hydoxy$C_1$-$C_6$alkyl, ester, carbamate, urea, sulfonamide, —$C_1$-$C_6$alkyl(heterocyclo), $C_1$-$C_6$alkyl(heteroaryl), —$C_1$-$C_6$alkyl($C_3$-$C_7$cycloalkyl), O—$C_1$-$C_6$alkyl($C_3$-$C_7$cycloalkyl), B(OH)$_2$, phosphate, phosphonate and $C_1$-$C_2$haloalkoxy.

"Alkyl" is a branched or straight chain saturated aliphatic hydrocarbon group. In one embodiment, the alkyl contains from 1 to about 12 carbon atoms, more generally from 1 to about 6 carbon atoms or from 1 to about 4 carbon atoms. In one embodiment, the alkyl contains from 1 to about 8 carbon atoms. In certain embodiments, the alkyl is $C_1$-$C_2$, $C_1$-$C_3$, or $C_1$-$C_6$. The specified ranges as used herein indicate an alkyl group having each member of the range described as an independent species. For example, the term $C_1$-$C_6$ alkyl as used herein indicates a straight or branched alkyl group having from 1, 2, 3, 4, 5, or 6 carbon atoms and is intended to mean that each of these is described as an independent species. For example, the term $C_1$-$C_4$alkyl as used herein indicates a straight or branched alkyl group having from 1, 2, 3, or 4 carbon atoms and is intended to mean that each of these is described as an independent species. When $C_0$-$C_n$ alkyl is used herein in conjunction with another group, for example, ($C_3$-$C_7$cycloalkyl)$C_0$-$C_4$ alkyl, or —$C_0$-$C_4$alkyl($C_3$-$C_7$cycloalkyl), the indicated group, in this case cycloalkyl, is either directly bound by a single covalent bond ($C_0$alkyl), or attached by an alkyl chain in this case 1, 2, 3, or 4 carbon atoms. Alkyls can also be attached via other groups such as heteroatoms as in —O—$C_0$-$C_4$alkyl($C_3$-$C_7$cycloalkyl). Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, 2,3-dimethylbutane, and hexyl. In one embodiment, the alkyl group is optionally substituted as described above.

In one embodiment, when a term is used that includes "alk" it should be understood that "cycloalkyl" or "carbocyclic" can be considered part of the definition, unless unambiguously excluded by the context. For example and without limitation, the terms alkyl, alkenyl, alkynyl, alkoxy, alkanoyl, alkenloxy, haloalkyl, aminoalkyl, alkylene, alkenylene, alkynylene, etc. can all be considered to include the cyclic forms of alkyl, unless unambiguously excluded by context.

"Alkenyl" is a branched or straight chain aliphatic hydrocarbon group having one or more carbon-carbon double bonds that may occur at a stable point along the chain. Non-limiting examples are $C_2$-$C_8$alkenyl, $C_2$-$C_6$alkenyl and $C_2$-$C_4$alkenyl. The specified ranges as used herein indicate an alkenyl group having each member of the range described as an independent species, as described above for the alkyl moiety. Examples of alkenyl include, but are not limited to, ethenyl and propenyl. In one embodiment, the alkenyl group is optionally substituted as described above.

"Alkynyl" is a branched or straight chain aliphatic hydrocarbon group having one or more carbon-carbon triple bonds that may occur at any stable point along the chain, for example, $C_2$-$C_8$alkynyl or $C_2$-$C_6$alkynyl. The specified ranges as used herein indicate an alkynyl group having each member of the range described as an independent species, as described above for the alkyl moiety. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. In one embodiment, the alkynyl group is optionally substituted as described above.

"Alkylene" is a bivalent saturated hydrocarbon. Alkylenes, for example, can be a 1 to 8 carbon moiety, 1 to 6 carbon moiety, or an indicated number of carbon atoms, for example $C_1$-$C_4$alkylene, $C_1$-$C_3$alkylene, or $C_1$-$C_2$alkylene.

"Alkenylene" is a bivalent hydrocarbon having at least one carbon-carbon double bond. Alkenylenes, for example, can be a 2 to 8 carbon moiety, 2 to 6 carbon moiety, or an indicated number of carbon atoms, for example $C_2$-$C_4$alkenylene.

"Alkynylene" is a bivalent hydrocarbon having at least one carbon-carbon triple bond. Alkynylenes, for example, can be a 2 to 8 carbon moiety, 2 to 6 carbon moiety, or an indicated number of carbon atoms, for example $C_2$-$C_4$alkynylene.

"Alkoxy" is an alkyl group as defined above covalently bound through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Similarly an "alkylthio" or a "thioalkyl" group is an alkyl group as defined above with the indicated number of carbon atoms covalently bound through a sulfur bridge (—S—). In one embodiment, the alkoxy group is optionally substituted as described above.

"Alkenyloxy" is an alkenyl group as defined covalently bound to the group it substitutes by an oxygen bridge (—O—).

"Alkanoyl" is an alkyl group as defined above covalently bound through a carbonyl (C=O) bridge. The carbonyl carbon is included in the number of carbons, that is $C_2$alkanoyl is a $CH_3(C=O)$— group. In one embodiment, the alkanoyl group is optionally substituted as described above.

"Alkylester" is an alkyl group as defined herein covalently bound through an ester linkage. The ester linkage may be in either orientation, e.g., a group of the formula —O(C=O)alkyl or a group of the formula —(C=O)Oalkyl.

"Amide" or "carboxamide" is —C(O)NR$^a$R$^b$ wherein R$^a$ and R$^b$ are each independently selected from hydrogen, alkyl, for example, $C_1$-$C_6$alkyl, alkenyl, for example, $C_2$-$C_6$alkenyl, alkynyl, for example, $C_2$-$C_6$alkynyl, —$C_0$-$C_4$alkyl($C_3$-$C_7$cycloalkyl), —$C_0$-$C_4$alkyl($C_3$-$C_7$heterocycloalkyl), —$C_0$-$C_4$alkyl(aryl), and —$C_0$-$C_4$alkyl(heteroaryl); or together with the nitrogen to which they are bonded, R$^a$ and R$^b$ can form a $C_3$-$C_7$heterocyclic ring. In one embodiment, the R$^a$ and R$^b$ groups are each independently optionally substituted as described above.

"Carbocyclic group", "carbocyclic ring", or "cycloalkyl" is a saturated or partially unsaturated (i.e., not aromatic) group containing all carbon ring atoms. A carbocyclic group typically contains 1 ring of 3 to 7 carbon atoms or 2 fused rings each containing 3 to 7 carbon atoms. Cycloalkyl substituents may be pendant from a substituted nitrogen or carbon atom, or a substituted carbon atom that may have two substituents can have a cycloalkyl group, which is attached as a spiro group. Examples of carbocyclic rings include cyclohexenyl, cyclohexyl, cyclopentenyl, cyclopentyl, cyclobutenyl, cyclobutyl and cyclopropyl rings. In one embodiment, the carbocyclic ring is optionally substituted as described above. In one embodiment, the cycloalkyl is a partially unsaturated (i.e., not aromatic) group containing all carbon ring atoms. In another embodiment, the cycloalkyl is a saturated group containing all carbon ring atoms.

"Carbocyclic-oxy group" is a monocyclic carbocyclic ring or a mono- or bi-cyclic carbocyclic group as defined above attached to the group it substitutes via an oxygen, —O—, linker.

"Haloalkyl" indicates both branched and straight-chain alkyl groups substituted with 1 or more halogen atoms, up to the maximum allowable number of halogen atoms. Examples of haloalkyl include, but are not limited to, trifluoromethyl, monofluoromethyl, difluoromethyl, 2-fluoroethyl, and penta-fluoroethyl.

"Haloalkoxy" indicates a haloalkyl group as defined herein attached through an oxygen bridge (oxygen of an alcohol radical).

"Hydroxyalkyl" is an alkyl group as previously described, substituted with at least one hydroxyl substituent.

"Aminoalkyl" is an alkyl group as previously described, substituted with at least one amino substituent.

"Halo" or "halogen" indicates independently any of fluoro, chloro, bromo or iodo.

"Aryl" indicates an aromatic group containing only carbon in the aromatic ring or rings. In one embodiment, the aryl groups contain 1 to 3 separate or fused rings and is 6 to about 14 or 18 ring atoms, without heteroatoms as ring members. When indicated, such aryl groups may be further substituted with carbon or non-carbon atoms or groups. Such substitution may include fusion to a 4 to 7 or a 5 to 7-membered saturated or partially unsaturated cyclic group that optionally contains 1, or 3 heteroatoms independently selected from N, O, B, P, Si and/or S, to form, for example, a 3,4-methylenedioxyphenyl group. Aryl groups include, for example, phenyl and naphthyl, including 1-naphthyl and 2-naphthyl. In one embodiment, aryl groups are pendant. An example of a pendant ring is a phenyl group substituted with a phenyl group. In one embodiment, the aryl group is optionally substituted as described above.

The term "heterocycle," or "heterocyclic ring" as used herein refers to a saturated or a partially unsaturated (i.e., having one or more double and/or triple bonds within the ring without aromaticity) carbocyclic moiety of 3 to about 12, and more typically 3, 5, 6, 7 to 10 ring atoms in which at least one ring atom is a heteroatom selected from nitrogen, oxygen, phosphorus and sulfur, the remaining ring atoms being C, where one or more ring atoms is optionally substituted independently with one or more substituents described above. A heterocycle may be a monocycle having 3 to 7 ring members (2 to 6 carbon atoms and 1 to 4 heteroatoms selected from N, O, P, and S) or a bicycle having 6 to 10 ring members (4 to 9 carbon atoms and 1 to 6 heteroatoms selected from N, O, P, and S), for example: a bicyclo [4,5], [5,5], [5,6], or [6,6] system. In one embodiment, the only heteroatom is nitrogen. In one embodiment, the only heteroatom is oxygen. In one embodiment, the only heteroatom is sulfur. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. Examples of heterocyclic rings include, but are not limited to, pyrrolidinyl, dihydrofuranyl, tetrahydrothienyl, tetrahydropyranyl, dihydropyranyl, tetrahydrothiopyranyl, piperidino, piperidonyl, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, dihydroisoquinolinyl, tetrahydroisoquinolinyl, pyrazolidinylimidazolinyl, imidazolidinyl, 2-oxa-5-azabicyclo[2.2.2]octane, 3-oxa-8-azabicyclo[3.2.1]octane, 8-oxa-3-azabicyclo[3.2.1]octane, 6-oxa-3-azabicyclo[3.1.1]heptane, 2-oxa-5-azabicyclo[2.2.1]heptane, 3-azabicyco[3.1.0]hexanyl, 3-azabicyclo[4.1.0]heptanyl, azabicyclo[2.2.2]hexanyl, 3H-indolyl, quinolizinyl, N-pyridyl ureas, and pyrrolopyrimidine. Spiro moieties are also included within the scope of this definition. Examples of a heterocyclic group wherein 1 or 2 ring carbon atoms are substituted with oxo (═O) moieties are pyrimidinonyl and 1,1-dioxo-thiomorpholinyl. The heterocycle groups herein are optionally substituted independently with one or more substituents described herein.

"Heterocyclicoxy group" is a monocyclic heterocyclic ring or a bicyclic heterocyclic group as described previously linked to the group it substitutes via an oxygen, —O—, linker.

"Heteroaryl" indicates a stable monocyclic aromatic ring which contains from 1 to 3, or in some embodiments from 1, 2 or 3 heteroatoms selected from N, O, S, B or P with remaining ring atoms being carbon, or a stable bicyclic or tricyclic system containing at least one 4 to 7 or 5- to 7-membered aromatic ring which contains from 1 to 3, or in some embodiments from 1 to 2, heteroatoms selected from N, O, S, B or P with remaining ring atoms being carbon. In one embodiment, the only heteroatom is nitrogen. In one embodiment, the only heteroatom is oxygen. In one embodiment, the only heteroatom is sulfur. Monocyclic heteroaryl groups typically have from 5 to 7 ring atoms. In some embodiments bicyclic heteroaryl groups are 9- to 10-membered heteroaryl groups, that is, groups containing 9 or 10 ring atoms in which one 5- to 7-member aromatic ring is fused to a second aromatic or non-aromatic ring. When the total number of S and O atoms in the heteroaryl group exceeds 1, these heteroatoms are not adjacent to one another. In one embodiment, the total number of S and O atoms in the heteroaryl group is not more than 2. In another embodiment, the total number of S and O atoms in the aromatic heterocycle is not more than 1. Examples of heteroaryl groups include, but are not limited to, pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, tetrahydrofuranyl, and furopyridinyl. Heteroaryl groups are optionally substituted independently with one or more substituents described herein. "Heteroaryloxy" is a heteroaryl group as described bound to the group it substituted via an oxygen, —O—, linker.

"Heterocycloalkyl" is a saturated ring group. It may have, for example, 1, 2, 3, or 4 heteroatoms independently selected from N, S, and O, with remaining ring atoms being carbon. In a typical embodiment, nitrogen is the heteroatom. Monocyclic heterocycloalkyl groups typically have from 3 to about 8 ring atoms or from 4 to 6 ring atoms. Examples of heterocycloalkyl groups include morpholinyl, piperazinyl, piperidinyl, and pyrrolinyl.

The term "mono- and/or di-alkylamino" indicate a secondary or tertiary alkylamino group, wherein the alkyl groups are independently selected alkyl groups, as defined herein. The point of attachment of the alkylamino group is on the nitrogen. Examples of mono- and di-alkylamino groups include ethylamino, dimethylamino, and methyl-propyl-amino.

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like. A "dosage form" can also include an implant, for example an optical implant.

"Pharmaceutical compositions" are compositions comprising at least one active agent, and at least one other substance, such as a carrier. "Pharmaceutical combinations" are combinations of at least two active agents which may be combined in a single dosage form or provided together in separate dosage forms with instructions that the active agents are to be used together to treat any disorder described herein.

A "pharmaceutically acceptable salt" is a derivative of the disclosed compound in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like, or using a different acid that produces the same counterion. Lists of additional suitable salts may be found, e.g., in *Remington's Pharmaceutical Sciences*, 17th ed., Mack Publishing Company, Easton, Pa., p. 1418 (1985).

The term "carrier" applied to pharmaceutical compositions/combinations of the invention refers to a diluent, excipient, or vehicle with which an active compound is provided.

A "pharmaceutically acceptable excipient" means an excipient that is useful in preparing a pharmaceutical composition/combination that is generally safe, non-toxic and neither biologically nor otherwise inappropriate for administration to a host, typically a human. In one embodiment, an excipient is used that is acceptable for veterinary use.

A "patient" or "host" or "subject" is a human or non-human animal in need of treatment or prevention of any of the disorders as specifically described herein, including but not limited to by modulation of the complement Factor D pathway. Typically the host is a human. A "patient" or "host" or "subject" also refers to for example, a mammal, primate (e.g., human), cows, sheep, goat, horse, dog, cat, rabbit, rat, mice, fish, bird and the like.

A "prodrug" as used herein, means a compound which when administered to a host in vivo is converted into a parent drug. As used herein, the term "parent drug" means any of the presently described chemical compounds described herein. Prodrugs can be used to achieve any desired effect, including to enhance properties of the parent drug or to improve the pharmaceutic or pharmacokinetic properties of the parent. Prodrug strategies exist which provide choices in modulating the conditions for in vivo generation of the parent drug, all of which are deemed included herein. Non-limiting examples of prodrug strategies include covalent attachment of removable groups, or removable portions of groups, for example, but not limited to acylation, phosphorylation, phosphonylation, phosphoramidate derivatives, amidation, reduction, oxidation, esterification, alkylation, other carboxy derivatives, sulfoxy or sulfone derivatives, carbonylation or anhydride, among others.

"Providing a compound with at least one additional active agent," for example, in one embodiment can mean that the compound and the additional active agent(s) are provided simultaneously in a single dosage form, provided concomitantly in separate dosage forms, or provided in separate dosage forms for administration. In one embodiment, the compound administrations are separated by some amount of time that is within the blood stream of a patient. In certain embodiments the compound and the additional active agent need not be prescribed for a patient by the same medical care worker. In certain embodiments the additional active agent or agents need not require a prescription. Administration of the compound or the at least one additional active agent can occur via any appropriate route, for example, oral tablets, oral capsules, oral liquids, inhalation, injection, suppositories, parenteral, sublingual, buccal, intravenous, intraaortal, transdermal, polymeric controlled delivery, non-polymeric controlled delivery, nano or microparticles, liposomes, and/or topical contact.

A "therapeutically effective amount" of a pharmaceutical composition/combination of this invention means an amount effective, when administered to a host, to provide a therapeutic benefit such as an amelioration of symptoms or reduction or diminution of the disease itself. In one embodiment, a therapeutically effective amount is an amount sufficient to prevent a significant increase or will significantly reduce the detectable level of complement Factor D in the patient's blood, serum, or tissues.

II. Detailed Description of the Active Compounds

PCT Patent Application No. PCT/US2015/017538 and U.S. patent application Ser. No. 14/631,233 titled "Amide Compounds for Treatment of Complement Mediated Disorders" defines a compound of Formula I as:

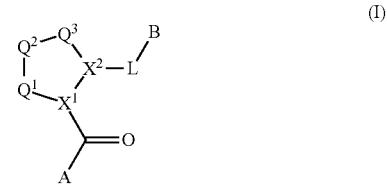

as well as the pharmaceutically acceptable salts and compositions thereof. In one embodiment, the invention is the use of a compound of Formula I, or a pharmaceutically acceptable salt or composition thereof, wherein $R^{12}$ or $R^{13}$ on the A group is an amide substituent, including those compounds set out in Table 1, for the treatment of a disorder in a host, typically a human, wherein the disorder is selected from the group disclosed in the Detailed Description, Part IV, Section A.

Formula I can be considered to have a central core, an L substituent, a B substituent (which can be an L-B substituent), and a (C=O)A substituent. Non-limiting examples of compounds falling within Formula I with variations in the variables e.g., A, B, $R^1$-$R^{3'}$, the central core, and L, are illustrated below. The disclosure includes the use of all combinations of these definitions so long as a stable compound results. In one embodiment, the compound of Formula I is selected from the compounds in Table 1 below.

in certain embodiments, any of the active compounds can be provided in its N-oxide form to a patient in need thereof. In a different embodiment, an N-oxide of one of the active compounds or a precursor of the active compound is used in a manufacturing scheme. In yet another embodiment, the N-oxide is a metabolite of administration of one of the active compounds herein, and may have independent activity. The N-oxide can be formed by treating the compound of interest with an oxidizing agent, for example a suitable peroxyacid or peracid, to generate an N-oxide compound. For example, a heteroaryl group, for example a pyridyl group, can be treated with an oxidizing agent such as sodium percarbonate in the presence of a rhenium-based catalyst under mild reaction conditions to generate an N-oxide compound. A person skilled in the art will understand that appropriate protecting groups may be necessary to carry out the chemistry. See, Jain, S. L. et al., "Rhenium-Catalyzed Highly Efficient Oxidations of Tertiary Nitrogen Compounds to N-Oxides Using Sodium Percarbonate as Oxygen Source, Synlett, 2261-2663, 2006.

In one embodiment, a sulfur atom in a selected compound as described herein can be oxidized to form a sulfoxide

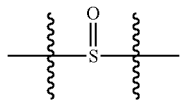 [SMILES: *S(*)=O]

or a sulfone

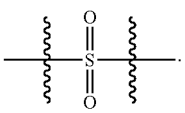 [SMILES: *S(*)(=O)=O]

For example, the compound 1,3,5-triazo-2,4,6-triphosphorine-2,2,4,4,6,6-tetrachloride (TAPC) is an efficient promoter for the oxidation of sulfides to sulfoxides. See, Bahrami, M. et al., "TAPC-Promoted Oxidation of sulfides and Deoxygenation of Sulfoxides", J. Org. Chem., 75, 6208-6213 (2010). Oxidation of sulfides with 30% hydrogen peroxide catalyzed by tantalum carbide provides sulfoxides in high yields, see, Kirihara, A., et al., "Tantalum Carbide or Niobium Carbide Catalyzed Oxidation of Sulfides with Hydrogen Peroxide: Highly Efficient and Chemoselective Syntheses of Sulfoxides and Sulfones", Synlett, 1557-1561 (2010). Sulfides can be oxidized to sulfones using, for example, niobium carbide as the catalyst, see, Kirihara, A., et al., "Tantalum Cardide or Niobium Carbide Catalyzed Oxidation of Sulfides with Hydrogen Peroxide: Highly Efficient and Chemoselective Syntheses of Sulfoxides and Sulfones", Synlett, 1557-1561 (2010). Urea-hydrogen peroxide adduct is a stable inexpensive and easily handled reagent for the oxidation of sulfides to sulfones, see Varma, R. S. and Naicker, K. P., "The Urea-Hydrogen Peroxide Complex: Solid-State Oxidative Protocols for Hydroxylated Aldehydes and Ketones (Dakin Reaction), Nitriles, Sulfides, and Nitrogen Heterocycles", Org. Lett., 1, 189-191 (1999). One skilled in the art will appreciate that other heteroatoms, such as nitrogen, may need to be protected and then deprotected while carrying out the oxidation of a sulfur atom to produce the desired compound.

Formulas II-XXX

In one aspect, the disclosure includes the use, as further described herein, of a compound or salt of Formula II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX and XXX. The variables shown in Formula II-XXX carry the definitions set forth in the SUMMARY section for Formula I or any of the definitions set forth in this disclosure.

Formula II

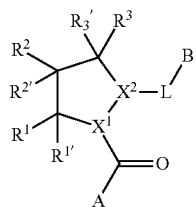

Formula III

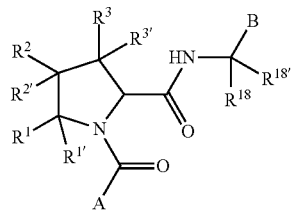

Formula IV

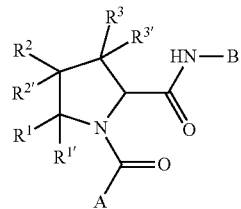

Formula V

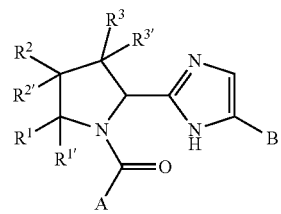

Formula VI

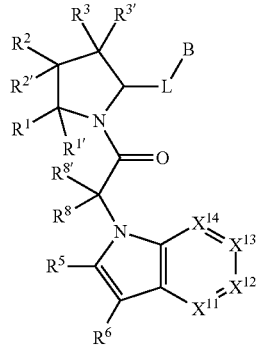

Formula VII

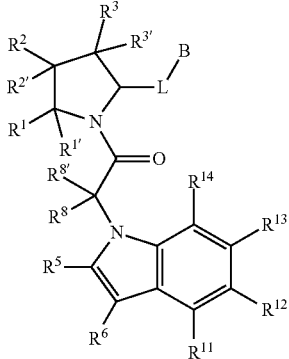

-continued
Formula VIII
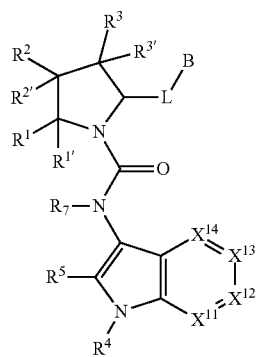
Formula IX
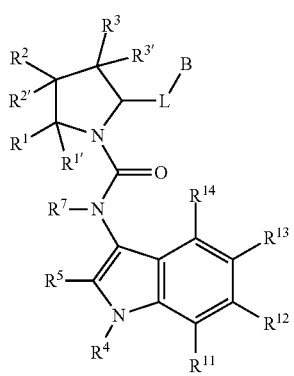
Formula X
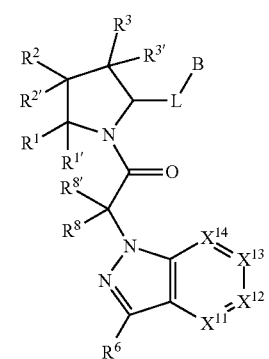
Formula XI
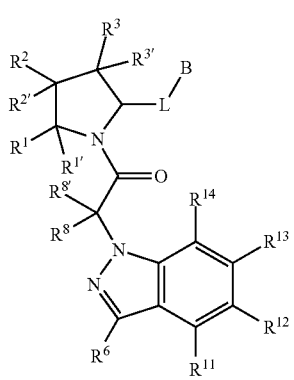
-continued
Formula XII
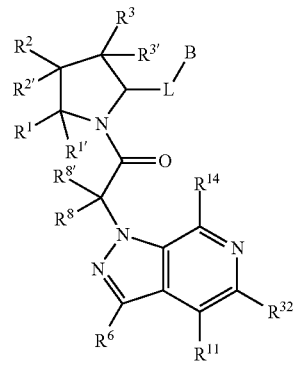
Formula XIII
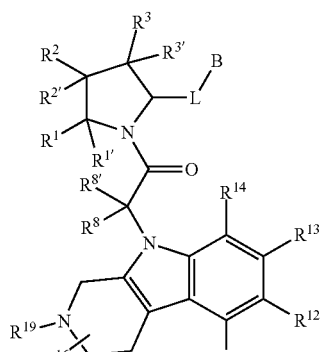
Formula XIV
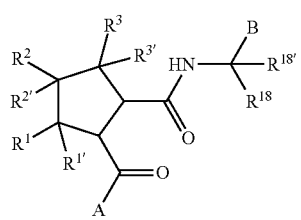
Formula XV
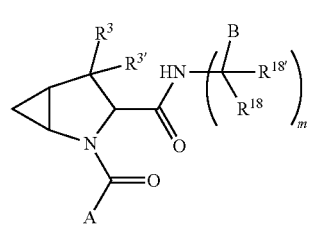
m is 0 or 1.
Formula XVI
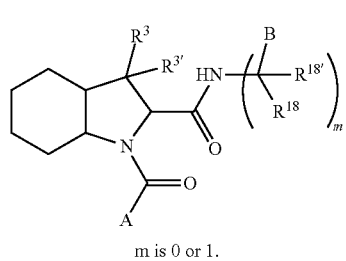
m is 0 or 1.

Formula XVII
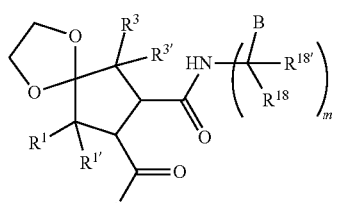
m is 0 or 1.
Formula XVIII
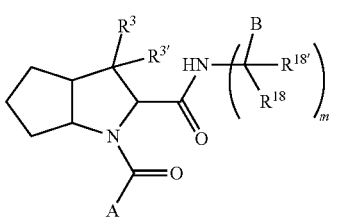
m is 0 or 1.
Formula XIX
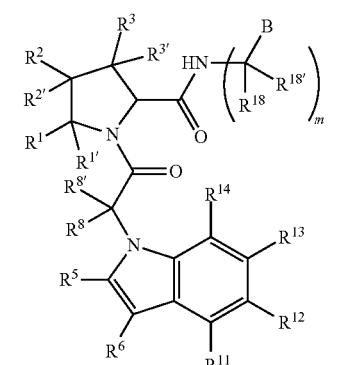
m is 0 or 1.
Formula XX
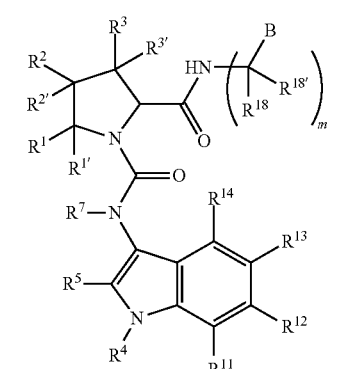
m is 0 or 1.
Formula XXI
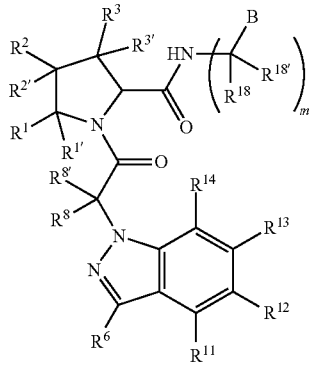
m is 0 or 1.
Formula XXII
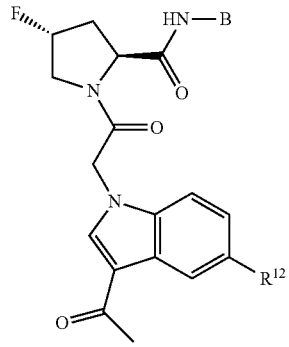
Formula XXIII
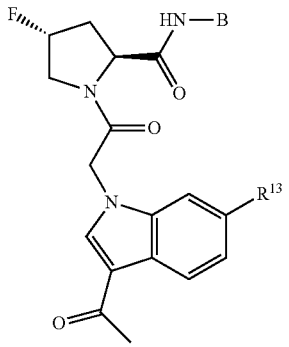
Formula XXIV
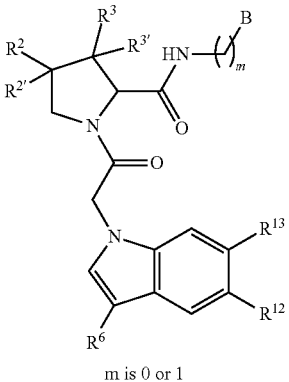
m is 0 or 1

Formula XXV

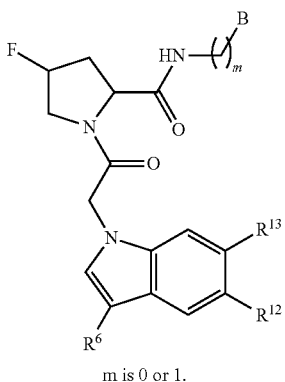

m is 0 or 1.

Formula XXVI

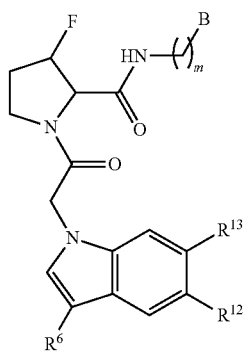

m is 0 or 1.

Formula XXVII

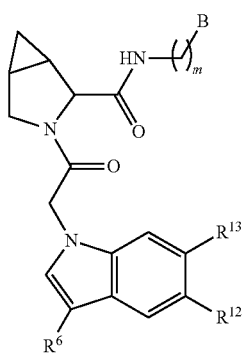

m is 0 or 1.

Formula XXVIII

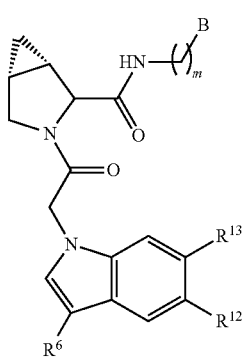

m is 0 or 1.

Formula XXIX

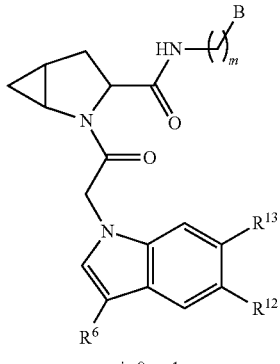

m is 0 or 1.

Formula XXX

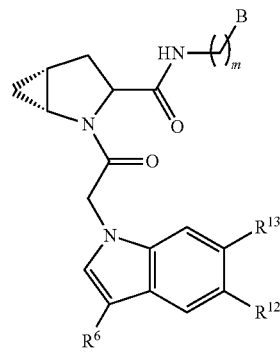

m is 0 or 1.

Additionally, the disclosure includes the use of compounds and salts of Formula I and pharmaceutically acceptable compositions thereof, and any of its subformulae (II-XXX) in which at least one of the following conditions is met in the embodiments described below.

The $R^{12}$ and $R^{13}$ Amide Substituents

In one embodiment, the invention is the use of a compound of Formula I, or a pharmaceutically acceptable salt or composition thereof, wherein at least one of $R^{12}$ or $R^{13}$ on the A group is an amide substituent, including those compounds set out in Table 1, for the treatment of a disorder in a host, typically a human, wherein the disorder is selected from the group disclosed in the Detailed Description, Part IV, Section A.

One of $R^{12}$ or $R^{13}$ is $R^{32}$. In one embodiment, one of $R^{12}$ and $R^{13}$ is selected from $R^{31}$ and the other of $R^{12}$ and $R^{13}$ is selected from $R^{32}$. In an alternative embodiment, $R^{12}$ and $R^{13}$ are each independently selected from an $R^{32}$ moiety.

$R^{31}$ is selected from hydrogen, halogen, hydroxyl, nitro, cyano, amino, —COOH, $C_1$-$C_2$haloalkyl, $C_1$-$C_2$haloalkoxy, $C_1$-$C_6$alkyl, —$C_0$-$C_4$alkyl($C_3$-$C_7$cycloalkyl), $C_2$-$C_6$alkenyl, $C_2$-$C_6$alkanoyl, $C_1$-$C_6$alkoxy, $C_2$-$C_6$alkenyloxy, —C(O)OR$^9$, $C_1$-$C_6$thioalkyl, —$C_0$-$C_4$alkylNR$^9$R$^{10}$, —C(O)NR$^9$R$^{10}$, —SO$_2$R$^9$, —SO$_2$NR$^9$R$^{10}$, —OC(O)R$^9$, and —C(NR$^9$)NR$^9$R$^{10}$, each of which $R^{31}$ other than hydrogen, halogen, hydroxyl, nitro, cyano, $C_1$-$C_2$haloalkyl, and $C_1$-$C_2$haloalkoxy is unsubstituted or substituted with one or more substituents independently selected from halogen, hydroxyl, nitro, cyano, amino, —COOH, —CONH$_2$C$_1$-C$_2$haloalkyl, and $C_1$-$C_2$haloalkoxy, and each of which $R^{31}$ is also optionally substituted with one substituent selected from phenyl and 4- to 7-membered heterocycle containing 1, 2, or 3 heteroatoms independently selected from N, O, and S; which phenyl or 4- to 7-membered heterocycle is unsubstituted or substituted with one or more substituents independently selected from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), $C_1$-$C_2$haloalkyl, and $C_1$-$C_2$haloalkoxy;

$R^{32}$ is selected from $C(O)NR^{21}R^{37}$, —$C(O)NR^{24}R^{25}$, —$C(O)NR^9R^{37}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, and —$NR^9C(O)NR^{24}R^{25}$, each of which is optionally substituted.

In one embodiment, when $R^{32}$ is $C(O)NR^{21}R^{37}$, —$C(O)NR^{24}R^{25}$, —$C(O)NR^9R^{37}$, B is not $C_2$-$C_6$ alkenyl; ($C_0$-$C_4$ alkyl)(heteroaryl); monocyclic or bicyclic carbocyclic; or monocyclic heterocyclic.

When A is an indole or indazole and $X^{12}$ is N, $X^{13}$ is $CR^{13}$ wherein $R^{13}$ is $R^{32}$.

When A is an indole or indazole and $X^{13}$ is N, $X^{12}$ is $CR^{12}$, wherein $R^{12}$ is $R^{32}$.

Figure 6A:
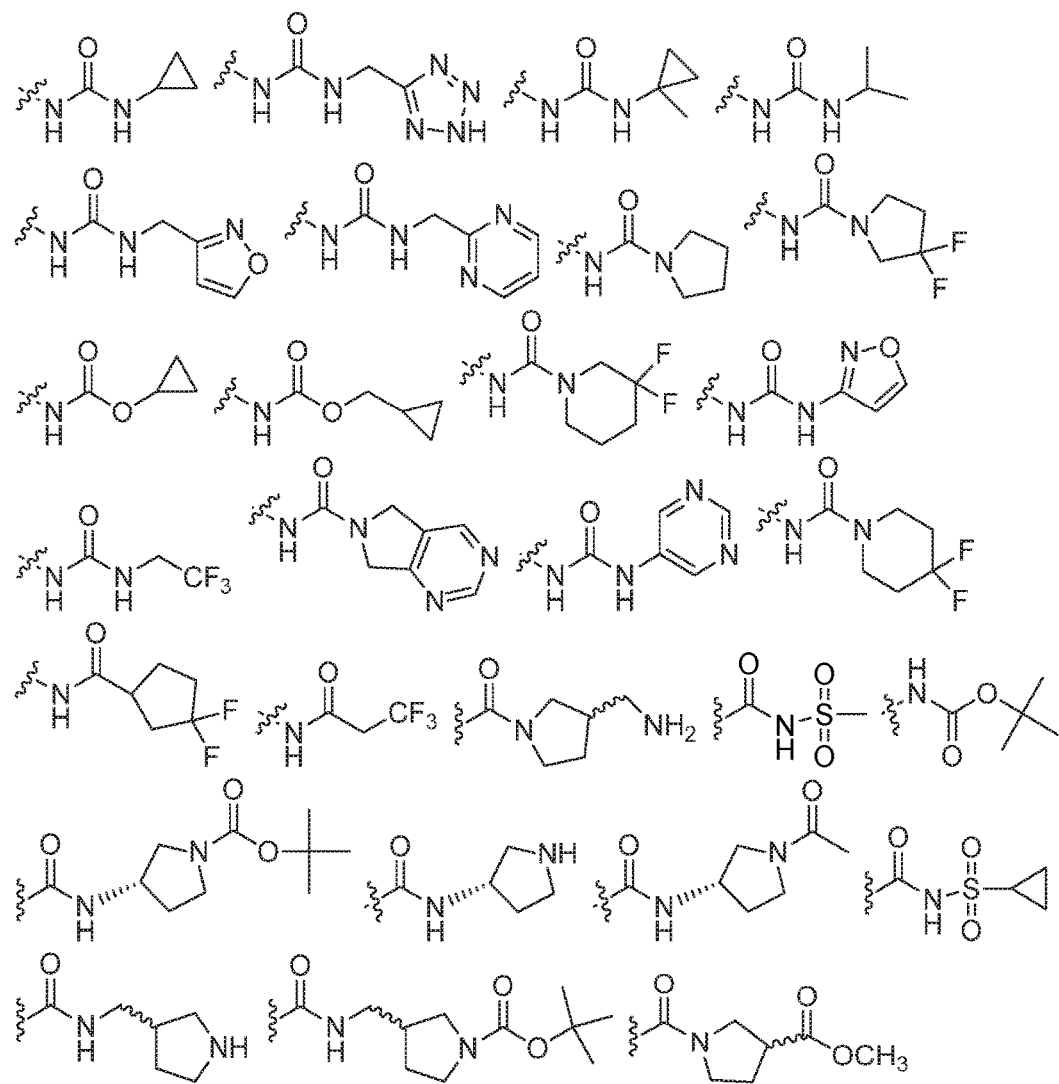
FIGS. 6A, 6B, and 6C, provide non-limiting specific embodiments of $R^{32}$.
Figure 6B:
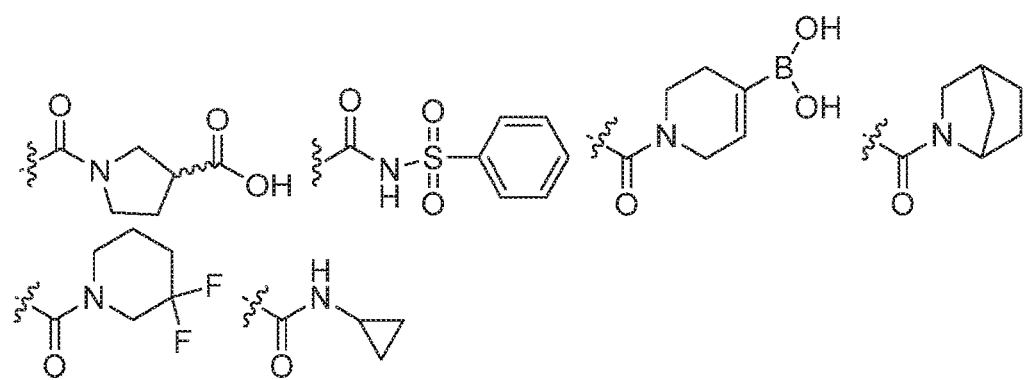
Figure 6C:
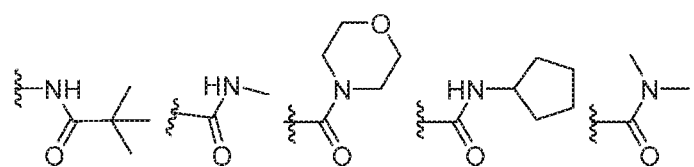
Figure 7A:
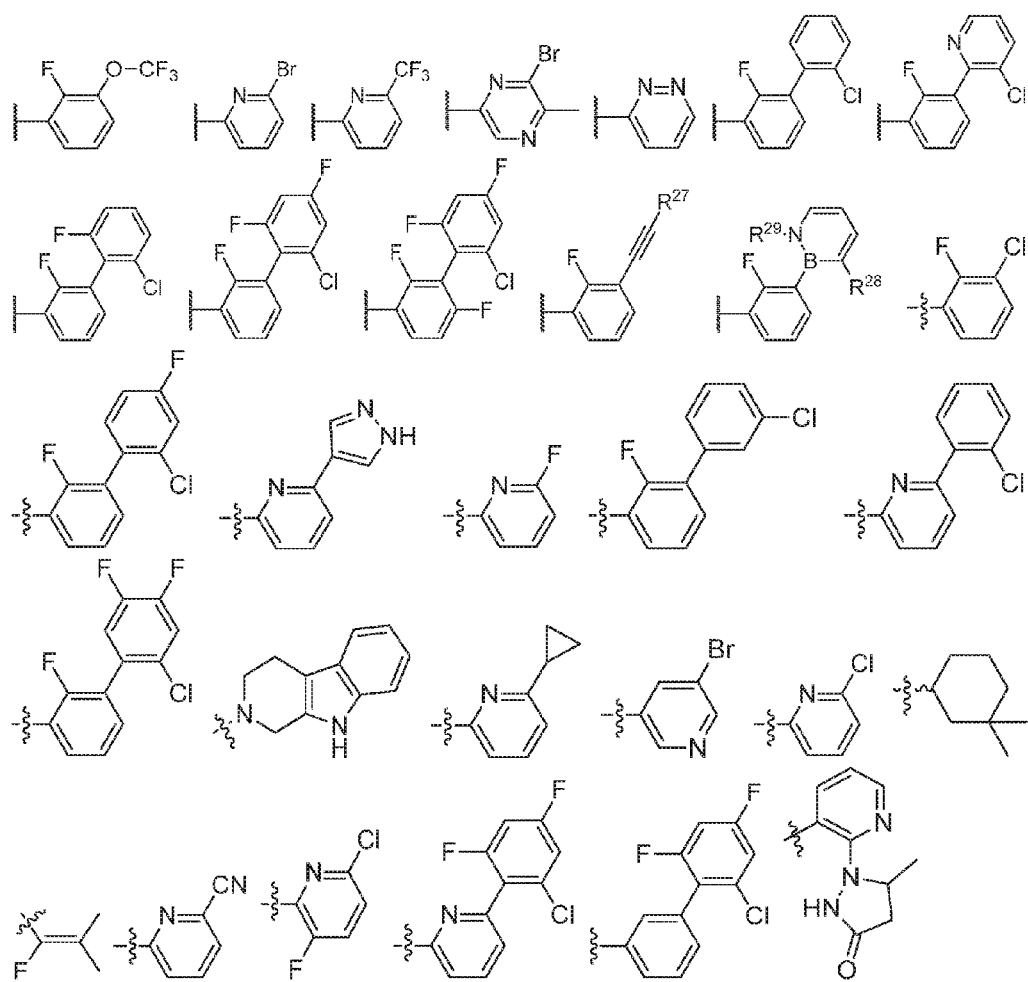
FIGS. 7A, 7B, 7C, 7D, 7E, 7F and 7G provide non-limiting specific embodiments of the B ring, wherein $R^{27}$, $R^{28}$, and $R^{29}$ are defined below.
Figure 7B:
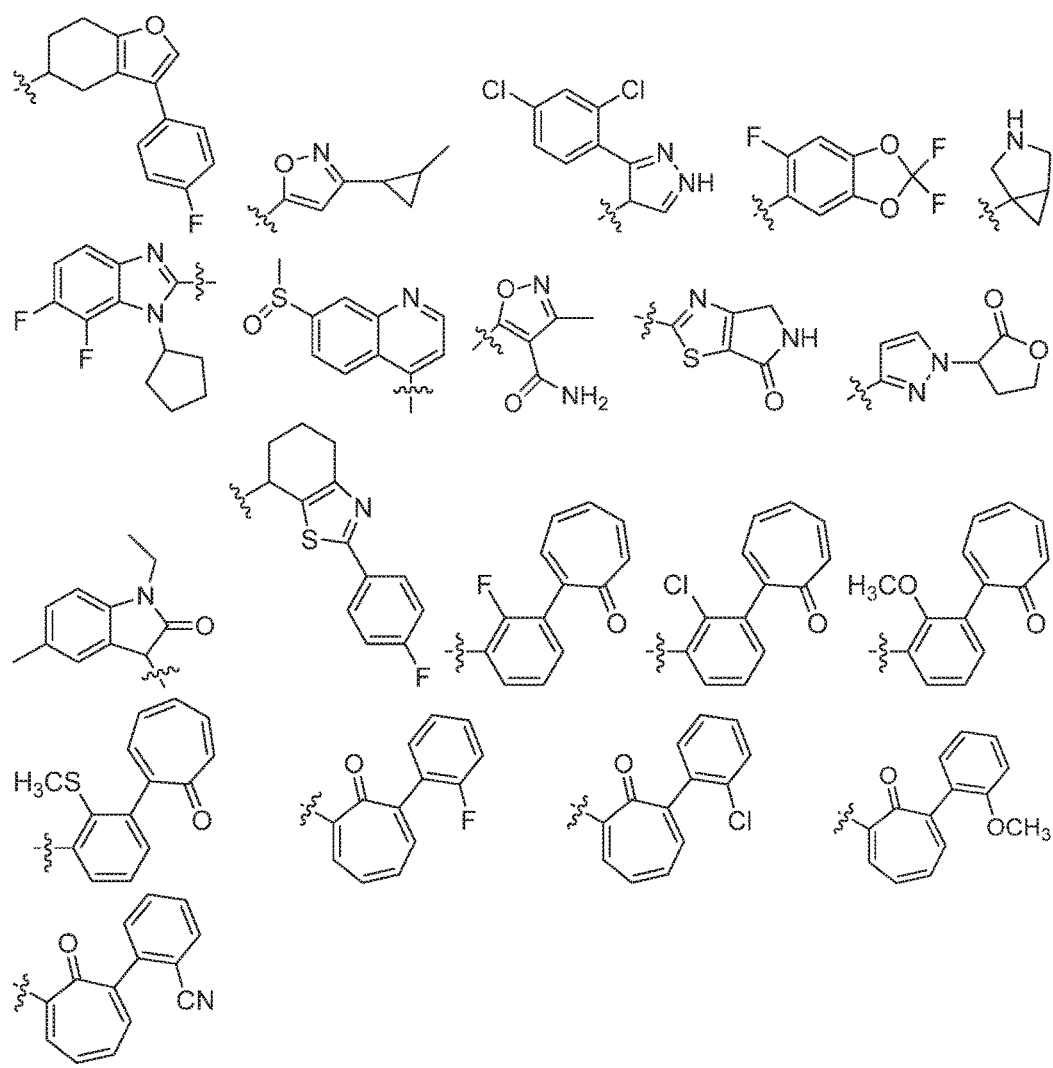
Figure 7C:
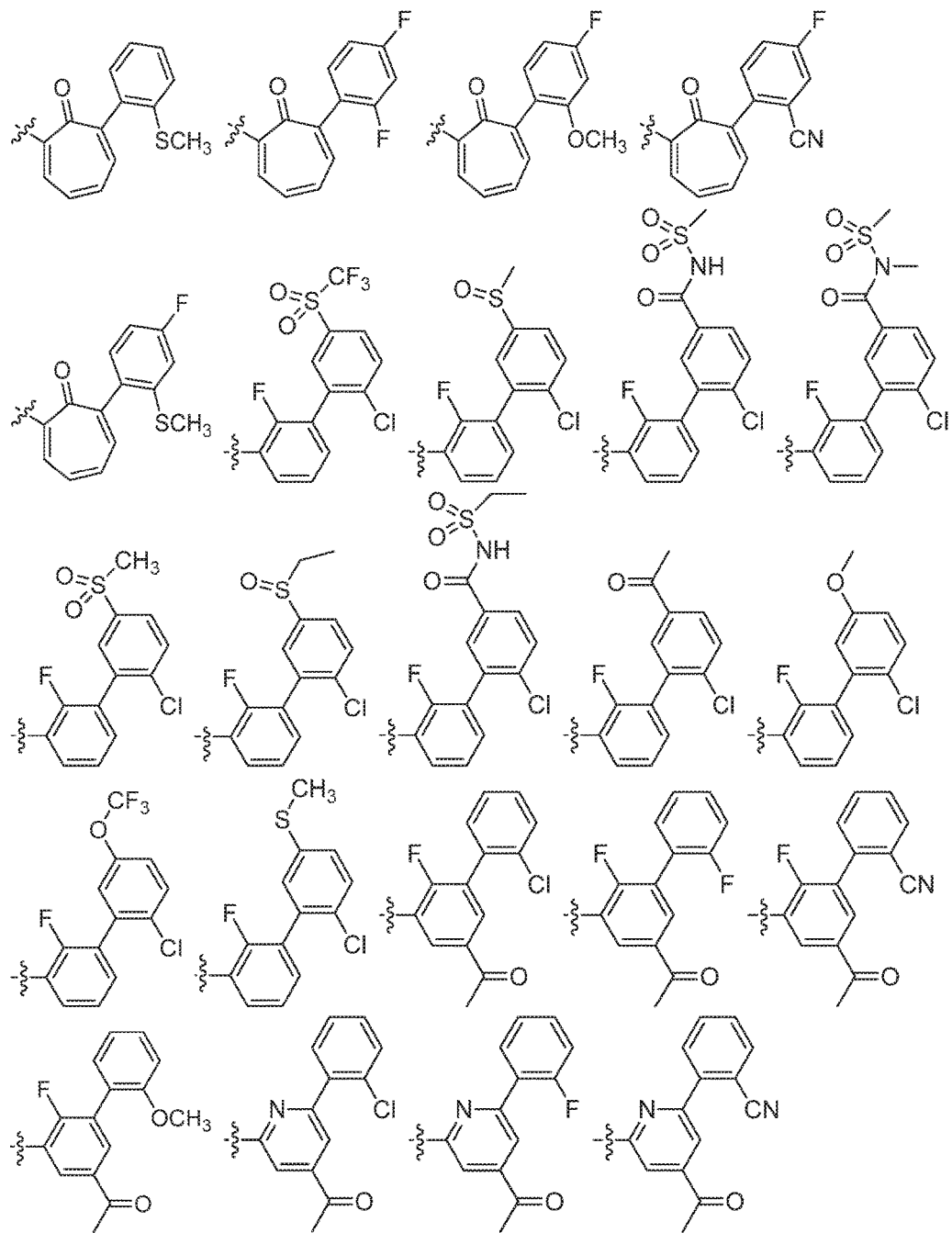
Figure 7D:
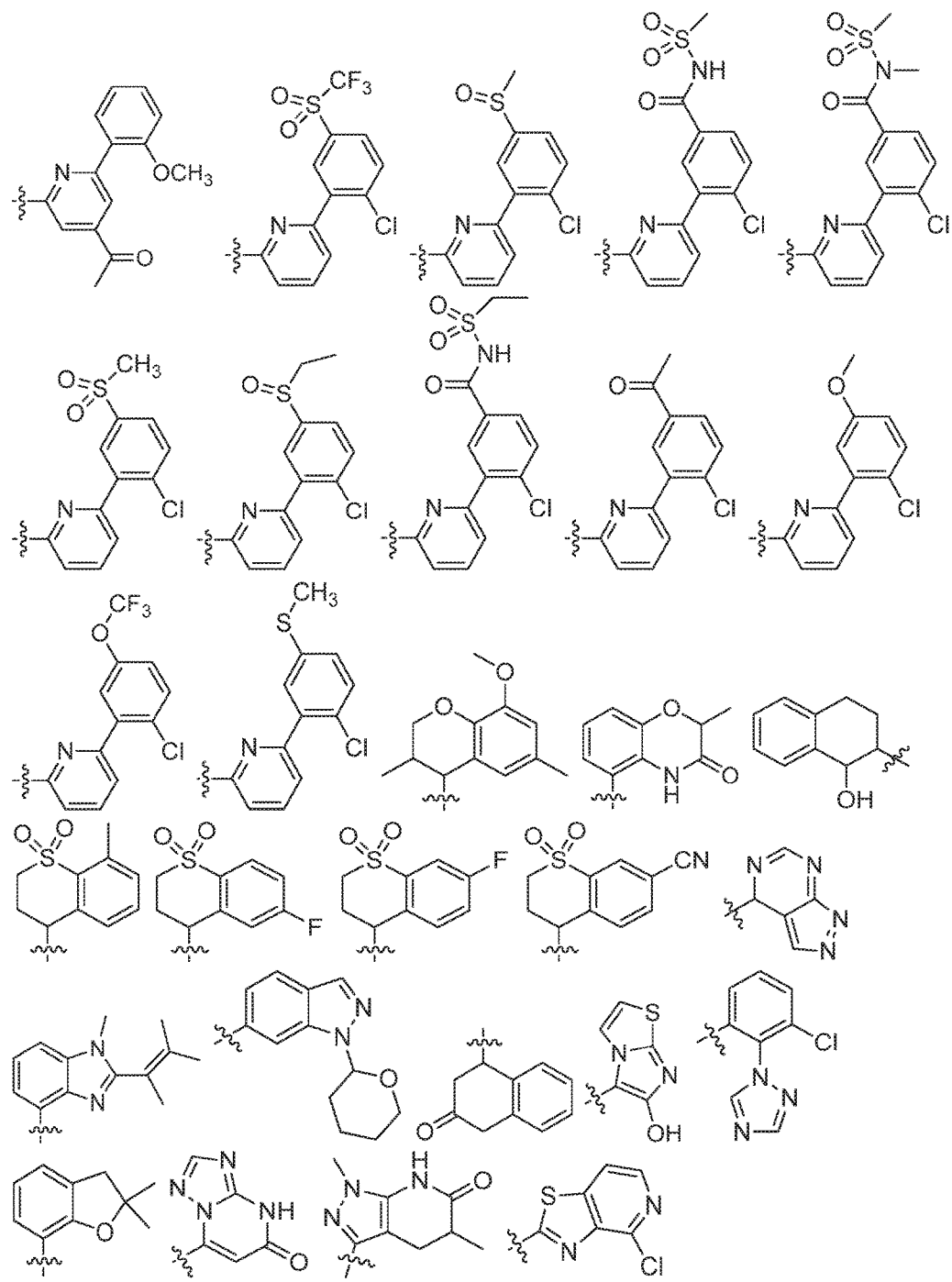
Figure 7E:
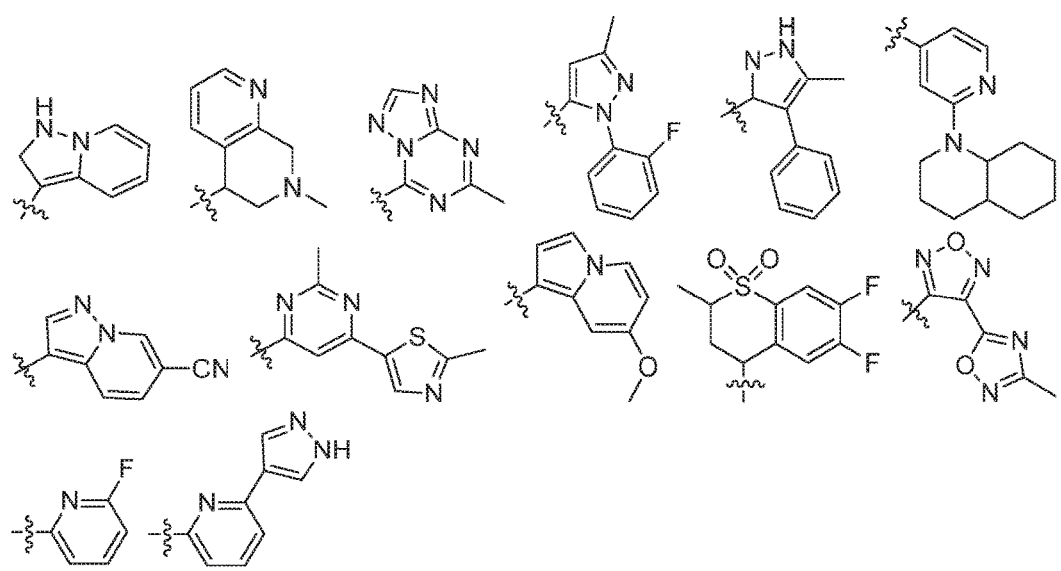
Figure 7F:
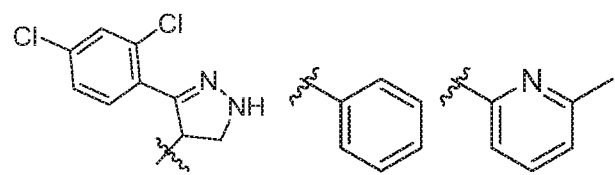
Figure 7G:
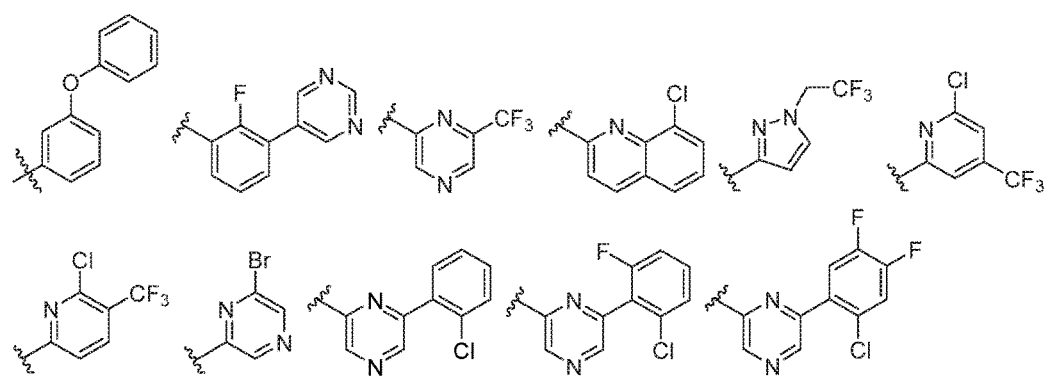

Non-limiting examples of $R^{32}$ include the structures of FIGS. 6A and 6B.

Non-Limiting $R^{12}$/$R^{13}$ Embodiments

In one embodiment, $R^{12}$ is $R^{32}$.
In one embodiment, $R^{13}$ is $R^{32}$.
In one embodiment, $R^{12}$ is $R^{32}$, which is —$C(O)NR^{21}R^{37}$.
In one embodiment, $R^{12}$ is $R^{32}$, which is —$C(O)NR^{24}R^{25}$.
In one embodiment, $R^{12}$ is $R^{32}$, which is —$C(O)NR^9R^{37}$.
In one embodiment, $R^{12}$ is $R^{32}$, which is —$C(O)NR^{21}SO_2R^{22}$.
In one embodiment, $R^{12}$ is $R^{32}$, which is —$NR^9C(O)OR^{10}$.
In one embodiment, $R^{12}$ is $R^{32}$, which is —$NR^9C(O)OR^{23}$.
In one embodiment, $R^{12}$ is $R^{32}$, which is —$NR^9C(O)R^{21}$.
In one embodiment, $R^{12}$ is $R^{32}$, which is —$NR^9C(O)NR^9R^{10}$.
In one embodiment, $R^{12}$ is $R^{32}$, which is —$NR^9C(O)NR^{10}R^{23}$.
In one embodiment, $R^{12}$ is $R^{32}$, which is —$NR^9C(O)NR^{24}R^{25}$.
In one embodiment, $R^{13}$ is $R^{32}$, which is —$C(O)NR^{21}R^{37}$.
In one embodiment, $R^{13}$ is $R^{32}$, which is —$C(O)NR^{24}R^{25}$.
In one embodiment, $R^{13}$ is $R^{32}$, which is —$C(O)NR^9R^{37}$.
In one embodiment, $R^{13}$ is $R^{32}$, which is —$C(O)NR^{21}SO_2R^{22}$.
In one embodiment, $R^{13}$ is $R^{32}$, which is —$NR^9C(O)OR^{10}$.
In one embodiment, $R^{13}$ is $R^{32}$, which is —$NR^9C(O)OR^{23}$.
In one embodiment, $R^{13}$ is $R^{32}$, which is —$NR^9C(O)R^{21}$.
In one embodiment, $R^{13}$ is $R^{32}$, which is —$NR^9C(O)NR^9R^{10}$.
In one embodiment, $R^{13}$ is $R^{32}$, which is —$NR^9C(O)NR^{10}R^{23}$.
In one embodiment, $R^{13}$ is $R^{32}$, which is —$NR^9C(O)NR^{24}R^{25}$.

In one embodiment, the disclosure provides compounds of Formula I, wherein; one of $R^{12}$ and $R^{13}$ is H and the other of $R^{12}$ and $R^{13}$ is $R^{32}$, where:

$R^{32}$ is selected from $C(O)NR^{21}R^{37}$, —$C(O)NR^{24}R^{25}$, —$C(O)NR^9R^{37}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, and —$NR^9C(O)NR^{24}R^{25}$, each of which is optionally substituted;

wherein $R^9$, $R^{10}$, $R^{21}$, $R^{22}$, $R^{23}$, $R^{24}$, $R^{25}$, and $R^{37}$ are as defined in the summary section above.

In another embodiment, the disclosure provides compounds of Formula I, wherein;

$R^1$, $R^{1'}$, $R^2$, and $R^{3'}$ are all hydrogen;

$R^2$ is fluoro and $R^3$ is hydrogen, —$C_0$-$C_4$alkyl($C_3$-$C_7$cycloalkyl), or —O—$C_0$-$C_4$alkyl($C_3$-$C_7$cycloalkyl);

$R^5$ is hydrogen, halogen, or $C_1$-$C_2$alkyl;

$R^{11}$, $R^{13}$, $R^{14}$, and $R^{15}$, if present, are independently selected at each occurrence from hydrogen, halogen, hydroxyl, amino, $C_1$-$C_4$alkyl, $C_1$-$C_4$alkoxy, —$C_0$-$C_2$alkyl (mono- and di-$C_1$-$C_2$alkylamino), trifluoromethyl, and trifluoromethoxy;

$X^{12}$ is $CR^{12}$; and $R^{12}$ is selected from $C(O)NR^{21}R^{37}$, —$C(O)NR^{24}R^{25}$, —$C(O)NR^9R^{37}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, and —$NR^9C(O)NR^{24}R^{25}$, each of which is optionally substituted;

wherein $R^9$, $R^{10}$, $R^{21}$, $R^{22}$, $R^{23}$, $R^{24}$, $R^{25}$, and $R^{37}$ are as defined in the summary section above.

In one embodiment, when $R^{32}$ is $C(O)NR^{21}R^{37}$, —$C(O)NR^{24}R^{25}$, —$C(O)NR^9R^{37}$, B is not $C_2$-$C_6$ alkenyl; ($C_0$-$C_4$ alkyl)(heteroaryl); monocyclic or bicyclic carbocyclic; or monocyclic heterocyclic.

In one embodiment, the disclosure provides compounds of Formula I, wherein;

m is 0 or 1;

$R^2$ is halogen, $R^{2'}$ is hydrogen or halogen, and $R^3$ is hydrogen, halogen, —$C_0$-$C_4$alkyl($C_3$-$C_7$cycloalkyl), or —O—$C_0$-$C_4$alkyl($C_3$-$C_7$cycloalkyl);

$R^6$ is —$C(O)C_1$-$C_4$alkyl, —$C(O)NH_2$, —$C(O)CF_3$, —$C(O)(C_3$-$C_7$cycloalkyl), or -ethyl(cyanoimino);

one of $R^{12}$ and $R^{13}$ is selected from hydrogen, halogen, $C_1$-$C_4$alkyl, $C_1$-$C_4$alkoxy, trifluoromethyl, and trifluoromethoxy; the other of $R^{12}$ and $R^{13}$ is $R^{32}$, where $R^{32}$ is selected from $C(O)NR^{21}R^{37}$, —$C(O)NR^{24}R^{25}$, —$C(O)NR^9R^{37}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, and —$NR^9C(O)NR^{24}R^{25}$, each of which is optionally substituted;

wherein $R^9$, $R^{10}$, $R^{21}$, $R^{22}$, $R^{23}$, $R^{24}$, $R^{25}$, and $R^{37}$ are as defined in the summary section above.

In one embodiment, the disclosure provides compounds of Formula I, wherein;

one of $R^{12}$ and $R^{13}$ is hydrogen, hydroxyl, halogen, methyl, or methoxy; and the other of $R^{12}$ and $R^{13}$ is $R^{32}$, where $R^{32}$ is selected from $C(O)NR^{21}R^{37}$, —$C(O)NR^{24}R^{25}$, —$C(O)NR^9R^{37}$, —$C(O)NR^{21}SO_2R^{22}$, —$NR^9C(O)OR^{10}$, —$NR^9C(O)OR^{23}$, —$NR^9C(O)R^{21}$, —$NR^9C(O)NR^9R^{10}$, —$NR^9C(O)NR^{10}R^{23}$, and —$NR^9C(O)NR^{24}R^{25}$, each of which is optionally substituted;

wherein $R^9$, $R^{10}$, $R^{21}$, $R^{22}$, $R^{23}$, $R^{24}$, $R^{25}$, and $R^{37}$ are as defined in the summary section above.

In one embodiment, $R^{32}$ may be unsubstituted or substituted with one or more substituents independently selected from halogen, hydroxyl, nitro, cyano, amino, oxo, —$B(OH)_2$, —$Si(CH_3)_3$, —COOH, —$CONH_2$, —$P(O)(OH)_2$, $C_1$-$C_6$alkyl, $C_1$-$C_6$alkoxy, —$C_0$-$C_2$alkyl(mono- and di-$C_1$-$C_4$alkylamino), $C_1$-$C_6$alkylester, $C_1$-$C_4$alkylamino, $C_1$-$C_4$hydroxylalkyl, $C_1$-$C_2$haloalkyl, and $C_1$-$C_2$haloalkoxy.

Central Core Moiety

The central core moiety in Formula I is illustrated below:

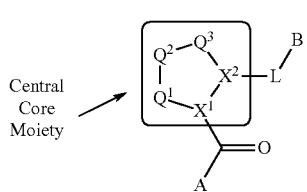

wherein:

Q$^1$ is N(R$^1$) or C(R$^1$R$^{1'}$);

Q$^2$ is C(R$^2$R$^{2'}$), C(R$^2$R$^{2'}$)—C(R$^2$R$^{2'}$), S, O, N(R$^2$) or C(R$^2$R$^{2'}$)O;

Q$^3$ is N(R$^3$), S, or C(R$^3$R$^{3'}$);

X$^1$ and X$^2$ are independently N, CH, or CZ, or X$^1$ and X$^2$ together are C=C; and wherein Q$^1$, Q$^2$, Q$^3$, X$^1$, and X$^2$ are selected such that a stable compound results.

Any of the structures illustrated herein, e.g., A, B, L or central core can be optionally substituted with 0, 1, 2, 3, or 4, as appropriate, and independently, selected from R$^{75}$, wherein R$^{75}$ is selected from hydrogen, halogen, hydroxyl, nitro, cyano, amino, C$_1$-C$_6$alkyl, C$_1$-C$_6$haloalkyl, C$_2$-C$_6$alkenyl, C$_2$-C$_6$alkynyl, C$_1$-C$_6$thioalkyl, C$_1$-C$_6$alkoxy, -JC$_3$-C$_7$cycloalkyl, —B(OH)$_2$, -JC(O)NR$^9$R$^{23}$, -JOSO$_2$OR$^{21}$, —C(O)(CH$_2$)$_{1-4}$S(O)R$^{21}$, —O(CH$_2$)$_{1-4}$S(O)NR$^{21}$R$^{22}$, -JOP(O)(OR$^{21}$)(OR$^{22}$), -JP(O)(OR$^{21}$)(OR$^{22}$), -JOP(O)(OR$^{21}$)R$^{22}$, -JP(O)(OR$^{21}$)R$^{22}$, -JOP(O)R$^{21}$R$^{22}$, -JP(O)R$^{21}$R$^{22}$, -JSP(O)(OR$^{21}$)(OR$^{22}$), -JSP(O)(OR$^{21}$)(R$^{22}$), -JSP(O)(R$^{21}$)(R$^{22}$), -JNR$^9$P(O)(NHR$^{21}$)(NHR$^{22}$), -JNR$^9$P(O)(OR$^{21}$)(NHR$^{22}$), -JNR$^9$P(O)(OR$^{21}$)(OR$^{22}$), -JC(S)R$^{21}$, -JNR$^{21}$SO$_2$R$^{22}$, -JNR$^9$S(O)NR$^{10}$R$^{22}$, -JNR$^9$SO$_2$NR$^{10}$R$^{22}$, -JSO$_2$NR$^9$COR$^{22}$, -JSO$_2$NR$^9$CONR$^{21}$R$^{22}$, -JNR$^{21}$SO$_2$R$^{22}$, -JC(O)NR$^{21}$SO$_2$R$^{22}$, -JC(NH$_2$)=NR$^{22}$, -JCH(NH$_2$)NR$^9$S(O)$_2$R$^{22}$, -JOC(O)NR$^{21}$R$^{22}$, -JNR$^{21}$C(O)OR$^{22}$, -JNR$^{21}$OC(O)R$^{22}$, —(CH$_2$)$_{1-4}$C(O)NR$^{21}$R$^{22}$, -JC(O)NR$^{24}$R$^{25}$, -JNR$^9$C(O)R$^{21}$, -JC(O)R$^{21}$, -JNR$^9$C(O)NR$^{10}$R$^{22}$, —CCR$^{21}$, —(CH$_2$)$_1$OC(O)R$^{21}$, -JC(O)OR$^{23}$; SC$_1$-C$_6$alkyl(O)=NH; each of which R$^{75}$ may be unsubstituted or substituted with one or more substituents independently selected from halogen, hydroxyl, nitro, cyano, amino, oxo, —B(OH)$_2$, —Si(CH$_3$)$_3$, —COOH, —CONH$_2$, —P(O)(OH)$_2$, C$_1$-C$_6$alkyl, —C$_0$-C$_4$alkyl(C$_3$-C$_7$cycloalkyl), C$_1$-C$_6$alkoxy, —C$_0$-C$_4$alkyl(mono- and)di-C$_1$-C$_4$alkylNR$^9$R$^{10}$, C$_1$-C$_6$alkylester, C$_1$-C$_4$alkylamino, C$_1$-C$_4$hydroxylalkyl, C$_1$-C$_2$haloalkyl, C$_1$-C$_2$haloalkoxy, —OC(O)R$^9$, —NR$^9$C(O)R$^{10}$, —C(O)NR$^9$R$^{10}$, —OC(O)NR$^9$R$^{10}$, —NR$^9$C(O)OR$^{10}$, C$_1$-C$_2$haloalkyl, and C$_1$-C$_2$haloalkoxy, S(O)=NHR$^{21}$, SF$_5$, and JC(R$^9$)=NR$^{21}$ and SO$_2$OR$^{21}$.

Non-limiting examples of the

Figure 5:
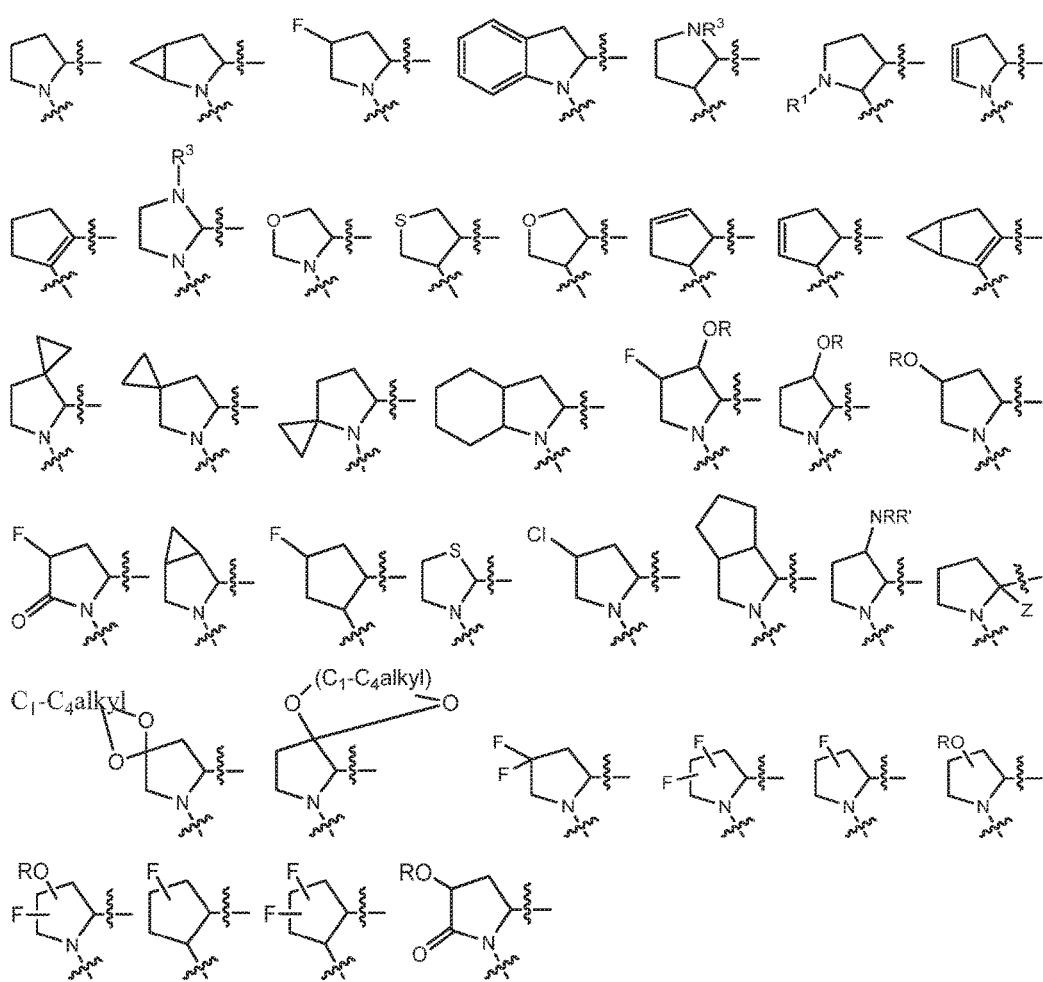
FIG. 5 provides non-limiting specific embodiments of the Central Core ring, wherein R, R', and $R^3$ are defined below.

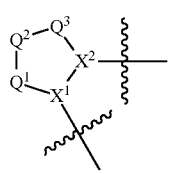

ring are illustrated in FIG. 5 (any of which can be otherwise substituted with R$^1$, R$^{1'}$, R$^2$, R$^{2'}$, R$^3$, and R$^{3'}$).

In an alternate embodiment, the

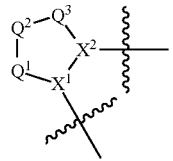

ring is replaced by one of the following core structures:

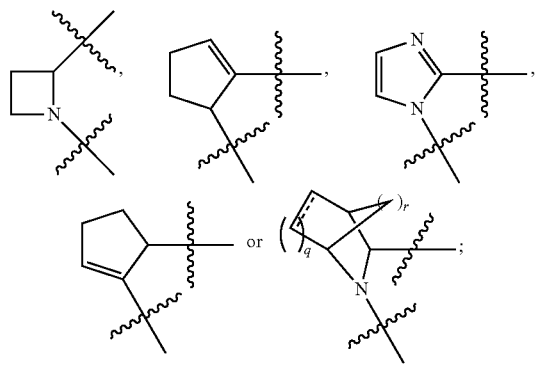

wherein q is 0, 1, 2 or 3, r is 1, 2 or 3, ≈≈≈ is a single or double bond.

It is clear that when q is 0, ≈≈≈ is not a double bond.

Any of the structures illustrated herein, e.g., A, B, L or central core can be optionally substituted with 0, 1, 2, 3, or 4, as appropriate, and independently, selected from R$^{75}$, wherein R$^{75}$ is selected from hydrogen, halogen, hydroxyl, nitro, cyano, amino, C$_1$-C$_6$alkyl, C$_1$-C$_6$haloalkyl, C$_2$-C$_6$alkenyl, C$_2$-C$_6$alkynyl, C$_1$-C$_6$thioalkyl, C$_1$-C$_6$alkoxy, -JC$_3$-C$_7$cycloalkyl, —B(OH)$_2$, -JC(O)NR$^9$R$^{23}$, -JOSO$_2$OR$^{21}$, —C(O)(CH$_2$)$_{1-4}$S(O)R$^{21}$, —O(CH$_2$)$_{1-4}$S(O)NR$^{21}$R$^{22}$, -JOP(O)(OR$^{21}$)(OR$^{22}$), -JP(O)(OR$^{21}$)(OR$^{22}$), -JOP(O)(OR$^{21}$)R$^{22}$, -JP(O)(OR$^{21}$)R$^{22}$, -JOP(O)R$^{21}$R$^{22}$, -JP(O)R$^{21}$R$^{22}$, -JSP(O)(OR$^{21}$)(OR$^{22}$), -JSP(O)(OR$^{21}$)(R$^{22}$), -JSP(O)(R$^{21}$)(R$^{22}$), -JNR$^9$P(O)(NHR$^{21}$)(NHR$^{22}$), -JNR$^9$P(O)(OR$^{21}$)(NHR$^{22}$), -JNR$^9$P(O)(OR$^{21}$)(OR$^{22}$), -JC(S)R$^{21}$, -JNR$^{21}$SO$_2$R$^{22}$, -JNR$^9$S(O)NR$^{10}$R$^{22}$, -JNR$^9$SO$_2$NR$^{10}$R$^{22}$, -JSO$_2$NR$^9$COR$^{22}$, -JSO$_2$NR$^9$CONR$^{21}$R$^{22}$, -JNR$^{21}$SO$_2$R$^{22}$, -JC(O)NR$^{21}$SO$_2$R$^{22}$, -JC(NH$_2$)=NR$^{22}$, -JCH(NH$_2$)NR$^9$S(O)$_2$R$^{22}$, -JOC(O)NR$^{21}$R$^{22}$, -JNR$^{21}$C(O)OR$^{22}$, -JNR$^{21}$OC(O)R$^{22}$, —(CH$_2$)$_{1-4}$C(O)NR$^{21}$R$^{22}$, JC(O)NR$^{24}$R$^{25}$, -JNR$^9$C(O)R$^{21}$, -JC(O)R$^{21}$, -JNR$^9$C(O)NR$^{10}$R$^{22}$, —CCR$^{21}$, —(CH$_2$)$_{1-4}$OC(O)R$^{21}$, -JC(O)OR$^{23}$; SC$_1$-C$_6$alkyl(O)=NH; each of which R$^{75}$ may be unsubstituted or substituted with one or more substituents independently selected from halogen, hydroxyl, nitro, cyano, amino, oxo, —B(OH)$_2$, —Si(CH$_3$)$_3$, —COOH, —CONH$_2$, —P(O)(OH)$_2$, C$_1$-C$_6$alkyl, —C$_0$-C$_4$alkyl(C$_3$-C$_7$cycloalkyl), C$_1$-C$_6$alkoxy, —C$_0$-C$_4$alkyl(mono- and di-C$_1$-C$_4$alkylNR$^9$R$^{10}$), C$_1$-C$_6$alkylester, C$_1$-C$_4$alkylamino, C$_1$-C$_4$hydroxylalkyl, C$_1$-C$_2$haloalkyl, C$_1$-C$_2$haloalkoxy, —OC(O)R$^9$, —NR$^9$C(O)R$^{10}$, —C(O)NR$^9$R$^{10}$, —OC(O)NR$^9$R$^{10}$, —NR$^9$C(O)OR$^{10}$, C$_1$-C$_2$haloalkyl, and C$_1$-C$_2$haloalkoxy, S(O)=NHR$^{21}$, SF$_5$, and JC(R$^9$)=NR$^{21}$ and SO$_2$OR$^{21}$.

R and R' are independently selected from H, alkyl, cycloalkyl, cycloalkylalkyl, heterocycle, heterocycloalkyl, aryl, aralkyl, heteroaryl, heteroarylalkyl wherein each group can be optionally substituted or any other substituent group herein that provides the desired properties. In some embodiments, the ring includes one or more chiral carbon atoms.

The invention includes embodiments in which the chiral carbon can be provided as an enantiomer, or mixtures of enantiomers, including a racemic mixture. Where the ring includes more than one stereocenter, all of the enantiomers and diastereomers are included in the invention as individual species.

Z is F, Cl, $NH_2$, $CH_3$, $CH_2D$, $CHD_2$, or $CD_3$.

$R^1$, $R^{1'}$, $R^2$, $R^{2'}$, $R^3$, and $R^{3'}$ are independently selected at each occurrence, as appropriate, and only where a stable compound results, from hydrogen, halogen, hydroxyl, nitro, cyano, amino, $C_1$-$C_6$alkyl, $C_2$-$C_6$alkenyl, $C_2$-$C_6$alkynyl, $C_1$-$C_6$alkoxy, $C_2$-$C_6$alkynyl, $C_2$-$C_6$alkanoyl, $C_1$-$C_6$thioalkyl, hydroxy$C_1$-$C_6$alkyl, amino$C_1$-$C_6$alkyl, —$C_0$-$C_4$alkylNR$^9$R$^{10}$, —C(O)OR$^9$, —OC(O)OR$^9$, —NR$^9$C(O)R$^{10}$, —C(O)NR$^9$R$^{10}$, —OC(O)NR$^9$R$^{10}$, —NR$^9$C(O)OR$^{10}$, $C_1$-$C_2$haloalkyl, and $C_1$-$C_2$haloalkoxy, where $R^9$ and $R^{10}$ are independently selected at each occurrence from hydrogen, $C_1$-$C_6$alkyl, ($C_3$-$C_7$cycloalkyl)$C_0$-$C_4$alkyl, —$C_0$-$C_4$alkyl($C_3$-$C_7$cycloalkyl), and —O—$C_0$-$C_4$alkyl($C_3$-$C_7$cycloalkyl).

Examples of central cores include, but are not limited to:

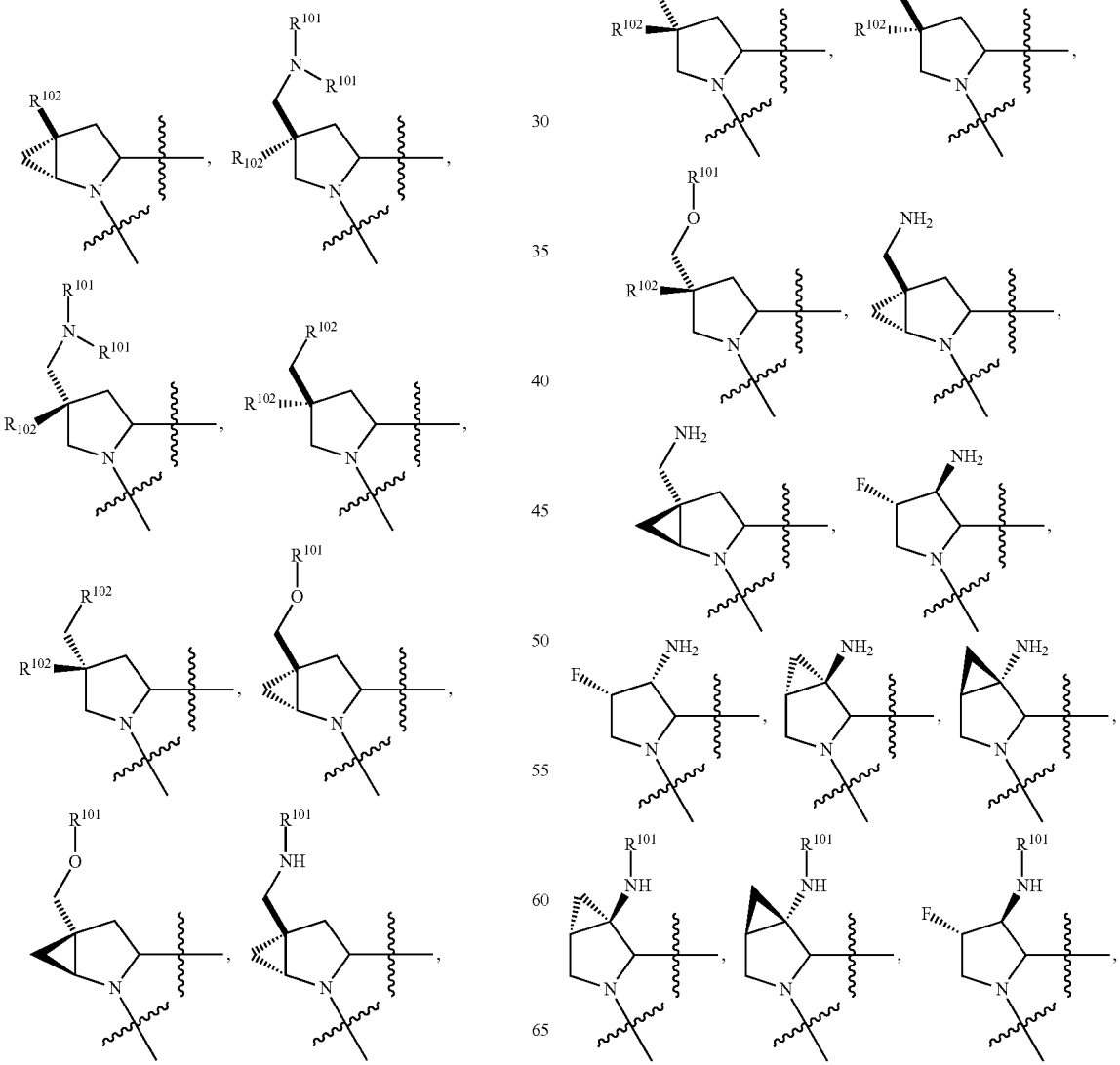

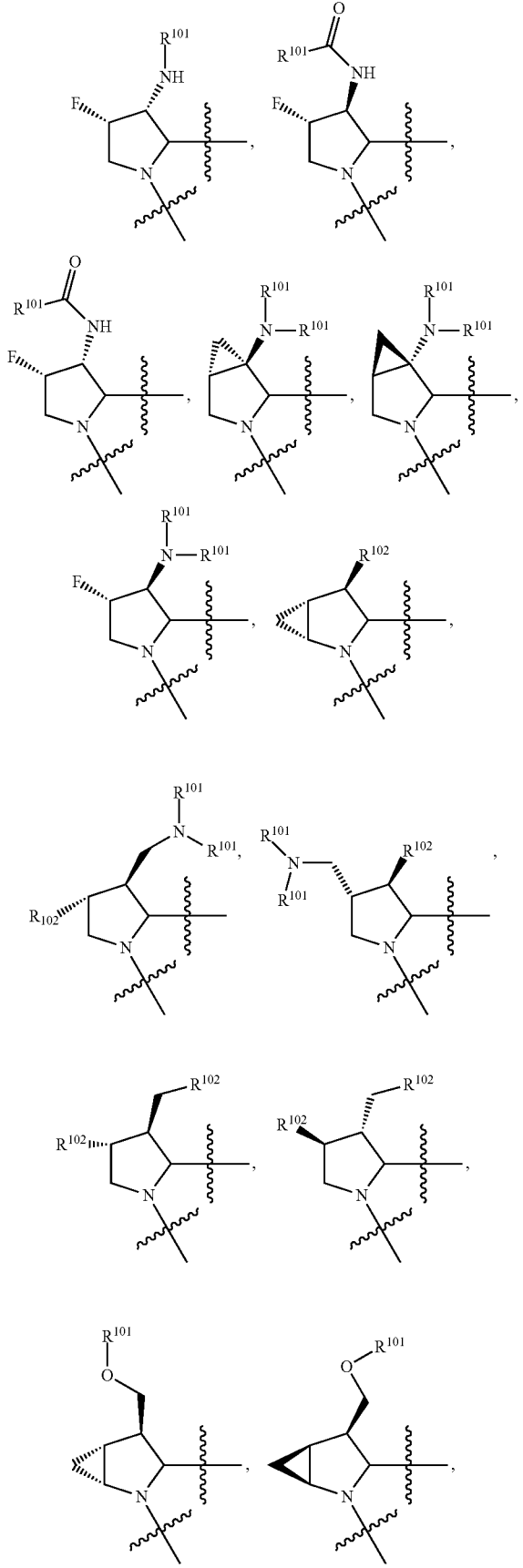
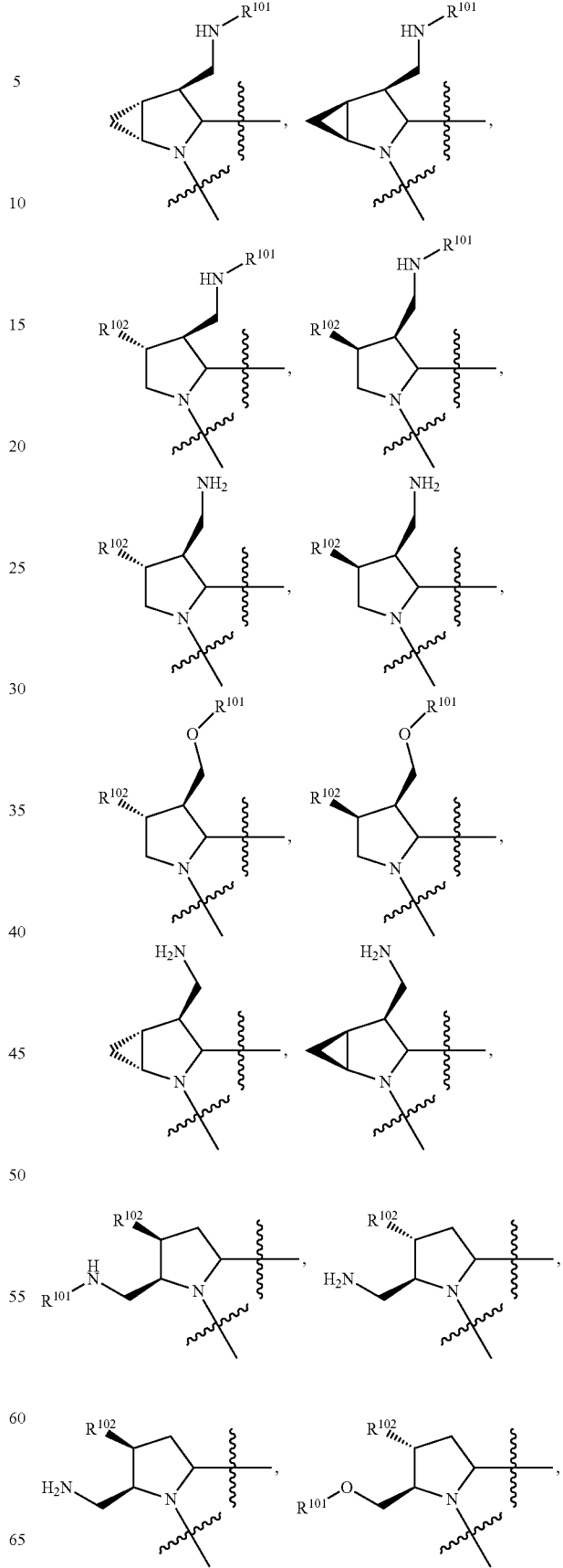

-continued

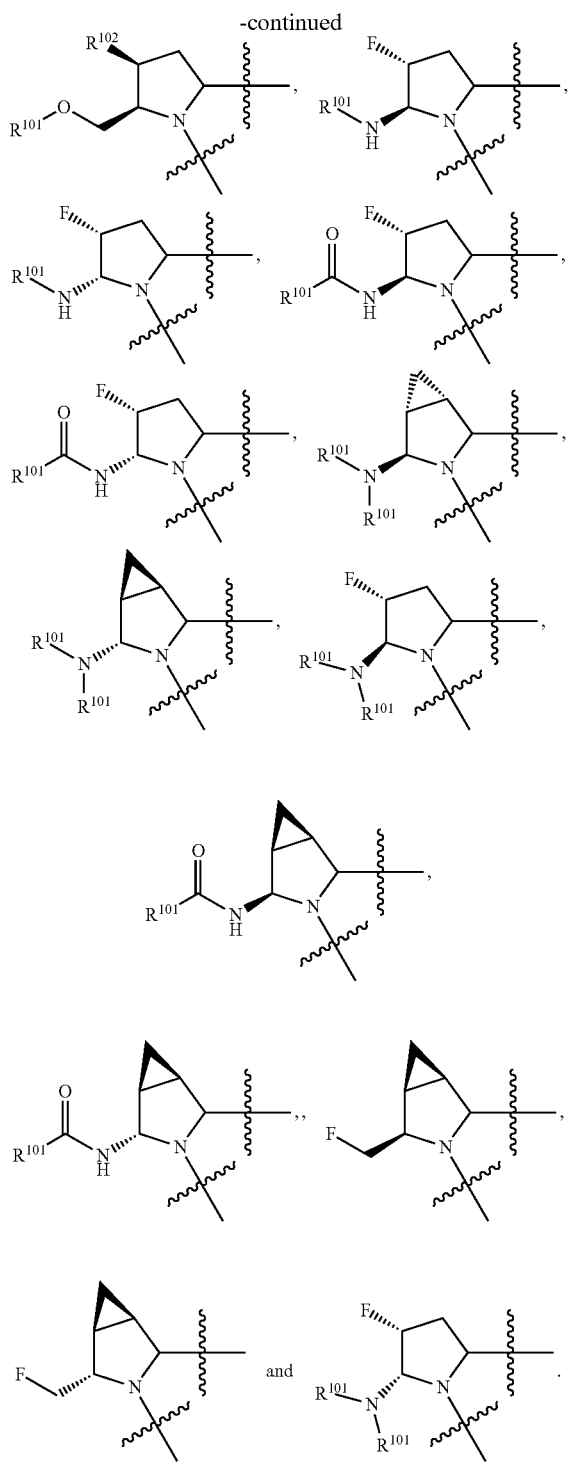

$R^{101}$ is $C_1$-$C_4$ alkyl or $C_3$-$C_7$ cycloalkyl.
$R^{102}$ is $C_1$-$C_4$ alkyl, fluorine, chlorine, or bromine.

Non-Limiting Central Core Embodiments

In alternative embodiments, $R^1$ and $R^{1'}$ or $R^3$ and $R^{3'}$ may be taken together to form a 3- to 6-membered carbocyclic spiro ring or a 3- to 6-membered heterocyclic spiro ring containing 1 or 2 heteroatoms independently selected from N, O, or S; $R^2$ and $R^{2'}$ may be taken together to form a 3- to 6-membered carbocyclic spiro ring; or $R^2$ and $R^{2'}$ may be taken together to form a 3- to 6-membered heterocyclic spiro ring; each of which ring may be unsubstituted or substituted with 1 or more substituents independently selected from halogen (and in particular F), hydroxyl, cyano, —COOH, $C_1$-$C_4$alkyl (including in particular methyl), $C_2$-$C_4$alkenyl, $C_2$-$C_4$alkynyl, $C_1$-$C_4$alkoxy, $C_2$-$C_4$alkanoyl, hydroxy$C_1$-$C_4$alkyl, (mono- and di-$C_1$-$C_4$alkylamino)$C_0$-$C_4$alkyl, —$C_0$-$C_4$alkyl($C_3$-$C_7$cycloalkyl), —O—$C_0$-$C_4$alkyl($C_3$-$C_7$cycloalkyl), $C_1$-$C_2$haloalkyl, and $C_1$-$C_2$haloalkoxy.

In alternative embodiments, $R^1$ and $R^2$ may be taken together to form a 3-membered carbocyclic ring; $R^1$ and $R^2$ may be taken together to form a 4- to 6-membered carbocyclic or aryl ring or a 4- to 6-membered heterocyclic or heteroaryl ring containing 1 or 2 heteroatoms independently selected from N, O, and S; or $R^2$ and $R^3$, if bound to adjacent carbon atoms, may be taken together to form a 3- to 6-membered carbocyclic or aryl ring or a 3- to 6-membered heterocyclic or heteroaryl ring; each of which ring may be unsubstituted or substituted with 1 or more substituents independently selected from halogen (and in particular F), hydroxyl, cyano, —COOH, $C_1$-$C_4$alkyl (including in particular methyl), $C_2$-$C_4$alkenyl, $C_2$-$C_4$alkynyl, $C_1$-$C_4$alkoxy, $C_2$-$C_4$alkanoyl, hydroxy$C_1$-$C_4$alkyl, (mono- and di-$C_1$-$C_4$alkylamino)$C_0$-$C_4$alkyl, —$C_0$-$C_4$alkyl($C_3$-$C_7$cycloalkyl), —O—$C_0$-$C_4$alkyl($C_3$-$C_7$cycloalkyl), $C_1$-$C_2$haloalkyl, and $C_1$-$C_2$haloalkoxy.

In one embodiment, the central core moiety is proline.

In one embodiment, the central core moiety is 4-fluoroproline.

In one embodiment, $R^1$, $R^{1'}$, $R^{2'}$, $R^3$, and $R^{3'}$, if present, are all hydrogen; and $R^2$ is fluoro.

In one embodiment, $R^1$, $R^{1'}$, $R^{2'}$, and $R^{3'}$, if present, are all hydrogen; and $R^2$ is fluoro and $R^3$ is —$C_0$-$C_4$alkyl($C_3$-$C_7$cycloalkyl) or —O—$C_0$-$C_4$alkyl($C_3$-$C_7$cycloalkyl).

In one embodiment, $R^1$ and $R^2$ are taken together to form a 3- to 6-membered cycloalkyl group, and $R^{1'}$, $R^{2'}$, $R^3$, and $R^{3'}$, where present, are all hydrogen.

In one embodiment, $R^1$, $R^{1'}$, $R^3$, and $R^{3'}$, if present, are all hydrogen, and $R^2$ and $R^{2'}$ are taken together to form a 5- or 6-membered heterocycloalkyl group having 1 or 2 oxygen atoms.

In one embodiment, $R^1$ is hydrogen and $R^2$ is fluoro.

In one embodiment, $R^1$ and $R^2$ are joined to form a 3 membered ring.

The disclosure includes the use of compounds of Formula I in which the central pyrrolidine is vinyl substituted, for example:

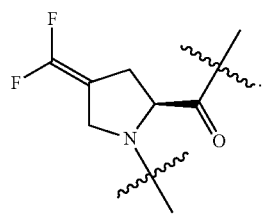 [SMILES: *C(=O)[C@@H]1CC(=C(F)F)CN1*]

In one embodiment, the compound of Formula I has the structure:

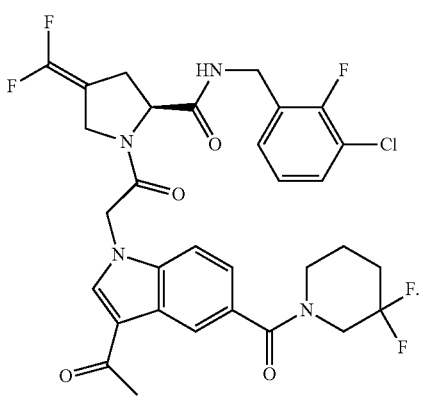 [SMILES: CC(=O)c1cn(CC(=O)N2CC(=C(F)F)C[C@H]2C(=O)NCc2cccc(Cl)c2F)c2ccc(C(=O)N3CCCC(F)(F)C3)cc12]

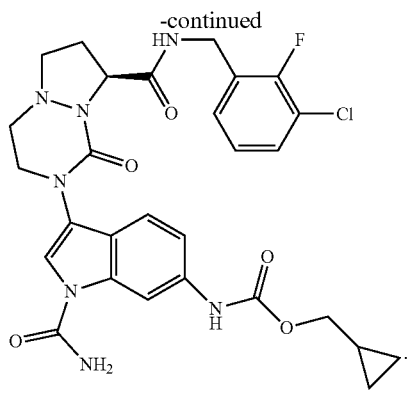

In one embodiment, the central pyrrolidine is modified by addition of a second heteroatom to a pyrrolidine ring, such as N, O, S, Si, or B, for example:

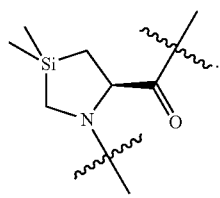 [SMILES: *C(=O)[C@@H]1C[Si](C)(C)CN1*]

Another modification within the scope of the disclosure is joining a substituent on the central pyrrolidine ring to $R^7$ or $R^8$ to form a 5- to 6-membered heterocyclic ring, for example:

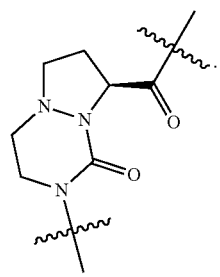 [SMILES: *C(=O)[C@@H]1CCN2CCN(*)C(=O)N12]

Example compounds having the modifications disclosed above include:

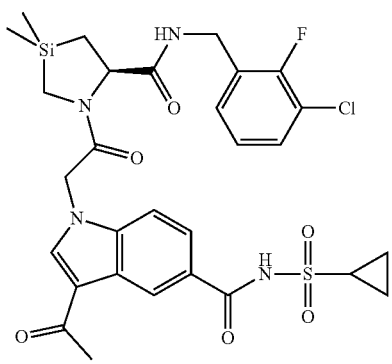

Central Core L-B Substituents

The central core L substituents and B substituents in Formula I are illustrated below:

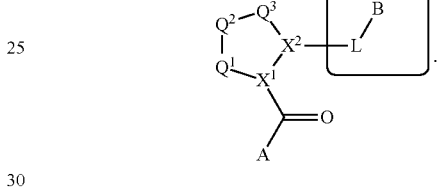

L is a bond or is selected from the formulas:

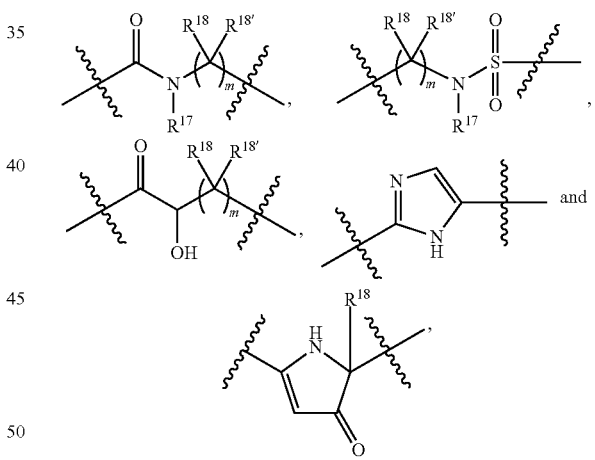

where $R^{17}$ is hydrogen, $C_1$-$C_6$alkyl, or —$C_0$-$C_4$alkyl($C_3$-$C_7$cycloalkyl) and $R^{18}$ and $R^{18'}$ are independently selected from hydrogen, halogen, hydroxymethyl, and methyl; and m is 0, 1, 2, or 3.

B is a monocyclic or bicyclic carbocyclic; a monocyclic or bicyclic carbocyclicoxy group; a monocyclic, bicyclic, or tricyclic heterocyclic group having 1, 2, 3, or 4 heteroatoms independently selected from N, O, and S and from 4 to 7 ring atoms per ring; $C_2$-$C_6$alkenyl; $C_2$-$C_6$alkynyl; —($C_0$-$C_4$alkyl)(aryl); —($C_0$-$C_4$alkyl)(heteroaryl); or —($C_0$-$C_4$alkyl)(biphenyl).

Each of which B is unsubstituted or substituted with one or more substituents independently selected from $R^{33}$ and $R^{34}$, and 0 or 1 substituents selected from $R^{35}$ and $R^{36}$:

$R^{33}$ is independently selected from halogen, hydroxyl, —COOH, cyano, $C_1$-$C_6$alkyl, $C_2$-$C_6$alkanoyl, $C_1$-$C_6$alkoxy, —$C_0$-$C_4$alkylNR$^9$R$^{10}$, —SO$_2$R$^9$, $C_1$-$C_2$haloalkyl, and $C_1$-$C_2$haloalkoxy;

$R^{34}$ is independently selected from nitro, $C_2$-$C_6$alkenyl, $C_2$-$C_6$alkynyl, $C_1$-$C_6$thioalkyl, -JC$_3$-C$_7$cycloalkyl, —B(OH)$_2$, -JC(O)NR$^9$R$^{23}$, -JOSO$_2$OR$^{21}$, —C(O)(CH$_2$)$_{1-4}$S(O)R$^{21}$, —O(CH$_2$)$_{1-4}$S(O)NR$^{21}$R$^{22}$, -JOP(O)(OR$^{21}$)(OR$^{22}$), -JP(O)(OR$^{21}$)(OR$^{22}$), -JOP(O)(OR$^{21}$)R$^{22}$, -JP(O)(OR$^{21}$)R$^{22}$, -JOP(O)R$^{21}$R$^{22}$, -JP(O)R$^{21}$R$^{22}$, -JSP(O)(OR$^{21}$)(OR$^{22}$), -JSP(O)(OR$^{21}$)(R$^{22}$), -JSP(O)(R$^{21}$)(R$^{22}$), -JNR$^9$P(O)(NHR$^{21}$)(NHR$^{22}$), -JNR$^9$P(O)(OR$^{21}$)(NHR$^{22}$), -JNR$^9$P(O)(OR$^{21}$)(OR$^{22}$), -JC(S)R$^{21}$, -JNR$^{21}$SO$_2$R$^{22}$, -JNR$^9$S(O)NR$^{10}$R$^{22}$, -JNR$^9$SO$_2$NR$^{10}$R$^{22}$, -JSO$_2$NR$^9$COR$^{22}$, -JSO$_2$NR$^9$CONR$^{21}$R$^{22}$, -JNR$^{21}$SO$_2$R$^{22}$, -JC(O)NR$^{21}$SO$_2$R$^{22}$, -JC(NH$_2$)NR$^{22}$, -JC(NH$_2$)NR$^9$S(O)$_2$R$^{22}$, -JOC(O)NR$^{21}$R$^{22}$, -JNR$^{21}$C(O)OR$^{22}$, -JNR$^{21}$OC(O)R$^{22}$, —(CH$_2$)$_{1-4}$C(O)NR$^{21}$R$^{22}$, -JC(O)NR$^{24}$R$^{25}$, -JNR$^9$C(O)R$^{21}$, -JC(O)R$^{21}$, -JNR$^9$C(O)NR$^{10}$R$^{22}$, —CCR$^{21}$, —(CH$_2$)$_{1-4}$OC(O)R$^{21}$, and -JC(O)OR$^{23}$; each of which $R^{34}$ may be unsubstituted or substituted with one or more substituents independently selected from halogen, hydroxyl, nitro, cyano, amino, oxo, —B(OH)$_2$, —Si(CH$_3$)$_3$, —COOH, —CONH$_2$, —P(O)(OH)$_2$, $C_1$-$C_6$alkyl, —$C_0$-$C_4$alkyl($C_3$-$C_7$cycloalkyl), $C_1$-$C_6$alkoxy, —$C_0$-$C_2$alkyl(mono- and di-$C_1$-$C_4$alkylamino), $C_1$-$C_6$alkylester, $C_1$-$C_4$alkylamino, $C_1$-$C_4$hydroxylalkyl, $C_1$-$C_2$haloalkyl, and $C_1$-$C_2$haloalkoxy;

$R^{35}$ is independently selected from naphthyl, naphthyloxy, indanyl, (4- to 7-membered heterocycloalkyl)$C_0$-$C_4$alkyl containing 1 or 2 heteroatoms selected from N, O, and S, and bicyclic heterocycle containing 1, 2, or 3 heteroatoms independently selected from N, O, and S, and containing 4- to 7-ring atoms in each ring; each of which $R^{35}$ is unsubstituted or substituted with one or more substituents independently selected from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), —SO$_2$R$^9$, $C_1$-$C_2$haloalkyl, and $C_1$-$C_2$haloalkoxy; and $R^{36}$ is independently selected from tetrazolyl, (phenyl)$C_0$-$C_2$alkyl, (phenyl)$C_1$-$C_2$alkoxy, phenoxy, and 5- or 6-membered heteroaryl containing 1, 2, or 3 heteroatoms independently selected from N, O, B, and S, each of which $R^{36}$ is unsubstituted or substituted with one or more substituents independently selected from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), —SO$_2$R$^9$, —OSi(CH$_3$)$_2$C(CH$_3$)$_3$, —Si(CH$_3$)$_2$C(CH$_3$)$_3$, $C_1$-$C_2$haloalkyl, and $C_1$-$C_2$haloalkoxy.

J is independently selected at each occurrence from a covalent bond, $C_1$-$C_4$alkylene, —O$C_1$-$C_4$alkylene, $C_2$-$C_4$alkenylene, and $C_2$-$C_4$alkynylene.

Examples of B moieties include, but are not limited to

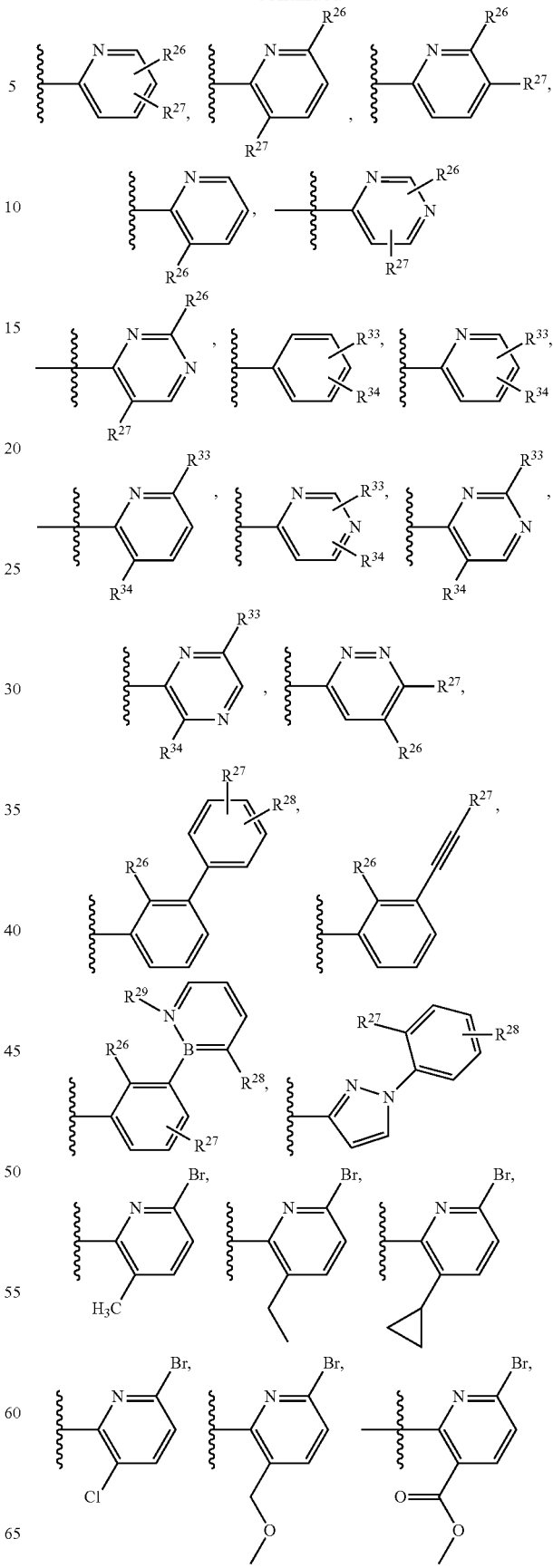

-continued

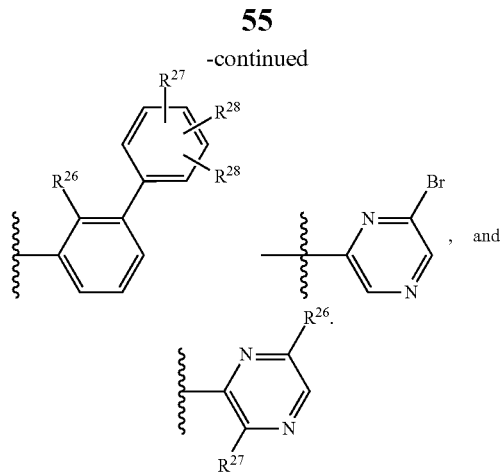

Non-Limiting L-B Embodiments

In one embodiment, -L-B— is

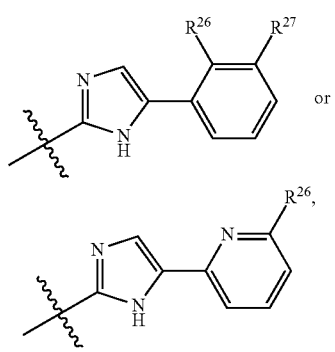

where

R$^{26}$ and R$^{27}$ are independently selected from hydrogen, halogen, hydroxyl, nitro, cyano, C$_1$-C$_6$alkyl, C$_2$-C$_6$alkenyl, C$_2$-C$_6$alkanoyl, C$_1$-C$_6$alkoxy, C$_1$-C$_6$thioalkyl, —C$_0$-C$_4$alkyl(mono- and di-C$_1$-C$_6$alkylamino), —C$_0$-C$_4$alkyl(C$_3$-C$_7$cycloalkyl), —C$_0$-C$_4$alkoxy(C$_3$-C$_7$cycloalkyl), C$_1$-C$_2$haloalkyl, C$_1$-C$_2$haloalkoxy, and C$_1$-C$_2$haloalkylthio.

In another embodiment, -L-B— is

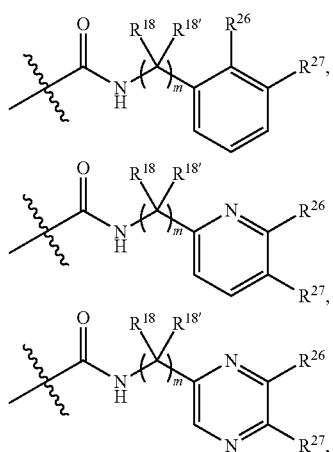

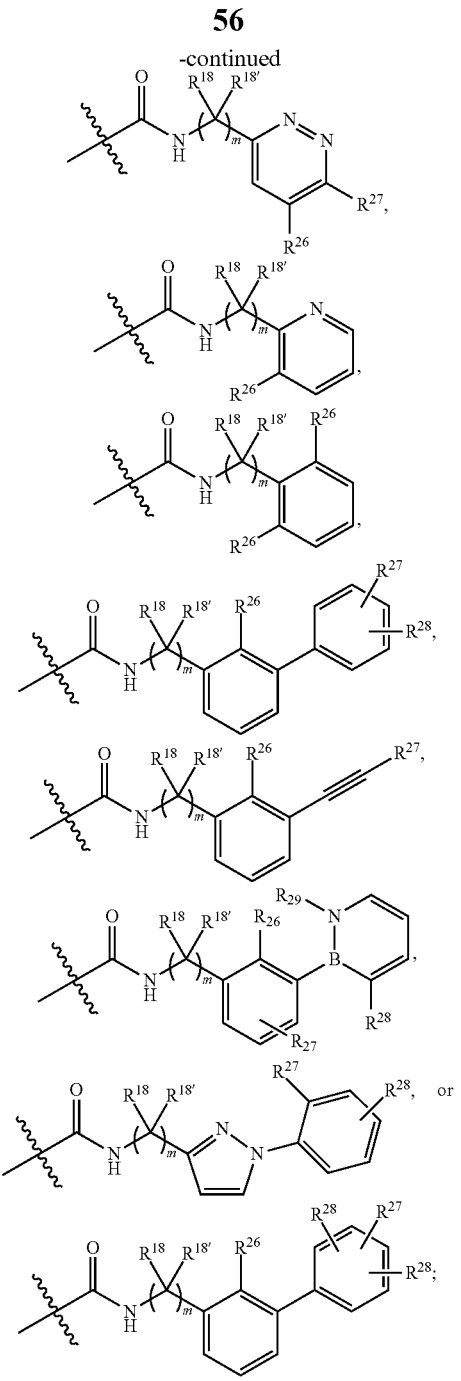

wherein

R$^{18}$ and R$^{18'}$ are independently selected from hydrogen, halogen, hydroxymethyl, and methyl; and m is 0 or 1; and R$^{26}$, R$^{27}$, and R$^{28}$ are independently selected from hydrogen, halogen, hydroxyl, nitro, cyano, C$_1$-C$_6$alkyl, C$_2$-C$_6$alkenyl, C$_2$-C$_6$alkanoyl, C$_1$-C$_6$alkoxy, C$_1$-C$_6$thioalkyl, (mono- and di-C$_1$-C$_6$alkylamino)C$_0$-C$_4$alkyl, (C$_3$-C$_7$cycloalkyl)C$_0$-C$_4$alkyl, (aryl)C$_0$-C$_4$alkyl-, (heteroaryl)C$_0$-C$_4$alkyl-, and —C$_0$-C$_4$alkoxy(C$_3$-C$_7$cycloalkyl); each of which R$^{26}$, R$^{27}$, and R$^{28}$ other than hydrogen, halogen, hydroxyl, nitro, cyano, is unsubstituted or substituted with one or more substituents independently selected from halogen, hydroxyl, amino, C$_1$-C$_2$alkoxy, C$_1$-C$_2$haloalkyl, (C$_3$-C$_7$cycloalkyl)C$_0$-C$_4$alkyl-, and C$_1$-C$_2$haloalkoxy; and R$^{29}$ is hydrogen, C$_1$-C$_2$alkyl, C$_1$C$_2$haloalkyl or —Si(CH$_3$)$_2$C(CH$_3$)$_3$.

In one embodiment, m is 0.

In one embodiment, the disclosure further includes the use of compounds and salts of Formula I in which B is 2-fluoro-3-chlorophenyl. In another embodiment, another carbocyclic, aryl, heterocyclic, or heteroaryl group such as 2-bromo-pyridin-6-yl, 1-(2,2,2-trifluoroethyl)-1H-pyrazol-3-yl, 2,2-dichlorocyclopropylmethyl, or 2-fluoro-3-trimethylsilylphenyl is used.

In another embodiment, B is phenyl, pyridyl, or indanyl each of which is unsubstituted or substituted with one or more substituents independently selected from hydrogen, halogen, hydroxyl, nitro, cyano, $C_1$-$C_6$alkyl, $C_2$-$C_6$alkenyl, $C_2$-$C_6$alkanoyl, $C_1$-$C_6$alkoxy, $C_1$-$C_6$thioalkyl, (mono- and di-$C_1$-$C_6$alkylamino)$C_0$-$C_4$alkyl, ($C_3$-$C_7$cycloalkyl)$C_0$-$C_4$alkyl, —$C_0$-$C_4$alkoxy($C_3$-$C_7$cycloalkyl), (phenyl)$C_0$-$C_2$alkyl, (pyridyl)$C_0$-$C_2$alkyl; each of which substituents other than hydrogen, halogen, hydroxyl, nitro, cyano, is unsubstituted or substituted with one or more substituents independently selected from halogen, hydroxyl, amino, $C_1$-$C_2$alkyl, $C_1$-$C_2$alkoxy, —OSi(CH$_3$)$_2$C(CH$_3$)$_3$, —Si(CH$_3$)$_2$C(CH$_3$)$_3$, $C_1$-$C_2$haloalkyl, and $C_1$-$C_2$haloalkoxy.

In another embodiment, B is phenyl or pyridyl substituted with 1, 2, or 3 substituents selected from chloro, bromo, hydroxyl, —SCF$_3$, $C_1$-$C_2$alkyl, $C_1$-$C_2$alkoxy, trifluoromethyl, phenyl and trifluoromethoxy each of which substituents other than chloro, bromo, hydroxyl, —SCF$_3$, can be optionally substituted.

In certain embodiments, B is a 2-fluoro-3-chlorophenyl or a 2-fluoro-3-trifluoromethoxyphenyl group.

In one embodiment, B is pyridyl, optionally substituted with halogen, $C_1$-$C_2$alkoxy, and trifluoromethyl.

In one embodiment, B is phenyl, substituted with 1, 2, or 3 substituents independently selected from halogen, $C_1$-$C_2$alkyl, $C_1$-$C_2$alkoxy, trifluoromethyl, and optionally substituted phenyl.

In one embodiment, $R^{23}$ is independently selected at each occurrence from ($C_3$-$C_7$cycloalkyl)$C_0$-$C_4$alkyl, (phenyl)$C_0$-$C_4$alkyl, (4- to 7-membered heterocycloalkyl)$C_0$-$C_4$alkyl having 1, 2, or 3 heteroatoms independently selected from N, O, and S, and (5- or 6-membered unsaturated or aromatic heterocycle)$C_0$-$C_4$alkyl having 1, 2, or 3 heteroatoms independently selected from N, O, and S.

In one embodiment, B is selected from the structures of FIGS. 7A, 7B, 7C, 7D, and 7E, wherein $R^{27}$ is hydrogen, methyl, or trifluoromethyl; $R^{28}$ is hydrogen or halogen; and $R^{29}$ is hydrogen, methyl, trifluoromethyl, or —Si(CH$_3$)$_2$C(CH$_3$)$_3$.

Figure 8:
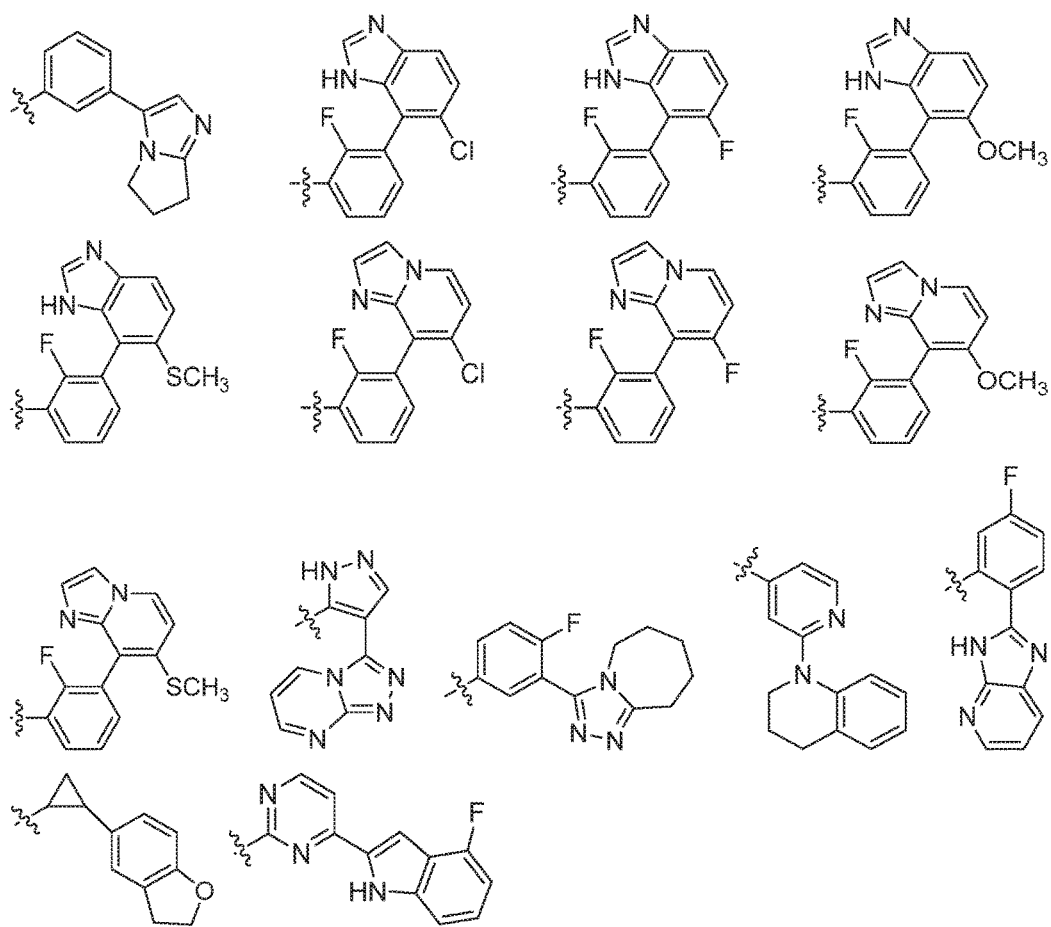
FIG. 8 provides non-limiting specific embodiments of the B ring.
Figure 9A:
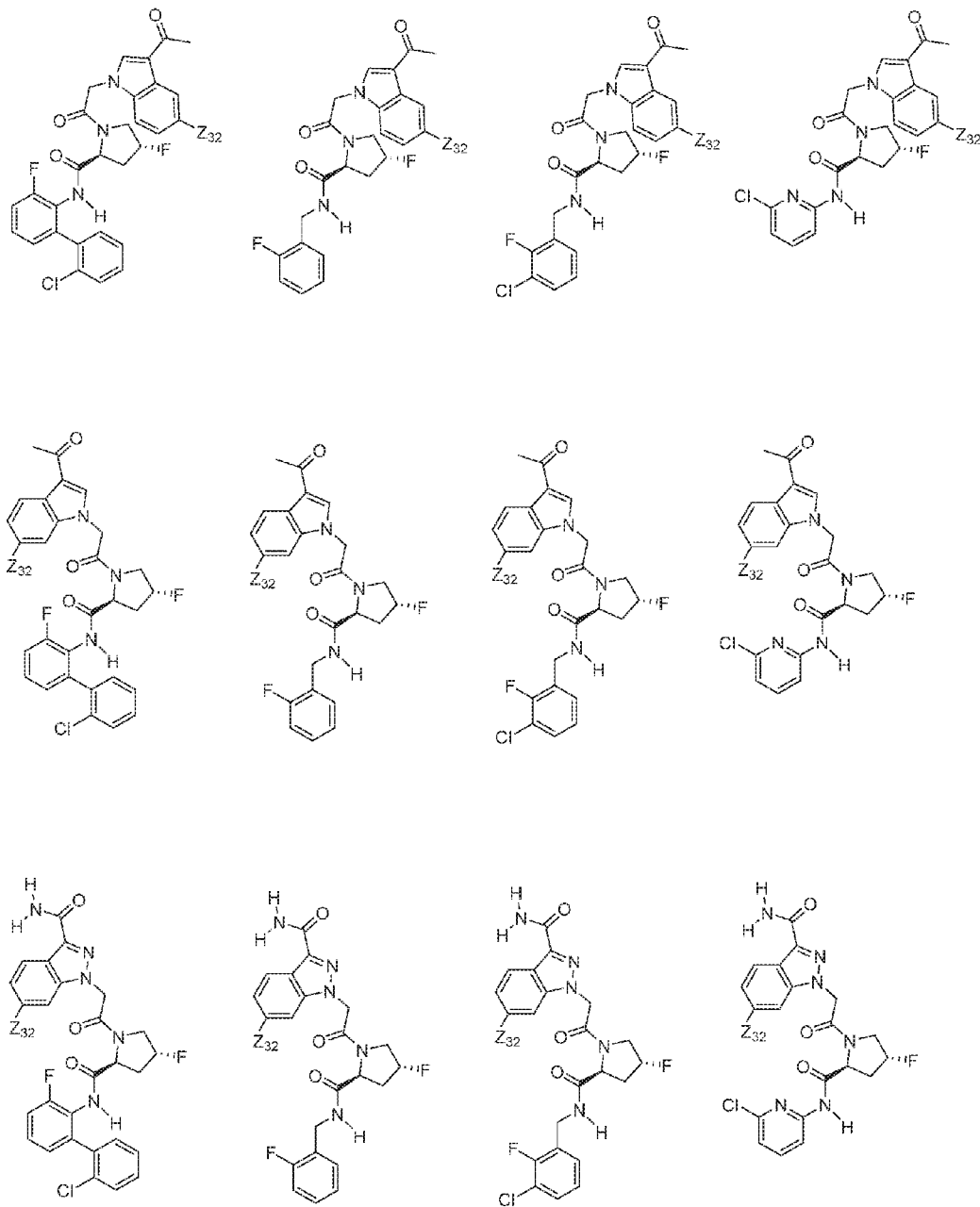
FIGS. 9A, 9B, 9C, 9D, 9E, 9F, 9G and 9H provide non-limiting examples of compounds included in the present invention, wherein $Z_{32}$ is the same as $R^{32}$ as used herein.
Figure 9B:
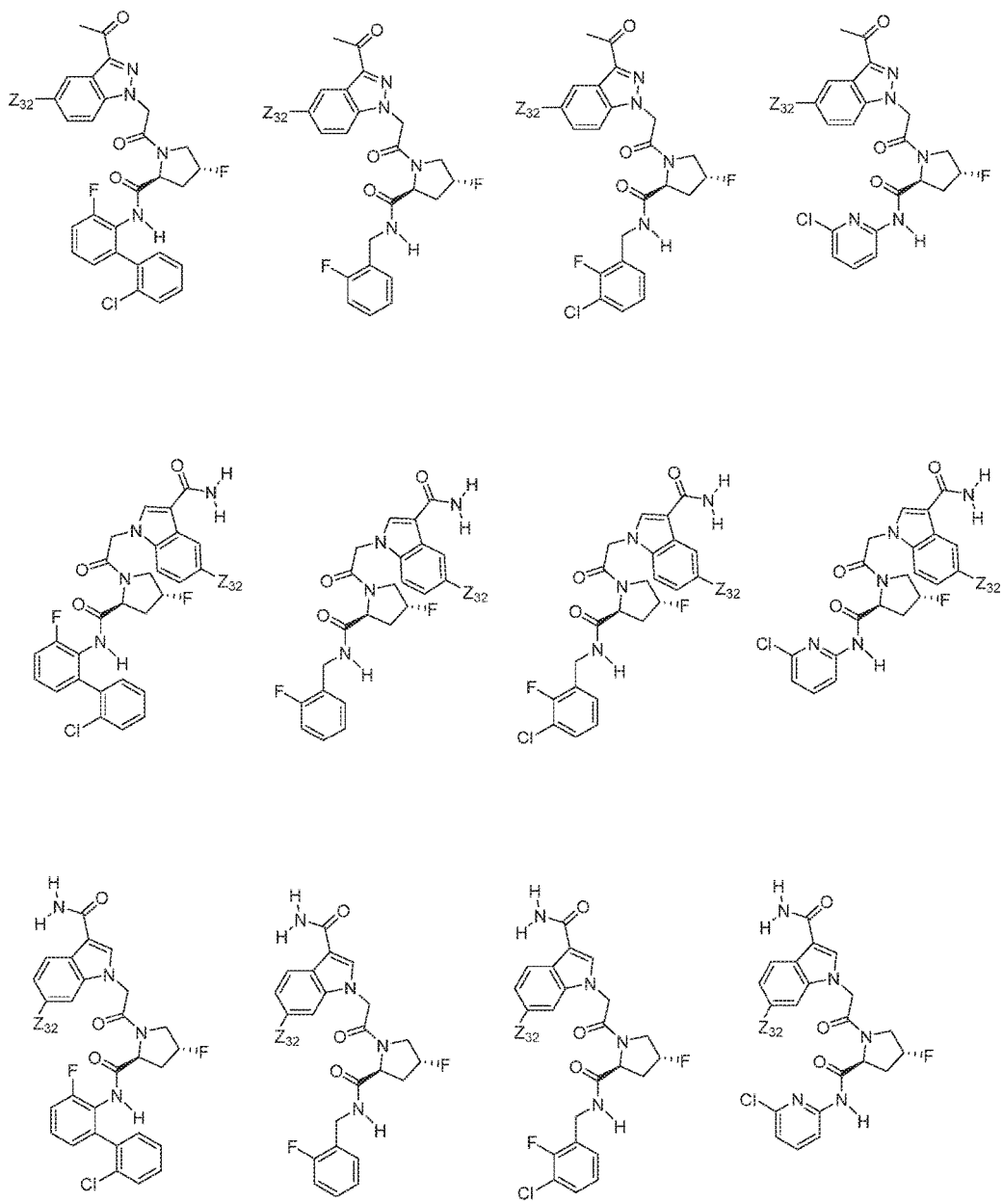
Figure 9C:
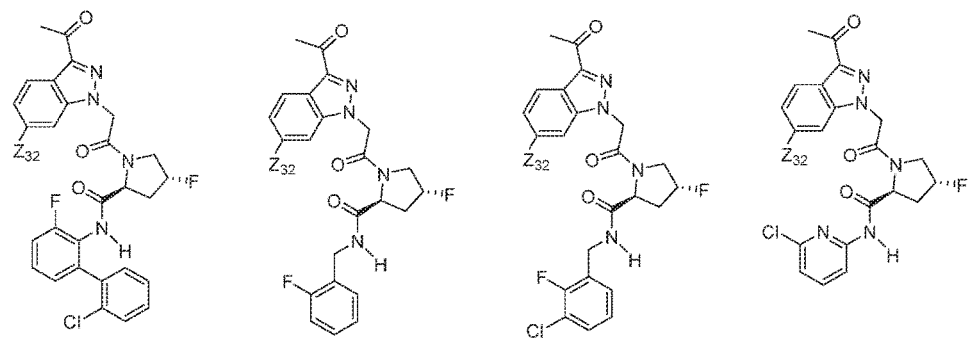
Figure 9C:
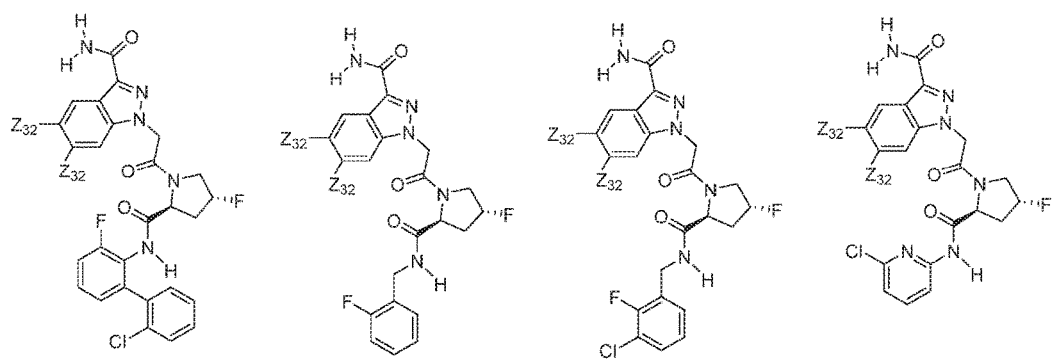
Figure 9C:
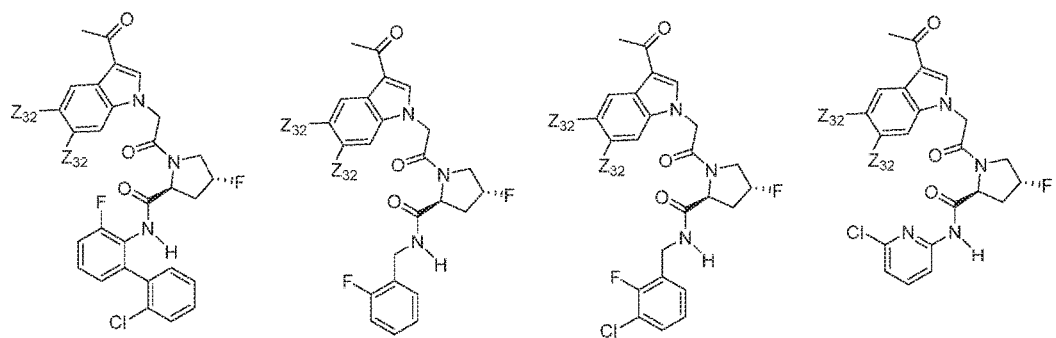
Figure 9D:
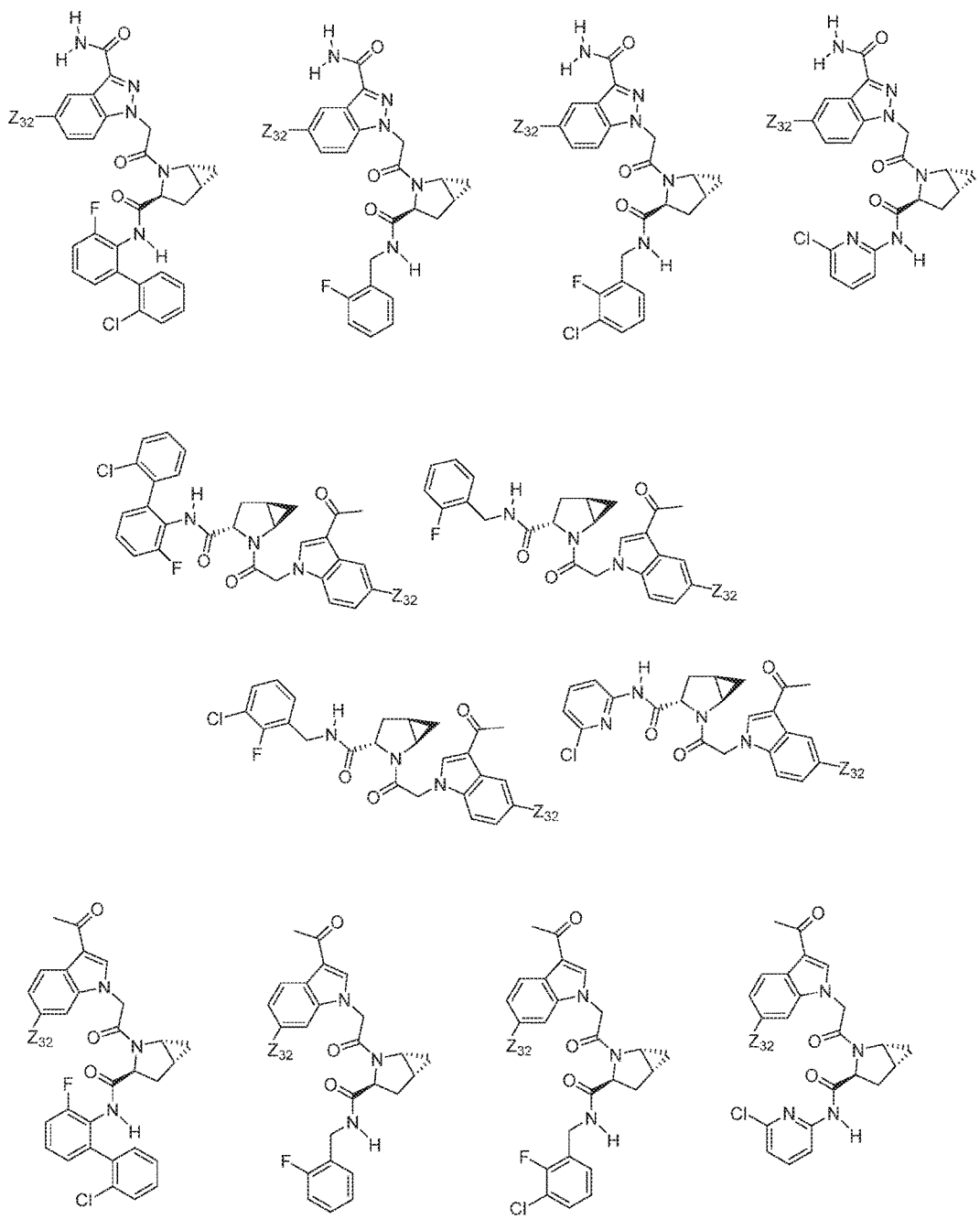
Figure 9E:
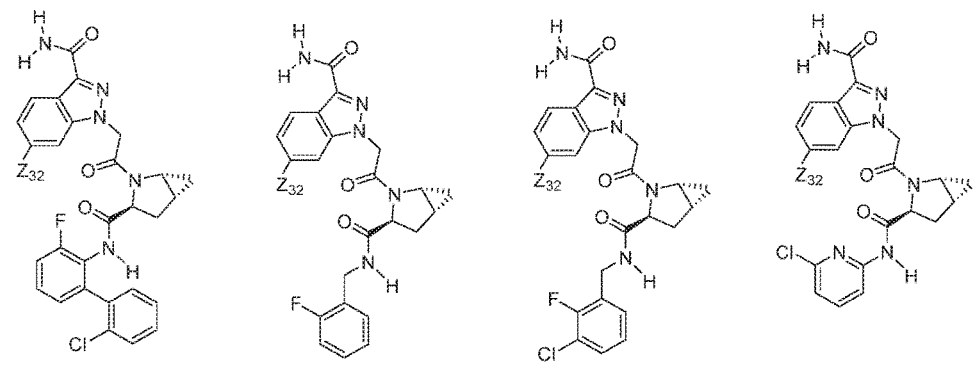
Figure 9E:
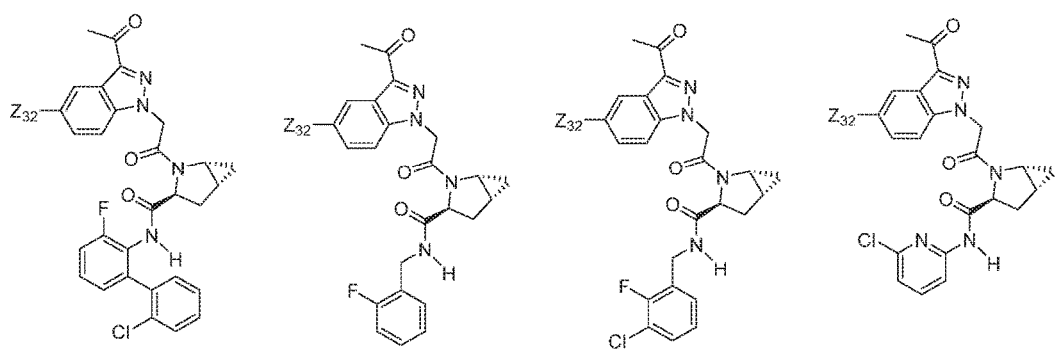
Figure 9E:
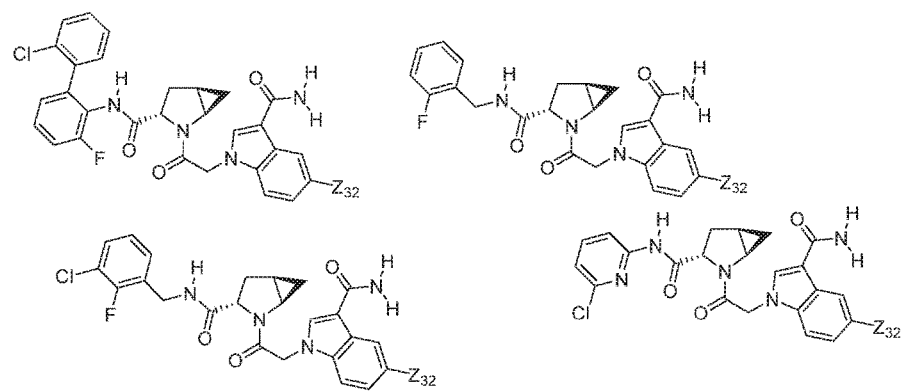
Figure 9F:
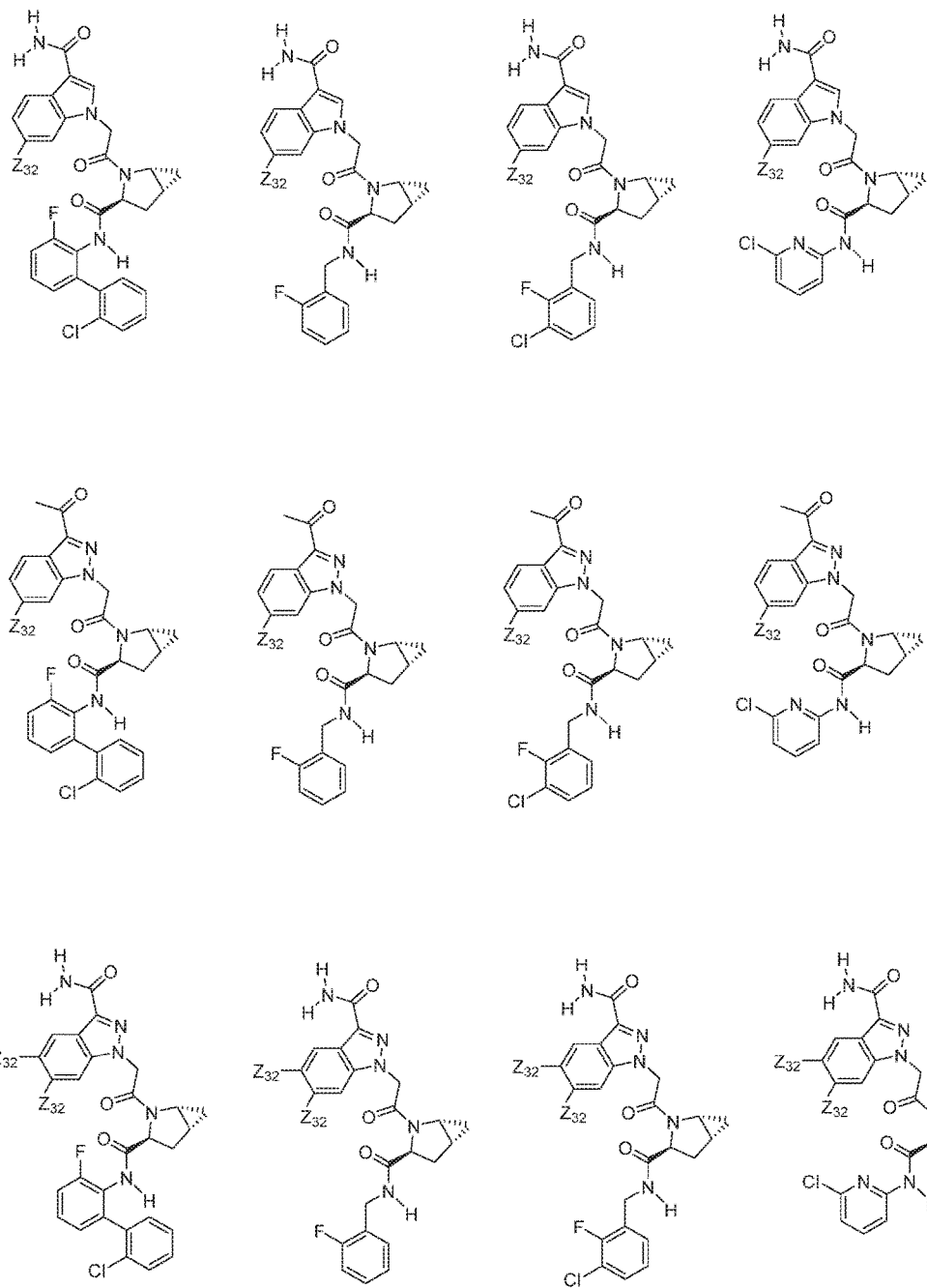
Figure 9G:
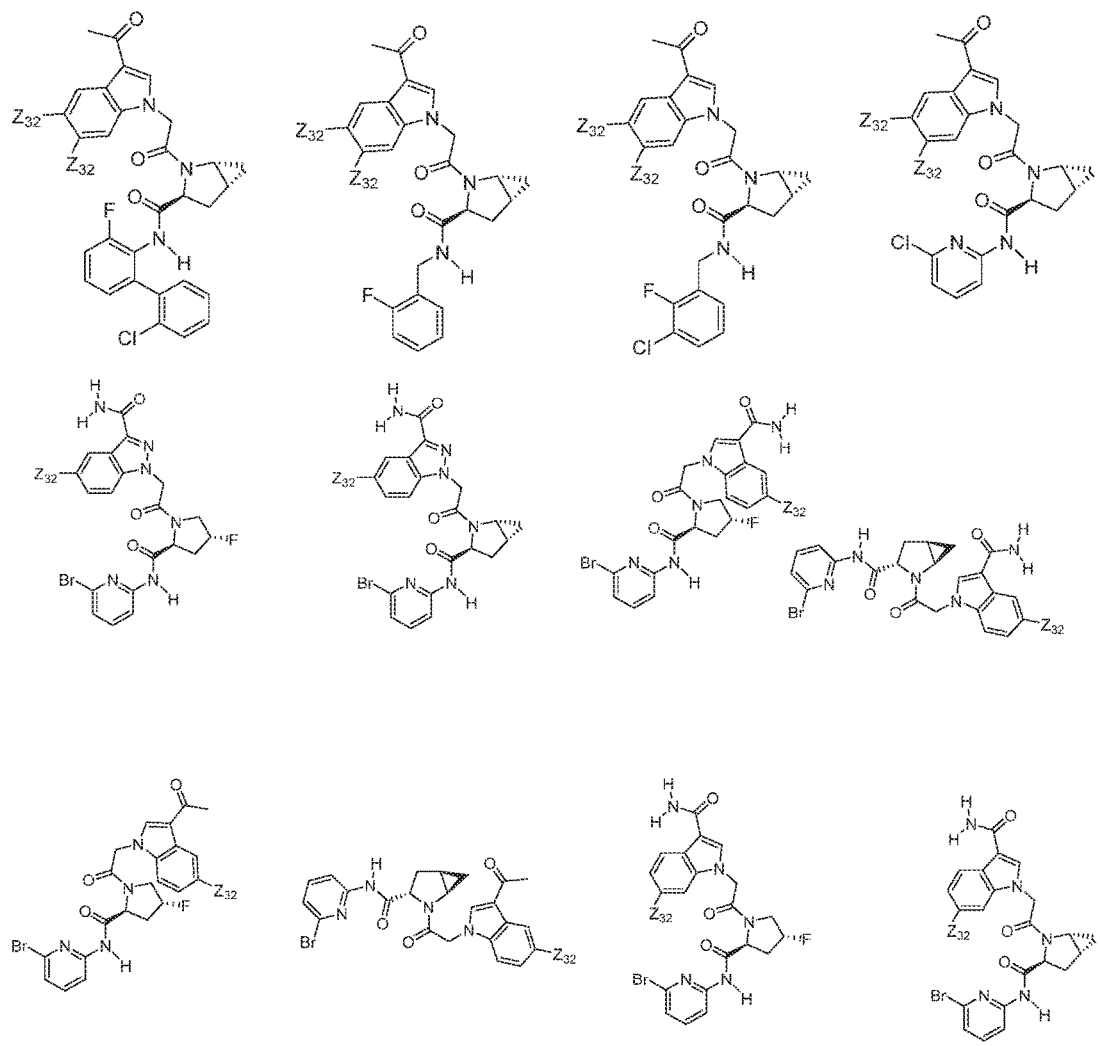
Figure 9H:
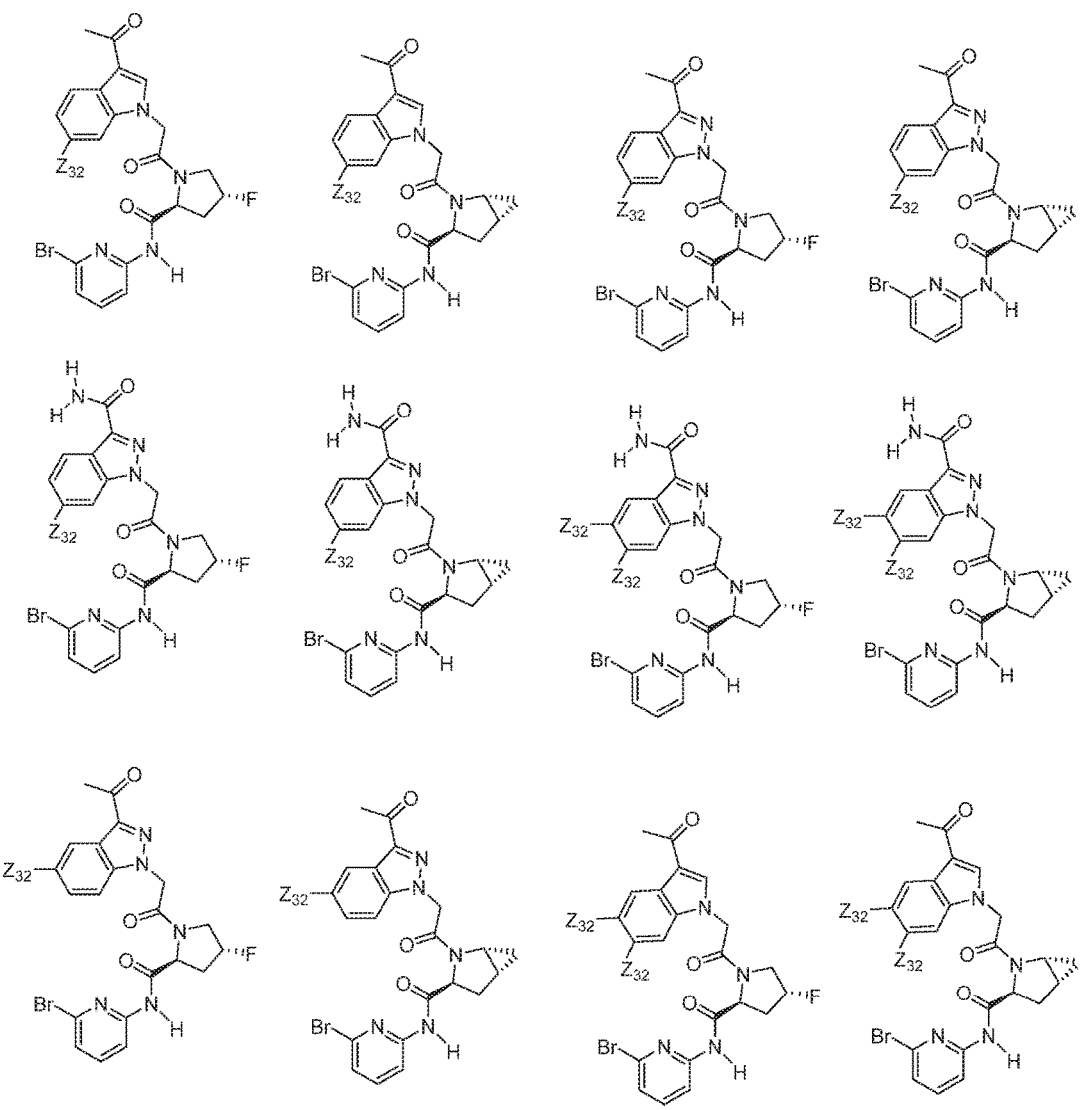

In an alternative embodiment, B is selected from the structures of FIG. 8.

Central Core (C=O)A Substituent

The central core (C=O)A substituent in Formula I is illustrated below:

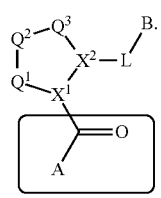

A is a group selected from:

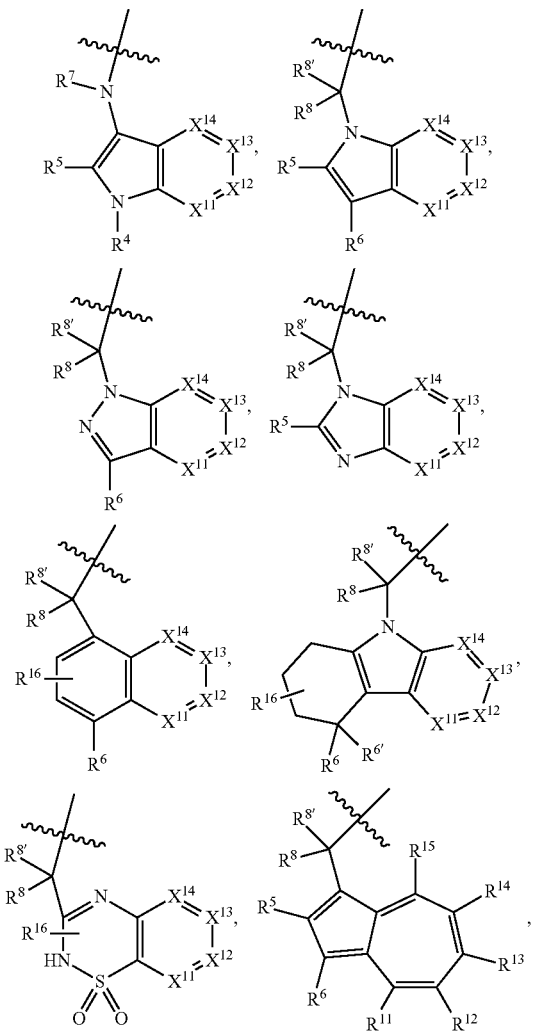

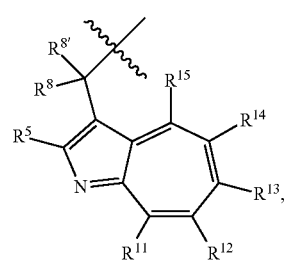

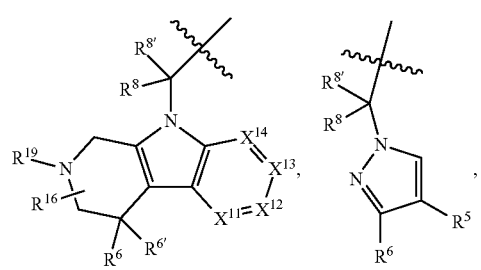

-continued

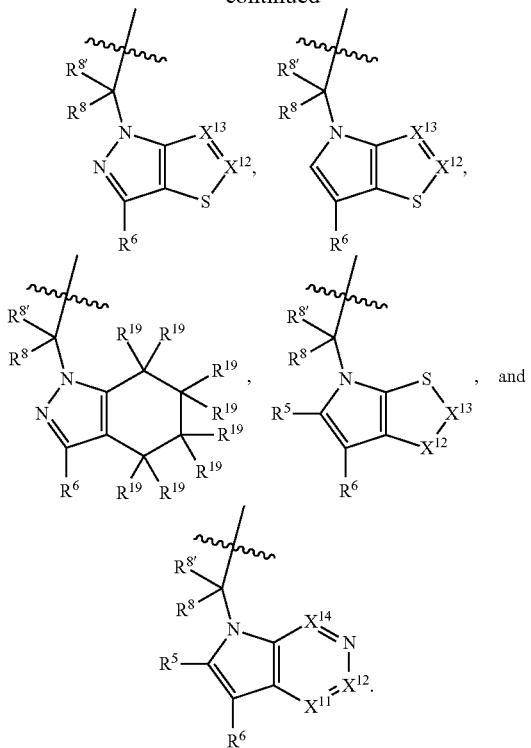

$R^4$ is selected from —CHO, —CONH$_2$, C$_2$-C$_6$alkanoyl, hydrogen, —SO$_2$NH$_2$, —C(CH$_2$)$_2$F, —CH(CF$_3$)NH$_2$, C$_1$-C$_6$alkyl, —C$_0$-C$_4$alkyl(C$_3$-C$_7$cycloalkyl), —C(O)C$_0$-C$_2$alkyl(C$_3$-C$_7$cycloalkyl),

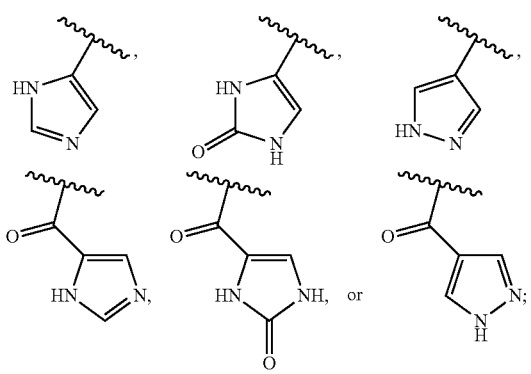

each of which R$^4$ other than hydrogen, —CHO, and —CONH$_2$, is unsubstituted or substituted with one or more of amino, imino, halogen, hydroxyl, cyano, cyanoimino, C$_1$-C$_2$alkyl, C$_1$-C$_2$alkoxy, —C$_0$-C$_2$alkyl(mono- and di-C$_1$-C$_4$alkylamino), C$_1$-C$_2$haloalkyl, and C$_1$-C$_2$haloalkoxy.

R$^5$ and R$^6$ are independently selected from —CHO, —C(O)NH$_2$, —C(O)NH(CH$_3$), C$_2$-C$_6$alkanoyl, hydrogen, hydroxyl, halogen, cyano, nitro, —COOH, —SO$_2$NH$_2$, vinyl, C$_1$-C$_6$alkyl (including methyl), C$_2$-C$_6$alkenyl, C$_1$-C$_6$alkoxy, —C$_0$-C$_4$alkyl(C$_3$-C$_7$cycloalkyl), —C(O)C$_0$-C$_4$alkyl(C$_3$-C$_7$cycloalkyl), —P(O)(OR$^9$)$_2$, —OC(O)R$^9$, —C(O)OR$^9$, —C(O)N(CH$_2$CH$_2$R$^9$)(R$^{10}$), —NR$^9$C(O)R$^{10}$, phenyl, or 5- to 6-membered heteroaryl.

Each R$^5$ and R$^6$ other than hydrogen, hydroxyl, cyano, and —COOH is unsubstituted or optionally substituted. For example, R$^5$ and R$^6$ other than hydrogen, hydroxyl, cyano, and —COOH may be substituted with one or more substituents independently selected from halogen, hydroxyl, amino, imino, cyano, cyanoimino, C$_1$-C$_2$alkyl, C$_1$-C$_4$alkoxy, —C$_0$-C$_2$alkyl(mono- and di-C$_1$-C$_4$alkylamino), C$_1$-C$_2$haloalkyl, and C$_1$-C$_2$haloalkoxy.

R$^{6'}$ is hydrogen, halogen, hydroxyl, C$_1$-C$_4$alkyl, —C$_0$-C$_4$alkyl(C$_3$-C$_7$cycloalkyl), or C$_1$-C$_4$alkoxy; or R$^6$ and R$^{6'}$ may be taken together to form an oxo, vinyl, or imino group.

R$^7$ is hydrogen, C$_1$-C$_6$alkyl, or —C$_0$-C$_4$alkyl(C$_3$-C$_7$cycloalkyl).

R$^8$ and R$^{8'}$ are independently selected from hydrogen, halogen, hydroxyl, C$_1$-C$_6$alkyl, —C$_0$-C$_4$alkyl(C$_3$-C$_7$cycloalkyl), C$_1$-C$_6$alkoxy, and (C$_1$-C$_4$alkylamino)C$_0$-C$_2$alkyl; or R$^8$ and R$^{8'}$ are taken together to form an oxo group; or R$^8$ and R$^{8'}$ can be taken together with the carbon that they are bonded to form a 3-membered carbocyclic ring.

R$^{16}$ is absent or may include one or more substituents independently selected from halogen, hydroxyl, nitro, cyano, C$_1$-C$_6$alkyl, C$_2$-C$_6$alkenyl, C$_2$-C$_6$alkanoyl, C$_1$-C$_6$alkoxy, —C$_0$-C$_4$alkyl(mono- and di-C$_1$-C$_6$alkylamino), —C$_0$-C$_4$alkyl(C$_3$-C$_7$cycloalkyl), C$_1$-C$_2$haloalkyl, and C$_1$-C$_2$haloalkoxy.

R$^{19}$ is hydrogen, C$_1$-C$_6$alkyl, C$_2$-C$_6$alkenyl, C$_2$-C$_6$alkanoyl, —SO$_2$C$_1$-C$_6$alkyl, (mono- and di-C$_1$-C$_6$alkylamino)C$_1$-C$_4$alkyl, —C$_0$-C$_4$alkyl(C$_3$-C$_7$cycloalkyl), —C$_0$-C$_4$alkyl(C$_3$-C$_7$heterocycloalkyl), —C$_0$-C$_4$alkyl(aryl), C$_0$-C$_4$alkyl(heteroaryl), and wherein R$^{19}$ other than hydrogen is unsubstituted or substituted with one or more substituents independently selected from halogen, hydroxyl, amino, —COOH, and —C(O)OC$_1$-C$_4$alkyl.

X$^{11}$ is N or CR$^{11}$.
X$^{12}$ is N or CR$^{12}$.
X$^{13}$ is N or CR$^{13}$.
X$^{14}$ is N or CR$^{14}$.
No more than 2 of X$^{11}$, X$^{12}$, X$^{13}$, and X$^{14}$ are N.
R$^{11}$, R$^{14}$, and R$^{15}$ are independently selected at each occurrence from hydrogen, halogen, hydroxyl, nitro, cyano, —O(PO)(OR$^9$)$_2$, —(PO)(OR$^9$)$_2$, C$_1$-C$_6$alkyl, C$_2$-C$_6$alkenyl, C$_2$-C$_6$alkynyl, C$_2$-C$_6$alkenyl(aryl), C$_2$-C$_6$alkenyl(cycloalkyl), C$_2$-C$_6$alkenyl(heterocycle), C$_2$-C$_6$alkenyl(heteroaryl), C$_2$-C$_6$alkynyl, C$_2$-C$_6$alkynyl(aryl), C$_2$-C$_6$alkynyl(cycloalkyl), C$_2$-C$_6$alkynyl(heterocycle), C$_2$-C$_6$alkynyl(heteroaryl), C$_2$-C$_6$alkanoyl, C$_1$-C$_6$alkoxy, C$_1$-C$_6$thioalkyl, —C$_0$-C$_4$alkyl(mono- and di-C$_1$-C$_6$alkylamino), —C$_0$-C$_4$alkyl(C$_3$-C$_7$cycloalkyl), —C$_0$-C$_4$alkoxy(C$_3$-C$_7$cycloalkyl), C$_1$-C$_2$haloalkyl, and C$_1$-C$_2$haloalkoxy.

In one embodiment, R$^5$ and R$^6$ are independently selected from —CHO, —C(O)NH$_2$, —C(O)NH(CH$_3$), C$_2$-C$_6$alkanoyl, and hydrogen.

In one embodiment, each R$^5$ and R$^6$ other than hydrogen, hydroxyl, cyano, and —COOH is unsubstituted or substituted with one or more substituents independently selected from halogen, hydroxyl, amino, imino, cyano, cyanoimino, C$_1$-C$_2$alkyl, C$_1$-C$_4$alkoxy, —C$_0$-C$_2$alkyl(mono- and di-C$_1$-C$_4$alkylamino), C$_1$-C$_2$haloalkyl, and C$_1$-C$_2$haloalkoxy.

In one embodiment, R$^8$ and R$^{8'}$ are independently hydrogen or methyl.

In one embodiment, R$^8$ and R$^{8'}$ are hydrogen.
In one embodiment, R$^7$ is hydrogen or methyl.
In one embodiment, R$^7$ is hydrogen.

Embodiments of Formulas IA, IB, IC, and ID

To further illustrate the invention, various embodiments of Formula IA, IB, IC and ID are provided. These are presented by way of example to show some of the variations among presented compounds to be used within the invention and can be applied to any of the Formulas I-XXX.

In one aspect, this disclosure includes the use of compounds and salts of Formula IA:

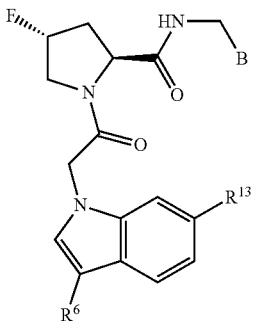

(IA)

where $R^6$, $R^{13}$, and B may carry any of the definitions set forth herein for this variable.

In another aspect, this disclosure includes the use of compounds and salts of Formula IB, IC, and ID.

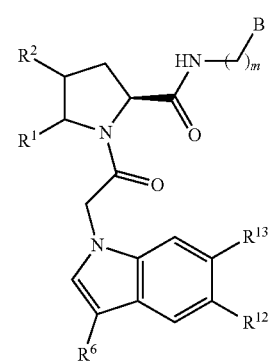

IB

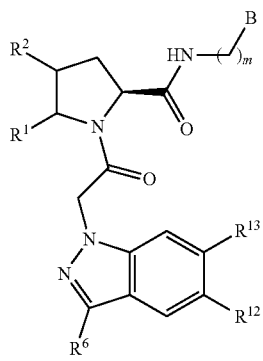

IC

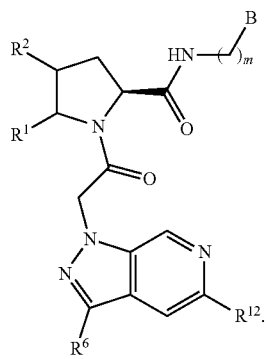

ID

In Formulas IA, IB, IC, and ID, the variables may include any of the definitions set forth herein that results in a stable compound. In certain embodiments, the following conditions apply for Formula IB and IC.

In some embodiments, uses of compounds are provided, as described herein, comprising the administration of an effective amount of a compound of Formula IB or IC, wherein m=0, $R^1$ is H, $R^2$ is F, $R^6$ is alkanoyl, $R^{12}$ is $R^{32}$, $R^{32}$ is —C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, or —NR$^9$C(O)NR$^{24}$R$^{25}$, each of which is optionally substituted, $R^{13}$ is H, and B is heteroaryl.

In some embodiments, uses of compounds are provided, as described herein, comprising the administration of an effective amount of a compound of Formula IB or IC, wherein m=0, $R^1$ and $R^2$ are joined to form a 3 membered ring, $R^6$ is alkanoyl, $R^{12}$ is $R^{32}$, $R^{32}$ is —C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, or —NR$^9$C(O)NR$^{24}$R$^{25}$, each of which is optionally substituted, $R^{13}$ is H, and B is heteroaryl.

In some embodiments, uses of compounds are provided, as described herein, comprising the administration of an effective amount of a compound of Formula IB or IC, wherein m=0, $R^1$ is H, $R^2$ is F, $R^6$ is amide, $R^{12}$ is $R^{32}$, $R^{32}$ is —C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, or —NR$^9$C(O)NR$^{24}$R$^{25}$, each of which is optionally substituted, $R^{13}$ is H, and B is heteroaryl.

In some embodiments, uses of compounds are provided, as described herein, comprising the administration of an effective amount of a compound of Formula IB or IC, wherein m=0, $R^1$ and $R^2$ are joined to form a 3 membered ring, $R^6$ is amide, $R^{12}$ is $R^{32}$, $R^{32}$ is —C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, or —NR$^9$C(O)NR$^{24}$R$^{25}$, each of which is optionally substituted, $R^{13}$ is H, and B is heteroaryl.

In some embodiments, uses of compounds are provided, as described herein, comprising the administration of an effective amount of a compound of Formula IB or IC, wherein m=0, $R^1$ is H, $R^2$ is F, $R^6$ is alkanoyl, $R^{12}$ is H, $R^{13}$ is $R^{32}$, $R^{32}$ is —C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C (O)NR$^{10}$R$^{23}$, or —NR$^9$C(O)NR$^{24}$R$^{25}$, each of which is optionally substituted, and B is heteroaryl.

In some embodiments, uses of compounds are provided, as described herein, comprising the administration of an effective amount of a compound of Formula IB or IC, wherein m=0, R$^1$ and R$^2$ are joined to form a 3 membered ring, R$^6$ is alkanoyl, R$^{12}$ is H, R$^{13}$ is R$^{32}$, R$^{32}$ is —C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, or —NR$^9$C(O)NR$^{24}$R$^{25}$, each of which is optionally substituted, and B is heteroaryl.

In some embodiments, uses of compounds are provided, as described herein, comprising the administration of an effective amount of a compound of Formula IB or IC, wherein m=0, R$^1$ is H, R$^2$ is F, R$^6$ is amide, R$^{12}$ is H, R$^{13}$ is R$^{32}$, R$^{32}$ is —C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, or —NR$^9$C(O)NR$^{24}$R$^{25}$, each of which is optionally substituted, and B is heteroaryl.

In some embodiments, uses of compounds are provided, as described herein, comprising the administration of an effective amount of a compound of Formula IB or IC, wherein m=0, R$^1$ and R$^2$ are joined to form a 3 membered ring, R$^6$ is amide, R$^{12}$ is H, R$^{13}$ is R$^{32}$, R$^{32}$ is —C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, or —NR$^9$C(O)NR$^{24}$R$^{25}$, each of which is optionally substituted, and B is heteroaryl.

In some embodiments, uses of compounds are provided, as described herein, comprising the administration of an effective amount of a compound of Formula IB or IC, wherein m=0, R$^1$ is H, R$^2$ is F, R$^6$ is alkanoyl, R$^{12}$ is R$^{32}$, R$^{32}$ is —C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, or —NR$^9$C(O)NR$^{24}$R$^{25}$, each of which is optionally substituted, R$^{13}$ is H, and B is phenyl.

In some embodiments, uses of compounds are provided, as described herein, comprising the administration of an effective amount of a compound of Formula IB or IC, wherein m=0, R$^1$ and R$^2$ are joined to form a 3 membered ring, R$^6$ is alkanoyl, R$^{12}$ is R$^{32}$, R$^{32}$ is —C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, or —NR$^9$C(O)NR$^{24}$R$^{25}$, each of which is optionally substituted, R$^{13}$ is H, and B is phenyl.

In some embodiments, uses of compounds are provided, as described herein, comprising the administration of an effective amount of a compound of Formula IB or IC, wherein m=0, R$^1$ is H, R$^2$ is F, R$^6$ is amide, R$^{12}$ is R$^{32}$, R$^{32}$ is —C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, or —NR$^9$C(O)NR$^{24}$R$^{25}$, each of which is optionally substituted, R$^{13}$ is H, and B is phenyl.

In some embodiments, uses of compounds are provided, as described herein, comprising the administration of an effective amount of a compound of Formula IB or IC, wherein m=0, R$^1$ and R$^2$ are joined to form a 3 membered ring, R$^6$ is amide, R$^{12}$ is R$^{32}$, R$^{32}$ is —C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, or —NR$^9$C(O)NR$^{24}$R$^{25}$, each of which is optionally substituted, R$^{13}$ is H, and B is phenyl.

In some embodiments, uses of compounds are provided, as described herein, comprising the administration of an effective amount of a compound of Formula IB or IC, wherein m=0, R$^1$ is H, R$^2$ is F, R$^6$ is alkanoyl, R$^{12}$ is H, R$^{13}$ is R$^{32}$, R$^{32}$ is —C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, or —NR$^9$C(O)NR$^{24}$R$^{25}$, each of which is optionally substituted, and B is phenyl.

In some embodiments, uses of compounds are provided, as described herein, comprising the administration of an effective amount of a compound of Formula IB or IC, wherein m=0, R$^1$ and R$^2$ are joined to form a 3 membered ring, R$^6$ is alkanoyl, R$^{12}$ is H, R$^{13}$ is R$^{32}$, R$^{32}$ is —C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, or —NR$^9$C(O)NR$^{24}$R$^{25}$, each of which is optionally substituted, and B is phenyl.

In some embodiments, uses of compounds are provided, as described herein, comprising the administration of an effective amount of a compound of Formula IB or IC, wherein m=0, R$^1$ is H, R$^2$ is F, R$^6$ is amide, R$^{12}$ is H, R$^{13}$ is R$^{32}$, R$^{32}$ is —C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, or —NR$^9$C(O)NR$^{24}$R$^{25}$, each of which is optionally substituted, and B is phenyl.

In some embodiments, uses of compounds are provided, as described herein, comprising the administration of an effective amount of a compound of Formula IB or IC, wherein m=0, R$^1$ and R$^2$ are joined to form a 3 membered ring, R$^6$ is amide, R$^{12}$ is H, R$^{13}$ is R$^{32}$, R$^{32}$ is —C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, or —NR$^9$C(O)NR$^{24}$R$^{25}$, each of which is optionally substituted, and B is phenyl.

In some embodiments, uses of compounds are provided, as described herein, comprising the administration of an effective amount of a compound of Formula IB or IC, wherein m=1, R$^1$ is H, R$^2$ is F, R$^6$ is alkanoyl, R$^{12}$ is R$^{32}$, R$^{32}$ is —C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, or —NR$^9$C(O)NR$^{24}$R$^{25}$, each of which is optionally substituted, R$^{13}$ is H, and B is heteroaryl.

In some embodiments, uses of compounds are provided, as described herein, comprising the administration of an effective amount of a compound of Formula IB or IC, wherein m=1, R$^1$ and R$^2$ are joined to form a 3 membered ring, R$^6$ is alkanoyl, R$^{12}$ is R$^{32}$, R$^{32}$ is —C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, or —NR$^9$C(O)NR$^{24}$R$^{25}$, each of which is optionally substituted, R$^{13}$ is H, and B is heteroaryl.

In some embodiments, uses of compounds are provided, as described herein, comprising the administration of an effective amount of a compound of Formula IB or IC, wherein m=1, R$^1$ is H, R$^2$ is F, R$^6$ is amide, R$^{12}$ is R$^{32}$, R$^{32}$ is —C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, or —NR$^9$C(O)NR$^{24}$R$^{25}$, each of which is optionally substituted, R$^{13}$ is H, and B is heteroaryl.

In some embodiments, uses of compounds are provided, as described herein, comprising the administration of an effective amount of a compound of Formula IB or IC, wherein m=1, R$^1$ and R$^2$ are joined to form a 3 membered ring, R$^6$ is amide, R$^{12}$ is R$^{32}$, R$^{32}$ is —C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, or —NR$^9$C(O)NR$^{24}$R$^{25}$, each of which is optionally substituted, R$^{13}$ is H, and B is heteroaryl.

In some embodiments, uses of compounds are provided, as described herein, comprising the administration of an effective amount of a compound of Formula IB or IC, wherein m=1, R$^1$ is H, R$^2$ is F, R$^6$ is alkanoyl, R$^{12}$ is H, R$^{13}$ is R$^{32}$, R$^{32}$ is —C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, or —NR$^9$C(O)NR$^{24}$R$^{25}$, each of which is optionally substituted, and B is heteroaryl.

In some embodiments, uses of compounds are provided, as described herein, comprising the administration of an effective amount of a compound of Formula IB or IC, wherein m=1, R$^1$ and R$^2$ are joined to form a 3 membered ring, R$^6$ is alkanoyl, R$^{12}$ is H, R$^{13}$ is R$^{32}$, R$^{32}$ is —C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, or —NR$^9$C(O)NR$^{24}$R$^{25}$, each of which is optionally substituted, and B is heteroaryl.

In some embodiments, uses of compounds are provided, as described herein, comprising the administration of an effective amount of a compound of Formula IB or IC, wherein m=1, R$^1$ is H, R$^2$ is F, R$^6$ is amide, R$^{12}$ is H, R$^{13}$ is R$^{32}$, R$^{32}$ is —C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, or —NR$^9$C(O)NR$^{24}$R$^{25}$, each of which is optionally substituted, and B is heteroaryl.

In some embodiments, uses of compounds are provided, as described herein, comprising the administration of an effective amount of a compound of Formula IB or IC, wherein m=1, R$^1$ and R$^2$ are joined to form a 3 membered ring, R$^6$ is amide, R$^{12}$ is H, R$^{13}$ is R$^{32}$, R$^{32}$ is —C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, or —NR$^9$C(O)NR$^{24}$R$^{25}$, each of which is optionally substituted, and B is heteroaryl.

In some embodiments, uses of compounds are provided, as described herein, comprising the administration of an effective amount of a compound of Formula IB or IC, wherein m=1, R$^1$ is H, R$^2$ is F, R$^6$ is alkanoyl, R$^{12}$ is R$^{32}$, R$^{32}$ is —C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, or —NR$^9$C(O)NR$^{24}$R$^{25}$, each of which is optionally substituted, R$^{13}$ is H, and B is phenyl.

In some embodiments, uses of compounds are provided, as described herein, comprising the administration of an effective amount of a compound of Formula IB or IC, wherein m=1, R$^1$ and R$^2$ are joined to form a 3 membered ring, R$^6$ is alkanoyl, R$^{12}$ is R$^{32}$, R$^{32}$ is —C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, or —NR$^9$C(O)NR$^{24}$R$^{25}$, each of which is optionally substituted, R$^{13}$ is H, and B is phenyl.

In some embodiments, uses of compounds are provided, as described herein, comprising the administration of an effective amount of a compound of Formula IB or IC, wherein m=1, R$^1$ is H, R$^2$ is F, R$^6$ is amide, R$^{12}$ is R$^{32}$, R$^{32}$ is —C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, or —NR$^9$C(O)NR$^{24}$R$^{25}$, each of which is optionally substituted, R$^{13}$ is H, and B is phenyl.

In some embodiments, uses of compounds are provided, as described herein, comprising the administration of an effective amount of a compound of Formula IB or IC, wherein m=1, R$^1$ and R$^2$ are joined to form a 3 membered ring, R$^6$ is amide, R$^{12}$ is R$^{32}$, R$^{32}$ is —C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, or —NR$^9$C(O)NR$^{24}$R$^{25}$, each of which is optionally substituted, R$^{13}$ is H, and B is phenyl.

In some embodiments, uses of compounds are provided, as described herein, comprising the administration of an effective amount of a compound of Formula IB or IC, wherein m=1, R$^1$ is H, R$^2$ is F, R$^6$ is alkanoyl, R$^{12}$ is H, R$^{13}$ is R$^{32}$, R$^{32}$ is —C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, or —NR$^9$C(O)NR$^{24}$R$^{25}$, each of which is optionally substituted, and B is phenyl.

In some embodiments, uses of compounds are provided, as described herein, comprising the administration of an effective amount of a compound of Formula IB or IC, wherein m=1, R$^1$ and R$^2$ are joined to form a 3 membered ring, R$^6$ is alkanoyl, R$^{12}$ is H, R$^{13}$ is R$^{32}$, R$^{32}$ is —C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, or —NR$^9$C(O)NR$^{24}$R$^{25}$, each of which is optionally substituted, and B is phenyl.

In some embodiments, uses of compounds are provided, as described herein, comprising the administration of an effective amount of a compound of Formula IB or IC, wherein m=1, R$^1$ is H, R$^2$ is F, R$^6$ is amide, R$^{12}$ is H, R$^{13}$ is R$^{32}$, R$^{32}$ is —C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, or —NR$^9$C(O)NR$^{24}$R$^{25}$, each of which is optionally substituted, and B is phenyl.

In some embodiments, uses of compounds are provided, as described herein, comprising the administration of an effective amount of a compound of Formula IB or IC, wherein m=1, R$^1$ and R$^2$ are joined to form a 3 membered ring, R$^6$ is amide, R$^{12}$ is H, R$^{13}$ is R$^{32}$, R$^{32}$ is —C(O)NR$^{21}$R$^{37}$, —C(O)NR$^{24}$R$^{25}$, —C(O)NR$^9$R$^{37}$, —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, or —NR$^9$C(O)NR$^{24}$R$^{25}$, each of which is optionally substituted, and B is phenyl.

Embodiments of Formula VII

To further illustrate the invention, various embodiments of Formula VII are provided that can be used as further described in this application. In one aspect, the disclosure includes uses, as described herein, of compounds and salts of Formula VII:

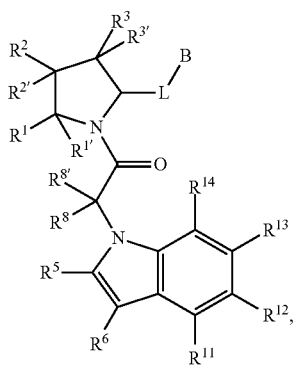

(VII)

wherein:

$R^1$, $R^2$, $R^{2'}$, and $R^3$ are independently selected from hydrogen, halogen, $C_1$-$C_4$alkyl, $C_1$-$C_4$alkoxy, —$C_0$-$C_2$alkylNR$^9$R$^{10}$, —$C_0$-$C_4$alkyl($C_3$-$C_7$cycloalkyl), —O—$C_0$-$C_4$alkyl($C_3$-$C_7$cycloalkyl), $C_1$-$C_2$haloalkyl, and $C_1$-$C_2$haloalkoxy;

$R^8$ and $R^{8'}$ are independently selected from hydrogen, halogen, and methyl;

$R^5$ is hydrogen, hydroxyl, cyano, —COOH, $C_1$-$C_6$alkyl, $C_1$-$C_6$alkoxy, $C_2$-$C_6$alkanoyl —$C_0$-$C_4$alkyl($C_3$-$C_7$cycloalkyl), —C(O)$C_0$-$C_4$alkyl($C_3$-$C_7$cycloalkyl), $C_1$-$C_2$haloalkyl, or $C_1$-$C_2$haloalkoxy;

$R^6$ is —C(O)CH$_3$, —C(O)NH$_2$, —C(O)CF$_3$, —C(O)(cyclopropyl), or -ethyl(cyanoimino); and $R^{11}$ and $R^{14}$ are independently selected from hydrogen, halogen, hydroxyl, amino, nitro, cyano, $C_1$-$C_6$alkyl, $C_2$-$C_6$alkenyl, $C_2$-$C_6$alkanoyl, $C_1$-$C_6$alkoxy, $C_1$-$C_6$thioalkyl, —$C_0$-$C_4$alkyl(mono- and di-$C_1$-$C_6$alkylamino), —$C_0$-$C_4$alkyl($C_3$-$C_7$cycloalkyl), —O$C_0$-$C_4$alkyl($C_3$-$C_7$cycloalkyl), $C_1$-$C_2$haloalkyl, and $C_1$-$C_2$haloalkoxy.

Non-limiting examples of compounds of the invention provided herein include the structures of FIGS. 9A, 9B, 9C, 9D, 9E, 9F, 9G, and 9H.

The use of prodrugs of Formula I and Table 1 for the treatment of a disorder in a host, typically a human, wherein the disorder is selected from the group disclosed in the Detailed Description, Part IV, Section A are within the scope of the disclosure. Prodrugs of compounds selected from Table 2 or an embodiment of the active compound as described in the Figures are also within the scope of the disclosure. The use of prodrugs of compounds selected from Table 2 or an embodiment of the active compound as described in the Figures for the treatment of a disorder in a host, typically a human, wherein the disorder is selected from the group disclosed in the Detailed Description, Part IV, Section A and Section B, are also within the scope of the disclosure.

III. Pharmaceutical Preparations

Active compounds described herein can be administered to a host in need thereof as the neat chemical, but are more typically administered as a pharmaceutical composition that includes an effective amount for a host, typically a human, in need of such treatment of an active compound as described herein or its pharmaceutically acceptable salt.

Thus, in one embodiment, the disclosure provides pharmaceutical compositions comprising an effective amount of compound or pharmaceutically acceptable salt together with at least one pharmaceutically acceptable carrier for any of the uses described herein. The pharmaceutical composition may contain a compound or salt as the only active agent, or, in an alternative embodiment, the compound and at least one additional active agent.

An effective amount of an active compound as described herein, or the active compound described herein in combination or alternation with, or preceded by, concomitant with or followed by another active agent, can be used in an amount sufficient to (a) inhibit the progression of a disorder mediated by the complement pathway, including an inflammatory, immune, including an autoimmune, disorder or complement Factor D related disorder; (b) cause a regression of an inflammatory, immune, including an autoimmune, disorder or complement Factor D related disorder; (c) cause a cure of an inflammatory, immune, including an autoimmune, disorder or complement Factor D related disorder; or inhibit or prevent the development of an inflammatory, immune, including an autoimmune, disorder or complement Factor D related disorder.

The exact amount of the active compound or pharmaceutical composition described herein to be delivered to the host, typically a human, in need thereof, will be determined by the health care provider to achieve the desired clinical benefit.

In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples are dosage forms with at least about 25, 50, 100, 200, 250, 300, 400, 500, 600, 700, 750, 800, 900, 1000, 1100, 1200, 1300, 1400, 1500, 1600, or 1700 mg of active compound, or its salt. In one embodiment, the dosage form has at least about 100 mg, 200 mg, 400 mg, 500 mg, 600 mg, 1000 mg, 1200 mg, or 1600 mg of active compound, or its salt. The amount of active compound in the dosage form is calculated without reference to the salt. The dosage form can be administered, for example, once a day (q.d.), twice a day (b.i.d.), three times a day (t.i.d.), four times a day (q.i.d.), once every other day (Q2d), once every third day (Q3d), as needed, or any dosage schedule that provides treatment of a disorder described herein.

The pharmaceutical composition may for example include any molar ratio of the active compound and additional active agent that achieves the desired result. For example, the pharmaceutical composition may contain a molar ratio of about 0.5:1, about 1:1, about 2:1, about 3:1 or from about 1.5:1 to about 4:1 of an additional active agent in combination with the active compound (additional active agent:active compound), or its salt, described herein. In one embodiment, the additional active agent is an anti-inflammatory or immunosuppressing agent.

Compounds disclosed herein or used as described herein may be administered orally, topically, parenterally, by inhalation or spray, sublingually, via implant, including ocular implant, transdermally, via buccal administration, rectally, as an ophthalmic solution, injection, including ocular injection, intravenous, intra-aortal, intracranial, subdermal, intraperitoneal, subcutaneous, transnasal, sublingual, intrathecal, or rectal or by other means, in dosage unit formulations containing conventional pharmaceutically acceptable carriers. For ocular delivery, the compound can be administered, as desired, for example, as a solution, suspension, or other formulation via intravitreal, intrastromal, intracameral, sub-tenon, sub-retinal, retro-bulbar, peribulbar, suprachorodial, subchorodial, chorodial, conjunctival, subconjunctival, episcleral, periocular, transscleral, retrobulbar, posterior juxtascleral, circumcorneal, or tear duct injections, or through a mucus, mucin, or a mucosal barrier, in an immediate or controlled release fashion or via an ocular device, injection, or topically administered formulation, for example a solution or suspension provided as an eye drop.

The pharmaceutical composition may be formulated as any pharmaceutically useful form, e.g., as an aerosol, a cream, a gel, a gel cap, a pill, a microparticle, a nanoparticle, an injection or infusion solution, a capsule, a tablet, a syrup, a transdermal patch, a subcutaneous patch, a dry powder, an inhalation formulation, in a medical device, suppository, buccal, or sublingual formulation, parenteral formulation, or an ophthalmic solution or suspension. Some dosage forms, such as tablets and capsules, are subdivided into suitably sized unit doses containing appropriate quantities of the active components, e.g., an effective amount to achieve the desired purpose.

Pharmaceutical compositions, and methods of manufacturing such compositions, suitable for administration as contemplated herein are known in the art. Examples of known techniques include, for example, U.S. Pat. Nos. 4,983,593, 5,013,557, 5,456,923, 5,576,025, 5,723,269, 5,858,411, 6,254,889, 6,303,148, 6,395,302, 6,497,903, 7,060,296, 7,078,057, 7,404,828, 8,202,912, 8,257,741, 8,263,128, 8,337,899, 8,431,159, 9,028,870, 9,060,938, 9,211,261, 9,265,731, 9,358,478, and 9,387,252, incorporated by reference herein.

The pharmaceutical compositions contemplated here can optionally include a carrier. Carriers must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound. Classes of carriers include, but are not limited to binders, buffering agents, coloring agents, diluents, disintegrants, emulsifiers, fillers, flavorants, glidents, lubricants, pH modifiers, preservatives, stabilizers, surfactants, solubilizers, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Examples of other matrix materials, fillers, or diluents include lactose, mannitol, xylitol, microcrystalline cellulose, calcium diphosphate, and starch. Examples of surface active agents include sodium lauryl sulfate and polysorbate 80. Examples of drug complexing agents or solubilizers include the polyethylene glycols, caffeine, xanthene, gentisic acid and cylodextrins. Examples of disintegrants include sodium starch gycolate, sodium alginate, carboxymethyl cellulose sodium, methyl cellulose, colloidal silicon dioxide, and croscarmellose sodium. Examples of binders include methyl cellulose, microcrystalline cellulose, starch, and gums such as guar gum, and tragacanth. Examples of lubricants include magnesium stearate and calcium stearate. Examples of pH modifiers include acids such as citric acid, acetic acid, ascorbic acid, lactic acid, aspartic acid, succinic acid, phosphoric acid, and the like; bases such as sodium acetate, potassium acetate, calcium oxide, magnesium oxide, trisodium phosphate, sodium hydroxide, calcium hydroxide, aluminum hydroxide, and the like, and buffers generally comprising mixtures of acids and the salts of said acids. Optional other active agents may be included in a pharmaceutical composition, which do not substantially interfere with the activity of the compound of the present invention.

In certain embodiments, the pharmaceutical composition for administration further includes an active compound as described herein and optionally comprises one or more of a phosphoglyceride; phosphatidylcholine; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohol such as polyethylene glycol (PEG); polyoxyethylene-9-lauryl ether; a surface active fatty acid, such as palmitic acid or oleic acid; fatty acid; fatty acid monoglyceride; fatty acid diglyceride; fatty acid amide; sorbitan trioleate (Span®85) glycocholate; sorbitan monolaurate (Span®20); polysorbate 20 (Tween®20); polysorbate 60 (Tween®60); polysorbate 65 (Tween®65); polysorbate 80 (Tween®80); polysorbate 85 (Tween®85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebroside; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidyletanolamine; poly(ethylene glycol)400-monostearate; phospholipid; synthetic and/or natural detergent having high surfactant properties; deoxycholate; cyclodextrin; chaotropic salt; ion pairing agent; glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid; pullulan, cellulose, microcrystalline cellulose, hydroxypropyl methylcellulose (HPMC), hydroxycellulose (HC), methylcellulose (MC), dextran, cyclodextran, glycogen, hydroxyethyl starch, carageenan, glycon, amylose, chitosan, N,O-carboxylmethylchitosan, algin and alginic acid, starch, chitin, inulin, konjac, glucommannan, pustulan, heparin, hyaluronic acid, curdlan, and xanthan, mannitol, sorbitol, xylitol, erythritol, maltitol, and lactitol, a pluronic polymer, polyethylene, polycarbonate (e.g. poly(1,3-dioxan-2one)), polyanhydride (e.g. poly(sebacic anhydride)), polypropylfumerate, polyamide (e.g. polycaprolactam), polyacetal, polyether, polyester (e.g., polylactide, polyglycolide, polylactide-co-glycolide, polycaprolactone, polyhydroxyacid (e.g. poly((β-hydroxyalkanoate))), poly(orthoester), polycyanoacrylate, polyvinyl alcohol, polyurethane, polyphosphazene, polyacrylate, polymethacrylate, polyurea, polystyrene, and polyamine, polylysine, polylysine-PEG copolymer, and poly(ethyleneimine), poly(ethylene imine)-PEG copolymer, glycerol monocaprylocaprate, propylene glycol, Vitamin E TPGS (also known as d-α-Tocopheryl polyethylene glycol 1000 succinate), gelatin, titanium dioxide, polyvinylpyrrolidone (PVP), hydroxypropyl methyl cellulose (HPMC), hydroxypropyl cellulose (HPC), methyl cellulose (MC), block copolymers of ethylene oxide and propylene oxide (PEO/PPO), polyethyleneglycol (PEG), sodium carboxymethylcellulose (NaCMC), hydroxypropylmethyl cellulose acetate succinate (HPMCAS).

In some embodiments, the pharmaceutical preparation may include a polymer for controlled delivery of the described compounds, including, but not limited to, a pluronic polymer, polyester (e.g., polylactic acid, poly(lactic-co-glycolic acid), polycaprolactone, polyvalerolactone, poly(1,3-dioxan-2one)); polyanhydride (e.g., poly(sebacic anhydride)); polyether (e.g., polyethylene glycol); polyurethane; polymethacrylate; polyacrylate; and polycyanoacrylate. In some embodiments, the polymer may be modified with polyethylene glycol (PEG), with a carbohydrate, and/or with an acyclic polyacetal derived from a polysaccharide. See, e.g., Papisov, 2001, ACS Symposium Series, 786:301, incorporated by reference herein.

The compounds of the present invention can be formulated as particles. In one embodiment the particles are or include microparticles. In an alternative embodiment the particles are or include nanoparticles.

In an additional alternative embodiment, common techniques for preparing particles include, but are not limited to, solvent evaporation, solvent removal, spray drying, phase inversion, coacervation, and low temperature casting. Suitable methods of particle formulation are briefly described below. Pharmaceutically acceptable excipients, including pH modifying agents, disintegrants, preservatives, and antioxidants, can optionally be incorporated into the particles during particle formation.

In one embodiment, the particles are derived through a solvent evaporation method. In this method, a compound described herein (or polymer matrix and one or more compounds described herein) is dissolved in a volatile organic solvent, such as methylene chloride. The organic solution containing a compound described herein is then suspended in an aqueous solution that contains a surface active agent such as poly(vinyl alcohol). The resulting emulsion is stirred until most of the organic solvent evaporated, leaving solid nanoparticles or microparticles. The resulting nanoparticles or microparticles are washed with water and dried overnight in a lyophilizer. Nanoparticles with different sizes and morphologies can be obtained by this method.

Pharmaceutical compositions which contain labile polymers, such as certain polyanhydrides, may degrade during the fabrication process due to the presence of water. For these polymers, methods which are performed in completely or substantially anhydrous organic solvents can be used to make the particles.

Solvent removal can also be used to prepare particles of a compound that is hydrolytically unstable. In this method, the compound (or polymer matrix and one or more compounds) is dispersed or dissolved in a volatile organic solvent such as methylene chloride. This mixture is then suspended by stirring in an organic oil (such as silicon oil) to form an emulsion. Solid particles form from the emulsion, which can subsequently be isolated from the supernatant. The external morphology of spheres produced with this technique is highly dependent on the identity of the drug.

In one embodiment an active compound as described herein is administered to a patient in need thereof as particles formed by solvent removal. In another embodiment the present invention provides particles formed by solvent removal comprising a compound of the present invention and one or more pharmaceutically acceptable excipients as defined herein. In another embodiment the particles formed by solvent removal comprise a compound of the present invention and an additional therapeutic agent. In a further embodiment the particles formed by solvent removal comprise a compound of the present invention, an additional therapeutic agent, and one or more pharmaceutically acceptable excipients. In another embodiment any of the described particles formed by solvent removal can be formulated into a tablet and then coated to form a coated tablet. In an alternative embodiment the particles formed by solvent removal are formulated into a tablet but the tablet is uncoated.

In one embodiment, the particles are derived by spray drying. In this method, a compound (or polymer matrix and one or more compounds) is dissolved in an organic solvent such as methylene chloride. The solution is pumped through a micronizing nozzle driven by a flow of compressed gas, and the resulting aerosol is suspended in a heated cyclone of air, allowing the solvent to evaporate from the micro droplets, forming particles. Microparticles and nanoparticles can be obtained using this method.

In one embodiment an active compound as described herein is administered to a patient in need thereof as a spray dried dispersion (SDD). In another embodiment the present invention provides a spray dried dispersion (SDD) comprising a compound of the present invention and one or more pharmaceutically acceptable excipients as defined herein. In another embodiment the SDD comprises a compound of the present invention and an additional therapeutic agent. In a further embodiment the SDD comprises a compound of the present invention, an additional therapeutic agent, and one or more pharmaceutically acceptable excipients. In another embodiment any of the described spray dried dispersions can be coated to form a coated tablet. In an alternative embodiment the spray dried dispersion is formulated into a tablet but is uncoated.

Particles can be formed from the active compound as described herein using a phase inversion method. In this method, the compound (or polymer matrix and one or more active compounds) is dissolved in a suitable solvent, and the solution is poured into a strong non-solvent for the compound to spontaneously produce, under favorable conditions, microparticles or nanoparticles. The method can be used to produce nanoparticles in a wide range of sizes, including, for example, from nanoparticles to microparticles, typically possessing a narrow particle size distribution.

In one embodiment, an active compound as described herein is administered to a patient in need thereof as particles formed by phase inversion. In another embodiment the present invention provides particles formed by phase inversion comprising a compound of the present invention and one or more pharmaceutically acceptable excipients as defined herein. In another embodiment the particles formed by phase inversion comprise a compound of the present invention and an additional therapeutic agent. In a further embodiment the particles formed by phase inversion comprise a compound of the present invention, an additional therapeutic agent, and one or more pharmaceutically acceptable excipients. In another embodiment any of the described particles formed by phase inversion can be formulated into a tablet and then coated to form a coated tablet. In an alternative embodiment the particles formed by phase inversion are formulated into a tablet but the tablet is uncoated.

Techniques for particle formation using coacervation are known in the art, for example, as described in GB-B-929 406; GB-B-929 40 1; and U.S. Pat. Nos. 3,266,987, 4,794, 000, and 4,460,563. Coacervation involves the separation of a compound (or polymer matrix and one or more compounds) solution into two immiscible liquid phases. One phase is a dense coacervate phase, which contains a high concentration of the compound, while the second phase contains a low concentration of the compound. Within the dense coacervate phase, the compound forms nanoscale or microscale droplets, which harden into particles. Coacervation may be induced by a temperature change, addition of a non-solvent or addition of a micro-salt (simple coacervation), or by the addition of another polymer thereby forming an interpolymer complex (complex coacervation).

In one embodiment an active compound as described herein is administered to a patient in need thereof as particles formed by coacervation. In another embodiment the present invention provides particles formed by coacervation comprising a compound of the present invention and one or more pharmaceutically acceptable excipients as defined herein. In another embodiment the particles formed by coacervation comprise a compound of the present invention and an additional therapeutic agent. In a further embodiment the particles formed by coacervation comprise a compound of the present invention, an additional therapeutic agent, and one or more pharmaceutically acceptable excipients. In another embodiment any of the described particles formed by coacervation can be formulated into a tablet and then coated to form a coated tablet. In an alternative embodiment the particles formed by coacervation are formulated into a tablet but the tablet is uncoated.

Methods for very low temperature casting of controlled release microspheres are described in U.S. Pat. No. 5,019,400 to Gombotz et al. In this method, the compound is dissolved in a solvent. The mixture is then atomized into a vessel containing a liquid non-solvent at a temperature below the freezing point of the drug solution which freezes the compound droplets. As the droplets and non-solvent for the compound are warmed, the solvent in the droplets thaws and is extracted into the non-solvent, hardening the microspheres.

In one embodiment, a compound of the present invention is administered to a patient in need thereof as particles formed by low temperature casting. In another embodiment the present invention provides particles formed by low temperature casting comprising a compound of the present invention and one or more pharmaceutically acceptable excipients as defined herein. In another embodiment the particles formed by low temperature casting comprise a compound of the present invention and an additional therapeutic agent. In a further embodiment the particles formed by low temperature casting comprise a compound of the present invention, an additional therapeutic agent, and one or more pharmaceutically acceptable excipients. In another embodiment any of the described particles formed by low temperature casting can be formulated into a tablet and then coated to form a coated tablet. In an alternative embodiment the particles formed by low temperature casting are formulated into a tablet but the tablet is uncoated.

In one aspect of the present invention, an effective amount of an active compound as described herein is incorporated into a nanoparticle, e.g. for convenience of delivery and/or extended release delivery. The use of materials in nanoscale provides one the ability to modify fundamental physical properties such as solubility, diffusivity, blood circulation half-life, drug release characteristics, and/or immunogenicity. A number of nanoparticle-based therapeutic and diagnostic agents have been developed for the treatment of cancer, diabetes, pain, asthma, allergy, and infections. These nanoscale agents may provide more effective and/or more convenient routes of administration, lower therapeutic toxicity, extend the product life cycle, and ultimately reduce health-care costs. As therapeutic delivery systems, nanoparticles can allow targeted delivery and controlled release.

In addition, nanoparticle-based compound delivery can be used to release compounds at a sustained rate and thus lower the frequency of administration, deliver drugs in a targeted manner to minimize systemic side effects, or to deliver two or more drugs simultaneously for combination therapy to generate a synergistic effect and suppress drug resistance. A number of nanotechnology-based therapeutic products have been approved for clinical use. Among these products, liposomal drugs and polymer-based conjugates account for a large proportion of the products. See, Zhang, L., et al., Nanoparticles in Medicine: Therapeutic Applications and Developments, Clin. Pharm. and Ther., 83(5):761-769, 2008.

Methods for producing nanoparticles are known in the art. For example, see Muller, R. H., et al., Solid lipid nanoparticles (SLN) for controlled drug delivery—a review of the state of the art, Eur. H. Pharm. Biopharm., 50:161-177, 2000; U.S. Pat. No. 8,691,750 to Consien et al.; WO 2012/145801 to Kanwar. U.S. Pat. No. 8,580,311 to Armes, S. et al.; Petros, R. A. and DeSimone, J. M., Strategies in the design of nanoparticles for therapeutic applications, Nature Reviews/Drug Discovery, vol. 9:615-627, 2010; U.S. Pat. No. 8,465,775; U.S. Pat. No. 8,444,899; U.S. Pat. No. 8,420,124; U.S. Pat. No. 8,263,129; U.S. Pat. Nos. 8,158,728; 8,268,446; Pellegrino et al., 2005, Small, 1:48; Murray et al., 2000, Ann. Rev. Mat. Sci., 30:545; and Trindade et al., 2001, Chem. Mat., 13:3843; all incorporated herein by reference. Additional methods have been described in the literature (see, e.g., Doubrow, Ed., "Microcapsules and Nanoparticles in Medicine and Pharmacy," CRC Press, Boca Raton, 1992; Mathiowitz et al., 1987, J. Control. Release, 5:13; Mathiowitz et al., 1987, Reactive Polymers, 6:275; and Mathiowitz et al., 1988, J. Appl. Polymer Sci., 35:755; U.S. Pat. Nos. 5,578,325 and 6,007,845; P. Paolicelli et al., "Surface-modified PLGA-based Nanoparticles that can Efficiently Associate and Deliver Virus-like Particles" Nanomedicine. 5(6):843-853 (2010)), U.S. Pat. No. 5,543,158 to Gref et al., or WO publication WO2009/051837 by Von Andrian et al. Zauner et al., 1998, Adv. Drug Del. Rev., 30:97; and Kabanov et al., 1995, Bioconjugate Chem., 6:7; (PEI; Boussif et al., 1995, Proc. Natl. Acad. Sci., USA, 1995, 92:7297), and poly(amidoamine) dendrimers (Kukowska-Latallo et al., 1996, Proc. Natl. Acad. Sci., USA, 93:4897; Tang et al., 1996, Bioconjugate Chem., 7:703; and Haensler et al., 1993, Bioconjugate Chem., 4:372; Putnam et al., 1999, Macromolecules, 32:3658; Barrera et al., 1993, J. Am. Chem. Soc., 115:11010; Kwon et al., 1989, Macromolecules, 22:3250; Lim et al., 1999, J. Am. Chem. Soc., 121:5633; and Zhou et al., 1990, Macromolecules, 23:3399). Examples of these polyesters include poly(L-lactide-co-L-lysine) (Barrera et al., 1993, J. Am. Chem. Soc., 115:11010), poly(serine ester) (Zhou et al., 1990, Macromolecules, 23:3399), poly(4-hydroxy-L-proline ester) (Putnam et al., 1999, Macromolecules, 32:3658; and Lim et al., 1999, J. Am. Chem. Soc., 121:5633), and poly(4-hydroxy-L-proline ester) (Putnam et al., 1999, Macromolecules, 32:3658; and Lim et al., 1999, J. Am. Chem. Soc., 121:5633; U.S. Pat. No. 6,123,727; U.S. Pat. No. 5,804,178; U.S. Pat. No. 5,770,417; U.S. Pat. No. 5,736,372; U.S. Pat. No. 5,716,404; U.S. Pat. No. 6,095,148; U.S. Pat. No. 5,837,752; U.S. Pat. No. 5,902,599; U.S. Pat. No. 5,696,175; U.S. Pat. No. 5,514,378; U.S. Pat. No. 5,512,600; U.S. Pat. No. 5,399,665; U.S. Pat. No. 5,019,379; U.S. Pat. No. 5,010,167; U.S. Pat. No. 4,806,621; U.S. Pat. No. 4,638,045; and U.S. Pat. No. 4,946,929; Wang et al., 2001, J. Am. Chem. Soc., 123:9480; Lim et al., 2001, J. Am. Chem. Soc., 123:2460; Langer, 2000, Acc. Chem. Res., 33:94; Langer, 1999, J. Control.

Release, 62:7; and Uhrich et al., 1999, Chem. Rev., 99:3181; Concise Encyclopedia of Polymer Science and Polymeric Amines and Ammonium Salts, Ed. by Goethals, Pergamon Press, 1980; Principles of Polymerization by Odian, John Wiley & Sons, Fourth Edition, 2004; Contemporary Polymer Chemistry by Allcock et al., Prentice-Hall, 1981; Deming et al., 1997, Nature, 390:386; and in U.S. Pat. Nos. 6,506,577, 6,632,922, 6,686,446, and 6,818,732; C. Astete et al., "Synthesis and characterization of PLGA nanoparticles" J. Biomater. Sci. Polymer Edn, Vol. 17, No. 3, pp. 247-289 (2006); K. Avgoustakis "Pegylated Poly(Lactide) and Poly(Lactide-Co-Glycolide) Nanoparticles: Preparation, Properties and Possible Applications in Drug Delivery" Current Drug Delivery 1:321-333 (2004); C. Reis et al., "Nanoencapsulation I. Methods for preparation of drug-loaded polymeric nanoparticles" Nanomedicine 2:8-21 (2006); P. Paolicelli et al., "Surface-modified PLGA-based Nanoparticles that can Efficiently Associate and Deliver Virus-like Particles" Nanomedicine. 5(6):843-853 (2010); U.S. Pat. No. 6,632,671 to Unger Oct. 14, 2003, all incorporated herein by reference.

In one embodiment, the polymeric particle is between about 0.1 nm to about 10000 nm, between about 1 nm to about 1000 nm, between about 10 nm and 1000 nm, between about 1 and 100 nm, between about 1 and 10 nm, between about 1 and 50 nm, between about 100 nm and 800 nm, between about 400 nm and 600 nm, or about 500 nm. In one embodiment, the micro-particles are no more than about 0.1 nm, 0.5 nm, 1.0 nm, 5.0 nm, 10 nm, 25 nm, 50 nm, 75 nm, 100 nm, 150 nm, 200 nm, 250 nm, 300 nm, 400 nm, 450 nm, 500 nm, 550 nm, 600 nm, 650 nm, 700 nm, 750 nm, 800 nm, 850 nm, 900 nm, 950 nm, 1000 nm, 1250 nm, 1500 nm, 1750 nm, or 2000 nm. In some embodiments, a compound described herein may be covalently coupled to a polymer used in the nanoparticle, for example a polystyrene particle, PLGA particle, PLA particle, or other nanoparticle.

The pharmaceutical compositions can be formulated for oral administration. These compositions can contain any amount of active compound that achieves the desired result, for example between 0.1 and 99 weight % (wt. %) of the compound and usually at least about 5 wt. % of the compound. Some embodiments contain at least about 10%, 15%, 20%, 25 wt. % to about 50 wt. % or from about 5 wt. % to about 75 wt. % of the compound.

Pharmaceutical compositions suitable for rectal administration are typically presented as unit dose suppositories. These may be prepared by admixing the active compound with one or more conventional solid carriers, for example, cocoa butter, and then shaping the resulting mixture.

Pharmaceutical compositions suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Pharmaceutical compositions suitable for transdermal administration may be presented as discrete patches adapted to remain in intimate contact with the epidermis of the recipient for a prolonged period of time. Pharmaceutical compositions suitable for transdermal administration may also be delivered by iontophoresis (see, for example, *Pharmaceutical Research* 3 (6):318 (1986)) and typically take the form of an optionally buffered aqueous solution of the active compound. In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Pharmaceutical compositions suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

Additional non-limiting examples of inhalation drug delivery devices and methods include, for example, U.S. Pat. No. 7,383,837 titled "Inhalation device" (SmithKline Beecham Corporation); WO/2006/033584 titled "Powder inhaler" (Glaxo SmithKline Pharmaceuticals SA); WO/2005/044186 titled "Inhalable pharmaceutical formulations employing desiccating agents and methods of administering the same" (Glaxo Group Ltd and SmithKline Beecham Corporation); U.S. Pat. No. 9,095,670 titled "Inhalation device and method of dispensing medicament", U.S. Pat. No. 8,205,611 titled "Dry powder inhaler" (Astrazeneca AB); WO/2013/038170 titled "Inhaler" (Astrazeneca AB and Astrazeneca UK Ltd.); US/2014/0352690 titled "Inhalation Device with Feedback System", U.S. Pat. No. 8,910,625 and US/2015/0165137 titled "Inhalation Device for Use in Aerosol Therapy" (Vectura GmbH); U.S. Pat. No. 6,948,496 titled "Inhalers", US/2005/0152849 titled "Powders comprising anti-adherent materials for use in dry powder inhalers", U.S. Pat. No. 6,582,678, U.S. Pat. No. 8,137,657, US/2003/0202944, and US/2010/0330188 titled "Carrier particles for use in dry powder inhalers", U.S. Pat. No. 6,221,338 titled "Method of producing particles for use in dry powder inhalers", U.S. Pat. No. 6,989,155 titled "Powders", US/2007/0043030 titled "Pharmaceutical compositions for treating premature ejaculation by pulmonary inhalation", U.S. Pat. No. 7,845,349 titled "Inhaler", US/2012/0114709 and U.S. Pat. No. 8,101,160 titled "Formulations for Use in Inhaler Devices", US/2013/0287854 titled "Compositions and Uses", US/2014/0037737 and U.S. Pat. No. 8,580,306 titled "Particles for Use in a Pharmaceutical Composition", US/2015/0174343 titled "Mixing Channel for an Inhalation Device", U.S. Pat. No. 7,744,855 and US/2010/0285142 titled "Method of making particles for use in a pharmaceutical composition", U.S. Pat. No. 7,541,022, US/2009/0269412, and US/2015/0050350 titled "Pharmaceutical formulations for dry powder inhalers" (Vectura Limited).

Many methods and devices for drug delivery to the eye are known in the art. Non-limiting examples are described in the following patents and patent applications (fully incorporated herein by reference). Examples are U.S. Pat. No. 8,192,408 titled "Ocular trocar assembly" (Psivida Us, Inc.); U.S. Pat. No. 7,585,517 titled "Transcleral delivery" (Macusight, Inc.); U.S. Pat. No. 5,710,182 and U.S. Pat. No. 5,795,913 titled "Ophthalmic composition" (Santen O Y); U.S. Pat. No. 8,663,639 titled "Formulations for treating ocular diseases and conditions", U.S. Pat. No. 8,486,960 titled "Formulations and methods for vascular permeability-related diseases or conditions", U.S. Pat. No. 8,367,097 and U.S. Pat. No. 8,927,005 titled "Liquid formulations for treatment of diseases or conditions", U.S. Pat. No. 7,455,855 titled "Delivering substance and drug delivery system using the same" (Santen Pharmaceutical Co., Ltd.); WO/2011/050365 titled "Conformable Therapeutic Shield For Vision and Pain" and WO/2009/145842 titled "Therapeutic Device for Pain Management and Vision" (Forsight Labs, LLC); U.S. Pat. No. 9,066,779 and U.S. Pat. No. 8,623,395 titled "Implantable therapeutic device", WO/2014/160884 titled "Ophthalmic Implant for Delivering Therapeutic Substances", U.S. Pat. No. 8,399,006, U.S. Pat. No. 8,277,830, U.S. Pat. No. 8,795,712, U.S. Pat. No. 8,808,727, U.S. Pat. No. 8,298,578, and WO/2010/088548 titled "Posterior segment drug delivery", WO/2014/152959 and US20140276482 titled "Systems for Sustained Intraocular Delivery of Low Solubility Compounds from a Port Delivery System Implant", U.S. Pat. No. 8,905,963 and U.S. Pat. No. 9,033,911 titled "Injector apparatus and method for drug delivery", WO/2015/057554 titled "Formulations and Methods for Increasing or Reducing Mucus", U.S. Pat. No. 8,715,712 and U.S. Pat. No. 8,939,948 titled "Ocular insert apparatus and methods", WO/2013/116061 titled "Insertion and Removal Methods and Apparatus for Therapeutic Devices", WO/2014/066775 titled "Ophthalmic System for Sustained Release of Drug to the Eye", WO/2015/085234 and WO/2012/019176 titled "Implantable Therapeutic Device", WO/2012/065006 titled "Methods and Apparatus to determine Porous Structures for Drug Delivery", WO/2010/141729 titled "Anterior Segment Drug Delivery", WO/2011/050327 titled "Corneal Denervation for Treatment of Ocular Pain", WO/2013/022801 titled "Small Molecule Delivery with Implantable Therapeutic Device", WO/2012/019047 titled "Subconjunctival Implant for Posterior Segment Drug Delivery", WO/2012/068549 titled "Therapeutic Agent Formulations for Implanted Devices", WO/2012/019139 titled "Combined Delivery Methods and Apparatus", WO/2013/040426 titled "Ocular Insert Apparatus and Methods", WO/2012/019136 titled "Injector Apparatus and Method for Drug Delivery", WO/2013/040247 titled "Fluid Exchange Apparatus and Methods" (ForSight Vision4, Inc.).

Additional non-limiting examples of how to deliver the active compounds are provided in WO/2015/085251 titled "Intracameral Implant for Treatment of an Ocular Condition" (Envisia Therapeutics, Inc.); WO/2011/008737 titled "Engineered Aerosol Particles, and Associated Methods", WO/2013/082111 titled "Geometrically Engineered Particles and Methods for Modulating Macrophage or Immune Responses", WO/2009/132265 titled "Degradable compounds and methods of use thereof, particularly with particle replication in non-wetting templates", WO/2010/099321 titled "Interventional drug delivery system and associated methods", WO/2008/100304 titled "Polymer particle composite having high fidelity order, size, and shape particles", WO/2007/024323 titled "Nanoparticle fabrication methods, systems, and materials" (Liquidia Technologies, Inc. and the University of North Carolina at Chapel Hill); WO/2010/009087 titled "Iontophoretic Delivery of a Controlled-Release Formulation in the Eye", (Liquidia Technologies, Inc. and Eyegate Pharmaceuticals, Inc.) and WO/2009/132206 titled "Compositions and Methods for Intracellular Delivery and Release of Cargo", WO/2007/133808 titled "Nanoparticles for cosmetic applications", WO/2007/056561 titled "Medical device, materials, and methods", WO/2010/065748 titled "Method for producing patterned materials", WO/2007/081876 titled "Nanostructured surfaces for biomedical/biomaterial applications and processes thereof" (Liquidia Technologies, Inc.).

Additional non-limiting examples of methods and devices for drug delivery to the eye include, for example, WO2011/106702 and U.S. Pat. No. 8,889,193 titled "Sustained delivery of therapeutic agents to an eye compartment", WO2013/138343 and U.S. Pat. No. 8,962,577 titled "Controlled release formulations for the delivery of HIF-1 inhibitors", WO/2013/138346 and US2013/0272994 titled "Non-Linear Multiblock Copolymer-Drug Conjugates for the Delivery of Active Agents", WO2005/072710 and U.S. Pat. No. 8,957,034 titled "Drug and Gene Carrier Particles that Rapidly Move Through Mucus Barriers", WO2008/030557, US2010/0215580, US2013/0164343 titled "Compositions and Methods for Enhancing Transport Through Mucous", WO2012/061703, US2012/0121718, and US2013/0236556 titled "Compositions and Methods Relating to Reduced Mucoadhesion", WO2012/039979 and US2013/0183244 titled "Rapid Diffusion of Large Polymeric Nanoparticles in the Mammalian Brain", WO2012/109363 and US2013/0323313 titled "Mucus Penetrating Gene Carriers", WO 2013/090804 and US2014/0329913 titled "Nanoparticles with enhanced mucosal penetration or decreased inflammation", WO2013/110028 titled "Nanoparticle formulations with enhanced mucosal penetration", WO2013/166498 and US2015/0086484 titled "Lipid-based drug carriers for rapid penetration through mucus linings" (The Johns Hopkins University); WO2013/166385 titled "Pharmaceutical Nanoparticles Showing Improved Mucosal Transport", US2013/0323179 titled "Nanocrystals, Compositions, And Methods that Aid Particle Transport in Mucus" (The Johns Hopkins University and Kala Pharmaceuticals, Inc.); WO/2015/066444 titled "Compositions and methods for ophthalmic and/or other applications", WO/2014/020210 and WO/2013/166408 titled "Pharmaceutical nanoparticles showing improved mucosal transport" (Kala Pharmaceuticals, Inc.); U.S. Pat. No. 9,022,970 titled "Ophthalmic injection device including dosage control device", WO/2011/153349 titled "Ophthalmic compositions comprising pbo-peo-pbo block copolymers", WO/2011/140203 titled "Stabilized ophthalmic galactomannan formulations", WO/2011/068955 titled "Ophthalmic emulsion", WO/2011/037908 titled "Injectable aqueous ophthalmic composition and method of use therefor", US2007/0149593 titled "Pharmaceutical Formulation for Delivery of Receptor Tyrosine Kinase Inhibiting (RTKi) Compounds to the Eye", U.S. Pat. No. 8,632,809 titled "Water insoluble polymer matrix for drug delivery" (Alcon, Inc.).

Additional non-limiting examples of drug delivery devices and methods include, for example, US20090203709 titled "Pharmaceutical Dosage Form For Oral Administration Of Tyrosine Kinase Inhibitor" (Abbott Laboratories); US20050009910 titled "Delivery of an active drug to the posterior part of the eye via subconjunctival or periocular delivery of a prodrug", US 20130071349 titled "Biodegradable polymers for lowering intraocular pressure", U.S. Pat. No. 8,481,069 titled "Tyrosine kinase microspheres", U.S. Pat. No. 8,465,778 titled "Method of making tyrosine kinase microspheres", U.S. Pat. No. 8,409,607 titled "Sustained release intraocular implants containing tyrosine kinase inhibitors and related methods", U.S. Pat. No. 8,512,738 and US 2014/0031408 titled "Biodegradable intravitreal tyrosine kinase implants", US 2014/0294986 titled "Microsphere Drug Delivery System for Sustained Intraocular Release", U.S. Pat. No. 8,911,768 titled "Methods For Treating Retinopathy With Extended Therapeutic Effect" (Allergan, Inc.); U.S. Pat. No. 6,495,164 titled "Preparation of injectable suspensions having improved inj ectability" (Alkermes Controlled Therapeutics, Inc.); WO 2014/047439 titled "Biodegradable Microcapsules Containing Filling Material" (Akina, Inc.); WO 2010/132664 titled "Compositions And Methods For Drug Delivery" (Baxter International Inc. Baxter Healthcare SA); US20120052041 titled "Polymeric nanoparticles with enhanced drugloading and methods of use thereof" (The Brigham and Women's Hospital, Inc.); US20140178475, US20140248358, and US20140249158 titled "Therapeutic Nanoparticles Comprising a Therapeutic Agent and Methods of Making and Using Same" (BIND Therapeutics, Inc.); U.S. Pat. No. 5,869,103 titled "Polymer microparticles for drug delivery" (Danbiosyst UK Ltd.); U.S. Pat. No. 8,628,801 titled "Pegylated Nanoparticles" (Universidad de Navarra); US2014/0107025 titled "Ocular drug delivery system" (Jade Therapeutics, LLC); U.S. Pat. No. 6,287,588 titled "Agent delivering system comprised of microparticle and biodegradable gel with an improved releasing profile and methods of use thereof", U.S. Pat. No. 6,589,549 titled "Bioactive agent delivering system comprised of microparticles within a biodegradable to improve release profiles" (Macromed, Inc.); U.S. Pat. No. 6,007,845 and U.S. Pat. No. 5,578,325 titled "Nanoparticles and microparticles of non-linear hydrophilichydrophobic multi-block copolymers" (Massachusetts Institute of Technology); US20040234611, US20080305172, US20120269894, and US20130122064 titled "Ophthalmic depot formulations for periocular or subconjunctival administration (Novartis Ag); U.S. Pat. No. 6,413,539 titled "Block polymer" (Poly-Med, Inc.); US 20070071756 titled "Delivery of an agent to ameliorate inflammation" (Peyman); US 20080166411 titled "Injectable Depot Formulations And Methods For Providing Sustained Release Of Poorly Soluble Drugs Comprising Nanoparticles" (Pfizer, Inc.); U.S. Pat. No. 6,706,289 titled "Methods and compositions for enhanced delivery of bioactive molecules" (PR Pharmaceuticals, Inc.); and U.S. Pat. No. 8,663,674 titled "Microparticle containing matrices for drug delivery" (Surmodics).

IV. Uses of Active Compounds for Treatment of Selected Disorders

In one aspect, an active compound or its salt or composition, as described herein is used to treat a medical disorder which is an inflammatory or immune condition, a disorder mediated by the complement cascade (including a dysfunctional cascade) including a complement D-related disorder, a disorder or abnormality of a cell that adversely affects the ability of the cell to engage in or respond to normal complement activity, or an undesired complement-mediated response to a medical treatment, such as surgery or other medical procedure or a pharmaceutical or biopharmaceutical drug administration, a blood transfusion, or other allogenic tissue or fluid administration.

Section A Disorders

In one embodiment, the invention is the use of a compound of Formula I, or a pharmaceutically acceptable salt or composition thereof, as well as the compounds of Table 1, Table 2, Table 3 or an embodiment of the active compound as described in the Figures for the treatment of a disorder as described in this Section A herein.

In one embodiment, the disorder is selected from fatty liver and conditions stemming from fatty liver, such as nonalcoholic steatohepatitis (NASH), liver inflammation, cirrhosis and liver failure. In one embodiment of the present invention, a method is provided for treating fatty liver disease in a host by administering an effective amount of a compound of Formula I, Table 1, Table 2, Table 3 or an embodiment of the active compound as described in the Figures or a pharmaceutically acceptable salt thereof, optionally in a pharmaceutically acceptable carrier. In one embodiment of the present invention, a method is provided for treating nonalcoholic steatohepatitis (NASH) in a host by administering an effective amount of a compound of Formula I, Table 1, Table 2, Table 3 or an embodiment of the active compound as described in the Figures, or a pharmaceutically acceptable salt thereof, optionally in a pharmaceutically acceptable carrier.

In another embodiment, the active compound is used to modulate an immune response prior to or during surgery or other medical procedure. One non-limiting example is use in connection with acute or chronic graft versus host disease, which is a common complication as a result of allogeneic tissue transplant, and can also occur as a result of a blood transfusion.

In one embodiment, the present invention provides a method of treating or preventing dermatomyositis by administering to a host in need thereof an effective amount of a composition comprising a compound of the current invention. In one embodiment, the present invention provides a method of treating or preventing amyotrophic lateral sclerosis by administering to a host in need thereof an effective amount of a composition comprising a compound of the current invention.

In another embodiment, a method is provided for the treatment or prevention of cytokine or inflammatory reactions in response to the administration of biotherapeutics (e.g. CAR T-cell therapy or monoclonal antibody therapy) in a host by administering an effective amount of a compound of Formula I, Table 1, Table 2, Table 3 or an embodiment of the active compound as described in the Figures, or a pharmaceutically acceptable salt thereof, optionally in a pharmaceutically acceptable carrier, or a pharmaceutically acceptable salt thereof, optionally in a pharmaceutically acceptable carrier. Various types of cytokine or inflammatory reactions may occur in response to biotherapeutics. In one embodiment, the cytokine or inflammatory reaction is cytokine release syndrome. In one embodiment, the cytokine or inflammatory reaction is tumor lysis syndrome (which also leads to cytokine release). Symptoms of cytokine release syndrome range from fever, headache, and skin rashes to bronchospasm, hypotension and even cardiac arrest. Severe cytokine release syndrome is described as cytokine storm, and can be fatal. Fatal cytokine storms have been observed in response to infusion with several monoclonal antibody therapeutics. See, Abramowicz D, et al. "Release of tumor necrosis factor, interleukin-2, and gamma-interferon in serum after injection of OKT3 monoclonal antibody in kidney transplant recipients" *Transplantation* (1989) 47(4):606-8; Chatenoud L, et al. "In vivo cell activation following OKT3 administration. Systemic cytokine release and modulation by corticosteroids" *Transplantation* (1990) 49(4):697-702; and Lim L C, Koh L P, and Tan P. "Fatal cytokine release syndrome with chimeric anti-CD20 monoclonal antibody rituximab in a 71-year-old patient with chronic lymphocytic leukemia" *J. Clin Oncol.* (1999) 17(6):1962-3.

Also contemplated herein, is the use of a compound of Formula I, Table 1, Table 2, Table 3 or an embodiment of the active compound as described in the Figures, or a pharmaceutically acceptable salt thereof, optionally in a pharmaceutically acceptable carrier to mediate an adverse immune response in patients receiving bi-specific T-cell engagers (BiTE). A bi-specific T-cell engager directs T-cells to target and bind with a specific antigen on the surface of a cancer cell. For example, Blinatumomab (Amgen), a BiTE has recently been approved as a second line therapy in Philadelphia chromosome-negative relapsed or refractory acute lymphoblastic leukemia. Blinatumomab is given by continuous intravenous infusion in 4-week cycles. The use of BiTE agents has been associated with adverse immune responses, including cytokine release syndrome. The most significantly elevated cytokines in the CRS associated with ACT include IL-10, IL-6, and IFN-γ (Klinger et al., Immunopharmacologic response of patients with B-lineage acute lymphoblastic leukemia to continuous infusion of T cell-engaging CD19/CD3-bispecific BiTE antibody blinatumomab. Blood (2012) 119:6226-6233).

In another embodiment, the disorder is episcleritis, idiopathic episcleritis, anterior episcleritis, or posterior episcleritis. In one embodiment, the disorder is idiopathic anterior uveitis, HLA-B27 related uveitis, herpetic keratouveitis, Posner Schlossman syndrome, Fuch's heterochromic iridocyclitis, or cytomegalovirus anterior uveitis.

In yet another embodiment, the disorder is selected from:
(i) vitritis, sarcoidosis, syphilis, tuberculosis, or Lyme disease;
(ii) retinal vasculitis, Eales disease, tuberculosis, syphilis, or toxoplasmosis;
(iii) neuroretinitis, viral retinitis, or acute retinal necrosis;
(iv) varicella zoster virus, herpes simplex virus, cytomegalovirus, Epstein-Barr virus, lichen planus, or Dengue-associated disease (e.g., hemorraghic Dengue Fever);
(v) Masquerade syndrome, contact dermatitis, trauma induced inflammation, UVB induced inflammation, eczema, granuloma annulare, or acne.

In an additional embodiment, the disorder is selected from:
(i) acute myocardial infarction, aneurysm, cardiopulmonary bypass, dilated cardiomyopathy, complement activation during cardiopulmonary bypass operations, coronary artery disease, restenosis following stent placement, or percutaneous transluminal coronary angioplasty (PTCA);
(ii) antibody-mediated transplant rejection, anaphylactic shock, anaphylaxis, allogenic transplant, humoral and vascular transplant rejection, graft dysfunction, graft-versus-host disease, Graves' disease, adverse drug reactions, or chronic graft vasculopathy;
(iii) allergic bronchopulmonary aspergillosis, allergic neuritis, drug allergy, radiation-induced lung injury, eosinophilic pneumonia, radiographic contrast media allergy, bronchiolitis obliterans, or interstitial pneumonia;
(iv) amyotrophic lateral sclerosis, parkinsonism-dementia complex, sporadic frontotemporal dementia, frontotemporal dementia with Parkinsonism linked to chromosome 17, frontotemporal lobar degeneration, tangle only dementia, cerebral amyloid angiopathy, cerebrovascular disorder, certain forms of frontotemporal dementia, chronic traumatic encephalopathy (CTE), PD with dementia (PDD), argyrophilic grain dementia, dementia pugilistica, dementia with Lewy Bodies (DLB), or multi-infarct dementia;
(v) Creutzfeldt-Jakob disease, Huntington's disease, multifocal motor neuropathy (MMN), prion protein cerebral amyloid angiopathy, polymyositis, postencephalitic parkinsonism, subacute sclerosing panencephalitis, non-Guamanian motor neuron disease with neurofibrillary tangles, neural regeneration, or diffuse neurofibrillary tangles with calcification.

In one embodiment, the disorder is selected from:
(i) atopic dermatitis, dermatitis, dermatomyositis, dermatomyositis bullous pemphigoid, scleroderma, sclerodermatomyositis, psoriatic arthritis, pemphigus vulgaris, cutaneous lupus, discoid lupus erythematosus, chilblain lupus erythematosus, or lupus erythematosus-lichen planus overlap syndrome;
(ii) cryoglobulinemic vasculitis, mesenteric/enteric vascular disorder, peripheral vascular disorder, antineutrophil cytoplasm antibody (ANCA)-associated vasculitis (AAV), IL-2 induced vascular leakage syndrome, or immune complex vasculitis;
(iii) angioedema, low platelets (HELLP) syndrome, sickle cell disease, platelet refractoriness, red cell casts, or typical or infectious hemolytic uremic syndrome (tHUS);
(iv) hematuria, hemodialysis, hemolysis, hemorrhagic shock, immunothrombocytopenic purpura (ITP), thrombotic thrombocytopenic purpura (TTP), idiopathic thrombocytopenic purpura (ITP), drug-induced thrombocytopenia, autoimmune hemolytic anemia (AIHA), azotemia, blood vessel and/or lymph vessel inflammation, rotational atherectomy, or delayed hemolytic transfusion reaction;
(v) British type amyloid angiopathy, Buerger's disease, bullous pemphigoid, Clq nephropathy, cancer, or catastrophic antiphospholipid syndrome.

In another embodiment, the disorder is selected from:
(i) wet AMD, dry AMD, chorioretinal degeneration, choroidal neovascularization (CNV), choroiditis, loss of RPE function, loss of vision (including loss of visual acuity or visual field), loss of vision from AMD, retinal damage in response to light exposure, retinal degeneration, retinal detachment, retinal dysfunction, retinal neovascularization (RNV), retinopathy of prematurity, or RPE degeneration;
(ii) pseudophakic bullous keratopathy, symptomatic macular degeneration related disorder, optic nerve degeneration, photoreceptor degeneration, cone degeneration, loss of photoreceptor cells, pars planitis, scleritis, proliferative vitreoretinopathy, or formation of ocular drusen;
(iii) chronic urticaria, Churg-Strauss syndrome, cold agglutinin disease (CAD), corticobasal degeneration (CBD), cryoglobulinemia, cyclitis, damage of the Bruch's membrane, Degos disease, diabetic angiopathy, elevated liver enzymes, endotoxemia, epidermolysis bullosa, or epidermolysis bullosa acquisita;
(iv) essential mixed cryoglobulinemia, excessive blood urea nitrogen-BUN, focal segmental glomerulosclerosis, Gerstmann-Straussler-Scheinker disease, giant cell arteritis, gout, Hallervorden-Spatz disease, Hashimoto's thyroiditis, Henoch-Schonlein purpura nephritis, or abnormal urinary sediments;
(v) hepatitis, hepatitis A, hepatitis B, hepatitis C or human immunodeficiency virus (HIV),
(vi) a viral infection more generally, for example selected from Flaviviridae, Retroviruses, Coronaviridae, Poxviridae, Adenoviridae, Herpesviridae, Caliciviridae, Reoviridae, Picornaviridae, Togaviridae, Orthomyxoviridae, Rhabdoviridae, or Hepadnaviridae;
(vii) *Neisseria meningitidis*, shiga toxin *E. coli*-related hemolytic uremic syndrome (STEC-HUS), *Streptococcus*, or poststreptococcal glomerulonephritis.

In a further embodiment, the disorder is selected from:
(viii) hyperlipidemia, hypertension, hypoalbuminemia, hypobolemic shock, hypocomplementemic urticarial vasculitis syndrome, hypophosphastasis, hypovolemic shock, idiopathic pneumonia syndrome, or idiopathic pulmonary fibrosis;
(ix) inclusion body myositis, intestinal ischemia, iridocyclitis, iritis, juvenile chronic arthritis, Kawasaki's disease (arteritis), or lipiduria;

(x) membranoproliferative glomerulonephritis (MPGN) I, microscopic polyangiitis, mixed cryoglobulinemia, molybdenum cofactor deficiency (MoCD) type A, pancreatitis, panniculitis, Pick's disease, polyarteritis nodosa (PAN), progressive subcortical gliosis, proteinuria, reduced glomerular filtration rate (GFR), or renovascular disorder;

(xi) multiple organ failure, multiple system atrophy (MSA), myotonic dystrophy, Niemann-Pick disease type C, chronic demyelinating diseases, or progressive supranuclear palsy;

(xii) spinal cord injury, spinal muscular atrophy, spondyloarthropathies, Reiter's syndrome, spontaneous fetal loss, recurrent fetal loss, pre-eclampsia, synucleinopathy, Takayasu's arteritis, post-partum thryoiditis, thyroiditis, Type I cryoglobulinemia, Type II mixed cryoglobulinemia, Type III mixed cryoglobulinemia, ulcerative colitis, uremia, urticaria, venous gas embolus (VGE), or Wegener's granulomatosis;

In one embodiment, a compound described herein is useful for treating or preventing a disorder selected from autoimmune oophoritis, endometriosis, autoimmune orchitis, Ord's thyroiditis, autoimmune enteropathy, coeliac disease, Hashimoto's encephalopathy, antiphospholipid syndrome (APLS) (Hughes syndrome), aplastic anemia, autoimmune lymphoproliferative syndrome (Canale-Smith syndrome), autoimmune neutropenia, Evans syndrome, pernicious anemia, pure red cell aplasia, thrombocytopenia, adipose dolorosa (Dercum's disease), adult onset Still's disease, ankylosing spondylitis, CREST syndrome, drug-induced lupus, eosinophilic fasciitis (Shulman's syndrome), Felty syndrome, IgG4-related disease, mixed connective tissue disease (MCTD), palindromic rheumatism (Hench-Rosenberg syndrome), Parry-Romberg syndrome, Parsonage-Turner syndrome, relapsing polychondritis (Meyenburg-Altherr-Uehlinger syndrome), retroperitonial fibrosis, rheumatic fever, Schnitzler syndrome, fibromyalgia, neuromyotonia (Isaac's disease), paraneoplastic degeneration, autoimmune inner ear disease, Meniere's disease, interstitial cystitis, autoimmune pancreatitis, zika virus-related disorders, chikungunya virus-related disorders, subacute bacterial endocarditis (SBE), IgA nephropathy, IgA vasculitis, polymyalgia rheumatic, rheumatoid vasculitis, alopecia areata, autoimmune progesterone dermatitis, dermatitis herpetiformis, erythema nodosum, gestational pemphigoid, hidradenitis suppurativa, lichen sclerosus, linear IgA disease (LAD), morphea, myositis, pityriasis lichenoides et varioliformis acuta, vitiligo post-myocardial infarction syndrome (Dressler's syndrome), post-pericardiotomy syndrome, autoimmune retinopathy, Cogan syndrome, Graves opthalmopathy, ligneous conjunctivitis, Mooren's ulcer, opsoclonus myoclonus syndrome, optic neuritis, retinocochleocerebral vasculopathy (Susac's syndrome), sympathetic opthalmia, Tolosa-Hunt syndrome, interstitial lung disease, antisynthetase syndrome, Addison's disease, autoimmune polyendocrine syndrome (APS) type I, autoimmune polyendocrine syndrome (APS) type II, autoimmune polyendocrine syndrome (APS) type III, disseminated sclerosis (multiple sclerosis, pattern II), rapidly progressing glomerulonephritis (RPGN), juvenile rheumatoid arthritis, enthesitis-related arthritis, reactive arthritis (Reiter's syndrome), autoimmune hepatitis or lupoid hepatitis, primary biliary cirrhosis (PBS), primary sclerosing cholangitis, microscopic colitis, latent lupus (undifferentiated connective tissue disease (UCTD)), acute disseminated encephalomyelitis (ADEM), acute motor axonal neuropathy, anti-n-methyl-D-aspartate receptor encephalitis, Balo concentric sclerosis (Schilders disease), Bickerstaff's encephalitis, chronic inflammatory demyelinating polyneuropathy, idiopathic inflammatory demyelinating disease, Lambert-Eaton myasthenic syndrome, Oshtoran syndrome, pediatric autoimmune neuropsychiatric disorder associated with streptococcus (PANDAS), progressive inflammatory neuropathy, restless leg syndrome, stiff person syndrome, Sydenhem syndrome, transverse myelitis, lupus vasculitis, leukocytoclastic vasculitis, Microscopic Polyangiitis, polymyositis, ischemic-reperfusion injury of the eye.

In one embodiment, a method for the treatment of sickle cell in a host is provided that includes the administration of an effective amount of a compound described herein, or its salt, optionally in a pharmaceutically acceptable carrier. In one embodiment, a method for the treatment of immuno-thrombocytopenic purpura (ITP), thrombotic thrombocytopenic purpura (TTP), or idiopathic thrombocytopenic purpura (ITP) in a host is provided that includes the administration of an effective amount of a compound described herein, or its salt, optionally in a pharmaceutically acceptable carrier. In one embodiment, a method for the treatment of ANCA-vasculitis in a host is provided that includes the administration of an effective amount of a compound described herein, or its salt, optionally in a pharmaceutically acceptable carrier. In one embodiment, a method for the treatment of IgA nephropathy in a host is provided that includes the administration of an effective amount of a compound described herein, or its salt, optionally in a pharmaceutically acceptable carrier. In one embodiment, a method for the treatment of rapidly progressing glomerulonephritis (RPGN), in a host is provided that includes the administration of an effective amount of a compound described herein, or its salt, optionally in a pharmaceutically acceptable carrier. In one embodiment, a method for the treatment of lupus nephritis, in a host is provided that includes the administration of an effective amount of a compound described herein, or its salt, optionally in a pharmaceutically acceptable carrier. In one embodiment, a method for the treatment of hemorraghic dengue fever, in a host is provided that includes the administration of an effective amount of a compound described herein, or its salt, optionally in a pharmaceutically acceptable carrier.

Section B Disorders

The compound of Table 2 or Table 3 or their pharmaceutically acceptable salts or pharmaceutical compositions are useful for treating any of the disorders described herein. In one embodiment, the compound is useful for treating or preventing a disorder that is mediated by the complement pathway, and in particular, a pathway that is modulated by complement Factor D. In another embodiment, the compound is effective to treat the named disorder, albeit through a different mechanism.

In certain embodiments, the disorder is an inflammatory disorder, an immune disorder, an autoimmune disorder, or complement Factor D related disorders in a host. In one embodiment, the disorder is an ocular disorder or an eye disorder.

Examples of eye disorders that may be treated according to the compositions and methods disclosed herein include amoebic keratitis, fungal keratitis, bacterial keratitis, viral keratitis, onchorcercal keratitis, bacterial keratoconjunctivitis, viral keratoconjunctivitis, corneal dystrophic diseases, Fuchs' endothelial dystrophy, Sjogren's syndrome, Stevens-Johnson syndrome, autoimmune dry eye diseases, environmental dry eye diseases, corneal neovascularization diseases, post-corneal transplant rejection prophylaxis and treatment, autoimmune uveitis, infectious uveitis, anterior uveitis, posterior uveitis (including toxoplasmosis), pan-uveitis, an inflammatory disease of the vitreous or retina, endophthalmitis prophylaxis and treatment, macular edema, macular degeneration, age related macular degeneration, proliferative and non-proliferative diabetic retinopathy, hypertensive retinopathy, an autoimmune disease of the retina, primary and metastatic intraocular melanoma, other intraocular metastatic tumors, open angle glaucoma, closed angle glaucoma, pigmentary glaucoma and combinations thereof.

In a further embodiment, the disorder is selected from age-related macular degeneration, glaucoma, diabetic retinopathy, neuromyelitis optica (NMO), vasculitis, hemodialysis, blistering cutaneous diseases (including bullous pemphigoid, pemphigus, and epidermolysis bullosa), ocular cicatrical pemphigoid, uveitis, adult macular degeneration, diabetic retinopa retinitis pigmentosa, macular edema, Behcet's uveitis, multifocal choroiditis, Vogt-Koyangi-Harada syndrome, imtermediate uveitis, birdshot retino-chorioditis, sympathetic ophthalmia, ocular dicatricial pemphigoid, ocular pemphigus, nonartertic ischemic optic neuropathy, post-operative inflammation, and retinal vein occlusion, or uveitis (including Behcet's disease and other sub-types of uveitis).

In some embodiments, complement mediated diseases include ophthalmic diseases (including early or neovascular age-related macular degeneration and geographic atrophy), autoimmune diseases (including arthritis, rheumatoid arthritis), respiratory diseases, cardiovascular diseases. In other embodiments, the compounds of the invention are suitable for use in the treatment of diseases and disorders associated with fatty acid metabolism, including obesity and other metabolic disorders.

Complement mediated disorders that may be treated or prevented by the compounds of Table 2 or Table 3 include, but are not limited to:
(i) paroxysmal nocturnal hemoglobinuria (PNH), hereditary angioedema, capillary leak syndrome, atypical hemolytic uremic syndrome (aHUS), hemolytic uremic syndrome (HUS), abdominal aortic aneurysm, hemodialysis complications, hemolytic anemia, or hemodialysis;
(ii) myasthenia gravis, multiple sclerosis, C3 glomerulonephritis (C3GNs), MPGN II (dense deposit disease), neurological disorders, Guillain Barre Syndrome, diseases of the central nervous system and other neurodegenerative conditions, glomerulonephritis (including membrane proliferative glomerulonephritis), SLE nephritis, proliferative nephritis, liver fibrosis, tissue regeneration and neural regeneration, or Barraquer-Simons Syndrome;
(iii) inflammatory effects of sepsis, systemic inflammatory response syndrome (SIRS), disorders of inappropriate or undesirable complement activation, interleukin-2 induced toxicity during IL-2 therapy, inflammatory disorders, inflammation of autoimmune diseases, system lupus erythematosus (SLE), Crohn's disease, rheumatoid arthritis, inflammatory bowel disease, lupus nephritides, arthritis, immune complex disorders and autoimmune diseases, systemic lupus, or lupus erythematosus;
(iv) ischemia/reperfusion injury (FR injury), myocardial infarction, myocarditis, post-ischemic reperfusion conditions, balloon angioplasty, atherosclerosis, post-pump syndrome in cardiopulmonary bypass or renal bypass, renal ischemia, mesenteric artery reperfusion after aortic reconstruction, antiphospholipid syndrome, autoimmune heart disease, ischemia-reperfusion injuries, obesity, or diabetes;
(v) Alzheimer's dementia, stroke, schizophrenia, traumatic brain injury, trauma, Parkinson's disease, epilepsy, transplant rejection, prevention of fetal loss, biomaterial reactions (e.g. in hemodialysis, implants), hyperacute allograft rejection, xenograft rejection, transplantation, psoriasis, burn injury, thermal injury including burns or frostbite;
(vi) asthma, allergy, acute respiratory distress syndrome (ARDS), cystic fibrosis, adult respiratory distress syndrome, dyspnea, hemoptysis, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), bronchoconstriction, hypersensitivity pneumonitis, parasitic diseases, Goodpasture's Syndrome (anti-glomerular basement membrane nephritis), pulmonary vasculitis, Pauci-immune vasculitis, or immune complex-associated inflammation.

In one embodiment, a method for the treatment of paroxysmal nocturnal hemoglobinuria (PNH) is provided that includes the administration of an effective amount of a compound selected from Table 2 or Table 3, or a pharmaceutically acceptable salt thereof, optionally in a pharmaceutically acceptable carrier.

In another embodiment, a method for the treatment of age-related macular degeneration (AMD) is provided that includes the administration of an effective amount of a compound selected from Table 2 or Table 3, or a pharmaceutically acceptable salt thereof, optionally in a pharmaceutically acceptable carrier.

In another embodiment, a method for the treatment of rheumatoid arthritis is provided that includes the administration of an effective amount of a compound selected from Table 2 or Table 3, or a pharmaceutically acceptable salt thereof, optionally in a pharmaceutically acceptable carrier.

In another embodiment, a method for the treatment of multiple sclerosis is provided that includes the administration of an effective amount of a compound selected from Table 2 or Table 3, or a pharmaceutically acceptable salt thereof, optionally in a pharmaceutically acceptable carrier.

In another embodiment, a method for the treatment of myasthenia gravis is provided that includes the administration of an effective amount of a compound selected from Table 2 or Table 3, or a pharmaceutically acceptable salt thereof, optionally in a pharmaceutically acceptable carrier.

In another embodiment, a method for the treatment of atypical hemolytic uremic syndrome (aHUS) is provided that includes the administration of an effective amount of a compound selected from Table 2 or Table 3, or a pharmaceutically acceptable salt thereof, optionally in a pharmaceutically acceptable carrier.

In another embodiment, a method for the treatment of C3 glomerulonephritis is provided that includes the administration of an effective amount of a compound selected from Table 2 or Table 3, or a pharmaceutically acceptable salt thereof, optionally in a pharmaceutically acceptable carrier.

In another embodiment, a method for the treatment of abdominal aortic aneurysm is provided that includes the administration of an effective amount of a compound selected from Table 2 or Table 3, or a pharmaceutically acceptable salt thereof, optionally in a pharmaceutically acceptable carrier.

In another embodiment, a method for the treatment of neuromyelitis optica (NMO) is provided that includes the administration of an effective amount of a compound selected from Table 2 or Table 3, or a pharmaceutically acceptable salt thereof, optionally in a pharmaceutically acceptable carrier.

In some embodiments, the present invention provides methods of treating or preventing an inflammatory disorder or a complement related disease, by administering to a host in need thereof an effective amount of a compound selected from Table 2 or Table 3 of the invention. In some embodiments, the present invention provides methods of treating or preventing an inflammatory disorder more generally, an immune disorder, autoimmune disorder, or complement Factor D related disorder, by providing an effective amount of a compound or pharmaceutically acceptable salt of a compound selected from Table 2 or Table 3 to patient with a Factor D mediated inflammatory disorder. A compound selected from Table 2 or Table 3 may be provided as the only active agent or may be provided together with one or more additional active agents.

In one embodiment, a method for the treatment of a disorder associated with a dysfunction in the complement cascade is provided that includes the administration of an effective amount of a compound selected from Table 2 or Table 3, or a pharmaceutically acceptable salt thereof, optionally in a pharmaceutically acceptable carrier. In one embodiment, a method of inhibiting activation of the alternative complement pathway in a host is provided that includes the administration of an effective amount of a compound selected from Table 2 or Table 3, or a pharmaceutically acceptable salt thereof, optionally in a pharmaceutically acceptable carrier. In one embodiment, a method of modulating Factor D activity in a host is provided that includes the administration of an effective amount of a compound selected from Table 2 or Table 3, or a pharmaceutically acceptable salt thereof, optionally in a pharmaceutically acceptable carrier.

In an additional alternative embodiment, the compound selected from Table 2 or Table 3, or a pharmaceutically acceptable salt thereof, optionally in a pharmaceutically acceptable carrier is used in the treatment of an autoimmune disorder.

The complement pathway enhances the ability of antibodies and phagocytic cells to clear microbes and damaged cells from the body. It is part of the innate immune system and in healthy individuals is an essential process. Inhibiting the complement pathway will decrease the body's immune system response. Therefore, it is an object of the present invention to treat autoimmune disorders by administering an effective does of a compound of Table 2 or Table 3, or a pharmaceutically acceptable salt thereof, optionally in a pharmaceutically acceptable carrier, to a host in need thereof.

In one embodiment the autoimmune disorder is caused by activity of the complement system. In one embodiment the autoimmune disorder is caused by activity of the alternative complement pathway. In one embodiment the autoimmune disorder is caused by activity of the classical complement pathway. In another embodiment the autoimmune disorder is caused by a mechanism of action that is not directly related to the complement system, such as the over-proliferation of T-lymphocytes or the over-production of cytokines.

Non-limiting examples of autoimmune disorders include: allograft rejection, autoimmune thyroid diseases (such as Graves' disease and Hashimoto's thyroiditis), autoimmune uveoretinitis, giant cell arteritis, inflammatory bowel diseases (including Crohn's disease, ulcerative colitis, regional enteritis, granulomatous enteritis, distal ileitis, regional ileitis, and terminal ileitis), diabetes, multiple sclerosis, pernicious anemia, psoriasis, rheumatoid arthritis, sarcoidosis, and scleroderma.

In one embodiment, a compound selected from Table 2 or Table 3, or a pharmaceutically acceptable salt thereof, optionally in a pharmaceutically acceptable carrier, is used in the treatment of lupus. Non-limiting examples of lupus include lupus erythematosus, cutaneous lupus, discoid lupus erythematosus, chilblain lupus erythematosus, lupus erythematosus-lichen planus overlap syndrome.

Lupus erythematosus is a generic category of disease that includes both systemic and cutaneous disorders. The systemic form of the disease can have cutaneous as well as systemic manifestations. However, there are also forms of the disease that are only cutaneous without systemic involvement. For example, SLE is an inflammatory disorder of unknown etiology that occurs predominantly in women, and is characterized by articular symptoms, butterfly erythema, recurrent pleurisy, pericarditis, generalized adenopathy, splenomegaly, as well as CNS involvement and progressive renal failure. The sera of most patients (over 98%) contain antinuclear antibodies, including anti-DNA antibodies. High titers of anti-DNA antibodies are essentially specific for SLE. Conventional treatment for this disease has been the administration of corticosteroids or immunosuppressants.

There are three forms of cutaneous lupus: chronic cutaneous lupus (also known as discoid lupus erythematosus or DLE), subacute cutaneous lupus, and acute cutaneous lupus. DLE is a disfiguring chronic disorder primarily affecting the skin with sharply circumscribed macules and plaques that display erythema, follicular plugging, scales, telangiectasia and atrophy. The condition is often precipitated by sun exposure, and the early lesions are erythematous, round scaling papules that are 5 to 10 mm in diameter and display follicular plugging. DLE lesions appear most commonly on the cheeks, nose, scalp, and ears, but they may also be generalized over the upper portion of the trunk, extensor surfaces of the extremities, and on the mucous membranes of the mouth. If left untreated, the central lesion atrophies and leaves a scar. Unlike SLE, antibodies against double-stranded DNA (e.g., DNA-binding test) are almost invariably absent in DLE.

Multiple sclerosis is an autoimmune demyelinating disorder that is believed to be T lymphocyte dependent. MS generally exhibits a relapsing-remitting course or a chronic progressive course. The etiology of MS is unknown, however, viral infections, genetic predisposition, environment, and autoimmunity all appear to contribute to the disorder. Lesions in MS patients contain infiltrates of predominantly T lymphocyte mediated microglial cells and infiltrating macrophages. CD4+ T lymphocytes are the predominant cell type present at these lesions. The hallmark of the MS lesion is plaque, an area of demyelination sharply demarcated from the usual white matter seen in MM scans. Histological appearance of MS plaques varies with different stages of the disease. In active lesions, the blood-brain barrier is damaged, thereby permitting extravasation of serum proteins into extracellular spaces. Inflammatory cells can be seen in perivascular cuffs and throughout white matter. CD4+ T-cells, especially Th1, accumulate around postcapillary venules at the edge of the plaque and are also scattered in the white matter. In active lesions, up-regulation of adhesion molecules and markers of lymphocyte and monocyte activation, such as IL2-R and CD26 have also been observed.

Demyelination in active lesions is not accompanied by destruction of oligodendrocytes. In contrast, during chronic phases of the disease, lesions are characterized by a loss of oligodendrocytes and hence, the presence of myelin oligodendrocyte glycoprotein (MOG) antibodies in the blood.

Diabetes can refer to either type 1 or type 2 diabetes. In one embodiment a compound of Table 2 or Table 3 or a pharmaceutically acceptable salt thereof, optionally in a pharmaceutically acceptable carrier, is provided at an effective dose to treat a patient with type 1 diabetes. In one embodiment a compound of Table 2 or Table 3, or a pharmaceutically acceptable salt thereof, optionally in a pharmaceutically acceptable carrier, is provided at an effective dose to treat a patient with type 2 diabetes.

Type 1 diabetes is an autoimmune disease. An autoimmune disease results when the body's system for fighting infection (the immune system) turns against a part of the body. The pancreas then produces little or no insulin.

V. Combination Therapy

In additional embodiments, an effective amount of an active compound or its salt or composition as described herein may be provided in combination or alternation with or preceded by, concomitant with or followed by, an effective amount of at least one additional therapeutic agent, for example, for treatment of a disorder listed herein. Non-limiting examples of additional therapeutic agents for such combination therapy are provided below.

In one embodiment, an effective amount of an active compound or its salt or composition as described herein may be provided in combination or alternation with an effective amount of at least one additional inhibitor of the complement system or a second active compound with a different biological mechanism of action. In the description below and herein generally, whenever any of the terms referring to an active compound or its salt or composition as described herein are used, it should be understood that pharmaceutically acceptable salts, prodrugs or compositions are considered included, unless otherwise stated or inconsistent with the text.

In non-limiting embodiments, an active compound or its salt or composition as described herein may be provided together with a protease inhibitor, a soluble complement regulator, a therapeutic antibody (monoclonal or polyclonal), complement component inhibitor, receptor agonist, or siRNA.

In other embodiments, an active compound described herein is administered in combination or alternation with an antibody against tumor necrosis factor (TNF), including but not limited to infliximab (Remicade), adalimumab, certolizumab, golimumab, or a receptor fusion protein such as etanercept (Embrel).

In another embodiment, an active compound as described herein can be administered in combination or alternation with an anti-CD20 antibody, including but not limited to rituximab (Rituxan), adalimumab (Humira), ofatumumab (Arzerra), tositumomab (Bexxar), obinutuzumab (Gazyva), or ibritumomab (Zevalin).

In an alternative embodiment, an active compound as described herein can be administered in combination or alternation with an anti-IL6 antibody, including but not limited to tocilizumab (Actemra) and siltuximab (Sylvant).

In an alternative embodiment, an active compound as described herein can be administered in combination or alternation with an IL17 inhibitor, including but not limited to secukibumab (Cosentyx).

In an alternative embodiment, an active compound as described herein can be administered in combination or alternation with a p40 (IL12/IL23) inhibitor, including but not limited to ustekinumab (Stelara).

In an alternative embodiment, an active compound as described herein can be administered in combination or alteration with an IL23 inhibitor, including but not limited to risankizumab.

In an alternative embodiment, an active compound as described herein can be administered in combination or alteration with an anti-interferon α antibody, for example but not limited to sifalimumab.

In an alternative embodiment, an active compound as described herein can be administered in combination or alteration with a kinase inhibitor, for example but not limited to a JAK1/JAK3 inhibitor, for example but not limited to tofacitinib (Xelianz). In an alternative embodiment, an active compound as described herein can be administered in combination or alteration with a JAK1/JAK2 inhibitor, for example but not limited to baracitibib.

In another embodiment, an active compound as described herein can be administered in combination or alternation with an immune checkpoint inhibitor. Non-limiting examples of checkpoint inhibitors are anti-PD-1 or anti-PDL1 antibodies (for example, Nivolumab, Pembrolizumab, Pidilizumab and Atezolizumab) and anti-CTLA4 antibodies (Ipilimumab and Tremelimumab).

Non-limiting examples of active agents that can be used in combination with active compounds described herein are:

Protease inhibitors: plasma-derived C1-INH concentrates, for example Cetor® (Sanquin), Berinert-P® (CSL Behring, Lev Pharma), and Cinryze®; recombinant human C1-inhibitors, for example Rhucin®; ritonavir (Norvir®, Abbvie, Inc.);

Soluble complement regulators: Soluble complement receptor 1 (TP10) (Avant Immunotherapeutics); sCR1-sLex/TP-20 (Avant Immunotherapeutics); MLN-2222/CAB-2 (Millenium Pharmaceuticals); Mirococept (Inflazyme Pharmaceuticals);

Therapeutic antibodies: Eculizumab/Soliris (Alexion Pharmaceuticals); Pexelizumab (Alexion Pharmaceuticals); Ofatumumab (Genmab A/S); TNX-234 (Tanox); TNX-558 (Tanox); TA106 (Taligen Therapeutics); Neutrazumab (G2 Therapies); Anti-properdin (Novelmed Therapeutics); HuMax-CD38 (Genmab A/S);

Complement component inhibitors: Compstatin/POT-4 (Potentia Pharmaceuticals); ARC1905 (Archemix);

Receptor agonists: PMX-53 (Peptech Ltd.); JPE-137 (Jerini); JSM-7717 (Jerini);

Others: Recombinant human MBL (rhMBL; Enzon Pharmaceuticals).

Imides and glutarimide derivatives such as thalidomide, lenalidomide, pomalidomide;

Additional non-limiting examples that can be used in combination or alternation with an active compound or its salt or composition as described herein include the following.

| Non-limiting examples of potential therapeutics for combination therapy | | | |
|---|---|---|---|
| Name | Target | Company | Class of Molecule |
| LFG316 | C5 | Novartis/Morphosys | Monoclonal antibody |
| 4(1MEW)APL-1,APL-2 | C3/C3b | Apella | Compstatin Family |
| 4(1MeW)POT-4 | C3/C3b | Potentia | Compstatin Family |
| Anti-C5 siRNA | C5 | Alnylam | Si-RNA |
| Anti-FB siRNA | CFB | Alnylam | SiRNA |
| ARC1005 | C5 | Novo Nordisk | Aptamers |
| ATA | C5 | N.A. | Chemical |
| Coversin | C5 | Volution Immuno-Pharmaceuticals | Small animal protein |
| CP40/AMY-101,PEG-Cp40 | C3/C3b | Amyndas | Compstatin Family |
| CRIg/CFH | CAP C3 convertase | NA | CFH-based protein |
| Cynryze | C1n/C1s | ViroPharma/Baxter | Human purified protein |
| FCFD4514S | CFD | Genentech/Roche | Monoclonal antibody |
| H17 | C3 (C3b/iC3b) | EluSys Therapeutics | Monoclonal antibody |
| Mini-CFH | CAP C3 convertase | Amyndas | CFH-based protein |
| Mirococept (APT070) | CAP and CCP C3 | NA | CR1-based protein |
| Mubodine | C5 | Adienne | Monoclonal antibody |
| RA101348 | C5 | Rapharma | Small molecule |
| sCR1 (CDX-1135) | CAP and CP C3 | Celldex | CR1-based protein |
| SOBI002 | C5 | Swedish Orphan Biovitrum | Affibody |
| SOMAmers | C5 | SomaLogic | Aptamers |
| SOMAmers | CFB and CFD | SomaLogic | Aptamers (SELEX) |
| TA106 | CFB | Alexion Pharmaceuticals | Monoclonal antibody |
| TNT003 | C1s | True North | Monoclonal antibody |
| TT30 (CR2/CFH) | CAP C3 convertase | Alexion | CFH-based protein |
| TT32 (CR2/CR1) | CAP and CCP C3 | Alexion Pharmaceuticals | CR1-based protein |
| Nafamostat (FUT-175, Futhan) | C1s, CFD, other proteases | Torri Pharmaceuticals | Small molecule |
| OMS721 | MASP-2 | Omeros | Monoclonal antibody |
| OMS906 | MASP-2 | Omeros | Monoclonal antibody |
| Bikaciomab, NM9308 | CFB | Novelmed | Monoclonal antibody |
| NM9401 | Properdin | Novelmed | Monoclonal antibody |
| CVF, HC-1496 | C3 | InCode | Recombinant peptide |
| ALXN1102/ALXN1103 (TT30) | C3-conv, C3b | Alexion Pharmaceuticals | Regulator |
| rFH | C3-conv, C3b | Optherion | Regulator |
| 5C6, AMY-301 | CFH | Amyndas | Regulator |
| Erdigna | C5 | Adienne Pharma | Antibody |
| ARC1905 | C5 | Opthotech | Monoclonal Antibody |
| MEDI7814 | C5/C5a | MedImmune | Monoclonal Antibody |
| NOX-D19 | C5a | Noxxon | Aptamer (Spiegelmer) |
| IFX-1, CaCP29 | C5a | InflaRx | Monoclonal Antibody |
| PMX53, PMX205 | C5aR | Cephalon, Teva | Peptidomimetic |
| CCX168 | C5aR | ChemoCentryx | Small molecule |
| ADC-1004 | C5aR | Alligator Bioscience | Small molecule |
| Anti-C5aR-151, NN8209; Anti-C5aR-215, NN8210 | C5aR | Novo Nordisk | Monoclonal Antibody |
| Imprime PGG | CR3 | Biothera | Soluble beta-glucan |

In one embodiment, an active compound or its salt or composition as described herein may be provided together with a compound that inhibits an enzyme that metabolizes an administered protease inhibitor. In one embodiment, a compound or salt may be provided together with ritonavir.

In one embodiment, an active compound or its salt or composition as described herein may be provided in combination with a complement C5 inhibitor or C5 convertase inhibitor. In another embodiment, an active compound or its salt or composition as described herein may be provided in combination with eculizumab, a monoclonal antibody directed to the complement factor C5 and manufactured and marketed by Alexion Pharmaceuticals under the tradename Soliris. Eculizumab has been approved by the U.S. FDA for the treatment of PNH and aHUS.

In one embodiment, an active compound or its salt or composition as described herein may be provided together with a compound that inhibits complement factor D. In one embodiment of the invention, an active compound or its salt or composition as described herein as described herein can be used in combination or alternation with a compound described in Biocryst Pharmaceuticals U.S. Pat. No. 6,653,340 titled "Compounds useful in the complement, coagulate and kallikrein pathways and method for their preparation" describes fused bicyclic ring compounds that are potent inhibitors of Factor D; Novartis PCT patent publication WO2012/093101 titled "Indole compounds or analogues thereof useful for the treatment of age-related macular degeneration" describes certain Factor D inhibitors; Novartis PCT patent publications WO2014/002051, WO2014/002052, WO2014/002053, WO2014/002054, WO2014/002057, WO2014/002058, WO2014/002059, WO2014/005150, WO2014/009833, WO 2013/164802, WO 2015/009616, WO 2015/066241, Bristol-Myers Squibb PCT patent publication WO2004/045518 titled "Open chain prolyl urea-related modulators of androgen receptor function"; Japan Tobacco Inc. PCT patent publication WO1999/048492 titled "Amide derivatives and nociceptin antagonists"; Ferring B. V. and Yamanouchi Pharmaceutical Co. LTD. PCT patent publication WO1993/020099 titled "CCK and/or gastrin receptor ligands"; Alexion Pharmaceuticals PCT patent publication WO1995/029697 titled "Methods and compositions for the treatment of glomerulonephritis and other inflammatory diseases"; or Achillion Pharmaceuticals filed PCT Patent Application No. PCT/US2015/017523 and U.S. patent application Ser. No. 14/631,090 titled "Alkyne Compounds for Treatment of Complement Mediated Disorders"; PCT Patent Application No. PCT/US2015/017538 and U.S. patent application Ser. No. 14/631,233 titled "Amide Compounds for Treatment of Complement Mediated Disorders"; PCT Patent Application No. PCT/US2015/017554 and U.S. patent application Ser. No. 14/631,312 titled "Amino Compounds for Treatment of Complement Mediated Disorders"; PCT Patent Application No. PCT/US2015/017583 and U.S. patent application Ser. No. 14/631,440 titled "Carbamate, Ester, and Ketone Compounds for Treatment of Complement Mediated Disorders"; PCT Patent Application No. PCT/US2015/017593 and U.S. patent application Ser. No. 14/631,625 titled "Aryl, Heteroaryl, and Heterocyclic Compounds for Treatment of Complement Mediated Disorders"; PCT Patent Application No. PCT/US2015/017597 and U.S. patent application Ser. No. 14/631,683 titled "Ether Compounds for Treatment of Complement Mediated Disorders"; PCT Patent Application No. PCT/US2015/017600 and U.S. patent application Ser. No. 14/631,785 titled "Phosphonate Compounds for Treatment of Complement Mediated Disorders"; and PCT Patent Application No. PCT/US2015/017609 and U.S. patent application Ser. No. 14/631,828 titled "Compounds for Treatment of Complement Mediated Disorders."

In one embodiment, an active compound or its salt or composition as described herein is administered in combination with an anti-inflammatory drug, antimicrobial agent, anti-angiogenesis agent, immunosuppressant, antibody, steroid, ocular antihypertensive drug or combinations thereof. Examples of such agents include amikacin, anecortane acetate, anthracenedione, anthracycline, an azole, amphotericin B, bevacizumab, camptothecin, cefuroxime, chloramphenicol, chlorhexidine, chlorhexidine digluconate, clortrimazole, a clotrimazole cephalosporin, corticosteroids, dexamethasone, desamethazone, econazole, eftazidime, epipodophyllotoxin, fluconazole, flucytosine, fluoropyrimidines, fluoroquinolines, gatifloxacin, glycopeptides, imidazoles, itraconazole, ivermectin, ketoconazole, levofloxacin, macrolides, miconazole, miconazole nitrate, moxifloxacin, natamycin, neomycin, nystatin, ofloxacin, polyhexamethylene biguanide, prednisolone, prednisolone acetate, pegaptanib, platinum analogues, polymicin B, propamidine isethionate, pyrimidine nucleoside, ranibzumab, squalamine lactate, sulfonamides, triamcinolone, triamcinolone acetonide, triazoles, vancomycin, anti-vascular endothelial growth factor (VEGF) agents, VEGF antibodies, VEGF antibody fragments, vinca alkaloid, timolol, betaxolol, travoprost, latanoprost, bimatoprost, brimonidine, dorzolamide, acetazolamide, pilocarpine, ciprofloxacin, azithromycin, gentamycin, tobramycin, cefazolin, voriconazole, gancyclovir, cidofovir, foscarnet, diclofenac, nepafenac, ketorolac, ibuprofen, indomethacin, fluorometalone, rimexolone, anecortave, cyclosporine, methotrexate, tacrolimus and combinations thereof.

In one embodiment of the present invention, an active compound or its salt or composition as described herein can be administered in combination or alternation with at least one immunosuppressive agent. The immunosuppressive agent as non-limiting examples, may be a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g. ridaforolimus, azathioprine, campath 1H, a S1P receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3®), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SIMULECT®), Daclizumab (ZENAPAX®), mizorbine, methotrexate, dexamethasone, ISAtx-247, SDZ ASM 981 (pimecrolimus, Elidel®), CTLA41g (Abatacept), belatacept, LFA31g, etanercept (sold as Enbrel® by Immunex), adalimumab (Humira®), infliximab (Remicade®), an anti-LFA-1 antibody, natalizumab (Antegren®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, tocilizumab (Actemra), siltuximab (Sylvant), secukibumab (Cosentyx), ustekinumab (Stelara), risankizumab, sifalimumab, aspirin and ibuprofen.

Examples of anti-inflammatory agents include methotrexate, dexamethasone, dexamethasone alcohol, dexamethasone sodium phosphate, fluromethalone acetate, fluromethalone alcohol, lotoprednol etabonate, medrysone, prednisolone acetate, prednisolone sodium phosphate, difluprednate, rimexolone, hydrocortisone, hydrocortisone acetate, lodoxamide tromethamine, aspirin, ibuprofen, suprofen, piroxicam, meloxicam, flubiprofen, naproxan, ketoprofen, tenoxicam, diclofenac sodium, ketotifen fumarate, diclofenac sodium, nepafenac, bromfenac, flurbiprofen sodium, suprofen, celecoxib, naproxen, rofecoxib, glucocorticoids, diclofenac, and any combination thereof. In one embodiment, an active compound or its salt or composition as described herein is combined with one or more non-steroidal anti-inflammatory drugs (NSAIDs) selected from naproxen sodium (Anaprox), celecoxib (Celebrex), sulindac (Clinoril), oxaprozin (Daypro), sal salate (Disalcid), diflunisal (Dolobid), piroxicam (Feldene), indomethacin (Indocin), etodolac (Lodine), meloxicam (Mobic), naproxen (Naprosyn), nabumetone (Relafen), ketorolac tromethamine (Toradol), naproxen/esomeprazole (Vimovo), and diclofenac (Voltaren), and combinations thereof.

In one embodiment, an active compound or its salt or composition as described herein is administered in combination or alteration with an omega-3 fatty acid or a peroxisome proliferator-activated receptor (PPARs) agonist. Omega-3 fatty acids are known to reduce serum triglycerides by inhibiting DGAT and by stimulating peroxisomal and mitochondrial beta oxidation. Two omega-3 fatty acids, eicosapentaenoic acid (EPA) and docosahexaenoic acid (DHA), have been found to have high affinity for both PPAR-alpha and PPAR-gamma. Marine oils, e.g., fish oils, are a good source of EPA and DHA, which have been found to regulate lipid metabolism. Omega-3 fatty acids have been found to have beneficial effects on the risk factors for cardiovascular diseases, especially mild hypertension, hypertriglyceridemia and on the coagulation factor VII phospholipid complex activity. Omega-3 fatty acids lower serum triglycerides, increase serum HDL-cholesterol, lower systolic and diastolic blood pressure and the pulse rate, and lower the activity of the blood coagulation factor VII-phospholipid complex. Further, omega-3 fatty acids seem to be well tolerated, without giving rise to any severe side effects. One such form of omega-3 fatty acid is a concentrate of omega-3, long chain, polyunsaturated fatty acids from fish oil containing DHA and EPA and is sold under the trademark Omacor®. Such a form of omega-3 fatty acid is described, for example, in U.S. Pat. Nos. 5,502,077, 5,656,667 and 5,698,594, the disclosures of which are incorporated herein by reference.

Peroxisome proliferator-activated receptors (PPARs) are members of the nuclear hormone receptor superfamily ligand-activated transcription factors that are related to retinoid, steroid and thyroid hormone receptors. There are three distinct PPAR subtypes that are the products of different genes and are commonly designated PPAR-alpha, PPAR-beta/delta (or merely, delta) and PPAR-gamma. General classes of pharmacological agents that stimulate peroxisomal activity are known as PPAR agonists, e.g., PPAR-alpha agonists, PPAR-gamma agonists and PPAR-delta agonists. Some pharmacological agents are combinations of PPAR agonists, such as alpha/gamma agonists, etc., and some other pharmacological agents have dual agonist/antagonist activity. Fibrates such as fenofibrate, bezafibrate, clofibrate and gemfibrozil, are PPAR-alpha agonists and are used in patients to decrease lipoproteins rich in triglycerides, to increase HDL and to decrease atherogenic-dense LDL. Fibrates are typically orally administered to such patients. Fenofibrate or 2-[4-(4-chlorobenzoyl)phenoxy]-2-methyl-propanoic acid, 1-methylethyl ester, has been known for many years as a medicinally active principle because of its efficacy in lowering blood triglyceride and cholesterol levels.

In one embodiment, the present invention provides a method of treating or preventing age-related macular degeneration (AMD) by administering to a host in need thereof an effective amount of an active compound or its salt or composition as described herein in combination with an anti-VEGF agent. Non-limiting examples of anti-VEGF agents include, but are not limited to, aflibercept (Eylea®; Regeneron Pharmaceuticals); ranibizumab (Lucentis®: Genentech and Novartis); and pegaptanib (Macugen®; OSI Pharmaceuticals and Pfizer); Bevacizumab (Avastin; Genentech/Roche); anecortane acetate, squalamine lactate, and corticosteroids, including, but not limited to, triamcinolone acetonide.

In one embodiment, the present invention provides a method of treating or preventing paroxysmal nocturnal hemoglobinuria (PNH) by administering to a host in need thereof an effective amount of an active compound or its salt or composition as described herein with an additional inhibitor of the complement system or another active compound with a different biological mechanism of action. In another embodiment, the present invention provides a method of treating or preventing paroxysmal nocturnal hemoglobinuria (PNH) by administering to a host in need thereof an effective amount of an active compound or its salt or composition as described herein in combination or alternation with eculizumab. In another embodiment, the present invention provides a method of treating or preventing paroxysmal nocturnal hemoglobinuria (PNH) by administering to a host in need thereof an effective amount of an active compound or its salt or composition as described herein in combination or alternation with CP40. In one embodiment, the additional agent is PEGylated-CP40. CP40 is a peptide inhibitor that shows a strong binding affinity for C3b and inhibits hemolysis of paroxysmal nocturnal hemoglobinuria (PNH) erythrocytes.

In one embodiment, the present invention provides a method of treating or preventing rheumatoid arthritis by administering to a host in need thereof an effective amount of a composition comprising an active compound or its salt or composition as described herein in combination or alternation with an additional inhibitor of the complement system, or an active agent that functions through a different mechanism of action. In another embodiment, the present invention provides a method of treating or preventing rheumatoid arthritis by administering to a host in need thereof an effective amount of an active compound or its salt or composition as described herein in combination or alternation with methotrexate. In certain embodiments, an active compound or its salt or composition as described herein is administered in combination or alternation with at least one additional therapeutic agent selected from: salicylates including aspirin (Anacin, Ascriptin, Bayer Aspirin, Ecotrin) and salsalate (Mono-Gesic, Salgesic); nonsteroidal anti-inflammatory drugs (NSAIDs); nonselective inhibitors of the cyclo-oxygenase (COX-1 and COX-2) enzymes, including diclofenac (Cataflam, Voltaren), ibuprofen (Advil, Motrin), ketoprofen (Orudis), naproxen (Aleve, Naprosyn), piroxicam (Feldene), etodolac (Lodine), indomethacin, oxaprozin (Daypro), nabumetone (Relafen), and meloxicam (Mobic); selective cyclo-oxygenase-2 (COX-2) inhibitors including Celecoxib (Celebrex); disease-modifying anti-rheumatic drugs (DMARDs), including azathioprine (Imuran), cyclosporine (Sandimmune, Neoral), gold salts (Ridaura, Solganal, Aurolate, Myochrysine), hydroxychloroquine (Plaquenil), leflunomide (Arava), methotrexate (Rheumatrex), penicillamine (Cuprimine), and sulfasalazine (Azulfidine); biologic drugs including abatacept (Orencia), etanercept (Enbrel), infliximab (Remicade), adalimumab (Humira), and anakinra (Kineret); corticosteroids including betamethasone (Celestone Soluspan), cortisone (Cortone), dexamethasone (Decadron), methylprednisolone (SoluMedrol, DepoMedrol), prednisolone (Delta-Cortef), prednisone (Deltasone, Orasone), and triamcinolone (Aristocort); gold salts, including Auranofin (Ridaura); Aurothioglucose (Solganal); Aurolate; Myochrysine; or any combination thereof.

In one embodiment, the present invention provides a method of treating or preventing multiple sclerosis by administering to a host in need thereof an effective amount of an active compound or its salt or composition as described herein in combination or alternation with an additional inhibitor of the complement system, or an active agent that functions through a different mechanism of action. In another embodiment, the present invention provides a method of treating or preventing multiple sclerosis by administering to a host in need thereof an effective amount of an active compound or its salt or composition as described herein in combination or alternation with a corticosteroid. Examples of corticosteroids include, but are not limited to, prednisone, dexamethasone, solumedrol, and methylprednisolone. In one embodiment, an active compound or its salt or composition as described herein is combined with at least one anti-multiple sclerosis drug, for example, selected from: Aubagio (teriflunomide), Avonex (interferon beta-1a), Betaseron (interferon beta-1b), Copaxone (glatiramer acetate), Extavia (interferon beta-1b), Gilenya (fingolimod), Lemtrada (alemtuzumab), Novantrone (mitoxantrone), Plegridy (peginterferon beta-1a), Rebif (interferon beta-1a), Tecfidera (dimethyl fumarate), Tysabri (natalizumab), Solu-Medrol (methylprednisolone), High-dose oral Deltasone (prednisone), H.P. Acthar Gel (ACTH), or a combination thereof.

In one embodiment, an active compound or its salt or composition as described herein is useful in a combination with another pharmaceutical agent to ameliorate or reduce a side effect of the agent. For example, in one embodiment, an active compound or its salt or composition as described herein may be used in combination with adoptive cell transfer therapies to reduce an associated inflammatory response associated with such therapies, for example, a cytokine mediated response such as cytokine release syndrome. In one embodiment, the adoptive cell transfer therapy includes the use of a chimeric antigen receptor T-Cell (CAR T). In one embodiment, the adoptive cell transfer therapy includes the use of a chimeric antigen receptor T-Cell (CAR T) or a dendritic cell to treat a hematologic or solid tumor, for example, a B-cell related hematologic cancer. In one embodiment, the hematologic or solid tumor is acute lymphoblastic leukemia (ALL), acute myeloid leukemia (AML), non-Hodgkin's lymphoma, chronic lymphocytic leukemia (CLL), pancreatic cancer, glioblastoma, or a cancer that expresses CD19.

In an additional alternative embodiment, an active compound or its salt or composition as described herein may be provided in combination with eculizumab for the treatment of PNH, aHUSs, STEC-HUS, ANCA-vasculitis, AMD, CAD, chronic hemolysis, neuromyelitis optica, or transplantation rejection. In one embodiment, an active compound or its salt or composition as described herein may be provided in combination with compstatin or a compstatin derivative for the treatment of PNH, aHUSs, STEC-HUS, ANCA-vasculitis, AMD, CAD, chronic hemolysis, neuromyelitis optica, or transplantation rejection.

In one embodiment, an active compound or its salt or composition as described herein may be provided in combination with rituxan for the treatment of a complement mediated disorder. In one embodiment, the complement mediated disorder is, for example, rheumatoid arthritis, Granulomatosis with Polyangiitis (GPA) (Wegener's Granulomatosis), and Microscopic Polyangiitis (MPA). In one embodiment, the disorder is Lupus.

In one embodiment, an active compound or its salt or composition as described herein may be provided in combination with cyclophosphamide for the treatment of a complement mediated disorder. In one embodiment, the disorder is an autoimmune disease. In one embodiment, the complement mediated disorder is, for example, rheumatoid arthritis, Granulomatosis with Polyangiitis (GPA) (Wegener's Granulomatosis), and Microscopic Polyangiitis (MPA). In one embodiment, the disorder is Lupus.

In one embodiment, an active compound or its salt or composition as described herein is dosed in combination with a conventional DLE treatment for the treatment of lupus to a host in need thereof.

Examples of conventional DLE treatments include topical corticosteroid ointments or creams, such as triamcinolone acetonide, fluocinolone, flurandrenolide, betamethasone valerate, or betamethasone dipropionate. Resistant plaques can be injected with an intradermal corticosteroid. Other potential DLE treatments include calcineurin inhibitors such as pimecrolimus cream or tacrolimus ointment. Particularly resistant cases can be treated with systemic antimalarial drugs, such as hydroxychloroquine (PLAQUENIL).

In one embodiment, an active compound or its salt or composition as described herein may be provided in combination with methotrexate for the treatment of Lupus.

In one embodiment, an active compound or its salt or composition as described herein may be provided in combination with azathioprine for the treatment of Lupus.

In one embodiment, an active compound or its salt or composition as described herein may be provided in combination with a non-steroidal anti-inflammatory drug for the treatment of Lupus.

In one embodiment, an active compound or its salt or composition as described herein may be provided in combination with a corticosteroid for the treatment of Lupus.

In one embodiment, an active compound or its salt or composition as described herein may be provided in combination with a belimumab (Benlysta) for the treatment of Lupus.

In one embodiment, an active compound or its salt or composition as described herein may be provided in combination with hydroxychloroquine (Plaquenil) for the treatment of Lupus.

In one embodiment, an active compound or its salt or composition as described herein may be provided in combination with sifalimumab for the treatment of Lupus.

In one embodiment, an active compound or its salt or composition as described herein may be provided in combination with OMS721 (Omeros) for the treatment of a complement mediated disorder. In one embodiment, an active compound or its salt or composition as described herein may be provided in combination with OMS906 (Omeros) for the treatment of a complement mediated disorder. In one embodiment, the complement mediated disorder is, for example, thrombotic thrombocytopenic purpura (TTP) or aHUS.

In one embodiment, an active compound or its salt or composition as described herein may be provided in combination with an anti-inflammatory agent, immunosuppressive agent, or anti-cytokine agent for the treatment or prevention of cytokine or inflammatory reactions in response to the administration of biotherapeutics (e.g. adoptive T-cell therapy (ACT) such as CAR T-cell therapy, or monoclonal antibody therapy). In one embodiment, an active compound or its salt or composition as described herein may be provided in combination with a corticosteroid, for example prednisone, dexamethasone, solumedrol, and methylprednisolone, and/or anti-cytokine compounds targeting, e.g., IL-4, IL-10, IL-11, IL-13 and TGFβ. In one embodiment, an active compound or its salt or composition as described herein may be provided in combination with an anti-cytokine inhibitor including, but are not limited to, adalimumab, infliximab, etanercept, protopic, efalizumab, alefacept, anakinra, siltuximab, secukinumab, ustekinumab, golimumab, and tocilizumab, or a combination thereof. Additional anti-inflammatory agents that can be used in combination with an active compound or its salt or composition as described herein include, but are not limited to, non-steroidal anti-inflammatory drug(s) (NSAIDs); cytokine suppressive anti-inflammatory drug(s) (CSAIDs); CDP-571/BAY-10-3356 (humanized anti-TNFα antibody; Celltech/Bayer); cA2/infliximab (chimeric anti-TNFα antibody; Centocor); 75 kdTNFR-IgG/etanercept (75 kD TNF receptor-IgG fusion protein; Immunex); 55 kdTNF-IgG (55 kD TNF receptor-IgG fusion protein; Hoffmann-LaRoche); IDEC-CE9.1/SB 210396 (non-depleting primatized anti-CD4 antibody; IDEC/SmithKline); DAB 486-IL-2 and/or DAB 389-IL-2 (IL-2 fusion proteins; Seragen); Anti-Tac (humanized anti-IL-2Rα; Protein Design Labs/Roche); IL-4 (anti-inflammatory cytokine; DNAX/Schering); IL-10 (SCH 52000; recombinant IL-10, anti-inflammatory cytokine; DNAX/Schering); IL-4; IL-10 and/or IL-4 agonists (e.g., agonist antibodies); IL-1RA (IL-1 receptor antagonist; Synergen/Amgen); anakinra (Kineret®/Amgen); TNF-bp/s-TNF (soluble TNF binding protein); R973401 (phosphodiesterase Type IV inhibitor); MK-966 (COX-2 Inhibitor); Iloprost, leflunomide (anti-inflammatory and cytokine inhibiton); tranexamic acid (inhibitor of plasminogen activation); T-614 (cytokine inhibitor); prostaglandin E1; Tenidap (non-steroidal anti-inflammatory drug); Naproxen (non-steroidal anti-inflammatory drug); Meloxicam (non-steroidal anti-inflammatory drug); Ibuprofen (non-steroidal anti-inflammatory drug); Piroxicam (non-steroidal anti-inflammatory drug); Diclofenac (non-steroidal anti-inflammatory drug); Indomethacin (non-steroidal anti-inflammatory drug); Sulfasalazine; Azathioprine; ICE inhibitor (inhibitor of the enzyme interleukin-1β converting enzyme); zap-70 and/or lck inhibitor (inhibitor of the tyrosine kinase zap-70 or lck); TNF-convertase inhibitors; anti-IL-12 antibodies; anti-IL-18 antibodies; interleukin-11; interleukin-13; interleukin-17 inhibitors; gold; penicillamine; chloroquine; chlorambucil; hydroxychloroquine; cyclosporine; cyclophosphamide; anti-thymocyte globulin; anti-CD4 antibodies; CD5-toxins; orally-administered peptides and collagen; lobenzarit disodium; Cytokine Regulating Agents (CRAB) HP228 and HP466 (Houghten Pharmaceuticals, Inc.); ICAM-1 antisense phosphorothioate oligo-deoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids); auranofin; phenylbutazone; meclofenamic acid; flufenamic acid; intravenous immune globulin; zileuton; azaribine; mycophenolic acid (RS-61443); tacrolimus (FK-506); sirolimus (rapamycin); amiprilose (therafectin); cladribine (2-chlorodeoxyadenosine).

In a specific embodiment, an active compound or its salt or composition as described herein may be provided in combination with a corticosteroid for the treatment or prevention of cytokine or inflammatory reactions in response to the administration of biotherapeutics. In another embodiment, an active compound or its salt or composition as described herein may be provided in combination with etarnercept for the treatment or prevention of cytokine or inflammatory reactions in response to the administration of biotherapeutics. In another embodiment, an active compound or its salt or composition as described herein may be provided in combination with tocilizumab for the treatment or prevention of cytokine or inflammatory reactions in response to the administration of biotherapeutics. In another embodiment, an active compound or its salt or composition as described herein may be provided in combination with etarnercept and tocilizumab for the treatment or prevention of cytokine or inflammatory reactions in response to the administration of biotherapeutics. In another embodiment, an active compound or its salt or composition as described herein may be provided in combination with infliximab for the treatment or prevention of cytokine or inflammatory reactions in response to the administration of biotherapeutics. In another embodiment, an active compound or its salt or composition as described herein may be provided in combination with golimumab for the treatment or prevention of cytokine or inflammatory reactions in response to the administration of biotherapeutics.

VI. Combinations for Prophylactic or Concomitant Anti-Bacterial Therapy

In one aspect of the present invention, a method is provided for treating a host in need thereof that comprises administering an effective amount of a prophylactic anti-bacterial vaccine prior to administration of an active compound or its salt or composition for any of the disorders described herein. In another aspect of the present invention, a method is provided for treating a host in need thereof that comprises administering an effective amount of a prophylactic anti-bacterial drug, such as a pharmaceutical drug, prior to administration of an active compound or its salt or composition for any of the disorders described herein. In one aspect of the present invention, a method is provided for treating a host in need thereof that comprises administering an effective amount of an anti-bacterial vaccine after administration of an active compound or its salt or composition for any of the disorders described herein. In another aspect of the present invention, a method is provided for treating a host in need thereof that comprises administering an effective amount of an anti-bacterial drug, such as a pharmaceutical drug, after administration of an active compound or its salt or composition for any of the disorders described herein. In one embodiment, the disorder is PNH or aHUS. In one embodiment, the host has received an organ or other tissue or biological fluid transplant. In one embodiment, the host is also administered eculizumab.

In one aspect of the present invention, an active compound or its salt or composition as described herein is administered to a host concomitantly with the prophylactic administration of a vaccine against a bacterial infection. In one embodiment, the complement mediated disorder is PNH or aHUS. In one embodiment, the host has received an organ or other tissue or biological fluid transplant. In one embodiment, the host is also administered eculizumab.

In one aspect of the present invention, an active compound or its salt or composition as described herein is administered to a host and, during the administration period of the compound or salt, a vaccine against a bacterial infection is administered to the host. In one embodiment, the disorder is PNH or aHUS. In one embodiment, the host has received an organ or other tissue or biological fluid transplant. In one embodiment, the host is also administered eculizumab.

In one aspect of the present invention, the host is administered an active compound or its salt or composition as described herein in combination with an antibiotic compound for the duration of factor D inhibitor administration. In one embodiment, the disorder is PNH or aHUS. In one embodiment, the host has received an organ or other tissue or biological fluid transplant. In one embodiment, the host is also administered eculizumab.

In one aspect of the present invention, an active compound or its salt or composition as described herein is administered to a host following the prophylactic administration of a vaccine against a bacterial infection, and in combination with an antibiotic compound for the duration of factor D inhibitor administration. In one embodiment, the complement mediated disorder is PNH or aHUS. In one embodiment, the host has received an organ or other tissue or biological fluid transplant. In one embodiment, the host is also administered eculizumab.

In one embodiment, the host, prior to receiving an active compound or its salt or composition as described herein, is vaccinated against a bacterial infection caused by the bacterium *Neisseria meningitidis*. In one embodiment, the host is vaccinated against a bacterial infection caused by the bacterium *Haemophilus influenzae*. In one embodiment, the *Haemophilus influenzae* is *Haemophilus influenzae* serotype B (Hib). In one embodiment, the host is vaccinated against a bacterial infection caused by *Streptococcus pneumoniae*. In one embodiment, the host is vaccinated against a bacterial infection caused by the bacterium *Nisseria meningitidis*, *Haemophilus influenzae*, or *Streptococcus pneumoniae*, or a combination of one or more of *Nisseria meningitidis*, *Haemophilus influenzae*, or *Streptococcus pneumoniae*. In one embodiment, the host is vaccinated against a bacterial infection caused by the bacterium *Nisseria meningitidis*, *Haemophilus influenzae*, and *Streptococcus pneumoniae*.

In other embodiments, the host is vaccinated against a bacterial infection caused by a bacterium selected from a Gram-negative bacterium. In one embodiment, the host is vaccinated against a bacterial infection caused by a bacterium selected from a Gram-positive bacterium. In one embodiment, the host is vaccinated against a bacterial infection caused by the bacterium *Nisseria meningitidis*, *Haemophilus influenzae*, or *Streptococcus pneunemoniae*, or a combination of one or more of *Nisseria meningitidis*, *Haemophilus influenzae*, or *Streptococcus pneumoniae*, and one or more of, but not limited to, *Bacillus anthracis, Bordetella pertussis, Clostridium tetani, Corynebacterium diphtheria, Coxiella burnetii, Mycobacterium tuberculosis, Salmonella typhi, Vibrio cholerae, Anaplasma phagocytophilum, Ehrlichia ewingii, Ehrlichia chaffeensis, Ehrlichia canis, Neorickettsia sennetsu, Mycobacterium leprae, Borrelia burgdorferi, Borrelia mayonii, Borrelia afzelii, Borrelia garinii, Mycobacterium bovis, Staphylococcus aureus, Streptococcus pyogenes, Treponema pallidum, Francisella tularensis, Yersinia pestis,*

In one embodiment, the host is vaccinated with one or more vaccines selected from, but not limited to, typhoid vaccine, live (Vivotif Berna Vaccine, PaxVax), typhoid Vi polysaccharide vaccine (Typhim Vi, Sanofi), pneumococcal 23-polyvalent vaccine, PCV13 (Pneumovax 23, Merck), pneumococcal 7-valent vaccine, PCV7 (Prevnar, Pfizer), pneumococcal 13-valent vaccine, PCV13 (Prevnar 13, Pfizer), haemophilus b conjugate (prp-t) vaccine (ActHIB, Sanofi; Hibrix, GSK), haemophilus b conjugate (hboc) vaccine (HibTITER, Neuron Biotech), haemophilus b conjugate (prp-omp) vaccine (PedvaxHIB, Merck), haemophilus b conjugate (prp-t) vaccine/meningococcal conjugate vaccine (MenHibrix, GSK), haemophilus b conjugate (prp-t) vaccine/meningococcal conjugate vaccine/Hepatitis B vaccine (Comvax, Merck), meningococcal polysaccharide vaccine (Menomune A/C/Y/W-135, Sanofi), meningococcal conjugate vaccine/diphtheria CRM197 conjugate (Menveo, GSK; Menactra, Sanofi), meningococcal group B vaccine (Bexsero, GSK; Trumenba, Pfizer), anthrax vaccine adsorbed (Biothrax, Emergent Biosolutions), tetanus toxoid (Te Anatoxal Berna, Hendricks Regional Health), Bacillus Calmette and Guerin, live, intravesical (TheraCys, Sanofi; Tice BCG, Organon), cholera vaccine, live, oral (Vachora, Sanofi; Dukoral, SBL Vaccines; ShanChol, Shantha Biotec; Micromedex, Truven Health), tetanus toxoids and diphtheria absorbed (Tdap; Decavac, Sanofi; Tenivac, Sanofi; td, Massachusetts Biological Labs), diphtheria and tetanus toxois and pertussis (DTap; Daptacel, Sanofi; Infanrix, GSK; Tripedia, Sanofi), diphtheria and tetanus toxois and pertussis/polio (Kinrix, GSK; Quadracel, Sanofi), diphtheria and tetanus toxois and pertussis tetanus/hepatitis B/polio (Pediarix, GSK), diphtheria and tetanus toxois and pertussis/polio, haemophilus influenza tybe b (Pentacel, Sanofi), and/or diphtheria, and pertussis (Tdap; Boostrix, GSK; Adacel, Sanofi), or a combination thereof.

As described above, a host receiving a compound of the present invention to treat disorder is prophylactically administered an antibiotic compound in addition to a factor D inhibitor described herein. In one embodiment, the host is administered an antibiotic compound for the duration of administration of the active compound to reduce the development of a bacterial infection. Antibiotic compounds for concomitant administration with a factor D inhibitor described herein can be any antibiotic useful in preventing or reducing the effect of a bacterial infection. Antibiotics are well known in the art and include, but are not limited to, amikacin (Amikin), gentamicin (Garamycin), kanamycin (Kantrex), neomycin (Neo-Fradin), netilmicin (Netromycin), tobramycin (Nebcin), paromomycin (Humatin), streptomycin, spectinomycin (Trobicin), geldanamycin, herbimycin, rifaximin (Xifaxan), loracarbef (Lorabid), ertapenem (Invanz), doripenem (Doribax), imipenem/cilastatin (Primaxin), meropenem (Merrem), cefadroxil (Duricef), cefazolin (Ancef), cefalotin/cefalothin (Keflin), cephalexin (Keflex), cefaclor (Distaclor), cefamandole (Mandol), cefoxitin (Mefoxin), cefprozil (Cefzil), cefuroxime (Ceftin, Zinnat), cefixime (Cefspan), cefdinir (Omnicef, Cefdiel), cefditoren (Spectracef, Meiact), cefoperazone (Cefobid), cefotaxime (Claforan), cefpodoxime (Vantin) ceftazidime (Fortaz), ceftibuten (Cedax), ceftizoxime (Cefizox), ceftriaxone (Rocephin), cefepime (Maxipime), ceftaroline fosamil (Teflaro), ceftobiprole (Zeftera), teicoplanin (Targocid), vancomycin (Vancocin), telavancin (Vibativ), dalbavancin (Dalvance), oritavancin (Orbactiv), clindamycin (Cleocin), lincomycin (Lincocin), daptomycin (Cubicin), azithromycin (Zithromax, Sumamed, Xithrone), clarithromycin (Biaxin), dirithromycin (Dynabac), erythromycin (Erythocin, Erythroped), roxithromycin, troleandomycin (Tao), telithromycin (Ketek), spiramycin (Rovamycine), aztreonam (Azactam), furazolidone (Furoxone), nitrofurantoin (Macrodantin, Macrobid), linezolid (Zyvox), posizolid, radezolid, torezolid, amoxicillin (Novamox, Amoxil), ampicillin (Principen),azlocillin, carbenicillin (Geocillin), cloxacillin (Tegopen), dicloxacillin (Dynapen), flucloxacillin (Floxapen), mezlocillin (Mezlin), methicillin (Staphcillin), nafcillin (Unipen),oxacillin (Prostaphlin), penicillin G (Pentids),penicillin V (Veetids (Pen-Vee-K), piperacillin (Pipracil), penicillin G (Pfizerpen), temocillin (Negaban),ticarcillin (Ticar), amoxicillin/clavulanate (Augmentin), ampicillin/sulbactam (Unasyn), piperacillin/tazobactam (Zosyn), ticarcillin/clavulanate (Timentin),bacitracin, colistin (Coly-Mycin-S), polymyxin B, ciprofloxacin (Cipro, Ciproxin, Ciprobay), enoxacin (Penetrex), gatifloxacin (Tequin), gemifloxacin (Factive), levofloxacin (Levaquin), lomefloxacin (Maxaquin), moxifloxacin (Avelox), nalidixic acid (NegGram), norfloxacin (Noroxin), ofloxacin (Floxin, Ocuflox), trovafloxacin (Trovan), grepafloxacin (Raxar), sparfloxacin (Zagam), temafloxacin (Omniflox), mafenide (Sulfamylon), sulfacetamide (Sulamyd, Bleph-10), sulfadiazine (Micro-Sulfon), silver sulfadiazine (Silvadene), sulfadimethoxine (Di-Methox, Albon), sulfamethizole (Thiosulfil Forte), sulfamethoxazole (Gantanol), sulfanilamide, sulfasalazine (Azulfidine), sulfisoxazole (Gantrisin), trimethoprim-sulfamethoxazole (Co-trimoxazole) (TMP-SMX) (Bactrim, Septra), sulfonamidochrysoidine (Prontosil), demeclocycline (Declomycin), doxycycline (Vibramycin), minocycline (Minocin), oxytetracycline (Terramycin), tetracycline (Sumycin, Achromycin V, Steclin), clofazimine (Lamprene), dapsone (Avlosulfon), capreomycin (Capastat), cycloserine (Seromycin), ethambutol (Myambutol), ethionamide (Trecator), isoniazid (I.N.H.), pyrazinamide (Aldinamide), rifampicin (Rifadin, Rimactane), rifabutin (Mycobutin), rifapentine (Priftin), streptomycin, arsphenamine (Salvarsan), chloramphenicol (Chloromycetin), fosfomycin (Monurol, Monuril), fusidic acid (Fucidin), metronidazole (Flagyl), mupirocin (Bactroban), platensimycin, quinupristin/dalfopristin (Synercid), thiamphenicol, tigecycline (Tigacyl), tinidazole (Tindamax Fasigyn), trimethoprim (Proloprim, Trimpex), and/or teixobactin, or a combination thereof.

In one embodiment, the host is administered a prophylactic antibiotic selected from cephalosporin, for example, ceftriaxone or cefotaxime, ampicillin-sulbactam, Penicillin G, ampicillin, chloramphenicol, fluoroquinolone, aztreonam, levofloxacin, moxifloxacin, gemifloxacin, vancomycin, clindamycin, cefazolin, azithromycin, meropenem, ceftaroline, tigecycline, clarithromycin, moxifloxacin, trimethoprim/sulfamethoxazole, cefuroxime, axetil, ciprofloxacin, rifampin, minocycline, spiramycin, and cefixime, or a combination of two or more thereof.

VII. Process of Preparation of Active Compounds

Abbreviations (Boc)20 di-tert-butyl dicarbonate
CAN Acetonitrile
AcOEt, EtOAc Ethyl acetate
$CH_3OH$, MeOH Methanol
CsF Cesium fluoride
CuI Cuprous iodide
DCM, $CH_2Cl_2$ Dichloromethane
DIEA, DIPEA N,N-diisopropylethylamine
DMA N,N-dimethylacetamide
DMF N,N-dimethylformamide
DMSO Dimethyl sulfoxide
DPPA Diphenyl phosphoryl azide
$Et_3N$, TEA Triethylamine
EtOAc Ethylacetate
EtOH Ethanol
HATU 1-[Bis(dimethylamino)methylene]-1H-1,2,3-triazolo[4,5-b]pyridinium 3-oxide hexafluorophosphate
HCl Hydrochloric acid
$^iPr_2$Net N,N-diisopropylethylamine
$K_2CO_3$ Potassium carbonate
LiOH Lithium hydroxide
MTBE Methyl tert-butylether
$Na_2SO_4$ Sodium sulfate
NaCl Sodium chloride
NaH Sodium hydride
$NaHCO_3$ Sodium bicarbonate
$NEt_3$ Trimethylamine
$Pd(OAc)_2$ Palaldium acetate
$Pd(dppf)Cl_2$ [1,1'-Bis(diphenylphosphino) ferrocene]dichloropalladium(II)
$Pd(PPh_3)_2Cl_2$ Bis(triphenylphosphine)palladium(II) dichloride
$Pd(PPh_3)_4$ Tetrakis(triphenylphosphine)palladium(0)-Tetrakis
$Pd_2$ $(dba)_3$ Tris(dibenzylideneacetone)dipalladium(0)
$PPh_3$ Triphenylphosphine
RT Room temperature
tBuOK Potassium tert-butoxide
TEA Trimethylamine
TFA Trifluoroacetic acid
$Tf_2O$ Trifluoromethanesulfonic anhydride
TFA Trifluoroacetic acid
THF Tetrahydrofuran
TMSBr Bromotrimethylsilane
$t_R$ Retention time
Zn $(CN)_2$ Zinc cyanide General Methods All nonaqueous reactions were performed under an atmosphere of dry argon or nitrogen gas using anhydrous solvents. The progress of reactions and the purity of target compounds were determined using one of the two liquid chromatography (LC) methods listed below. The structure of starting materials, intermediates, and final products was confirmed by standard analytical techniques, including NMR spectroscopy and mass spectrometry.

LC Method A
Instrument: Waters Acquity Ultra Performance LC
Column: ACQUITY UPLC BEH C18 2.1×50 mm, 1.7 µm
Column Temperature: 40° C.
Mobile Phase: Solvent A: $H_2O$+0.05% FA; Solvent B: $CH_3CN$+0.05% FA
Flow Rate: 0.8 mL/min
Gradient: 0.24 min @ 15% B, 3.26 min gradient (15-85% B), then 0.5 min @ 85% B
Detection: UV (PDA), ELS, and MS (SQ in EI mode)

LC Method B
Instrument: Shimadzu LC-2010A HT
Column: Athena, C18-WP, 50×4.6 mm, 5 µm
Column Temperature: 40° C.
Mobile Phase: Solvent A: $H_2O/CH_3OH/FA$=90/10/0.1; Solvent B: $H_2O/CH_3OH/FA$=10/90/0.1
Flow Rate: 3 mL/min
Gradient: 0.4 min @ 30% B, 3.4 min gradient (30-100% B), then 0.8 min @ 100% B
Detection: UV (220/254 nm)

LC Method C
Instrument: Agilent 1100/1200 series LC system with DAD detector
Column: Atlantis dC18 (250×4.6) mm, 5 µm
Column Temperature: Ambient
Mobile Phase A: 0.1% TFA in water, Mobile Phase B: Acetonitrile
Flow Rate: 1.0 mL/min
Gradient:

| | Time (min) | | | | |
|---|---|---|---|---|---|
| | 0.0 | 15 | 20 | 23 | 30 |
| % B | 10 | 100 | 100 | 10 | 10 |

Detection: (210-400 nm)

LC Method D
Instrument: Shimadzu LC 20AD system with PDA detector
Column: Phenomenex Gemini NX C18 (150×4.6) mm, 5 µm
Column Temperature: Ambient
Mobile Phase A: 10 mM $NH_4OAC$ in water, Mobile Phase B: Acetonitrile
Flow Rate: 1.0 mL/min Gradient:

| Time (min) | | | | |
|---|---|---|---|---|
| 0.0 | 15 | 20 | 23 | 30 |
| % B 10 | 100 | 100 | 10 | 10 |

Detection: (210-400 nm)

Example 1. General Route of Synthesis

A compound of the present invention can be prepared, for example, from a central core. In one embodiment, for example, the central core Structure 1 is an N-protected aminoacid where $X^1$ is nitrogen and PG=protecting group. In one embodiment, the central core is coupled to an amine to generate an amide of Structure 2 (wherein L-B includes a C(O)N moiety). Structure 2 can then be deprotected to generate Structure 3. Structure 3 is coupled to Structure 4 (A-COOH) to generate a second amide bond, forming a compound within Formula I. The chemistry is illustrated in Route 1.

Route 1

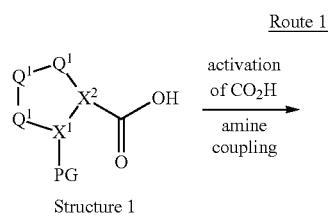

Structure 1

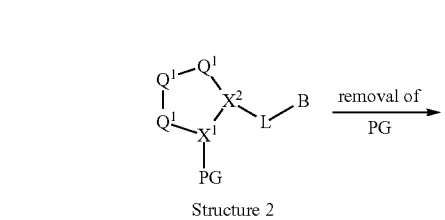

Structure 3 → Formula I

In an alternative embodiment, central core Structure 5 is reacted with a heterocyclic or heteroaryl compound to generate a compound of Structure 6. In one embodiment, Structure 6 is deprotected to generate a carboxylic acid, Structure 7. In one embodiment, Structure 7 is coupled to an amine to generate a compound of Formula I. This chemistry is illustrated in Route 2.

Route 2

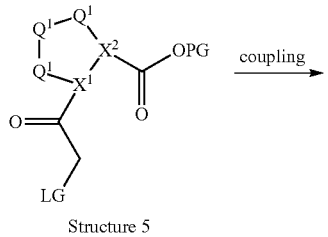

Structure 5

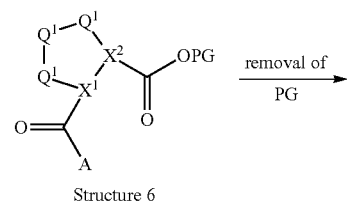

Structure 6

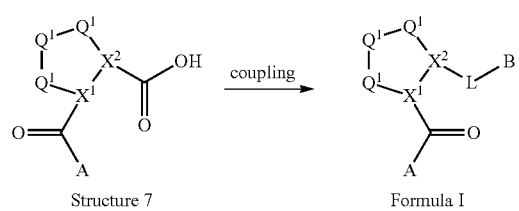

Structure 7 → Formula I

In an alternative embodiment, Structure 8 is deprotected to generate an amine which is Structure 9. Structure 9 is then coupled to generate an amide which is Structure 6. Structure 6 is then deprotected to generate a carboxylic acid which is Structure 7. Structure 7 is then coupled to form the amide which falls within Formula I. The chemistry is illustrated in Route 3.

Route 3

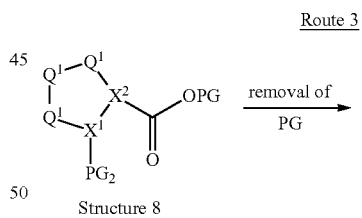

Structure 8

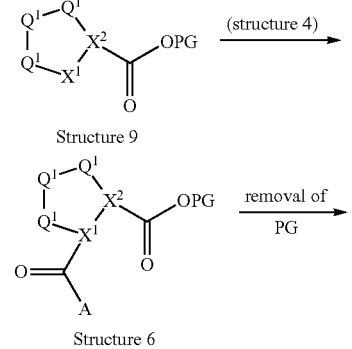

Structure 9

Structure 6

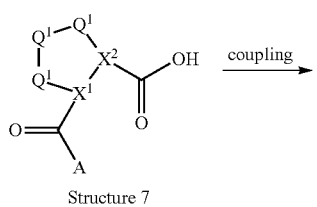

Structure 7

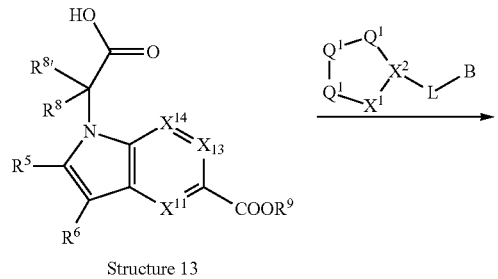

Structure 13

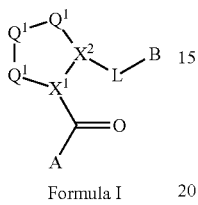

Formula I

In an alternate embodiment, a heteroaryl compound of Structure 10 is coupled to an activated ester, Structure 11, to generate Structure 12. The ester is hydrolyzed to form acid Structure 13. Structure 13 is coupled to Structure 3 from Route 1 to generate Structure 14. Structure 14 is treated with a base such as, but not limited to, lithium hydroxide to generate Structure 15. This chemistry is illustrated in Route 4.

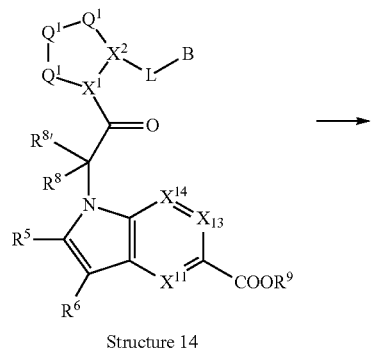

Structure 14

Route 4

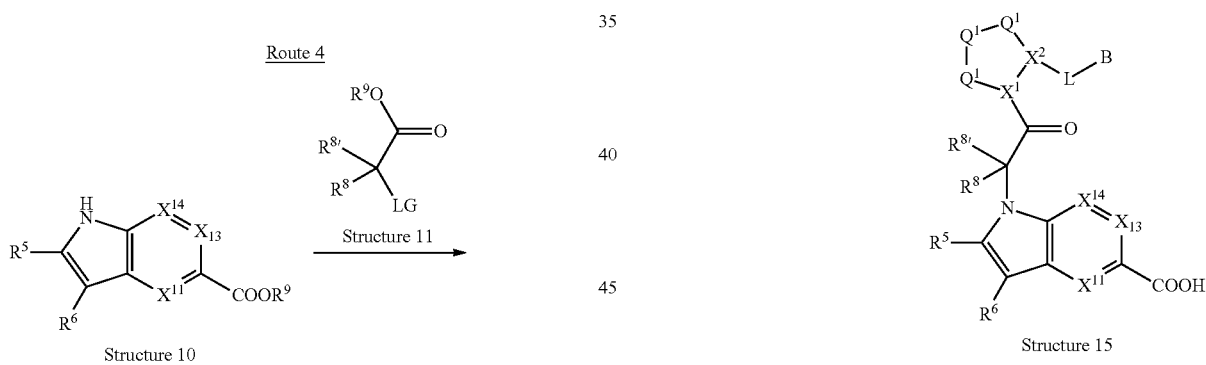

Structure 10 → Structure 11 → Structure 15

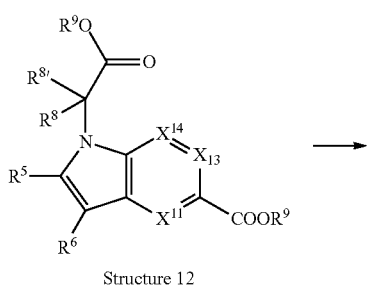

Structure 12

In another embodiment, Structure 15 is treated with diphenylphosphoryl azide (DPPA) to generate the isocyanate, Structure 16. Structure 16 is then treated with an amine or alcohol to generate ureas and carbamates compounds of Formula I, wherein the $R^{12}$ substituent is $NR^9C(O)NR^9R^{10}$, $NR^9C(O)NR^{10}R^{23}$, $NR^9C(O)NR^{24}R^{25}$, $NR^9C(O)OR^{10}$ or $NR^9C(O)OR^{23}$. In some embodiments, $R^9$ is hydrogen. Structure 15 can be coupled to amines to generate amides of Formula I, wherein the $R^{12}$ substituent is, $C(O)NR^{24}R^{25}$, $C(O)NR^9R^{37}$, or $C(O)NR^{21}SO_2R^{22}$. In some embodiments, $R^9$ is hydrogen. The chemistry is illustrated in Route 5.

Route 5

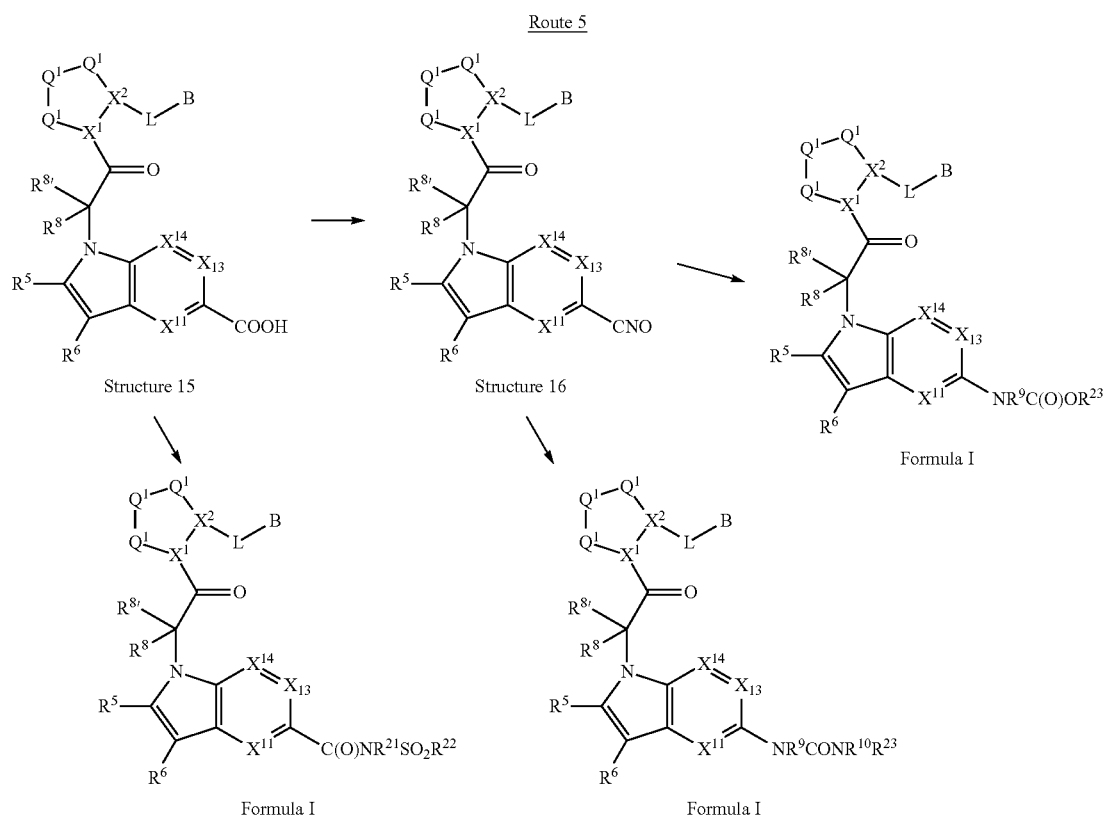

In an alternate embodiment, a heteroaryl compound of Structure 17 is coupled to an activated ester to generate Structure 18. The ester is hydrolyzed to form acid Structure 19. Structure 19 is coupled to Structure 3 from Route 1 to generate Structure 20. Structure 20 is treated with a base such as, but not limited to, lithium hydroxide to generate Structure 21. This chemistry is illustrated in Route 6.

Route 6

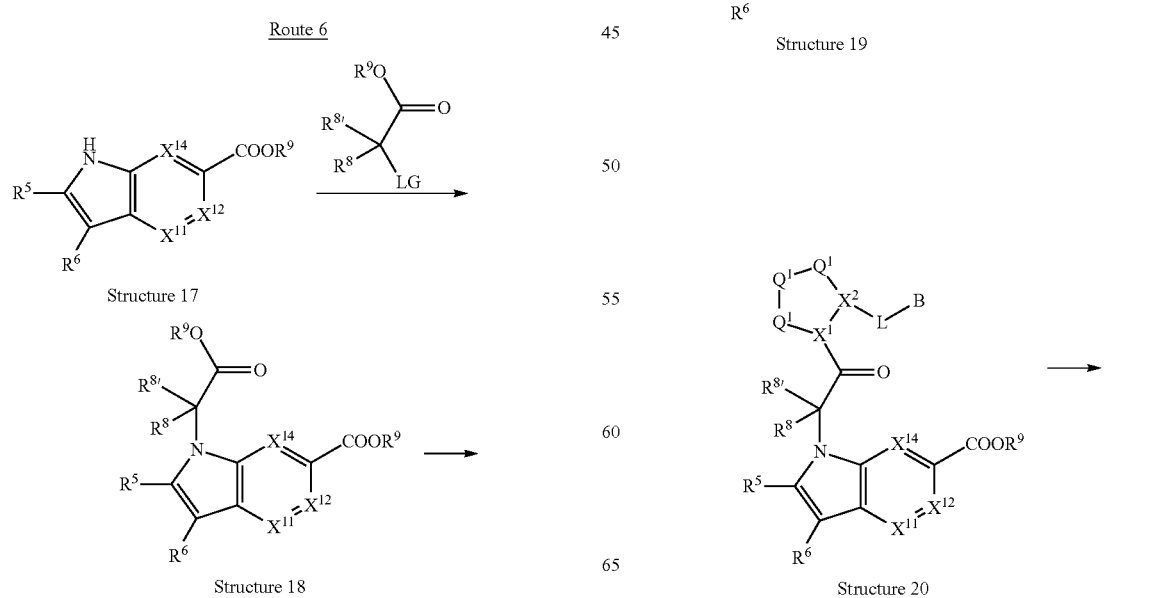

-continued

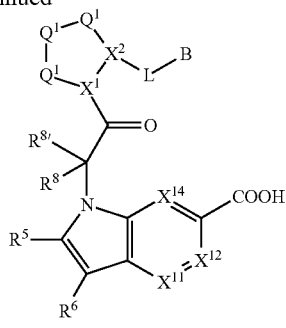

Structure 21

In one embodiment, Structure 21 from Route 6, is treated with, for example, diphenylphosphoryl azide (DPPA) to generate an isocyanate, Structure 22. Structure 22 is then treated with an amine or alcohol to generate urea and carbamate compounds within Formula I, wherein the $R^{13}$ substituent is $NR^9C(O)NR^9R^{10}$, $NR^9C(O)NR^{10}R^{23}$, $NR^9C(O)R^{24}R^{25}$, $NR^9C(O)OR^{10}$ and $NR^9C(O)OR^{23}$. In some embodiments, $R^9$ is hydrogen. Structure 21 can be coupled to amines to generate amides within Formula I, wherein the $R^{13}$ substituent is $C(O)NR^{24}R^{25}$, $C(O)NR^9R^{37}$, or $C(O)NR^{21}SO_2R^{22}$. In some embodiments, $R^9$ is hydrogen. The chemistry is illustrated in Route 7.

In an alternate embodiment, a heteroaryl or aryl moiety is coupled to a central core to generate 8-2. The protected acid, 8-2 is deblocked to form the carboxylic acid, 8-3. The carboxylic acid is coupled to form an amide bond (L-B) and 8-4. The heteroaryl or aryl moiety, A', can then be further derivitized to add substituents at the $X^{11}$, $X^{12}$, $X^{13}$ and $X^{14}$ positions to generate compounds within Formula I. This chemistry is illustrated in Route 8.

Route 8

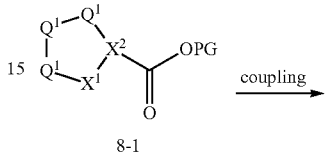

8-1

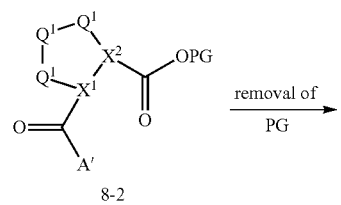

8-2

Route 7

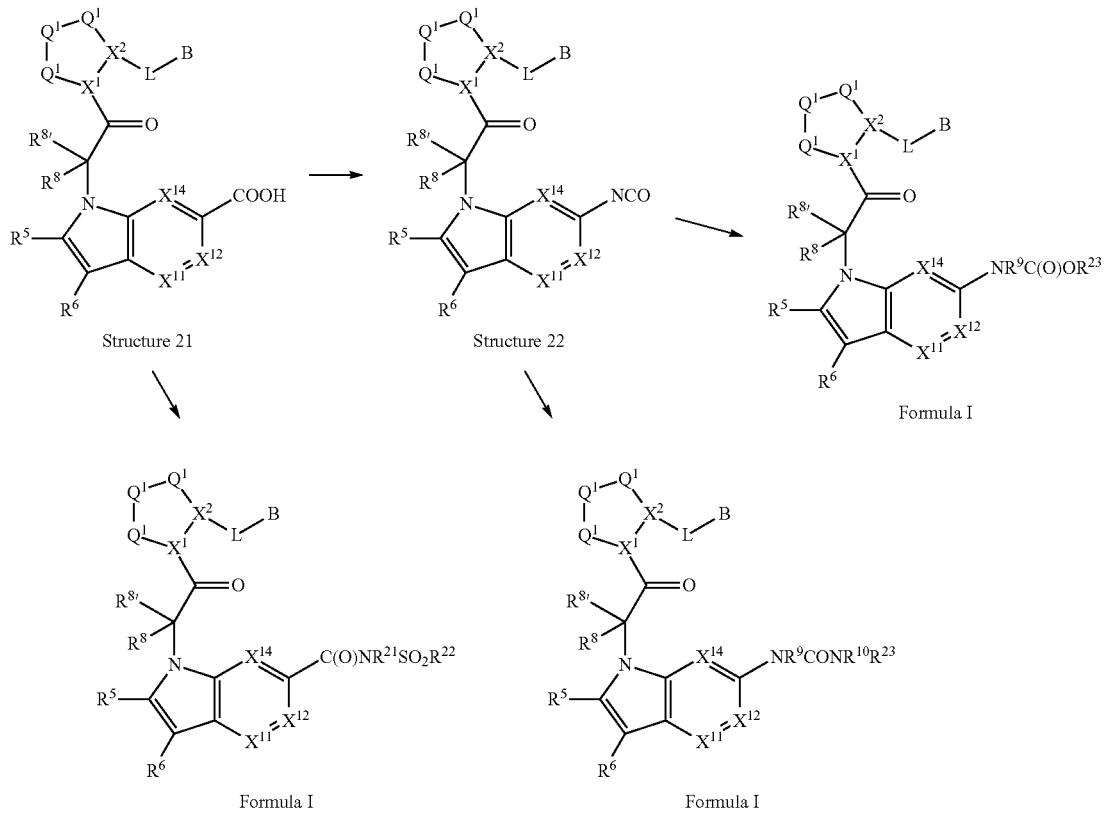

-continued

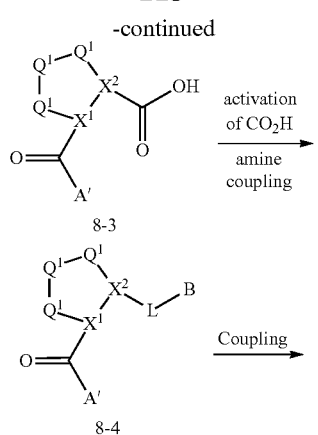

In an alternate embodiment, Structure 9-1 is coupled to an acid, Structure 9-2, to generate Structure 9-3. The carboxylic acid, Structure 9-3, is deblocked to generate carboxylic acid, Structure 9-4. Carboxylic acid Structure 9-4 is coupled to an amine to form an amide bond (L-B) and compounds within Formula I. This chemistry is illustrated in Route 9.

Route 9

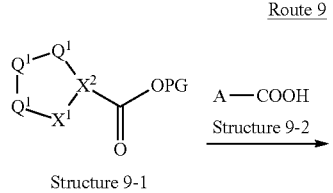

Structure 9-1

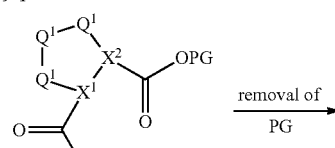

Structure 9-3

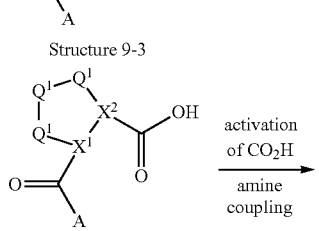

Structure 9-4

Formula I

In an alternate embodiment, a heteroaryl compound of Structure 10-1 is treated with a carboxylic acid to generate Structure 10-2. The heteroaryl Structure 10-2 can be treated with an acylating agent to generate Structure 10-3. In an alternate embodiment, Structure 10-2 is treated with coupling conditions to generate $R^6$=CN. The nitrile can be treated with an oxime to generate an amide at the $R^6$ position. Structure 10-3 is treated with an activated ester to generate Structure 10-4. In some embodiments, the leaving group, LG, is a halide. Structure 10-4 is treated with a base to generate the acid, Structure 10-5. Structure 10-5 can be coupled to Structure 3 from Route 1 to generate compounds within Formula I. This chemistry is illustrated in Route 10.

Route 10

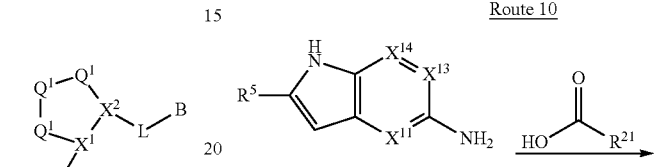

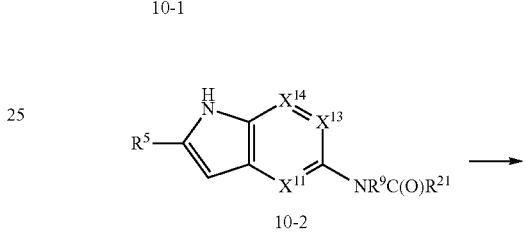

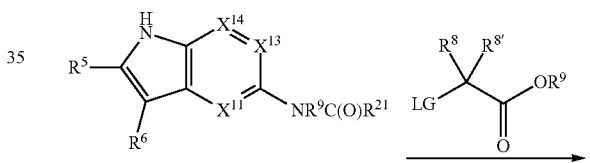

-continued

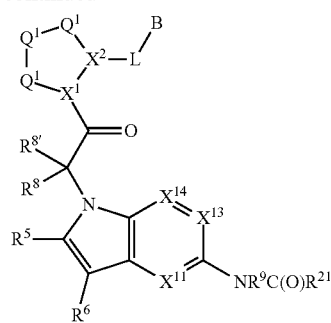

Formula I

In an alternate embodiment, a heteroaryl compound of Structure 11-1 is treated with a carboxylic acid to generate Structure 11-2. The heteroaryl Structure 11-2 can be treated with an acylating agent to generate Structure 11-3. In an alternate embodiment, Structure 11-2 is treated with coupling conditions to generate $R^6$=CN. The nitrile can be treated with an oxime to generate an amide at the $R^6$ position. Structure 11-3 is treated with an activated ester to generate Structure 11-4. In some embodiments, the leaving group, LG, is a halide. Structure 11-4 is treated with a base to generate the acid, Structure 11-5. Structure 11-5 is coupled to Structure 3 from Route 1 to generate compounds within Formula I. The chemistry is illustrated in Route 11.

Route 11

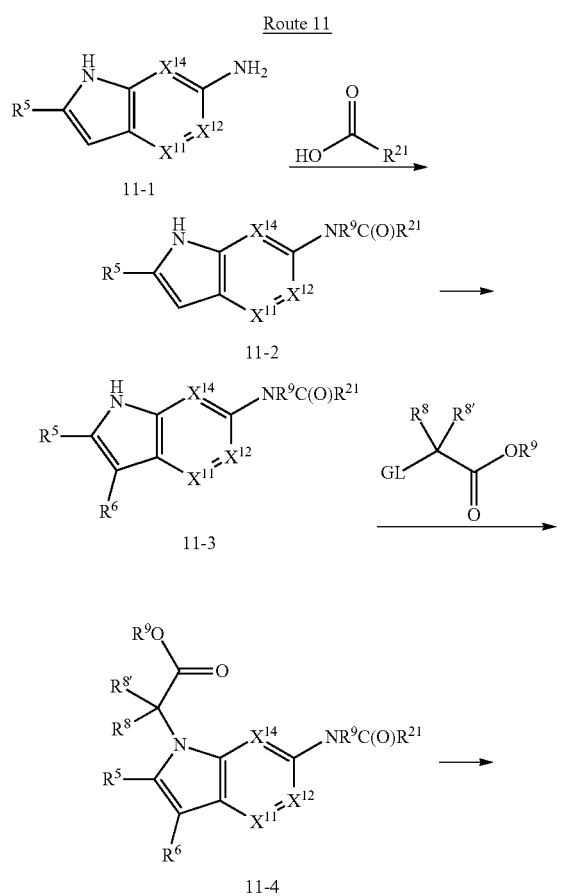

-continued

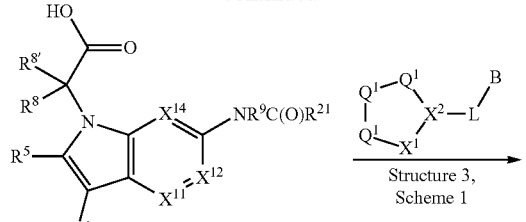

11-5

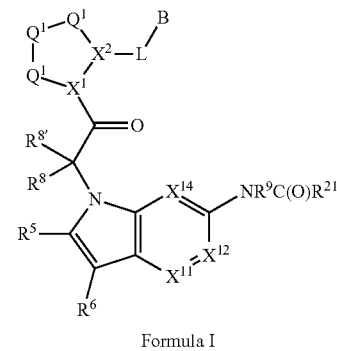

Formula I

In an alternate embodiment, a heteroaryl compound of Structure 12-1 is treated with a carboxylic acid to generate Structure 12-2. The heteroaryl Structure 12-2 can be treated with an acylating agent to generate Structure 12-3. In an alternate embodiment, Structure 12-2 is treated with coupling conditions to generate $R^6$=CN. The nitrile can be treated with an oxime to generate an amide at the $R^6$ position. Structure 12-3 is treated with an activated ester to generate Structure 12-4. In some embodiments, the leaving group, LG, is a halide. Structure 12-4 is treated with a base to generate the acid, Structure 12-5. Structure 12-5 can be coupled to Structure 3 from Route 1 to generate compounds within Formula I. This chemistry is illustrated in Route 12.

Route 12

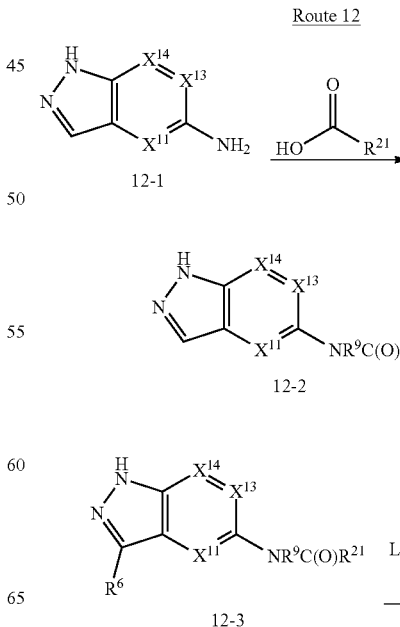

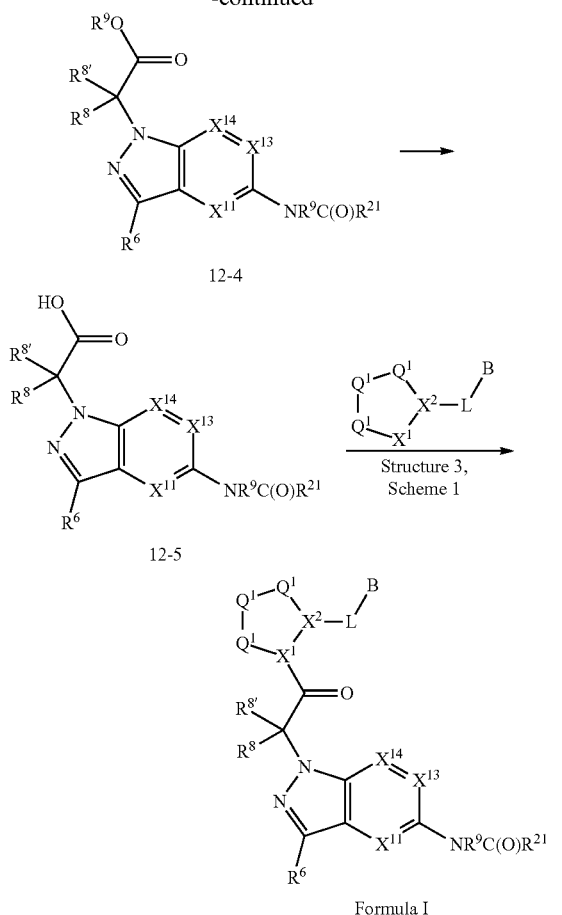

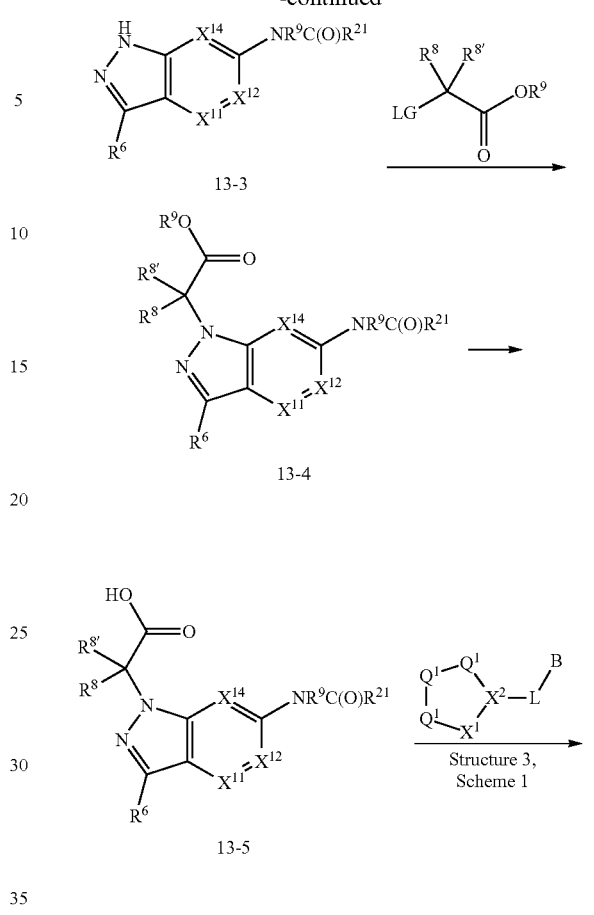

In an alternate embodiment, a heteroaryl compound of Structure 13-1 is treated with a carboxylic acid to generate Structure 13-2. The heteroaryl Structure 13-2 can be treated with an acylating agent to generate Structure 13-3. In an alternate embodiment, Structure 13-2 is treated with coupling conditions to generate $R^6$=CN. The nitrile can be treated with an oxime to generate an amide at the $R^6$ position. Structure 13-3 is treated with an activated ester to generate Structure 13-4. In some embodiments, the leaving group, LG, is a halide. Structure 13-4 is treated with a base to generate the acid, Structure 13-5. Structure 13-5 can be coupled to Structure 3 from Route 1 to generate compounds within Formula I. The chemistry is illustrated in Route 13.

Route 13

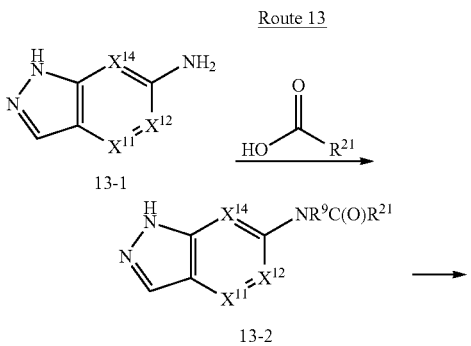

In an alternate embodiment, Structure 14-1 is coupled to an amine to generate an amide bond (L-B), and Structure 14-2. Structure 14-2, is coupled to an amine to generate compounds within Formula I. This chemistry is illustrated in Route 14.

Route 14

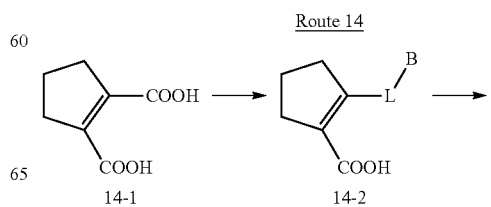

Example 2. Examples of Central Synthons
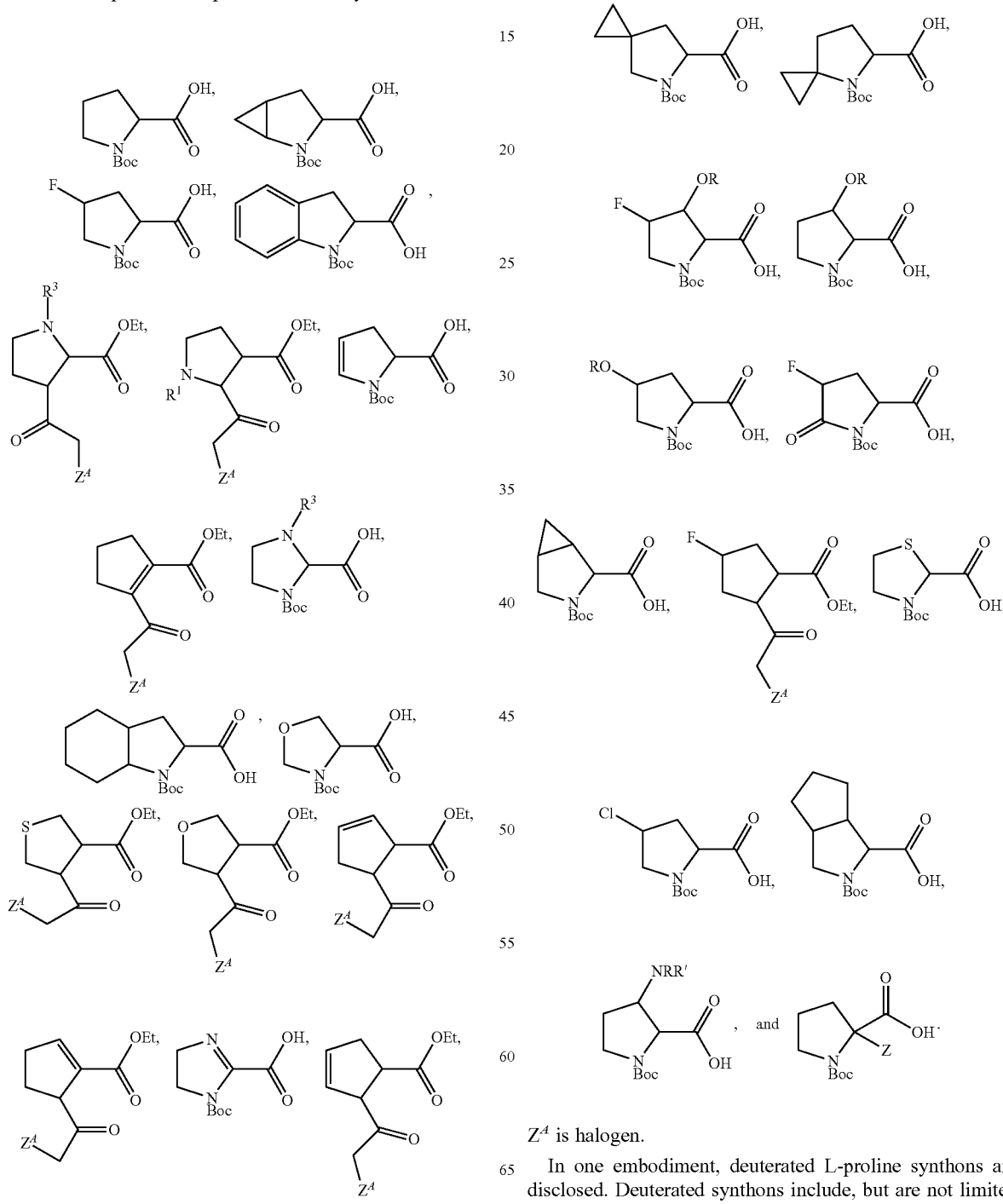
$Z^A$ is halogen.
In one embodiment, deuterated L-proline synthons are disclosed. Deuterated synthons include, but are not limited to, for example, the following compounds:

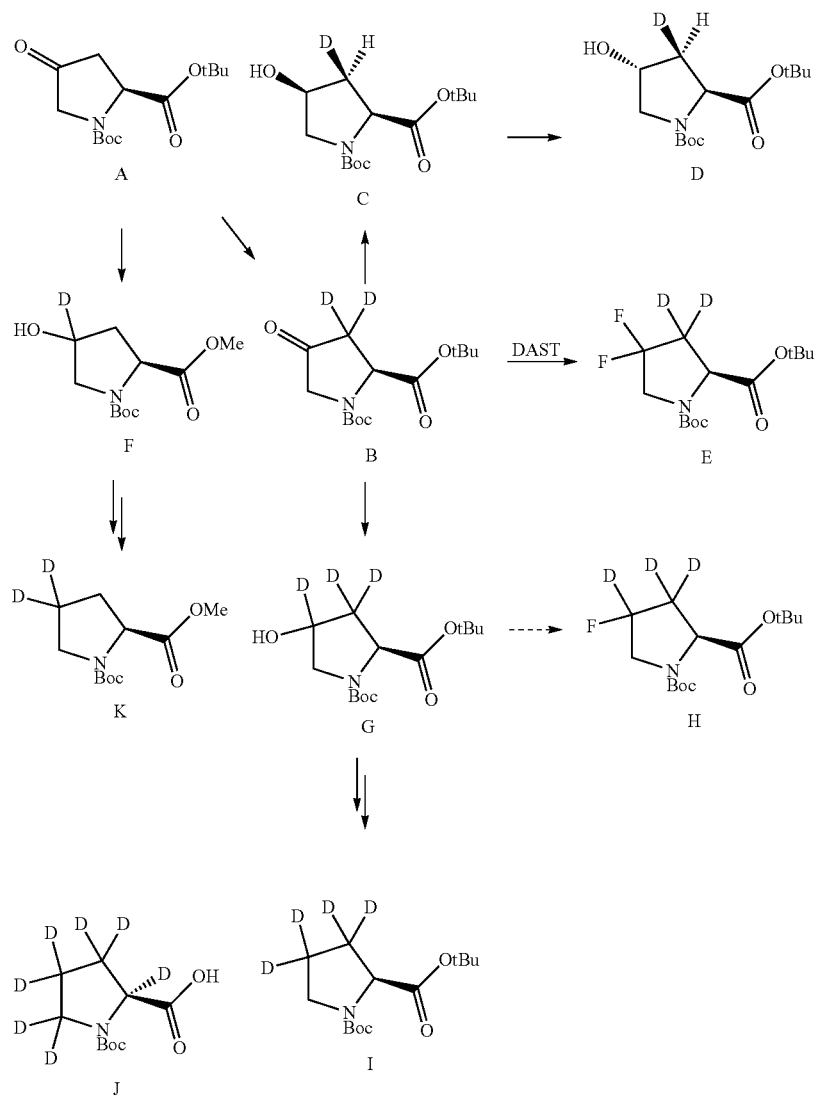

Structure A can be treated with deuterium oxide to generate Structure B. See, Barraclough, P. et al. Tetrahedron Lett. 2005, 46, 4653-4655; Barraclough, P. et al. Org. Biomol. Chem. 2006, 4, 1483-1491 and WO 2014/037480 (p. 103). Structure B can be reduced to generate Structure C. See, Barraclough, P. et al. Tetrahedron Lett. 2005, 46, 4653-4655; Barraclough, P. et al. Org. Biomol. Chem. 2006, 4, 1483-1491. Structure C can be treated with Mitsunobu reaction conditions to generate Structure D. Structure B can be treated with DAST to generate Structure E. See, WO 2014/037480. Structure A can be treated with sodium borodeuteride to generate Structure F. See, Dormoy, J.-R.; Castro, B. Synthesis 1986, 81-82. Compound F can be used to generate Structure K. See, Dormoy, J.-R.; Castro, B. Synthesis 1986, 81-82. Structure B can be treated with a deuterated reducing agent, for example sodium borodeuteride to generate Structure G. Structure G can be treated with DAST to generate Structure H. Structure F can be used to generate Structure K. See, Dormoy, J.-R.; Castro, B. Synthesis 1986, 81-82. Structure G can be used to generate Structure I. Structure J can be prepared according to Hruby, V. J. et al. J. Am. Chem. Soc. 1979, 101, 202-212. Structures A-J can be used to prepare compounds of Formula I.

Example 3. Preparation of Central-L-B Synthons

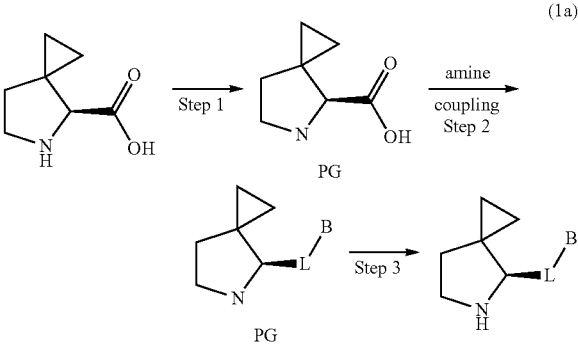

Routes 1a, 1b and 1c.

(1a)

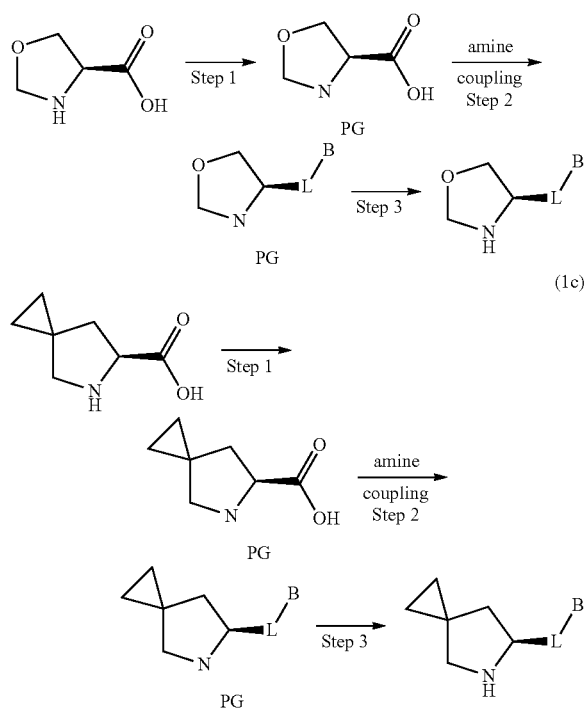

In Route 1a, 5-azaspiro[2.4]heptane-4,5-dicarboxylic acid, 5-(1,1-dimethylethyl) ester, (4S)-, CAS 209269-08-9, can be prepared as described in Tandon, M. et al. Bioorg. Med. Chem. Lett. 1998, 8, 1139-1144. In Step 2, the protected azaspiro[2.4]heptane is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 3, the protecting group is removed. In one embodiment, the starting material is reacted with an acid in the presence of an organic solvent. In one embodiment, the acid is 4N hydrochloric acid. In one embodiment, the organic solvent is dioxane.

In Route 1b, (4S) 4-oxazolidinecarboxylic acid, hydrochloride is treated with an amine protecting reagent. In one embodiment, the amine protecting reagent is di-tert-butyl dicarbonate. In another embodiment, 3,4-oxazolidinedicarboxylic acid, 3-(1,1-dimethylethyl) ester, (4S)-, is commercially available from JPM2 Pharmaceuticals. In one embodiment the reaction is carried out in an organic solvent in the presence of a base. In one embodiment, the organic solvent is acetonitrile. In one embodiment, the base is 4-dimentylaminopyridine (DMAP). In Step 2, the protected 4-oxazolidinecarboxylic acid is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 3, the protecting group is removed. In one embodiment, the starting material is reacted with an acid in the presence of an organic solvent. In one embodiment, the acid is 4N hydrochloric acid. In one embodiment, the organic solvent is dioxane.

In Route 1c, (S)-5-(tert-Butoxycarbonyl)-5-azaspiro[2.4] heptane-6-caboxylic acid, CAS 1129634-44-1, is commercially available from Ark Pharm. In Step 2, the carboxylic acid is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 3, the protecting group is removed. In one embodiment, the starting material is reacted with an acid in the presence of an organic solvent. In one embodiment, the acid is 4N hydrochloric acid. In one embodiment, the organic solvent is dioxane.

Routes 2a, 2b, 2c, and 2d.

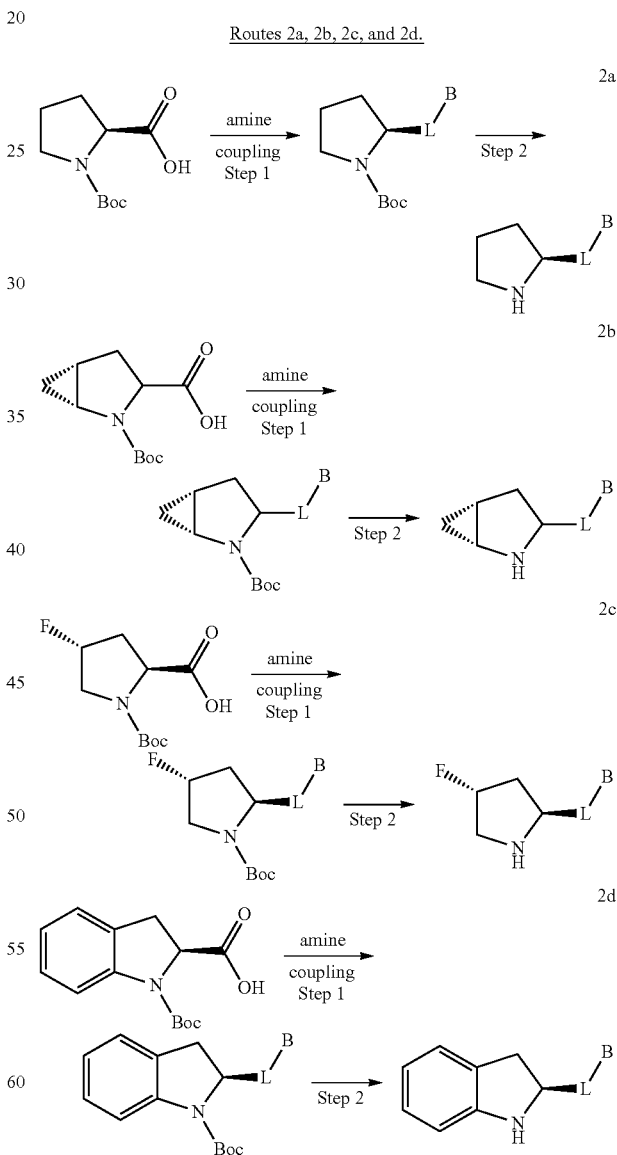

In Route 2a, commercially available Boc-L-proline is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane.

In Route 2b, commercially available (1R,3S,5R)-2-[(tert-butoxy)carbonyl]-2-azabicyclo[3.1.0]hexane-3-carboxylic acid, from Enamine, is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane.

In Route 2c, commercially available (2S,4R)-1-(tert-butoxycarbonyl)-4-fluoropyrrolidine-2-carboxylic acid, from Manchester Organics, is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane.

In Route 2d, commercially available (S)-1-(tert-butoxycarbonyl)indoline-2-carboxylic acid, from Chem-Impex, is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane. This chemistry is illustrated in Scheme 2.

Additional starting materials that can readily be converted to Central-L-B-Synthons include, but are not limited to: (S)-1-(tert-butoxycarbonyl)-2,3-dihydro-1H-pyrrole-2-carboxylic acid, CAS 90104-21-5, available from Ark Pharm; cyclopent-1-ene-1,2-dicarboxylic acid, CAS 3128-15-2, purchased from Ark Pharm; imidazole, 1H-imidazole-1,2-dicarboxylic acid, 1-(1,1-dimethylethyl) 2-ethyl ester, CAS 553650-00-3, commercially available from FCH Group; Boc-L-octahydroindole-2-carboxylic acid can be purchased from Chem Impex. The compound,

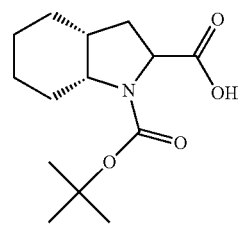 [SMILES: CC(C)(C)OC(=O)N1C(C(=O)O)C[C@H]2CCCC[C@H]21]

can be prepared according to the procedures disclosed in WO 2004/111041; (S)-Boc-5-oxopyrrolidine-2-carboxylic acid is available from the Aldrich Chemical Co.; (1S,2S,5R)-3-(tert-butoxycarbonyl)-3-azabicyclo[3.3.0]hexane-2-carboxylic acid is available from Ark Pharm; (S)-3-Boc-thiazolidine-2-carboxylic acid is available from Alfa Aesar; (2S,4R)-1-(tert-butoxycarbonyl)-4-chloropyrrolidine-2-carboxylic acid is available from Arch Bioscience; (1S,3aR,6aS)-2-(tert-butoxycarbonyl)octahydrocyclopenta[c]pyrrole-1-carboxylic acid is available from Ark Pharm; 1,2-pyrrolidinedicarboxylic acid, 3-[[(phenylmethoxy)carbonyl]amino]-, 1-(1,1-dimethylethyl) ester, (2S,3R) can be prepared as disclosed in WO 2004/007501. The Cbz group can be removed and the amino group can be alkylated to generate central core compounds of the present invention.

The compound

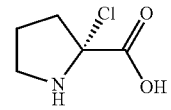

can be prepared as disclosed by Braun, J. V.; Heymons, Albrecht Berichte der Deutschen Chemischen Gesellschaft [Abteilung] B: Abhandlungen (1930) 63B, 502-7.

The compounds (2S,3S,4S)-4-fluoro-3-methoxy-pyrrolidine-1,2-dicarboxylic acid 1-tert-butyl ester and (2R,3R,4R)-3-fluoro-4-methoxy-pyrrolidine-1,2-dicarboxylic acid 1-tert-butyl ester can be prepared as a mixture according to WO 2012/093101 to Novartis and the regioisomers can be ultimately separated once coupled to generate the central core-L-B synthons. The compound (S)-Boc-5-oxopyrrolidine-2-carboxylic acid is available from the Aldrich Chemical Co.

Example 4. Preparation of A-C(O)-Moiety

Examples of the preparation of the A-C(O)-Moiety can be found in Example 1 and below.

In an alternate embodiment, a heteroaryl compound of Structure 1 is acylated to generate a compound of Structure 2. Structure 2 is coupled to an activated ester of Structure 3 to generate Structure 4. The ester is hydrolyzed to form acid Structure 5. This chemistry is illustrated in Scheme 4a.

Scheme 4a

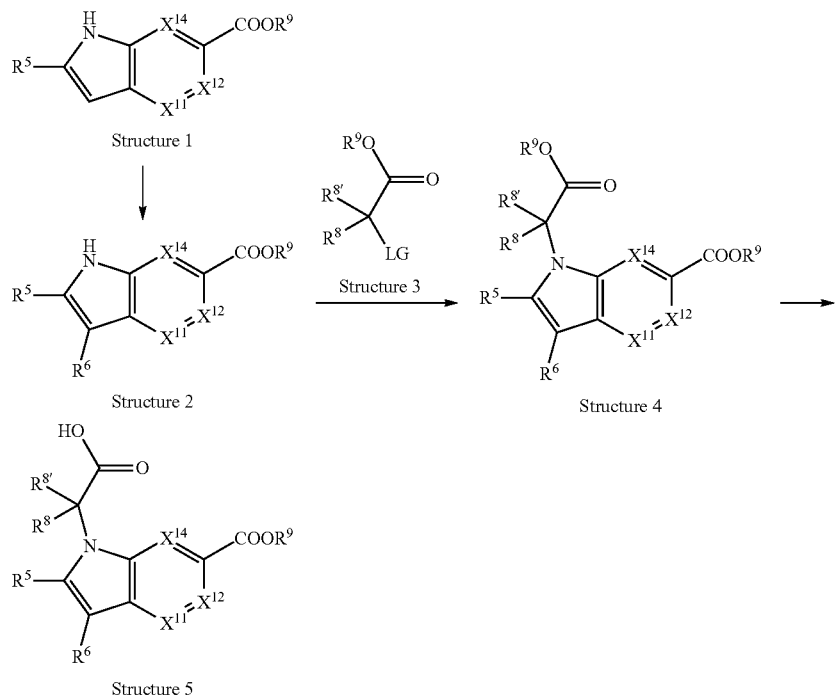

In an alternate embodiment, a heteroaryl compound, Structure 2-1, is treated with a halogen to generate Structure 2-2. In some embodiments, the halogen is iodine. Structure 2-2 is treated with an activated ester to generate Structure 2-3. The halide is treated with zinc cyanide to generate nitrile, Structure 2-4. The nitrile, Structure 2-4 is treated with an oxime to generate the amide Structure 2-5. The ester is treated with an acid to generate acid, Structure 2-6. This chemistry is illustrated in Scheme 4b.

Scheme 4b

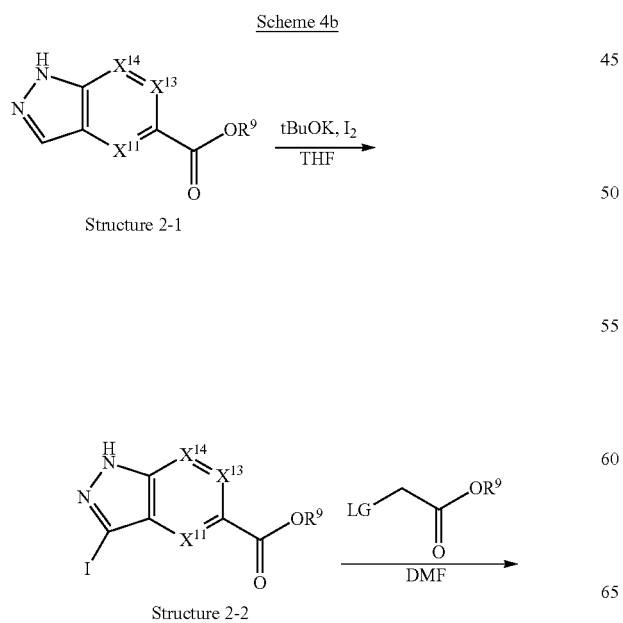

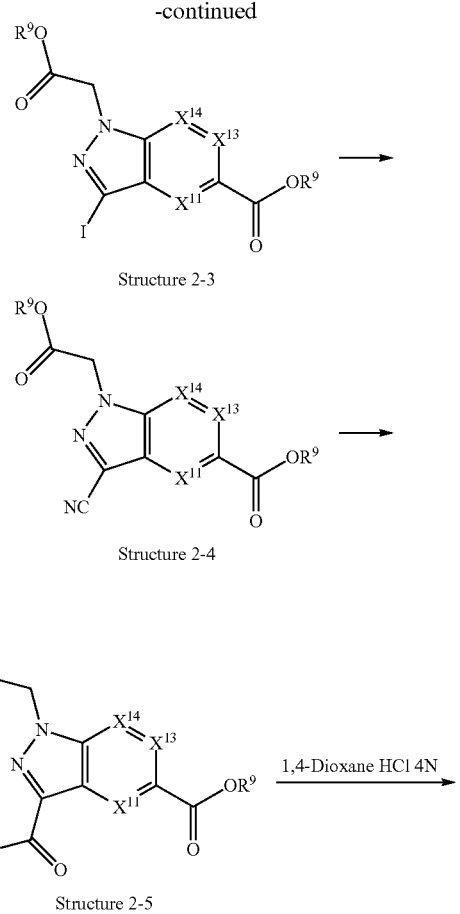

-continued

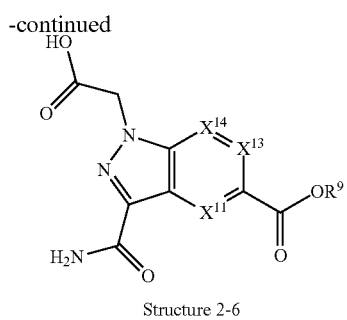

Structure 2-6

Example 5. Coupling of Central-L-B-Synthons to A-C(O)-Moieties

Examples of the coupling of central-L-B-synthons to A-C(O)-moieties can be found in Example 1.

In an alternate embodiment, Structure 5, from Example 4 Scheme 4a, is coupled to Structure 3 from Route 1 to generate Structure 6. Structure 6 is treated with a base such as, but not limited to, lithium hydroxide to generate Structure 7. This chemistry is illustrated in Scheme 5a.

Scheme 5a

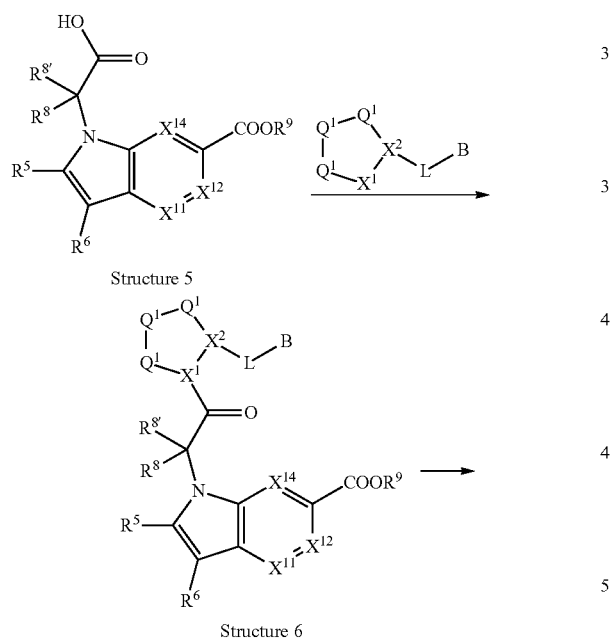

In one embodiment, Structure 2-6 from Example 4b, is coupled to a central core-L-B to generate Structure 2-7. Structure 2-7 is treated with a base to generate a carboxylic acid, Structure 2-8. In one embodiment, the base is lithium hydroxide. This chemistry is illustrated in Scheme 5b Scheme 5b.

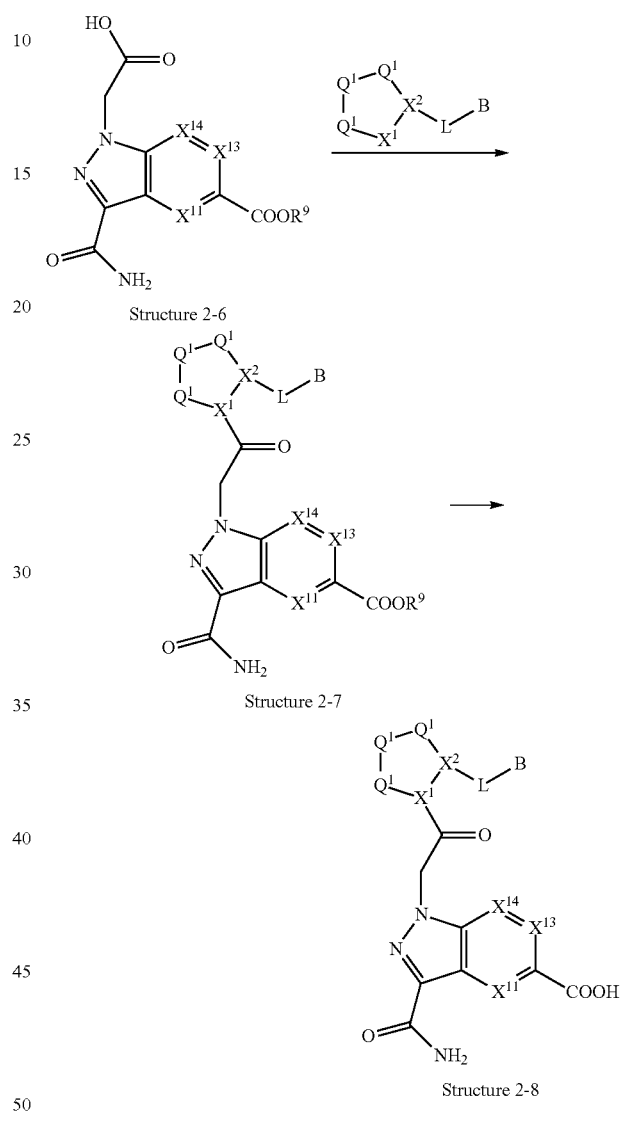

Example 6. Synthesis of Amides, Carbamates, and Ureas Within Formula I

Examples of the synthesis of amides, carbamates and ureas within Formula I can be found in Example 1 and below.

In one embodiment, Structure 1 is treated with, for example, diphenylphosphoryl azide (DPPA) to generate an isocyanate, Structure 2. Structure 2 is then treated with an amine or alcohol to generate urea and carbamate compounds within Formula I, wherein the $R^{13}$ substituent is $NR^9C(O)$ $NR^9R^{10}$, $NR^9C(O)NR^{10}R^{23}$, $NR^9C(O)R^{24}R^{25}$, $NR^9C(O)$ $OR^{10}$ and $NR^9C(O)OR^{23}$. In some embodiments, $R^9$ is hydrogen. Structure 1 can be coupled to amines to generate amides within Formula I, wherein the $R^{13}$ substituent is $C(O)NR^{24}R^{25}$, $C(O)NR^9R^{37}$, or $C(O)NR^{21}SO_2R^{22}$. In some embodiments, $R^9$ is hydrogen. The chemistry is illustrated in Scheme 6a.

Scheme 6a

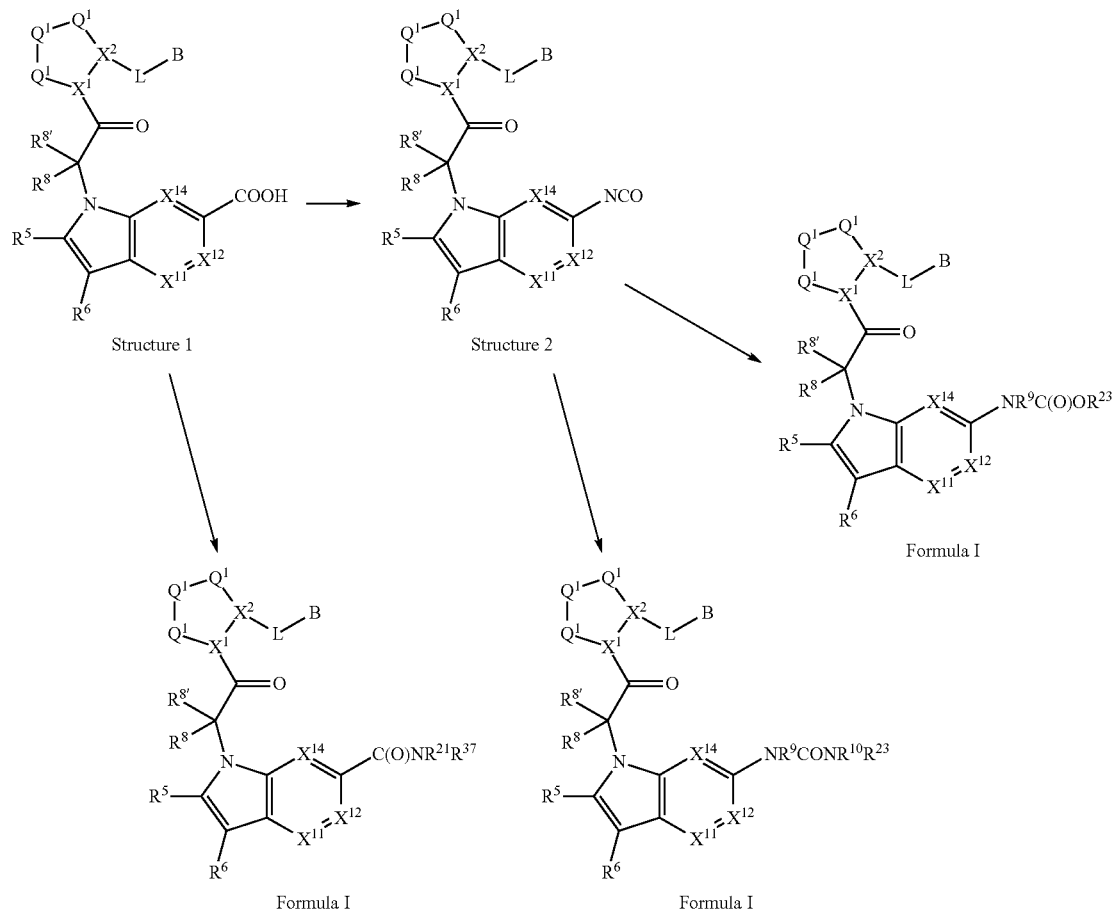

Structure 1

Structure 2

Formula I

Formula I

Formula I

Example 7. Synthesis of Intermediates

7A. (2S,4R)-Tert-Butyl 2-((3-Chloro-2-Fluorobenzyl)Carbamoyl)-4-Fluoropyrrolidine-1-Carboxylate (65)

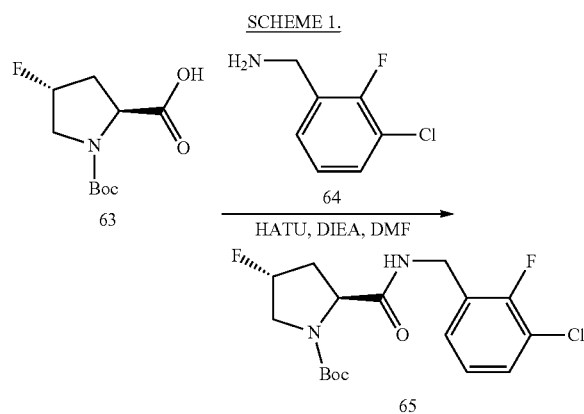

SCHEME 1.

(2S,4R)-1-(tert-butoxycarbonyl)-4-fluoropyrrolidine-2-carboxylic acid (2.33 g, 10 mmol) was dissolved in DMF (50 ml) and $^iPr_2NEt$ (8.6 ml, 5 eq.) was added followed by the addition of (3-chloro-2-fluorophenyl) methanamine (3.18 g 20 mmol) at 5° C. Then HATU (8 g, 2.1 eq) was added slowly at the same temperature. The reaction mixture was then stirred for 18 h at RT. After the completion of the reaction, monitored by HPLC, the reaction mixture was diluted with 1M citric acid solution (200 ml+NaCl solid 20 g) and extracted with DCM (150 mL×2). The organic layer was then washed with an aqueous solution of $NaHCO_3$ (100 ml), washed with water (100 ml), brine (100 ml), dried over $Na_2SO_4$ and concentrated under reduced pressure. The remaining residue was purified by column chromatography (eluted with DCM/EtOAc) to afford compound (63) and (2S,4R)-tert-butyl 2-((3-chloro-2-fluorobenzyl)carbamoyl)-4-fluoropyrrolidine-1-carboxylate (65).

7B. (2S,4R)—N-(3-Chloro-2-Fluorobenzyl)-4-Fluoropyrrolidine-2-Carboxamide Hydrochloride (66)

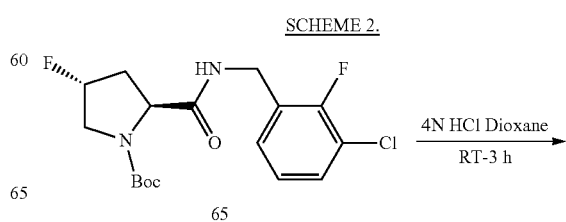

SCHEME 2.

133

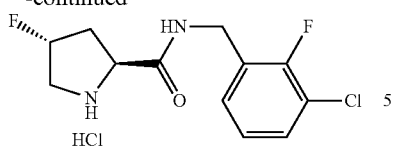

66

(2S,4R)-tert-butyl 2-((3-chloro-2-fluorobenzyl)carbamoyl)-4-fluoropyrrolidine-1-carboxylate 65 (500 mg) was taken in 4N HCl dioxane (30 ml) and resulting reaction mixture was stirred at rt for 3 h. After completion of the reaction, monitored by HPLC, the solvent was removed under reduced pressure. The residue, 66, was used directly in the next step.

7C. 2-(3-Acetyl-1H-Indol-1-Yl)Acetic Acid (69)

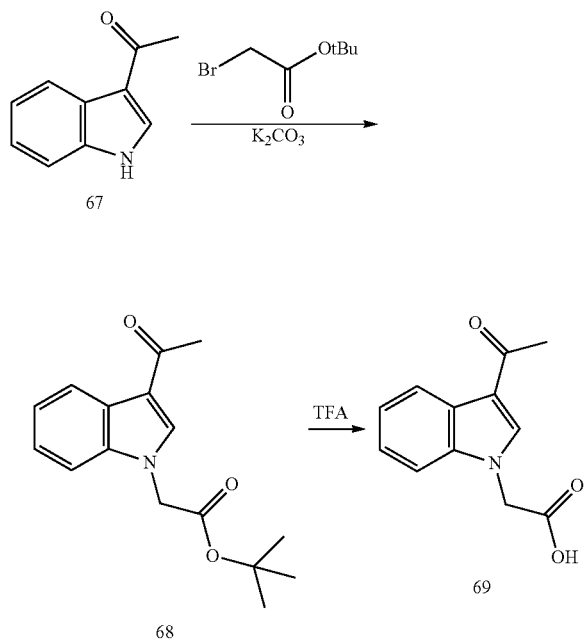

A mixture of 3-acetylindole (67) (10.09 g) and t-butyl-bromoacetate (13.71 g) was heated at reflux in acetonitrile in the presence of potassium carbonate (9.7 g) for 24 h. The reaction mixture was cooled to room temperature, filtered and evaporated to dryness. The residue was purified by chromatography over silica gel and eluted with a mixture of ethyl acetate in methylene chloride to afford tert-butyl 2-(3-acetyl-1H-indol-1-yl)acetate (68).

Tert-butyl 2-(3-acetyl-1H-indol-1-yl)acetate (68) was stirred overnight in a mixture of trifluoroacetic acid amd methylene chloride, diluted with methanol and evaporated to dryness. The residue was treated with 1M sodium hydroxide and extracted with methylene chloride. The aqueous layer was acidified with 6M HCl and the residue filtered, washed with water and dried to afford 2-(3-acetyl-1H-indol-1-yl)acetic acid (69).

134

7D. 1-(3-Amino-1H-Indol-1-Yl)Ethanone Hydrochloride (74)

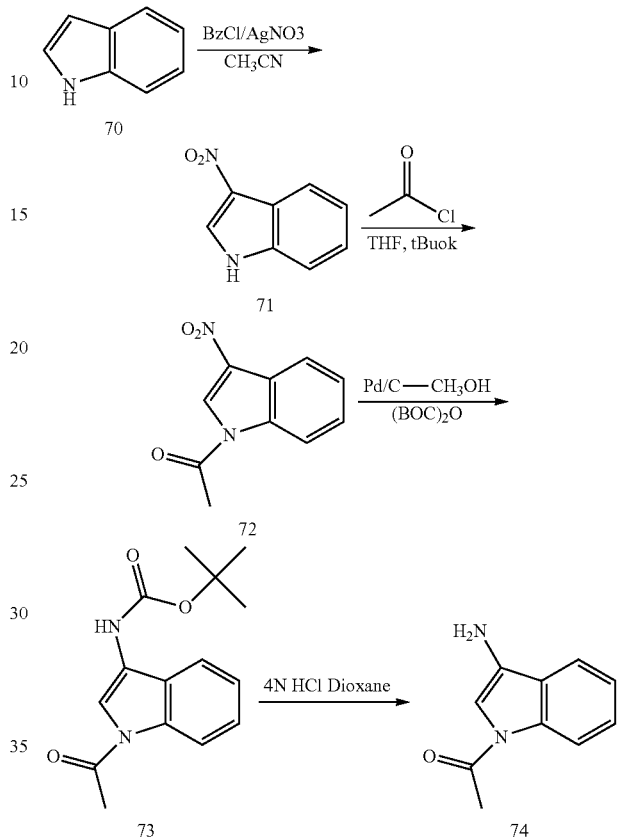

To a stirred solution of AgNO₃ (9.3 g, 1.07 equiv) in acetonitrile was added benzoyl chloride (7.47 g, 1.04 equiv) dropwise at 0° C. The mixture was stirred for 10 min, and a solution of 1H-indole (6 g, 1 equiv) in acetonitrile was added at 0° C. and stirred for 1 h at RT. The reaction mixture was poured into ice to afford a dark brown precipitate. The precipitate was filtered, washed with water and dried. The crude residue was purified by flash column chromatography (ISCO with hexanes/EtOAc) to afford 3-nitro-1H-indole (71).

A stirred solution of 3-nitro-1H-indole (1 g, 1 equiv) in dry THF was cooled to 5° C. Then tBuOK (830 mg, 1.2 equiv) was added slowly and the resulting mixture was stirred 10 min. Acetyl chloride (525 mg, 1.2 equiv) was added and the reaction mixture was stirred for 30 min. After completion of the reaction as monitored by HPLC, solvent was removed under reduced pressure, diluted with DCM and washed with an aqueous solution of NaHCO₃. The organic layer was separated, washed with brine and concentrated under reduced pressure. The remaining residue was purified by flash column chromatography (ISCO eluted with DCM/EtOAc) to afford 1-(3-nitro-1H-indol-1-yl)ethanone (72).

To a mixture of 1-(3-nitro-1H-indol-1-yl)ethanone (600 mg, 2.942 mmol) and di-tert-butyl dicarbonate (1.925 g, 8.826 mmol) in methanol (50 mL) was added 5% Pd/C (20 mg). The resulting reaction mixture was stirred under hydrogen for 24 h. After completion of the reaction, Pd/C was filtered using Celite®, and the filtrate was concentrated under reduced pressure. The remaining residue was purified by flash column chromatography (ISCO eluted with DCM/EtOAc) to afford tert-butyl (1-acetyl-1H-indol-3-yl)carbamate (73).

Tert-butyl (1-acetyl-1H-indol-3-yl) carbamate (300 mg, 1.1 mmol) was taken in 4N HCl dioxane (10 ml) and resulting reaction mixture was stirred at rt for 3 h. After completion of the reaction, solvent was removed under reduced pressure. This material, 1-(3-amino-1H-indol-1-yl)ethanone hydrochloride (74), was used directly in the next synthetic step.

7E. 2-(3-Acetyl-6-Hydroxy-1H-Indol-1-Yl)Acetic Acid (80)

SCHEME 5.

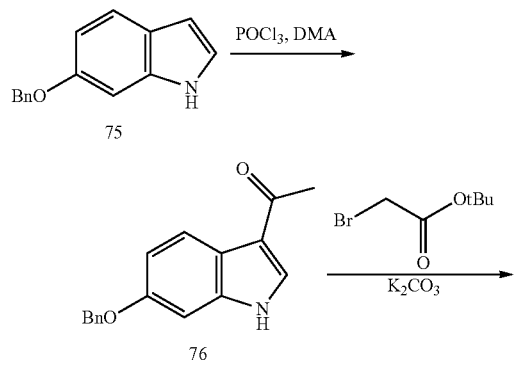

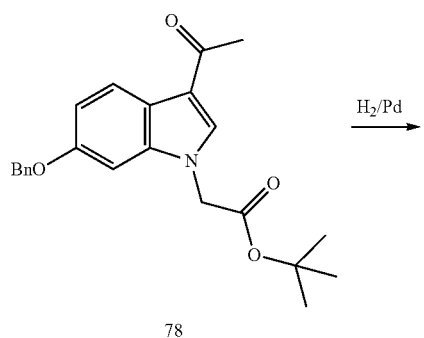

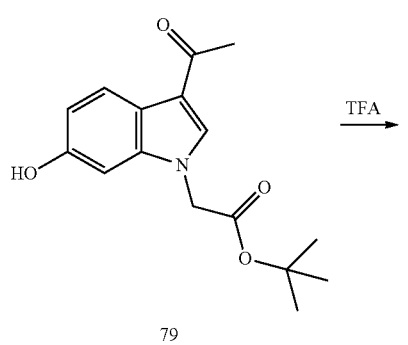

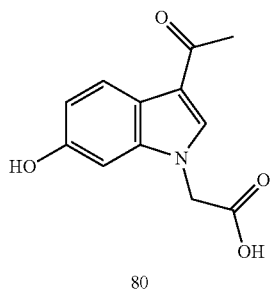

80

6-Benzyloxyindole was acetylated using the reported procedure (Eur. J. Med Chem., (2011), 46, 756) and alkylated following the procedure describe for compound 69. The benzyl group was removed by hydrogenation over palladium on charcoal and the t-butyl group removed again as described for compound 69.

7F. 2-(3-Acetyl-5-Hydroxy-1H-Indol-1-Yl)Acetic Acid (85)

SCHEME 6.

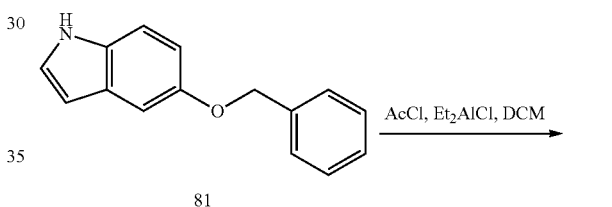

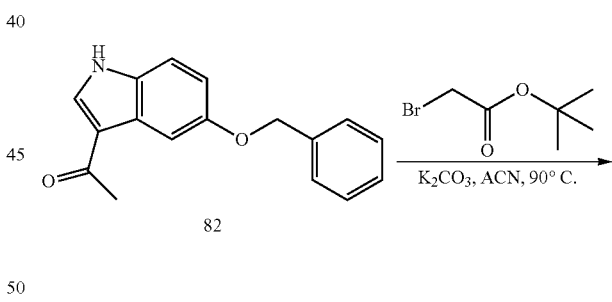

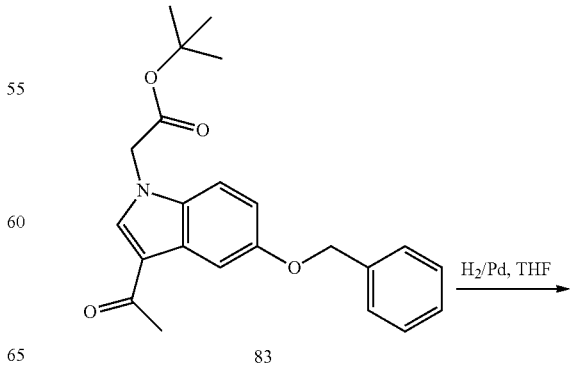

137

-continued

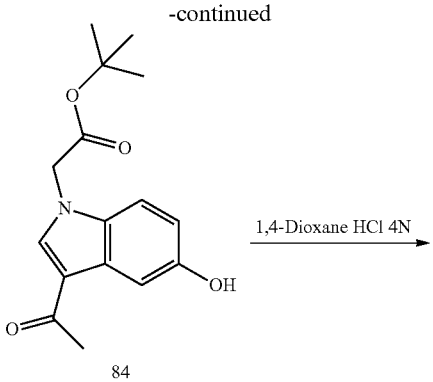

84

85

To a stirred solution of 5-(benzyloxy)-1H-indole (81) (11.08 g, 1 equiv) in DCM (200 mL) was added diethylaluminium chloride (1 M solution in Hexane; 74.6 mL, 1.5 equiv) drop wise at 0° C. The mixture was stirred for 30 min, and then a solution of acetyl chloride (5.3 mL, 1.5 equiv) in DCM (150 mL) was added at 0° C. and the reaction was stirred for 1 h at 0° C. A 5% aqueous citric acid solution was added at 0° C. and the reaction was stirred for 15 min at RT. The precipitate was filtered, washed with water, and the organic filtrate was dried and concentrated under reduced pressure. The residue was purified by flash column chromatography (silica gel eluted with DCM/CH$_3$OH) to afford 1-(5-(benzyloxy)-1H-indol-3-yl)ethanone (82).

To a suspension of 1-(5-(benzyloxy)-1H-indol-3-yl)ethanone (6.5 g, 1 equiv) and K$_2$CO$_3$ (3.72 g, 1.1 equiv) in acetonitrile (50 mL) was added tert-butyl 2-bromoacetate (3.92 mL, 1.1 equiv) dropwise at RT. The resulting mixture was then heated at reflux for 18 h. After cooling to RT, the mixture was diluted with DCM (100 mL) and filtered through a Celite® pad. The filtrate was concentrated under reduced pressure. The remaining residue was purified by flash column chromatography (silica gel eluted with DCM/EtOAc) to afford tert-butyl 2-(3-acetyl-5-(benzyloxy)-1H-indol-1-yl)acetate (83).

To tert-butyl 2-(3-acetyl-5-(benzyloxy)-1H-indol-1-yl)acetate (6 g) in THF (80 mL) was added Pd/C (0.05 equiv). The reaction mixture was stirred at RT for 5 h under H$_2$ (1 atm). The reaction mixture was filtered through a pad of Celite® and the pad was washed with CH$_2$Cl$_2$ and MeOH. The filtrate was concentrated under reduced pressure and the remaining residue was purified by flash column chromatography (silica gel eluted with DCM/EtOAc) to afford tert-butyl 2-(3-acetyl-5-hydroxy-1H-indol-1-yl)acetate (84).

Tert-Butyl 2-(3-acetyl-5-hydroxy-1H-indol-1-yl)acetate (814 mg, 2.8 mmol) was taken up in 4 N HCl dioxane (10 mL) and the resulting reaction mixture was stirred at RT for 48 h. The solvent was then removed under reduced pressure to afford 2-(3-acetyl-5-hydroxy-1H-indol-1-yl)acetic acid (85) which could be used directly in the next synthetic step.

138

7G. N-(2-((2R,4R)-4-fluoropyrrolidin-2-yl)ethyl)benzenesulfonamide hydrochloride (91)

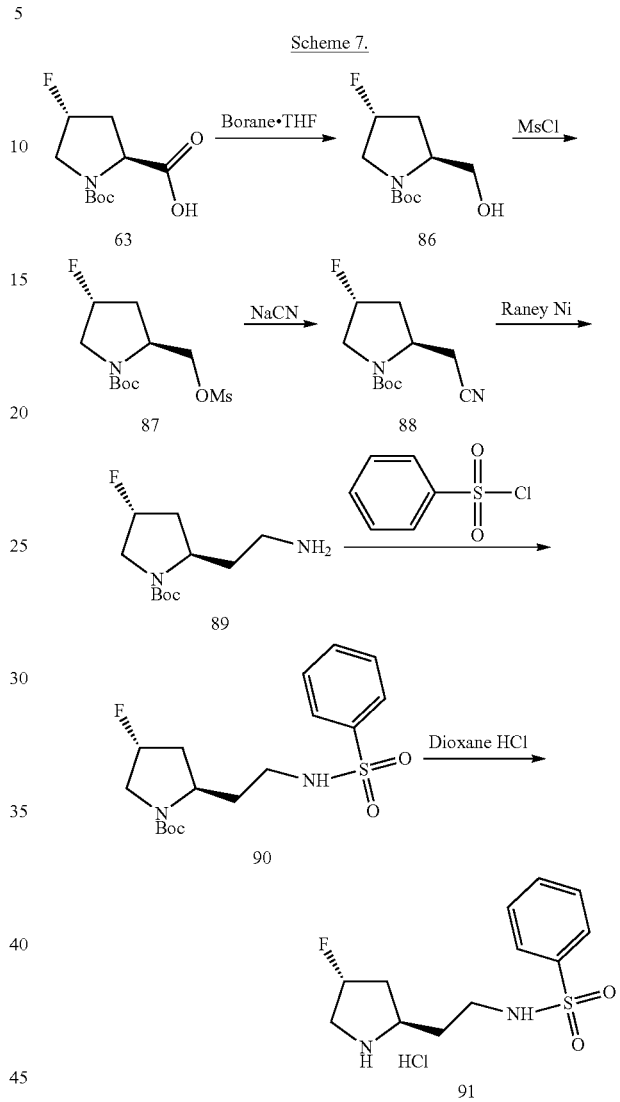

Scheme 7.

To a solution of (2S,4R)-1-(tert-butoxycarbonyl)-4-fluoropyrrolidine-2-carboxylic acid (1 equiv) in THF (10 vol) at 0° C. was added borane tetrahydrofuran complex (2.1 equiv). The reaction mixture was stirred at room temperature for 2 h and then cooled at 0° C. The resulting mixture was quenched with saturated K$_2$CO$_3$ solution and extracted with ethyl acetate. The organic layer was separated, dried over anhydrous Na$_2$SO$_4$, filtered and concentrated. The residue was purified by column chromatography on silica gel using DCM/MeOH to afford the title compound (86).

To a solution of tert-butyl (2S,4R)-4-fluoro-2-(hydroxymethyl)pyrrolidine-1-carboxylate (1 equiv) in DCM (20 Vol) at 0° C. was added methanesulfonyl chloride (1.5 equiv) and triethylamine (3 equiv). The reaction mixture was stirred at 0° C. for 1 h. The resulting mixture was diluted with ethyl acetate, washed with 1N HCl and saturated NaHCO$_3$ solution. The organic layer was separated, dried over anhydrous Na$_2$SO$_4$, filtered and concentrated. Crude tert-butyl (2S,4R)-4-fluoro-2-(((methylsulfonyl)oxy)methyl)pyrrolidine-1-carboxylate (87) was dissolved in DMSO (10 Vol) and sodium cyanide (3 equiv) was added. The reaction mixture was stirred at 50° C. for 15 h. The resulting mixture was cooled to room temperature and quenched with water and was extracted with ethyl acetate. The organic layer was separated, dried over anhydrous Na$_2$SO$_4$, filtered and concentrated. The residue was purified by column chromatography on silica gel using Hexane/EtOAc to afford tert-butyl (2R,4R)-2-(cyanomethyl)-4-fluoropyrrolidine-1-carboxylate (88).

To a solution of tert-butyl (2R,4R)-2-(cyanomethyl)-4-fluoropyrrolidine-1-carboxylate (88) (1 equiv) in methanol (5 Vol) was added Raney Ni (1.2 equiv) and triethylamine (2 equiv). The reaction mixture was stirred at room temperature at 3.5 millibar pressure under hydrogen atmosphere for 16 h. The resulting mixture was filtered and concentrated. The residue was purified by column chromatography on silica gel using DCM/MeOH to afford tert-butyl (2R,4R)-2-(2-aminoethyl)-4-fluoropyrrolidine-1-carboxylate (89).

To a solution of tert-butyl (2R,4R)-2-(2-aminoethyl)-4-fluoropyrrolidine-1-carboxylate (89) (1 equiv) in THF (10 vol) at 0° C. under nitrogen atmosphere was added benzenesulfonyl chloride (1.5 equiv) and triethylamine (3 equiv). The reaction mixture was stirred at room temperature for 16 h and then concentrated. The residue was purified by column chromatography on silica gel using Hexane/EtOAc to afford tert-butyl (2R,4R)-4-fluoro-2-(2-(phenylsulfonamido)ethyl)pyrrolidine-1-carboxylate (90).

To a solution of tert-butyl (2R,4R)-4-fluoro-2-(2-(phenylsulfonamido)ethyl)pyrrolidine-1-carboxylate (1 equiv) in 1,4-dioxane (2 vol) at 0° C. was added 4 N HCl in dioxane (10 vol). The reaction mixture was stirred at room temperature for 4 h and then concentrated. The residue was taken up in MTBE and stirred for 30 min. The resultant solid was filtered and dried to afford 91.

Example 8. Synthesis of (2S,4R)—N2-(1-Acetyl-1H-Indol-3-Yl)-N1-(3-Chloro-2-Fluorobenzyl)-4-Fluoropyrrolidine-1,2-Dicarboxamide (97)

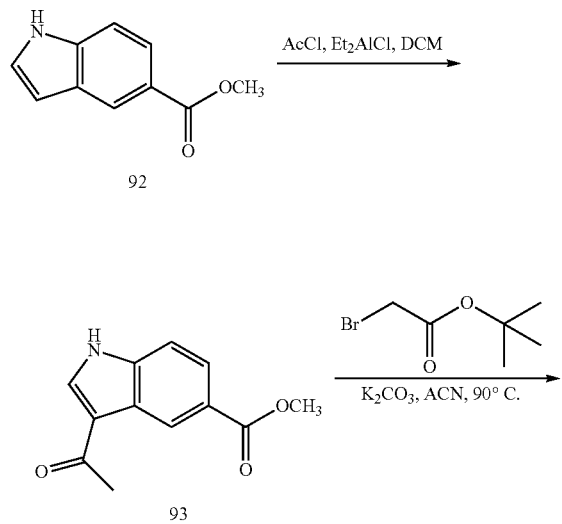

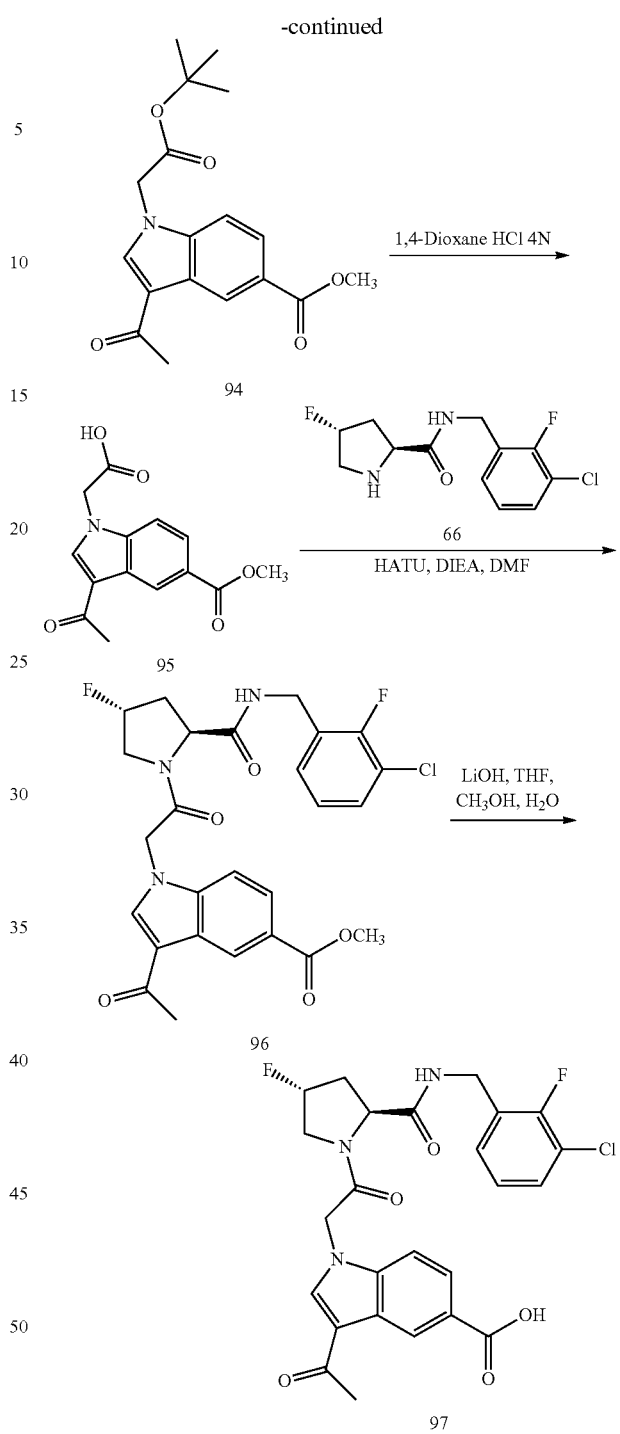

To a stirred solution of methyl 1H-indole-5-carboxylate (92) (10 g, 1 equiv) in DCM (200 mL) was added diethylaluminium chloride (1 M solution in hexane; 85.71 mL, 1.5 equiv) dropwise at 0° C. The mixture was stirred for 30 min and then a solution of acetyl chloride (6 mL, 1.5 equiv) in DCM (150 mL) was added at 0° C. and stirred for 1 h at 0° C. A 5% aqueous citric acid solution was added at 0° C. and the reaction mixture was stirred for 15 min at RT. The precipitate was collected by filtration, washed with water, and dried. The residue was purified by flash column chromatography (silica gel eluted with DCM/CH$_3$OH) to afford methyl 3-acetyl-1H-indole-5-carboxylate (93).

To a suspension of methyl 3-acetyl-1H-indole-5-carboxylate (93) (6 g, 1 equiv) and K₂CO₃ (4.19 g, 1.1 equiv) in 50 mL acetonitrile was added tert-butyl 2-bromoacetate (4.42 mL, 1.1 equiv) dropwise at RT. The resulting mixture was then heated at reflux for 18 h. After cooling to RT, the mixture was diluted with DCM (100 mL), filtered through a pad of Celite® and the filtrate was concentrated under reduced pressure. The remaining residue was purified by flash column chromatography (silica gel eluted with DCM/EtOAc) to afford Methyl 3-acetyl-1-(2-(tert-butoxy)-2-oxoethyl)-1H-indole-5-carboxylate (94).

Methyl 3-acetyl-1-(2-(tert-butoxy)-2-oxoethyl)-1H-indole-5-carboxylate (3 g, 9.06 mmol) was taken up in 4 N HCl dioxane (50 mL) and the resulting reaction mixture was stirred at RT for 48 h. The solvent was then removed under reduced pressure and the remaining material 2-(3-acetyl-5-(methoxycarbonyl)-1H-indol-1-yl)acetic acid (95) was used directly in the next synthetic step.

2-(3-Acetyl-5-(methoxycarbonyl)-1H-indol-1-yl)acetic acid (95) (2 g, 1 equiv) was dissolved in DMF (50 mL) and ⁱPr₂NEt (3.95 mL, 5 equiv) was added, followed by the sequential addition of (2S,4R)—N-(3-chloro-2-fluorobenzyl)-4-fluoropyrrolidine-2-carboxamide hydrochloride 66 (2.254 g, 1 equiv) and HATU (5.8 g, 2.1 equiv) slowly at 5° C. The reaction mixture was then stirred for 18 h at RT, diluted with 1 M citric acid solution (100 mL, containing 10 g NaCl), and extracted with DCM (50 mL×2). The organic layer was washed with an aqueous solution of NaHCO₃ (40 mL), washed with water (40 mL), brine (40 mL), dried over Na₂SO₄, and concentrated under reduced pressure. The remaining residue was purified by flash column chromatography (silica gel eluted with DCM/CH₃OH) to afford methyl 3-acetyl-1-(2-((2S,4R)-2-((3-chloro-2-fluorobenzyl)carbamoyl)-4-fluoropyrrolidin-1-yl)-2-oxoethyl)-1H-indole-5-carboxylate (96).

Methyl 3-acetyl-1-(2-((2S,4R)-2-((3-chloro-2-fluorobenzyl)carbamoyl)-4-fluoropyrrolidin-1-yl)-2-oxoethyl)-1H-indole-5-carboxylate (96) (3.86 g, 1 equiv) was taken up in a mixture of THF (20 mL) and methanol (20 mL), and then LiOH (1.832 g, 6 equiv) in water (20 mL) was added. The resulting reaction mixture was stirred at RT for 48 h. The solvent was removed under reduced pressure and water (30 mL) was added. Acidification with 4 N HCl produced a white precipitate that was collected by filtration and dried in vacuo. This material 3-acetyl-1-(2-((2S,4R)-2-((3-chloro-2-fluorobenzyl)carbamoyl)-4-fluoropyrrolidin-1-yl)-2-oxoethyl)-1H-indole-5-carboxylic acid (97) was used directly in the next synthetic step.

Example 9. Synthesis of Cyclopropyl (3-Acetyl-1-(2-((2S,4R)-2-((3-Chloro-2-Fluorobenzyl)Carbamoyl)-4-Fluoropyrrolidin-1-Yl)-2-Oxoethyl)-1H-Indol-5-Yl)Carbamate (Compound 14)

SCHEME 9.

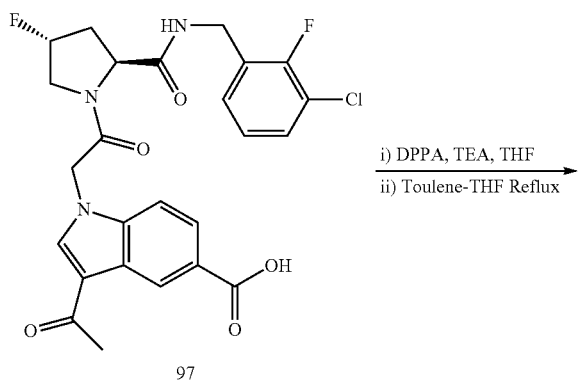

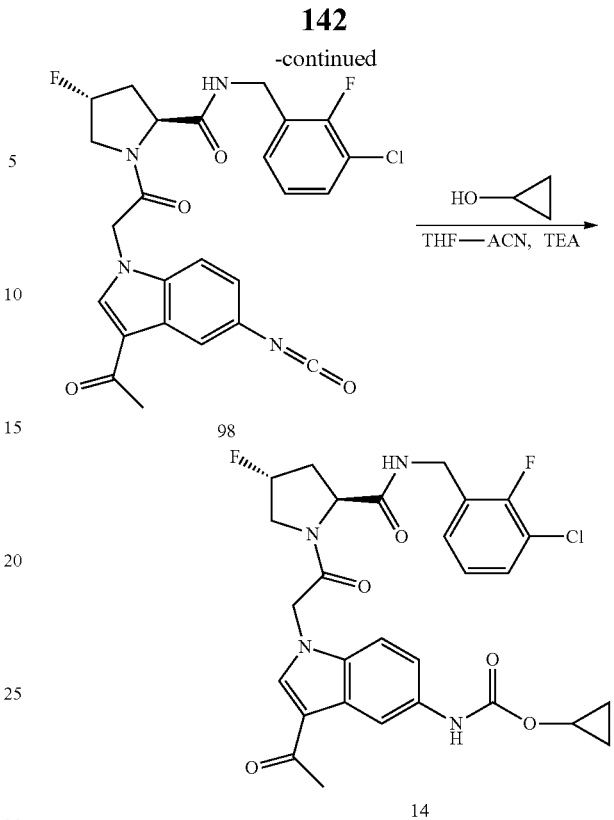

To a suspension of 3-acetyl-1-(2-((2S,4R)-2-((3-chloro-2-fluorobenzyl)carbamoyl)-4-fluoropyrrolidin-1-yl)-2-oxoethyl)-1H-indole-5-carboxylic acid (97) (155 mg, 0.3 mmol, 1 equiv) in THF (20 mL) was added Et₃N (38 µL, 1 equiv) and the resulting solution was stirred at RT under a nitrogen atmosphere for 15 min. DPPA (64 µL, 1 equiv) was added and the reaction was further stirred at RT under nitrogen for 18 h. The reaction mixture was concentrated under reduced pressure and the residue acyl azide intermediate was suspended in a mixture of toluene (20 mL) and THF (5 mL). This mixture was refluxed under nitrogen for 4 h and evaporated to dryness under reduce pressure. The remaining crude isocyanate (2S,4R)-1-(2-(3-acetyl-5-isocyanato-1H-indol-1-yl)acetyl)-N-(3-chloro-2-fluorobenzyl)-4-fluoropyrrolidine-2-carboxamide (98) was used directly in the next step.

Compound 98 was dissolved in a mixture of THF (7 mL), ACN (3 mL), and cyclopropanol (35 mg, 2 equiv), followed by the addition of NEt₃ (76 µL, 2 equiv) at 0° C. The reaction mixture was then stirred for 24 h at RT. The reaction mixture was concentrated under reduced pressure and the remaining residue was purified by flash column chromatography (silica gel eluted with DCM/CH₃OH) to afford the product cyclopropyl (3-acetyl-1-(2-((2S,4R)-2-((3-chloro-2-fluorobenzyl)carbamoyl)-4-fluoropyrrolidin-1-yl)-2-oxoethyl)-1H-indol-5-yl)carbamate (14).

$^1$H NMR (400 MHz, DMSO-d₆): (major rotamer) δ 0.68-0.72 (m, 4H), 2.00-2.17 (m, 1H), 2.40 (s, 3H), 2.49-2.56 (m, 1H), 3.89 (ddd, J=22.8, 9.6, 2.8 Hz, 1H), 4.05-4.14 (m, 1H), 4.32 (dd, J=20.8, 6.0 Hz, 1H), 4.42-4.49 (m, 2H), 5.12 (d, J=17.2 Hz, 1H), 5.33 (d, J=17.2 Hz, 1H), 5.50 (d, J=52.8 Hz, 1H), 6.97-7.01 (m, 1H), 7.15-7.45 (m, 4H), 8.18 (s, 1H), 8.31 (s, 1H), 8.59 (t, J=5.6 Hz, 1H), 9.49 (s, 1H). $^{19}$F NMR (376 MHz, DMSO-d₆): (major rotamer) δ−121.8, −176.1. LC (method 1): t$_R$=1.78 min. LC/MS (EI) m/z: [M+H]⁺ calcd for C₂₈H₂₇ClF₂N₄O₅, 573; found, 573.

Example 10. Synthesis of N-(3-Acetyl-1-(2-((2S,4R)-2-((3-Chloro-2-Fluorobenzyl)Carbamoyl)-4-Fluoropyrrolidin-1-Yl)-2-Oxoethyl)-1H-Indol-5-Yl)-3,3-Difluoropiperidine-1-Carboxamide (Compound 16)

Example 11. Synthesis of 3-Acetyl-1-(2-((2S,4R)-2-((3-Chloro-2-Fluorobenzyl)Carbamoyl)-4-Fluoropyrrolidin-1-Yl)-2-Oxoethyl)-N-Cyclopropylsulfonyl)-1H-Indole-6-Carboxamide (Compound 48)

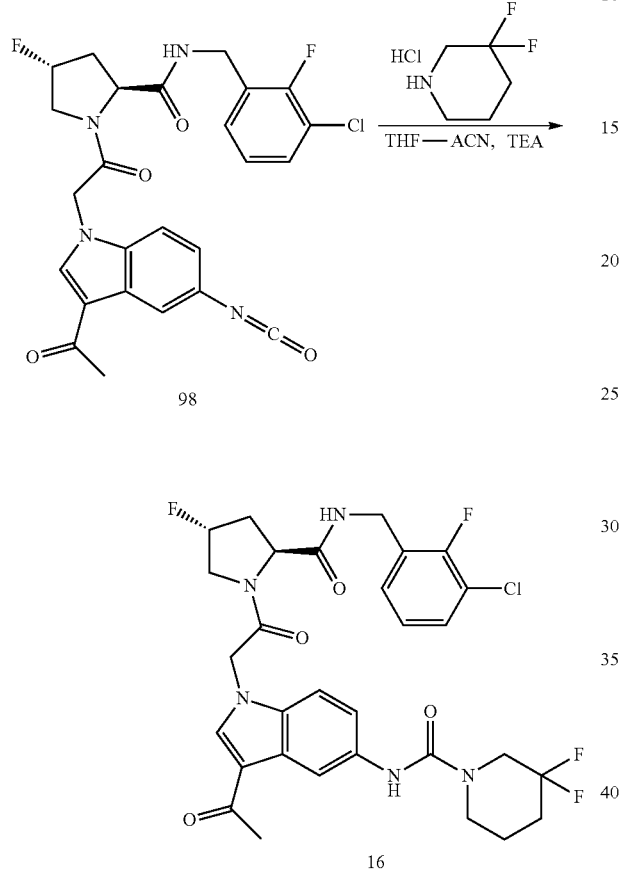

SCHEME 10.

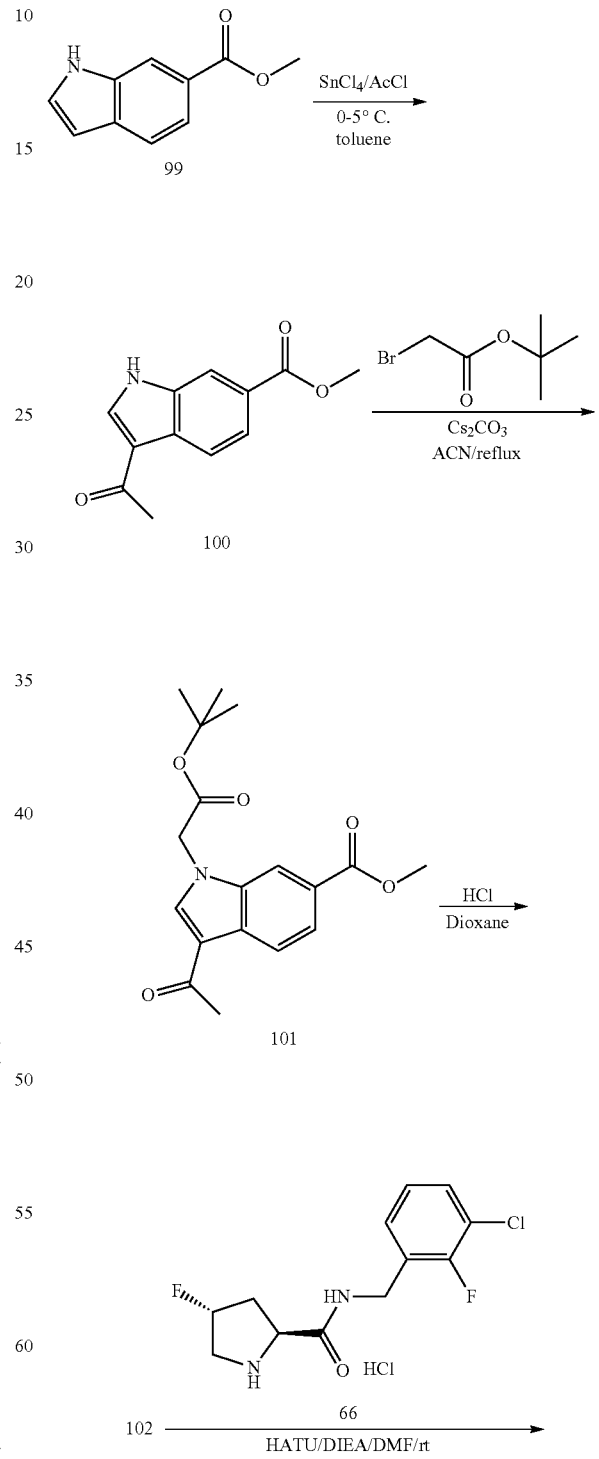

SCHEME 11.

Compound 98 was dissolved in a mixture of THF (7 mL), ACN (3 mL), and 3,3-difluoropiperidine hydrochloride (51.81 mg, 1.1 equiv), followed by the addition of NEt$_3$ (76 μL, 2 equiv) at 0° C. The reaction mixture was then stirred for 24 h at RT. The reaction mixture was concentrated under reduced pressure and the remaining residue was purified by flash column chromatography (silica gel eluted with DCM/CH$_3$OH) to afford N-(3-Acetyl-1-(2-((2S,4R)-2-((3-chloro-2-fluorobenzyl)carbamoyl)-4-fluoropyrrolidin-1-yl)-2-oxoethyl)-1H-indol-5-yl)-3,3-difluoropiperidine-1-carboxamide (16).

$^1$H NMR (400 MHz, DMSO-d$_6$): (major rotamer) δ 1.69-1.76 (m, 2H), 2.01-2.17 (m 3H), 2.41 (s, 3H), 3.52 (t, J=5.2 Hz, 1H), 3.78-3.95 (m, 3H), 4.13 (dd, J=9.2, 12.4 Hz, 1H), 4.32 (dd, J=20.4, 6.0 Hz, 1H), 4.42-4.49 (m, 2H), 5.12 (d, J=17.2 Hz, 1H), 5.33 (d, J=17.2 Hz, 1H), 5.50 (d, J=52.8 Hz, 1H), 6.99-7.03 (m, 1H), 7.22-7.25 (m, 1H), 7.29-7.48 (m, 3H), 8.16 (s, 1H), 8.19 (d, J=2 Hz, 1H), 8.59 (t, J=6 Hz, 1H), 8.62 (s, 1H). $^{19}$F NMR (376 MHz, DMSO-d$_6$): (major rotamer) δ −101.06, −121.25, −176.1. LC (method 1): t$_R$=1.82 min. LC/MS (EI) m/z: [M+H]$^+$ calcd for C$_{30}$H$_{30}$ClF$_4$N$_5$O$_4$, 636; found, 636.

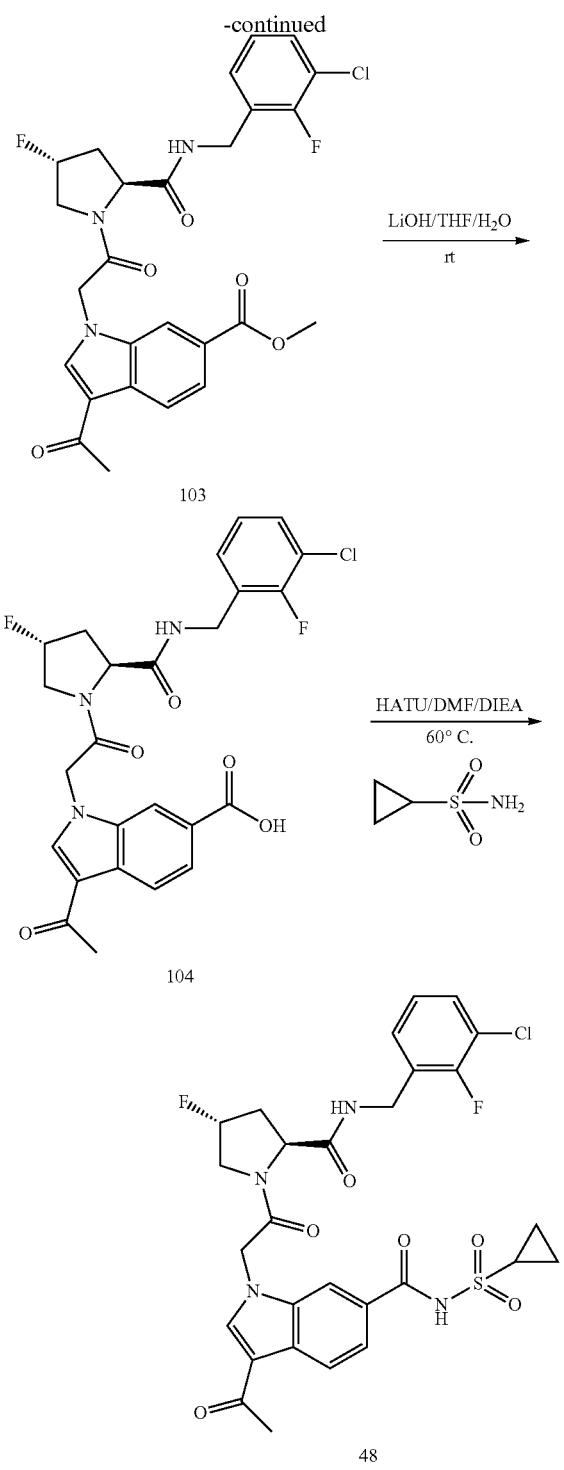

residue was taken up in a 2:1 mixture of EtOAc and water (30 mL: 15 mL). The two layers were separated and the organic layer was washed with brine (2×15 mL). Finally, the organic layer was dried ($Na_2SO_4$) and concentrated to obtain 283 mg of the product methyl 3-acetyl-1-(2-tert-butoxy)-2-oxoethyl)-1H-indole-6-carboxylate (100) as a yellow solid.

100 mg of methyl 3-acetyl-1-(2-tert-butoxy)-2-oxoethyl)-1H-indole-6-carboxylate (0.3 mmol) was stirred in 4 N HCl in dioxane (15 mL) at RT for 18 h. The volatiles were removed under reduced pressure. The residue was dissolved in 5 mL of DMF. To this solution was added 140 mg (0.36 mmol) of the TFA salt of 66, followed by 0.26 mL of N,N-diisopropylethylamine (1.5 mmol). HATU (137 mg, 0.36 mmol) was added and the reaction mixture was stirred overnight at RT. The reaction mixture was diluted with EtOAc (20 mL) and water (15 mL). The organic layer was separated, washed with brine (3×15 mL), dried ($Na_2SO_4$), concentrated in vacuo, and the residue was purified by column chromatography (silica gel, 0-10% MeOH in $CH_2Cl_2$) to afford 128 mg of methyl-3-acetyl-1-(2-((2S,4R)-2-((3-chloro-2-fluorobenzyl)carbamoyl)-4-fluoropyrrolidin-1-yl)-2-oxoethyl)-1H-indole-6-carboxylate (103) as a yellow solid.

A mixture of 128 mg (0.24 mmol) of methyl-3-acetyl-1-(2-((2S,4R)-2-((3-chloro-2-fluorobenzyl)carbamoyl)-4-fluoropyrrolidin-1-yl)-2-oxoethyl)-1H-indole-6-carboxylate in THF (5 mL) and 1 N LiOH (10 mL) was stirred at RT for 18 h. The solvent (THF) was removed under reduced pressure and the remaining water layer was washed with EtOAc (5 mL), acidified with 2 N HCl, and extracted with EtOAc (20 mL). The organic layer was washed with water, dried, and concentrated to obtain 126 mg of the product 3-acetyl-1-(2-((2S,4R)-2-((3-chloro-2-fluorobenzyl)carbamoyl)-4-fluoropyrrolidin-1-yl)-2-oxoethyl)-1H-indole-6-carboxylic acid (104) as a yellow solid.

To a stirred solution of 177 mg (0.34 mmol) of 3-acetyl-1-(2-((2S,4R)-2-((3-chloro-2-fluorobenzyl)carbamoyl)-4-fluoropyrrolidin-1-yl)-2-oxoethyl)-1H-indole-6-carboxylic acid in DMF (8 mL) was added 207 mg (1.71 mmol) of cyclopropanesulfonamide, 390 mg (1.03 mmol) of HATU, and 0.4 mL (2.4 mmol) DIEA. The reaction mixture was heated at 60° C. for 36 h. The reaction mixture was cooled to RT and the solvent was removed under reduced pressure. The residue was purified by preparative HPLC to afford 63 mg of the desired product 3-acetyl-1-(2-((2S,4R)-2-((3-chloro-2-fluorobenzyl)carbamoyl)-4-fluoropyrrolidin-1-yl)-2-oxoethyl)-N-cyclopropylsulfonyl)-1H-indole-6-carboxamide (48) as a white solid.

$^1$H NMR (400 MHz, DMSO-$d_6$): (major rotamer) δ 1.12 (m, 4H), 2.11 (m, 1H), 2.48 (s, 3H), 3.15 (m, 1H), 3.92 (m, 1H), 4.16 (m, 2H), 4.32 (m, 2H), 4.49 (m, 2H), 5.48 (m, 2H), 6.92 (t, 1H), 7.21 (t, 1H), 7.43 (t, 1H), 7.81 (d, 1H), 8.30 (d, 1H), 8.44 (s, 1H), 8.65 (t, 1H). $^{31}$F NMR (376 MHz, DMSO-$d_6$): (major rotamer) δ −121.6, −176.0. LC (method 1): $t_R$=1.52 min. LC/MS (EI) m/z: [M+H]$^+$ calcd for $C_{28}H_{27}ClF_2N_4O_6S$, 621.05; found, 621.00.

Methyl 3-acetyl-1H-indole-6-carboxylate (99) was prepared according to the procedure published by MacKay et al. (MacKay, J. A.; Bishop, R.; Rawal, V. H. *Org. Lett.* 2005, 7, 3421-3424.)

A mixture of 150 mg (0.68 mmol) of methyl 3-acetyl-1H-indole-6-carboxylate, (0.12 mL (0.76 mmol) of tert-butyl bromoacetate, and 249 mg (0.76 mmol) cesium carbonate in anhydrous acetonitrile (15 mL) was heated at reflux for 18 h. The reaction mixture was then cooled to RT and the solvent was removed under reduced pressure. The

Example 12. Additional Examples of Compounds 2-(3-Carbamoyl-5-(methoxycarbonyl)-1H-indol-1-yl)acetic acid (110)

Scheme 12

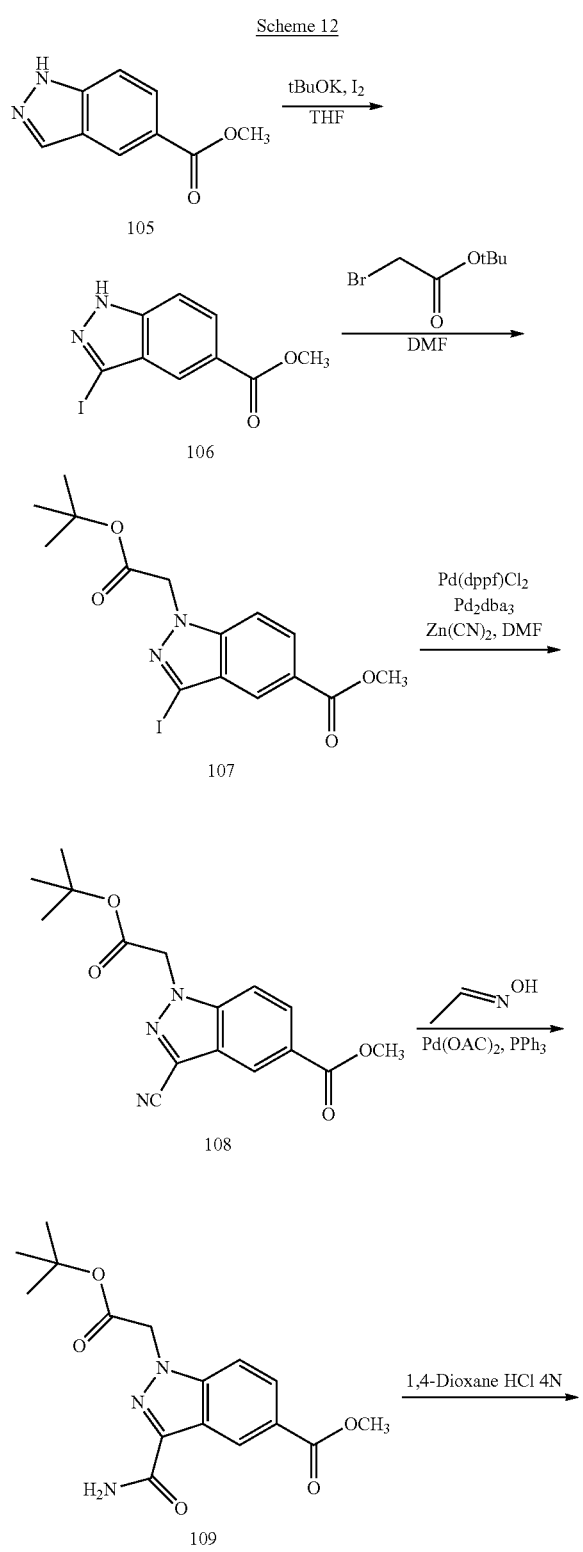

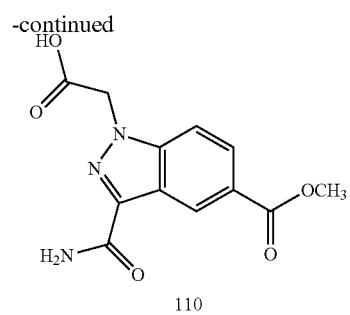

110

To a solution of methyl 1H-indazole-5-carboxylate (105) (10 g, 1 eq.) in THF (100 mL) was added iodine (21.6 g, 1.5 eq.) and potassium tert-butoxide (16 g, 2.5 eq.) at 0° C. The reaction mixture was stirred at room temperature for 2 h. The mixture was diluted with 10% sodium thiosulfate in water and extracted twice with EtOAc. The combined organic extracts were washed with brine and evaporated to dryness. The resultant solid was slurried with MTBE, filtered and dried to afford 106 (13 g).

To a mixture of methyl 3-iodo-1H-indazole-5-carboxylate (106) (30 g, 1 eq.) and potassium carbonate (34.3 g, 2.5 eq.) in DMF (300 mL) was added tert-butyl bromoacetate (17.6 mL, 1.2 eq.) drop wise at room temperature. The resulting mixture was stirred at 50° C. for 3 h. The reaction mixture was poured into water and extracted with EtOAc (2×100 mL). The combined organic extracts were concentrated under vacuum. The material thus obtained was used without further purification in the next step.

A mixture of methyl 1-(2-(tert-butoxy)-2-oxoethyl)-3-iodo-1H-indazole-5-carboxylate (107) (40 g, 1 eq.), Zn(CN)$_2$ (13.5 g, 1.2 eq.), Pd(dppf)Cl$_2$ (7.9 g, 0.1 eq.), Pd$_2$(dba)$_3$ (8.8 g, 0.1 eq.), water (80 mL) and DMF (400 mL) was stirred at 80° C. for 5 h under nitrogen. The reaction mixture was diluted with EtOAc and then successively washed with water, sat. aquoeous NaHCO$_3$ and brine. The organic layer was concentrated under vacuum. The residue was purified by column chromatography over silica gel (eluent: Hexane/EtOAc) to afford the compound 108.

A mixture of methyl 1-(2-(tert-butoxy)-2-oxoethyl)-3-cyano-1H-indazole-5-carboxylate (108) (20 g, 1 eq.), acetaldoxime (7.5 g, 2 eq.), Pd(OAc)$_2$ (0.7 g, 0.05 eq.) and PPh$_3$ (1.7 g, 0.1 eq.) in aqueous ethanol (500 mL, H$_2$O/EtOH (100 mL/400 mL) was heated at reflux for 3 h under a nitrogen atmosphere. The reaction mixture was filtered through Celite® and the solvent was removed under vacuum. The crude residue was purified by column chromatography over silica gel (eluent: Hexane/EtOAc) to afford compound 109.

Methyl 1-(2-(tert-butoxy)-2-oxoethyl)-3-carbamoyl-1H-indazole-5-carboxylate (3 g, 9.06 mmol) was taken up in 4N HCl in dioxane (50 mL) and resulting reaction mixture was stirred at RT for 48 h. After completion of the reaction, the solvent was removed under reduced pressure to afford compound 110.

(2S,4R)—N-(2'-Chloro-2-fluoro-[1,1'-biphenyl]-3-yl)-4-fluoropyrrolidine-2-carboxamide hydrochloride (115)

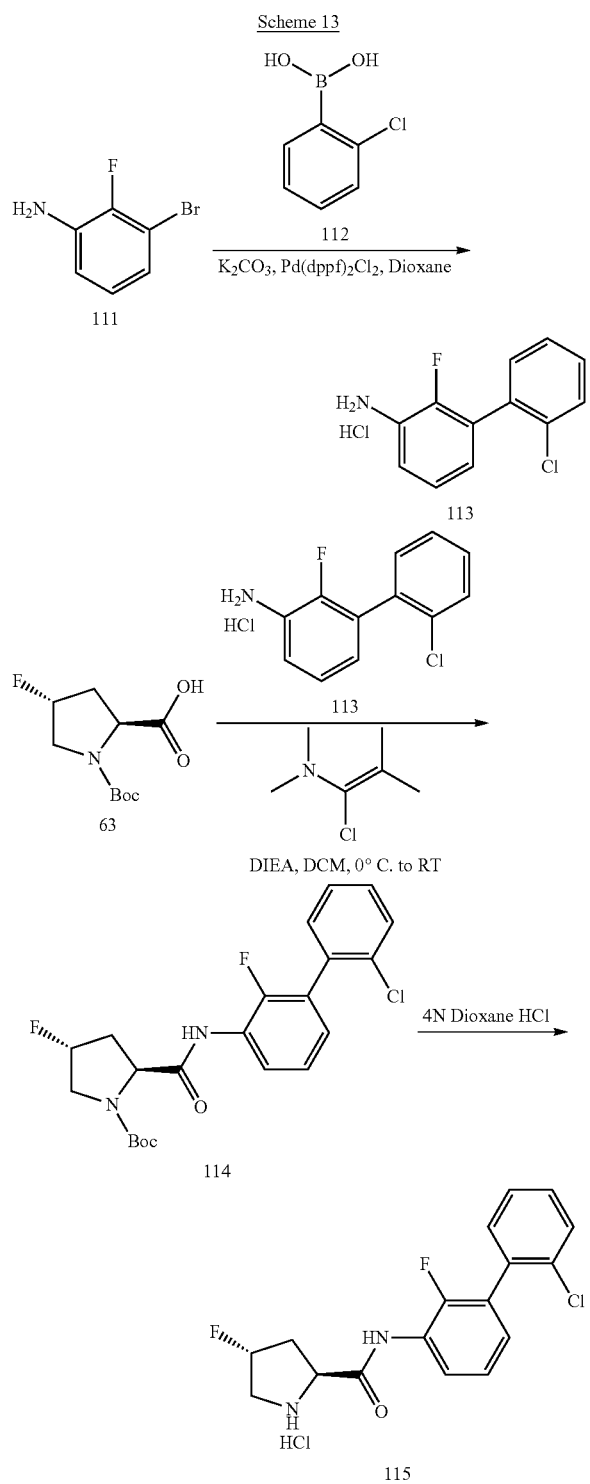

A mixture of 4-bromo-5-fluoroaniline (111) (30 g), 2-chlorophenylboronic acid (112) (60 g), K₂CO₃ (91 g) and Pd(dppf)₂Cl₂ (19.25 g) in aq. dioxane (dioxane 400 mL, H₂O 100 mL) was purged with argon in a pressure vessel for 5 min and stirred for 15 h at 100° C. The solvent was removed under reduced pressure and the residue was purified by flash column chromatography over silica gel. The purified material was then dissolved in MeOH and treated with HCl/MeOH. The solvent was removed and the solid was washed with IPA-heptane (1/1) to afford compound 113.

To an ice-cold solution of N-Boc-4-fluoroproline (63) (530 mg) in DCM (20 mL), was added 1-chloro-N,N,2-trimethyl-1-propenylamine (0.333 mL, 1.1 eq.) dropwise with stirring. Stirring was continued for 3 h at this temperature, then compound 113 (640 mg, 1.1 eq.) was added, followed by 1.12 mL of DIEA (3 eq.). The cooling bath was removed and the reaction mixture stirred overnight at RT. After completion of the reaction, the reaction mixture was added to water (20 mL) and extracted with DCM (2×25 mL). The organic layer was washed successively with aqueous NaHCO₃ (20 mL), water (20 mL), and brine (20 mL), dried over Na₂SO₄ and concentrated under reduced pressure. The residue was purified by flash column chromatography over silica gel (ISCO eluent: Hexanes/EtOAC) to afford compound 114.

(2S,4R)-tert-Butyl 2-((2'-chloro-2-fluoro-[1,1'-biphenyl]-3-yl)carbamoyl)-4-fluoro pyrrolidine-1-carboxylate (114) (700 mg) was taken up in 4N HCl in dioxane (25 mL) and the resulting reaction mixture was stirred at RT for 3 h. After completion of the reaction, the solvent was removed under reduced pressure. The residue, compound 115 was used without further purification.

(1R,3S,5R)—N-(3-Chloro-2-fluorobenzyl)-2-azabicyclo[3.1.0]hexane-3-carboxamide hydrochloride (118)

Scheme 14.

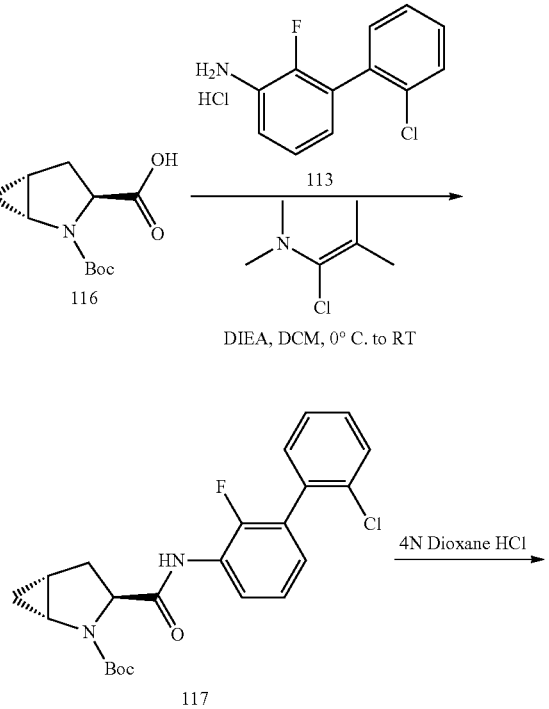

151
-continued

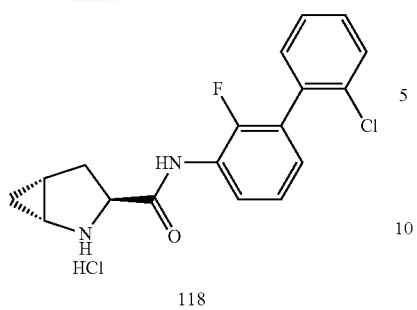
118

To an ice-cold solution of (1R,3S,5R)-2-(tert-butoxycarbonyl)-2-azabicyclo[3.1.0]hexane-3-carboxylic acid (116) (516 mg) in 20 mL of DCM was added 1-chloro-N,N,2-trimethyl-1-propenylamine (0.333 mL, 1.1 eq.) dropwise with stirring. The stirring was continued for 3 h at this temperature, then compound 113 (640 mg, 1.1 eq.) was added, followed by 1.12 mL of DIEA (3 eq.). The cooling bath was removed and the reaction mixture was stirred overnight at RT. The reaction mixture was added to water (20 mL) and extracted with DCM (2×25 mL). The organic layer was washed successively with an aqueous solution of NaHCO₃ (20 mL), water (20 mL), brine (20 mL), dried over Na₂SO₄ and concentrated under reduced pressure. The residue was purified by flash column chromatography over silica gel (ISCO eluent: Hexanes/EtOAC) to afford compound 117.

(2S,4R)-tert-Butyl 2-((2'-chloro-2-fluoro-[1,1'-biphenyl]-3-yl)carbamoyl)-4-fluoropyrrolidine-1-carboxylate (117) (700 mg) was taken up in 4N HCl in dioxane (25 mL) and the resulting reaction mixture was stirred at RT for 3 h. After completion of the reaction, the solvent was removed under reduced pressure. The residue, compound 118, was used without further purification.

(1R,3S,5R)—N-(3-chloro-2-fluorobenzyl)-2-azabicyclo[3.1.0]hexane-3-carboxamide hydrochloride (120)

Scheme 15.

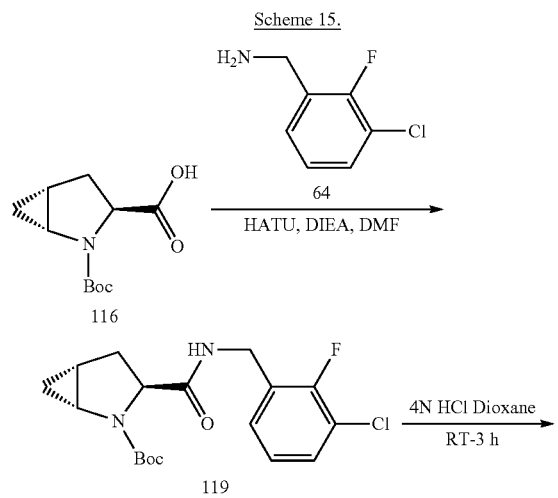

152
-continued

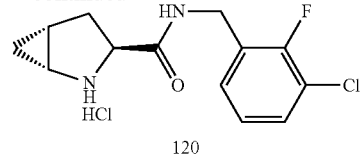
120

(1R,3S,5R)-2-(Tert-butoxycarbonyl)-2-azabicyclo[3.1.0]hexane-3-carboxylic acid (116, 2.27 g, 10 mmol) was dissolved in DMF (50 mL) and DIEA (8.6 mL, 5 eq.) was added followed by the addition of (3-chloro-2-fluorophenyl)methanamine (64, 3.18 g, 20 mmol) at 5° C. HATU (8 g, 2.1 eq) was added slowly at the same temperature and the reaction mixture was stirred for 18 h at RT. After completion of the reaction, the reaction mixture was diluted with 1M citric acid solution (200 mL+NaCl solid 20 g) and extracted with DCM (150 mL×2). The organic layer was washed with an aqueous solution of NaHCO₃ (100 mL), water (100 mL), brine (100 mL), dried over Na₂SO₄ and concentrated under reduced pressure. The residue was purified by column chromatography over silica gel (eluent: DCM/EtOAc) to afford (1R,3S,5R)-tert-butyl 3-((2'-chloro-2-fluoro-[1,1'-biphenyl]-3-yl)carbamoyl)-2-azabicyclo[3.1.0]hexane-2-carboxylate (119).

(2S,4R)-tert-butyl (1R,3S,5R)-tert-butyl 3-((2'-chloro-2-fluoro-[1,1'-biphenyl]-3-yl)carbamoyl)-2-azabicyclo[3.1.0]hexane-2-carboxylate (119, 500 mg) was taken up in 4N HCl in dioxane (30 mL) and resulting reaction mixture stirred at RT for 3 h. After completion of the reaction, solvent was removed under reduced pressure. The residue, compound 120, was used without any purification.

(2S,4R)—N-(3-(3-Chloropyridin-2-yl)-2-fluorophenyl)-4-fluoropyrrolidine-2-carboxamide hydrochloride (124)

Scheme 16

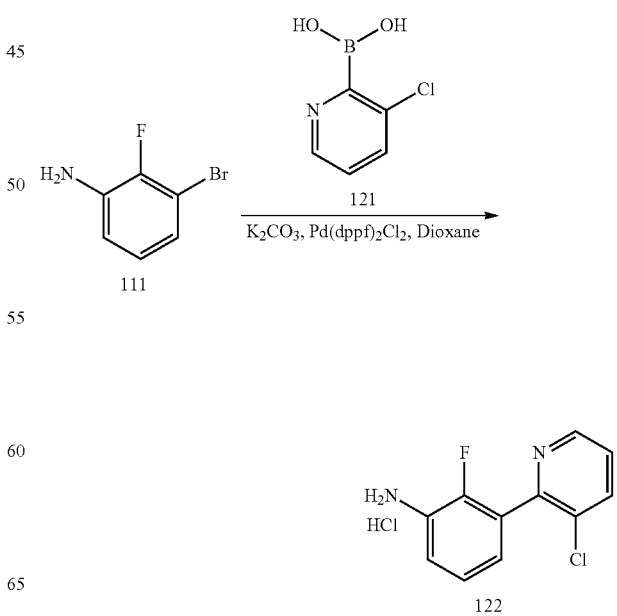

2-((3-(3-chloropyridin-2-yl)-2-fluorophenyl)carbamoyl)-4-fluoropyrrolidine-1-carboxylate, compound 123.

(2S,4R)-Tert-butyl 2-((3-(3-chloropyridin-2-yl)-2-fluorophenyl)carbamoyl)-4-fluoropyrrolidine-1-carboxylate (123, 700 mg) was taken up in 4N HCl dioxane (25 mL) and the resulting reaction mixture was stirred at RT for 3 h. After completion of the reaction, the solvent was removed under reduced pressure. The residue, compound 124 was used without further purification.

(2S,4R)—N-(6-Bromopyridin-2-yl)-4-fluoropyrrolidine-2-carboxamide hydrochloride (127)

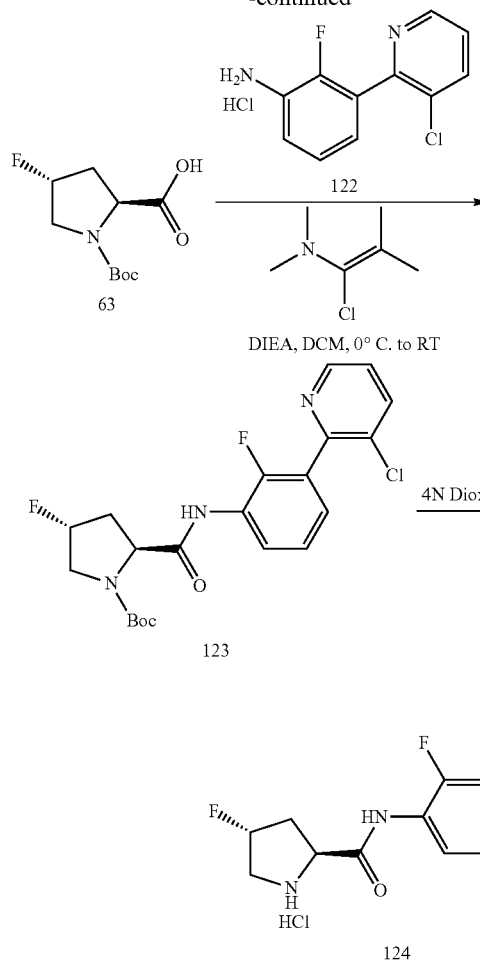

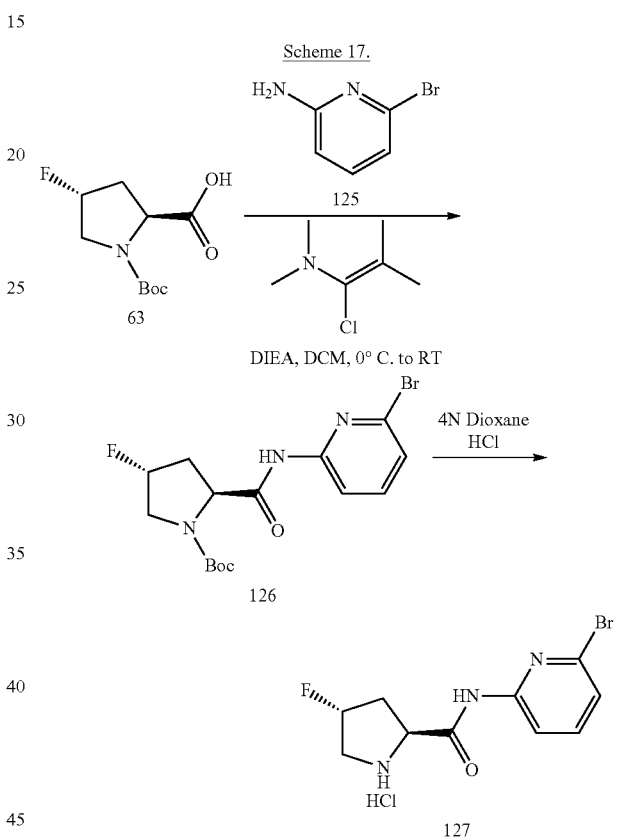

A mixture of 3-bromo-2-fluoroaniline (111, 10 g), (3-chloropyridin-2-yl)boronic acid (121, 20 g), $K_2CO_3$ (30 g) and $Pd(dppf)_2Cl_2$ (6.42 g) in solvent (dioxane 130 mL, $H_2O$ 33 mL) was purged with argon in a pressure vessel for 5 min and stirred for 15 h at 100° C. The solvent was removed under reduced pressure and the residue was purified by flash column chromatography over silica gel. The purified material was then dissolved in MeOH and treated with HCl/MeOH. The solvent was removed and the solid was washed with IPA-heptane (1/1) to afford 3-(3-chloropyridin-2-yl)-2-fluoroaniline hydrochloride (122).

To an ice-cold solution of (2S,4R)-1-(tert-butoxycarbonyl)-4-fluoropyrrolidine-2-carboxylic acid (63, 530 mg) in 20 mL of DCM, 1-chloro-N,N-2-trimethyl-1-propenylamine (0.333 mL, 1.1 eq.) was added dropwise with stirring. The stirring was continued for 3 h at this temperature and then 3-(3-chloropyridin-2-yl)-2-fluoroaniline hydrochloride (122) (642 mg, 1.1 eq.) was added followed by 1.12 mL of DIEA (3 eq.). The cooling bath was removed and the reaction mixture was stirred overnight at RT. The reaction mixture was added to water (20 mL) and extracted with DCM (2×25 mL). The organic layer was washed successively with an aqueous solution of $NaHCO_3$ (20 mL), water (20 mL), and brine (20 mL), then dried over $Na_2SO_4$ and concentrated under reduced pressure. The residue was purified by flash column chromatography over silica gel (ISCO eluted with hexanes/EtOAC) to afford (2S,4R)-tert-butyl 2-((3-(3-chloropyridin-2-yl)-2-fluorophenyl)carbamoyl)-4-fluoropyrrolidine-1-carboxylate (123, 700 mg) was taken up in 4N HCl dioxane (25 mL) and the resulting reaction mixture was stirred at RT for 3 h. After completion of the reaction, the solvent was removed under reduced pressure. The residue, compound 124 was used without further purification.

To an ice-cold solution of (2S,4R)-1-(tert-butoxycarbonyl)-4-fluoropyrrolidine-2-carboxylic acid (63, 530 mg) and DCM (20 mL) was added 1-chloro-N,N,2-trimethyl-1-propenylamine (0.333 mL, 1.1 eq.) dropwise with stirring. The stirring was continued for 3 h at this temperature and 6-bromopyridin-2-amine (125, 427 mg) was added followed by 1.12 mL of DIEA (3 eq.). The cooling bath was removed and the reaction mixture was stirred overnight at RT. After completion of the reaction, the reaction mixture was added to water (20 mL) and extracted with DCM (2×25 mL). The organic layer was washed successively with an aqueous solution of $NaHCO_3$ (20 mL), water (20 mL), and brine (20 mL), dried over $Na_2SO_4$ and concentrated under reduced pressure. The residue was purified by flash column chromatography over silica gel (eluent Hexanes/EtOAC) to afford (2S,4R)-tert-butyl 2-((6-bromopyridin-2-yl)carbamoyl)-4-fluoropyrrolidine-1-carboxylate (126).

(2S,4R)-Tert-butyl 2-((6-bromopyridin-2-yl)carbamoyl)-4-fluoropyrrolidine-1-carboxylate (126, 700 mg) was taken up in 4N HCl dioxane (25 mL) and the resulting reaction 3-Acetyl-1-(2-((1R,3S,5R)-3-((3-chloro-2-fluorobenzyl)carbamoyl)-2-azabicyclo[3.1.0]hexan-2-yl)-2-oxoethyl)-1H-indole-5-carboxylic acid (129)

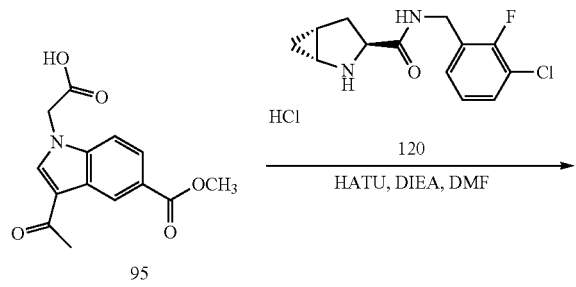

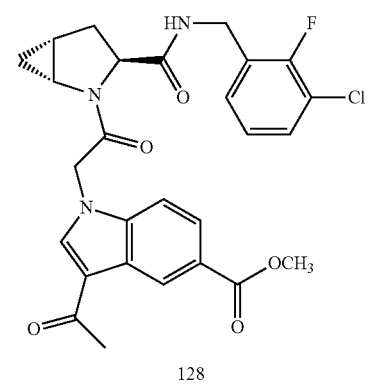

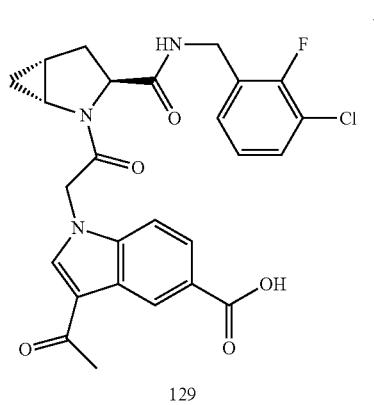

3-Acetyl-1-(2-((2S,4R)-2-((2'-chloro-2-fluoro-[1,1'-biphenyl]-3-yl)carbamoyl)-4-fluoropyrrolidin-1-yl)-2-oxoethyl)-1H-indole-5-carboxylic acid (131)

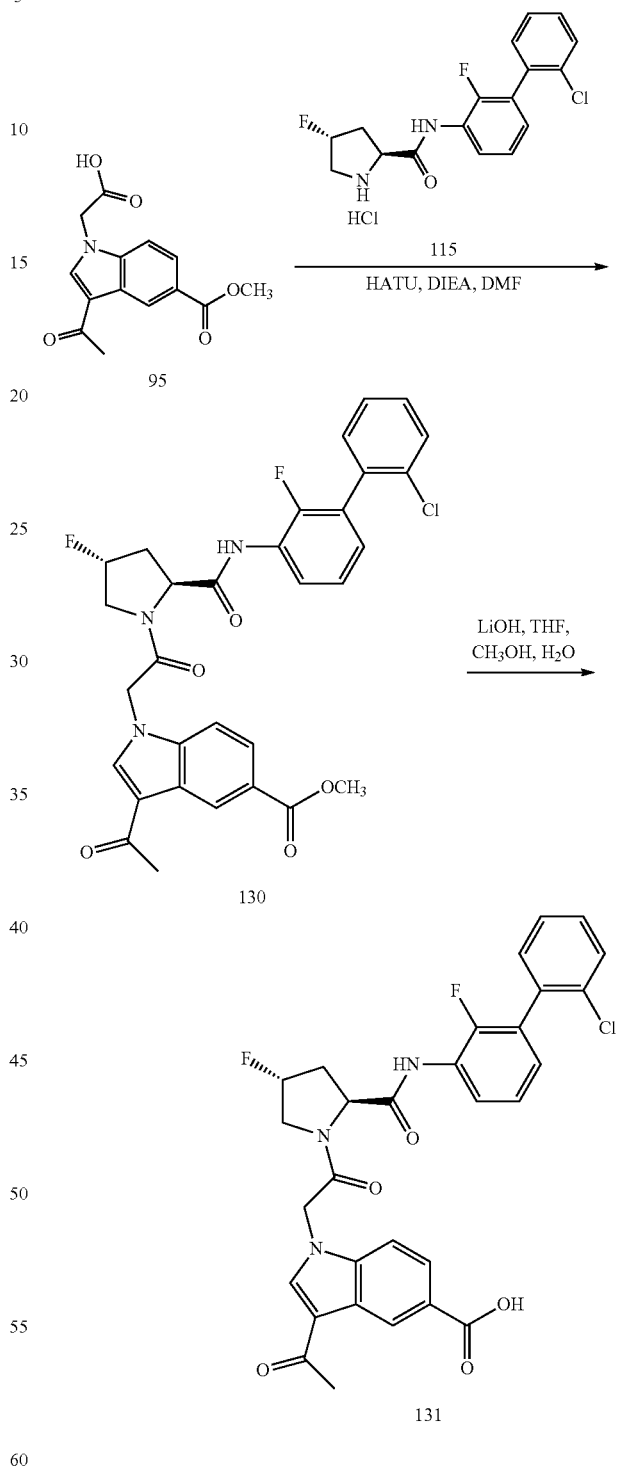

Compound 128 was prepared from 2-(3-acetyl-5-(methoxycarbonyl)-1H-indol-1-yl)acetic acid (95, 275 mg) and (1R,3S,5R)—N-(3-chloro-2-fluorobenzyl)-2-azabicyclo[3.1.0]hexane-3-carboxamide hydrochloride (120, 305 mg) as described in Scheme 15 and then hydrolyzed following procedures described in Scheme 8 to afford 129.

Compound 130 was prepared from 2-(3-acetyl-5-(methoxycarbonyl)-1H-indol-1-yl)acetic acid (95, 275 mg) and (2S,4R)—N-(2'-chloro-2-fluoro-[1,1'-biphenyl]-3-yl)-4-fluoropyrrolidine-2-carboxamide hydrochloride (115, 373 mg)) as described in Scheme 15 to afford compound 130 and then hydrolyzed following procedures described in Scheme 8 to afford compound 131.

3-Carbamoyl-1-(2-((2S,4R)-2-((2'-chloro-2-fluoro-[1,1'-biphenyl]-3-yl)carbamoyl)-4-fluoropyrrolidin-1-yl)-2-oxoethyl)-1H-indazole-5-carboxylic acid (133)

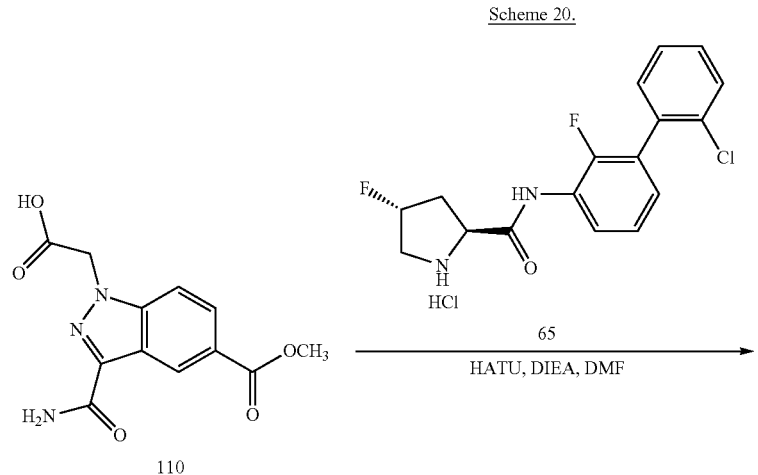

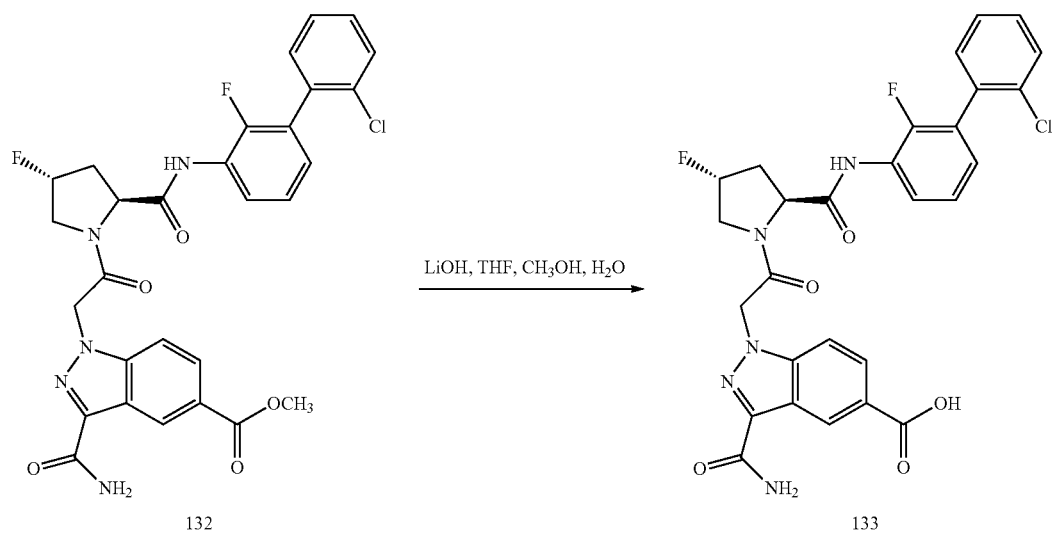

Compound 132 was prepared from 2-(3-carbamoyl-5-(methoxycarbonyl)-1H-indazol-1-yl)acetic acid (110, 277 mg) and (2S,4R)—N-(2'-chloro-2-fluoro-[1,1'-biphenyl]-3-yl)-4-fluoropyrrolidine-2-carboxamide hydrochloride (65, 373 mg) as described in Scheme 15 to afford compound 132 and then hydrolyzed following procedures described in Scheme 8 to afford compound 133.

3-Carbamoyl-1-(2-((1R,3S,5R)-3-((2'-chloro-2-fluoro-[1,1'-biphenyl]-3-yl)carbamoyl)-2-azabicyclo[3.1.0]hexan-2-yl)-2-oxoethyl)-1H-indazole-5-carboxylic acid (135)

Scheme 21.

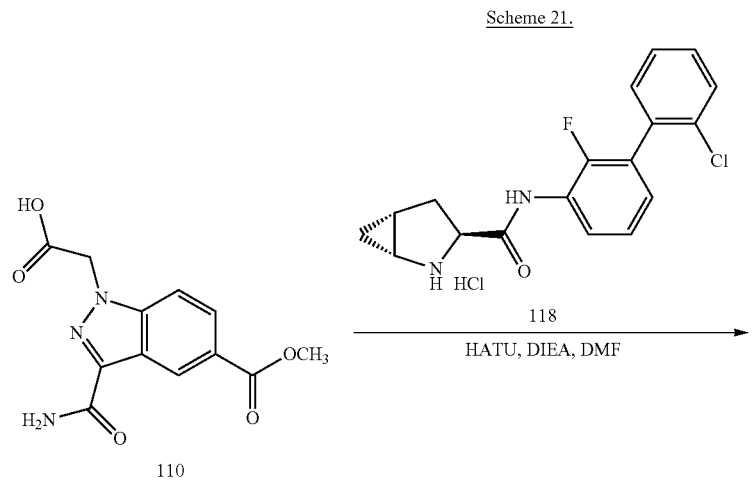

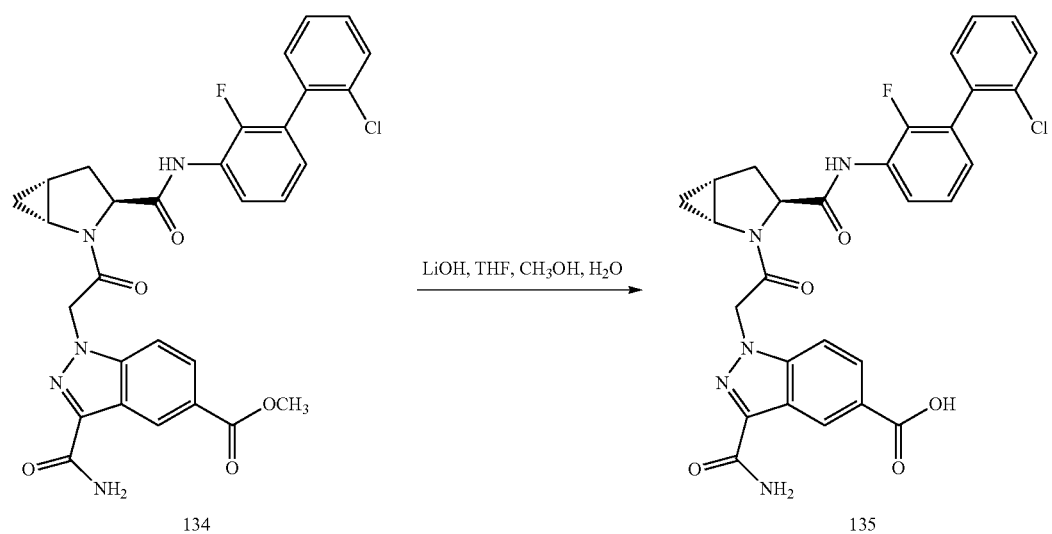

Compound 134 was prepared from 2-(3-carbamoyl-5-(methoxycarbonyl)-1H-indazol-1-yl)acetic acid (110, 277 mg) and (1R,3S,5R)—N-(2'-chloro-2-fluoro-[1,1'-biphenyl]-3-yl)-2-azabicyclo[3.1.0]hexane-3-carboxamide hydrochloride (119, 367 mg) as described in Scheme 15 to afford compound 134 and then hydrolyzed following procedures described in Scheme 8 to afford compound 135.

3-Carbamoyl-1-(2-((2S,4R)-2-((3-(3-chloropyridin-2-yl)-2-fluorophenyl)carbamoyl)-4-fluoropyrrolidin-1-yl)-2-oxoethyl)-1H-indazole-5-carboxylic acid (137)

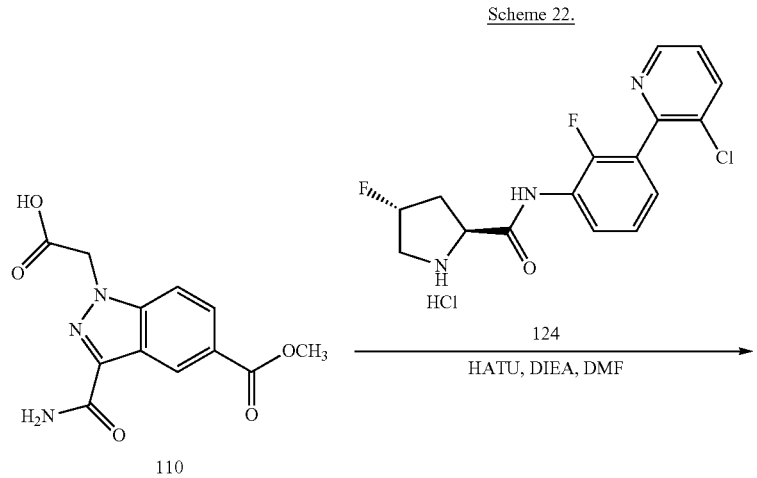

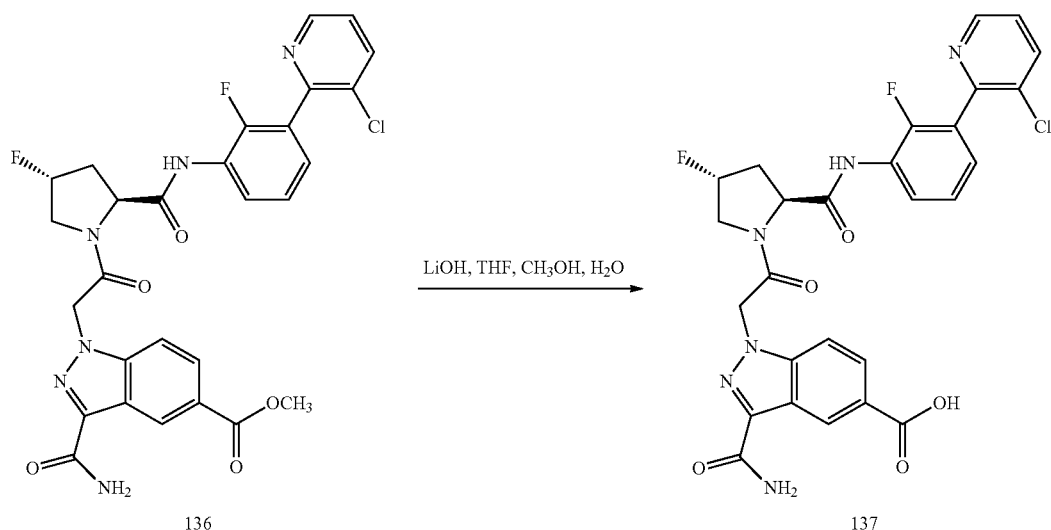

Compound 136 was prepared from 2-(3-carbamoyl-5-(methoxycarbonyl)-1H-indazol-1-yl)acetic acid (110, 277 mg) and (2S,4R)—N-(3-(3-chloropyridin-2-yl)-2-fluorophenyl)-4-fluoropyrrolidine-2-carboxamide hydrochloride (124, 374 mg) as described in Scheme 15 to afford compound 136 and then hydrolyzed following procedures described in Scheme 8 to afford 137.

163

1-(2-((2S,4R)-2-((6-bromopyridin-2-yl)carbamoyl)-4-fluoropyrrolidin-1-yl)-2-oxoethyl)-3-carbamoyl-1H-indazole-5-carboxylic acid (139)

Scheme 23.

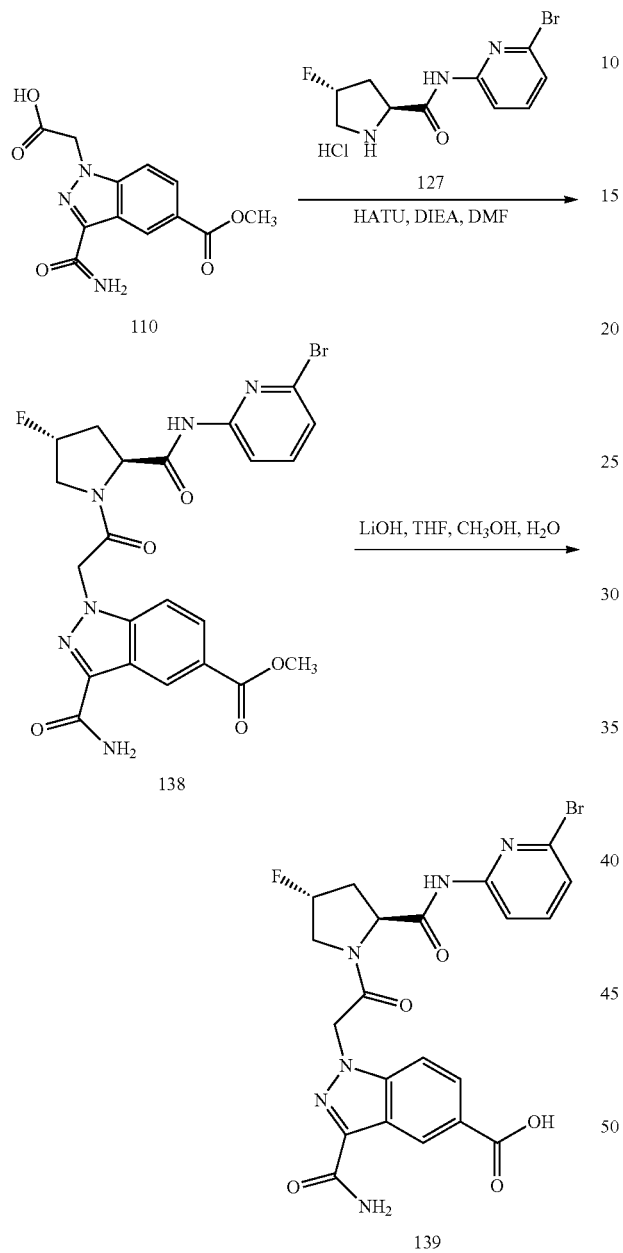

Compound 138 was prepared from 2-(3-carbamoyl-5-(methoxycarbonyl)-1H-indazol-1-yl)acetic acid (110, 277 mg) and (2S,4R)—N-(6-bromopyridin-2-yl)-4-fluoropyrrolidine-2-carboxamide hydrochloride (127, 325 mg) as described in Scheme 15 to afford compound 138 and then hydrolyzed following procedures described in Scheme 8 to afford 139.

164

(2S,4R)-1-(2-(3-acetyl-5-(3-cyclopropylureido)-1H-indol-1-yl)acetyl)-N-(3-chloro-2-fluorobenzyl)-4-fluoropyrrolidine-2-carboxamide (1)

Scheme 24.

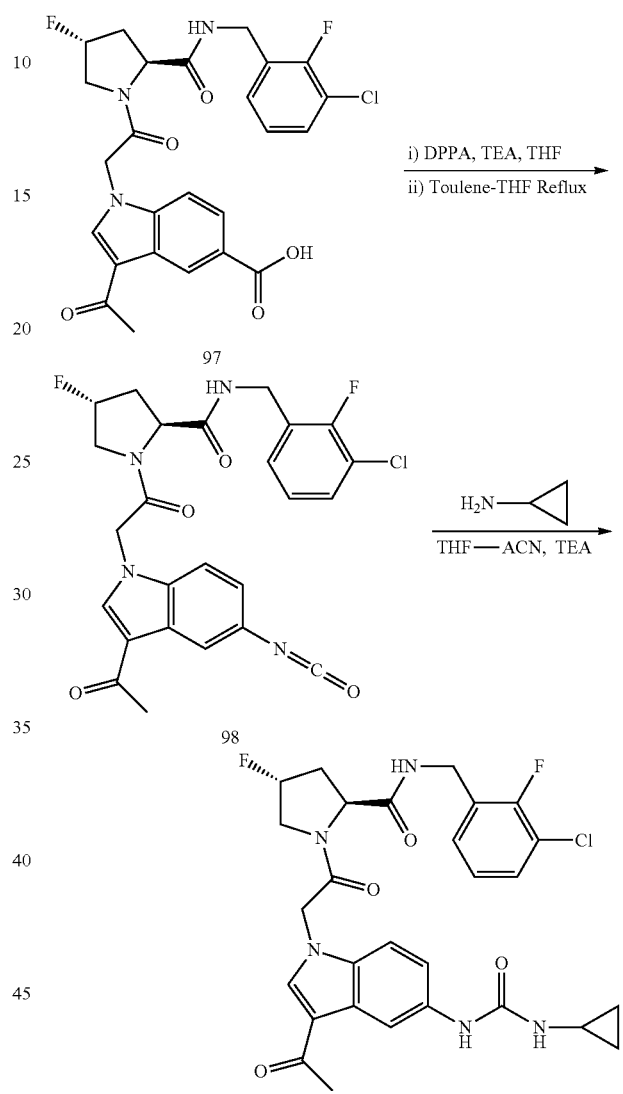

To a suspension of 3-acetyl-1-(2-((2S,4R)-2-((3-chloro-2-fluorobenzyl)carbamoyl)-4-fluoropyrrolidin-1-yl)-2-oxoethyl)-1H-indole-5-carboxylic acid (97, 517 mg, 1 mmol, 1 eq.) in THF (60 mL) was added $Et_3N$ (127 µl, 1 eq.) and the resulting solution was stirred at RT under nitrogen for 15 min. DPPA (213 µl, 1 eq.) was added and the reaction was further stirred at RT under nitrogen for 18 h. After completion of the reaction, THF was evaporated and the residue was suspended in toluene (60 mL) and THF (15 mL). The mixture was heated at reflux under nitrogen for 4 h until completion of the reaction to afford crude isocyanate, 98, which was used directly in the next step.

Isocyanate 98 was dissolved in THF (20 mL), ACN (10 mL) and cyclopropylamine (17 mg, 2 eq.) which was followed by the addition of $Et_3N$ (253 µl, 2 eq.) at 0° C. The reaction mixture was then stirred for 24 h at RT. After completion of the reaction, the reaction mixture was concentrated under reduced pressure. The residue was purified by flash column chromatography over silica gel (eluant DCM/CH$_3$OH) to afford compound 1.

$^1$H-NMR (400 MHz, DMSO-d$_6$): (major rotamer) δ 0.40-0.66 (m, 4H) 2.00-2.17 (m, 1H), 2.40 (s, 3H), 2.46-2.58 (m, 1H), 3.85-3.95 (m, 1H), 4.09-4.18 (m, 1H), 4.15 (dd, J=21.2, 12.4 Hz, 1H), 4.25-4.49 (m, 2H), 5.06 (d, J=17.2 Hz, 1H), 5.32 (d, J=17.2 Hz, 1H), 5.50 (d, J=53.2 Hz, 1H), 6.21 (s, 1H), 6.99-7.07 (m, 1H), 7.15-7.45 (m, 4H), 8.15 (s, 2H), 8.27 (s, 1H), 8.59 (t, J=5.6 Hz, 1H), 10.05 (s, 1H). LC (method 1): tR=1.24 min. LC/MS (APCI) m/z: [M+H]$^+$, 572

(1R,3S,5R)-2-(2-(3-acetyl-5-(3-cyclopropylureido)-1H-indol-1-yl)acetyl)-N-(3-chloro-2-fluorobenzyl)-2-azabicyclo[3.1.0]hexane-3-carboxamide (3)

1H-indole-5-carboxylic acid (129, 512 mg) was converted to the isocyanate, compound 140, and reacted with cyclopropanamine (114 mg) to afford compound 3 following procedures described in Scheme 24.

$^1$H NMR (400 MHz, DMSO-d$_6$): (major rotamer) δ 0.42-1.07 (m, 6H) 1.88 (m, 1H), 2.18-2.63 (m, 2H), 2.40 (s, 3H), 2.49-2.56 (m, 1H), 3.7 (m, 1H), 4.27-4.40 (m, 3H), 5.23 (d, J=17.2 Hz, 1H), 5.40 (d, J=17.2 Hz, 1H), 6.21 (d, J=2 Hz, 1H), 7.08 (m, 1H), 7.20 (m, 1H), 7.32-7.44 (m, 3H), 8.14 (s, 1H), 8.21 (s, 1H), 8.43 (s, 1H), 8.45 (m, 1H). LC (method 1): tR=1.52 min. LC/MS (APCI) m/z: [M+H]+ 566

N-(3-acetyl-1-(2-((2S,4R)-2-(2'-chloro-2-fluorobiphenyl-3-ylcarbamoyl)-4-fluoropyrrolidin-1-yl)-2-oxoethyl)-1H-indol-5-yl)-3,3-difluoropiperidine-1-carboxamide (18)

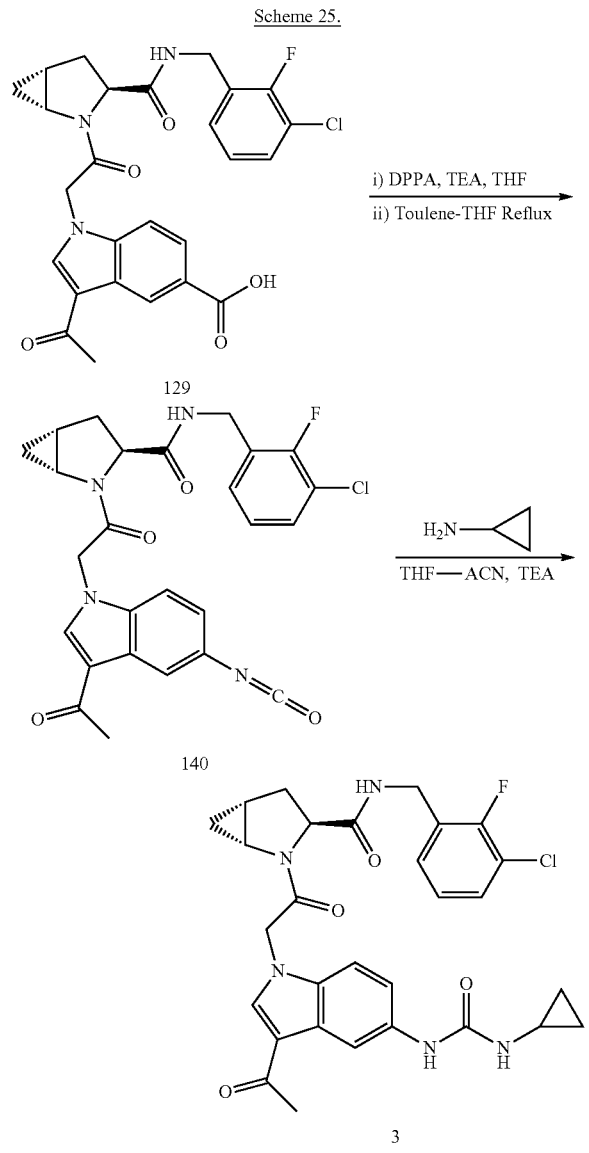

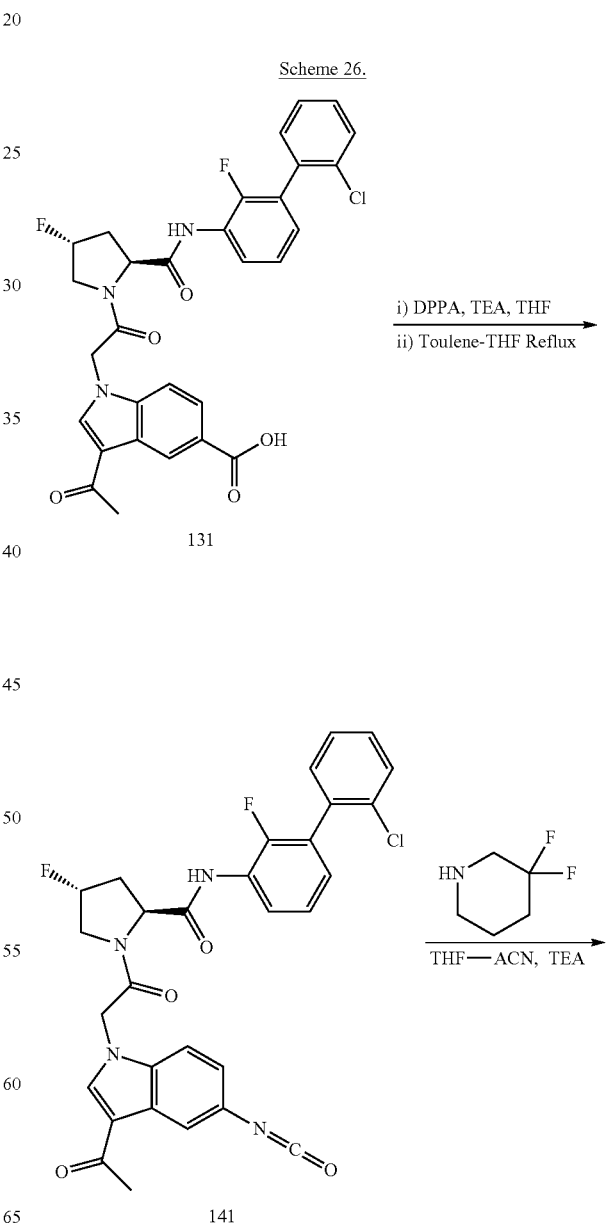

3-Acetyl-1-(2-((1R,3S,5R)-3-((3-chloro-2-fluorobenzyl) carbamoyl)-2-azabicyclo [3.1.0]hexan-2-yl)-2-oxoethyl)-

167
-continued

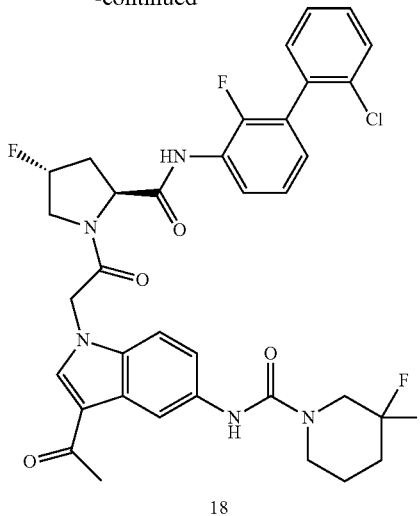

18

3-Acetyl-1-(2-((2S,4R)-2-((2'-chloro-2-fluoro-[1,1'-biphenyl]-3-yl)carbamoyl)-4-fluoropyrrolidin-1-yl)-2-oxoethyl)-1H-indole-5-carboxylic acid (131, 580 mg) was converted to the isocyanate, compound 141, and the reacted with 3,3-difluoropiperidine (242 mg) to afford compound 18 following procedures described in Scheme 24.

¹H NMR (400 MHz, DMSO-d₆): (major rotamer) δ 1.71 (m, 2H) 2.01-2.09 (m, 2H), 2.36 (s, 3H), 2.49-2.65 (m, 1H), 3.27 (m, 1H), 3.51 (m, 2H), 3.79 (m, 2H), 3.80-4.25 (m, 2H), 4.77 (m, 1H), 5.17 (d, J=17.2 Hz, 1H), 5.33 (d, J=17.2 Hz, 1H), 5.50 (d, J=52.8 Hz, 1H), 7.04-7.59 (m, 8H), 8.01 (m, 1H), 8.17 (s, 2H), 8.61 (s, 1H), 10.02 (s, 1H). LC (method 1): tR=2.25 min. LC/MS (APCI) m/z: [M+H]+ 698.

1-(2-((2S,4R)-2-(2'-chloro-2-fluorobiphenyl-3-ylcarbamoyl)-4-fluoropyrrolidin-1-yl)-2-oxoethyl)-5-(3,3-difluoropiperidine-1-carboxamido)-1H-indazole-3-carboxamide (24)

Scheme 27.

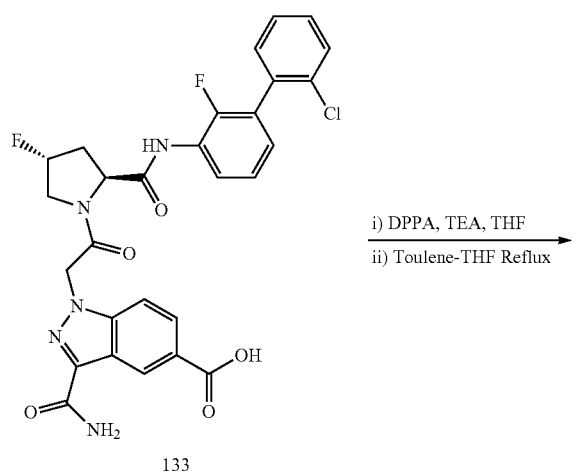

133 i) DPPA, TEA, THF
ii) Toulene-THF Reflux

168
-continued

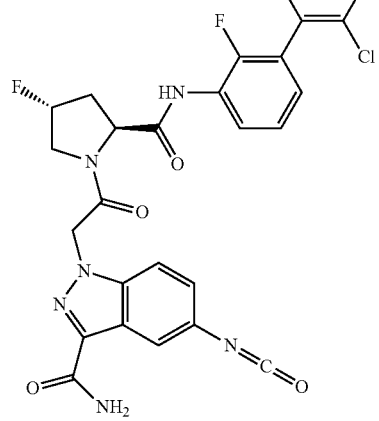

142

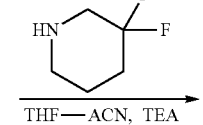

THF—ACN, TEA

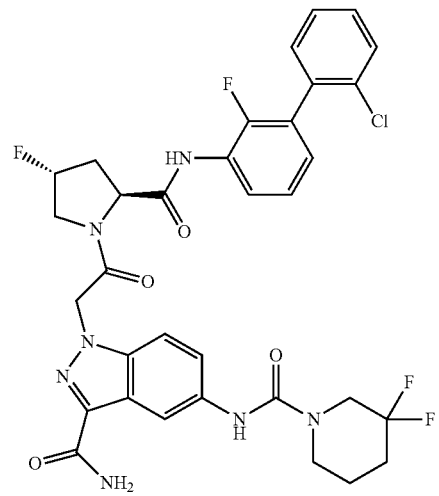

24

3-Carbamoyl-1-(2-((2S,4R)-2-((2'-chloro-2-fluoro-[1,1'-biphenyl]-3-yl)carbamoyl)-4-fluoropyrrolidin-1-yl)-2-oxoethyl)-1H-indazole-5-carboxylic acid (133, 582 mg) was converted to the isocyanate compound 142 and then treacted with 3,3-difluoropiperidine (242 mg) to afford compound 24 following procedures described in Scheme 24.

¹H NMR (400 MHz, DMSO-d₆): (major rotamer) δ 1.71 (m, 2H) 2.01-2.3 (m, 3H), 2.60 (m, 1H), 3.52 (m, 2H), 3.79-4.40 (m, 5H), 4.77 (m, 1H), 5.39-5.75 (m, 4H), 7.04-7.70 (m, 8H), 8.01 (m, 1H), 8.18 (s, 1H), 8.77 (s, 1H), 10.00 (s, 1H). LC (method 1): tR=2.09 min. LC/MS (APCI) m/z: [M+H]+ 700.

1-(2-((1R,3S,5R)-3-(2'-chloro-2-fluorobiphenyl-3-ylcarbamoyl)-2-azabicyclo[3.1.0]hexan-2-yl)-2-oxoethyl)-5-(3,3-difluoropiperidine-1-carboxamido)-1H-indazole-3-carboxamide (28)

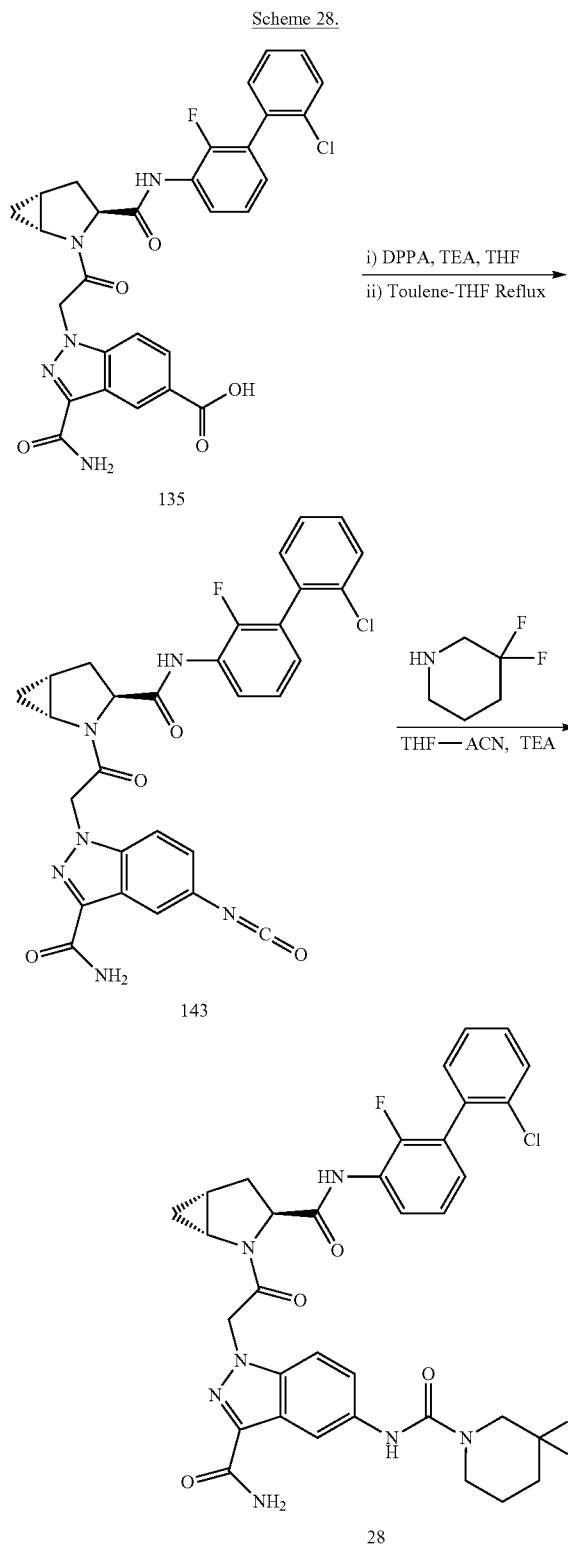

3-Carbamoyl-1-(2-((1R,3S,5R)-3-((2'-chloro-2-fluoro-[1,1'-biphenyl]-3-yl)carbamoyl)-2-azabicyclo[3.1.0]hexan-2-yl)-2-oxoethyl)-1H-indazole-5-carboxylic acid (135, 576 mg) was converted to the isocyanate 143 and then reacted with 3,3-difluoropiperidine (242 mg) to afford compound 28 following procedures described in Scheme 24.

$^1$H NMR (400 MHz, DMSO-d$_6$): (major rotamer) δ 0.74-1.30 (m, 3H) 1.72-2.35 (m, 7H), 3.30 (s, 1H), 3.55 (m, 2H), 3.80 (m, 3H), 4.55 (m, 1H), 5.45 (d, J=17.2 Hz, 1H), 5.74 (d, J=17.2 Hz, 1H), 7.15-7.70 (m, 8H), 7.92 (m, 1H), 8.19 (s, 1H), 8.75 (s, 1H), 9.75 (s, 1H). LC (method 1): tR=2.17 min. LC/MS (APCI) m/z: [M+H]+ 694.

1-(2-((2S,4R)-2-(3-(3-chloropyridin-2-yl)-2-fluorophenylcarbamoyl)-4-fluoropyrrolidin-1-yl)-2-oxoethyl)-5-(3,3-difluoropiperidine-1-carboxamido)-1H-indazole-3-carboxamide (29)

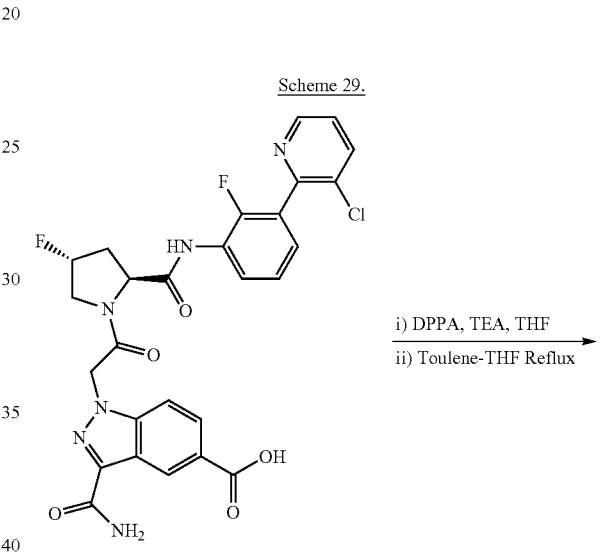

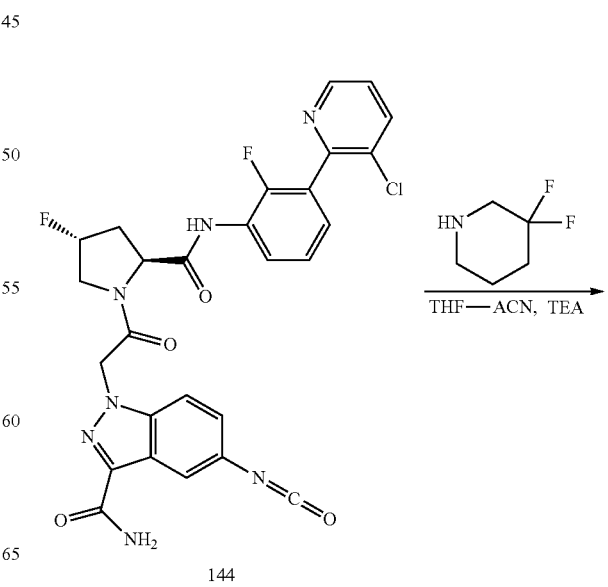

-continued

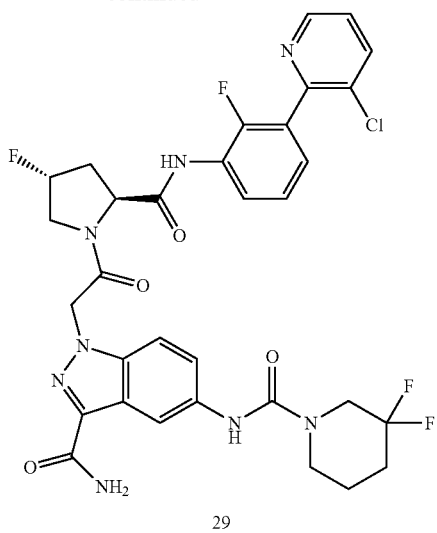

29

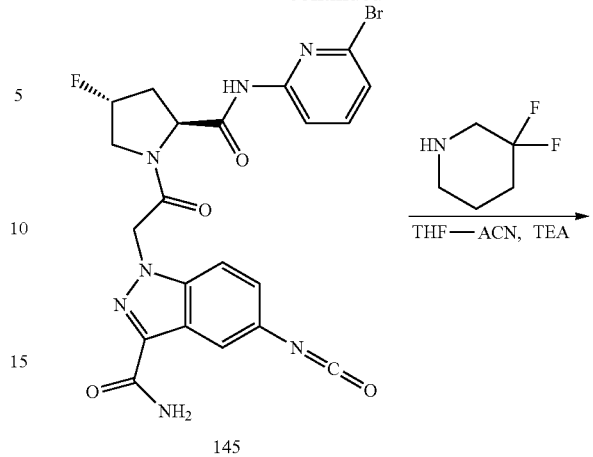

145

3-Carbamoyl-1-(2-((2S,4R)-2-((3-(3-chloropyridin-2-yl)-2-fluorophenyl)carbamoyl)-4-fluoropyrrolidin-1-yl)-2-oxo-ethyl)-1H-indazole-5-carboxylic acid (137, 583 mg) was converted to the isocyanate compound 144 and then reacted with 3,3-difluoropiperidine (242 mg) to afford compound 29 following procedures described in Scheme 24.

$^1$H NMR (400 MHz, DMSO-$d_6$): (major rotamer) δ 1.72 (m, 2H) 2.01-2.3 (m, 3H), 2.60 (m, 1H), 3.52 (m, 2H), 3.79-4.40 (m, 5H), 4.77 (m, 1H), 5.39-5.75 (m, 4H), 7.18-7.65 (m, 5H), 8.00 (m, 1H), 8.07 (m, 1H), 8.19 (s, 1H), 8.64 (m, 1H), 8.75 (s, 1H), 10.05 (s, 1H). LC (method 1): tR=1.65 min. LC/MS (APCI) m/z: [M+H]+ 701

1-(2-((2S,4R)-2-(6-bromopyridin-2-ylcarbamoyl)-4-fluoropyrrolidin-1-yl)-2-oxoethyl)-5-(3,3-difluoropi-peridine-1-carboxamido)-1H-indazole-3-carboxam-ide (33)

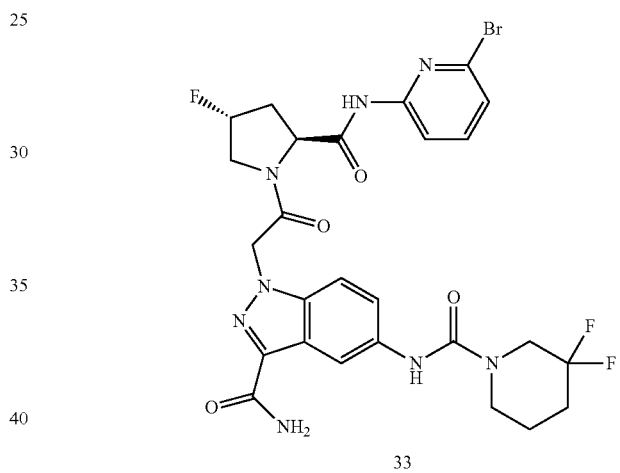

33

1-(2-((2S,4R)-2-((6-bromopyridin-2-yl)carbamoyl)-4-fluoropyrrolidin-1-yl)-2-oxoethyl)-3-carbamoyl-1H-inda-zole-5-carboxylic acid (139) (533 mg) was converted to the isocyanate compound 145 and then reacted with 3,3-difluo-ropiperidine (242 mg) to afford compound 33 following procedures described in Scheme 24.

$^1$H NMR (400 MHz, DMSO-$d_6$): (major rotamer) δ 1.72 (m, 2H) 2.01-2.3 (m, 3H), 2.60 (m, 1H), 3.52 (m, 2H), 3.79-4.40 (m, 5H), 4.77 (m, 1H), 5.39-5.75 (m, 4H), 7.30-7.75 (m, 4H), 8.02 (d, J=8.0 Hz, 1H), 8.28 (s, 1H), 8.74 (s, 1H), 11.00 (s, 1H). LC (method 1): tR=1.59 min. LC/MS (APCI) m/z: [M+H]+ 651.

Scheme 30.

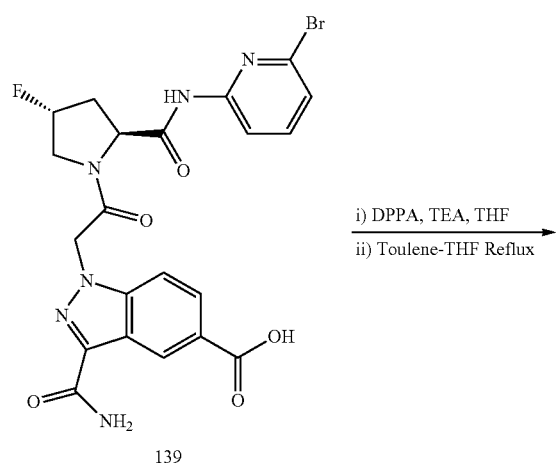

139 i) DPPA, TEA, THF
ii) Toulene-THF Reflux (2S,4R)-1-(2-(3-acetyl-5-(3,3-difluorocyclopentan-ecarboxamido)-1H-indol-1-yl)acetyl)-N-(2'-chloro-2-fluorobiphenyl-3-yl)-4-fluoropyrrolidine-2-carboxamide (30)

Scheme 31.

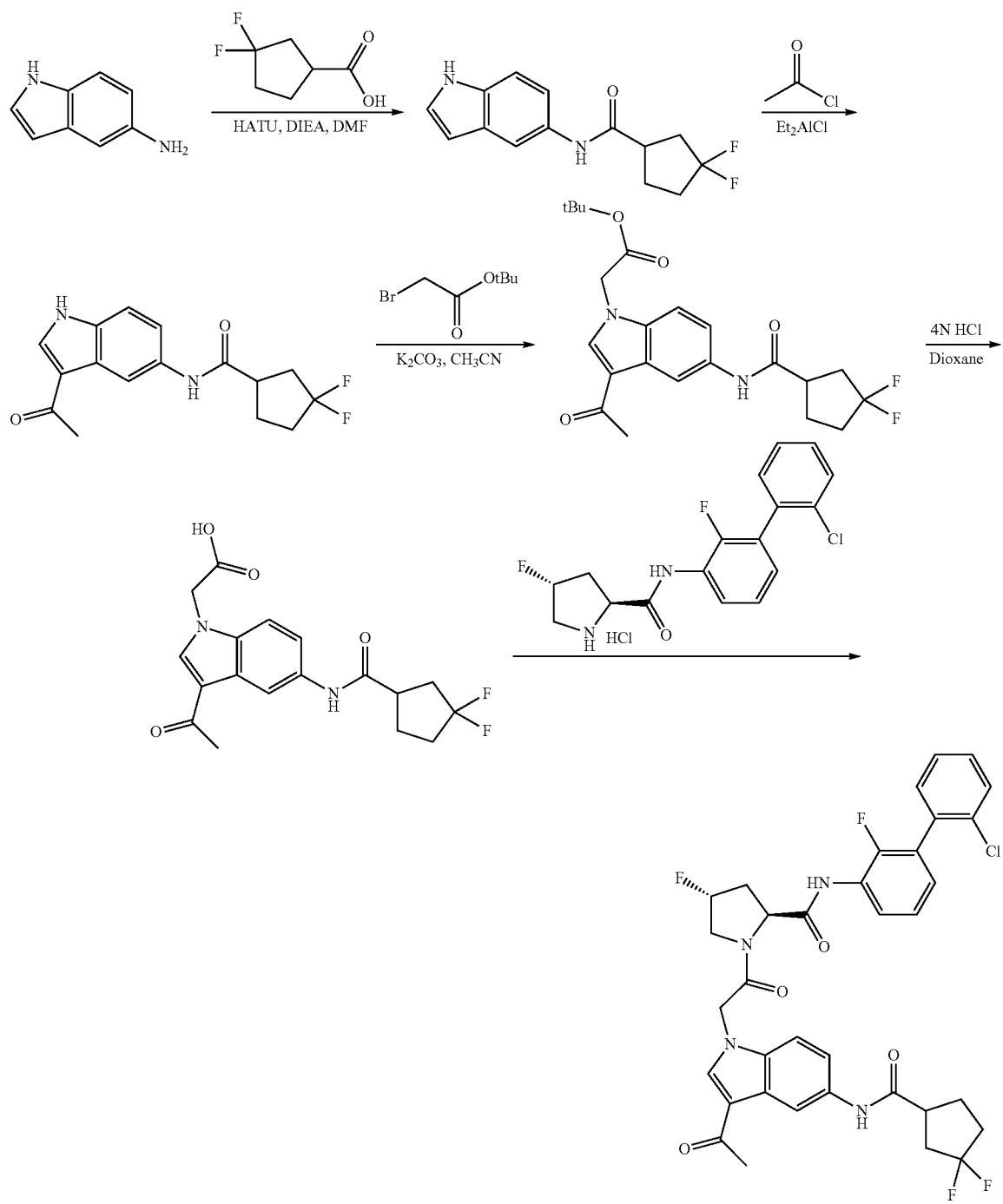

A mixture of 1H-indol-5-amine (220 mg), 3,3-difluoro-cyclopentanecarboxylic acid, (250 mg), HATU (1.2 eq), and DIEA (5.0 eq) in DMF (20 mL) was stirred overnight at rt. The solvent was removed and residue purified by chromatography over silica gel to afford 3,3-difluoro-N-(1H-indol-5-yl)cyclopentanecarboxamide.

To 3,3-difluoro-N-(1H-indol-5-yl)cyclopentanecarboxamide (287 mg), acetyl chloride (1.5 eq) in DCM was added diethylaluminum chloride (1.5 eq) at 0° C. The reaction mixture was stirred for 3 h and pour into ice-water and extracted with DCM. Solvent was removed and the residue was purified by chromatography over silica gel to afford N-(3-acetyl-1H-indol-5-yl)-3,3-difluorocyclopentanecarboxamide.

N-(3-acetyl-1H-indol-5-yl)-3,3-difluorocyclopentanecarboxamide (8 mg), tert-butyl 2-bromoacetate(5.6 mg) and K$_2$CO$_3$ (4.1 mg) in ACN (10 mL) was stirred at 60° C. for 5 h. The solvent was removed and the residue was purified by chromatography over silica gel to afford tert-butyl 2-(3-acetyl-5-(3,3-difluorocyclopentanecarboxamido)-1H-indol-1-yl)acetate.

To 2-(3-acetyl-5-(3,3-difluorocyclopentanecarboxamido)-1H-indol-1-yl)acetate (7 mg) was treated with 4 N HCl in dioxane and the reaction was stirred for 3 h at RT. The solvent was removed and the crude product was used directly in the next step.

2-(3-Acetyl-5-(3,3-difluorocyclopentanecarboxamido)-1H-indol-1-yl)acetic acid (5 mg) and (2S,4R)—N-(2'-chloro-2-fluoro-[1,1'-biphenyl]-3-yl)-4-fluoropyrrolidine-2-carboxamide hydrochloride (6.3 mg) were coupled using HATU as a coupling reagent as described in Scheme 14 to afford compound 30.

$^1$H NMR (400 MHz, DMSO-d$_6$): (major rotamer) δ 1.92-2.70 (m, 10H) 3.19 (m, 1H), 3.88-4.18 (m, 2H), 4.77 (m, 1H), 5.19 (d, J=17.2 Hz, 1H), 5.35 (d, J=17.2 Hz, 1H), 5.48 (m, 1H), 5.61 (m, 1H), 7.04-7.59 (m, 8H), 8.01 (m, 1H), 8.17 (s, 2H), 8.61 (s, 1H), 10.02 (s, 1H). LC (method 1): tR=2.61 min. LC/MS (APCI) m/z: [M+H]+ 683.

(2S,4R)-1-(2-(3-acetyl-5-(3,3,3-trifluoropropanamido)-1H-indol-1-yl)acetyl)-N-(2'-chloro-2-fluorobiphenyl-3-yl)-4-fluoropyrrolidine-2-carboxamide (36)

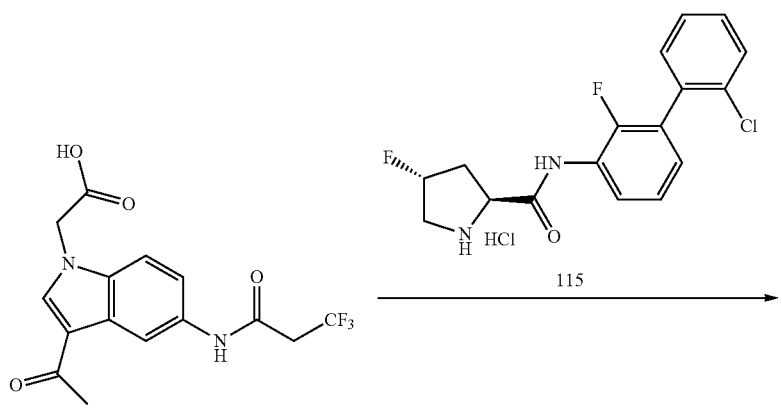

2-(3-Acetyl-5-(3,3,3-trifluoropropanamido)-1H-indol-1-yl)acetic acid (152, 10 mg) and (2S,4R)—N-(2'-chloro-2-fluoro-[1,1'-biphenyl]-3-yl)-4-fluoropyrrolidine-2-carboxamide hydrochloride (115, 10 mg) were coupled using HATU as a coupling agent following the procedures described in Scheme 8 to afford compound 36.

$^1$H NMR (400 MHz, DMSO-d$_6$): (major rotamer) δ 2.16-2.70 (m, 4H) 3.28 (m, 1H), 3.49 (ddd, J=22.4, 11.2, Hz, 2H), 3.89-4.01 (m, 1H), 4.13-4.22 (m, 1H), 4.75 (m, 1H), 5.16 (d, J=17.2 Hz, 1H), 5.32 (d, J=17.2 Hz, 1H), 5.43 (d, J=35.6 Hz, 1H), 7.04-7.59 (m, 8H), 8.01 (m, 1H), 8.17 (s, 2H), 8.61 (s, 1H), 10.27 (s, 1H). LC (method 1): tR=2.70 min. LC/MS (APCI) m/z: [M+H]+ 661.

177 tert-Butyl 3-acetyl-1-(2-((2S,4R)-2-(3-chloro-2-fluorobenzylcarbamoyl)-4-fluoro pyrrolidin-1-yl)-2-oxoethyl)-1H-indol-6-ylcarbamate (37)

178

(2S,4R)-1-(2-(3-acetyl-5-(2-azabicyclo[2.2.1]heptane-2-carbonyl)-1H-indol-1-yl)acetyl)-N-(3-chloro-2-fluorobenzyl)-4-fluoropyrrolidine-2-carboxamide (39)

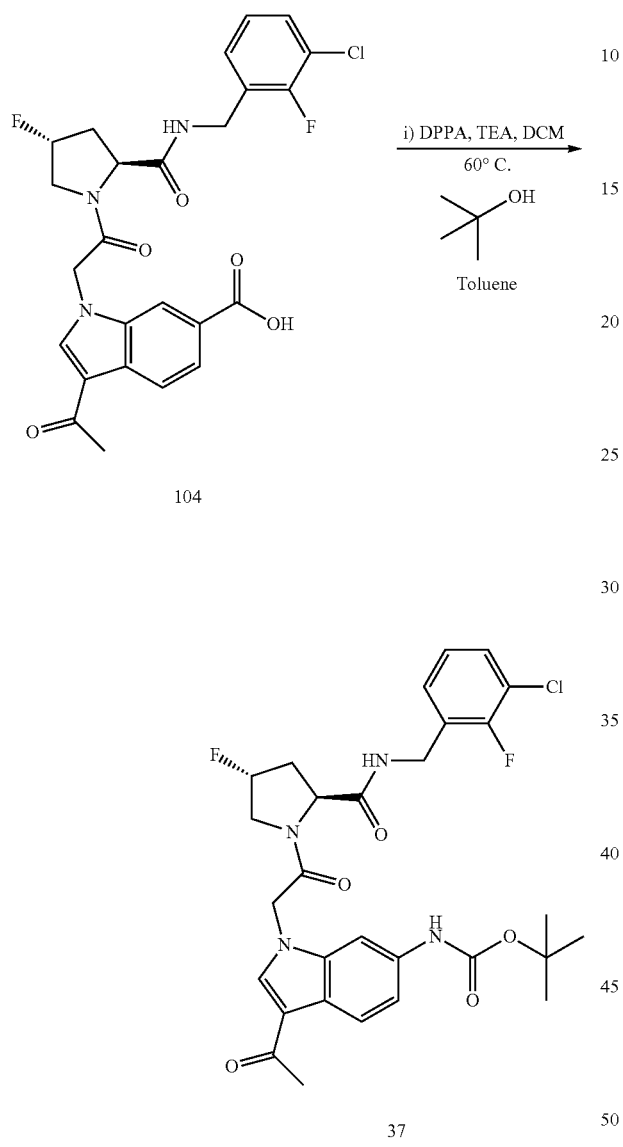

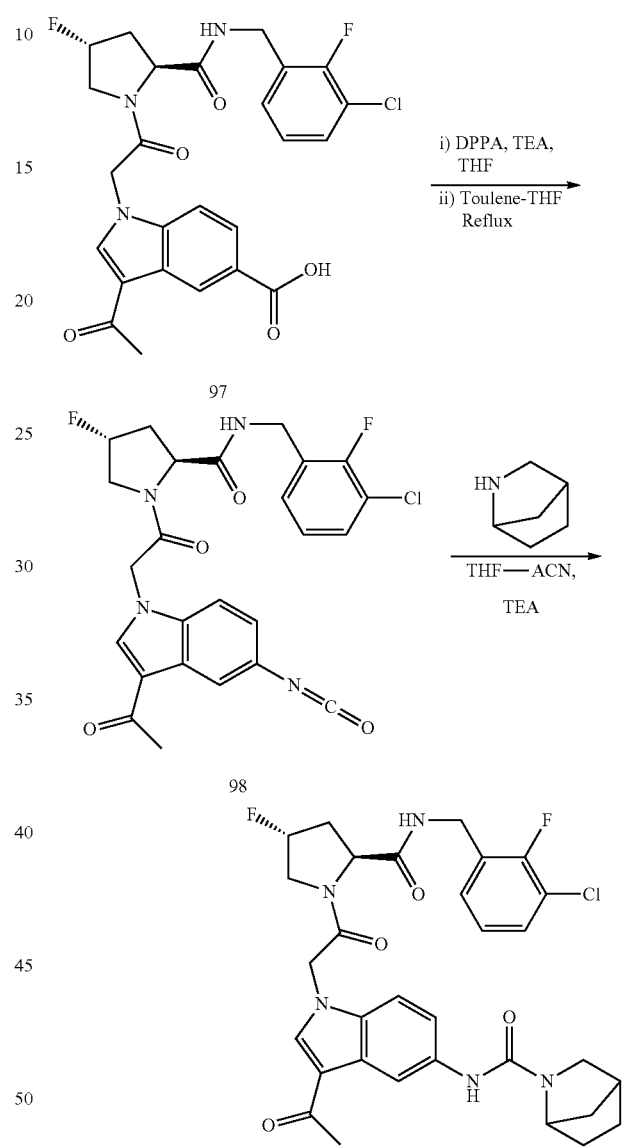

To a solution of 3-acetyl-1-(2-((2S,4R)-2-((3-chloro-2-fluorobenzyl)carbamoyl)-4-fluoropyrrolidin-1-yl)-2-oxoethyl)-1H-indole-5-carboxylic acid (104, 56 mg) and DCM (20 mL) was added TEA (0.02 mL, 1 eq.). The solution was stirred for 15 min. and DPPA (0.02 mL, 1 eq.) was added. The reaction mixture was stirred for 16 h at RT and DCM was removed. The residue was diluted with toluene (15 mL) and excess tert-BuOH and heated at reflux for 16 h. The solvent was evaporated and the residue was purified by chromatography over silica gel (MeOH in DCM gradient) to obtain tert-butyl 3-acetyl-1-(2-((2S,4R)-2-(3-chloro-2-fluorobenzylcarbamoyl)-4-fluoropyrrolidin-1-yl)-2-oxoethyl)-1H-indol-6-ylcarbamate (37) (46 mg, 0.08 mmol). LC (method 1): tR=1.90 min. LC/MS (APCI) m/z: [M+H]+ 589.

3-Acetyl-1-(2-((2S,4R)-2-((3-chloro-2-fluorobenzyl)carbamoyl)-4-fluoropyrrolidin-1-yl)-2-oxoethyl)-1H-indole-5-carboxylic acid (97, 518 mg) was converted to the isocyanate and the isocyante, 98, was reacted with 2-azabicyclo[2.2.1]heptane (194 mg) to afford compound 39 following procedures described in Scheme 24.

$^1$H NMR (400 MHz, DMSO-$d_6$): (major rotamer) δ 1.38-1.77 (m, 6H), 2.00-2.17 (m, 1H), 2.45 (s, 3H), 2.62 (s, 1H), 3.10 (d, J=10.8 Hz, 1H), 3.46-3.48 (m, 1H), 3.80-4.00 (m, 1H), 4.05-4.55 (m, 5H), 5.21 (d, J=17.2 Hz, 1H), 5.42 (d, J=53.2 Hz, 1H), 5.58 (s, 1H), 6.99-7.07 (m, 1H), 7.15-7.45

(m, 4H), 8.15 (s, 2H), 8.27 (s, 1H), 8.59 (t, J=5.6 Hz, 1H). LC (method 1): tR=1.76 min. LC/MS (APCI) m/z: [M+H]+ 597.

3-acetyl-1-(2-((2S,4R)-2-((3-chloro-2-fluorobenzyl)carbamoyl)-4-fluoropyrrolidin-1-yl)-2-oxoethyl)-N-(phenylsulfonyl)-1H-indole-6-carboxamide (53)

1-(2-((2S,4R)-2-((2'-Chloro-2-fluoro-[1,1'-biphenyl]-3-yl)carbamoyl)-4-fluoropyrrolidin-1-yl)-2-oxoethyl)-5-pivalamido-1H-pyrazolo[3,4-d]thiazole-3-carboxamide (55)

Scheme 35.

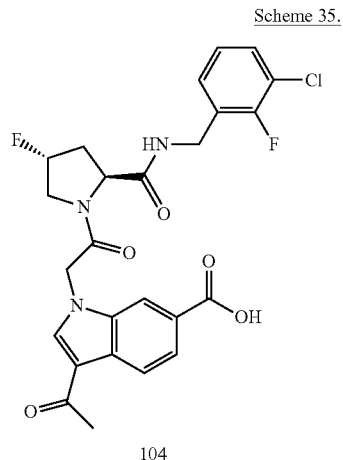

Scheme 36.

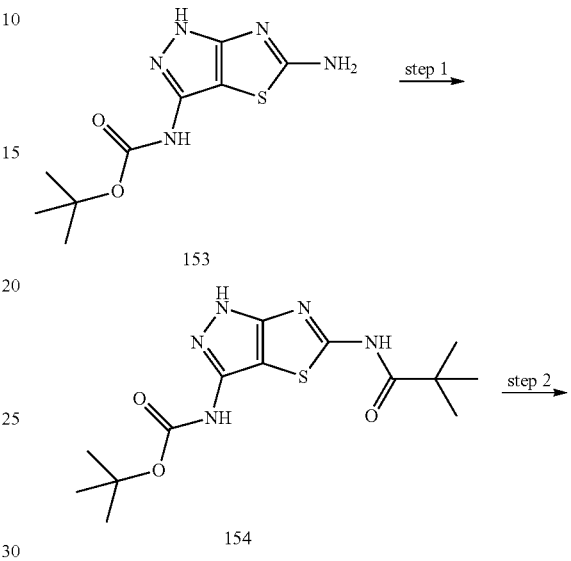

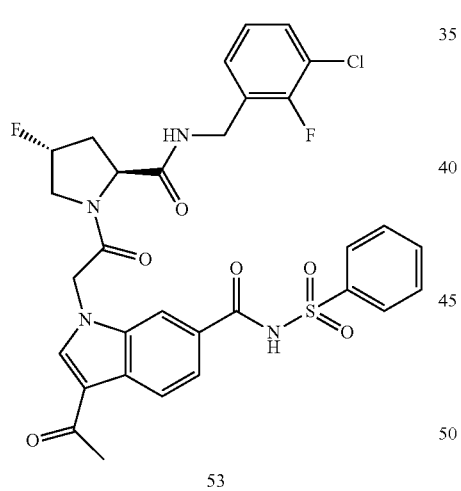

Compound 53 was prepared from 3-acetyl-1-(2-((2S,4R)-2-((3-chloro-2-fluorobenzyl)carbamoyl)-4-fluoropyrrolidin-1-yl)-2-oxoethyl)-1H-indole-6-carboxylic acid (104, 518 mg) and benzenesulfonamide (786 mg) using HATU as a coupling agent to afford compound 53 following procedures described in Scheme 11.

$^1$H NMR (400 MHz, CD$_3$OD): (major rotamer) δ2.06-2.25 (m, 1H), 2.41 (s, 3H), 2.51-2.59 (m, 1H), 3.82-4.15 (2H), 4.32 (m, 2H), 4.49 (m, 1H), 5.13-5.45 (m, 3H), 6.62 (t, J=7.0 Hz, 1H), 7.15 (dt, J=6.4 Hz, J=7.0 Hz 2H), 7.45 (t, 2H), 7.55 (m, 2H), 7.82 (d, 2H), 7.88 (s, 1H), 8.25 (m, 2H), 8.59 (t, J=5.6 Hz, 1H). LC (method 1): tR=1.71 min. LC/MS (EI) m/z: [M+H]+ 657.

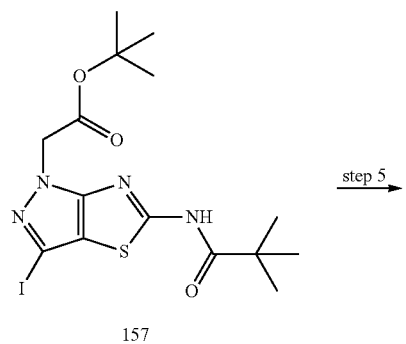

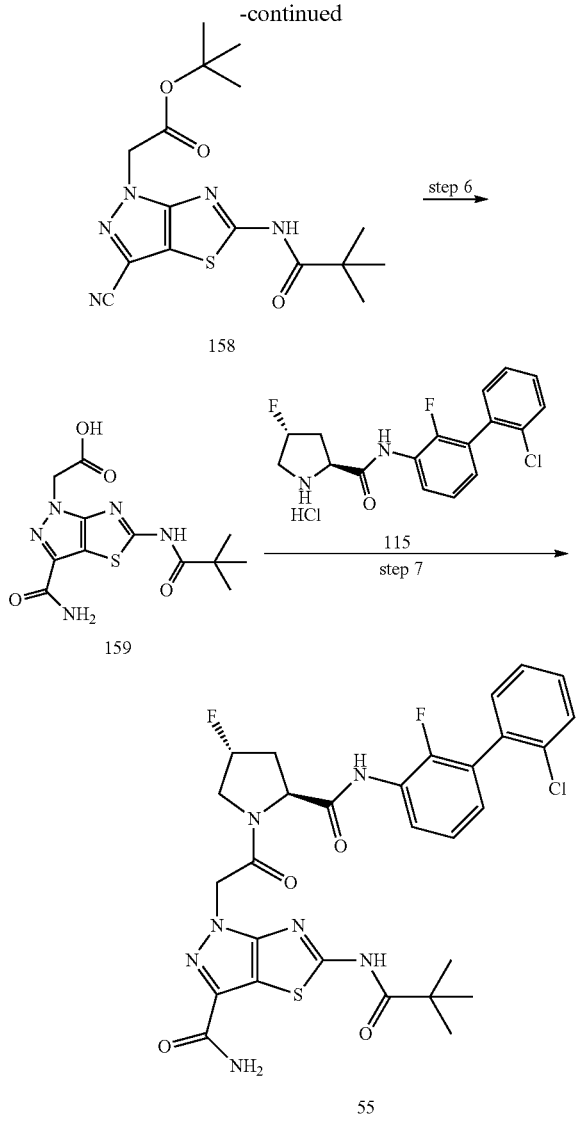

Step 1: tert-Butyl (5-pivalamido-1H-pyrazolo[3,4-d]thiazol-3-yl)carbamate (154)

tert-Butyl (5-amino-1H-pyrazolo[3,4-d]thiazol-3-yl)carbamate (1.19 g, 4.67 mmol) in THF (25 mL) was treated with pivaloyl chloride (2.89 mL, 23.35 mmol) in the presence of pyridine (2.26 mL, 28 mmol) at 70° C. for 2 h. DMEDA (2.56 mL, 23.35 mmol) was added and the mixture was stirred at 70° C. overnight. The solvent was removed by evaporation, and the residue was treated with 5% aq. citric acid (100 mL). The formed solid was collected by filtration, washed with water, and dried under vacuum to afford tert-butyl (5-pivalamido-1H-pyrazolo[3,4-d]thiazol-3-yl)carbamate (1.53 g).

Step 2: N-(3-Amino-1H-pyrazolo[3,4-d]thiazol-5-yl)pivalamide hydrochloride (155)

tert-Butyl (5-pivalamido-1H-pyrazolo[3,4-d]thiazol-3-yl)carbamate (1.53 g, 4.5 mmol) was treated with TFA (15 mL) in DCM (30 mL) at room temperature for 1 h. After the volatiles are removed under reduced pressure, the residue was co-evaporated with HCl/dioxane (4 N, 10 mL) and dried under vacuum to afford N-(3-amino-1H-pyrazolo[3,4-d]thiazol-5-yl)pivalamide hydrochloride (1.78 g) as a solid.

Step 3: N-(3-Iodo-1H-pyrazolo[3,4-d]thiazol-5-yl)pivalamide (156)

N-(3-Amino-1H-pyrazolo[3,4-d]thiazol-5-yl)pivalamide hydrochloride (1.78 g) suspended in $H_2SO_4$ (1 N, 40 mL) was treated with $NaNO_2$ (0.47 g, 6.75 mmol) in water (1 mL) at 0° C. After stirring for 10 min, KI (3.74 g, 22.5 mmol) was carefully added. The dark mixture was stirred at room temperature for 2 h. $Na_2SO_3$ (2.5 g) was added with stirring. The mixture was adjusted to pH 8-9 and extracted with EtOAc (100 mL×2). After washing the organic layer with brine and drying over anhydrous $Na_2SO_4$, the solvent was removed by evaporation to afford N-(3-iodo-1H-pyrazolo[3,4-d]thiazol-5-yl)pivalamide (1.41 g) as a brown powder.

Step 4: tert-Butyl 2-(3-iodo-5-pivalamido-1H-pyrazolo[3,4-d]thiazol-1-yl)acetate (157)

A mixture of N-(3-iodo-1H-pyrazolo[3,4-d]thiazol-5-yl)pivalamide (1.41 g, 4.03 mmol), tert-butyl 2-bromoacetate (0.62 mL, 4.23 mmol) and $K_2CO_3$ was refluxed in acetonitrile (40 mL) for 4 h. The mixture was filtered and the filtrate was concentrated under reduced pressure. The remaining residue was purified by column chromatography (silica gel, hexanes/EtOAc=1:1) to afford tert-butyl 2-(3-iodo-5-pivalamido-1H-pyrazolo[3,4-d]thiazol-1-yl)acetate (0.706 g).

Step 5: tert-Butyl 2-(3-cyano-5-pivalamido-1H-pyrazolo[3,4-d]thiazol-1-yl)acetate (158)

Into an argon-purged solution of tert-butyl 2-(3-iodo-5-pivalamido-1H-pyrazolo[3,4-d]thiazol-1-yl)acetate (0.706 g, 1.52 mmol) and DMF-water (15 mL/1.5 mL) was added $Zn(CN)_2$ (0.267 g, 2.28 mmol) followed by $Pd(dppf)_2$ (0.124 g, 0.152 mmol) and $Pd_2(dba)_3$ (0.139 g, 0.152 mmol). The mixture was stirred at 90° C. for 4 h. EtOAc (50 mL) was added and the mixture was filtered through a pad of Celite®. The filtrate was concentrated under reduced pressure and the remaining residue was purified by column chromatography (silica gel, 40% EtOAc in hexanes) to afford tert-butyl 2-(3-cyano-5-pivalamido-1H-pyrazolo[3,4-d]thiazol-1-yl)acetate (0.25 g) as a solid.

Step 6: 2-(3-Carbamoyl-5-pivalamido-1H-pyrazolo[3,4-d]thiazol-1-yl)acetic acid (159)

tert-Butyl 2-(3-cyano-5-pivalamido-1H-pyrazolo[3,4-d]thiazol-1-yl)acetate (51 mg, 0.14 mmol) in TFA (1.5 mL) and water (5 μL) was heated with microwave irradiation at 140° C. for 30 min. The volatiles were removed by evaporation and the residue was co-evaporated with toluene (5 mL) to afford 2-(3-carbamoyl-5-pivalamido-1H-pyrazolo[3,4-d]thiazol-1-yl)acetic acid which was used directly in the next synthetic step.

Step 7: 1-(2-((2S,4R)-2-((2'-Chloro-2-fluoro-[1,1'-biphenyl]-3-yl)carbamoyl)-4-fluoropyrrolidin-1-yl)-2-oxoethyl)-5-pivalamido-1H-pyrazolo[3,4-d]thiazole-3-carboxamide (55)

A mixture of 2-(3-carbamoyl-5-pivalamido-1H-pyrazolo[3,4-d]thiazol-1-yl)acetic acid and (2S,4R)—N-(2'-chloro-2-fluoro-[1,1'-biphenyl]-3-yl)-4-fluoropyrrolidine-2-carboxamide hydrochloride (57.5 mg, 0.154 mmol) in DMF was treated with TBTU (67.4 mg, 0.321 mmol) followed by DIEA (0.122 mL, 0.7 mmol) and the reaction was stirred at room temperature overnight. The reaction mixture was purified by HPLC to afford 1-(2-((2S,4R)-2-((2'-chloro-2-fluoro-[1,1'-biphenyl]-3-yl)carbamoyl)-4-fluoropyrrolidin-1-yl)-2-oxoethyl)-5-pivalamido-1H-pyrazolo[3,4-d]thiazole-3-carboxamide (62 mg).

$^1$H NMR (400 MHz, MeOD): (major rotamer) δ 1.29 (s, 9H), 2.29-2.41 (m, 1H), 2.67-2.72 (m, 1H), 3.94 (ddd, J=35.8, 12.6, 3.2 Hz, 1H), 4.18 (dd, J=19.8, 12 Hz, 1H), 5.34 (dd J=34, 16.8 Hz, 2H), 5.46 (d, J=52.4 Hz, 1H), 7.03-7.07 (m, 1H), 7.13 (t, J=7.6 Hz, 1H), 7.18-7.38 (m, 3H), 7.45-7.48 (m, 1H), 7.96-7.99 (m, 1H). $^{19}$F NMR (376 MHz, MeOD): δ−128.50, −177.98. LC (method A): $t_R$=2.20 min. LC/MS (EI) m/z: [M+H]$^+$ 644.

1-(2-((2S,4R)-2-((3-Chloro-2-fluorobenzyl)carbamoyl)-4-fluoropyrrolidin-1-yl)-2-oxoethyl)-5-pivalamido-1H-pyrazolo[3,4-d]thiazole-3-carboxamide (56)

Scheme 37.

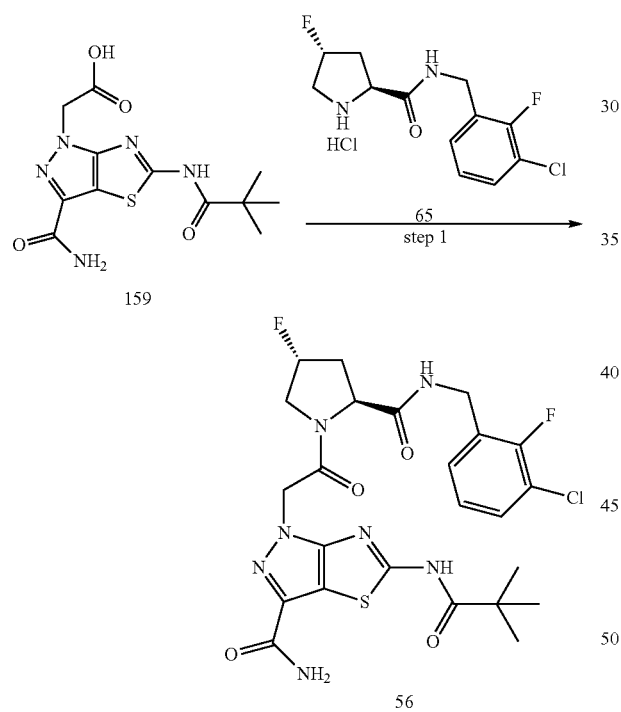

A mixture of 2-(3-carbamoyl-5-pivalamido-1H-pyrazolo[3,4-d]thiazol-1-yl)acetic acid, 159, (0.145 mmol) and (2S,4R)—N-(3-chloro-2-fluorobenzyl)-4-fluoropyrrolidine-2-carboxamide hydrochloride (65) (50 mg, 0.16 mmol) in DMF was treated with TBTU (70 mg, 0.22 mmol) followed by DIEA (0.126 mL, 0.725 mmol) at room temperature for 2 h. The reaction mixture was purified by HPLC to afford 1-(2-((2S,4R)-2-((3-chloro-2-fluorobenzyl)carbamoyl)-4-fluoropyrrolidin-1-yl)-2-oxoethyl)-5-pivalamido-1H-pyrazolo[3,4-d]thiazole-3-carboxamide, 56, (41 mg).

$^1$H NMR (400 MHz, MeOD): (major rotamer) δ 1.32 (s, 9H), 2.15-2.32 (m, 1H), 2.55-2.67 (m, 1H), 3.89 (ddd, J=35.4, 12.0, 2.8 Hz, 1H), 4.08 (dd, J=20.2, 12 Hz, 1H), 4.44-4.48 (m, 2H), 5.21-5.30 (m 2H), 5.41 (d, J=52 Hz, 1H), 6.93 (t, J=8 Hz, 1H), 7.20-7.40 (m, 3H), 8.49 (t, J=5.6 Hz, 1H). $^{19}$F NMR (376 MHz, MeOD): δ−121.99, −177.63. LC (method A): $t_R$=1.77 min. LC/MS (EI) m/z: [M+H]+ 582.

1-(2-((2S,4R)-2-((2'-Chloro-2-fluoro-[1,1'-biphenyl]-3-yl)carbamoyl)-4-fluoropyrrolidin-1-yl)-2-oxoethyl)-N5-cyclopropyl-1H-thieno[3,2-c]pyrazole-3,5-dicarboxamide (57)

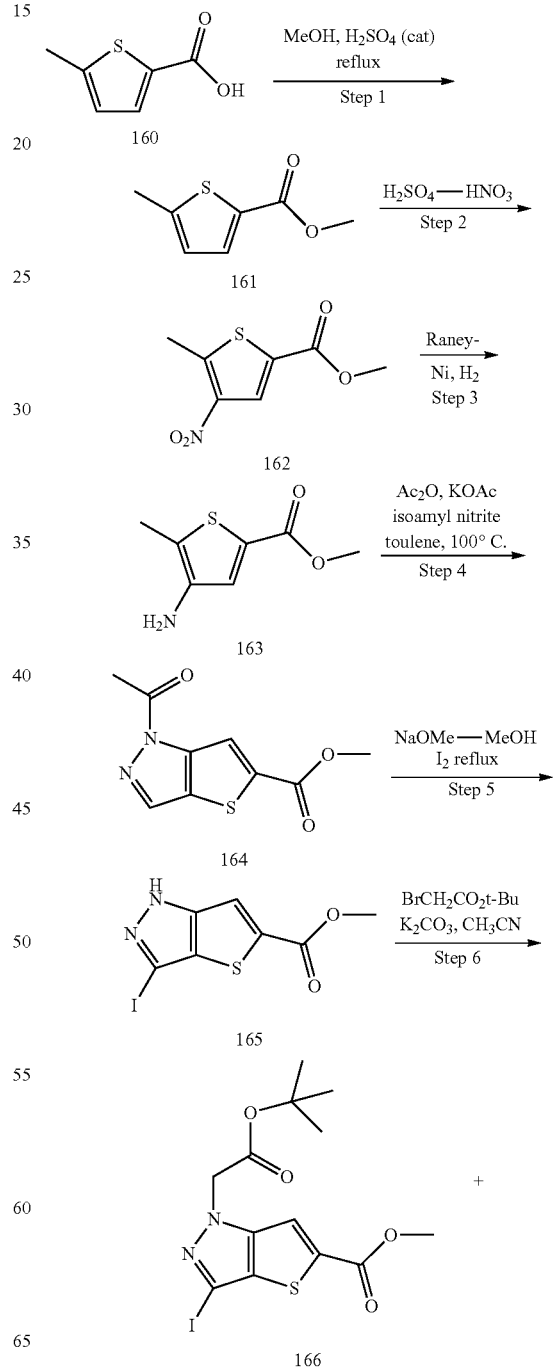

-continued

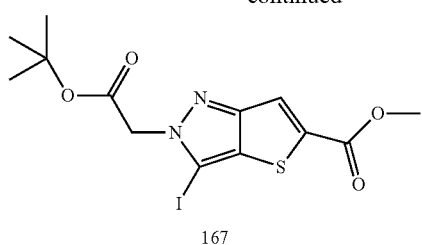
167

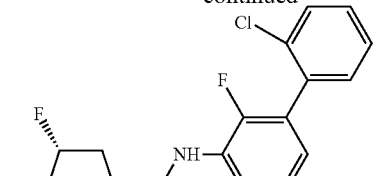

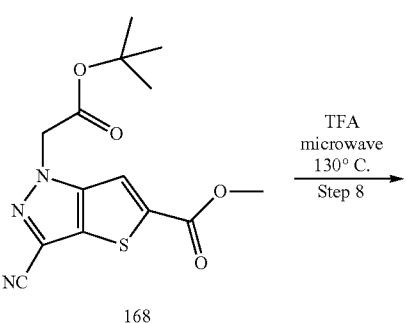
168

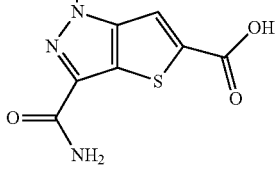

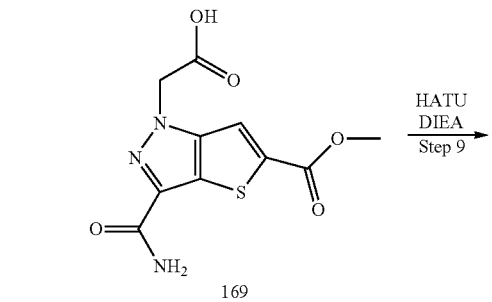
169

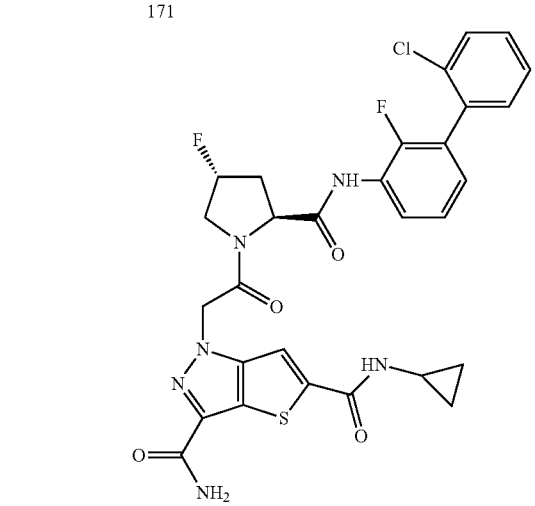
171

57

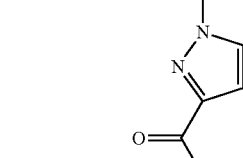

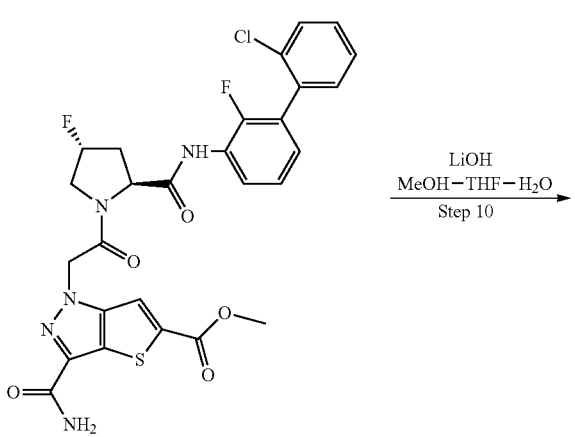
170

Step 1: Methyl 5-methylthiophene-2-carboxylate (161)

To a solution of 5-methylthiophene-2-carboxylic acid (25 g, 0.176 mol) in 300 mL of anhydrous methanol was added concentrated $H_2SO_4$ (3 mL). The mixture was heated at reflux for 60 h. The reaction was cooled to rt and the solvent was removed under reduced pressure. The residue was diluted with ethyl acetate (200 mL) and quenched carefully with saturated aq. sodium bicarbonate (adjust pH>7). The organic layer was collected and the aqueous phase was extracted with ethyl acetate twice. The combined organic solution was washed with brine, dried over $MgSO_4$, and filtered. The filtrate was concentrated to afford 25.8 g of the title compound as a pale yellow oil. LC (method A): $t_R$=1.70 min. LC/MS (EI) m/z: $[M+H]^+$ 156.9.

Step 2: Methyl 5-methyl-4-nitrothiophene-2-carboxylate (162)

Methyl 5-methylthiophene-2-carboxylate (25.8 g) was dissolved in 50 mL of cold concentrated sulfuric acid and the mixture was kept cold in an ice bath. To this solution, a prepared solution of fuming nitric acid (14 mL) and concentrated sulfuric acid (40 mL) was added dropwise. After completion of the addition, the mixture was stirred for an additional 15 min at 0° C. The reaction mixture was poured carefully into crushed ice and the solid was collected by filtration, washed with water, and dried. The desired product (24.3 g) was used directly in the next synthetic step.

$^1$H NMR (400 MHz, CDCl$_3$): (major isomer) δ: 2.84 (s, 3H), 3.91 (s, 3H), 8.20 (s, 1H) ppm. LC (method A): t$_R$=1.73 min. LC/MS (EI) m/z: [M+H]$^+$ 202.3.

Step 3: Methyl 4-amino-5-methylthiophene-2-carboxylate (163)

Methyl 5-methyl-4-nitrothiophene-2-carboxylate (24.3 g) was dissolved in a mixture of THF (100 mL) and methanol (100 mL) and then to this solution was added wet Raney Ni. The solution was degassed, refilled with hydrogen, and stirred over an atmosphere of hydrogen overnight. The mixture was filtered through a pad of Celite® and concentrated to afford the title product (17.1 g), which was used directly in the next synthetic step. LC (method A): t$_R$=0.55 min. LC/MS (EI) m/z: [M+H]$^-$ 172.2.

Step 4: Methyl 1-acetyl-1H-thieno[3,2-c]pyrazole-5-carboxylate (164)

To a solution of methyl 4-amino-5-methylthiophene-2-carboxylate (17.0 g, 0.1 mol) in 150 mL of anhydrous toluene, KOAc (5.88 g, 60 mmol) was added, followed by Ac$_2$O (17.4 g, 16.1 mL, 170 mmol). The mixture was heated at 100° C. for 3 h and then cooled to room temperature. Isoamyl nitrite (12.9 g, 14.8 mL, 110 mmol) was added and the reaction was heated at 120° C. for 3 h. The reaction was cooled to rt, diluted with ethyl acetate, and filtered. The filtrate was concentrated. The black solid residue was purified to afford the title product.

$^1$H NMR (400 MHz, CDCl$_3$): (major isomer) δ: 2.75 (s, 3H), 3.95 (s, 3H), 7.94 (s, 1H), 8.22 (s, 1H) ppm. LC (method A): t$_R$=1.61 min. LC/MS (EI) m/z: [M+H]$^-$ 225.0.

Step 5: Methyl 3-iodo-1H-thieno[3,2-c]pyrazole-5-carboxylate (165)

To a mixture of methyl 1-acetyl-1H-thieno[3,2-c]pyrazole-5-carboxylate (1.12 g, 5 mmol) in anhydrous methanol (20 mL) was added sodium methoxide (25% in methanol, 3 mL). The mixture was heated at 60° C. for 20 min. The solution was cooled to rt, then iodine (1.4 g, 5.5 mmol) was added in one portion. The mixture was heated at 60° C. for 2 h, then cooled to rt. The volatiles were removed under reduced pressure, and the remaining residue was used in the next synthetic step without further purification.

Step 6: Methyl 1-(2-(tert-butoxy)-2-oxoethyl)-3-iodo-1H-thieno[3,2-c]pyrazole-5-carboxylate (166)

To a solution of methyl 3-iodo-1H-thieno[3,2-c]pyrazole-5-carboxylate in 30 mL CH$_3$CN was added tert-butyl 2-bromoacetate (0.8 mL, 5.5 mmol) and solid potassium carbonate (1.5 g, 10.6 mmol). The mixture was heated at reflux overnight under an atmosphere of argon. LC-MS analysis indicated two isomers were formed in a ratio of 7:3. The reaction mixture was cooled to rt and filtered through a pad of Celite®. The solid cake was washed with CH$_3$CN (20 mL) and the combined filtrates were concentrated. The remaining residue was purified to afford pure separated major (1.08 g) and minor isomers.

$^1$H NMR (400 MHz, CDCl$_3$): (major isomer) δ: 1.46 (s, 9H), 3.93 (s, 3H), 4.96 (s, 2H), 7.67 (s, 1H) ppm. LC/MS tR=2.63 min, [M+H]$^+$ 422.91. $^1$H NMR (400 MHz, CDCl$_3$): (minor isomer) δ: 1.48 (s, 9H), 3.93 (s, 3H), 5.07 (s, 2H), 7.90 (s, 1H) ppm. LC (method A): t$_R$=2.47 min. LC/MS (EI) m/z: [M+H]$^+$ 423.0.

Step 7: Methyl 1-(2-(tert-butoxy)-2-oxoethyl)-3-cyano-1H-thieno[3,2-c]pyrazole-5-carboxylate (167)

To a degassed solution of methyl 1-(2-(tert-butoxy)-2-oxoethyl)-3-iodo-1H-thieno[3,2-c]pyrazole-5-carboxylate (1.08 g, 2.56 mmol) in DMF (25 mL) and water (3 mL) was added Zn(CN)$_2$ (364 mg, 3.07 mmol), Pd(dppf)$_2$Cl$_2$ (212 mg, 0.26 mmol) and Pd$_2$(dba)$_3$ (238 mg, 0.26 mmol) under argon. The mixture was heated at 100° C. overnight. The reaction was then cooled to rt and the volatiles were evaporated under reduced pressure. The residue was diluted with ethyl acetate (50 mL) and filtered through a pad of Celite®. The collected solid was washed with ethyl acetate (30 mL). The combined filtrates were concentrated and the remaining residue was purified to afford 364 mg of the title compound (168).

$^1$H NMR (400 MHz, CDCl$_3$) δ:1.48 (s, 9H), 3.95 (s, 3H), 5.03 (s, 2H), 7.67 (s, 1H) ppm. LC (method A): t$_R$=2.37 min. LC/MS (EI) m/z: [M+H]$^+$ 266.0.

Step 8: 2-(3-Carbamoyl-5-(methoxycarbonyl)-1H-thieno[3,2-c]pyrazol-1-yl)acetic acid (169)

A solution of methyl 1-(2-(tert-butoxy)-2-oxoethyl)-3-cyano-1H-thieno[3,2-c]pyrazole-5-carboxylate (120 mg, 0.37 mmol) in TFA (1.5 mL) and water (0.3 mL) was subjected to microwave irradiation at 130° C. for 30 min. The mixture was concentrated in vacuo and the residue was co-evaporated with toluene (10 mL) twice. The dried residue was used directly in the next synthetic step. LC (method A): t$_R$=0.61 min. LC/MS (EI) m/z: [M+H]$^+$ 284.0. (169)

Step 9: Methyl 3-carbamoyl-1-(2-((2S,4R)-2-((2'-chloro-2-fluoro-[1,1'-biphenyl]-3-yl)carbamoyl)-4-fluoropyrrolidin-1-yl)-2-oxoethyl)-1H-thieno[3,2-c]pyrazole-5-carboxylate (170)

To a solution of 2-(3-carbamoyl-5-(methoxycarbonyl)-1H-thieno[3,2-c]pyrazol-1-yl)acetic acid (0.47 mmol) and (2S,4R)—N-(2'-chloro-2-fluoro-[1,1'-biphenyl]-3-yl)-4-fluoropyrrolidine-2-carboxamide hydrochloride(177 mg, 0.47 mmol) in DMF (2 mL) was added HATU (214 mg, 0.56 mmol) followed by dropwise addition of DIEA (0.5 mL) at room temperature. The mixture was stirred for 1 h at rt and the volatiles were removed under reduced pressure. The residue was diluted with 20 mL of 10% sodium carbonate and extracted with ethyl acetate (3×20 mL). The combined organic solution was successively washed with water and brine, and dried over MgSO$_4$. The mixture was filtered and the filtrate was concentrated. The remaining residue was purified to afford the title compound (167.7 mg).

$^1$H NMR (400 MHz, DMSO-d$_6$): (major rotamer) δ 2.03-2.19 (m, 1H), 2.46-2.55 (m, 1H), 3.79 (s, 3H), 3.75-3.90 (m, 1H), 4.01-4.10 (m, 1H), 4.70 (t, J=8.4 Hz, 1H), 5.34-5.59 (m, 3H), 7.01 (t, J=6.4 Hz, 1H), 7.15 (t, J=8.0 Hz, 1H), 7.30-7.52 (m, 5H), 7.69 (s, 1H), 7.89-7.94 (m, 2H), 9.92 (s, 1H) ppm; $^{19}$F NMR (376 MHz, DMSO-d$_6$): (major rotamer) δ −126.79, −175.78. LC (method A): t$_R$=2.10 min. LC/MS (EI) m/z: [M+H]$^+$ 602.2.

Step 10: 3-Carbamoyl-1-(2-((2S,4R)-2-((2'-chloro-2-fluoro-[1,1'-biphenyl]-3-yl)carbamoyl)-4-fluoropyrrolidin-1-yl)-2-oxoethyl)-1H-thieno[3,2-c]pyrazole-5-carboxylic acid (171)

The compound from Step 9 (110 mg, 0.18 mmol) was dissolved in a mixture of CH$_3$OH-THF-H$_2$O (2 mL-2 mL-2 mL) and treated with LiOH (24 mg). The reaction mixture was stirred overnight at rt. The volatiles were removed under reduce pressure and the remaining residue was acidified with 10% citric acid (10 mL). The white solid was collected, washed with water, and dried for use in the next step.
$^1$H NMR (400 MHz, DMSO-d$_6$): (major rotamer) δ 2.03-2.19 (m, 1H), 2.46-2.55 (m, 1H), 3.77-3.90 (m, 1H), 4.01-4.10 (m, 1H), 4.71 (t, J=8.4 Hz, 1H), 5.27-5.57 (m, 3H), 7.0 (t, J=6.4 Hz, 1H), 7.15 (t, J=8.0 Hz, 1H), 7.30-7.41 (m, 4H), 7.50-7.53 (m, 1H), 7.65 (s, 1H), 7.76 (s, 1H), 7.93 (t, J=7.2 Hz, 1H), 9.95 (s, 1H) ppm; $^{19}$F NMR (376 MHz, DMSO-d$_6$): (major rotamer) δ −126.81, −175.80. LC (method A): t$_R$=1.78 min. LC/MS (EI) m/z: [M+H]$^+$ 588.

Step 11: 1-(2-((2S,4R)-2-((2'-Chloro-2-fluoro-[1,1'-biphenyl]-3-yl)carbamoyl)-4-fluoropyrrolidin-1-yl)-2-oxoethyl)-N5-cyclopropyl-1H-thieno[3,2-c]pyrazole-3,5-dicarboxamide To a solution of 3-carbamoyl-1-(2-((2S,4R)-2-((2'-chloro-2-fluoro-[1,1'-biphenyl]-3-yl)carbamoyl)-4-fluoropyrrolidin-1-yl)-2-oxoethyl)-1H-thieno[3,2-c]pyrazole-5-carboxylic acid (0.1 mmol) and HATU (0.15 mmol) in DMF (1 mL) was added DIEA (0.5 mmol) dropwise. The mixture was stirred for 30 min at rt, then cyclopropanamine (0.2 mmol) was added. The mixture was stirred for an additional 30 min and the volatiles were removed under reduced pressure. The solution was subjected to preparative HPLC purification to afford 17.9 mg of the title compound (57).
$^1$H NMR (400 MHz, DMSO-d$_6$): (major rotamer) δ 0.47-0.51 (m, 2H), 0.61-0.65 (m, 2H), 2.01-2.18 (m, 1H), 2.36-2.54 (m, 1H), 2.73-2.78 (m, 1H), 3.74-3.87 (m, 1H), 4.02-4.12 (m, 1H), 4.70 (t, J=8.4 Hz, 1H), 5.24-5.55 (m, 3H), 7.0 (t, J=6.8 Hz, 1H), 7.15 (t, J=8.0 Hz, 1H), 7.30-7.40 (m, 4H), 7.50-7.52 (m, 1H), 7.62 (s, 1H), 7.67 (s, 1H), 7.91 (t, J=7.2 Hz, 1H), 8.58 (m, 1H), 9.96 (s, 1H); $^{19}$F NMR (376 MHz, DMSO-d6): (major rotamer) δ −126.86, −175.74. LC (method A): t$_R$=1.96 min. LC/MS (EI) m/z: [M+H]$^+$ 627.1.

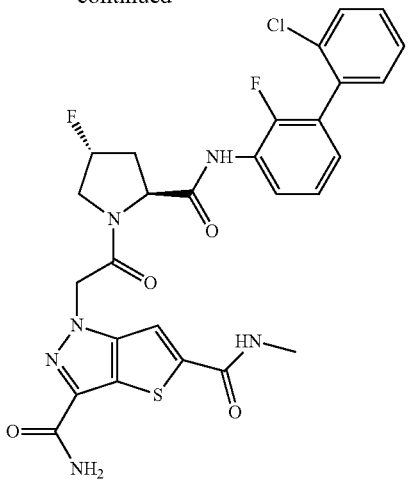

58

To a solution of 3-carbamoyl-1-(2-((2S,4R)-2-((2'-chloro-2-fluoro-[1,1'-biphenyl]-3-yl)carbamoyl)-4-fluoropyrrolidin-1-yl)-2-oxoethyl)-1H-thieno[3,2-c]pyrazole-5-carboxylic acid (0.1 mmoL) and HATU (0.15 mmol) in DMF (1 mL) was added DIEA (0.5 mmol) dropwise. The mixture was stirred for 30 min at rt, then CH$_3$NH$_2$ HCl (0.2 mmol) was added. The mixture was stirred for an additional 30 min and the volatiles are removed under reduced pressure. The remaining material was subjected to preparative HPLC purification to afford 11.4 mg of the title compound (58).
$^1$H NMR (400 MHz, DMSO-d$_6$): (major rotamer) δ 2.01-2.18 (m, 1H), 2.36-2.54 (m, 1H), 2.70 (d, J=4.4 Hz, 3H), 3.75-3.87 (m, 1H), 4.05-4.13 (m, 1H), 4.70 (t, J=8.4 Hz, 1H), 5.26-5.56 (m, 3H), 7.0 (t, J=6.8 Hz, 1H), 7.15 (t, J=8.0 Hz, 1H), 7.30-7.41 (m, 4H), 7.50-7.52 (m, 1H), 7.62 (s, 1H), 7.66 (s, 1H), 7.91 (t, J=7.2 Hz, 1H), 8.52 (m, 1H), 9.96 (s, 1H); $^{19}$F NMR (376 MHz, DMSO-d6): (major rotamer) δ −126.85, −175.81. LC (method A): t$_R$=1.82 min. LC/MS (EI) m/z: [M+H]$^+$ 601.1.

1-(2-((2S,4R)-2-((2'-Chloro-2-fluoro-[1,1'-biphenyl]-3-yl)carbamoyl)-4-fluoropyrrolidin-1-yl)-2-oxoethyl)-5-(morpholine-4-carbonyl)-1H-thieno[3,2-c]pyrazole-3-carboxamide (59)

Scheme 39

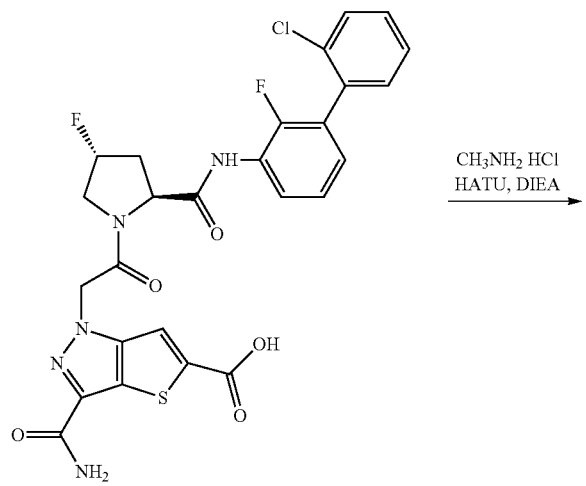

171

Scheme 40

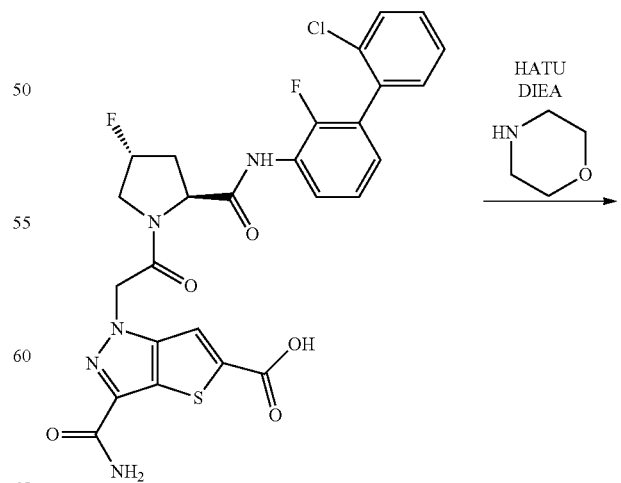

171

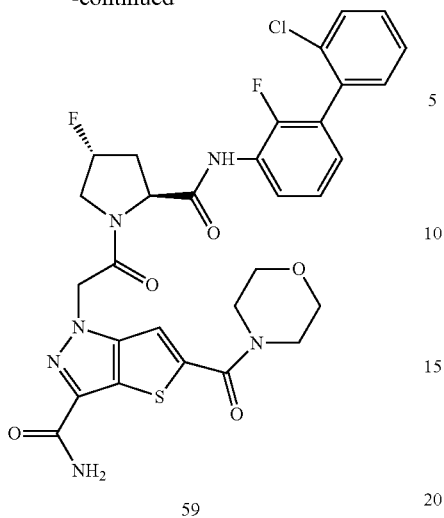

59

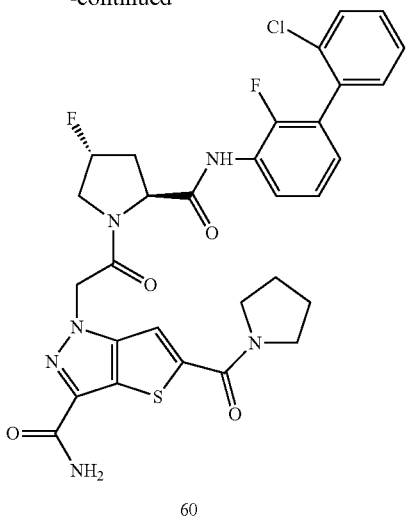

60

To a solution of 3-carbamoyl-1-(2-((2S,4R)-2-((2'-chloro-2-fluoro-[1,1'-biphenyl]-3-yl)carbamoyl)-4-fluoropyrrolidin-1-yl)-2-oxoethyl)-1H-thieno[3,2-c]pyrazole-5-carboxylic acid (0.1 mmol) and HATU (0.15 mmol) in DMF (1 mL) was added DIEA (0.5 mmol) dropwise. The mixture was stirred for 30 min at rt, then morpholine (0.2 mmol) was added. The mixture was stirred for an additional 30 min and the volatiles are removed under reduced pressure. The remaining material was subjected to preparative HPLC purification to afford 64.7 mg of the title compound (59).

$^1$H NMR (400 MHz, DMSO-d$_6$): (major rotamer) δ 2.02-2.1 (m, 1H), 2.36-2.59 (m, 1H), 3.55-3.57 (m, 8H), 3.76-3.88 (m, 1H), 4.02-4.11 (m, 1H), 4.71 (t, J=8.4 Hz, 1H), 5.30-5.53 (m, 3H), 7.0 (t, J=6.8 Hz, 1H), 7.15 (t, J=8.0 Hz, 1H), 7.31-7.43 (m, 5H), 7.51-7.53 (m, 1H), 7.64 (s, 1H), 7.89 (t, J=7.6 Hz, 1H), 9.96 (s, 1H); $^{19}$F NMR (376 MHz, DMSO-d6): (major rotamer) δ −126.75, −175.70. LC (method A): t$_R$=1.88 min. LC/MS (EI) m/z: [M+H]$^+$ 657.0.

1-(2-((2S,4R)-2-((2'-Chloro-2-fluoro-[1,1'-biphenyl]-3-yl)carbamoyl)-4-fluoropyrrolidin-1-yl)-2-oxoethyl)-N5-cyclopentyl-1H-thieno[3,2-c]pyrazole-3,5-dicarboxamide (60)

Scheme 41.

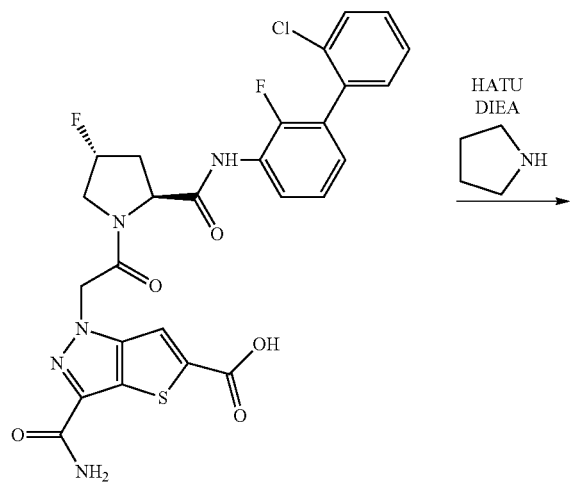

171

To a solution of 3-carbamoyl-1-(2-((2S,4R)-2-((2'-chloro-2-fluoro-[1,1'-biphenyl]-3-yl)carbamoyl)-4-fluoropyrrolidin-1-yl)-2-oxoethyl)-1H-thieno[3,2-c]pyrazole-5-carboxylic acid (0.1 mmol) and HATU (0.15 mmol) in DMF (1 mL) was added DIEA (0.5 mmol) dropwise. The mixture was stirred for 30 min at rt, then pyrrolidine (0.2 mmol) was added. The mixture was stirred for an additional 30 min and the volatiles are removed under reduced pressure. The remaining material was subjected to preparative HPLC purification to afford 55.9 mg of the title compound (60).

$^1$H NMR (400 MHz, DMSO-d$_6$): (major rotamer) δ 1.72-1.91 (m, 4H), 2.02-2.19 (m, 1H), 2.36-2.57 (m, 1H), 3.43 (br, 2H), 3.68 (br, 2H), 3.75-3.88 (m, 1H), 4.02-4.10 (m, 1H), 4.72 (t, J=8.4 Hz, 1H), 5.32-5.53 (m, 3H), 7.0 (t, J=6.8 Hz, 1H), 7.15 (t, J=8.0 Hz, 1H), 7.31-7.43 (m, 4H), 7.51-7.53 (m, 1H), 7.61-7.62 (m, 2H), 7.90 (t, J=7.6 Hz, 1H), 9.95 (s, 1H); $^{19}$F NMR (376 MHz, DMSO-d6): (major rotamer) δ −126.78, −175.67. LC (method A): t$_R$=2.01 min. LC/MS (EI) m/z: [M+H]$^+$ 641.0

1-(2-((2S,4R)-2-((2'-Chloro-2-fluoro-[1,1'-biphenyl]-3-yl)carbamoyl)-4-fluoropyrrolidin-1-yl)-2-oxoethyl)-N5-cyclopentyl-1H-thieno[3,2-c]pyrazole-3,5-dicarboxamide (61)

Scheme 42.

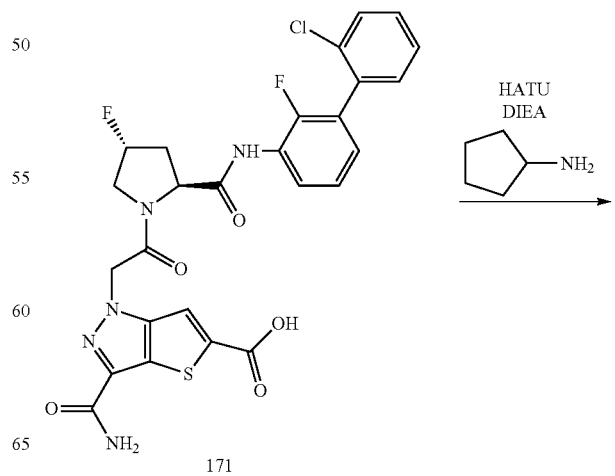

171

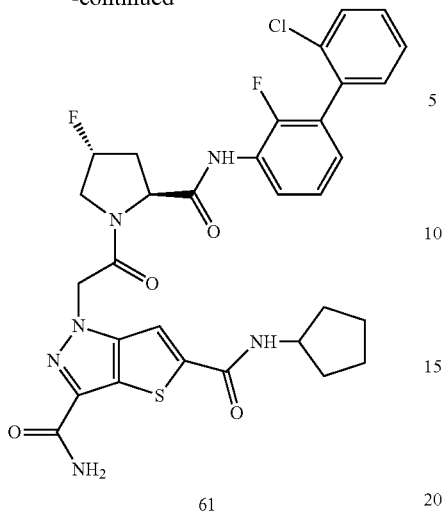

61

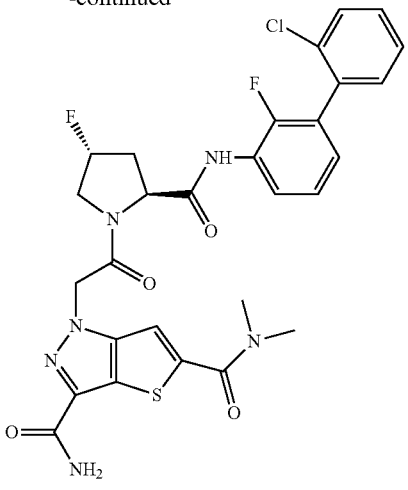

62

To a solution of 3-carbamoyl-1-(2-((2S,4R)-2-((2'-chloro-2-fluoro-[1,1'-biphenyl]-3-yl)carbamoyl)-4-fluoropyrrolidin-1-yl)-2-oxoethyl)-1H-thieno[3,2-c]pyrazole-5-carboxylic acid (0.1 mmol) and HATU (0.15 mmol) in DMF (1 mL) was added DIEA (0.5 mmol) dropwise. The mixture was stirred for 30 min at rt, then cyclopentanamine (0.2 mmol) was added. The mixture was stirred for an additional 30 min and the volatiles are removed under reduced pressure. The remaining material was subjected to preparative HPLC purification to afford 21.6 mg of the title compound (61).

$^1$H NMR (400 MHz, DMSO-d$_6$): (major rotamer) δ 1.41-1.52 (m, 4H), 1.57-1.68 (m, 2H), 1.77-1.87 (m, 2H), 2.01-2.18 (m, 1H), 2.36-2.54 (m, 1H), 3.74-3.87 (m, 1H), 4.04-4.15 (m, 1H), 4.70 (t, J=8.4 Hz, 1H), 5.24-5.57 (m, 3H), 7.0 (t, J=6.8 Hz, 1H), 7.14 (t, J=8.0 Hz, 1H), 7.30-7.42 (m, 4H), 7.50-7.54 (m, 1H), 7.62 (s, 1H), 7.77 (s, 1H), 7.91 (t, J=7.2 Hz, 1H), 8.45 (m, 1H), 9.97 (s, 1H); $^{19}$F NMR (376 MHz, DMSO-d6): (major rotamer) δ −126.86, −175.67. LC (method A): $t_R$=2.27 min. LC/MS (EI) m/z: [M+H]$^+$ 655.2.

1-(2-((2S,4R)-2-((2'-Chloro-2-fluoro-[1,1'-biphenyl]-3-yl)carbamoyl)-4-fluoropyrrolidin-1-yl)-2-oxoethyl)-N5,N5-dimethyl-1H-thieno[3,2-c]pyrazole-3,5-dicarboxamide (62)

Scheme 43.

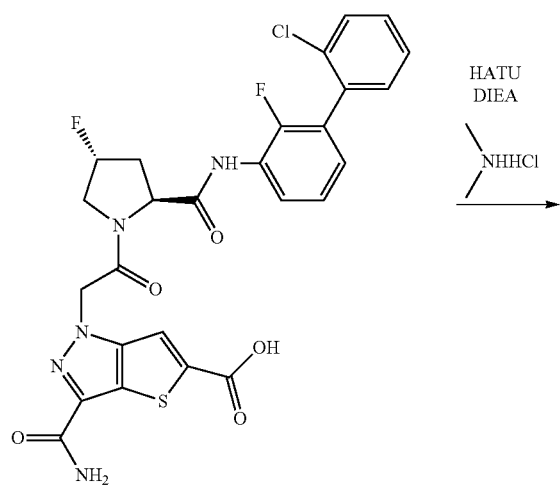

171

To a solution of 3-carbamoyl-1-(2-((2S,4R)-2-((2'-chloro-2-fluoro-[1,1'-biphenyl]-3-yl)carbamoyl)-4-fluoropyrrolidin-1-yl)-2-oxoethyl)-1H-thieno[3,2-c]pyrazole-5-carboxylic acid (0.1 mmol) and HATU (0.15 mmol) in DMF (1 mL) was added DIEA (0.5 mmol) dropwise. The mixture was stirred for 30 min at rt, then dimethylamine hydrochloride (0.2 mmol) was added. The mixture was stirred for an additional 30 min and the volatiles are removed under reduced pressure. The remaining material was subjected to preparative HPLC purification to afford 15.2 mg of the title compound (62).

$^1$H NMR (400 MHz, DMSO-d$_6$): (major rotamer) δ2.02-2.19 (m, 1H), 2.36-2.55 (m, 1H), 3.03 (s, 6H), 3.76-3.89 (m, 1H), 4.02-4.10 (m, 1H), 4.71 (t, J=8.4 Hz, 1H), 5.30-5.52 (m, 3H), 7.0 (t, J=6.8 Hz, 1H), 7.16 (t, J=8.0 Hz, 1H), 7.30-7.41 (m, 4H), 7.48 (s, 1H), 7.51-7.53 (m, 1H), 7.62 (s, 1H), 7.89 (t, J=7.2 Hz, 1H), 9.96 (s, 1H) ppm; $^{19}$F NMR (376 MHz, DMSO-d6): (major rotamer) δ −126.75, −175.72. LC (method A): $t_R$=1.89 min. LC/MS (EI) m/z: [M+H]$^+$ 615.2.

3-Acetyl-N-(cyclopropylsulfonyl)-1-(2-((2R,4R)-4-fluoro-2-(2-(phenylsulfonamido)ethyl)pyrrolidin-1-yl)-2-oxoethyl)-1H-indole-5-carboxamide (174)

Scheme 44.

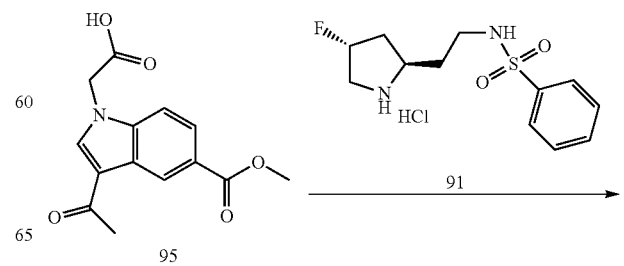

95   91

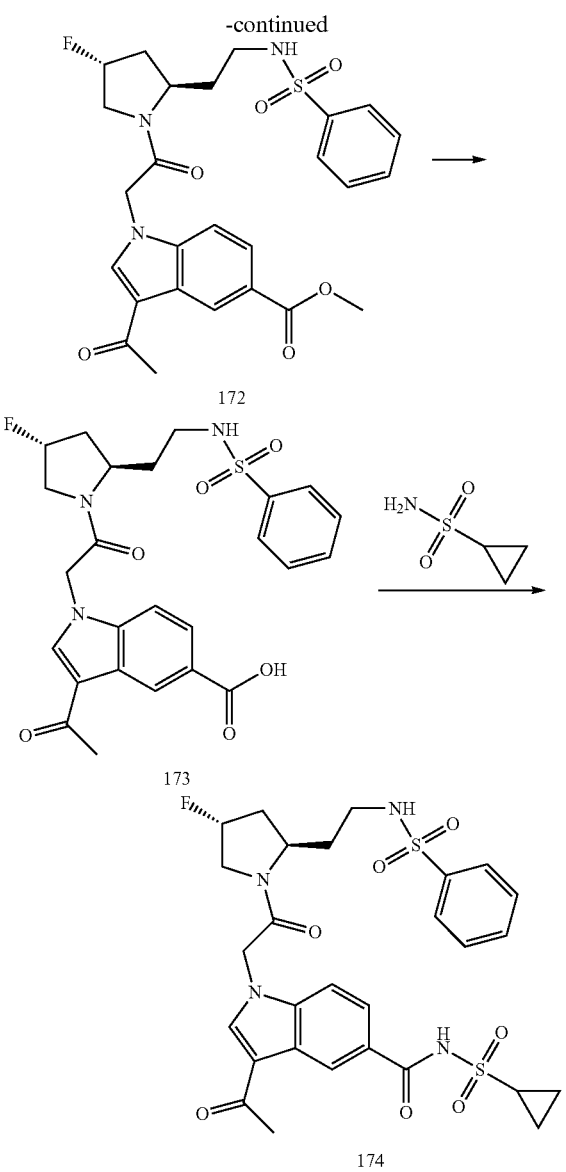

ethyl)-1H-indole-5-carboxylate. (1 equiv) in THF/water (8:2) was added LiOH (4 equiv). The reaction mixture was stirred at room temperature for 4 h and then quenched with 1 M citric acid. The resulting mixture was extracted with ethyl acetate. The organic layer was separated, dried over anhydrous Na$_2$SO$_4$, filtered and then concentrated to give methyl 3-acetyl-1-(2-((2R,4R)-4-fluoro-2-(2-(phenylsulfonamido)ethyl)pyrrolidin-1-yl)-2-oxoethyl)-1H-indole-5-carboxylate.

Step 3: 3-acetyl-N-(cyclopropylsulfonyl)-1-(2-((2R,4R)-4-fluoro-2-(2-(phenylsulfonamido)ethyl)pyrrolidin-1-yl)-2-oxoethyl)-1H-indole-5-carboxamide (173)

To a solution of methyl 3-acetyl-1-(2-((2R,4R)-4-fluoro-2-(2-(phenylsulfonamido)ethyl)pyrrolidin-1-yl)-2-oxoethyl)-1H-indole-5-carboxylate (1 equiv) in THF (10 vol) was added CDI (2 equiv). The reaction mixture was stirred at 70° C. for 4 h and then cooled to room temperature. Cyclopropylsulfonamide (2 equiv) and DBU (2.5 equiv) was added to the reaction mixture and the reaction mixture was stirred at room temperature for 16 h. After completion of the reaction, the reaction mixture was quenched with water (30 vol). The resulting mixture was extracted with DCM. The organic layer was washed with brine, dried over anhydrous Na$_2$SO$_4$, filtered and then concentrated. The residue was purified by column chromatography on silica gel using DCM/MeOH to give 3-acetyl-N-(cyclopropylsulfonyl)-1-(2-((2R,4R)-4-fluoro-2-(2-(phenylsulfonamido)ethyl)pyrrolidin-1-yl)-2-oxoethyl)-1H-indole-5-carboxamide (174).

$^1$H NMR (400 MHz, DMSO-d$_6$) δ 12.15 (s, 1H), 8.82 (s, 1H), 8.40 (s, 1H), 7.89-7.73 (m, 3H), 7.68-7.51 (m, 5H), 5.51-5.28 (m, 2H), 5.26-5.08 (m, 1H), 4.10-3.96 (m, 2H), 3.80-3.70 (m, 1H), 3.20-3.16 (m, 1H), 2.73-2.71 (m, 2H), 2.38 (s, 3H), 2.06-2.04 (m, 1H), 1.97-1.77 (m, 2H), 1.52-1.49 (m, 1H), 1.22-1.06 (m, 4H).

(2S,4R)—N-Benzyl-4-fluoropyrrolidine-2-carboxamide hydrochloride (176)

Step 1: Methyl 3-acetyl-1-(2-((2R,4R)-4-fluoro-2-(2-(phenylsulfonamido)ethyl)pyrrolidin-1-yl)-2-oxoethyl)-1H-indole-5-carboxylate To a solution of N-(2-((2R,4R)-4-fluoropyrrolidin-2-yl)ethyl)benzenesulfonamide hydrochloride (95) (1 equiv) in DMF (10 vol) at 0° C. under nitrogen atmosphere was added 91 (1.2 equiv), HATU (1.5 equiv) and DIPEA (5 equiv). The reaction mixture was stirred at room temperature for 16 h. After completion of the reaction, the reaction mixture was quenched with water (30 vol). The resulting solid was filtered and dried to give methyl 3-acetyl-1-(2-((2R,4R)-4-fluoro-2-(2-(phenyl sulfonamido)ethyl)pyrrolidin-1-yl)-2-oxoethyl)-1H-indole-5-carboxylate (172).

Step 2: 3-acetyl-1-(2-((2R,4R)-4-fluoro-2-(2-(phenylsulfonamido)ethyl)pyrrolidin-1-yl)-2-oxoethyl)-1H-indole-5-carboxylic acid (173)

To a solution of methyl 3-acetyl-1-(2-((2R,4R)-4-fluoro-2-(2-(phenylsulfonamido)ethyl)pyrrolidin-1-yl)-2-oxo- Scheme 45.

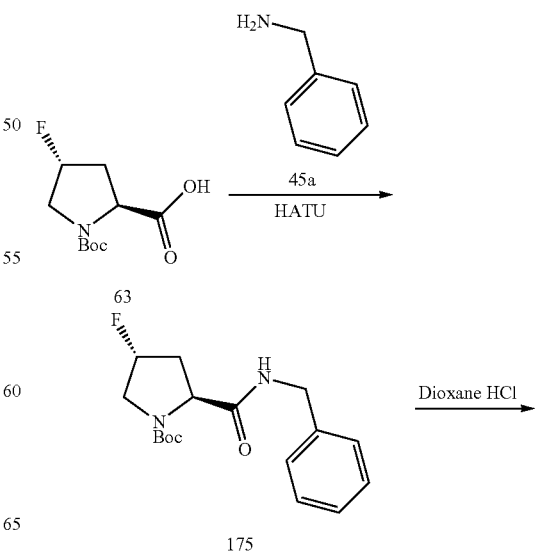

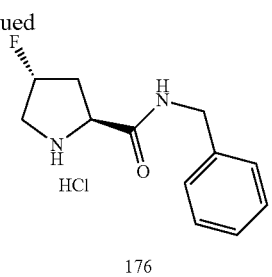

176

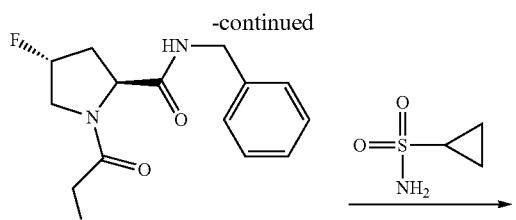

179

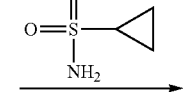

180

To a solution of 63 (1 equiv) in DMF (10 vol) at 0° C. under nitrogen atmosphere was added benzyl amine (1.2 equiv), HATU (1.5 equiv) and DIPEA (3 equiv). The reaction mixture was stirred at room temperature for 3 h. After completion of the reaction, the reaction mixture was quenched with water (30 vol). The resulting mixture was extracted with DCM. The organic layer was washed with brine, dried over anhydrous Na₂SO₄, filtered and then concentrated. The residue was purified by column chromatography on silica gel using DCM/MeOH to afford 45b. To a solution of 45b (1 equiv) in 1,4-dioxane (3 vol) at 0° C. under nitrogen atmosphere was added 4 N HCl in 1,4-dioxane (10 vol) and stirred at room temperature for 3 h. The reaction mixture was concentrated to afford 176.

3-Acetyl-1-(2-((2S,4R)-2-(benzylcarbamoyl)-4-fluoropyrrolidin-1-yl)-2-oxoethyl)-N-(cyclopropylsulfonyl)-1H-indole-5-carboxamide (180)

Scheme 46.

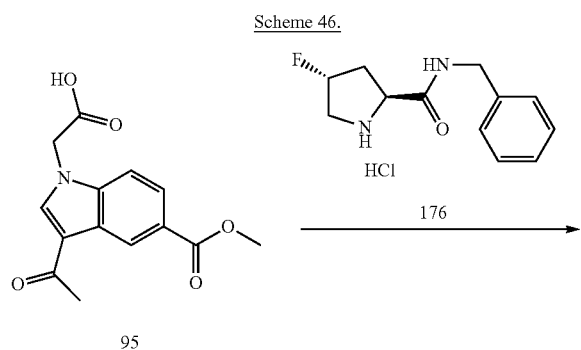

95    176

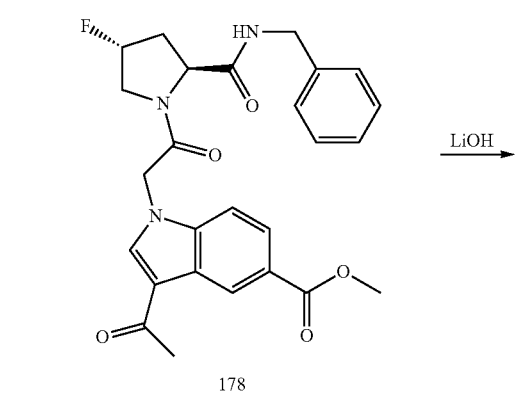

178

Step 1: Methyl 3-acetyl-1-(2-((2S,4R)-2-(benzylcarbamoyl)-4-fluoropyrrolidin-1-yl)-2-oxoethyl)-1H-indole-5-carboxylate (178)

To a solution of (2S,4R)—N-benzyl-4-fluoropyrrolidine-2-carboxamide hydrochloride (1 equiv) in DMF (10 vol) at 0° C. under nitrogen atmosphere was added Compound 176 (1.2 equiv), HATU (1.5 equiv) and DIPEA (5 equiv). The reaction mixture was stirred at room temperature for 16 h. After completion of the reaction, the reaction mixture was quenched with water (30 vol). The resulting solid was filtered, dried to give methyl 3-acetyl-1-(2-((2S,4R)-2-(benzylcarbamoyl)-4-fluoropyrrolidin-1-yl)-2-oxoethyl)-1H-indole-5-carboxylate (178).

Step 2: 3-acetyl-1-(2-((2S,4R)-2-(benzylcarbamoyl)-4-fluoropyrrolidin-1-yl)-2-oxoethyl)-1H-indole-5-carboxylic acid (179)

To a solution of methyl 3-acetyl-1-(2-((2S,4R)-2-(benzylcarbamoyl)-4-fluoropyrrolidin-1-yl)-2-oxoethyl)-1H-indole-5-carboxylate (1 equiv) in THF/water (8:2) was added LiOH (4 equiv). The reaction mixture was stirred at room temperature for 4 h and then quenched with 1 M citric acid. The resulting mixture was extracted with ethyl acetate. The organic layer was separated, dried over anhydrous Na₂SO₄, filtered and then concentrated to give 3-acetyl-1-(2-((2S,4R)-2-(benzylcarbamoyl)-4-fluoropyrrolidin-1-yl)-2-oxoethyl)-1H-indole-5-carboxylic acid.

Step 3: 3-acetyl-1-(2-((2S,4R)-2-(benzylcarbamoyl)-4-fluoropyrrolidin-1-yl)-2-oxoethyl)-N-(cyclopropylsulfonyl)-1H-indole-5-carboxamide (180)

To a solution of 3-acetyl-1-(2-((2S,4R)-2-(benzylcarbamoyl)-4-fluoropyrrolidin-1-yl)-2-oxoethyl)-1H-indole-5-carboxylic acid (1 equiv) in THF (10 vol) was added CDI (2 equiv). The reaction mixture was stirred at 70° C. for 4 h and then cooled to room temperature. Cyclopropylsulfonamide (2 equiv) and DBU (2.5 equiv) was added to the reaction mixture and the reaction mixture was stirred at room temperature for 16 h. After completion of the reaction, the reaction mixture was quenched with water (30 vol). The resulting mixture was extracted with DCM. The organic layer was washed with brine, dried over anhydrous $Na_2SO_4$, filtered and then concentrated. The residue was purified by column chromatography on silica gel using DCM/MeOH to give 3-acetyl-1-(2-(((2S,4R)-2-(benzylcarbamoyl)-4-fluoropyrrolidin-1-yl)-2-oxoethyl)-N-(cyclopropylsulfonyl)-1H-indole-5-carboxamide (180).

$^1$H NMR (400 MHz, DMSO-$d_6$) δ 8.88 (s, 1H), 8.55-8.52 (m, 1H), 8.37 (s, 1H), 7.79 (d, J=8.4 Hz, 1H), 7.58 (d, J=8.8 Hz, 1H), 7.34-7.30 (m, 1H), 7.23-7.18 (m, 4H), 5.58-5.43 (m, 2H), 5.27-5.23 (m, 1H), 4.47-4.10 (m, 4H), 4.10-3.98 (m, 1H), 3.17-3.14 (m, 1H), 2.49 (s, 3H), 2.48-2.47 (m, 1H), 2.20-2.01 (m, 1H), 1.15-1.11 (m, 4H).

(2S,4R)-4-Fluoro-N-phenethylpyrrolidine-2-carboxamide hydrochloride (182)

washed with brine, dried over anhydrous $Na_2SO_4$, filtered and then concentrated. The residue was purified by column chromatography on silica gel using DCM/MeOH to afford tert-butyl (2S,4R)-4-fluoro-2-(phenethylcarbamoyl)pyrrolidine-1-carboxylate. To a solution of tert-butyl (2S,4R)-4-fluoro-2-(phenethylcarbamoyl)pyrrolidine-1-carboxylate (1 equiv) in 1,4-dioxane (3 vol) at 0° C. under nitrogen atmosphere was added 4 N HCl in 1,4-dioxane (10 vol) and stirred at room temperature for 3 h. The reaction mixture was concentrated to afford (2S,4R)-4-fluoro-N-phenethylpyrrolidine-2-carboxamide hydrochloride (182).

3-Acetyl-N-(cyclopropylsulfonyl)-1-(2-((2S,4R)-4-fluoro-2-(phenethylcarbamoyl)pyrrolidin-1-yl)-2-oxoethyl)-1H-indole-5-carboxamide (185)

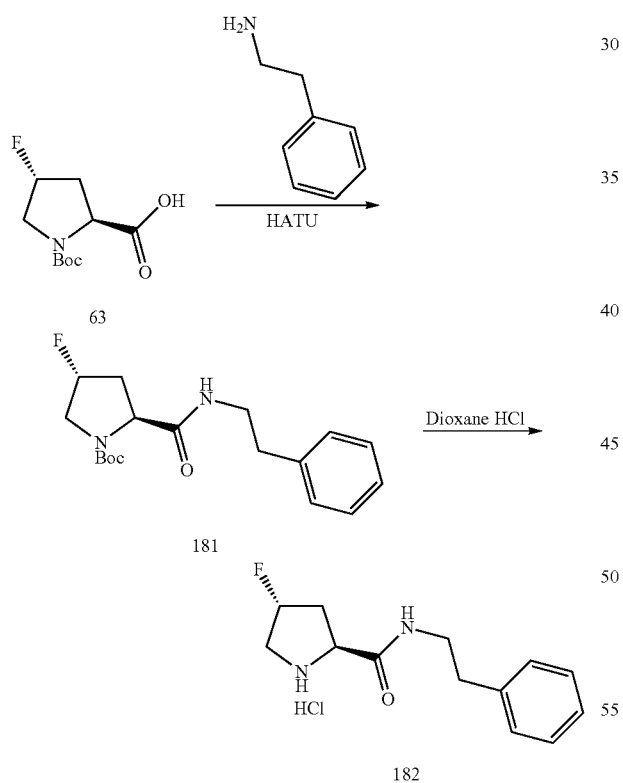

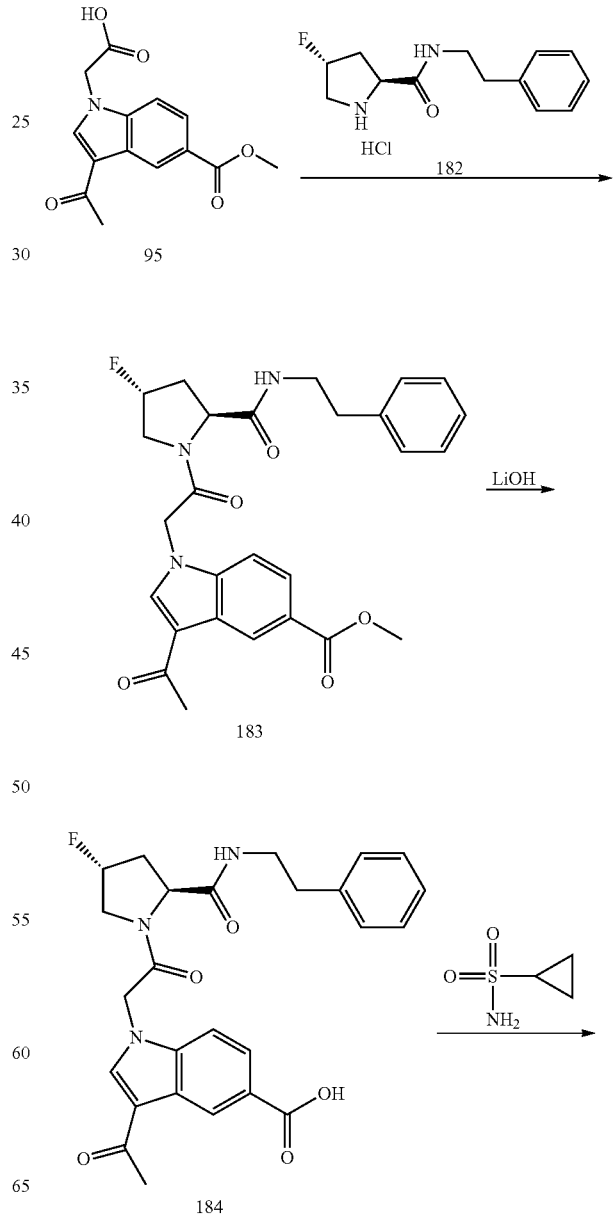

To a solution of (2S,4R)-1-(tert-butoxycarbonyl)-4-fluoropyrrolidine-2-carboxylic acid (1 equiv) in DMF (10 vol) at 0° C. under nitrogen atmosphere was added 2-phenylethan-1-amine (1.2 equiv), HATU (1.5 equiv) and DIPEA (3 equiv). The reaction mixture was stirred at room temperature for 3 h. After completion of the reaction, the reaction mixture was quenched with water (30 vol). The resulting mixture was extracted with DCM. The organic layer was -continued

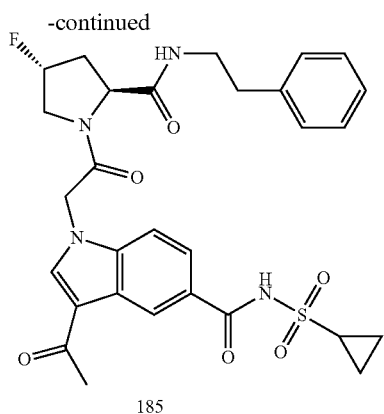

185

Step 1: Methyl 3-acetyl-1-(2-((2S,4R)-4-fluoro-2-(phenethylcarbamoyl)pyrrolidin-1-yl)-2-oxoethyl)-1H-indole-5-carboxylate (183)

To a solution of (2S,4R)-4-fluoro-N-phenethylpyrrolidine-2-carboxamide hydrochloride (1 equiv) in DMF (10 vol) at 0° C. under nitrogen atmosphere was added Compound 182 (1.2 equiv), HATU (1.5 equiv) and DIPEA (5 equiv). The reaction mixture was stirred at room temperature for 16 h. After completion of the reaction, the reaction mixture was quenched with water (30 vol). The resulting solid was filtered, dried to give methyl 3-acetyl-1-(2-((2S,4R)-4-fluoro-2-(phenethylcarbamoyl)pyrrolidin-1-yl)-2-oxoethyl)-1H-indole-5-carboxylate.

Step 2: 3-Acetyl-1-(2-((2S,4R)-4-fluoro-2-(phenethylcarbamoyl)pyrrolidin-1-yl)-2-oxoethyl)-1H-indole-5-carboxylic acid (184)

To a solution of methyl 3-acetyl-1-(2-((2S,4R)-4-fluoro-2-(phenethylcarbamoyl)pyrrolidin-1-yl)-2-oxoethyl)-1H-indole-5-carboxylate (1 equiv) in THF/water (8:2) was added LiOH (4 equiv). The reaction mixture was stirred at room temperature for 4 h and then quenched with 1 M citric acid. The resulting mixture was extracted with ethyl acetate. The organic layer was separated, dried over anhydrous Na$_2$SO$_4$, filtered and then concentrated to give 3-acetyl-1-(2-((2S,4R)-4-fluoro-2-(phenethylcarbamoyl)pyrrolidin-1-yl)-2-oxoethyl)-1H-indole-5-carboxylic acid.

Step 3: 3-acetyl-N-(cyclopropylsulfonyl)-1-(2-((2S,4R)-4-fluoro-2-(phenethylcarbamoyl)pyrrolidin-1-yl)-2-oxoethyl)-1H-indole-5-carboxamide (185)

To a solution of 3-acetyl-1-(2-((2S,4R)-4-fluoro-2-(phenethylcarbamoyl)pyrrolidin-1-yl)-2-oxoethyl)-1H-indole-5-carboxylic acid (1 equiv) in THF (10 vol) was added CDI (2 equiv). The reaction mixture was stirred at 70° C. for 4 h and then cooled to room temperature. Cyclopropylsulfonamide (2 equiv) and DBU (2.5 equiv) was added to the reaction mixture and the reaction mixture was stirred at room temperature for 16 h. After completion of the reaction, the reaction mixture was quenched with water (30 vol). The resulting mixture was extracted with DCM. The organic layer was washed with brine, dried over anhydrous Na$_2$SO$_4$, filtered and then concentrated. The residue was purified by column chromatography on silica gel using DCM/MeOH to give 3-acetyl-N-(cyclopropylsulfonyl)-1-(2-((2S,4R)-4-fluoro-2-(phenethylcarbamoyl)pyrrolidin-1-yl)-2-oxoethyl)-1H-indole-5-carboxamide.

$^1$H NMR (400 MHz, DMSO-d$_6$) δ 12.13 (s, 1H), 8.81 (s, 1H), 8.39 (s, 1H), 8.12 (d, J=5.7 Hz, 1H), 7.81 (d, J=8.7 Hz, 1H), 7.59 (d, J=8.8 Hz, 1H), 7.20-7.14 (m, 5H), 5.59-5.32 (m, 2H), 5.29-5.10 (m, 1H), 4.35 (t, J=8.5 Hz, 1H), 4.15-4.06 (m, 1H), 3.93-3.81 (m, 1H), 3.56-3.35 (m, 1H), 3.31-3.08 (m, 1H), 2.65-2.64 (m, 2H), 2.48 (s, 3H), 2.39-2.37 (m, 1H), 2.07-1.87 (m, 1H), 1.11-1.05 (m, 5H).

(2S,4R)-4-Fluoro-N-(3-phenylpropyl)pyrrolidine-2-carboxamidehydrochloride (187)

Scheme 49

To a solution of (2S,4R)-1-(tert-butoxycarbonyl)-4-fluoropyrrolidine-2-carboxylic acid (1 equiv) in DMF (10 vol) at 0° C. under nitrogen atmosphere was added 3-phenylpropan-1-amine (1.2 equiv), HATU (1.5 equiv) and DIPEA (3 equiv). The reaction mixture was stirred at room temperature for 3 h. After completion of the reaction, the reaction mixture was quenched with water (30 vol). The resulting mixture was extracted with DCM. The organic layer was washed with brine, dried over anhydrous Na$_2$SO$_4$, filtered and then concentrated. The residue was purified by column chromatography on silica gel using DCM/MeOH to afford tert-butyl (2S,4R)-4-fluoro-2-((3-phenylpropyl)carbamoyl)pyrrolidine-1-carboxylate. To a solution of tert-butyl (2S,4R)-4-fluoro-2-((3-phenylpropyl)carbamoyl)pyrrolidine-1-carboxylate (1 equiv) in 1,4-dioxane (3 vol) at 0° C. under nitrogen atmosphere was added 4 N HCl in 1,4-dioxane (10 vol) and stirred at room temperature for 3 h. The reaction mixture was concentrated to afford 2S,4R)-4-fluoro-N-(3-phenylpropyl)pyrrolidine-2-carboxamidehydrochloride (187).

3-Acetyl-N-(cyclopropylsulfonyl)-1-(2-((2S,4R)-4-fluoro-2-((3-phenylpropyl)carbamoyl)pyrrolidin-1-yl)-2-oxoethyl)-1H-indole-5-carboxamide (190)

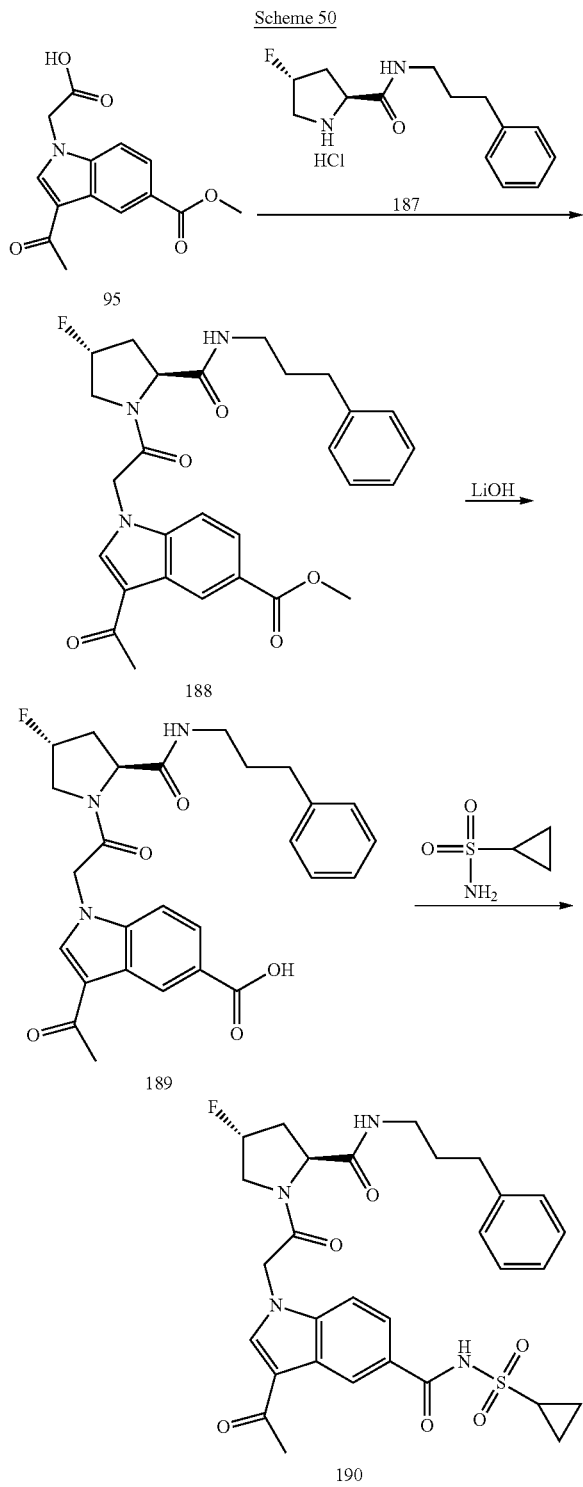

Step 1: Methyl 3-acetyl-1-(2-((2S,4R)-4-fluoro-2-((3-phenylpropyl)carbamoyl)pyrrolidin-1-yl)-2-oxoethyl)-1H-indole-5-carboxylate (188)

To a solution of (2S,4R)-4-fluoro-N-(3-phenylpropyl)pyrrolidine-2-carboxamidehydrochloride (1 equiv) in DMF (10 vol) at 0° C. under nitrogen atmosphere was added 187 (1.2 equiv), HATU (1.5 equiv) and DIPEA (5 equiv). The reaction mixture was stirred at room temperature for 16 h. After completion of the reaction, the reaction mixture was quenched with water (30 vol). The resulting solid was filtered, dried to give methyl 3-acetyl-1-(2-((2S,4R)-4-fluoro-2-((3-phenylpropyl)carbamoyl)pyrrolidin-1-yl)-2-oxoethyl)-1H-indole-5-carboxylate.

Step 2: 3-Acetyl-1-(2-((2S,4R)-4-fluoro-2-((3-phenylpropyl)carbamoyl)pyrrolidin-1-yl)-2-oxoethyl)-1H-indole-5-carboxylic acid (189)

To a solution of methyl 3-acetyl-1-(2-((2S,4R)-4-fluoro-2-((3-phenylpropyl)carbamoyl)pyrrolidin-1-yl)-2-oxoethyl)-1H-indole-5-carboxylate (1 equiv) in THF/water (8:2) was added LiOH (4 equiv). The reaction mixture was stirred at room temperature for 4 h and then quenched with 1 M citric acid. The resulting mixture was extracted with ethyl acetate. The organic layer was separated, dried over anhydrous $Na_2SO_4$, filtered and then concentrated to give 3-acetyl-1-(2-((2S,4R)-4-fluoro-2-((3-phenylpropyl)carbamoyl)pyrrolidin-1-yl)-2-oxoethyl)-1H-indole-5-carboxylic acid.

Step 3: 3-Acetyl-N-(cyclopropylsulfonyl)-1-(2-((2S,4R)-4-fluoro-2-((3-phenylpropyl)carbamoyl)pyrrolidin-1-yl)-2-oxoethyl)-1H-indole-5-carboxamide (190)

To a solution of 3-acetyl-1-(2-((2S,4R)-4-fluoro-2-((3-phenylpropyl)carbamoyl)pyrrolidin-1-yl)-2-oxoethyl)-1H-indole-5-carboxylic acid (1 equiv) in THF (10 vol) was added CDI (2 equiv). The reaction mixture was stirred at 70° C. for 4 h and then cooled to room temperature. Cyclopropylsulfonamide (2 equiv) and DBU (2.5 equiv) was added to the reaction mixture and the reaction mixture was stirred at room temperature for 16 h. After completion of the reaction, the reaction mixture was quenched with water (30 vol). The resulting mixture was extracted with DCM. The organic layer was washed with brine, dried over anhydrous $Na_2SO_4$, filtered and then concentrated. The residue was purified by column chromatography on silica gel using DCM/MeOH to give 3-acetyl-N-(cyclopropylsulfonyl)-1-(2-((2S,4R)-4-fluoro-2-((3-phenylpropyl)carbamoyl)pyrrolidin-1-yl)-2-oxoethyl)-1H-indole-5-carboxamide (190).

$^1$H NMR (400 MHz, DMSO-$d_6$) δ 12.13 (s, 1H), 8.81 (s, 1H), 8.38 (s, 1H), 8.04-8.03 (m, 1H), 7.79 (d, J=8.4 Hz, 1H), 7.61 (d, J=8.8 Hz, 1H), 7.20-7.05 (m, 5H), 5.47-5.42 (m, 2H), 5.27-5.23 (m, 1H), 4.60-4.38 (m, 2H), 4.35-3.81 (m, 3H), 3.18-3.00 (m, 3H), 2.50-2.32 (m, 3H), 2.11-1.90 (m, 2H), 1.81-1.60 (m, 2H), 1.17-1.16 (m, 4H).

205
(2S,4R)-4-Fluoro-N-(4-phenylbutyl)pyrrolidine-2-carboxamide (192)

206
3-acetyl-N-(cyclopropylsulfonyl)-1-(2-((2S,4R)-4-fluoro-2-((4-phenylbutyl)carbamoyl)pyrrolidin-1-yl)-2-oxoethyl)-1H-indole-5-carboxamide (195)

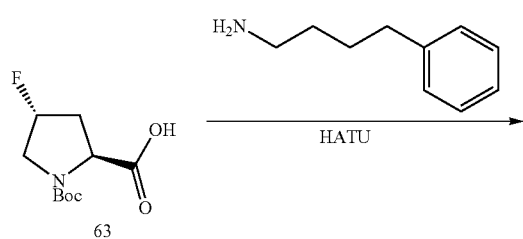

Scheme 51

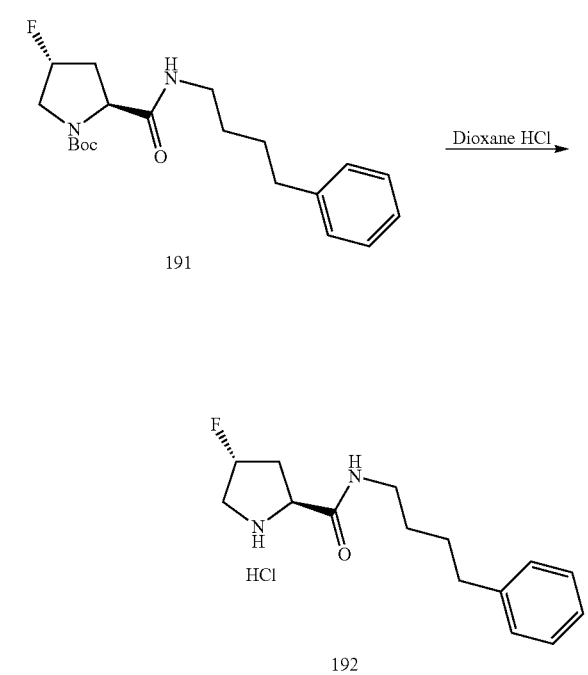

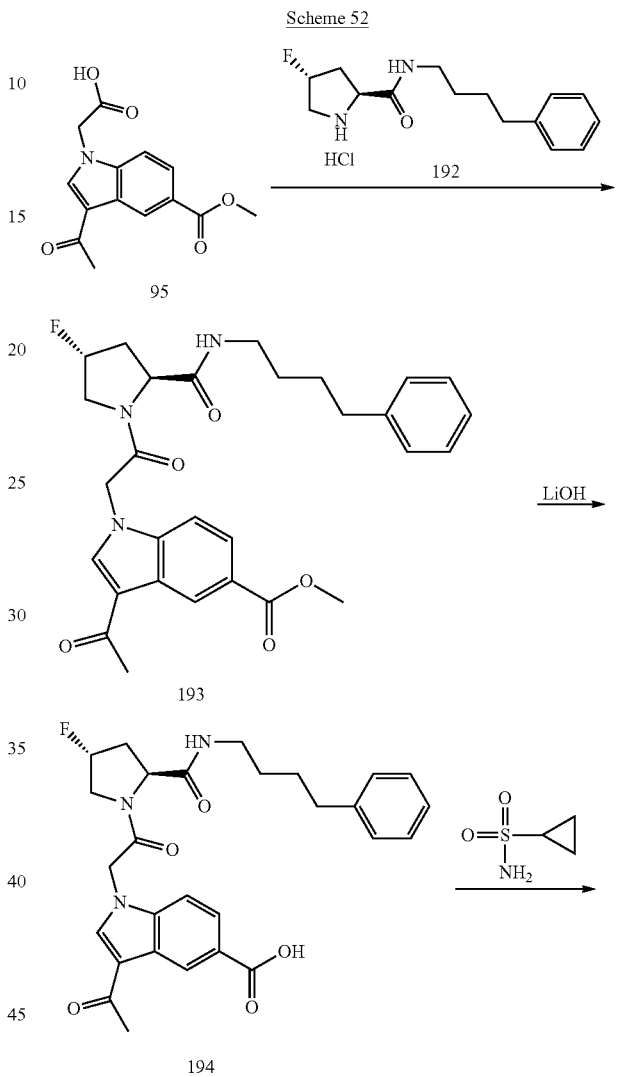

Scheme 52

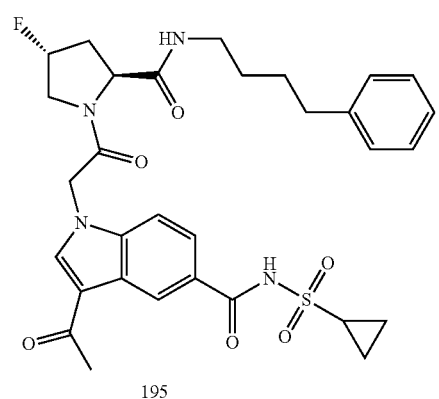

To a solution of (2S,4R)-1-(tert-butoxycarbonyl)-4-fluoropyrrolidine-2-carboxylic acid (1 equiv) in DMF (10 vol) at 0° C. under nitrogen atmosphere was added 4-phenylbutan-1-amine (1.2 equiv), HATU (1.5 equiv) and DIPEA (3 equiv). The reaction mixture was stirred at room temperature for 3 h. After completion of the reaction, the reaction mixture was quenched with water (30 vol). The resulting mixture was extracted with DCM. The organic layer was washed with brine, dried over anhydrous $Na_2SO_4$, filtered and then concentrated. The residue was purified by column chromatography on silica gel using DCM/MeOH to afford tert-butyl (2S,4R)-4-fluoro-2-((4-phenylbutyl)carbamoyl)pyrrolidine-1-carboxylate. To a solution of tert-butyl (2S,4R)-4-fluoro-2-((4-phenylbutyl)carbamoyl)pyrrolidine-1-carboxylate (1 equiv) in 1,4-dioxane (3 vol) at 0° C. under nitrogen atmosphere was added 4 N HCl in 1,4-dioxane (10 vol) and stirred at room temperature for 3 h. The reaction mixture was concentrated to afford (2S,4R)-4-fluoro-N-(4-phenylbutyl)pyrrolidine-2-carboxamide.

Step 1: Methyl 3-acetyl-1-(2-((2S,4R)-4-fluoro-2-((4-phenylbutyl)carbamoyl)pyrrolidin-1-yl)-2-oxo-ethyl)-1H-indole-5-carboxylate (193)

To a solution of (2S,4R)-4-fluoro-N-(4-phenylbutyl)pyrrolidine-2-carboxamide (1 equiv) in DMF (10 vol) at 0° C. under nitrogen atmosphere was added Compound 192 (1.2 equiv), HATU (1.5 equiv) and DIPEA (5 equiv). The reaction mixture was stirred at room temperature for 16 h. After completion of the reaction, the reaction mixture was quenched with water (30 vol). The resulting solid was filtered, dried to give methyl 3-acetyl-1-(2-((2S,4R)-4-fluoro-2-((4-phenylbutyl)carbamoyl)pyrrolidin-1-yl)-2-oxoethyl)-1H-indole-5-carboxylate.

Step 2: 3-acetyl-1-(2-((2S,4R)-4-fluoro-2-((4-phenylbutyl)carbamoyl)pyrrolidin-1-yl)-2-oxoethyl)-1H-indole-5-carboxylic acid (194)

To a solution of methyl 3-acetyl-1-(2-((2S,4R)-4-fluoro-2-((4-phenylbutyl)carbamoyl)pyrrolidin-1-yl)-2-oxoethyl)-1H-indole-5-carboxylate (1 equiv) in THF/water (8:2) was added LiOH (4 equiv). The reaction mixture was stirred at room temperature for 4 h and then quenched with 1 M citric acid. The resulting mixture was extracted with ethyl acetate. The organic layer was separated, dried over anhydrous $Na_2SO_4$, filtered and then concentrated to give 3-acetyl-1-(2-((2S,4R)-4-fluoro-2-((4-phenylbutyl)carbamoyl)pyrrolidin-1-yl)-2-oxoethyl)-1H-indole-5-carboxylic acid.

Step 3: 3-acetyl-N-(cyclopropylsulfonyl)-1-(2-((2S,4R)-4-fluoro-2-((4-phenylbutyl)carbamoyl)pyrrolidin-1-yl)-2-oxoethyl)-1H-indole-5-carboxamide (195)

To a solution of 3-acetyl-1-(2-((2S,4R)-4-fluoro-2-((4-phenylbutyl)carbamoyl)pyrrolidin-1-yl)-2-oxoethyl)-1H-indole-5-carboxylic acid (1 equiv) in THF (10 vol) was added CDI (2 equiv). The reaction mixture was stirred at 70° C. for 4 h and then cooled to room temperature. Cyclopropylsulfonamide (2 equiv) and DBU (2.5 equiv) was added to the reaction mixture and the reaction mixture was stirred at room temperature for 16 h. After completion of the reaction, the reaction mixture was quenched with water (30 vol). The resulting mixture was extracted with DCM. The organic layer was washed with brine, dried over anhydrous $Na_2SO_4$, filtered and then concentrated. The residue was purified by column chromatography on silica gel using DCM/MeOH to give 3-acetyl-N-(cyclopropylsulfonyl)-1-(2-((2S,4R)-4-fluoro-2-((4-phenylbutyl)carbamoyl)pyrrolidin-1-yl)-2-oxoethyl)-1H-indole-5-carboxamide.

$^1$H NMR (400 MHz, DMSO-$d_6$) δ 12.14 (s, 1H), 8.81 (s, 1H), 8.38 (s, 1H), 7.97 (t, J=5.7 Hz, 1H), 7.81 (d, J=8.8 Hz, 1H), 7.59 (d, J=8.8 Hz, 1H), 7.25-7.05 (m, 5H), 5.59-5.38 (m, 2H), 5.24 (d, J=17.2 Hz, 1H), 4.34 (t, J=8.4 Hz, 1H), 4.21-4.11 (m, 1H), 3.95-3.75 (m, 1H), 3.20-2.96 (m, 3H), 2.46 (s, 3H), 2.45-2.33 (m, 3H), 2.11-1.94 (m, 1H), 1.50-1.46 (m, 2H), 1.37-1.33 (m, 2H), 1.12-1.07 (m, 4H)

N-(3-acetyl-1-(2-((2S,4R)-2-(benzylcarbamoyl)-4-fluoropyrrolidin-1-yl)-2-oxoethyl)-1H-indol-5-yl)-3,3-difluoropiperidine-1-carboxamide (196)

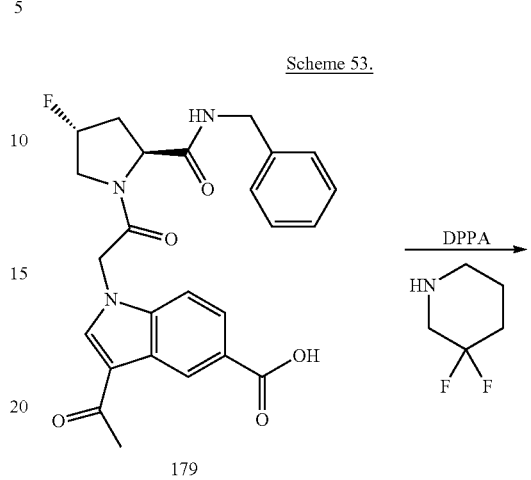

Scheme 53.

To a solution of compound 179 (1 equiv) in benzene (10 vol) was added TEA (1.5 equiv) and DPPA (1.2 equiv). The reaction mixture was stirred at 50° C. for 1 h and then cooled to room temperature. 3,3-difluoropiperidine hydrochloride (4 equiv) and TEA (8 equiv) was added to the reaction mixture and stirred at 80° C. for 16 h. After completion of the reaction, the reaction mixture was concentrated and the residue was purified by preparative HPLC to give compound 196.

$^1$H NMR (400 MHz, DMSO-$d_6$) δ 8.66 (s, 1H), 8.57-8.55 (m, 1H), 8.20-8.17 (m, 2H), 7.36-7.20 (m, 6H), 5.56-5.43 (m, 1H), 5.35-5.31 (m, 1H), 5.15-5.11 (m, 1H), 4.46-4.40 (m, 1H), 4.29 (d, J=5.9 Hz, 1H), 4.25 (d, J=5.6 Hz, 1H), 3.80-3.77 (m, 3H), 3.52-3.51 (m, 4H), 2.40 (s, 3H), 2.09-2.02 (m, 3H), 1.72-1.71 (m, 2H).

209
N-(3-Acetyl-1-(2-((2S,4R)-4-fluoro-2-(phenethylcarbamoyl)pyrrolidin-1-yl)-2-oxoethyl)-1H-indol-5-yl)-3,3-difluoropiperidine-1-carboxamide (197)

Scheme 54.

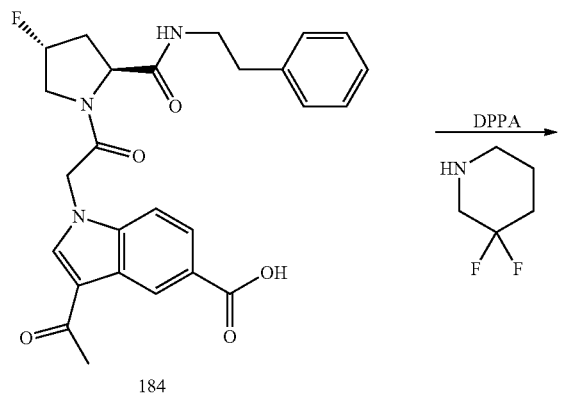

184

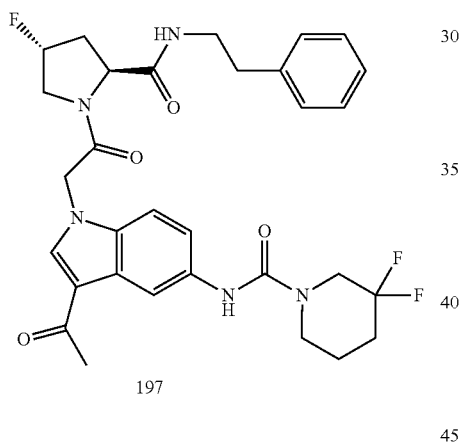

197

To a solution of compound 184 (1 equiv) in benzene (10 vol) was added TEA (1.5 equiv) and DPPA (1.2 equiv). The reaction mixture was stirred at 50° C. for 1 h and then cooled to room temperature. 3,3-difluoropiperidine hydrochloride (4 equiv) and TEA (8 equiv) was added to the reaction mixture and stirred at 80° C. for 16 h. After completion of the reaction, the reaction mixture was concentrated and the residue was purified by preparative HPLC to give compound 197.

$^1$H NMR (400 MHz, DMSO-d$_6$) δ 8.63 (s, 1H), 8.16 (s, 1H), 8.12-8.07 (m, 1H), 7.39-7.13 (m, 7H), 5.51-5.38 (m, 1H), 5.30-5.26 (m, 1H), 5.12-5.08 (m, 1H), 4.35-4.31 (m, 2H), 4.13-3.81 (m, 2H), 3.78-3.76 (m, 2H), 3.51-3.50 (m, 2H), 3.29-3.16 (m, 2H), 2.66-2.65 (m, 2H), 2.40 (s, 3H), 2.06-2.00 (m, 3H), 1.69-1.68 (m, 2H).

210
N-(3-Acetyl-1-(2-((2S,4R)-4-fluoro-2-((3-phenylpropyl)carbamoyl)pyrrolidin-1-yl)-2-oxoethyl)-1H-indol-5-yl)-3,3-difluoropiperidine-1-carboxamide (198)

Scheme 55.

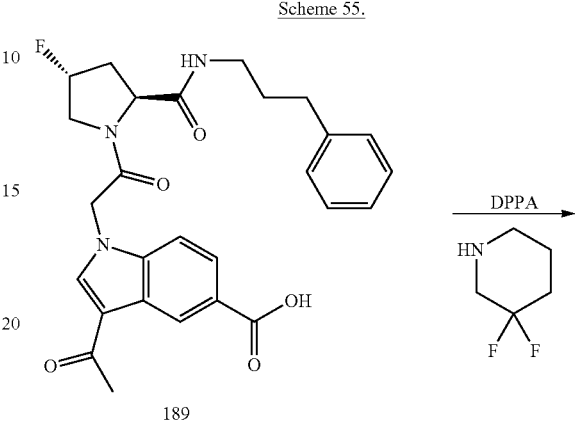

189

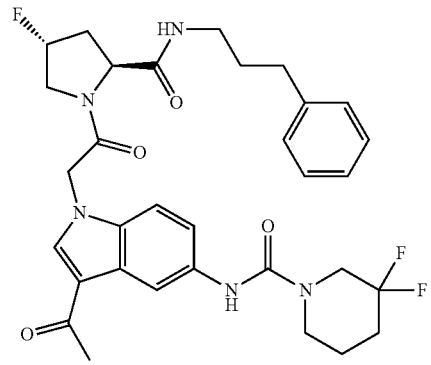

198

To a solution of compound 189 (1 equiv) in benzene (10 vol) was added TEA (1.5 equiv) and DPPA (1.2 equiv). The reaction mixture was stirred at 50° C. for 1 h and then cooled to room temperature. 3,3-difluoropiperidine hydrochloride (4 equiv) and TEA (8 equiv) was added to the reaction mixture and stirred at 80° C. for 16 h. After completion of the reaction, the reaction mixture was concentrated and the residue was purified by preparative HPLC to give compound 198.

$^1$H NMR (400 MHz, DMSO-d$_6$) δ 8.63 (s, 1H), 8.19-8.15 (m, 2H), 8.04-8.01 (m, 1H), 7.39-7.08 (m, 6H), 5.51-5.41 (m, 1H), 5.32-5.27 (m, 1H), 5.13-5.09 (m, 1H), 4.37-4.33 (m, 2H), 4.18-3.90 (m, 2H), 3.82-3.76 (m, 2H), 3.52-3.49 (m, 2H), 3.06-2.99 (m, 2H), 2.59-2.58 (m, 2H), 2.36 (s, 3H), 2.09-1.99 (m, 3H), 1.70-1.60 (m, 4H).

211

N-(3-Acetyl-1-(2-((2S,4R)-4-fluoro-2-((4-phenylbutyl)carbamoyl)pyrrolidin-1-yl)-2-oxoethyl)-1H-indol-5-yl)-3,3-difluoropiperidine-1-carboxamide (199)

Scheme 56.

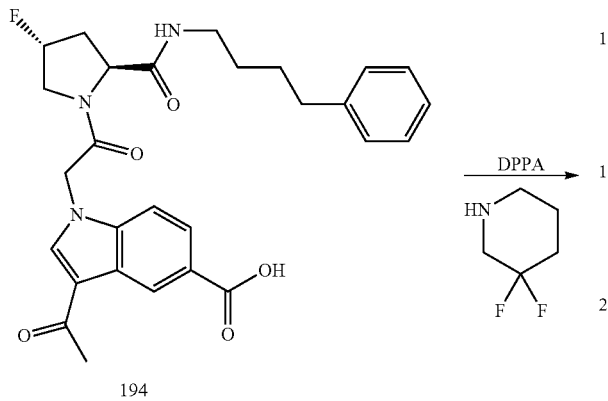

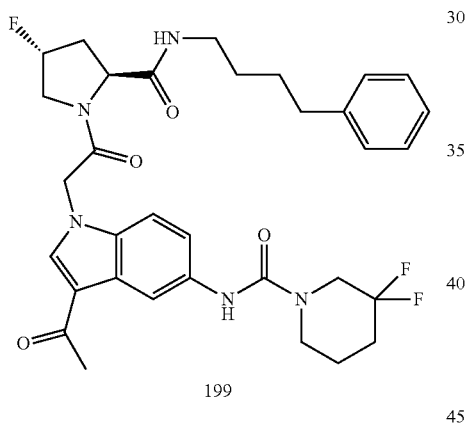

To a solution of compound 194 (1 equiv) in benzene (10 vol) was added TEA (1.5 equiv) and DPPA (1.2 equiv). The reaction mixture was stirred at 50° C. for 1 h and then cooled to room temperature. 3,3-difluoropiperidine hydrochloride (4 equiv) and TEA (8 equiv) was added to the reaction mixture and stirred at 80° C. for 16 h. After completion of the reaction, the reaction mixture was concentrated and the residue was purified by preparative HPLC to give compound 199.

$^1$H NMR (400 MHz, DMSO-d$_6$) δ 8.64 (s, 1H), 8.19-8.16 (m, 2H), 7.96-7.95 (m, 1H), 7.42-7.07 (m, 6H), 5.51-5.41 (m, 1H), 5.31-5.27 (m, 1H), 5.13-5.09 (m, 1H), 4.34-4.33 (m, 2H), 4.18-3.84 (m, 2H), 3.83-3.80 (m, 2H), 3.52-3.51 (m, 2H), 3.07-2.99 (m, 2H), 2.46-2.44 (m, 2H), 2.40 (s, 3H), 2.08-2.03 (m, 3H), 1.71-1.70 (m, 2H), 1.53-1.49 (m, 2H), 1.38-1.34 (m, 2H), 1.24-1.23 (m, 2H).

212

N-(3-Acetyl-1-(2-((2S,4R)-2-((3-chloro-2-fluorobenzyl)carbamoyl)-4-fluoropyrrolidin-1-yl)-2-oxoethyl)-1H-indol-5-yl)-3,3-difluoropiperidine-1-carboxamide (40)

Scheme 57.

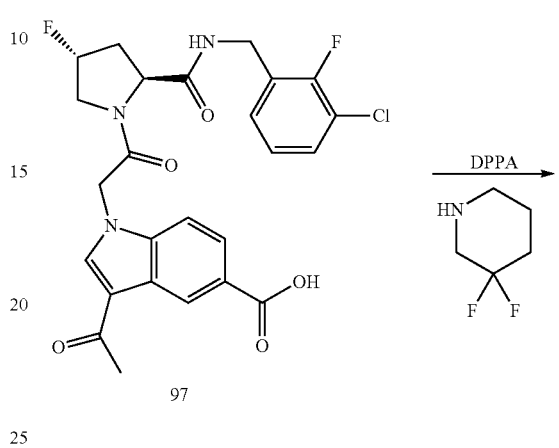

To a solution of compound 97 (1 equiv) in benzene (10 vol) was added TEA (1.5 equiv) and DPPA (1.2 equiv). The reaction mixture was stirred at 50° C. for 1 h and then cooled to room temperature. 3,3-difluoropiperidine hydrochloride (4 equiv) and TEA (8 equiv) was added to the reaction mixture and stirred at 80° C. for 16 h. After completion of the reaction, the reaction mixture was concentrated and the residue was purified by preparative HPLC to give compound 40.

$^1$H NMR (400 MHz, DMSO-d$_6$) δ 8.63 (s, 1H), 8.18-8.11 (s, 2H), 7.42-7.20 (m, 4H), 7.01-6.97 (m, 1H), 5.55-5.42 (m, 1H), 5.34-5.30 (m, 1H), 5.14-5.09 (m, 1H), 4.48-4.23 (m, 3H), 4.14-4.08 (m, 1H), 3.93-3.76 (m, 4H), 3.52-3.51 (m, 2H), 2.49 (s, 3H), 2.09-1.99 (m, 3H), 1.71-1.69 (m, 2H).

213
N-(3-Acetyl-1-(2-((2R,4R)-4-fluoro-2-(2-(phenylsulfonamido)ethyl)pyrrolidin-1-yl)-2-oxoethyl)-1H-indol-5-yl)-3,3-difluoropiperidine-1-carboxamide (201)

214
(S)—N-(3-Acetyl-1-(2-(2-(((6-methylpyridin-2-yl)carbamoyl)azetidin-1-yl)-2-oxoethyl)-1H-indol-5-yl)-3,3-difluoropiperidine-1-carboxamide (205)

Scheme 58.

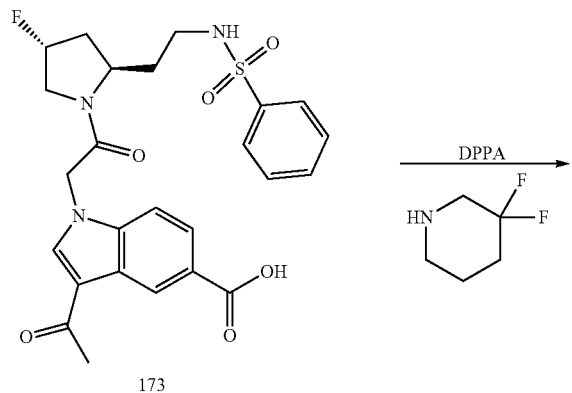

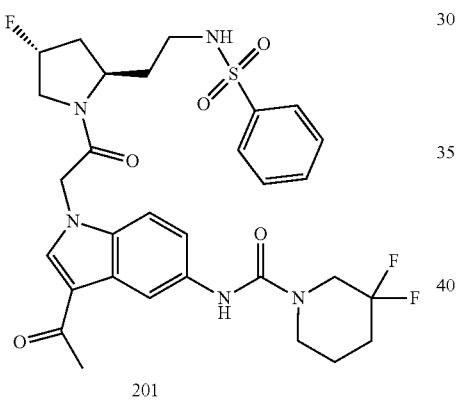

Scheme 59.

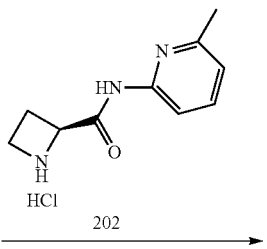

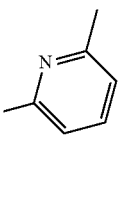

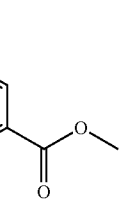

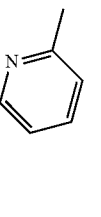

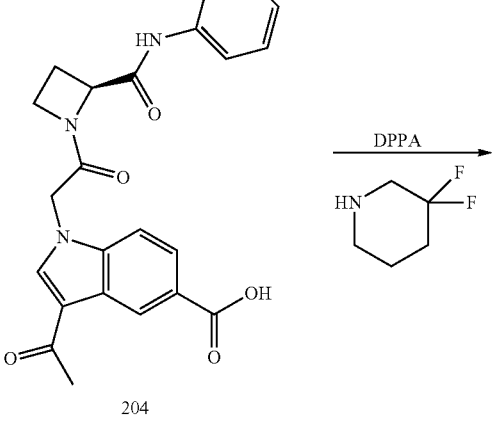

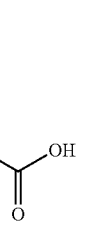

To a solution of compound 173 (1 equiv) in benzene (10 vol) was added TEA (1.5 equiv) and DPPA (1.2 equiv). The reaction mixture was stirred at 50° C. for 1 h and then cooled to room temperature. 3,3-difluoropiperidine hydrochloride (4 equiv) and TEA (8 equiv) was added to the reaction mixture and stirred at 80° C. for 16 h. After completion of the reaction, the reaction mixture was concentrated and the residue was purified by preparative HPLC to give compound 201.

$^1$H NMR (400 MHz, DMSO-d$_6$) δ 8.65 (s, 1H), 8.19 (s, 2H), 7.76 (d, J=7.2 Hz, 2H), 7.63-7.54 (m, 3H), 7.40 (d, J=8.8 Hz, 1H), 7.27 (d, J=8.8 Hz, 1H), 5.43-5.19 (m, 2H), 5.09-5.05 (m, 1H), 4.06-4.03 (m, 2H), 3.84-3.78 (m, 3H), 3.52-3.51 (m, 2H), 2.74-2.67 (m, 2H), 2.41 (s, 3H), 2.09-2.02 (m, 3H), 1.92-1.71 (m, 4H), 1.49-1.48 (m, 1H).

-continued

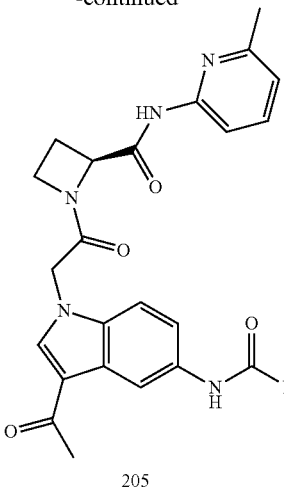

205

Step 1: Methyl (S)-3-acetyl-1-(2-(2-(((6-methylpyridin-2-yl)carbamoyl)azetidin-1-yl)-2-oxoethyl)-1H-indole-5-carboxylate (203)

To a solution of 202 (1 equiv) in DMF (10 vol) at 0° C. under nitrogen atmosphere was added INT-9 (1.2 equiv), HATU (1.5 equiv) and DIPEA (3 equiv). The reaction mixture was stirred at room temperature for 3 h. After completion of the reaction, the reaction mixture was quenched with water (30 vol). The resulting mixture was extracted with DCM. The organic layer was washed with brine, dried over anhydrous $Na_2SO_4$, filtered and then concentrated. The residue was purified by column chromatography on silica gel using DCM/MeOH to give compound 203.

Step 2: (S)-3-Acetyl-1-(2-(2-(((6-methylpyridin-2-yl)carbamoyl)azetidin-1-yl)-2-oxoethyl)-1H-indole-5-carboxylic acid (204)

To a solution of compound 203 (1 equiv) in THF/water (8:2) was added LiOH (4 equiv). The reaction mixture was stirred at room temperature for 4 h and then quenched with 1 M citric acid. The resulting mixture was extracted with ethyl acetate. The organic layer was separated, dried over anhydrous $Na_2SO_4$, filtered and then concentrated to give compound 204.

Step 3: (S)—N-(3-Acetyl-1-(2-(2-(((6-methylpyridin-2-yl)carbamoyl)azetidin-1-yl)-2-oxoethyl)-1H-indol-5-yl)-3,3-difluoropiperidine-1-carboxamide (205)

To a solution of compound 204 (1 equiv) in benzene (10 vol) was added TEA (1.5 equiv) and DPPA (1.2 equiv). The reaction mixture was stirred at 50° C. for 1 h and then cooled to room temperature. 3,3-difluoropiperidine hydrochloride (4 equiv) and TEA (8 equiv) was added to the reaction mixture and stirred at 80° C. for 16 h. After completion of the reaction, the reaction mixture was concentrated and the residue was purified by preparative HPLC to give compound 205.

$^1$H NMR (400 MHz, $CD_3OD$) δ 8.17-8.16 (m, 2H), 7.98-7.85 (m, 1H), 7.75-7.71 (m, 1H), 7.41-7.35 (m, 2H), 7.05-7.02 (m, 1H), 5.09-4.99 (m, 3H), 4.28-4.27 (m, 2H), 3.81-3.78 (m, 2H), 3.59-3.57 (m, 2H), 2.52 (s, 3H), 2.47 (s, 3H), 2.36-2.34 (m, 1H), 2.13-2.04 (m, 3H), 1.84-1.83 (m, 2H).

(1R,3S,4S)—N-(6-methylpyridin-2-yl)-2-azabicyclo[2.2.1]heptane-3-carboxamide hydrochloride (218)

Scheme 60.

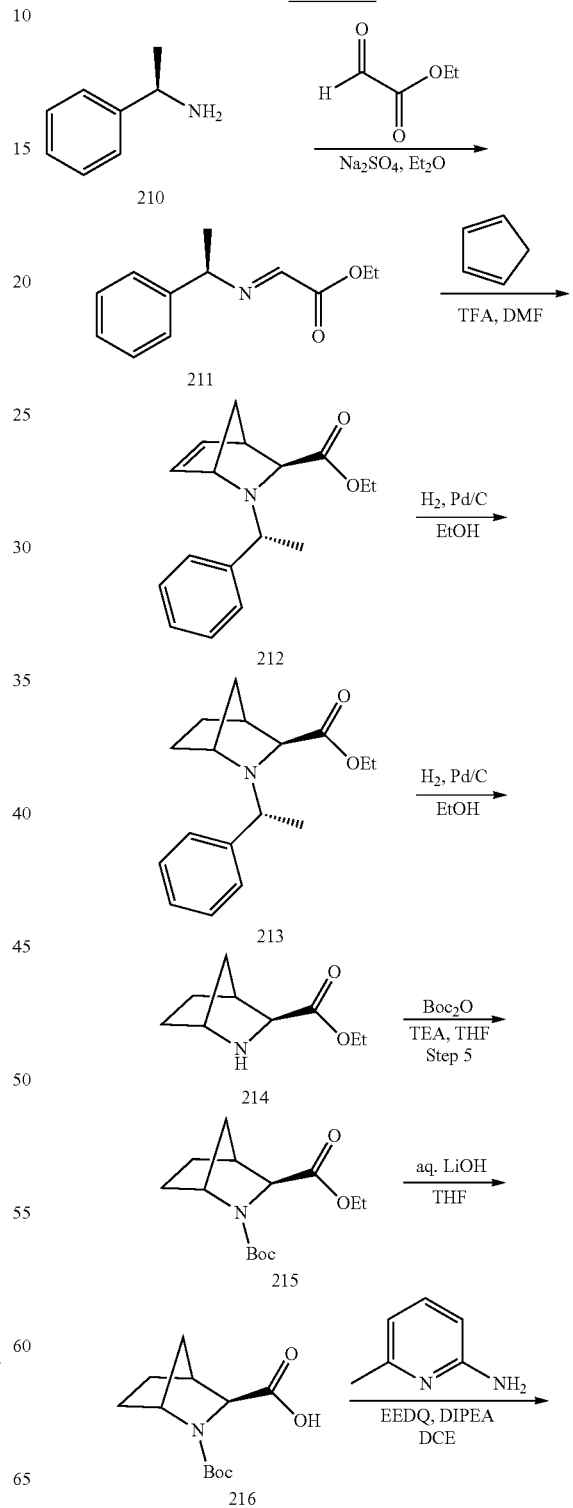

-continued

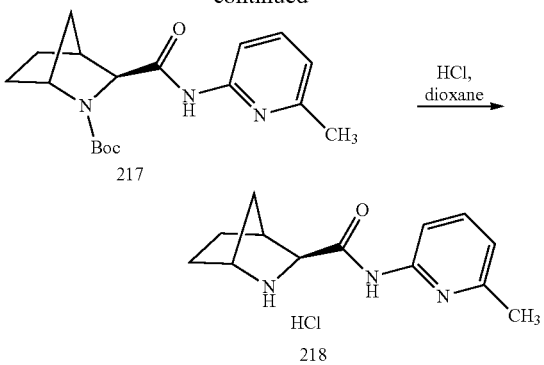

Step 1: (R,E)-ethyl 2-((1-phenylethyl)imino)acetate (211)

To a solution of compound 210 (15 g, 0.12 mol) in diethyl ether (200 mL) was added Na$_2$SO$_4$ (42.6 g, 0.3 mol) and ethyl glyoxalate (18.36 g, 0.12 mmol) at 0° C. The reaction mixture was stirred at room temperature for 16 hrs. The reaction filtered and the filtrated was concentrated under reduced pressure to give 2 (23 g, 90.6% yield) as a colorless oil.

Step 2: (1S,3S,4R)-ethyl 2-((R)-1-phenylethyl)-2-azabicyclo[2.2.1]hept-5-ene-3-carboxylate (212)

To a solution of compound 211 (23 g, 0.11 mol) in DMF (200 mL) was added 1,3-cyclopentadiene (18.48 g, 0.24 mmol) and trifluoroacetic acid (16 g, 0.14 mmol) at 0° C. The reaction mixture was stirred at room temperature for 16 hrs The mixture was diluted with EtOAc and washed with 10% aq. LiCl solution and brine successively, dried over anhydrous Na$_2$SO$_4$, filtered and then concentrated. The residue was purified by column chromatography on silica gel (eluted with petroleum ether:ethyl acetate=60:1) to give the title compound 212 (17 g, 57% yield) as a colorless oil. LC/MS (ESI) m/z: 272 [M+H]$^+$.

Step 3: (1R,3S,4S)-ethyl 2-((R)-1-phenylethyl)-2-azabicyclo[2.2.1]heptane-3-carboxylate (213)

To a solution of compound 212 (6 g, 22.1 mmol) in EtOH (60 mL) was added Pd/C (5% wt, 0.3 g) and the mixture was degassed under N$_2$ atmosphere for three times and stirred under H$_2$ balloon at room temperature for 1 hr. After filtration through Celite, the filter cake was washed with EtOH. To the filtrate, conc. HCl solution (7 mL) was added and then the resulting mixture was concentrated to dryness under reduced pressure. This procedure was repeated several times until a semi-crystalline residue was formed. The residue was precipitated in Et$_2$O/i-PrOH (50 mL, 5:1) at 0° C. for 1 hr and filtered. The filter cake was dried under vacuum to give the title compound (213) (5 g, 82.8% yield) as white solid. LC/MS (ESI) m/z: 274 [M+H]$^+$.

Step 4: (1R,3S,4S)-Ethyl 2-azabicyclo[2.2.1]heptane-3-carboxylate (214)

To a solution of compound 213 (5 g, 18.3 mmol) in ethanol (10 mL) was degassed under N$_2$ atmosphere for three times and Pd(OH)$_2$ (500 mg, 10% wt) was added. The mixture was degassed again and stirred under H$_2$ balloon at room temperature for 16 hrs. The mixture was filtered and the filtrate was concentrated under reduced pressure to give the title compound (3.3 g, 98.5% yield) as a colorless oil. LC/MS (ESI) m/z: 170 [M+H]$^+$.

Step 5: (1R,3S,4S)-2-tert-Butyl 3-ethyl 2-azabicyclo[2.2.1]heptane-2,3-dicarboxylate (215)

To a solution of compound 214 (3.3 g, 18 mmol) was in DCM (30 mL) was added triethylamine (7.5 mL, 54 mmol) and di-tert-butyl dicarbonate (7.85 g, 36 mmol) at room temperature. The reaction mixture was stirred at room temperature for 16 hrs and then diluted with DCM. The resulting mixture was washed with water and brine, dried over anhydrous Na$_2$SO$_4$, filtered and then concentrated. The residue was purified by column chromatography on silica gel (eluted with petroleum ether:ethyl acetate=20:1) to give the title compound (3.6 g, 71% yield) as a colorless oil. LC/MS (ESI) m/z: 214 [M+H-56]$^+$.

Step 6: (1R,3S,4S)-2-(tert-butoxycarbonyl)-2-azabicyclo[2.2.1]heptane-3-carboxylic acid (216)

To a solution of compound 215 (3.6 g, 0.18 mmol) in THF (20 mL) and was added aq. NaOH solution (2 M, 27 mL, 0.54 mmol) at room temperature. The reaction mixture was stirred at room temperature for 16 hrs and washed with ethyl acetate (20 mL×2). The aqueous phase was acidified to pH=3 with aq. HCl (1 M) and extracted with DCM twice. The combined organic phases are dried over anhydrous Na$_2$SO$_4$, filtered and then concentrated to give the title compound (216) (3.2 g, 99.2% yield) as white solid. LC/MS (ESI) m/z: 186 [M+H-56]$^+$.

Step 7: (1R,3S,4S)-tert-butyl3-((6-methylpyridin-2-yl)carbamoyl)-2-azabicyclo[2.2.1]heptane-2-carboxylate (217)

To a solution of compound 216 (2 g, 8.3 mmol) was in 1,2-Dichloroethane (20 ml) was added N-Ethoxycarbonyl-2-ethoxy-1,2-dihydroquinoline (4.1 g, 16.6 mmol) and 2-Amino-6-methylpyridine (0.9 g, 8.3 mmol) at 0° C. The reaction mixture was stirred at 85° C. for 16 hrs and concentrated to dryness to give crude product, which was purified by column chromatography on silica gel (eluted with petroleum ether:ethyl acetate=10:1) to give the title compound (2.1 g, 79% yield) as white solid. LC/MS (ESI) m/z: 276 [M+H-56]$^+$.

Step 8: (1R,3S,4S)—N-(6-methylpyridin-2-yl)-2-azabicyclo[2.2.1]heptane-3-carboxamide (218)

To a solution compound 217 (2.1 g, 6.5 mmol) in dioxane (15 mL) was added HCl dioxane solutions (15 mL) was at 0° C. The reaction was stirred at room temperature for 3 hrs and concentrated to dryness to give compound INT-5 (2.3 g, 99.7% yield) as yellow solid, which was directly used to the next reaction without purification. LC/MS (ESI) m/z: 232 [M+H]$^+$.

219

2-(3-Carbamoyl-5-(cyclopropylsulfonylcarbamoyl)-1H-indol-1-yl)acetic acid (229)

Scheme 61.

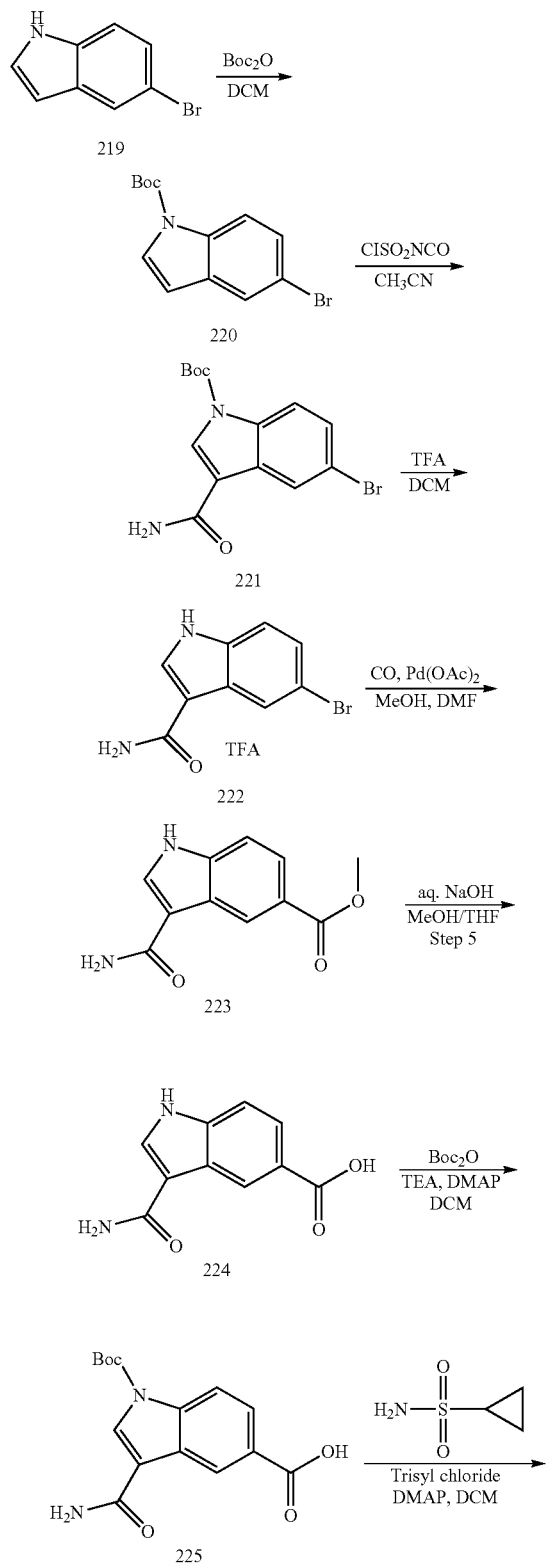

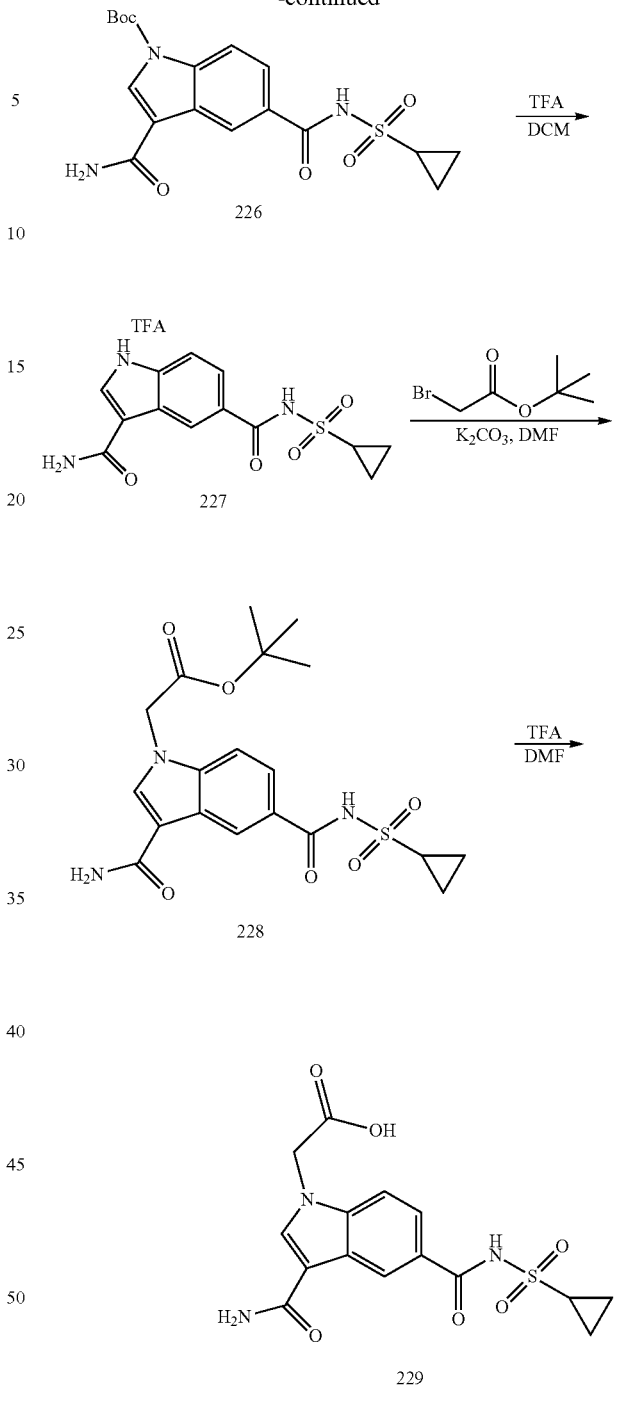

Step 1: tert-Butyl 5-bromo-1H-indole-1-carboxylate (220)

A mixture of 5-bromo-1H-indole (10.0 g, 51.0 mmol), Boc$_2$O (16.7 g, 76.5 mmol), TEA (14.2 mL, 102.0 mmol) and DMAP (622 mg, 5.1 mmol) in DCM (150 mL) was stirred at room temperature for 16 hrs. The mixture was evaporated under reduced pressure and the residue was purified by chromatography on silica gel (PE:EtOAc=50:1) to give the title compound (14.6 g, 97.0% yield) as white solid.

Step 2: tert-Butyl 5-bromo-3-carbamoyl-1H-indole-1-carboxylate (221)

To a solution of tert-butyl 5-bromo-1H-indole-1-carboxylate (5.0 g, 16.9 mmol) in dry CH$_3$CN (60 mL) was added sulfurwasocyanatidic chloride (1.55 mL, 17.7 mmol) dropwise at 0° C. under N$_2$ atmosphere. Then the reaction was stirred at room temperature for 16 hrs, followed by addition of acetone (100 mL) and water (12 mL). The resulting mixture was basified with 10% aq. NaOH solution and extracted with EtOAc (50 mL*2). The combined organic phases are dried over anhydrous Na$_2$SO$_4$, filtered and concentrated under reduced pressure. The residue was re-crystallized with EtOAc to afford the desired product (221) (3.6 g, 63.1% yield) as white solid.

Step 3: 5-Bromo-1H-indole-3-carboxamide (222)

To a solution of tert-butyl 5-bromo-3-carbamoyl-1H-indole-1-carboxylate (3.0 g) in DCM (30 mL) at 0° C. was added TFA (10 mL). The reaction was stirred at room temperature for 2 hrs and then filtered. The filter cake was dried under vacuum to give the title compound (3.5 g, TFA salt) as white solid, which was directly used to the next reaction without purification.

Step 4: Methyl 3-carbamoyl-1H-indole-5-carboxylate (223)

A mixture of 5-bromo-1H-indole-3-carboxamide (3.5 g, 10.41 mmol), Pd(OAc)$_2$ (108 mg, 0.48 mmol), TEA (2.8 mL, 19.2 mmol) and Xant-phos (347 mg, 0.60 mmol) in MeOH (10 mL) and DMF (50 mL) was degassed under N$_2$ atmosphere for three times and the reaction mixture was stirred at 100° C. under 45 psi of CO atmosphere for 16 hrs. The mixture was filtered and the residue was evaporated under reduced pressure. The residue was purified by chromatography on silica gel (DCM:MeOH=50:1 to 40:1) to give the title compound (223) (1.2 g, 52.82% yield) as yellow solid.

Step 5: 3-Carbamoyl-1H-indole-5-carboxylic acid (224)

To a solution of methyl 3-carbamoyl-1H-indole-5-carboxylate (1.2 g, 5.5 mmol) in MeOH (5 mL) and THF (5 mL) was added 2 M aq. NaOH solution (5.5 mL) and the reaction mixture was stirred at 60° C. for 2 hr. The volatility was removed under reduced pressure and the mixture was washed with EtOAc twice. The aqueous layer was acidified with 2 M aq. HCl until pH=~3. The slurry was filtered and the filter cake was dried under vacuum to give the title compound (224) (650 mg, 57.88% yield) as white solid.

Step 6: 1-(tert-Butoxycarbonyl)-3-carbamoyl-1H-indole-5-carboxylic acid (225)

A mixture of 224 (500 mg, 2.45 mmol), Boc$_2$O (801 mg, 3.67 mmol), TEA (0.85 mL, 6.13 mmol) and DMAP (30 mg, 0.25 mmol) in THF (15 mL) was stirred at room temperature overnight. The mixture was evaporated under reduced pressure and the residue was purified by chromatography on silica gel (DCM:MeOH=50:1 to 10:1) to give the title compound (224) (350 mg, 47.0% yield) as white solid.

Step 7: tert-Butyl 3-carbamoyl-5-((cyclopropylsulfonyl)carbamoyl)-1H-indole-1-carboxylate (226)

To a mixture of 225 (350 mg, 1.15 mmol), DIPEA (0.6 mL, 3.45 mmol) and DMAP (12.2 mg, 0.1 mmol) in dry DCM (5 mL) at 0° C. was added a solution of trwasyl chloride (418 mg, 1.38 mmol) in DCM (5 mL) and the reaction was stirred at 0° C. for 30 min. Then to the mixture was added cyclopropane sulfonamide (209 mg, 1.73 mmol) and the mixture was stirred at room temperature overnight. The reaction was quenched with AcOH (0.5 mL). The mixture was diluted with DCM and washed with water, brine, dried over anhydrous Na$_2$SO$_4$, filtered and concentrated. The residue was purified by chromatography on silica gel (DCM:MeOH=50:1 to 30:1) to give the title compound (225) (230 mg, 49.08% yield) as yellow solid.

Step 8: N5-(cyclopropylsulfonyl)-1H-indole-3,5-dicarboxamide (227)

To a solution of tert-butyl 3-carbamoyl-5-((cyclopropylsulfonyl)carbamoyl)-1H-indole-1-carboxylate (230 mg, 0.564 mmol) in DCM (6 mL) was added TFA (2 mL) and the reaction was stirred at room temperature for 1 hr. The mixture was evaporated to give the title compound (350 mg, 100% yield) as yellow solid, which was directly used to the next reaction without further purification.

Step 9: tert-Butyl 2-(3-carbamoyl-5-((cyclopropylsulfonyl)carbamoyl)-1H-indol-1-yl) acetate (228)

A mixture of 227 (350 mg, 0.564 mmol), tert-butyl 2-bromoacetate (143 mg, 0.733 mmol), K$_2$CO$_3$ (117 mg, 0.85 mmol) in DMF (10 mL) was stirred at room overnight. The mixture was diluted with EtOAc and washed with aq. LiCl solution. The organic phase was dried over anhydrous Na$_2$SO$_4$ and evaporated under reduced pressure. The residue was purified by chromatography on silica gel (DCM:MeOH=50:1 to 30:1) to afford the desired product (170 mg, 71.51% yield) as white solid.

Step 10: 2-(3-Carbamoyl-5-((cyclopropylsulfonyl)carbamoyl)-1H-indol-1-yl)acetic acid (229)

To a solution of tert-butyl 2-(3-carbamoyl-5-((cyclopropylsulfonyl)carbamoyl)-1H-indol-1-yl) acetate (170 mg) in DCM (2 mL) was added TFA (1 mL) and the reaction was stirred at room temperature for 16 hrs. The mixture was evaporated under reduced to give 229 (190 mg, 100% yield) as yellow solid, which was directly used to the next reaction without further purification.

N[5]-(cyclopropylsulfonyl)-1-(2-((1R,3S,4S)-3-((6-methylpyridin-2-yl)carbamoyl)-2-azabicyclo[2.2.1]heptan-2-yl)-2-oxoethyl)-1H-indole-3,5-dicarboxamide (209)

Scheme 62.

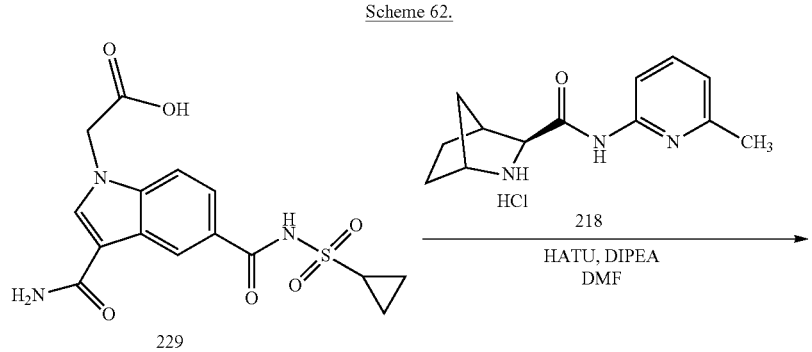

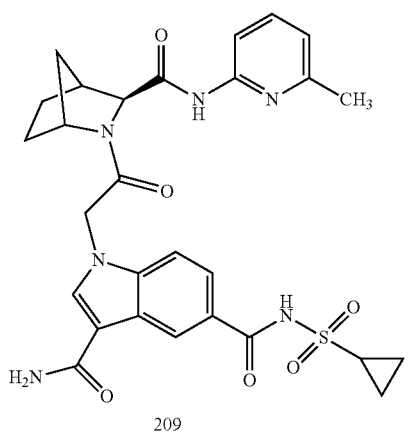

209

To a mixture of 2-(3-carbamoyl-5-((cyclopropylsulfonyl)carbamoyl)-1H-indol-1-yl)acetic acid (30 mg, 0.082 mmol), (1R,3S,4S)—N-(6-methylpyridin-2-yl)-2-azabicyclo[2.2.1]heptane-3-carboxamide hydrochloride (23 mg, 0.086 mmol) in DMF (2 mL) at 0° C. was added DIPEA (0.04 mL, 0.246 mmol) followed by HATU (46.7 mmol, 0.123 mmol). The reaction was stirred at room temperature for 16 hrs. The mixture was diluted with 10% aq. LiCl solution (10 mL) and extracted with i-PrOH/CHC13 (10 mL*3, 3/1). The combined organic layers are dried over anhydrous $Na_2SO_4$ and concentrated to dryness. The residue was purified by preparative HPLC to give compound 209 (6.5 mg, 13.7% yield) as white solid.

$^1$H NMR (400 MHz, DMSO-$d_6$) δ 12.02 (s, 1H), 10.94 (s, 1H), 10.46 (s, 1H), 8.76 (d, J=1.5 Hz, 1H), 8.05 (m, 1H), 7.84-7.71 (m, 2H), 7.64 (t, J=7.9 Hz, 1H), 7.58-7.44 (m, 2H), 6.99 (m, 1H), 5.47 (d, J=17.3 Hz, 1H), 5.18 (d, J=17.2 Hz, 2H), 4.67-4.44 (m, 3H), 4.12 (s, 1H), 3.23-3.11 (m, 1H), 2.67 (s, 1H), 2.42 (d, J=16.9 Hz, 3H), 2.10 (d, J=9.9 Hz, 1H), 1.78 (d, J=8.4 Hz, 3H), 1.47 (m, 2H), 1.20-1.05 (m, 4H). LC/MS (ESI) m/z: 579 [M+H]$^-$.

Example 13. Examples of Embodiments of Active Compounds

The Figures provide additional examples of the moieties of the active compounds described herein, namely, A, B, L, and the central core. All combinations of the A, B, L, and central core are considered specifically and individually disclosed, and are provided by groupings only for efficiency.

Example 14. Non-Limiting Examples of Compounds of Formula I

Table 1 shows illustrative compounds of Formula I with characterizing data. The compounds of Table 1 are described in PCT Patent Application No. PCT/US2015/017538 and U.S. patent application Ser. No. 14/631,233 titled "Amide Compounds for Treatment of Complement Mediated Disorders" The assay of Example 15 was used to determine the $IC_{50}$'s of the compounds. Other standard Factor D inhibition assays are also available. Three *s are used to denote compounds with an $IC_{50}$ less than 1 micromolar; two s indicate compound with an $IC_{50}$ between 1 micromolar and 10 micromolar, and one * denotes compounds with an $IC_{50}$ greater than 10 micromolar.

TABLE 1

Non-limiting Examples of Compounds of Formula I

| Cmp No. | Structure | Name | IC$_{50}$ | RT min (Method A or B) | MS (M + 1) |
|---|---|---|---|---|---|
| 1 | 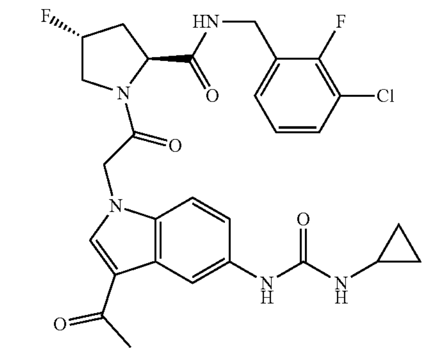 | (2S,4R)-1-(2-(3-acetyl-5-(3-cyclopropylureido)-1H-indol-1-yl)acetyl)-N-(3-chloro-2-fluorobenzyl)-4-fluoropyrrolidine-2-carboxamide | *** | 1.24 (A) | 572 |
| 2 | 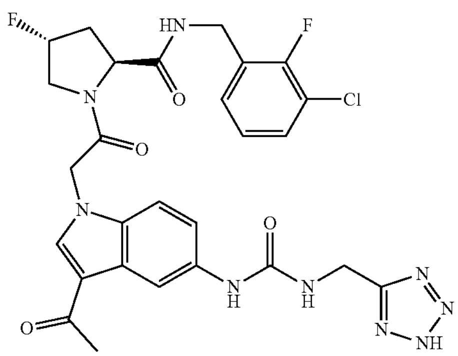 [SMILES: CC(=O)c1cn(CC(=O)N2C[C@H](F)C[C@H]2C(=O)NCc2cccc(Cl)c2F)c2ccc(NC(=O)NCc3nn[nH]n3)cc12] | (2S,4R)-1-(2-(5-(3-((2H-tetrazol-5-yl)methyl)ureido)-3-acetyl-1H-indol-1-yl)acetyl)-N-(3-chloro-2-fluorobenzyl)-4-fluoropyrrolidine-2-carboxamide | *** | 1.01 (A) | 614 |
| 3 | 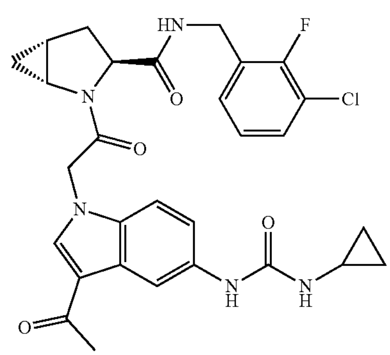 [SMILES: CC(=O)c1cn(CC(=O)N2[C@@H]3C[C@@H]3C[C@H]2C(=O)NCc2cccc(Cl)c2F)c2ccc(NC(=O)NC3CC3)cc12] | (1R,3S,5R)-2-(2-(3-acetyl-5-(3-cyclopropylureido)-1H-indol-1-yl)acetyl)-N-(3-chloro-2-fluorobenzyl)-2-azabicyclo[3.1.0]hexane-3-carboxamide | *** | 1.52 (A) | 566 |
| 4 | 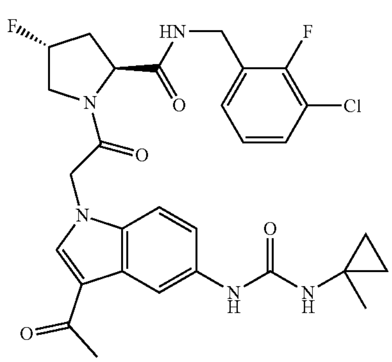 [SMILES: CC(=O)c1cn(CC(=O)N2C[C@H](F)C[C@H]2C(=O)NCc2cccc(Cl)c2F)c2ccc(NC(=O)NC3(C)CC3)cc12] | (2S,4R)-1-(2-(3-acetyl-5-(3-(1-methylcyclopropyl)ureido)-1H-indol-1-yl)acetyl)-N-(3-chloro-2-fluorobenzyl)-4-fluoropyrrolidine-2-carboxamide | *** | 1.66 (A) | 586 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 5 | 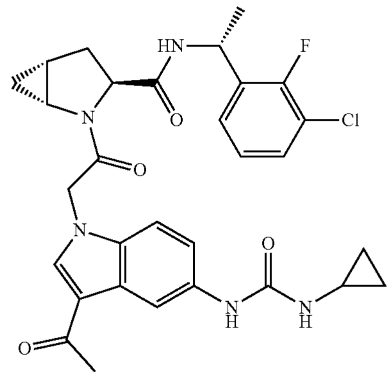 [SMILES: CC(=O)c1cn(CC(=O)N2[C@@H]3C[C@@H]3C[C@H]2C(=O)N[C@H](C)c2cccc(Cl)c2F)c2ccc(NC(=O)NC3CC3)cc12] | (1R,3S,5R)-2-(2-(3-acetyl-5-(3-cyclopropylureido)-1H-indol-1-yl)acetyl)-N-((R)-1-(3-chloro-2-fluorophenyl)ethyl)-2-azabicyclo[3.1.0]hexane-3-carboxamide | *** | 1.74 (A) | 580 |
| 6 | 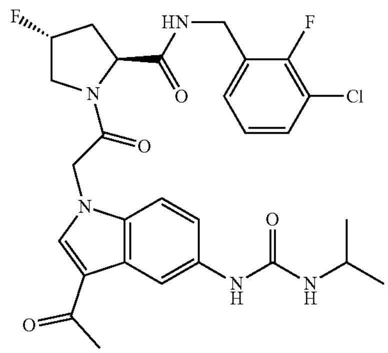 [SMILES: CC(=O)c1cn(CC(=O)N2C[C@H](F)C[C@H]2C(=O)NCc2cccc(Cl)c2F)c2ccc(NC(=O)NC(C)C)cc12] | (2S,4R)-1-(2-(3-acetyl-5-(3-isopropylureido)-1H-indol-1-yl)acetyl)-N-(3-chloro-2-fluorobenzyl)-4-fluoropyrrolidine-2-carboxamide | *** | 1.65 (A) | 574 |
| 7 | 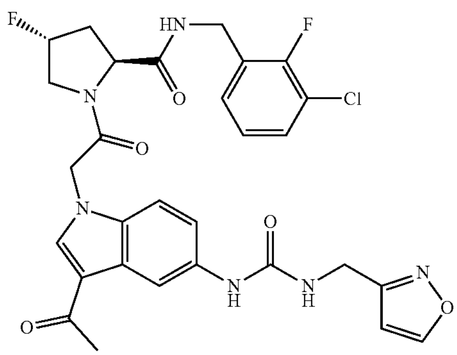 [SMILES: CC(=O)c1cn(CC(=O)N2C[C@H](F)C[C@H]2C(=O)NCc2cccc(Cl)c2F)c2ccc(NC(=O)NCc3ccon3)cc12] | (2S,4R)-1-(2-(3-acetyl-5-(3-(isoxazol-3-ylmethyl)ureido)-1H-indol-1-yl)acetyl)-N-(3-chloro-2-fluorobenzyl)-4-fluoropyrrolidine-2-carboxamide | *** | 1.49 (A) | 613 |
| 8 | 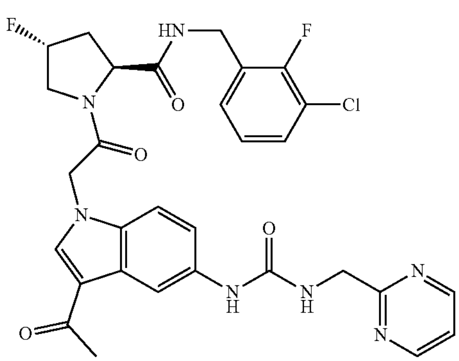 [SMILES: CC(=O)c1cn(CC(=O)N2C[C@H](F)C[C@H]2C(=O)NCc2cccc(Cl)c2F)c2ccc(NC(=O)NCc3ncccn3)cc12] | (2S,4R)-1-(2-(3-acetyl-5-(3-(pyrimidin-2-ylmethyl)ureido)-1H-indol-1-yl)acetyl)-N-(3-chloro-2-fluorobenzyl)-4-fluoropyrrolidine-2-carboxamide | *** | 1.35 (A) | 624 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 9 | 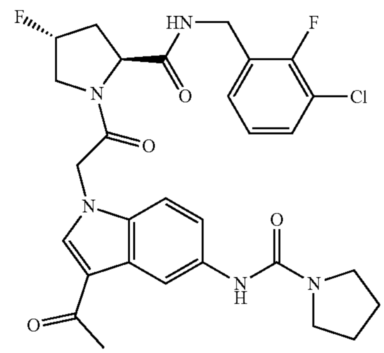 [SMILES: CC(=O)c1cn(CC(=O)N2C[C@H](F)C[C@H]2C(=O)NCc2cccc(Cl)c2F)c2ccc(NC(=O)N3CCCC3)cc12] | N-(3-acetyl-1-(2-((2S,4R)-2-(3-chloro-2-fluorobenzylcarbamoyl)-4-fluoropyrrolidin-1-yl)-2-oxoethyl)-1H-indol-5-yl)pyrrolidine-1-carboxamide | *** | 1.61 (A) | 586 |
| 10 | 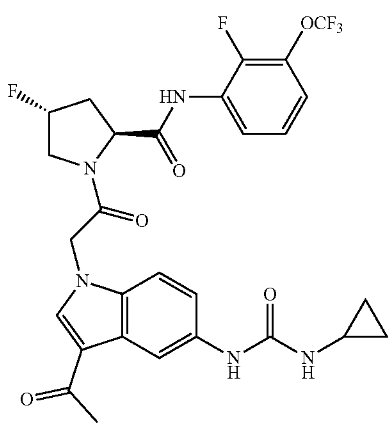 [SMILES: CC(=O)c1cn(CC(=O)N2C[C@H](F)C[C@H]2C(=O)Nc2cccc(OC(F)(F)F)c2F)c2ccc(NC(=O)NC3CC3)cc12] | (2S,4R)-1-(2-(3-acetyl-5-(3-cyclopropylureido)-1H-indol-1-yl)acetyl)-4-fluoro-N-(2-fluoro-3-(trifluoromethoxy)phenyl)pyrrolidine-2-carboxamide | *** | 1.80 (A) | 608 |
| 11 | 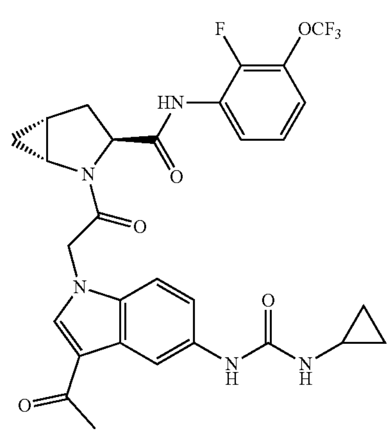 [SMILES: CC(=O)c1cn(CC(=O)N2[C@@H]3C[C@@H]3C[C@H]2C(=O)Nc2cccc(OC(F)(F)F)c2F)c2ccc(NC(=O)NC3CC3)cc12] | (1R,3S,5R)-2-(2-(3-acetyl-5-(3-cyclopropylureido)-1H-indol-1-yl)acetyl)-N-(2-fluoro-3-(trifluoromethoxy)phenyl)-2-azabicyclo[3.1.0]hexane-3-carboxamide | *** | 1.88 (A) | 602 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 12 | 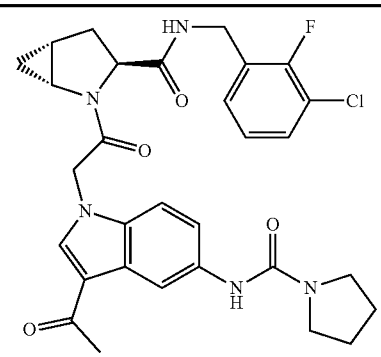 | (1R,3S,5R)-2-(2-(3-acetyl-5-(pyrrolidine-1-carboxamido)-1H-indol-1-yl)acetyl)-N-(3-chloro-2-fluorobenzyl)-2-azabicyclo[3.1.0]hexane-3-carboxamide | *** | 1.72 (A) | 581 |
| 13 | 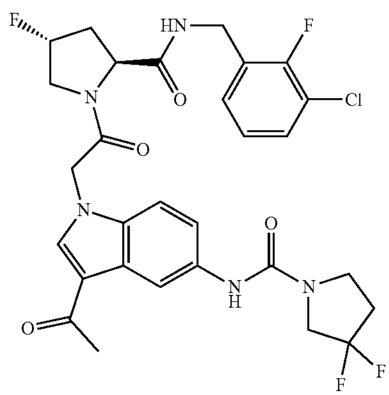 [SMILES: CC(=O)c1cn(CC(=O)N2C[C@H](F)C[C@H]2C(=O)NCc2cccc(Cl)c2F)c2ccc(NC(=O)N3CCC(F)(F)C3)cc12] | N-(3-acetyl-1-(2-((2S,4R)-2-(3-chloro-2-fluorobenzylcarbamoyl)-4-fluoropyrrolidin-1-yl)-2-oxoethyl)-1H-indol-5-yl)-3,3-difluoropyrrolidine-1-carboxamide | *** | 1.77 (A) | 622 |
| 14 | 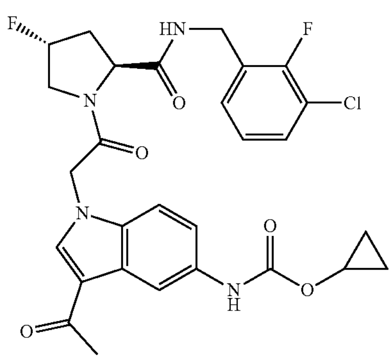 [SMILES: CC(=O)c1cn(CC(=O)N2C[C@H](F)C[C@H]2C(=O)NCc2cccc(Cl)c2F)c2ccc(NC(=O)OC3CC3)cc12] | cyclopropyl 3-acetyl-1-(2-((2S,4R)-2-(3-chloro-2-fluorobenzylcarbamoyl)-4-fluoropyrrolidin-1-yl)-2-oxoethyl)-1H-indol-5-ylcarbamate | *** | 1.78 (A) | 573 |
| 15 | 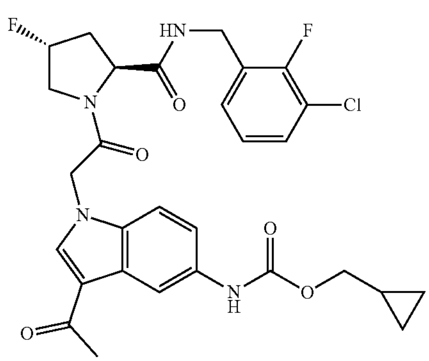 [SMILES: CC(=O)c1cn(CC(=O)N2C[C@H](F)C[C@H]2C(=O)NCc2cccc(Cl)c2F)c2ccc(NC(=O)OCC3CC3)cc12] | cyclopropylmethyl 3-acetyl-1-(2-((2S,4R)-2-(3-chloro-2-fluorobenzylcarbamoyl)-4-fluoropyrrolidin-1-yl)-2-oxoethyl)-1H-indol-5-ylcarbamate | *** | 1.96 (A) | 587 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 16 | 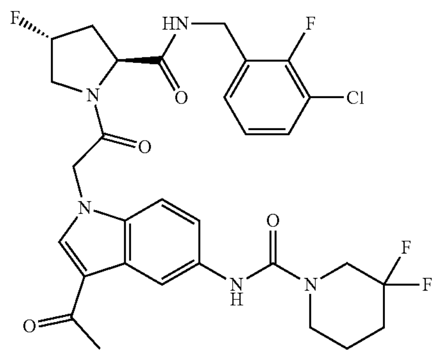 [SMILES: CC(=O)c1cn(CC(=O)N2C[C@H](F)C[C@H]2C(=O)NCc2cccc(Cl)c2F)c2ccc(NC(=O)N3CCCC(F)(F)C3)cc12] | N-(3-acetyl-1-(2-((2S,4R)-2-(3-chloro-2-fluorobenzylcarbamoyl)-4-fluoropyrrolidin-1-yl)-2-oxoethyl)-1H-indol-5-yl)-3,3-difluoropiperidine-1-carboxamide | *** | 1.82 (A) | 636 |
| 17 | 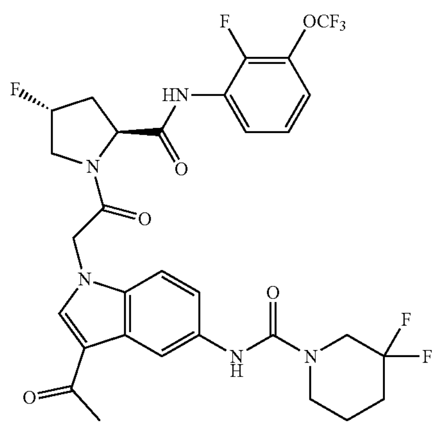 [SMILES: CC(=O)c1cn(CC(=O)N2C[C@H](F)C[C@H]2C(=O)Nc2cccc(OC(F)(F)F)c2F)c2ccc(NC(=O)N3CCCC(F)(F)C3)cc12] | N-(3-acetyl-1-(2-((2S,4R)-4-fluoro-2-(2-fluoro-3-(trifluoromethoxy)phenylcarbamoyl)pyrrolidin-1-yl)-2-oxoethyl)-1H-indol-5-yl)-3,3-difluoropiperidine-1-carboxamide | *** | 2.06 (A) | 672 |
| 18 | 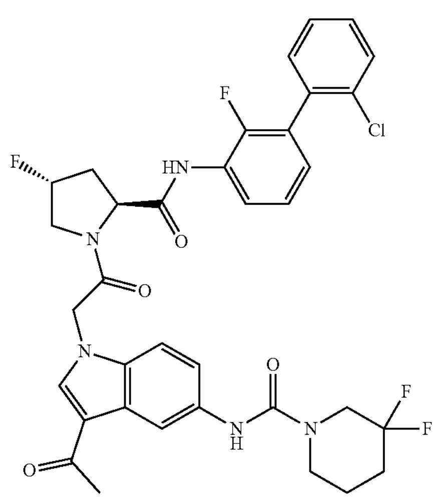 [SMILES: CC(=O)c1cn(CC(=O)N2C[C@H](F)C[C@H]2C(=O)Nc2cccc(-c3ccccc3Cl)c2F)c2ccc(NC(=O)N3CCCC(F)(F)C3)cc12] | N-(3-acetyl-1-(2-((2S,4R)-2-(2'-chloro-2-fluorobiphenyl-3-ylcarbamoyl)-4-fluoropyrrolidin-1-yl)-2-oxoethyl)-1H-indol-5-yl)-3,3-difluoropiperidine-1-carboxamide | *** | 2.25 (A) | 698 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 19 | 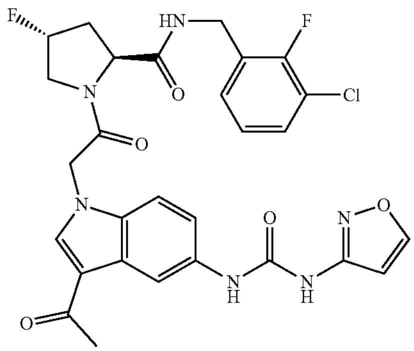 [SMILES: CC(=O)c1cn(CC(=O)N2C[C@H](F)C[C@H]2C(=O)NCc2cccc(Cl)c2F)c2ccc(NC(=O)Nc3ccon3)cc12] | (2S,4R)-1-(2-(3-acetyl-5-(3-isoxazol-3-ylureido)-1H-indol-1-yl)acetyl)-N-(3-chloro-2-fluorobenzyl)-4-fluoropyrrolidine-2-carboxamide | *** | 1.60 (A) | 599 |
| 20 | 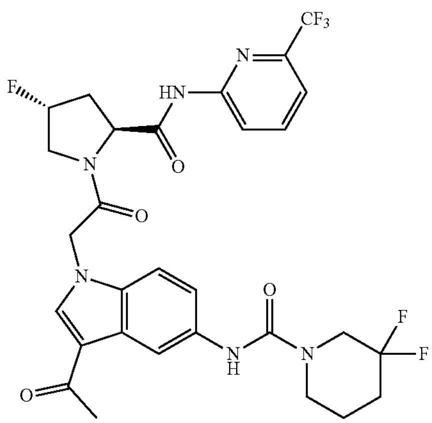 [SMILES: CC(=O)c1cn(CC(=O)N2C[C@H](F)C[C@H]2C(=O)Nc2cccc(C(F)(F)F)n2)c2ccc(NC(=O)N3CCCC(F)(F)C3)cc12] | N-(3-acetyl-1-(2-((2S,4R)-4-fluoro-2-(6-(trifluoromethyl)pyridin-2-ylcarbamoyl)pyrrolidin-1-yl)-2-oxoethyl)-1H-indol-5-yl)-3,3-difluoropiperidine-1-carboxamide | *** | 1.89 (A) | 639 |
| 21 | 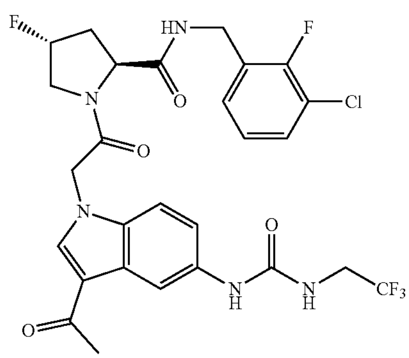 [SMILES: CC(=O)c1cn(CC(=O)N2C[C@H](F)C[C@H]2C(=O)NCc2cccc(Cl)c2F)c2ccc(NC(=O)NCC(F)(F)F)cc12] | (2S,4R)-1-(2-(3-acetyl-5-(3-(2,2,2-trifluoroethyl)ureido)-1H-indol-1-yl)acetyl)-N-(3-chloro-2-fluorobenzyl)-4-fluoropyrrolidine-2-carboxamide | *** | 1.72 (A) | 614 |
| 22 | 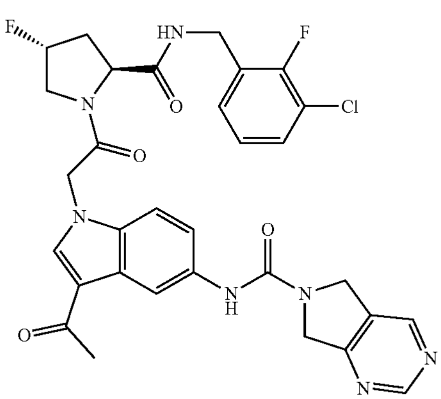 [SMILES: CC(=O)c1cn(CC(=O)N2C[C@H](F)C[C@H]2C(=O)NCc2cccc(Cl)c2F)c2ccc(NC(=O)N3Cc4cncnc4C3)cc12] | N-(3-acetyl-1-(2-((2S,4R)-2-(3-chloro-2-fluorobenzylcarbamoyl)-4-fluoropyrrolidin-1-yl)-2-oxoethyl)-1H-indol-5-yl)-5H-pyrrolo[3,4-d]pyrimidine-6(7H)-carboxamide | *** | 1.38 (A) | 636 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 23 | 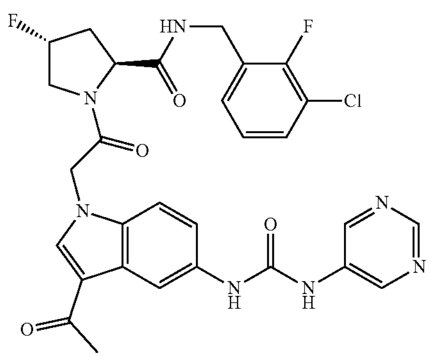 [SMILES: CC(=O)c1cn(CC(=O)N2C[C@H](F)C[C@H]2C(=O)NCc2cccc(Cl)c2F)c2ccc(NC(=O)Nc3cncnc3)cc12] | (2S,4R)-1-(2-(3-acetyl-5-(3-pyrimidin-5-ylureido)-1H-indol-1-yl)acetyl)-N-(3-chloro-2-fluorobenzyl)-4-fluoropyrrolidine-2-carboxamide | *** | 1.40 (A) | 610 |
| 24 | 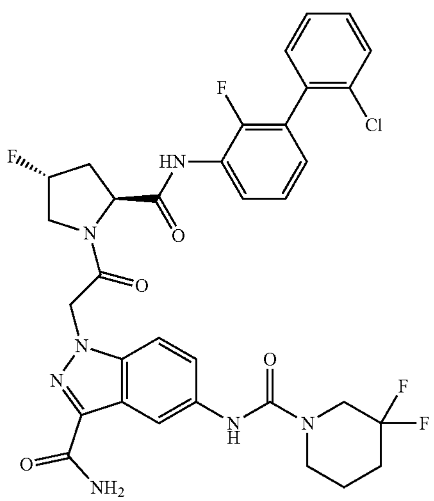 | 1-(2-((2S,4R)-2-(2'-chloro-2-fluorobiphenyl-3-ylcarbamoyl)-4-fluoropyrrolidin-1-yl)-2-oxoethyl)-5-(3,3-difluoropiperidine-1-carboxamido)-1H-indazole-3-carboxamide | *** | 2.09 (A) | 700 |
| 25 | 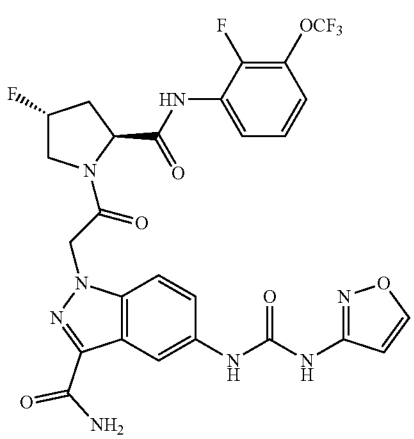 [SMILES: NC(=O)c1nn(CC(=O)N2C[C@H](F)C[C@H]2C(=O)Nc2cccc(OC(F)(F)F)c2F)c2ccc(NC(=O)Nc3ccon3)cc12] | 1-(2-((2S,4R)-4-fluoro-2-(2-fluoro-3-(trifluoromethoxy)phenylcarbamoyl)pyrrolidin-1-yl)-2-oxoethyl)-5-(3-isoxazol-3-ylureido)-1H-indazole-3-carboxamide | *** | 1.71 (A) | 637 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 26 | 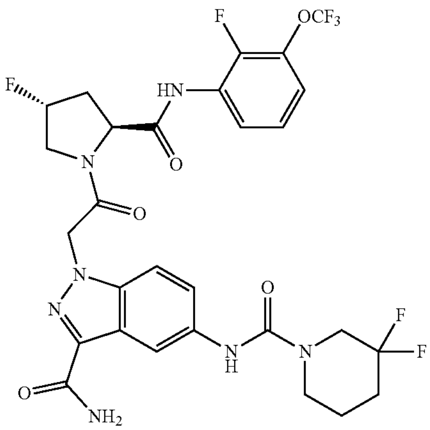 [SMILES: NC(=O)c1nn(CC(=O)N2C[C@H](F)C[C@H]2C(=O)Nc2cccc(OC(F)(F)F)c2F)c2ccc(NC(=O)N3CCCC(F)(F)C3)cc12] | 5-(3,3-difluoropiperidine-1-carboxamido)-1-(2-((2S,4R)-4-fluoro-2-(2-fluoro-3-(trifluoromethoxy)phenylcarbamoyl)-2-azabicylco[3.1.0]hexan-2-yl)-2-oxoethyl)-1H-indazole-3-carboxamide | *** | 1.90 (A) | 674 |
| 27 | 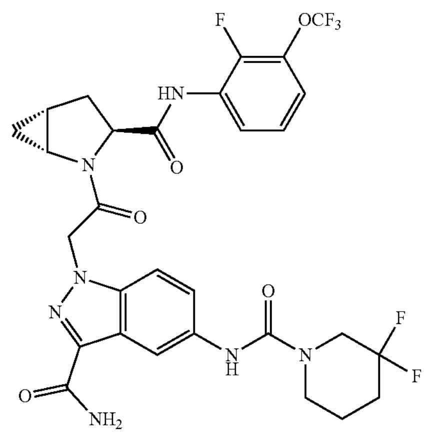 [SMILES: NC(=O)c1nn(CC(=O)N2[C@@H]3C[C@@H]3C[C@H]2C(=O)Nc2cccc(OC(F)(F)F)c2F)c2ccc(NC(=O)N3CCCC(F)(F)C3)cc12] | 5-(3,3-difluoropiperidine-1-carboxamido)-1-(2-((1R,3S,5R)-3-(2-fluoro-3-(trifluoromethoxy)phenylcarbamoyl)-2-azabicylco[3.1.0]hexan-2-yl)-2-oxoethyl)-1H-indazole-3-carboxamide | *** | 1.97 (A) | 668 |
| 28 | 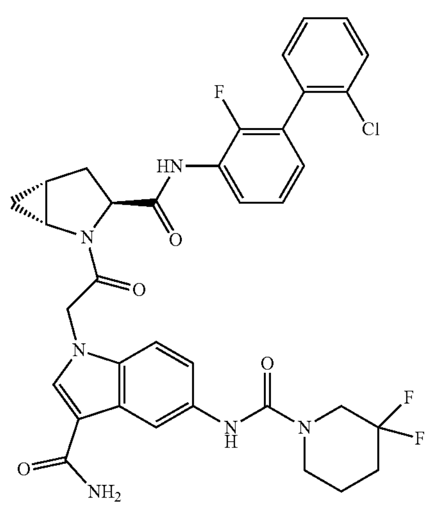 [SMILES: NC(=O)c1cn(CC(=O)N2[C@@H]3C[C@@H]3C[C@H]2C(=O)Nc2cccc(-c3ccccc3Cl)c2F)c2ccc(NC(=O)N3CCCC(F)(F)C3)cc12] | 1-(2-((1R,3S,5R)-3-(2'-chloro-2-fluorobiphenyl-3-ylcarbamoyl)-2-azabicyclo[3.1.0]hexan-2-yl)-2-oxoethyl)-5-(3,3-difluoropiperidine-1-carboxamido)-1H-indazole-3-carboxamide | *** | 2.17 (A) | 694 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 29 | 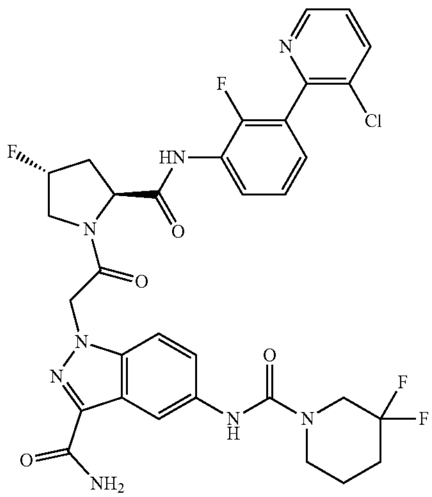 [SMILES: NC(=O)c1nn(CC(=O)N2C[C@H](F)C[C@H]2C(=O)Nc2cccc(-c3ncccc3Cl)c2F)c2ccc(NC(=O)N3CCCC(F)(F)C3)cc12] | 1-(2-((2S,4R)-2-(3-(3-chloropyridin-2-yl)-2-fluorophenylcarbamoyl)-4-fluoropyrrolidin-1-yl)-2-oxoethyl)-5-(3,3-difluoropiperidine-1-carboxamido)-1H-indazole-3-carboxamide | *** | 1.65 (A) | 701 |
| 30 | 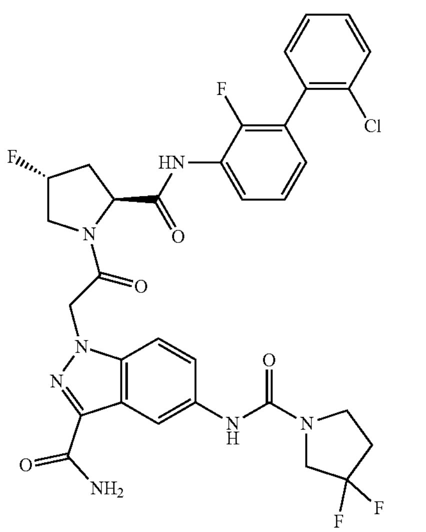 [SMILES: NC(=O)c1nn(CC(=O)N2C[C@H](F)C[C@H]2C(=O)Nc2cccc(-c3ccccc3Cl)c2F)c2ccc(NC(=O)N3CCC(F)(F)C3)cc12] | 1-(2-((2S,4R)-2-(2'-chloro-2-fluorobiphenyl-3-ylcarbamoyl)-4-fluoropyrrolidin-1-yl)-2-oxoethyl)-5-(3,3-difluoropyrrolidine-1-carboxamido)-1H-indazole-3-carboxamide | *** | 2.03 (A) | 686 |
| 31 | 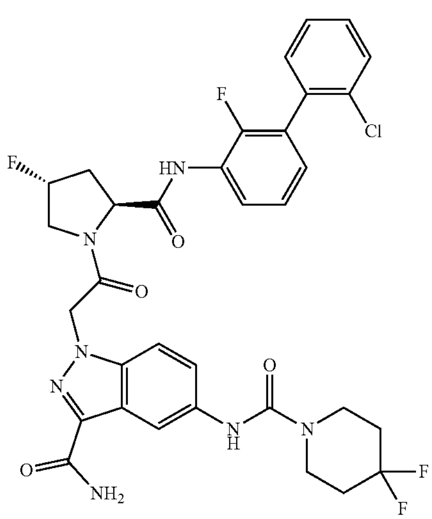 [SMILES: NC(=O)c1nn(CC(=O)N2C[C@H](F)C[C@H]2C(=O)Nc2cccc(-c3ccccc3Cl)c2F)c2ccc(NC(=O)N3CCC(F)(F)CC3)cc12] | 1-(2-((2S,4R)-2-(2'-chloro-2-fluorobiphenyl-3-ylcarbamoyl)-4-fluoropyrrolidin-1-yl)-2-oxoethyl)-5-(4,4-difluoropiperidine-1-carboxamido)-1H-indazole-3-carboxamide | *** | 2.11 (A) | 700 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 32 | 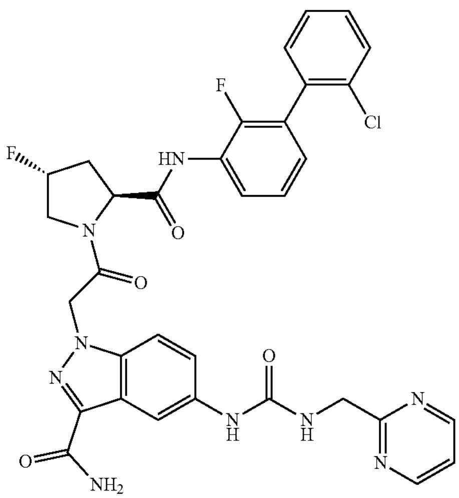 [SMILES: NC(=O)c1nn(CC(=O)N2C[C@H](F)C[C@H]2C(=O)Nc2cccc(-c3ccccc3Cl)c2F)c2ccc(NC(=O)NCc3ncccn3)cc12] | 1-(2-((2S,4R)-2-(2'-chloro-2-fluorobiphenyl-3-ylcarbamoyl)-4-fluoropyrrolidin-1-yl)-2-oxoethyl)-5-(3-(pyrimidin-2-ylmethyl)ureido)-1H-indazole-3-carboxamide | *** | 1.69 (A) | 688 |
| 33 | 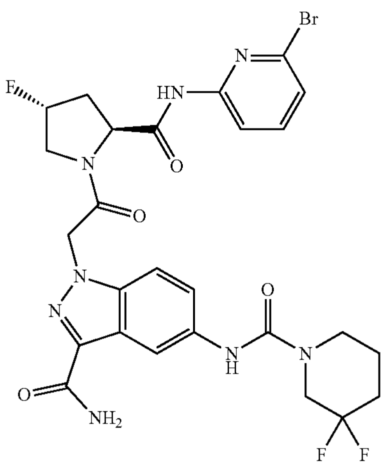 [SMILES: NC(=O)c1nn(CC(=O)N2C[C@H](F)C[C@H]2C(=O)Nc2cccc(Br)n2)c2ccc(NC(=O)N3CCCC(F)(F)C3)cc12] | 1-(2-((2S,4R)-2-(6-bromopyridin-2-ylcarbamoyl)-4-fluoropyrrolidin-1-yl)-2-oxoethyl)-5-(3,3-difluoropiperidine-1-carboxamido)-1H-indazole-3-carboxamide | *** | 1.59 (A) | 651 |
| 34 | 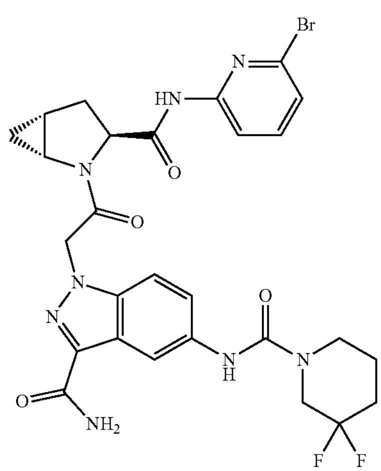 [SMILES: NC(=O)c1nn(CC(=O)N2[C@@H]3C[C@@H]3C[C@H]2C(=O)Nc2cccc(Br)n2)c2ccc(NC(=O)N3CCCC(F)(F)C3)cc12] | 1-(2-((1R,3S,5R)-3-(6-bromopyridin-2-ylcarbamoyl)-2-azabicylco[3.1.0]hexan-2-yl)-2-oxoethyl)-5-(3,3-difluoropiperidine-1-carboxamido)-1H-indazole-3-carboxamide | *** | 1.75 (A) | 645 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 35 | 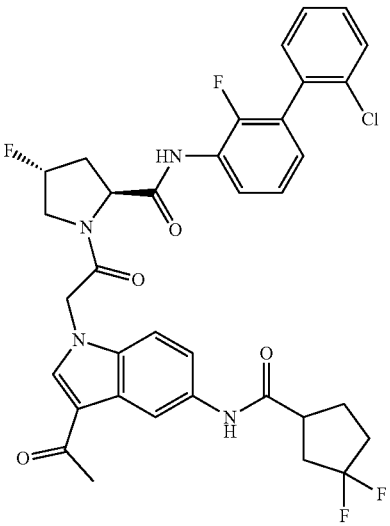 [SMILES: CC(=O)c1cn(CC(=O)N2C[C@H](F)C[C@H]2C(=O)Nc2cccc(-c3ccccc3Cl)c2F)c2ccc(NC(=O)C3CCC(F)(F)C3)cc12] | (2S,4R)-1-(2-(3-acetyl-5-(3,3-difluorocyclopentane-carboxamido)-1H-indol-1-yl)acetyl)-N-(2'-chloro-2-fluorobiphenyl-3-yl)-4-fluoropyrrolidine-2-carboxamide | *** | 2.61 (A) | 683 |
| 36 | 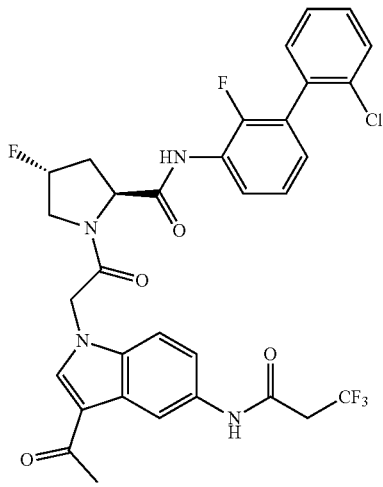 [SMILES: CC(=O)c1cn(CC(=O)N2C[C@H](F)C[C@H]2C(=O)Nc2cccc(-c3ccccc3Cl)c2F)c2ccc(NC(=O)CC(F)(F)F)cc12] | (2S,4R)-1-(2-(3-acetyl-5-(3,3,3-trifluoropropanamido)-1H-indol-1-yl)acetyl)-N-(2'-chloro-2-fluorobiphenyl-3-yl)-4-fluoropyrrolidine-2-carboxamide | *** | 2.70 (A) | 661 |
| 37 | 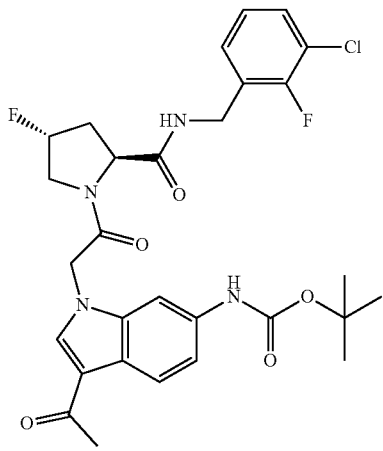 [SMILES: CC(=O)c1cn(CC(=O)N2C[C@H](F)C[C@H]2C(=O)NCc2cccc(Cl)c2F)c2cc(NC(=O)OC(C)(C)C)ccc12] | tert-butyl 3-acetyl-1-(2-((2S,4R)-2-(3-chloro-2-fluorobenzylcarbamoyl)-4-fluoropyrrolidin-1-yl)-2-oxoethyl)-1H-indol-6-ylcarbamate | *** | 1.90 (A) | 589 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 38 | 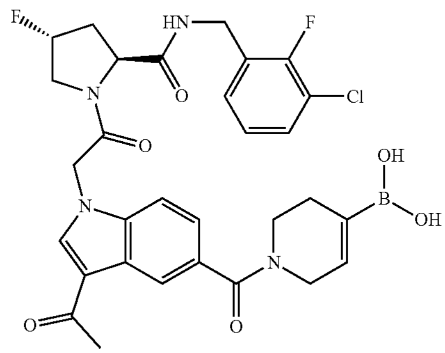 [SMILES: CC(=O)c1cn(CC(=O)N2C[C@H](F)C[C@H]2C(=O)NCc2cccc(Cl)c2F)c2ccc(C(=O)N3CC=C(B(O)O)CC3)cc12] | 1-(3-acetyl-1-(2-((2S,4R)-2-(3-chloro-2-fluorobenzylcarbamoyl)-4-fluoropyrrolidin-1-yl)-2-oxoethyl)-1H-indole-5-carbonyl)-1,2,3,6-tetrahydropyridin-4-ylboronic acid | *** | 0.93 (A) | 627 |
| 39 | 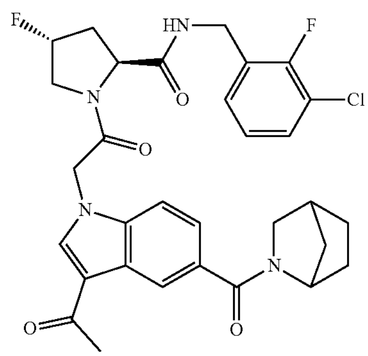 [SMILES: CC(=O)c1cn(CC(=O)N2C[C@H](F)C[C@H]2C(=O)NCc2cccc(Cl)c2F)c2ccc(C(=O)N3CC4CCC3C4)cc12] | (2S,4R)-1-(2-(3-acetyl-5-(2-azabicyclo[2.2.1]heptane-2-carbonyl)-1H-indol-1-yl)acetyl)-N-(3-chloro-2-fluorobenzyl)-4-fluoropyrrolidine-2-carboxamide | *** | 1.76 (A) | 597 |
| 40 | 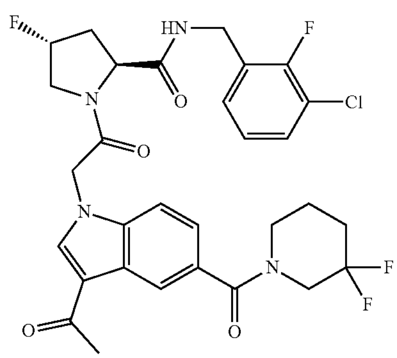 [SMILES: CC(=O)c1cn(CC(=O)N2C[C@H](F)C[C@H]2C(=O)NCc2cccc(Cl)c2F)c2ccc(C(=O)N3CCCC(F)(F)C3)cc12] | (2S,4R)-1-(2-(3-acetyl-5-(3,3-difluoropiperidine-1-carbonyl)-1H-indol-1-yl)acetyl)-N-(3-chloro-2-fluorobenzyl)-4-fluoropyrrolidine-2-carboxamide | *** | 1.83 (A) | 621 |
| 41 | 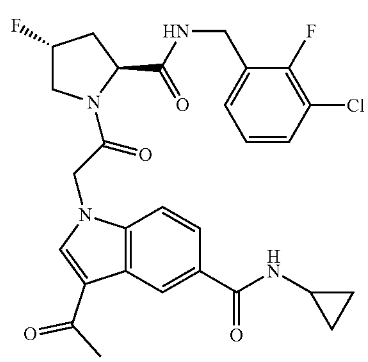 [SMILES: CC(=O)c1cn(CC(=O)N2C[C@H](F)C[C@H]2C(=O)NCc2cccc(Cl)c2F)c2ccc(C(=O)NC3CC3)cc12] | 3-acetyl-1-(2-((2S,4R)-2-(3-chloro-2-fluorobenzylcarbamoyl)-4-fluoropyrrolidin-1-yl)-2-oxoethyl)-N-cyclopropyl-1H-indole-5-carboxamide | *** | 1.54 (A) | 557 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 42 | 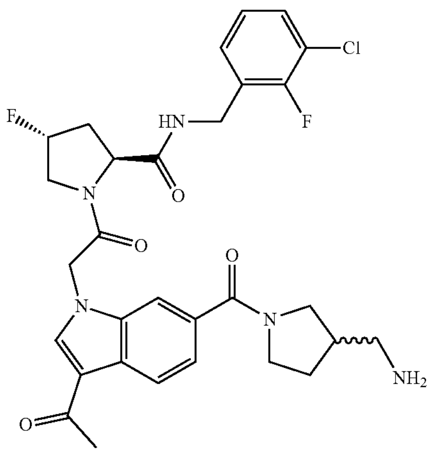 [SMILES: CC(=O)c1cn(CC(=O)N2C[C@H](F)C[C@H]2C(=O)NCc2cccc(Cl)c2F)c2cc(C(=O)N3CCC(CN)C3)ccc12] | (2S,4R)-1-(2-(3-acetyl-6-(3-(aminomethyl)-pyrrolidine-1-carbonyl)-1H-indol-1-yl)acetyl)-N-(3-chloro-2-fluorobenzyl)-4-fluoropyrrolidine-2-carboxamide | *** | 1.02 (A) | 600 |
| 43 | 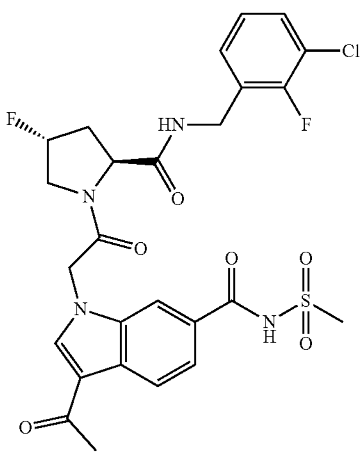 [SMILES: CC(=O)c1cn(CC(=O)N2C[C@H](F)C[C@H]2C(=O)NCc2cccc(Cl)c2F)c2cc(C(=O)NS(C)(=O)=O)ccc12] | 3-acetyl-1-(2-((2S,4R)-2-(3-chloro-2-fluorobenzyl-carbamoyl)-4-fluoropyrrolidin-1-yl)-2-oxoethyl)-N-(methylsulfonyl)-1H-indole-6-carboxamide | *** | 1.60 (A) | 595 |
| 44 | 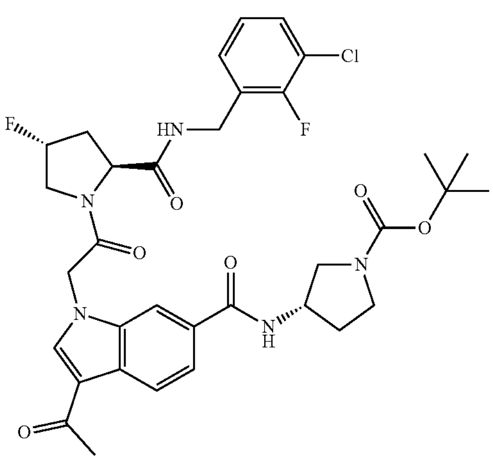 [SMILES: CC(=O)c1cn(CC(=O)N2C[C@H](F)C[C@H]2C(=O)NCc2cccc(Cl)c2F)c2cc(C(=O)N[C@H]3CCN(C(=O)OC(C)(C)C)C3)ccc12] | (S)-tert-butyl 3-(3-acetyl-1-(2-((2S,4R)-2-(3-chloro-2-fluorobenzyl-carbamoyl)-4-fluoropyrrolidin-1-yl)-2-oxoethyl)-1H-indole-6-carboxamido)pyrrolidine-1-carboxylate | *** | 1.92 (A) | 686 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 45 | 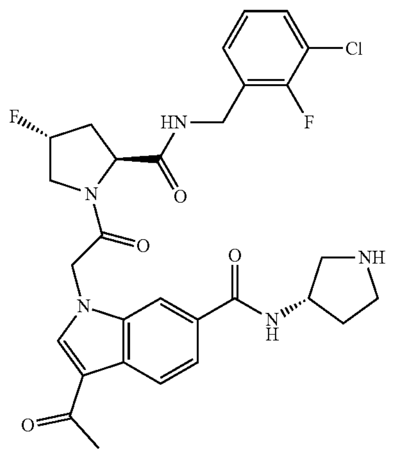 [SMILES: CC(=O)c1cn(CC(=O)N2C[C@H](F)C[C@H]2C(=O)NCc2cccc(Cl)c2F)c2cc(C(=O)N[C@H]3CCNC3)ccc12] | 3-acetyl-1-(2-((2S,4R)-2-(3-chloro-2-fluorobenzyl-carbamoyl)-4-fluoropyrrolidin-1-yl)-2-oxoethyl)-N-((S)-pyrrolidin-3-yl)-1H-indole-6-carboxamide | *** | 1.10 (A) | 586 |
| 46 | 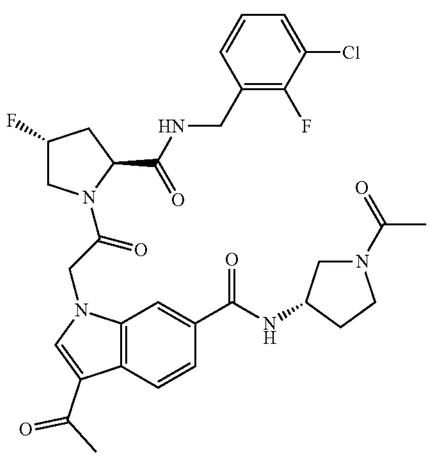 [SMILES: CC(=O)c1cn(CC(=O)N2C[C@H](F)C[C@H]2C(=O)NCc2cccc(Cl)c2F)c2cc(C(=O)N[C@H]3CCN(C(C)=O)C3)ccc12] | 3-acetyl-N-((S)-1-acetylpyrrolidin-3-yl)-1-(2-((2S,4R)-2-(3-chloro-2-fluorobenzylcarbamoyl)-4-fluoropyrrolidin-1-yl)-2-oxoethyl)-1H-indole-6-carboxamide | *** | 1.30 (A) | 628 |
| 48 | 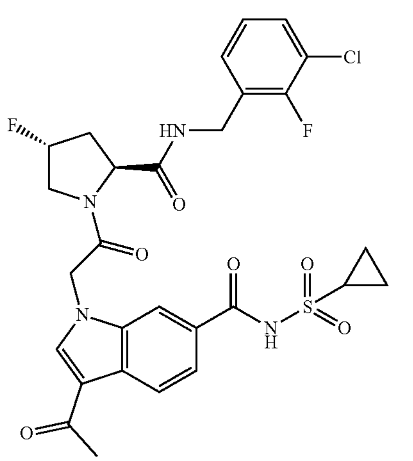 [SMILES: CC(=O)c1cn(CC(=O)N2C[C@H](F)C[C@H]2C(=O)NCc2cccc(Cl)c2F)c2cc(C(=O)NS(=O)(=O)C3CC3)ccc12] | 3-acetyl-1-(2-((2S,4R)-2-(3-chloro-2-fluorobenzylcarbamoyl)-4-fluoropyrrolidin-1-yl)-2-oxoethyl)-N-(cyclopropylsulfonyl)-1H-indole-6-carboxamide | *** | 1.52 (A) | 621 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 49 | 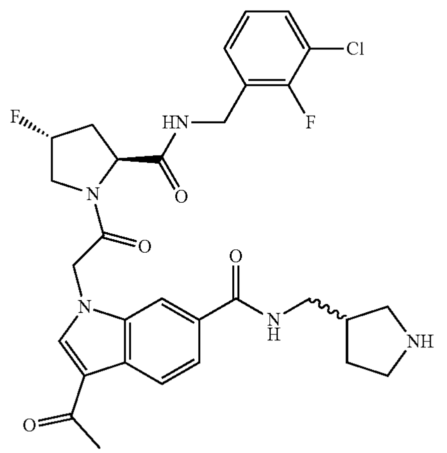 [SMILES: CC(=O)c1cn(CC(=O)N2C[C@H](F)C[C@H]2C(=O)NCc2cccc(Cl)c2F)c2cc(C(=O)NCC3CCNC3)ccc12] | 3-acetyl-1-(2-((2S,4R)-2-(3-chloro-2-fluorobenzylcarbamoyl)-4-fluoropyrrolildin-1-yl)-2-oxoethyl)-N-(pyrrolidin-3-ylmethyl)-1H-indole-6-carboxamide | *** | 0.70 (A) | 600 |
| 50 | 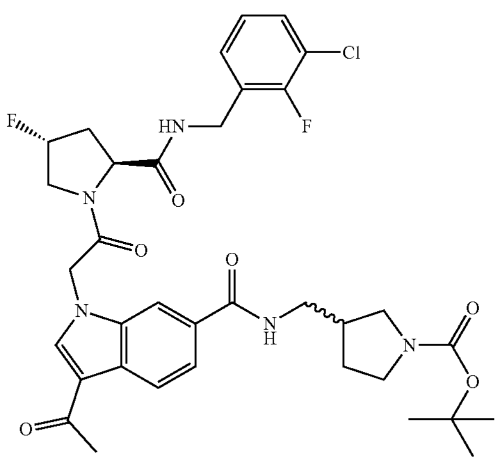 [SMILES: CC(=O)c1cn(CC(=O)N2C[C@H](F)C[C@H]2C(=O)NCc2cccc(Cl)c2F)c2cc(C(=O)NCC3CCN(C(=O)OC(C)(C)C)C3)ccc12] | tert-butyl 3-((3-acetyl-1-(2-((2S,4R)-2-(3-chloro-2-fluorobenzylcarbamoyl)-4-fluoropyrrolidin-1-yl)-2-oxoethyl)-1H-indole-6-carboxamido)methyl)pyrrolidine-1-carboxylate | *** | 1.77 (A) | 700 |
| 51 | 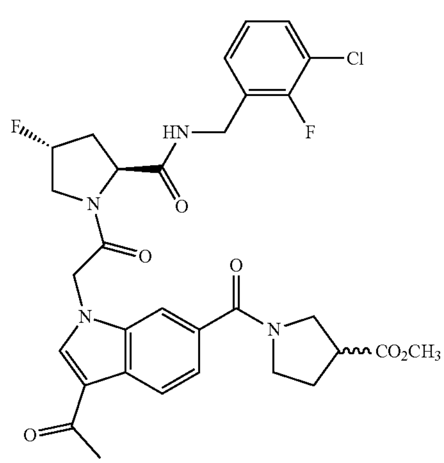 [SMILES: COC(=O)C1CCN(C(=O)c2ccc3c(C(C)=O)cn(CC(=O)N4C[C@H](F)C[C@H]4C(=O)NCc4cccc(Cl)c4F)c3c2)C1] | methyl 1-(3-acetyl-1-(2-((2S,4R)-2-(3-chloro-2-fluorobenzylcarbamoyl)-4-fluoropyrrolidin-1-yl)-2-oxoethyl)-1H-indole-6-carbonyl)pyrrolidine-3-carboxylate | *** | 1.28 (A) | 629 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 52 | 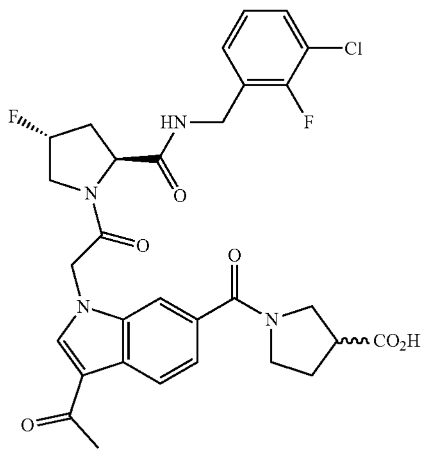 [SMILES: CC(=O)c1cn(CC(=O)N2C[C@H](F)C[C@H]2C(=O)NCc2cccc(Cl)c2F)c2cc(C(=O)N3CCC(C(=O)O)C3)ccc12] | 1-(3-acetyl-1-(2-((2S,4R)-2-(3-chloro-2-fluorobenzylcarbamoyl)-4-fluoropyrrolidin-1-yl)-2-oxoethyl)-1H-indole-6-carbonyl)pyrrolidine-3-carboxylic acid | *** | 1.14 (A) | 615 |
| 53 | 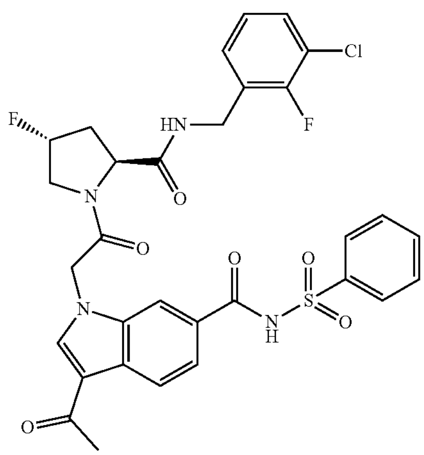 [SMILES: CC(=O)c1cn(CC(=O)N2C[C@H](F)C[C@H]2C(=O)NCc2cccc(Cl)c2F)c2cc(C(=O)NS(=O)(=O)c3ccccc3)ccc12] | 3-acetyl-1-(2-((2S,4R)-2-(3-chloro-2-fluorobenzylcarbamoyl)-4-fluoropyrrolidin-1-yl)-2-oxoethyl)-N-(phenylsulfonyl)-1H-indole-6-carboxamide | *** | 1.71 (A) | 657 |
| 54 | 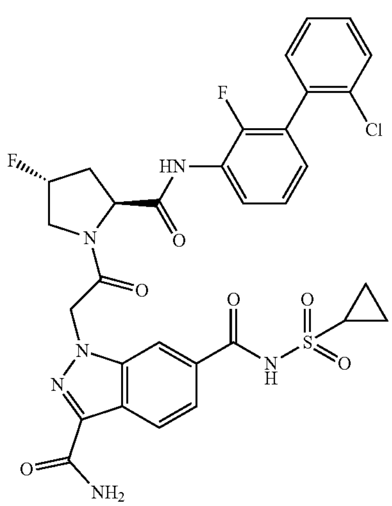 [SMILES: NC(=O)c1nn(CC(=O)N2C[C@H](F)C[C@H]2C(=O)Nc2cccc(-c3ccccc3Cl)c2F)c2cc(C(=O)NS(=O)(=O)C3CC3)ccc12] | 1-(2-((2S,4R)-2-(2'-chloro-2-fluorobiphenyl-3-ylcarbamoyl)-4-fluoropyrrolidin-1-yl)-2-oxoethyl)-N6-(cyclopropylsulfonyl)-1H-indazole-3,6-dicarboxamide | *** | 2.00 (A) | 685 |

Table 2 provides additional compounds within the scope of the present invention. The assay of Example 15 was used to determine the IC$_{50}$'s of the compounds. Other standard Factor D inhibition assays are also available. Three *s are used to denote compounds with an IC$_{50}$ less than 1 micromolar; two s indicate compound with an IC$_{50}$ between 1 micromolar and 10 micromolar, and one * denotes compounds with an IC$_{50}$ greater than 10 micromolar.

TABLE 2

Additional Compounds of the Present Invention

| Cmp No. | Structure | Name | IC$_{50}$ | RT min (Method A or B) | MS (M + 1) |
|---|---|---|---|---|---|
| 55 | 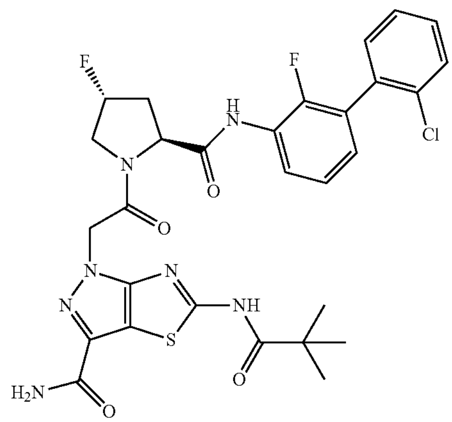 [SMILES: CC(C)(C)C(=O)Nc1nc2c(s1)c(C(N)=O)nn2CC(=O)N1C[C@H](F)C[C@H]1C(=O)Nc1cccc(-c2ccccc2Cl)c1F] | 1-(2-((2S,4R)-2-(2'-chloro-2-fluorobiphenyl-3-ylcarbamoyl)-4-fluoropyrrolidin-1-yl)-2-oxoethyl)-5-pivalamido-1H-pyrazolo[3,4-d]thiazole-3-carboxamide | *** | 2.20 (A) | 644 |
| 56 | 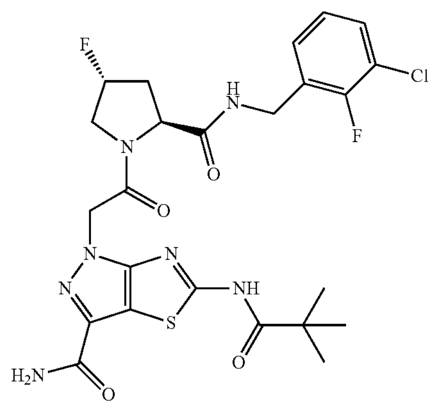 [SMILES: CC(C)(C)C(=O)Nc1nc2c(s1)c(C(N)=O)nn2CC(=O)N1C[C@H](F)C[C@H]1C(=O)NCc1cccc(Cl)c1F] | 1-(2-((2S,4R)-2-(3-chloro-2-fluorobenzylcarbamoyl)-4-fluoropyrrolidin-1-yl)-2-oxoethyl)-5-pivalamido-1H-pyrazolo[3,4-d]thiazole-3-carboxamide | *** | 1.77 (A) | 582 |
| 57 | 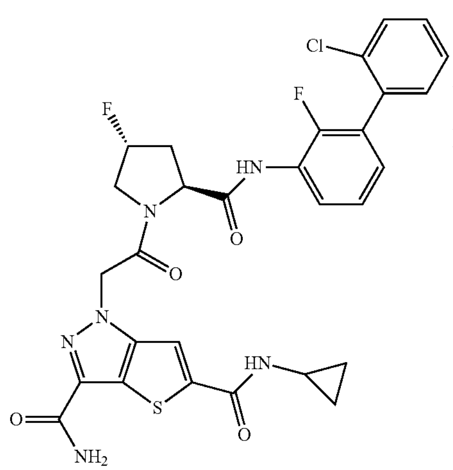 [SMILES: NC(=O)c1nn(CC(=O)N2C[C@H](F)C[C@H]2C(=O)Nc2cccc(-c3ccccc3Cl)c2F)c2cc(C(=O)NC3CC3)sc12] | 1-(2-((2S,4R)-2-(2'-chloro-2-fluorobiphenyl-3-ylcarbamoyl)-4-fluoropyrrolidin-1-yl)-2-oxoethyl)-N5-cyclopropyl-1H-thieno[3,2-c]pyrazole-3,5-dicarboxamide | *** | 1.96 (A) | 627 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 58 | 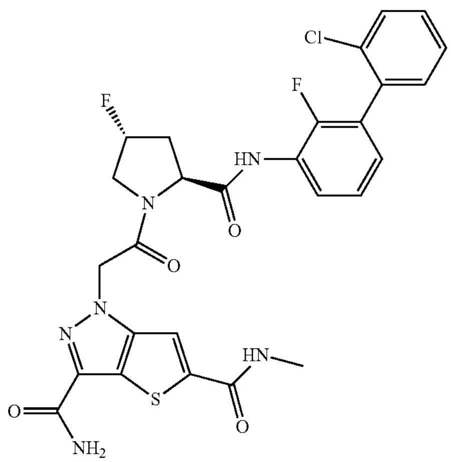 [SMILES: CNC(=O)c1cc2c(s1)c(C(N)=O)nn2CC(=O)N1C[C@H](F)C[C@H]1C(=O)Nc1cccc(-c2ccccc2Cl)c1F] | 1-(2-((2S,4R)-2-(2'-chloro-2-fluorobiphenyl-3-ylcarbamoyl)-4-fluoropyrrolidin-1-yl)-2-oxoethyl)-N5-methyl-1H-thieno[3,2-c]pyrazole-3,5-dicarboxamide | *** | 1.82 (A) | 601 |
| 59 | 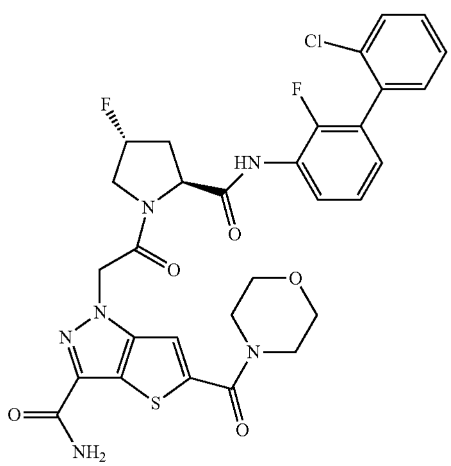 [SMILES: NC(=O)c1nn(CC(=O)N2C[C@H](F)C[C@H]2C(=O)Nc2cccc(-c3ccccc3Cl)c2F)c2cc(C(=O)N3CCOCC3)sc12] | 1-(2-((2S,4R)-2-(2'-chloro-2-fluorobiphenyl-3-ylcarbamoyl)-4-fluoropyrrolidin-1-yl)-2-oxoethyl)-5-(morpholine-4-carbonyl)-1H-thieno[3,2-c]pyrazole-3-carboxamide | *** | 1.88 (A) | 657 |
| 60 | 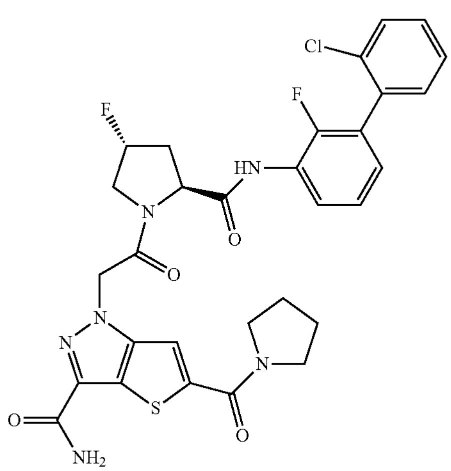 [SMILES: NC(=O)c1nn(CC(=O)N2C[C@H](F)C[C@H]2C(=O)Nc2cccc(-c3ccccc3Cl)c2F)c2cc(C(=O)N3CCCC3)sc12] | 1-(2-((2S,4R)-2-(2'-chloro-2-fluorobiphenyl-3-ylcarbamoyl)-4-fluoropyrrolidin-1-yl)-2-oxoethyl)-5-(pyrrolidine-1-carbonyl)-1H-thieno[3,2-c]pyrazole-3-carboxamide | *** | 2.01 (A) | 641 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 61 | 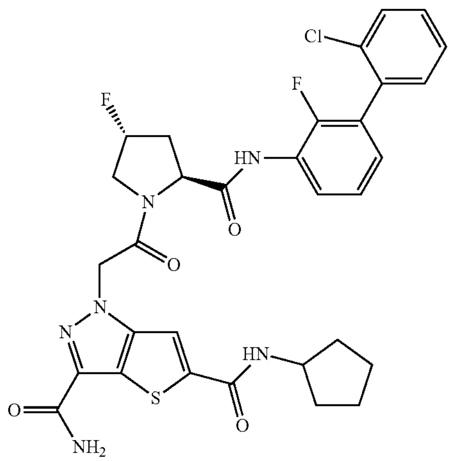 [SMILES: NC(=O)c1nn(CC(=O)N2C[C@H](F)C[C@H]2C(=O)Nc2cccc(-c3ccccc3Cl)c2F)c2cc(C(=O)NC3CCCC3)sc12] | 1-(2-((2S,4R)-2-(2'-chloro-2-fluorobiphenyl-3-ylcarbamoyl)-4-fluoropyrrolidin-1-yl)-2-oxoethyl)-N5-cyclopentyl-1H-thieno[3,2-c]pyrazole-3,5-dicarboxamide | *** | 2.27 (A) | 655 |
| 62 | 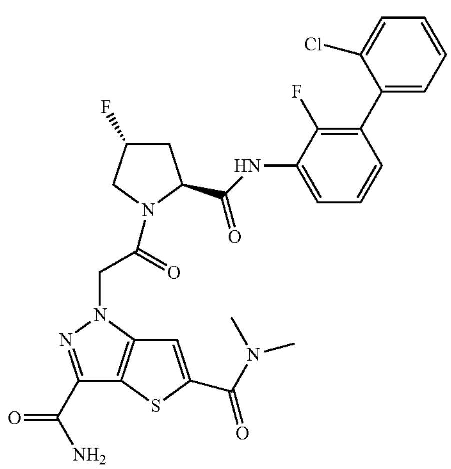 [SMILES: CN(C)C(=O)c1cc2c(s1)c(C(N)=O)nn2CC(=O)N1C[C@H](F)C[C@H]1C(=O)Nc1cccc(-c2ccccc2Cl)c1F] | 1-(2-((2S,4R)-2-(2'-chloro-2-fluorobiphenyl-3-ylcarbamoyl)-4-fluoropyrrolidin-1-yl)-2-oxoethyl)-N5,N5-dimethyl-1H-thieno[3,2-c]pyrazole-3,5-dicarboxamide | *** | 1.89 (A) | 615 |

Table 3 shows illustrative compounds of Formula I with characterizing data. The assay of Example 12 was used to determine the IC$_{50}$'s of the compounds. Other standard factor D inhibition assays are also available. Three *s are used to denote compounds with an IC$_{50}$ less than 1 micromolar; two s indicate compound with an IC$_{50}$ between 1 micromolar and 10 micromolar, and one * denotes compounds with an IC$_{50}$ greater than 10 micromolar.

TABLE 3

Additional Compounds of the Present Invention

| Cmp No. | Structure | Name | IC$_{50}$ (Stars) | RT min (Method A, B, C or D) | MS (M + 1) |
|---|---|---|---|---|---|
| 197 | 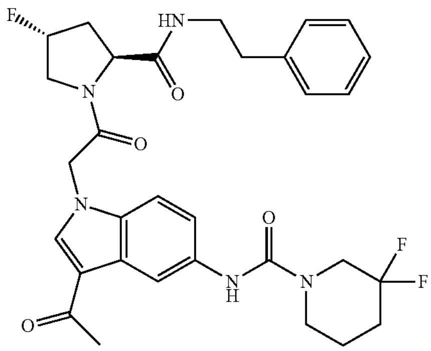 [SMILES: CC(=O)c1cn(CC(=O)N2C[C@H](F)C[C@H]2C(=O)NCCc2ccccc2)c2ccc(NC(=O)N3CCCC(F)(F)C3)cc12] | N-(3-acetyl-1-(2-((2S,4R)-4-fluoro-2-(phenethylcarbamoyl)pyrrolidin-1-yl)-2-oxoethyl)-1H-indol-5-yl)-3,3-difluoropiperidine-1-carboxamide | *** | 10.31 (D) | 598 |
| 198 | 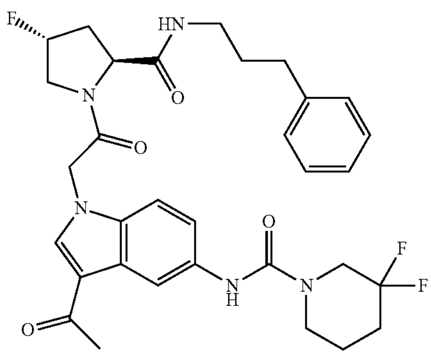 [SMILES: CC(=O)c1cn(CC(=O)N2C[C@H](F)C[C@H]2C(=O)NCCCc2ccccc2)c2ccc(NC(=O)N3CCCC(F)(F)C3)cc12] | N-(3-acetyl-1-(2-((2S,4R)-4-fluoro-2-((3-phenylpropyl)carbamoyl)pyrrolidin-1-yl)-2-oxoethyl)-1H-indol-5-yl)-3,3-difluoropiperidine-1-carboxamide | *** | 10.63 (D) | 612 |
| 199 | 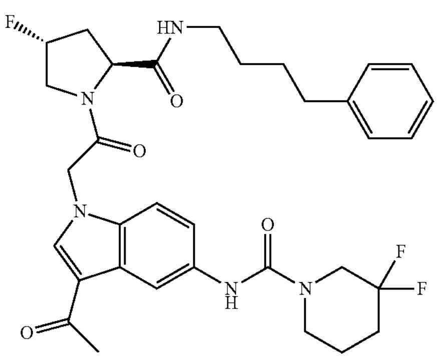 [SMILES: CC(=O)c1cn(CC(=O)N2C[C@H](F)C[C@H]2C(=O)NCCCCc2ccccc2)c2ccc(NC(=O)N3CCCC(F)(F)C3)cc12] | N-(3-acetyl-1-(2-((2S,4R)-4-fluoro-2-((4-phenylbutyl)carbamoyl)pyrrolidin-1-yl)-2-oxoethyl)-1H-indol-5-yl)-3,3-difluoropiperidine-1-carboxamide | *** | 11.28 (D) | 626 |
| 196 | 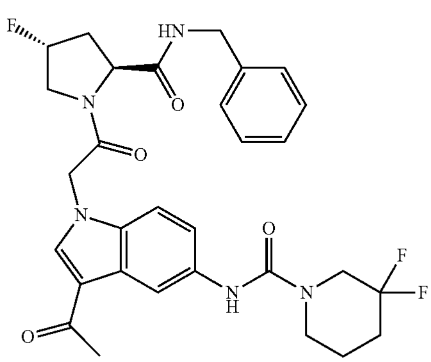 [SMILES: CC(=O)c1cn(CC(=O)N2C[C@H](F)C[C@H]2C(=O)NCc2ccccc2)c2ccc(NC(=O)N3CCCC(F)(F)C3)cc12] | N-(3-acetyl-1-(2-((2S,4R)-2-(benzocarbamoyl)-4-fluoropyrrolidin-1-yl)-2-oxoethyl)-1H-indol-5-yl)-3,3-difluoropiperidine-1-carboxamide | *** | 12.46 (C) | 584 |

TABLE 3-continued

Additional Compounds of the Present Invention

| Cmp No. | Structure | Name | IC$_{50}$ (Stars) | RT min (Method A, B, C or D) | MS (M + 1) |
|---|---|---|---|---|---|
| 205 | 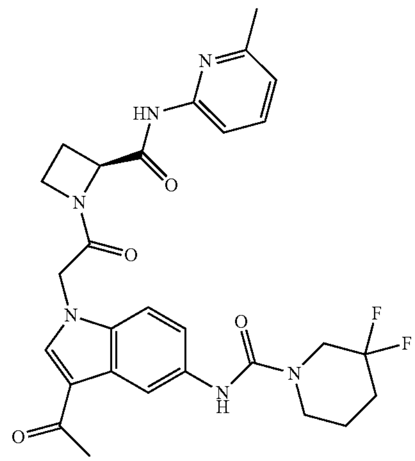 [SMILES: CC(=O)c1cn(CC(=O)N2CC[C@H]2C(=O)Nc2cccc(C)n2)c2ccc(NC(=O)N3CCCC(F)(F)C3)cc12] | (S)-N-(3-acetyl-1-(2-(2-((6-methylpyridin-2-yl)-carbamoyl)-azetidin-1-yl)-2-oxoethyl)-1H-indol-5-yl)-3,3-difluoropiperidine-1-carboxamide | * | 9.66 (D) | 553 |
| 201 | 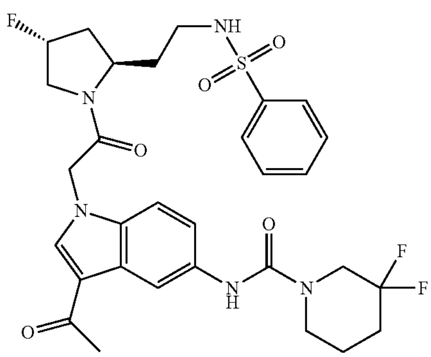 [SMILES: CC(=O)c1cn(CC(=O)N2C[C@H](F)C[C@H]2CCNS(=O)(=O)c2ccccc2)c2ccc(NC(=O)N3CCCC(F)(F)C3)cc12] | N-(3-acetyl-1-(2-((2R,4R)-4-fluoro-2-(2-(phenylsulfonamido)ethyl)pyrrolidin-1-yl)-2-oxoethyl)-1H-indol-5-yl)-3,3-difluoro-piperidine-1-carboxamide | ** | 10.55 (D) | 634 |
| 185 | 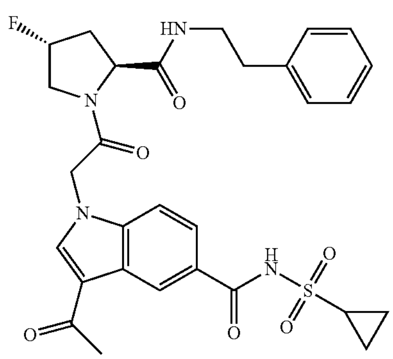 [SMILES: CC(=O)c1cn(CC(=O)N2C[C@H](F)C[C@H]2C(=O)NCCc2ccccc2)c2ccc(C(=O)NS(=O)(=O)C3CC3)cc12] | 3-acetyl-N-(cyclopropylsulfonyl)-1-(2-((2S,4R)-4-fluoro-2-(phenethylcarbamoyl)pyrrolidin-1-yl)-2-oxoethyl)-1H-indole-5-carboxamide | * | 7.73 (D) | 583 |

TABLE 3-continued

Additional Compounds of the Present Invention

| Cmp No. | Structure | Name | IC$_{50}$ (Stars) | RT min (Method A, B, C or D) | MS (M + 1) |
|---|---|---|---|---|---|
| 190 | 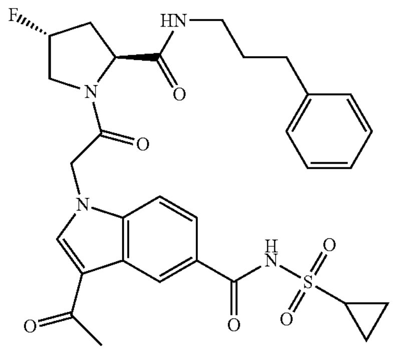 [SMILES: CC(=O)c1cn(CC(=O)N2C[C@H](F)C[C@H]2C(=O)NCCCc2ccccc2)c2ccc(C(=O)NS(=O)(=O)C3CC3)cc12] | 3-acetyl-N-(cyclopropylsulfonyl)-1-(2-((2S,4R)-4-fluoro-2-((3-phenylpropyl)carbamoyl)pyrrolidin-1-yl)-2-oxoethyl)-1H-indole-5-carboxamide | ** | 8.07 (D) | 595 (M − 1) |
| 180 | 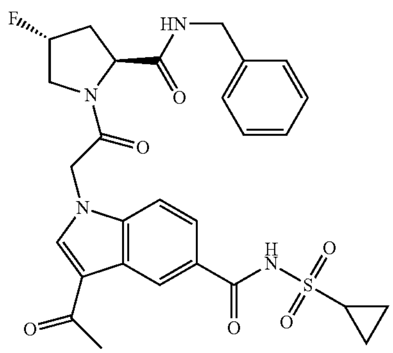 [SMILES: CC(=O)c1cn(CC(=O)N2C[C@H](F)C[C@H]2C(=O)NCc2ccccc2)c2ccc(C(=O)NS(=O)(=O)C3CC3)cc12] | 3-acetyl-1-(2-((2S,4R)-2-(benzylcarbamoyl)-4-fluoropyrrolidin-1-yl)-2-oxoethyl)-N-(cyclopropylsulfonyl)-1H-indole-5-carboxamide | ** | 11.11 (C) | 569 |
| 195 | 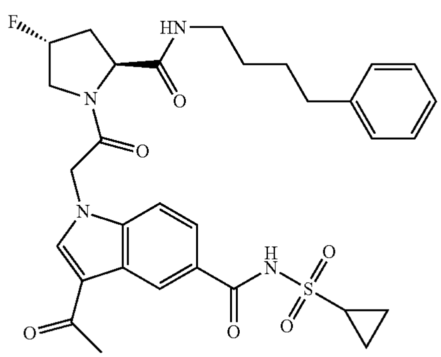 [SMILES: CC(=O)c1cn(CC(=O)N2C[C@H](F)C[C@H]2C(=O)NCCCCc2ccccc2)c2ccc(C(=O)NS(=O)(=O)C3CC3)cc12] | 3-acetyl-N-(cyclopropylsulfonyl)-1-(2-((2S,4R)-4-fluoro-2-((4-phenylbutyl)carbamoyl)pyrrolidin-1-yl)-2-oxoethyl)-1H-indole-5-carboxamide | * | 12.66 (C) | 609 (M − 1) |
| 174 | 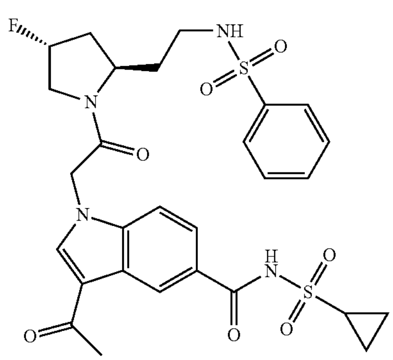 [SMILES: CC(=O)c1cn(CC(=O)N2C[C@H](F)C[C@H]2CCNS(=O)(=O)c2ccccc2)c2ccc(C(=O)NS(=O)(=O)C3CC3)cc12] | 3-acetyl-N-(cyclopropylsulfonyl)-1-(2-((2R,4R)-4-fluoro-2-(2-(phenylsulfonylamido)ethyl)pyrrolidin-1-yl)-2-oxoethyl)-1H-indole-5-carboxamide | * | 8.06 (D) | 617 (M − 1) |

TABLE 3-continued

Additional Compounds of the Present Invention

| Cmp No. | Structure | Name | IC$_{50}$ (Stars) | RT min (Method A, B, C or D) | MS (M + 1) |
|---|---|---|---|---|---|
| 206 | 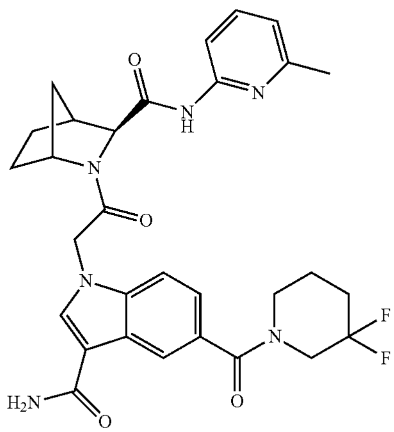 [SMILES: Cc1cccc(NC(=O)[C@@H]2C3CCC(C3)N2C(=O)Cn2cc(C(N)=O)c3cc(C(=O)N4CCCC(F)(F)C4)ccc32)n1] | 5-(3,3-difluoropiperidine-1-carbonyl)-1-(2-((1R,3S,4S)-3-((6-methylpyridin-2-yl)carbamoyl)-2-azabicyclo[2.2.1]heptan-2-yl)-2-oxoethyl)-1H-indole-3-carboxamide | ** | 2.07 (B) | 594 |
| 207 | 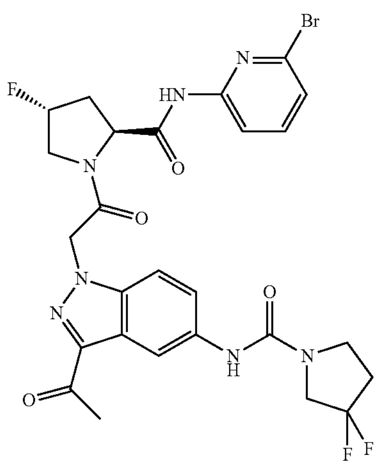 [SMILES: CC(=O)c1nn(CC(=O)N2C[C@H](F)C[C@H]2C(=O)Nc2cccc(Br)n2)c2ccc(NC(=O)N3CCC(F)(F)C3)cc12] | N-(3-acetyl-1-(2-((2S,4R)-2-((6-bromopyridin-2-yl)carbamoyl)-4-fluoropyrrolidin-1-yl)-2-oxoethyl)-1H-indazol-5-yl)-3,3-difluoropyrrolidine-1-carboxamide | *** | 12.88 (C) | 637 |
| 208 | 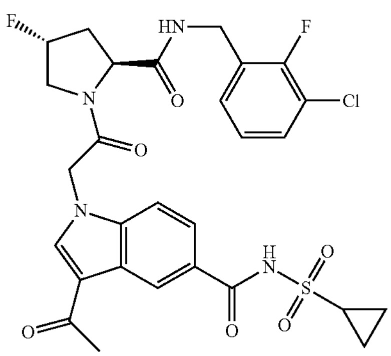 [SMILES: CC(=O)c1cn(CC(=O)N2C[C@H](F)C[C@H]2C(=O)NCc2cccc(Cl)c2F)c2ccc(C(=O)NS(=O)(=O)C3CC3)cc12] | 3-acetyl-1-(2-((2S,4R)-2-((3-chloro-2-fluorobenzyl)carbamoyl)-4-fluoropyrrolidin-1-yl)-2-oxoethyl)-N-(cyclopropylsulfonyl)-1H-indole-5-carboxamide | *** | 12.87 (C) | 622 |

TABLE 3-continued

Additional Compounds of the Present Invention

| Cmp No. | Structure | Name | IC$_{50}$ (Stars) | RT min (Method A, B, C or D) | MS (M + 1) |
|---|---|---|---|---|---|
| 209 | 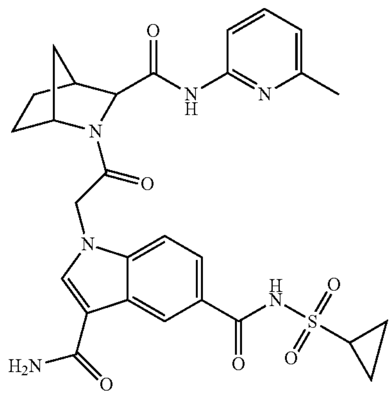 [SMILES: Cc1cccc(NC(=O)C2C3CCC(C3)N2C(=O)Cn2cc(C(N)=O)c3cc(C(=O)NS(=O)(=O)C4CC4)ccc32)n1] | N5-(cyclopropylsulfonyl)-1-(2-((1R,4S)-3-((6-methyl-pyridin-2-yl)carbamoyl)-2-aza-bicyclo[2.2.1]heptan-2-yl)-2-oxoethyl)-1H-indole-3,5-dicarboxamide | * | 1.30 (B) | 579 |
| 230 | 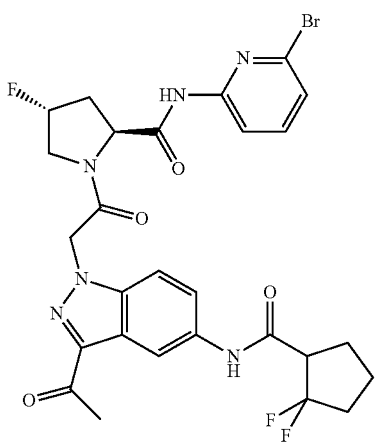 [SMILES: CC(=O)c1nn(CC(=O)N2C[C@H](F)C[C@H]2C(=O)Nc2cccc(Br)n2)c2ccc(NC(=O)C3CCCC3(F)F)cc12] | 2S,4R)-1-(2-(3-acetyl-5-(2,2-difluorocyclopentane-1-carboxamido)-1H-indazol-1-yl)acetyl)-N-(6-bromopyridin-2-yl)-4-fluoropyrrolidine-2-carboxamide | *** | 11.88 (D) | 633 (M − 2) |
| 231 | 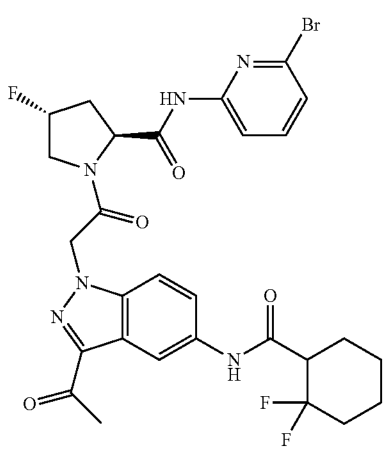 [SMILES: CC(=O)c1nn(CC(=O)N2C[C@H](F)C[C@H]2C(=O)Nc2cccc(Br)n2)c2ccc(NC(=O)C3CCCCC3(F)F)cc12] | 3-acetyl-N-(cyclopropylsulfonyl)-1-(2-((2S,4R)-4-fluoro-2-((3-phenylpropyl)carbamoyl)pyrrolidin-1-yl)-2-oxoethyl)-1H-indole-5-carboxamide | *** | 11.97 (D) | 647 (M − 2) |

TABLE 3-continued

Additional Compounds of the Present Invention

| Cmp No. | Structure | Name | IC$_{50}$ (Stars) | RT min (Method A, B, C or D) | MS (M + 1) |
|---|---|---|---|---|---|
| 232 | 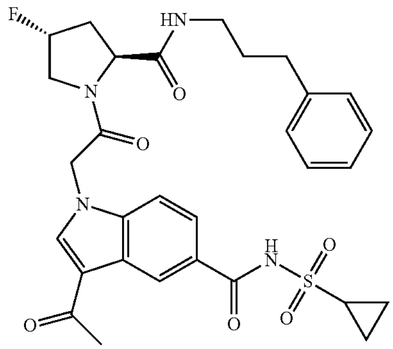 [SMILES: CC(=O)c1cn(CC(=O)N2C[C@H](F)C[C@H]2C(=O)NCCCc2ccccc2)c2ccc(C(=O)NS(=O)(=O)C3CC3)cc12] | 3-acetyl-1-(2-((2S,4R)-2-((6-bromopyridin-2-yl)carbamoyl)-4-fluoropyrrolidin-1-yl)-2-oxoethyl)-N-(cyclopropylsulfonyl)-1H-indazole-6-carboxamide | ** | 8.07 (D) | 595 (M − 1) |
| 233 | 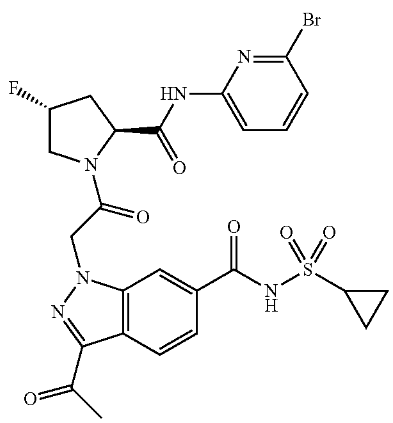 [SMILES: CC(=O)c1nn(CC(=O)N2C[C@H](F)C[C@H]2C(=O)Nc2cccc(Br)n2)c2cc(C(=O)NS(=O)(=O)C3CC3)ccc12] | 3-acetyl-1-(2-((2S,4R)-2-((6-bromopyridin-2-yl)-carbamoyl)-4-fluoro-pyrrolidin-1-yl)-2-oxoethyl)-N-(cyclopropylsulfonyl)-1H-indazole-6-carboxamide | *** | 8.36 (D) | 635 (M − 1) |
| 234 | 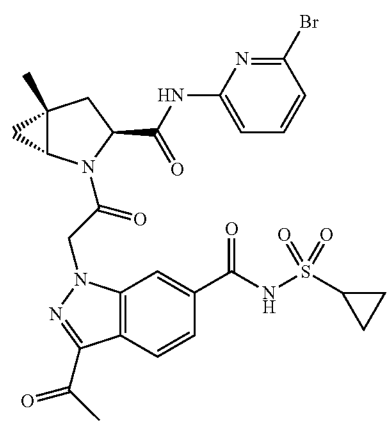 [SMILES: CC(=O)c1nn(CC(=O)N2[C@H](C(=O)Nc3cccc(Br)n3)C[C@@]3(C)C[C@@H]23)c2cc(C(=O)NS(=O)(=O)C3CC3)ccc12] | 3-acetyl-1-(2-((1R,3S,5R)-3-((6-bromopyridin-2-yl)carbamoyl)-5-methyl-2-azabicyclo[3.1.0]hexan-2-yl)-2-oxoethyl)-N-(cyclopropylsulfonyl)-1H-indazole-6-carboxamide | ** | 9.57 (C) | 644 |

Example 15. Human Factor D Assay

Human Factor D (purified from human serum, Complement Technology, Inc.) at 80 nM final concentration is incubated with test compound at various concentrations for 5 minutes at room temperature in 50 mM Tris, 1M NaCl, pH 7.5. A synthetic substrate Z-L-Lys-SBzl and DTNB (Ellman's reagent) are added to final concentrations of 100 µM each. Absorbance at 405 nm ($A_{405}$) is recorded at 30 second intervals for 30 minutes using a microplate spectrophotometer. IC$_{50}$ values are calculated by nonlinear regression of complement Factor D reaction rates as a function of test compound concentration.

Example 16. Hemolysis Assay

The hemolysis assay was previously described by G. Ruiz-Gomez, et al., J. Med. Chem. (2009) 52: 6042-6052. Prior to the assay, the optimum concentration of Normal Human Serum (NHS) needed to achieve 100% lysis of rabbit erythrocytes (RE) is determined by titration. In the assay, NHS (Complement Technology) is diluted in GVB⁰ Buffer (0.1% gelatin, 5 mM Veronal, 145 mM NaCl, 0.025% NaN$_3$, pH 7.3, Complement Technology) plus 10 mM Mg-EGTA and incubated with test compound at various concentrations for 15 minutes at 37° C. RE (Complement Technology) freshly suspended in GVB⁰ plus 10 mM Mg-EGTA are added to a final concentration of 1×10⁸ cells/mL and reactions are incubated for 30 minutes at 37° C. Positive control reactions (100% lysis) consist of GVB⁰ plus 10 mM Mg-EGTA with NHS and RE but without test compound; negative control reactions (0% lysis) consist of GVB⁰ plus 10 mM Mg-EGTA with RE only. Samples are centrifuged at 2000 g for 3 minutes and supernatants collected. Absorbance at 405 nm ($A_{405}$) is recorded using a microplate spectrophotometer. IC$_{50}$ values are calculated by nonlinear regression from the percentage of hemolysis as a function of test compound concentration.

Example 17. Effect of Combination Therapy

The combinatorial efficacy of two compounds on the complement alternative pathway (CAP) is assessed by determining the effect of two compounds mixed together at various concentrations with Normal Human Serum (NHS) on the hemolysis of rabbit erythrocytes (RE) or the production of terminal complement complex (TCC). In both assays the two test compounds are prepared individually in seven-point dilution series, with an eighth sample for each containing solvent alone, and each of the 64 possible combinations is tested in duplicate or triplicate wells.

In the hemolysis assay, NHS (Complement Technology) diluted to 10% in GVB⁰ Buffer (0.1% gelatin, 5 mM Veronal, 145 mM NaCl, 0.025% NaN$_3$, pH 7.3, Complement Technology) plus 10 mM Mg-EGTA is incubated with the compounds at various concentrations for 15 minutes at 37° C. RE (Complement Technology) freshly suspended in GVB⁰ plus 10 mM Mg-EGTA are added to a final concentration of 1×10⁸ cells/mL and reactions are incubated for 30 minutes at 37° C. Positive control reactions consist of GVB⁰ plus Mg-EGTA with NHS and RE but without test compounds; negative control reactions consist of GVB⁰ plus Mg-EGTA with RE only. Samples are centrifuged at 2000 g for 3 minutes and supernatants collected. Absorbance at 405 nM ($A_{405}$) is recorded using a microplate spectrophotometer.

The assay for TCC production is conducted using the Complement system Alternative Pathway Wieslab assay kit (Euro Diagnostica). NHS diluted to 5.56% in the provided diluent is incubated with each compound in the wells of the provided assay plates for 60 minutes at 37° C. The wells are emptied and washed with the provided wash solution, incubated with 100 enzyme-linked detection antibody at 37° C. for 30 minutes, emptied and washed again, and incubated with 100 µL substrate at room temperature for 30 minutes. The provided quantitation standards are used as described by the manufacturer. Positive control reactions consist of diluent with NHS but without test compounds; negative control reactions consist of diluent only. After the 30 minute incubation, the $A_{405}$ of each well is recorded using a microplate spectrophotometer. TCC production is quantitated from $A_{405}$ by reference to the quantitation standards.

Combinatorial effects in both assays are analyzed using the three-dimensional surface-graphing method of Prichard, M. N. and C. Shipman, Jr., Antiviral Research 1990, 14: 181-205, wherein the X-axis and Y-axis indicate test compound concentrations and the Z-axis indicates the difference between measured inhibition and a theoretically determined additive inhibition. For an additive combinatorial relationship the surface graph will resemble a horizontal plane of zero height, whereas positive surface peaks indicate greater inhibition than expected and therefore synergy, and negative surface peaks indicate less inhibition than expected and therefore antagonism.

Combinatorial efficacy on the hemolysis of rabbit erythrocytes (RE) can be examined using a compound described herein and a wide variety of second active agents. For example, one non-limiting example is the peptidic complement C3 inhibitor compstatin (Tocris Bioscience). In another example, the combinatorial efficacy of a compound as described herein and a complement Factor B inhibitor can be assessed, for example, using the structure below (See compound 84 in WO2013/192345). Alternatively, the combinatorial efficacy of a compound of the present invention and a monoclonal antibody directed against complement C5 protein (anti-C5, Quidel A217, murine monoclonal antibody to human complement C5, isotype IgG1K) on the production of terminal complement complex (TCC) can be assessed. In another non-limiting example, the combinatorial efficacy of an active compound of the invention and the broad spectrum inhibitor FUT-175 (BD Biosciences) on the hemolysis of rabbit erythrocytes (RE) is assessed.

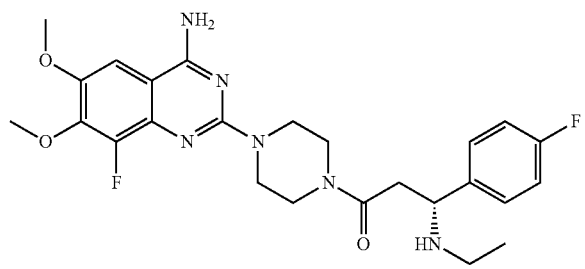

Structure of Complement Factor B Inhibitor

Synergy and antagonism volumes are the summed volumes of peaks respectively above and below the Z=0 plane on the surface graph. Volumes are determined using 95% confidence limits to assure significance. Compounds are considered additive for volumes between −25 and 25. Compounds are considered slightly synergistic for volumes between 25 and 50, moderately synergistic for volumes between 50 and 100, and strongly synergistic for volumes greater than 100. Compounds are considered slightly antagonistic for volumes between −25 and −50, moderately antagonistic for volumes between −50 and −100, and strongly antagonistic for volumes less than −100. Results are presented as means±standard deviations from two or three independent experiments.

This specification has been described with reference to embodiments of the invention. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

We claim:

1. A method for the treatment of a disorder mediated by complement factor D, comprising administering an effective amount to a host in need thereof a compound of Formula (I)

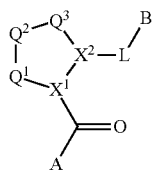

(I)

or a pharmaceutically acceptable salt thereof, wherein:
$Q^1$ is $C(R^1R^{1'})$;
$Q^2$ is $C(R^2R^{2'})$;
$Q^3$ is $C(R^3R^{3'})$;
$X^1$ is N and $X^2$ is CH;
$R^1$, $R^{1'}$, $R^2$, $R^{2'}$, $R^3$, and $R^{3'}$ are independently selected from hydrogen, halogen, hydroxyl, nitro, cyano, amino, $C_1$-$C_6$alkyl, $C_2$-$C_6$alkenyl, $C_2$-$C_6$alkynyl, $C_1$-$C_6$alkoxy, $C_2$-$C_6$alkynyl, $C_2$-$C_6$alkanoyl, $C_1$-$C_6$thioalkyl, hydroxy$C_1$-$C_6$alkyl, amino$C_1$-$C_6$alkyl, —$C_0$-$C_4$alkylNR$^9$R$^{10}$, —C(O)OR$^9$, —OC(O)R$^9$, —NR$^9$C(O)R$^{10}$, —C(O)NR$^9$R$^{10}$, —OC(O)NR$^9$R$^{10}$, —NR$^9$C(O)OR$^{10}$, $C_1$-$C_2$haloalkyl, and $C_1$-$C_2$haloalkoxy;
$R^9$ and $R^{10}$ are independently selected from hydrogen, $C_1$-$C_6$alkyl, ($C_3$-$C_7$cycloalkyl)$C_0$-$C_4$alkyl, —$C_0$-$C_4$alkyl($C_3$-$C_7$cycloalkyl), and —O—$C_0$-$C_4$alkyl($C_3$-$C_7$cycloalkyl);
or $R^1$ and $R^2$ are linked to form a 3- to 6-membered carbocyclic or aryl ring;
or $R^2$ and $R^3$ are linked to form a 3- to 6-membered carbocyclic ring;
or $R^1$ and $R^{1'}$, or $R^2$ and $R^{2'}$, or $R^3$ and $R^{3'}$ are linked to form a 3- to 6-membered carbocyclic spiro ring;
or $R^1$ and $R^{1'}$, or $R^2$ and $R^{2'}$, or $R^3$ and $R^{3'}$ are linked to form a 3- to 6-membered heterocyclic spiro ring;
each of which ring is unsubstituted or substituted with one or more substituents independently selected from halogen, hydroxyl, cyano, —COOH, $C_1$-$C_4$alkyl, $C_2$-$C_4$alkenyl, $C_2$-$C_4$alkynyl, $C_1$-$C_4$alkoxy, $C_2$-$C_4$alkanoyl, hydroxy$C_1$-$C_4$alkyl, (mono- and di-$C_1$-$C_4$alkylamino)$C_0$-$C_4$alkyl, —$C_0$-$C_4$alkyl($C_3$-$C_7$cycloalkyl), —O—$C_0$-$C_4$alkyl($C_3$-$C_7$cycloalkyl), $C_1$-$C_2$haloalkyl, and $C_1$-$C_2$haloalkoxy;
or $R^1$ and $R^{1'}$ or $R^2$ and $R^{2'}$ are taken together to form a carbonyl group;
A is a group selected from:

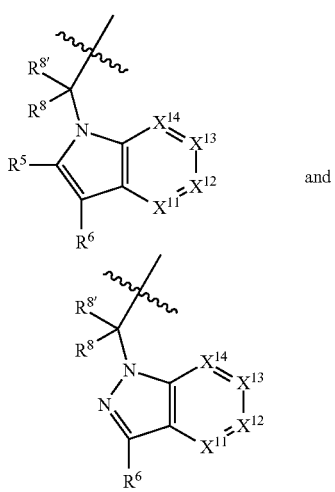

and $R^5$ and $R^6$ are independently selected from —CHO, —C(O)NH$_2$, —C(O)NH(CH$_3$), $C_2$-$C_6$alkanoyl, hydrogen, hydroxyl, halogen, cyano, nitro, —COOH, —SO$_2$NH$_2$, vinyl, $C_1$-$C_6$alkyl, $C_2$-$C_6$alkenyl, $C_1$-$C_6$alkoxy, —$C_0$-$C_4$alkyl($C_3$-$C_7$cycloalkyl), —C(O)$C_0$-$C_4$alkyl($C_3$-$C_7$cycloalkyl), —P(O)(OR$^9$)$_2$, —OC(O)R$^9$, —C(O)OR$^9$, —C(O)N(CH$_2$CH$_2$R$^9$)(R$^{10}$), —NR$^9$C(O)R$^{10}$, phenyl, and 5- to 6-membered heteroaryl;
$R^8$ and $R^{8'}$ are independently selected from hydrogen, halogen, hydroxyl, $C_1$-$C_6$alkyl, —$C_0$-$C_4$alkyl($C_3$-$C_7$cycloalkyl), $C_1$-$C_6$alkoxy, and ($C_1$-$C_4$alkylamino)$C_0$-$C_2$alkyl; or $R^8$ and $R^{8'}$ are taken together to form an oxo group; or $R^8$ and $R^{8'}$ can be taken together with the carbon that they are bonded to form a 3-membered carbocyclic ring;
$X^{11}$ is N or CR$^{11}$;
$X^{12}$ is CR$^{12}$;
$X^{13}$ is CR$^{13}$;
$X^{14}$ is N or CR$^{14}$;
one of $R^{12}$ and $R^{13}$ is selected from $R^{31}$ and the other of $R^{12}$ and $R^{13}$ is selected from $R^{32}$;
$R^{31}$ is selected from hydrogen, halogen, hydroxyl, nitro, cyano, amino, —COOH, $C_1$-$C_2$haloalkyl, $C_1$-$C_2$haloalkoxy, $C_1$-$C_6$alkyl, —$C_0$-$C_4$alkyl($C_3$-$C_7$cycloalkyl), $C_2$-$C_6$alkenyl, $C_2$-$C_6$alkanoyl, $C_1$-$C_6$alkoxy, $C_2$-$C_6$alkenyloxy, —C(O)OR$^9$, $C_1$-$C_6$thioalkyl, —$C_0$-$C_4$alkylNR$^9$R$^{10}$, —C(O)NR$^9$R$^{10}$, —SO$_2$R$^9$, —SO$_2$NR$^9$R$^{10}$, —OC(O)R$^9$, and —C(NR$^9$)NR$^9$R$^{10}$, each of which R$^{31}$ other than hydrogen, halogen, hydroxyl, nitro, cyano, $C_1$-$C_2$haloalkyl, and $C_1$-$C_2$haloalkoxy is unsubstituted or substituted with one or more substituents independently selected from halogen, hydroxyl, nitro, cyano, amino, —COOH, —CONH$_2$$C_1$-$C_2$haloalkyl, and $C_1$-$C_2$haloalkoxy, and each of which R$^{31}$ is also optionally substituted with one substituent selected from phenyl and 4- to 7-membered heterocycle containing 1, 2, or 3 heteroatoms independently selected from N, O, and S; which phenyl or 4- to 7-membered heterocycle is unsubstituted or substituted with one or more substituents independently selected from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl)($C_3$-$C_7$cycloalkyl), $C_1$-$C_2$haloalkyl, and $C_1$-$C_2$haloalkoxy;
$R^{32}$ is selected from —C(O)NR$^{21}$SO$_2$R$^{22}$, —NR$^9$C(O)OR$^{10}$, —NR$^9$C(O)OR$^{23}$, —NR$^9$C(O)R$^{21}$, —NR$^9$C(O)NR$^9$R$^{10}$, —NR$^9$C(O)NR$^{10}$R$^{23}$, and —NR$^9$C(O)NR$^{24}$R$^{25}$;
$R^{11}$ and $R^{14}$ are independently selected from hydrogen, halogen, hydroxyl, nitro, cyano, —O(PO)(OR$^9$)$_2$, —(PO)(OR$^9$)$_2$, $C_1$-$C_6$alkyl, $C_2$-$C_6$alkenyl, $C_2$-$C_6$alkynyl, $C_2$-$C_6$alkenyl(aryl), $C_2$-$C_6$alkenyl(cycloalkyl), $C_2$-$C_6$alkenyl(heterocycle), $C_2$-$C_6$alkenyl(heteroaryl), $C_2$-$C_6$alkynyl, $C_2$-$C_6$alkynyl(aryl), $C_2$-$C_6$alkynyl(cycloalkyl), $C_2$-$C_6$alkynyl(heterocycle), $C_2$-$C_6$alkynyl(heteroaryl), $C_2$-$C_6$alkanoyl, $C_1$-$C_6$alkoxy, $C_1$-$C_6$thioalkyl, —$C_0$-$C_4$alkyl(mono- and di-$C_1$-$C_6$alkylamino), —$C_0$-$C_4$alkyl($C_3$-$C_7$cycloalkyl), —$C_0$-$C_4$alkoxy($C_3$-$C_7$cycloalkyl), $C_1$-$C_2$haloalkyl, and $C_1$-$C_2$haloalkoxy;
$R^{21}$ and $R^{22}$ are independently selected from hydrogen, hydroxyl, cyano, amino, $C_1$-$C_6$alkyl, $C_1$-$C_6$haloalkyl, $C_1$-$C_6$alkoxy, ($C_3$-$C_7$cycloalkyl)$C_0$-$C_4$alkyl, (phenyl)$C_0$-$C_4$alkyl, —$C_1$-$C_4$alkylOC(O)OC$_1$-$C_6$alkyl, —$C_1$-

$C_4$alkylOC(O)$C_1$-$C_6$alkyl, —$C_1$-$C_4$alkylC(O)OC$_1$-$C_6$alkyl, (4- to 7-membered heterocycloalkyl)$C_0$-$C_4$alkyl having 1, 2, or 3 heteroatoms independently selected from N, O, and S, and (5- or 6-membered unsaturated or aromatic heterocycle)$C_0$-$C_4$alkyl having 1, 2, or 3 heteroatoms independently selected from N, O, and S;

$R^{23}$ is independently selected from $C_1$-$C_6$alkyl, $C_1$-$C_6$haloalkyl, ($C_3$-$C_7$cycloalkyl)$C_0$-$C_4$alkyl, (aryl)$C_0$-$C_4$alkyl, (4- to 7-membered heterocycloalkyl)$C_0$-$C_4$alkyl having 1, 2, or 3 heteroatoms independently selected from N, O, and S, and (5- or 6-membered unsaturated or aromatic heterocycle)$C_0$-$C_4$alkyl having 1, 2, or 3 heteroatoms independently selected from N, O, and S;

$R^{24}$ and $R^{25}$ are taken together with the nitrogen to which they are attached to form a 4- to 7-membered monocyclic heterocycloalkyl group, or a 6- to 10-membered bicyclic heterocyclic group having fused, spiro, or bridged rings and each $R^{24}$ and $R^{25}$;

L is

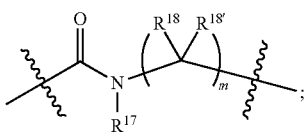

$R^{17}$ is hydrogen, $C_1$-$C_6$alkyl, or —$C_0$-$C_4$alkyl($C_3$-$C_7$cycloalkyl);

$R^{18}$ and $R^{18'}$ are independently selected from hydrogen, halogen, hydroxymethyl, and methyl;

m is 0, 1, 2, or 3;

B is a monocyclic or bicyclic carbocyclic; a monocyclic or bicyclic carbocyclic-oxy group; a monocyclic, bicyclic, or tricyclic heterocyclic group having 1, 2, 3, or 4 heteroatoms independently selected from N, O, and S and from 4 to 7 ring atoms per ring; $C_2$-$C_6$alkenyl; $C_2$-$C_6$alkynyl; —($C_0$-$C_4$alkyl)(aryl); —($C_0$-$C_4$alkyl)(heteroaryl); or —($C_0$-$C_4$alkyl)(biphenyl), and B is unsubstituted or substituted with one or more substituents independently selected from $R^{33}$ and $R^{34}$, and 0 or 1 substituents selected from $R^{35}$ and $R^{36}$;

$R^{33}$ is selected from halogen, hydroxyl, —COOH, cyano, $C_1$-$C_6$alkyl, $C_2$-$C_6$alkanoyl, $C_1$-$C_6$alkoxy, —$C_0$-$C_4$alkylNR$^9$R$^{10}$, —SO$_2$R$^9$, $C_1$-$C_2$haloalkyl, and $C_1$-$C_2$haloalkoxy;

$R^{34}$ is selected from nitro, $C_2$-$C_6$alkenyl, $C_2$-$C_6$alkynyl, $C_1$-$C_6$thioalkyl, -J$C_3$-$C_7$cycloalkyl, —B(OH)$_2$, -JC(O)NR$^9$R$^{23}$, -JOSO$_2$OR$^{21}$, —C(O)(CH$_2$)$_{1-4}$S(O)R$^{21}$, —O(CH$_2$)$_{1-4}$S(O)NR$^{21}$R$^{22}$, -JOP(O)(OR$^{21}$)(OR$^{22}$), -JP(O)(OR$^{21}$)(OR$^{22}$), -JOP(O)(OR$^{21}$)R$^{22}$, -JP(O)(OR$^{21}$)R$^{22}$, -JOP(O)R$^{21}$R$^{22}$, -JP(O)R$^{21}$R$^{22}$, -JSP(O)(OR$^{21}$)(OR$^{22}$), -JSP(O)(OR$^{21}$)(R$^{22}$), -JSP(O)(R$^{21}$)(R$^{22}$), -JNR$^9$P(O)(NHR$^{21}$)(NHR$^{22}$), -JNR$^9$P(O)(OR$^{21}$)(NHR$^{22}$), -JNR$^9$P(O)(OR$^{21}$)(OR$^{22}$), -JC(S)R$^{21}$, -JNR$^{21}$SO$_2$R$^{22}$, -JNR$^9$S(O)NR$^{10}$R$^{22}$, -JNR$^9$SO$_2$NR$^{10}$R$^{22}$, -JSO$_2$NR$^9$COR$^{22}$, -JSO$_2$NR$^9$CONR$^{21}$R$^{22}$, -JNR$^{21}$SO$_2$R$^{22}$, -JC(O)NR$^{21}$SO$_2$R$^{22}$, -JC(NH$_2$)NR$^{22}$, -JC(NH$_2$)NR$^9$S(O)$_2$R$^{22}$, -JOC(O)NR$^{21}$R$^{22}$, -JNR$^{21}$C(O)OR$^{22}$, -JNR$^{21}$OC(O)R$^{22}$, —(CH$_2$)$_{1-4}$C(O)NR$^{21}$R$^{22}$, -JC(O)NR$^{24}$R$^{25}$, -JNR$^9$C(O)R$^{21}$, -JC(O)R$^{21}$, -JNR$^9$C(O)NR$^1$R$^{22}$, —CCR$^{21}$, —(CH$_2$)$_{1-4}$OC(O)R$^{21}$, and -JC(O)OR$^{23}$; each of which $R^{34}$ may be unsubstituted or substituted with one or more substituents independently selected from halogen, hydroxyl, nitro, cyano, amino, oxo, —B(OH)$_2$, —Si(CH$_3$)$_3$, —COOH, —CONH$_2$, —P(O)(OH)$_2$, $C_1$-$C_6$alkyl, —$C_0$-$C_4$alkyl($C_3$-$C_7$cycloalkyl), $C_1$-$C_6$alkoxy, —$C_0$-$C_2$alkyl(mono- and di-$C_1$-$C_4$alkylamino), $C_1$-$C_6$alkylester, $C_1$-$C_4$alkylamino, $C_1$-$C_4$hydroxylalkyl, $C_1$-$C_2$haloalkyl, and $C_1$-$C_2$haloalkoxy;

$R^{35}$ is selected from naphthyl, naphthyloxy, indanyl, (4- to 7-membered heterocycloalkyl)$C_0$-$C_4$alkyl containing 1 or 2 heteroatoms selected from N, O, and S, and bicyclic heterocycle containing 1, 2, or 3 heteroatoms independently selected from N, O, and S, and containing 4- to 7-ring atoms in each ring; each of which $R^{35}$ is unsubstituted or substituted with one or more substituents independently selected from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), —SO$_2$R$^9$, $C_1$-$C_2$haloalkyl, and $C_1$-$C_2$haloalkoxy;

$R^{36}$ is selected from tetrazolyl, (phenyl)$C_0$-$C_2$alkyl, (phenyl)$C_1$-$C_2$alkoxy, phenoxy, and 5- or 6-membered heteroaryl containing 1, 2, or 3 heteroatoms independently selected from N, O, B, and S, each of which $R^{36}$ is unsubstituted or substituted with one or more substituents independently selected from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), —SO$_2$R$^9$, —OSi(CH$_3$)$_2$C(CH$_3$)$_3$, —Si(CH$_3$)$_2$C(CH$_3$)$_3$, $C_1$-$C_2$haloalkyl, and $C_1$-$C_2$haloalkoxy; and J is selected from a covalent bond, $C_1$-$C_4$alkylene, —O$C_1$-$C_4$alkylene, $C_2$-$C_4$alkenylene, and $C_2$-$C_4$alkynylene.

2. The method of claim 1, wherein the host is a human.

3. The method of claim 2, wherein the disorder is age-related macular degeneration (AMD) or retinal degeneration.

4. The method of claim 2, wherein the disorder is multiple sclerosis, arthritis, or COPD.

5. The method of claim 2, wherein the disorder is an ophthalmic disease.

6. The method of claim 2, wherein the disorder is paroxysmal nocturnal hemoglobinuria (PNH).

7. The method of claim 2, wherein the disorder is a respiratory disease.

8. The method of claim 2, wherein the disorder is cardiovascular disease.

9. The method of claim 2, wherein the disorder is atypical or typical hemolytic uremic syndrome.

10. The method of claim 2, wherein the disorder is rheumatoid arthritis.

11. The method of claim 2, wherein the disorder is C3 glomerulonephritis.

12. The method of claim 2, wherein the disorder is MPGN II.

13. The method of claim 2, wherein the disorder is membrane proliferative glomerulonephritis.

14. The method of claim 2, wherein the disorder is atypical hemolytic uremic syndrome.

15. The method of claim 2, wherein the

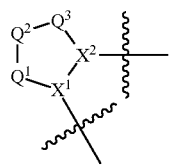

ring is selected from:

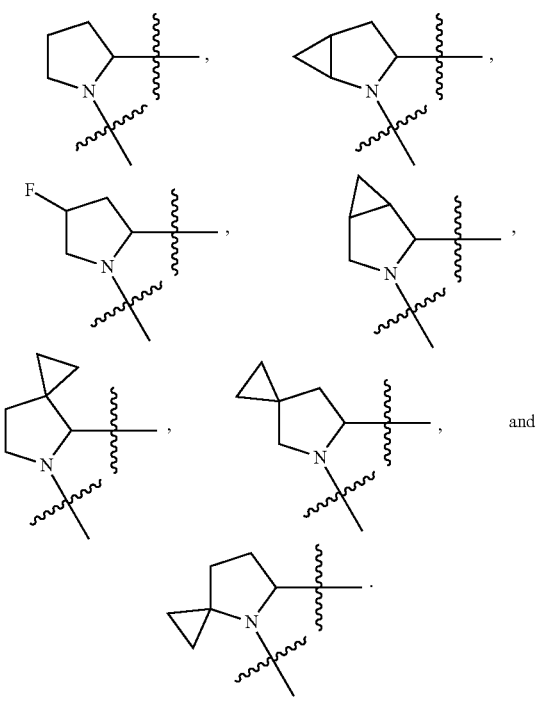

16. The method of claim 2, wherein:
a) $R^1$ and $R^{1'}$, or $R^2$ and $R^{2'}$, or $R^3$ and $R^{3'}$ are linked to form a 3- to 6-membered carbocyclic spiro ring; or
b) $R^1$ and $R^{1'}$, $R^2$ and $R^{2'}$ or $R^3$ and $R^{3'}$ are linked to form a 3- to 6-membered heterocyclic spiro ring; or
c) $R^1$ and $R^2$ are linked to form a 3- to 6-membered carbocyclic or aryl ring; or
d) $R^2$ and $R^3$ are linked to form a 3- to 6-membered carbocyclic ring.

17. The method of claim 2, wherein B is selected from —($C_0$-$C_4$alkyl)(aryl); —($C_0$-$C_4$alkyl)(heteroaryl); and —($C_0$-$C_4$alkyl)(biphenyl) wherein B is unsubstituted or substituted with one or more substituents independently chosen from $R^{33}$ and $R^{34}$, and 0 or 1 substituents chosen from $R^{35}$ and $R^{36}$.

18. The method of claim 3, wherein the —($C_0$-$C_4$alkyl)(aryl) group is phenyl or benzyl optionally substituted with halogen, hydroxyl, —COOH, cyano, $C_1$-$C_6$alkyl, $C_2$-$C_6$alkanoyl, $C_1$-$C_6$alkoxy, —$C_0$-$C_4$alkylNR$^9$R$^{10}$, —SO$_2$R$^9$, $C_1$-$C_2$haloalkyl, $C_1$-$C_2$haloalkoxy, $C_2$-$C_6$alkenyl, $C_2$-$C_6$alkynyl, $C_1$-$C_6$thioalkyl, or -J$C_3$-$C_7$cycloalkyl.

19. The method of claim 17, wherein the —($C_0$-$C_4$alkyl)(heteroaryl) group is imidazolyl, imidazopyridinyl, pyrimidinyl, pyrazolyl, triazolyl, pyrazinyl, furyl, thienyl, isoxazolyl, thiazolyl, oxadiazolyl, oxazolyl, isothiazolyl or pyrrolyl optionally substituted with halogen, hydroxyl, —COOH, cyano, $C_1$-$C_6$alkyl, $C_2$-$C_6$alkanoyl, $C_1$-$C_6$alkoxy, —$C_0$-$C_4$alkylNR$^9$R$^{10}$, —SO$_2$R$^9$, $C_1$-$C_2$haloalkyl, $C_1$-$C_2$haloalkoxy, $C_2$-$C_6$alkenyl, $C_2$-$C_6$alkynyl, $C_1$-$C_6$thioalkyl, or -J$C_3$-$C_7$cycloalkyl.

20. The method of claim 17, wherein the —($C_0$-$C_4$alkyl)(biphenyl) group is biphenyl optionally substituted with halogen, hydroxyl, —COOH, cyano, $C_1$-$C_6$alkyl, $C_2$-$C_6$alkanoyl, $C_1$-$C_6$alkoxy, —$C_0$-$C_4$alkylNR$^9$R$^{10}$, —SO$_2$R$^9$, $C_1$-$C_2$haloalkyl, $C_1$-$C_2$haloalkoxy, $C_2$-$C_6$alkenyl, $C_2$-$C_6$alkynyl, $C_1$-$C_6$thioalkyl, or -J$C_3$-$C_7$cycloalkyl.

21. The method of claim 2, wherein B is selected from:

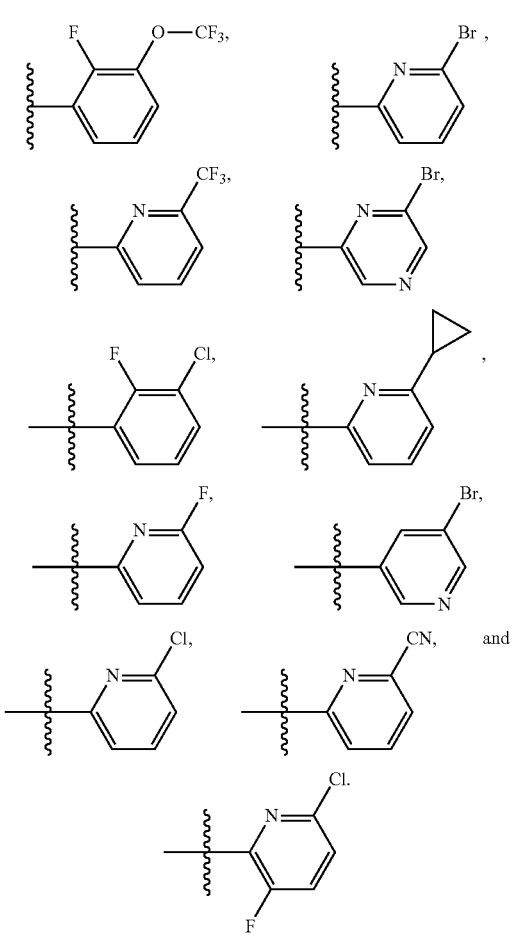

22. The method of claim 2, wherein B is selected from:

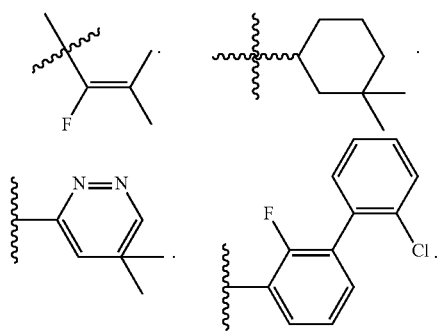

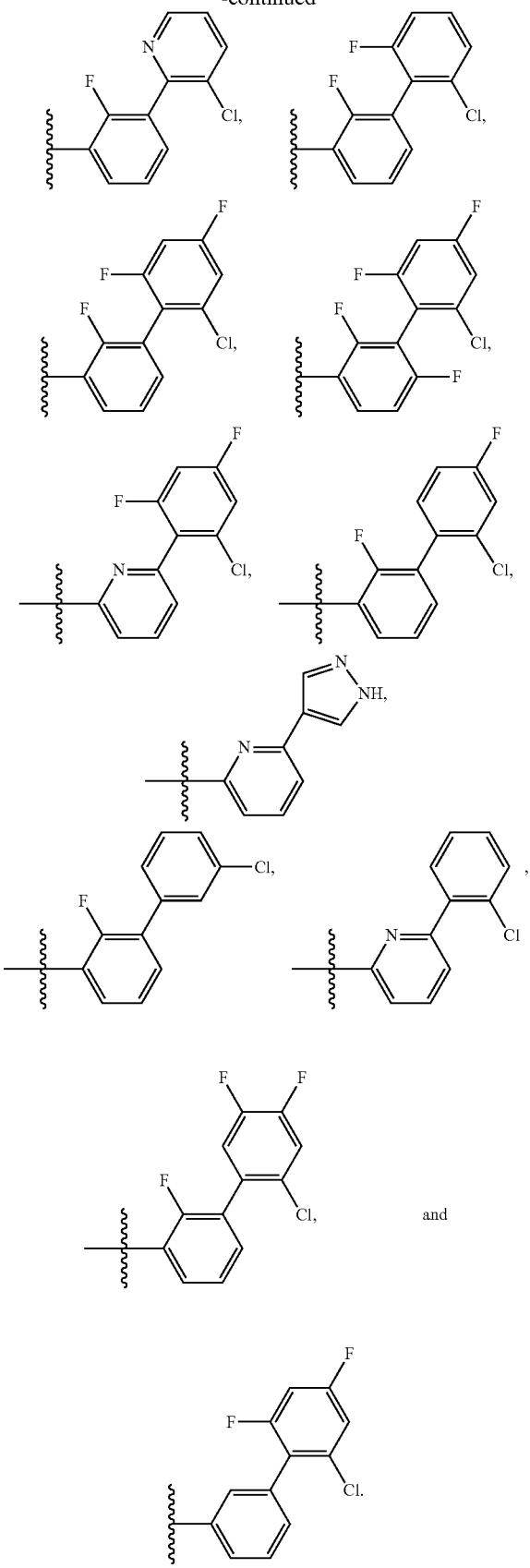
23. The method of claim 2, wherein $R^{32}$ is selected from:
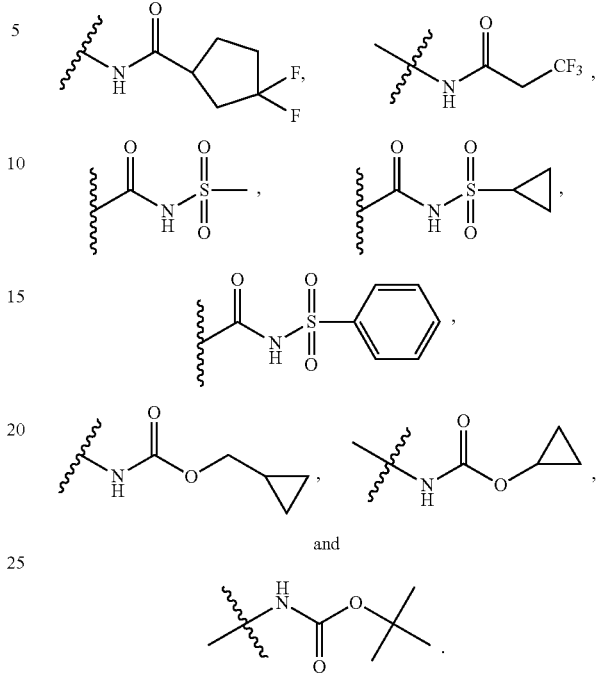
24. The method of claim 2, wherein the compound is selected from:
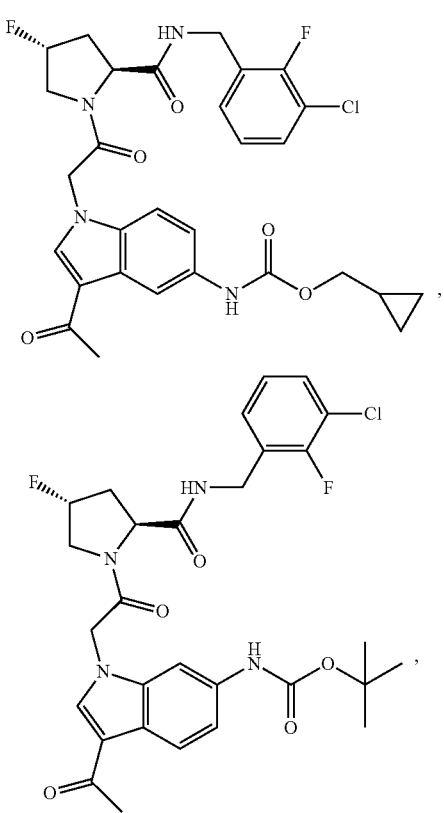

-continued

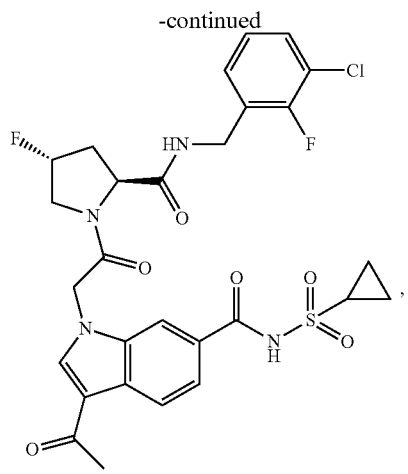

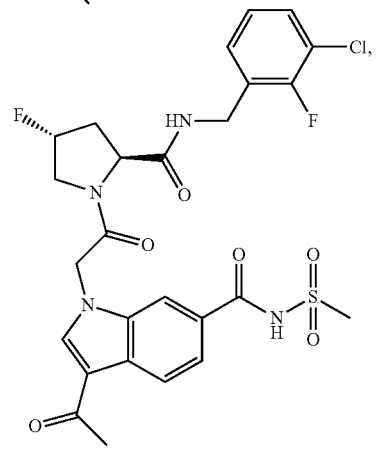

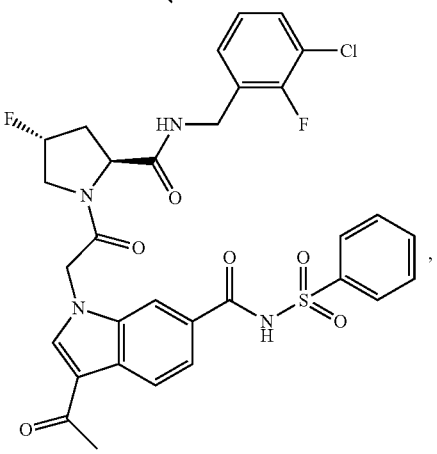
, and

-continued

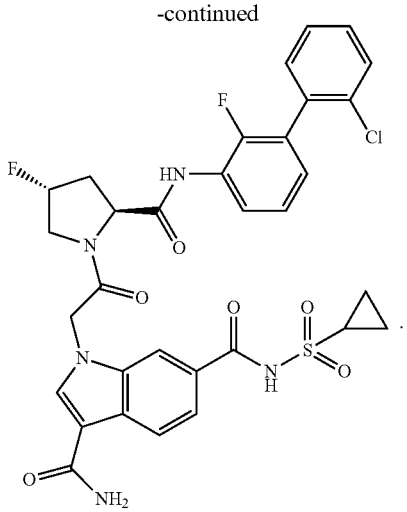
.

25. The method of claim 2, wherein the disorder is fatty liver disease.

26. The method of claim 2, wherein the disorder is liver inflammation, cirrhosis, or liver failure.

27. The method of claim 2, wherein the disorder is Dermatomyositis.

28. The method of claim 2, wherein the disorder is amyotrophic lateral sclerosis.

29. The method of claim 2, wherein the disorder is nonalcoholic steatohepatitis.

30. The method of claim 5, wherein the compound is administered to the intravitreal, subchoroidal, or suprachoroidal space of the eye.

31. The method of claim 2, wherein the compound is administered in combination with an effective amount of an additional active agent.

* * * * *